United States Patent
Goff et al.

(10) Patent No.: US 9,409,884 B2
(45) Date of Patent: *Aug. 9, 2016

(54) 5- OR 6-SUBSTITUTED BENZOFURAN-2-CARBOXAMIDE COMPOUNDS AND METHODS FOR USING THEM

(71) Applicant: Rigel Pharmaceuticals, Inc., South San Francisco, CA (US)

(72) Inventors: Dane Goff, Redwood City, CA (US); Donald Payan, Hillsborough, CA (US); David Carroll, San Francisco, CA (US); Simon Shaw, Oakland, CA (US); Hitoshi Yasumichi, Brisbane, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/376,098

(22) PCT Filed: Jan. 31, 2013

(86) PCT No.: PCT/US2013/024101
§ 371 (c)(1),
(2) Date: Jul. 31, 2014

(87) PCT Pub. No.: WO2013/116491
PCT Pub. Date: Aug. 8, 2013

(65) Prior Publication Data
US 2014/0378429 A1    Dec. 25, 2014

Related U.S. Application Data

(60) Provisional application No. 61/593,801, filed on Feb. 1, 2012.

(51) Int. Cl.
*C07D 401/14* (2006.01)
*A61K 31/453* (2006.01)
(Continued)

(52) U.S. Cl.
CPC ............ *C07D 401/14* (2013.01); *A61K 31/453* (2013.01); *A61K 31/454* (2013.01);
(Continued)

(58) Field of Classification Search
CPC .. C07D 211/46; C07D 211/58; C07D 211/98; C07D 401/12; C07D 401/14; C07D 409/14; C07D 413/14; C07D 417/14; C07D 471/04; C07D 487/08; A61K 31/5377; A61K 31/354; A61K 31/496; A61K 31/454; A61K 31/4545; A61K 31/4709
USPC .............. 514/210.2, 235.5, 253.01, 292, 314, 514/416, 318; 544/130, 360, 364; 546/87, 546/169, 187, 194, 196
See application file for complete search history.

(56) References Cited

U.S. PATENT DOCUMENTS 8,012,955 B2    9/2011  Singh et al.

8,119,809 B2 *  2/2012  Hong et al. ................... 546/187
(Continued)

FOREIGN PATENT DOCUMENTS

WO    2008/083124    7/2008
WO    2009/065131    5/2009
(Continued)

OTHER PUBLICATIONS

Braga et al. "Making crystals from crystals . . . " J. Roy Soc Chem Chem Commun.p. 3635-3645 (2005).*
Improper Markush, Fed. Reg. 76(27)p. 7162-7175, slides 1, 64-67 (2011).*
Sedoon "Pseudopolymorph . . . " Crys. Growth & design. v.4(6) p. 1087 (2005).*
Vippagunta et al. "Crystallline solids" Adv. Drug Del. Rev. 48 p. 3-26 (2001).*
Zhao et al. "Discovery and SAR . . . " Bioorg. Med. Chem. Lett. v.17, p. 3254-3257 (2007).*
"New Matter" USPTO connection v.II(1) p. 1-3 (2005).*
(Continued)

*Primary Examiner* — Celia Chang
(74) *Attorney, Agent, or Firm* — McDonnell Boehnen Hulbert & Berghoff LLP; Travis Young

(57) ABSTRACT

The disclosure relates particularly to certain carboxamide, sulfonamide and amine compounds and pharmaceutical compositions thereof, and to methods of treating and ameliorating disorders and conditions related to the adiponectin pathway, sphingolipid metabolism, oxidative stress, mitochondrial dysfunction, free radical damage and metabolic inefficiency, among others. In certain embodiments, the compounds have the structures (1-I), (2-I) and (3-I)

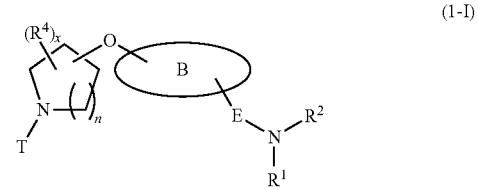

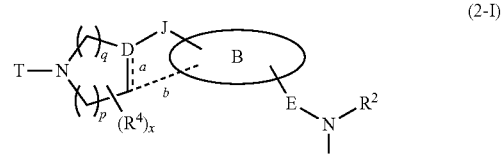

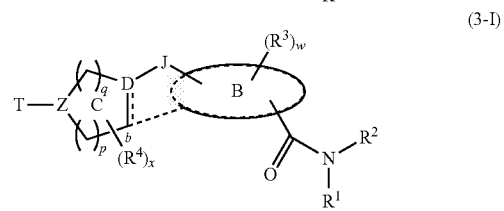

in which the variables are as described herein.

17 Claims, No Drawings

(51) Int. Cl.

| | |
|---|---|
| *A61K 31/454* | (2006.01) |
| *A61K 31/4545* | (2006.01) |
| *A61K 31/4709* | (2006.01) |
| *A61K 31/4725* | (2006.01) |
| *A61K 31/496* | (2006.01) |
| *A61K 31/5377* | (2006.01) |
| *C07D 405/14* | (2006.01) |
| *C07D 413/14* | (2006.01) |
| *C07D 401/12* | (2006.01) |
| *C07D 405/12* | (2006.01) |
| *C07D 409/14* | (2006.01) |
| *C07D 417/14* | (2006.01) |
| *C07D 471/04* | (2006.01) |
| *C07D 487/08* | (2006.01) |
| *C07D 211/46* | (2006.01) |
| *C07D 211/58* | (2006.01) |
| *C07D 211/98* | (2006.01) |
| *C12N 9/12* | (2006.01) |

(52) U.S. Cl.
CPC ......... *A61K31/4545* (2013.01); *A61K 31/4709* (2013.01); *A61K 31/4725* (2013.01); *A61K 31/496* (2013.01); *A61K 31/5377* (2013.01); *C07D 211/46* (2013.01); *C07D 211/58* (2013.01); *C07D 211/98* (2013.01); *C07D 401/12* (2013.01); *C07D 405/12* (2013.01); *C07D 405/14* (2013.01); *C07D 409/14* (2013.01); *C07D 413/14* (2013.01); *C07D 417/14* (2013.01); *C07D 471/04* (2013.01); *C07D 487/08* (2013.01); *C12N 9/12* (2013.01); *C12Y 207/11031* (2013.01)

(56) References Cited

U.S. PATENT DOCUMENTS

| | | | |
|---|---|---|---|
| 8,129,390 | B2 | 3/2012 | Darwish et al. |
| 8,314,107 | B2 | 11/2012 | Yu et al. |
| 8,362,235 | B2 | 1/2013 | Darwish et al. |
| 8,557,822 | B2 | 10/2013 | Darwish et al. |
| 8,569,340 | B2 | 10/2013 | Hong et al. |
| 8,697,727 | B2 | 4/2014 | Singh et al. |
| 8,785,449 | B2 | 7/2014 | Yu et al. |
| 8,791,136 | B2 | 7/2014 | Goff et al. |
| 8,796,254 | B2 * | 8/2014 | Payan et al. ................. 514/210.2 |
| 2009/0186894 | A1 | 7/2009 | Singh et al. |
| 2013/0131078 | A1 | 5/2013 | Darwish et al. |
| 2013/0203987 | A1 | 8/2013 | Goff et al. |
| 2013/0267701 | A1 | 10/2013 | Goff et al. |
| 2013/0267702 | A1 | 10/2013 | Goff et al. |
| 2014/0045882 | A1 | 2/2014 | Darwish et al. |
| 2014/0051673 | A1 | 2/2014 | Hong et al. |
| 2014/0148467 | A1 | 5/2014 | Yu et al. |
| 2014/0179738 | A1 | 6/2014 | Singh et al. |

FOREIGN PATENT DOCUMENTS

| | | |
|---|---|---|
| WO | 2009/076631 | 6/2009 |
| WO | 2009/132136 | 10/2009 |

OTHER PUBLICATIONS

DEA "position isomer" FR Doc E6-7979 [Federal Register:vol. 71, No. 10, p. 30097-30100 (2006).*
International Search Report and Written Opinion of PCT/US2013/024101 filed Jan. 31, 2013.
Pending U.S. Appl. No. 14/325,012, filed Jul. 7, 2014.
Pending U.S. Appl. No. 14/325,766, filed Jul. 8, 2014.

* cited by examiner

5- OR 6-SUBSTITUTED BENZOFURAN-2-CARBOXAMIDE COMPOUNDS AND METHODS FOR USING THEM

CROSS-REFERENCE TO RELATED APPLICATIONS

This application is a U.S. national phase application of International Patent Application No. PCT/US2013/024101 filed on Jan. 31, 2013, which claims the priority of U.S. Provisional Patent Application Ser. No. 61/593,801, which is hereby incorporated herein by reference in its entirety

BACKGROUND

1. Field

This disclosure relates generally to compounds, pharmaceutical compositions and methods of use of the compounds and compositions containing them. This disclosure relates more particularly to certain carboxamide, sulfonamide and amine compounds and pharmaceutical compositions thereof, and to methods of treating and ameliorating disorders and conditions related to the adiponectin pathway, sphingolipid metabolism, oxidative stress, mitochondrial dysfunction, free radical damage and metabolic inefficiency, among others.

2. Technical Background

The kinase 5'-AMP-activated protein kinase (AMPK) is well established as an important sensor and regulator of cellular energy homeostasis. Being a multi-substrate enzyme, AMPK regulates a variety of metabolic processes, such as glucose transport, glycolysis and lipid metabolism. It acts as a sensor of cellular energy homeostasis and is activated in response to certain hormones and muscle contraction as well as to intracellular metabolic stress signals such as exercise, ischemia, hypoxia and nutrient deprivation. Once activated, AMPK switches on catabolic pathways (such as fatty acid oxidation and glycolysis) and switches off ATP-consuming pathways (such as lipogenesis). Activation of the AMPK pathway improves insulin sensitivity by directly stimulating glucose uptake in adipocytes and muscle and by increasing fatty acid oxidation in liver and muscle, resulting in reduced circulating fatty acid levels and reduced intracellular triglyceride contents. Moreover, activation of the AMPK pathway decreases glycogen concentration by reducing the activity of glycogen synthase. Activation of the AMPK pathway also plays a protective role against inflammation and atherosclerosis. It suppresses the expression of adhesion molecules in vascular endothelial cells and cytokine production from macrophages, thus inhibiting the inflammatory processes that occur during the early phases of atherosclerosis. What is needed are compounds, pharmaceutical compositions and methods of using them to treat disease states wherein AMPK activation is beneficial, such as type II diabetes, atherosclerosis and cardiovascular disease.

SUMMARY

One aspect of the disclosure relates to compounds having any of structural formula (1-I), (2-I), (3-I), (4-I), (5-I), (5-XVII), (6-I) and (7-I):

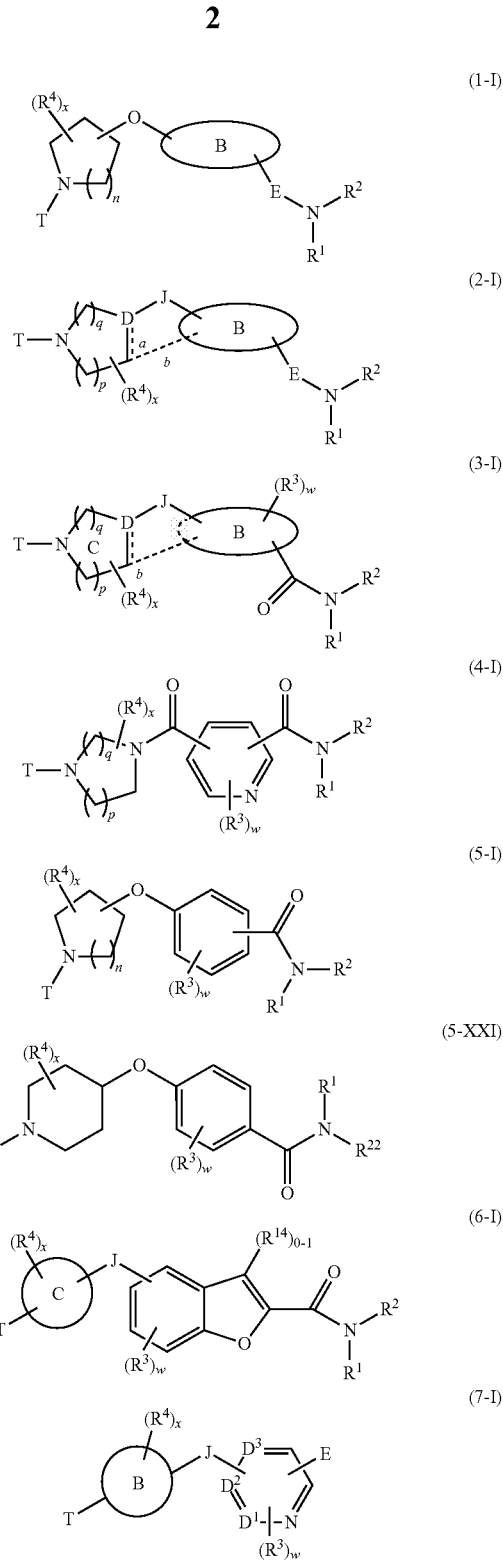

and pharmaceutically acceptable salts, prodrug and N-oxide thereof (and solvates and hydrates thereof), wherein the variables are as described herein.

Also disclosed herein are pharmaceutical compositions. Examples of such compositions include those having at least one pharmaceutically acceptable carrier, diluent or excipient; and a compound, pharmaceutically acceptable salt or N-oxide (or solvate or hydrate) disclosed herein.

Another aspect of the present disclosure includes methods for modulating metabolism in subjects. Accordingly, also disclosed are methods for treating metabolic disorders using the presently disclosed compounds and pharmaceutical compositions.

Another aspect of the present disclosure includes methods of treating or ameliorating disorders and conditions related to oxidative stress, mitochondrial dysfunction, free radical damage and metabolic inefficiency, using the presently disclosed compounds and pharmaceutical compositions.

Another aspect of the present disclosure includes methods for modulating sphingolipid metabolism, for example modulating ceramide signalling in subjects. In one aspect, modulating sphingolipid metabolism includes modulating ceramidase activity, for example by up-regulating ceramidase function. Accordingly, also disclosed are methods for treating ceramide-linked diseases and disorders using the presently disclosed compounds and pharmaceutical compositions Another aspect of the present disclosure relates to methods for increasing exercise endurance, exercise efficiency and aerobic workload in subjects using the compounds described herein.

Another aspect of the present disclosure relates to methods for using the compounds described herein as exercise mimetics.

Another aspect of the present disclosure relates to methods for increasing fiber oxidative capacity of muscle fiber using the compounds described herein.

DETAILED DESCRIPTION

One aspect of the disclosure provides compounds having structural formula (1-I):

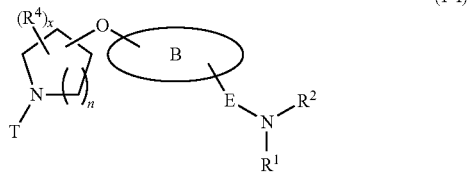

(1-I)

and pharmaceutically acceptable salts, and N-oxides thereof (and solvates and hydrates thereof), wherein "B" represents -(aryl or heteroaryl)- substituted by w $R^3$ and k $R^{14}$;

E is —C(O)—, —S(O)$_2$— or a single bond, provided that when "B" is phenyl, E is not —C(O)—;

$R^1$ is H, —(C$_1$-C$_4$ alkyl) or —C(O)O—(C$_1$-C$_4$ alkyl);

$R^2$ is -Hca, -Cak-N(R$^9$)-G-R$^{22}$ or —(C$_2$-C$_8$ alkyl)-N(R$^9$)—R$^{24}$ in which one or two carbons of the (C$_2$-C$_8$ alkyl) are optionally replaced by —O—, —S— or —N(R$^9$)— and $R^{24}$ is —R$^{23}$, -G-R$^{23}$, or —C(O)O—(C$_1$-C$_6$ alkyl);

each $R^3$ is substituted on a benzo or pyrido carbon of the ring system denoted by "B" and is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN;

w is 0, 1, 2 or 3;

each $R^{14}$ is substituted on a non-benzo, non-pyrido carbon of the ring system denoted by "B", and is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN;

k is 0, 1 or 2;

each $R^4$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two $R^4$ on the same carbon optionally combine to form oxo;

x is 0, 1, 2, 3 or 4;

n is 0, 1, 2 or 3;

T is —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$ or

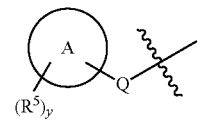

in which

Q is —(C$_0$-C$_3$ alkyl)-, in which each carbon of the —(C$_0$-C$_3$ alkyl)- is optionally and independently substituted with one or two R$^{16}$, or —S(O)$_2$—;

the ring system denoted by "A" is heteroaryl, aryl, cycloalkyl or heterocycloalkyl;

each $R^5$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, —(C$_0$-C$_6$ alkyl)-C(O)R$^{10}$, -halogen, —NO$_2$ and —CN; and y is 0, 1, 2, 3 or 4;

in which each L is independently selected from —NR$^9$C(O)O—, —OC(O)NR$^9$—, —NR$^9$C(O)—NR$^9$—, —NR$^9$C(O)S—, —SC(O)NR$^9$—, —NR$^9$C(O)—, —C(O)NR$^9$—, —NR$^9$C(S)O—, —OC(S)NR$^9$—, —NR$^9$C(S)—NR$^9$—, —NR$^9$C(S)S—, —SC(S)NR$^9$—, —NR$^9$C(S)—, —C(S)NR$^9$—, —SC(O)NR$^9$—, —NR$^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR$^9$C(NR$^2$)NR$^9$—, —NR$^9$SO$_2$—, —SO$_2$NR$^9$— and —NR$^9$SO$_2$NR$^9$—, each $R^6$, $R^7$, $R^8$ and $R^{10}$ is independently selected from H, —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-(C$_0$-C$_6$ alkyl), —(C$_0$-C$_6$ alkyl)-NR$^9$—(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), each $R^9$ is independently selected from —H, —(C$_1$-C$_4$ alkyl) and —C(O)O—(C$_1$-C$_4$ alkyl), each G is independently —(C$_0$-C$_3$ alkyl)-, in which each carbon of the —(C$_0$-C$_3$ alkyl)- is optionally and independently substituted with one or two R$^{16}$, or —S(O)$_2$—, each $R^{16}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and optionally two of $R^{16}$ on the same carbon combine to form oxo, each $R^{20}$, $R^{22}$ and $R^{23}$ is independently Ar or Het, each Ar is an optionally substituted aryl, each Het is an optionally substituted heteroaryl, each Cak is an optionally substituted cycloalkyl, each Hca is an optionally substituted heterocycloalkyl, and each alkyl is optionally substituted.

Various embodiments of compounds of structural formula (1-I) suitable for use in the methods described herein are described below. Information regarding certain of these compounds can also be found in U.S. Patent Application Publication no. 2009/0170829, which is hereby incorporated by reference in its entirety.

In certain embodiments of the presently disclosed compounds of structural formula (1-I), the ring system denoted by "B" is

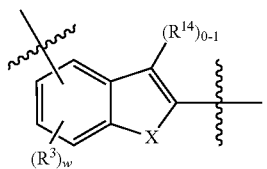

in which X is O or S, and E is —C(O)—. In certain such embodiments, one $R^{14}$ can be substituted on the furano or thieno carbon. In one such embodiment, $R^{14}$ is selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, $R^{14}$ is selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. $R^{14}$ can be, for example, halo (e.g., —Cl or —F), cyano, or unsubstituted —($C_1$-$C_4$ alkyl) (e.g., methyl or ethyl), unsubstituted —($C_1$-$C_4$ haloakyl) (e.g., trifluoromethyl). In other embodiments, no $R^{14}$ is substituted on the furano or thieno carbon. In certain embodiments, $R^{14}$ is H or methyl; in others, $R^{14}$ is halo (e.g., Cl).

In one embodiment of the presently disclosed compounds of structural formula (1-I), X is O.

In certain embodiments of the presently disclosed compounds of structural formula (1-I), the ring system denoted by "B" is

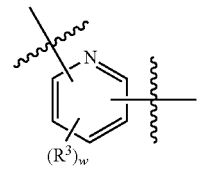

and E is —C(O)— or —S(O)$_2$—.

In certain embodiments of the presently disclosed compounds of structural formula (1-I), the ring system denoted by "B" is

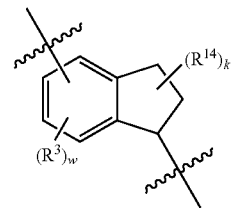

and E is a single bond. In one embodiment, k is 0. In another embodiment, k is 1 or 2. In certain embodiments, In each $R^{14}$ is independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{14}$ is independently selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. Each $R^{14}$ can be, for example, halo (e.g., —Cl or —F), cyano, unsubstituted —($C_1$-$C_4$ alkyl) (e.g., methyl or ethyl) or unsubstituted —($C_1$-$C_4$ haloakyl) (e.g., trifluoromethyl).

In certain embodiments of the presently disclosed compounds of structural formula (1-I), T is

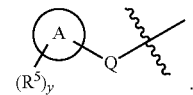

In such embodiments, Q is —S(O)$_2$— or —($C_0$-$C_3$ alkyl)- in which each carbon of the ($C_0$-$C_3$ alkyl) is optionally and independently substituted with one or two R$^{16}$, in which each R$^{16}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of R$^{16}$ on the same carbon combine to form oxo. In certain embodiments, each R$^{16}$ is independently selected from —(C$_1$-C$_6$ alkyl), —(C$_1$-C$_6$ haloalkyl) (e.g., trifluoromethyl), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two R$^{16}$ on the same carbon optionally combine to form an oxo, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl), and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in particular compounds, each R$^{16}$ is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, and two R$^{16}$ on the same carbon optionally combine to form an oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, Q has at most one R$^{16}$ or an oxo substituted thereon. Q can be, for example, an unsubstituted —(C$_0$-C$_3$ alkyl)-. In other embodiments, Q is a (C$_1$-C$_3$ alkyl) having as its only substitution a single oxo group. For example, in certain embodiments, Q is —CH$_2$—; a single bond; —S(O)$_2$—; —C(O)—; or —CH(CH$_3$)—.

In certain embodiments of the presently disclosed compounds of structural formula (1-I), the

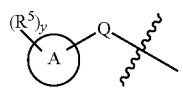

moiety is

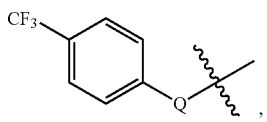

for example, p-(trifluoromethyl)phenyl. In other embodiments, the

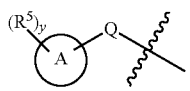

moiety is

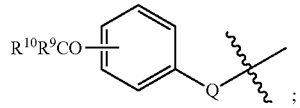

in one such embodiment, Q is a single bond.

The number of substituents on the ring system denoted by "A", y, is 0, 1, 2, 3 or 4. For example, in some embodiments, y is 0, 1, 2 or 3, for example 1. In one embodiment, y is not zero and at least one R$^5$ is halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ or —C(O)—Hca in which the Hca contains a ring nitrogen atom through which it is bound to the —C(O)—, and in which no alkyl, haloalkyl or heterocycloalkyl is substituted by an aryl, heteroaryl, cycloalkyl or heterocycloalkyl-containing group.

In certain embodiments of the presently disclosed compounds of structural formula (1-I), each R$^5$ is independently selected from —(C$_1$-C$_6$ alkyl), —(C$_1$-C$_6$ haloalkyl) (e.g., trifluoromethyl), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, in which each R$^7$, R$^8$ and R$^{10}$ is independently selected from H, —(C$_1$-C$_6$ alkyl), —(C$_1$-C$_6$ haloalkyl) (e.g., trifluoromethyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, each R$^5$ is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group.

In one embodiment of the compounds of structural formula (1-I), y is 0.

In the presently disclosed compounds, the ring system denoted by "A" is heteroaryl, aryl, cycloalkyl or heterocycloalkyl. For example, in one embodiment, the ring system denoted by "A" is an aryl or a heteroaryl. The ring system denoted by "A" can be, for example, a monocyclic aryl or heteroaryl. In one embodiment, when the "A" ring system is aryl, Q is a —(C$_0$-C$_3$ alkyl)- optionally substituted with oxo, and optionally substituted with one or more R$^{16}$. For example, Q can be a —(C$_1$-C$_3$ alkyl)- having its only substitution a single oxo, or an unsubstituted —(C$_0$-C$_3$ alkyl)-. For example, in certain embodiments, Q is —CH—; a single bond; —S(O)$_2$—; —C(O)—; or —CH(CH$_3$)—.

For example, in certain embodiments of the presently disclosed compounds, the ring system denoted by "A" is a phenyl. In one embodiment, y is 1 and R$^5$ is attached to the phenyl para to Q. In another embodiment, y is 1 and R$^5$ is selected from the group consisting of halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, and in which no ($C_0$-$C_4$ alkyl) or ($C_1$-$C_4$ alkyl) is substituted by an aryl, heteroaryl, cycloalkyl or heterocycloalkyl-containing group. $R^5$ can be, for example, —Cl, —F, cyano, —C(O)CH$_3$, —C(O)OH, —C(O)NH$_2$, trifluoromethyl, difluoromethyl, difluoromethoxy or trifluoromethoxy. In another embodiment, the

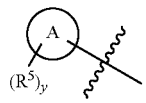

moiety is a 3,4-dihalophenyl.

In another embodiment of the presently disclosed compounds of structural formula (1-I), the ring system denoted by "A" is a heteroaryl. For example, in certain embodiments, the ring system denoted by "A" is a pyridyl, a thienyl, or a furanyl. In other embodiments, the ring system denoted by "A" is a pyrazolyl, imidazolyl, pyrrolyl, triazolyl or thiadiazolyl. In one embodiment, when the "A" ring system is heteroaryl, Q is a —($C_0$-$C_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. In certain embodiments, Q is —CH$_2$—; a single bond; —S(O)$_2$—; —C(O)—; or —CH(CH$_3$)—.

In certain embodiments of the presently disclosed compounds of structural formula (1-I), the

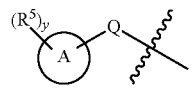

moiety is

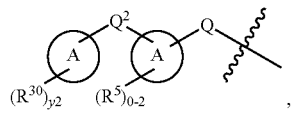

in which the ring system denoted by "A" is aryl or heteroaryl, the ring system denoted by "D" is cycloalkyl, heterocycloalkyl, aryl or heteroaryl; $Q^2$ is —S(O)$_2$—, —O— or —($C_0$-$C_3$ alkyl)- in which each carbon of the ($C_0$-$C_3$ alkyl) is optionally and independently substituted with one or two $R^{16}$, defined as described above with respect to Q; $y^2$ is 0, 1 or 2; and each $R^{30}$ is independently selected from —($C_1$-$C_3$ alkyl), —($C_1$-$C_3$ haloalkyl), —($C_0$-$C_3$ alkyl)-L-$R^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-NR$^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, $Q^2$ has at most one $R^{16}$ or an oxo substituted thereon. $Q^2$ can be, for example, an unsubstituted —($C_0$-$C_3$ alkyl)-. In other embodiments, $Q^2$ is a ($C_1$-$C_3$ alkyl) having as its only substitution a single oxo group. For example, in certain embodiments, $Q^2$ is —CH$_2$—; a single bond; —S(O)$_2$—; —O—; —C(O)—; or —CH(CH$_3$)—. In certain embodiments, at least one $R^{30}$ is halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), NO$_2$ or —C(O)—Hca in which the Hca contains a ring nitrogen atom through which it is bound to the —C(O)—, and in which no alkyl, haloalkyl or heterocycloalkyl is substituted by an aryl, heteroaryl, cycloalkyl or heterocycloalkyl-containing group. In certain embodiments, at least one $R^5$ is —SO$_2$($C_1$-$C_6$ alkyl), —SO$_2$($C_1$-$C_6$ haloalkyl), —SO$_2$N($C_0$-$C_6$ alkyl)($C_0$-$C_6$ alkyl), —SO$_2$($C_3$-$C_8$ cycloalkyl), —SO$_2$($C_3$-$C_8$ heterocycloalkyl), such as —SO$_2$Me, —SO$_2$Et, —SO$_2$Pr, —SO$_2$Bu, —SO$_2$cyclopropyl, —SO$_2$morphylinyl, SO$_2$pyrrolidinyl, SO$_2$NHEt, SO$_2$pyridyl or —SO$_2$phenyl. The number of substituents on the ring system denoted by "D", $y^2$, is 0, 1, or 2. For example, in some embodiments, $y^2$ is 0 or 1, for example 1. In other embodiments, $y^2$ is 0. $R^{30}$ can be further defined as described above with respect to $R^5$. In certain embodiments, the ring system denoted by "D" is cyclopropyl, morpholinyl, pyrazolyl, pyridyl, imidazolyl or phenyl.

In certain embodiments, at least one $R^5$ is —SO$_2$($C_1$-$C_6$ alkyl), —SO$_2$($C_1$-$C_6$ haloalkyl), —SO$_2$N($C_0$-$C_6$ alkyl)$_2$, —SO$_2$($C_3$-$C_8$ cycloalkyl), —SO$_2$($C_3$-$C_8$ heterocycloalkyl), such as —SO$_2$Me, —SO$_2$Et, —SO$_2$Pr, —SO$_2$Bu, —SO$_2$cyclopropyl, —SO$_2$morphylinyl, SO$_2$pyrrolidinyl, SO$_2$NHEt, SO$_2$pyridyl or —SO$_2$phenyl.

In one embodiment of the presently disclosed compounds, the compound has structural formula (1-II):

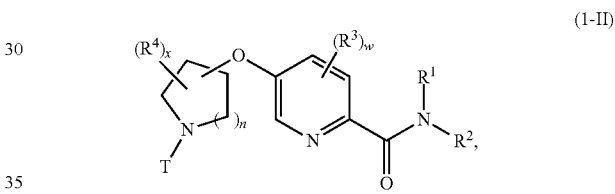

(1-II)

in which the variables are defined as described above with reference to structural formula (1-I).

In another embodiment of the presently disclosed compounds, the compound has structural formula (1-III):

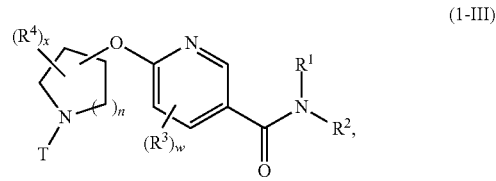

(1-III)

in which the variables are defined as described above with reference to structural formula (1-I).

In another embodiment of the presently disclosed compounds, the compound has structural formula (1-IV):

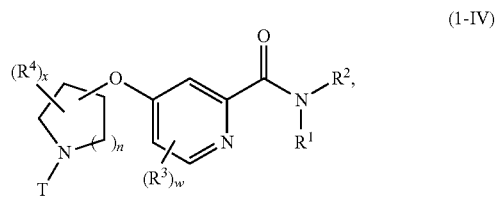

(1-IV)

in which the variables are defined as described above with reference to structural formula (1-I).

In another embodiment of the presently disclosed compounds, the compound has structural formula (1-V):

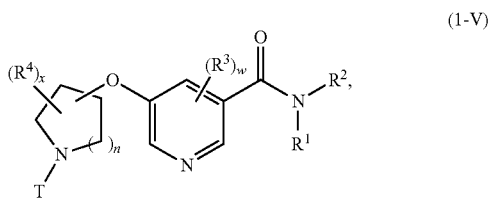

(1-V)

in which the variables are defined as described above with reference to structural formula (1-I).

In another embodiment of the presently disclosed compounds, the compound has structural formula (1-VI):

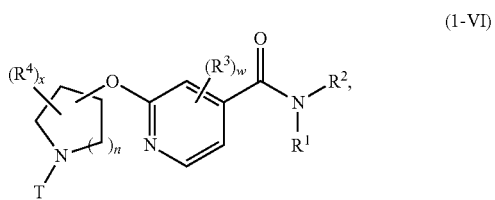

(1-VI)

in which the variables are defined as described above with reference to structural formula (1-I).

In another embodiment of the presently disclosed compounds, the compound has structural formula (1-VII):

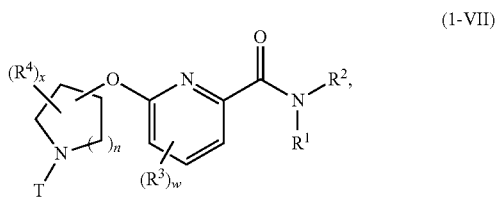

(1-VII)

in which the variables are defined as described above with reference to structural formula (1-I).

In another embodiment of the presently disclosed compounds, the compound has structural formula (1-VIII):

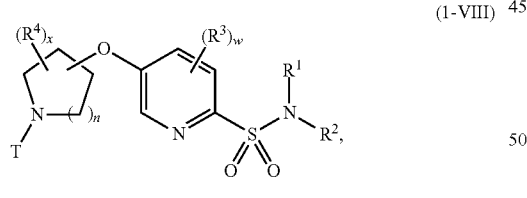

(1-VIII)

in which the variables are defined as described above with reference to structural formula (1-I).

In another embodiment of the presently disclosed compounds, the compound has structural formula (1-IX):

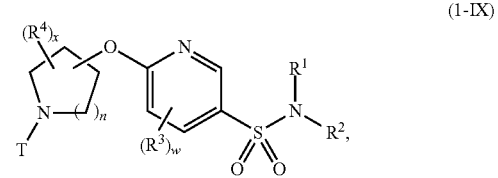

(1-IX)

in which the variables are defined as described above with reference to structural formula (1-I).

In another embodiment of the presently disclosed compounds, the compound has the structural formula (1-X):

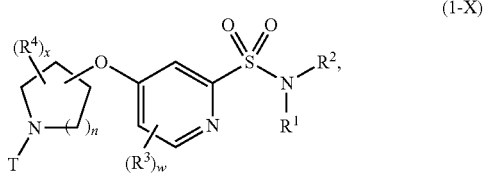

(1-X)

in which the variables are defined as described above with reference to structural formula (1-I).

In another embodiment of the presently disclosed compounds, the compound has structural formula (1-XI):

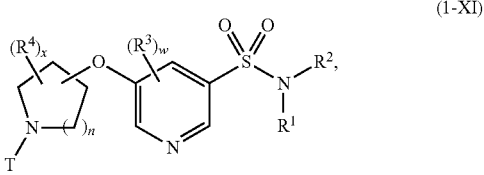

(1-XI)

in which the variables are defined as described above with reference to structural formula (1-I).

In another embodiment of the presently disclosed compounds, the compound has structural formula (1-XII):

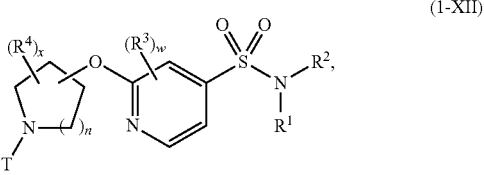

(1-XII)

in which the variables are defined as described above with reference to structural formula (1-I).

In another embodiment of the presently disclosed compounds, the compound has structural formula (1-XIII):

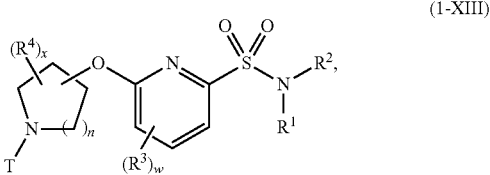

(1-XIII)

in which the variables are defined as described above with reference to structural formula (1-I).

In one embodiment of the presently disclosed compounds, the compound has structural formula (1-XIV):

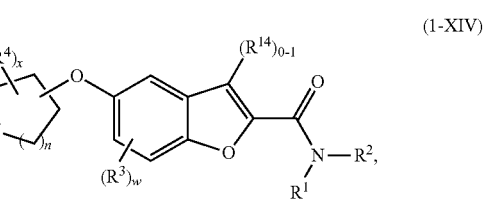

(1-XIV)

in which the variables are defined as described above with reference to structural formula (1-I). In certain embodiments, one $R^{14}$ is substituted on the furano carbon. In other embodiments, no $R^{14}$ is substituted on the furano carbon.

In another embodiment of the presently disclosed compounds, the compound has structural formula (1-XV):

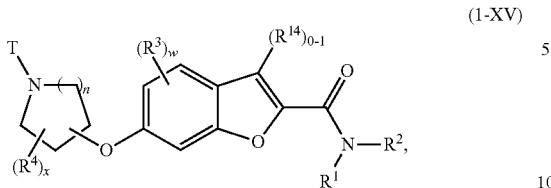

(1-XV)

in which the variables are defined as described above with reference to structural formula (1-I). In certain embodiments, one $R^{14}$ is substituted on the furano carbon. In other embodiments, no $R^{14}$ is substituted on the furano carbon.

In one embodiment of the presently disclosed compounds, the compound has structural formula (1-XVI):

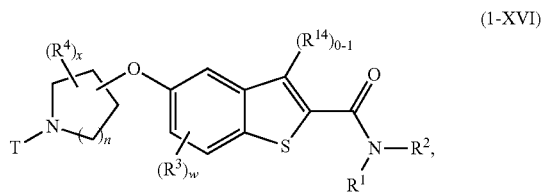

(1-XVI)

in which the variables are defined as described above with reference to structural formula (1-I). In certain embodiments, one $R^{14}$ is substituted on the thieno carbon. In other embodiments, no $R^{14}$ is substituted on the thieno carbon.

In another embodiment of the presently disclosed compounds, the compound has structural formula (1-XVII):

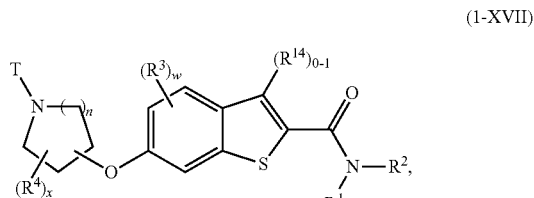

(1-XVII)

in which the variables are defined as described above with reference to structural formula (1-I). In certain embodiments, one $R^{14}$ is substituted on the thieno carbon. In other embodiments, no $R^{14}$ is substituted on the thieno carbon.

The presently disclosed compounds include S-oxidized forms of the benzothiophene compounds described (e.g., with reference to structural formulae (1-XVI) and (1-XVII). S-oxides include, for example, sulfoxides (—SO—) and sulfones (—SO$_2$—). Such compounds may be oxidized chemically or upon administration to e.g. a human subject, may be oxidized biologically. Chemically oxidized compounds may also be biologically reduced to the benzothiophene form.

In one embodiment of the presently disclosed compounds, the compound has structural formula (1-XVIII):

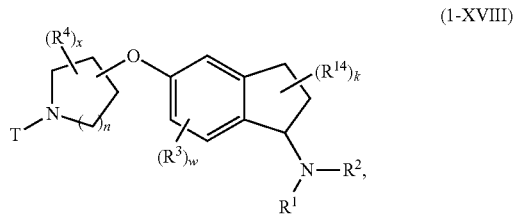

(1-XVIII)

in which the variables are defined as described above with reference to structural formula (1-I).

In another embodiment of the presently disclosed compounds, the compound has structural formula (1-XIX):

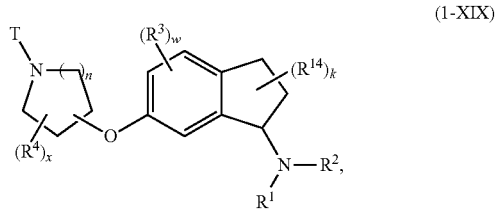

(1-XIX)

in which the variables are defined as described above with reference to structural formula (1-I).

In certain embodiments of the compounds disclosed with respect to structural formulae (1-I)-(1-XIX), n is 1 or 2. For example, in one embodiment, n is 2. In another embodiment, n is 1.

In one embodiment of the presently disclosed compounds, the compound has the structural formula (1-XX):

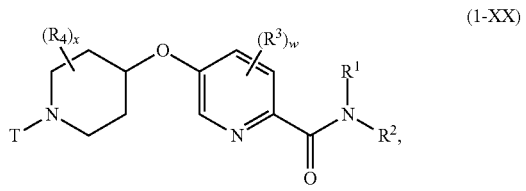

(1-XX)

in which the variables are defined as described above with reference to structural formula (1-I).

In another embodiment of the presently disclosed compounds, the compound has structural formula (1-XXI):

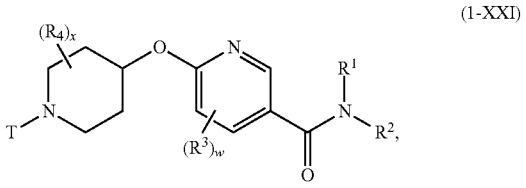

(1-XXI)

in which the variables are defined as described above with reference to structural formula (1-I).

In another embodiment of the presently disclosed compounds, the compound has structural formula (1-XXII):

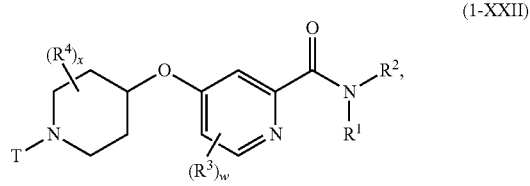

(1-XXII)

in which the variables are defined as described above with reference to structural formula (1-I).

In another embodiment of the presently disclosed compounds, the compound has structural formula (1-XXIII):

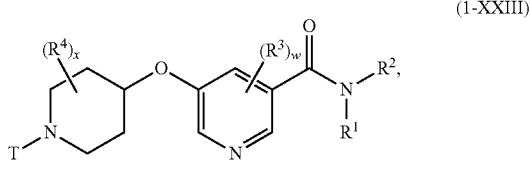

(1-XXIII)

in which the variables are defined as described above with reference to structural formula (1-I).

In another embodiment of the presently disclosed compounds, the compound has structural formula (1-XXIV):

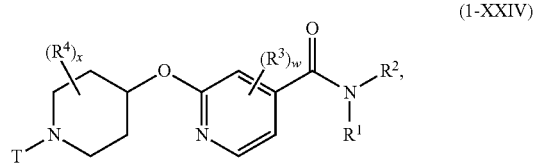

(1-XXIV)

in which the variables are defined as described above with reference to structural formula (1-I).

In another embodiment of the presently disclosed compounds, the compound has structural formula (1-XXV):

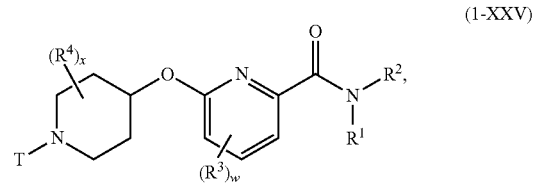

(1-XXV)

in which the variables are defined as described above with reference to structural formula (1-I).

In one embodiment of the presently disclosed compounds, the compound has structural formula (1-XXVI):

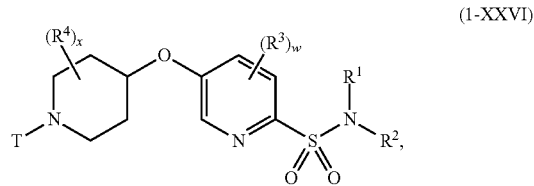

(1-XXVI)

in which the variables are defined as described above with reference to structural formula (1-I).

In another embodiment of the presently disclosed compounds, the compound has structural formula (1-XXVII):

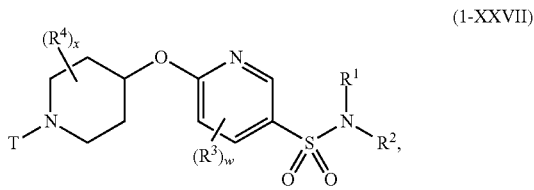

(1-XXVII)

in which the variables are defined as described above with reference to structural formula (1-I).

In another embodiment of the presently disclosed compounds, the compound has structural formula (1-XXVIII):

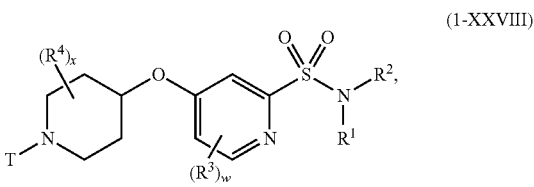

(1-XXVIII)

in which the variables are defined as described above with reference to structural formula (1-I).

In another embodiment of the presently disclosed compounds, the compound has structural formula (1-XXIX):

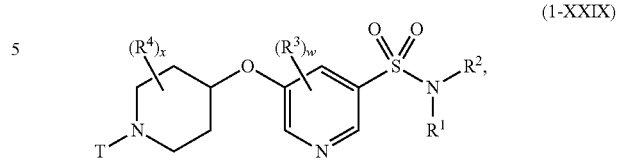

(1-XXIX)

in which the variables are defined as described above with reference to structural formula (1-I).

In another embodiment of the presently disclosed compounds, the compound has structural formula (1-XXX):

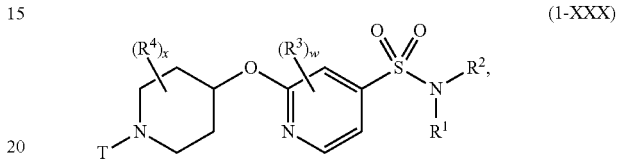

(1-XXX)

in which the variables are defined as described above with reference to structural formula (1-I).

In another embodiment of the presently disclosed compounds, the compound has structural formula (1-XXXI):

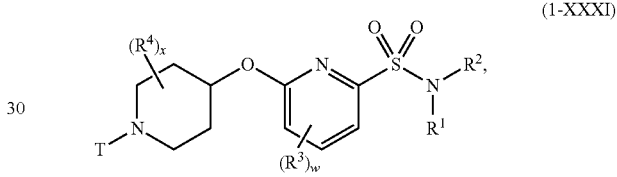

(1-XXXI)

in which the variables are defined as described above with reference to structural formula (1-I).

In one embodiment of the presently disclosed compounds, the compound has structural formula (1-XXXII):

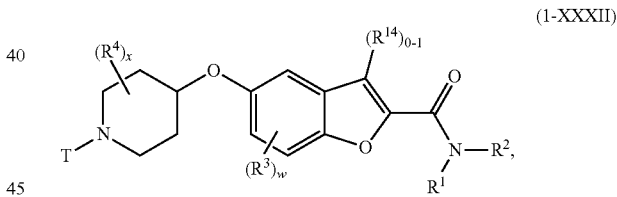

(1-XXXII)

in which the variables are defined as described above with reference to structural formula (1-I). In certain embodiments, one $R^{14}$ is substituted on the furano carbon. In other embodiments, no $R^{14}$ is substituted on the furano carbon.

In another embodiment of the presently disclosed compounds, the compound has structural formula (1-XXXIII):

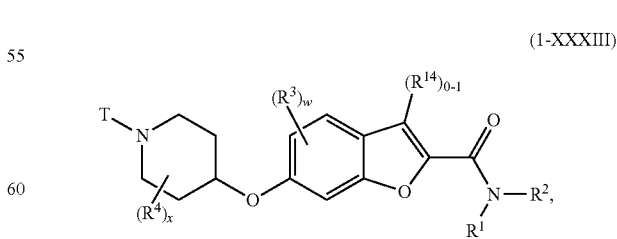

(1-XXXIII)

in which the variables are defined as described above with reference to structural formula (1-I). In certain embodiments, one $R^{14}$ is substituted on the furano carbon. In other embodiments, no $R^{14}$ is substituted on the furano carbon.

In one embodiment of the presently disclosed compounds, the compound has structural formula (1-XXXIV):

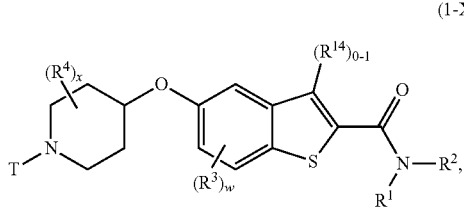

(1-XXXIV)

in which the variables are defined as described above with reference to structural formula (1-I). In certain embodiments, one $R^{14}$ is substituted on the thieno carbon. In other embodiments, no $R^{14}$ is substituted on the thieno carbon.

In another embodiment of the presently disclosed compounds, the compound has structural formula (1-XXXV):

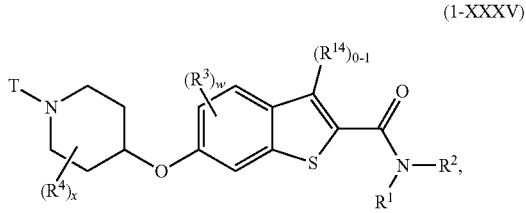

(1-XXXV)

in which the variables are defined as described above with reference to structural formula (1-I). In certain embodiments, one $R^{14}$ is substituted on the thieno carbon. In other embodiments, no $R^{14}$ is substituted on the thieno carbon.

In one embodiment of the presently disclosed compounds, the compound has structural formula (1-XXXVI):

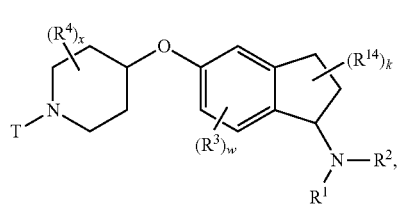

(1-XXXVI)

in which the variables are defined as described above with reference to structural formula (1-I).

In another embodiment of the presently disclosed compounds, the compound has structural formula (1-XXXVII):

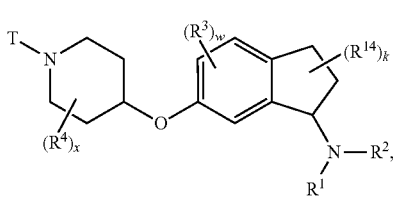

(1-XXXVII)

in which the variables are defined as described above with reference to structural formula (1-I).

In certain embodiments of the presently disclosed compounds of any of structural formulae (1-I)-(1-XXXVII), $R^1$ is —H. In other embodiments, $R^1$ is ($C_1$-$C_4$ alkyl), for example methyl, ethyl, n-propyl or isopropyl.

In certain embodiments of the presently disclosed compounds of any structural formulae (1-I)-(1-XXXVII), $R^2$ is -Hca. In certain embodiments, $R^2$ is an optionally-substituted monocyclic heterocycloalkyl. In another embodiment, $R^2$ is not an oxo-substituted heterocycloalkyl.

In certain particular compounds disclosed herein having any of structural formulae (1-I)-(1-XXXVII), $R^2$ is -(optionally-substituted azetidinyl), -(optionally-substituted pyrrolidinyl), -(optionally-substituted piperidinyl), or -(optionally-substituted azepanyl). For example, $R^2$ can be -(optionally substituted piperidinyl) or -(optionally substituted pyrrolidinyl). In one embodiment, $R^2$ is -(optionally substituted piperidinyl). In another embodiment, $R^2$ is -(optionally substituted pyrrolidinyl).

In particular embodiments of the presently disclosed compounds of any of structural formulae (1-I)-(1-XXXVII), $R^2$ is -(optionally-substituted azetidin-3-yl), -(optionally substituted piperidin-4-yl), -(optionally substituted pyrrolidin-3-yl) or -(optionally-substituted azepan-4-yl). For example, in one embodiment, $R^2$ is -(optionally substituted piperidin-4-yl). In another embodiment, $R^2$ is -(optionally substituted pyrrolidin-3-yl).

In certain embodiments of the presently disclosed compounds of any of structural formulae (1-I)-(1-XXXVII), the azetidinyl, pyrrolidinyl, piperidinyl and azepanyl $R^2$ moieties described above are substituted at their 1-positions. For example, in one embodiment, $R^2$ is substituted at its 1-position with —($C_0$-$C_3$ alkyl)-Ar or —($C_0$-$C_3$ alkyl)-Het, for example -(unsubstituted $C_0$-$C_3$ alkyl)-Ar or -(unsubstituted $C_0$-$C_3$ alkyl)-Het. For example, in one particular embodiment, the azetidinyl, pyrrolidinyl, piperidinyl or azepanyl $R^2$ moiety is substituted at its 1-position with an optionally substituted benzyl or an optionally substituted phenyl. In another embodiment, the azetidinyl, pyrrolidinyl, piperidinyl or azepanyl $R^2$ moiety is substituted at its 1-position with a benzyl substituted with an electron withdrawing group; or with a pyridinylmethyl optionally substituted with an electron withdrawing group. For example, the benzyl or pyridinylmethyl can be substituted with an electron withdrawing group selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In other embodiments, the azetidinyl, pyrrolidinyl, piperidinyl or azepanyl $R^2$ moiety is substituted at its 1-position with an unsubstituted benzyl or an unsubstituted phenyl.

In other embodiments of the compounds disclosed herein having any of structural formulae (1-I)-(1-XXXVII), the azetidinyl, pyrrolidinyl, piperidinyl or azepanyl $R^2$ moiety is substituted at its 1-position with an optionally substituted pyridinylmethyl, an optionally substituted furanylmethyl or an optionally substituted thienylmethyl. For example, the azetidinyl, pyrrolidinyl, piperidinyl or azepanyl $R^2$ moiety can be substituted with an unsubstituted pyridinylmethyl, an unsubstituted furanylmethyl, or an unsubstituted thienylmethyl.

In other embodiments of the presently disclosed compounds of any of structural formulae (1-I)-(1-XXXVII), the azetidinyl, pyrrolidinyl, piperidinyl or azepanyl $R^2$ moiety is substituted at its 1-position with —C(O)—O($C_0$-$C_6$ alkyl), —C(O)-Het, —C(O)—Ar, —S(O)$_2$-Het, —S(O)$_2$—Ar or —S(O)$_2$—O($C_0$-$C_6$ alkyl).

In certain embodiments of the compounds of any of structural formulae (1-I)-(1-XXXVII), $R^2$ is -Cak-N($R^9$)-G-$R^{22}$, as described above. For example, in one embodiment, $R^2$ has the structure

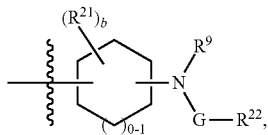

in which b is 0, 1, 2, 3 or 4, and each $R^{21}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN, and two $R^{21}$ on the same carbon optionally combine to form oxo. In certain embodiments of the presently disclosed compounds, each $R^{21}$ is independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN and two $R^{21}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-NR$^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{21}$ is —($C_1$-$C_3$ alkyl), —($C_1$-$C_3$ haloalkyl), —($C_0$-$C_3$ alkyl)-L-$R^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN and two $R^{21}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-NR$^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, b is 1 or 2. In other embodiments, b is 0. In certain embodiments, $R^9$ is H. In certain embodiments, G is a single bond.

In one embodiment of compounds of any of structural formulae (1-I)-(1-XXXVII), $R^2$ has the structure

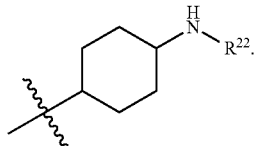

In certain embodiments of the compounds of any of structural formulae (1-I)-(1-XXXVII), $R^2$ is —($C_2$-$C_8$ alkyl)-N($R^9$)—$R^{24}$ in which one or two carbons of the ($C_2$-$C_8$ alkyl) are optionally replaced by —O— or —N($R^9$)— and $R^{24}$ is —$R^{23}$, -G$R^{23}$, or —C(O)O—($C_1$-$C_6$ alkyl). In certain embodiments, the ($C_2$-$C_8$ alkyl) is unsubstituted and no carbon is replaced by —O— or —N($R^9$)—. For example, in one embodiment, $R^2$ is —CH$_2$—CH$_2$—CH$_2$—N($R^9$)—$R^{24}$ or —CH$_2$—CH$_2$—CH$_2$—CH$_2$—N($R^9$)—$R^{24}$. In other embodiments, the ($C_2$-$C_8$ alkyl) is substituted and/or one or two carbons are replaced by —O— or —N($R^9$)—. For example, in one embodiment, $R^2$ is —CH$_2$—CH$_2$—O—CH$_2$—CH$_2$—N($R^9$)—$R^{24}$; —CH$_2$—CH(CH$_3$)—N($R^9$)—$R^{24}$; or —CH$_2$—CH$_2$—O—CH$_2$—C(O)—N($R^9$)—$R^{24}$. In certain embodiments, $R^9$ is H. In certain embodiments, $R^{24}$ is Ar or Het. In certain embodiments, the ($C_2$-$C_8$ alkyl) is a ($C_2$-$C_5$ alkyl).

In the compounds of any of structural formulae (1-I)-(1-XXXVII), w is 0, 1, 2 or 3. For example, in one embodiment, w is 0, 1 or 2. In another embodiment, w is 0. In other embodiments, w is at least 1, and at least one $R^3$ is selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In certain embodiments, an $R^3$ is substituted on the "B" ring system at a benzo or pyrido ring position meta to the alicyclic ethereal oxygen.

In certain embodiments of the compounds of any of structural formulae (1-I)-(1-XXXVII), each $R^3$ is independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-NR$^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^3$ is —($C_1$-$C_3$ alkyl), —($C_1$-$C_3$ haloalkyl), —($C_0$-$C_3$ alkyl)-L-$R^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-NR$^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group.

In certain embodiments of the compounds of of any of structural formulae (1-I)-(1-XXXVII), w is at least one, and at least one $R^3$ is —$NR^8R^9$. For example, in one embodiment, w is 1. In certain such embodiments, $R^3$ is substituted on the "B" ring system at a benzo or pyrido ring position meta to the alicyclic ethereal oxygen.

In other embodiments of the compounds of of any of structural formulae (1-I)-(1-XXXVII), w is at least one, and at least one $R^3$ is —($C_0$-$C_3$ alkyl)-$Y^1$—($C_1$-$C_3$ alkyl)-$Y^2$—($C_0$-$C_3$ alkyl), in which each of $Y^1$ and $Y^2$ is independently L, —O—, —S— or —$NR^9$—. For example, in one embodiment, w is 1. In certain such embodiments, $R^3$ is substituted on the "B" ring system at a benzo or pyrido ring position meta to the alicyclic ethereal oxygen. In one particular embodiment, $R^3$ is —$CH_2$—N($CH_3$)—$CH_2$—C(O)—$OCH_3$.

In the presently disclosed compounds of any of structural formulae (1-I)-(1-XXXVII), the number of substituents on the azacycloalkyl ring, x, is 0, 1, 2, 3 or 4. In one embodiment, x is 0, 1, 2 or 3. For example, x can be 0, or can be 1 or 2.

In certain embodiments of the presently disclosed compounds of any of structural formula (1-I)-(1-XXXVII), two $R^4$s combine to form an oxo. The oxo can be bound, for example, at the position alpha to the nitrogen of the azacycloalkyl ring. In other embodiments, no two $R^4$s combine to form an oxo.

In certain embodiments of the presently disclosed compounds of any of structural formulae (1-I)-(1-XXXVII), when x is 4, not all four $R^4$ moieties are ($C_1$-$C_6$ alkyl).

In certain embodiments of the presently disclosed compounds of any of structural formulae (1-I)-(1-XXXVII), each $R^4$ is independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}$$R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^4$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}$$R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group.

In certain embodiments, the presently disclosed compounds have the structural formula (1-XXXVIII):

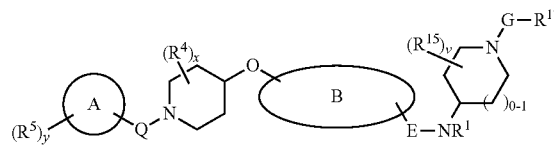

(1-XXXVIII)

in which Q and G are each independently a bond, —$CH_2$—, —C(H)($R^{16}$)—, —C($R^{16}$)$_2$— or —S(O)$_2$—; v is 0, 1, 2, 3 or 4; each $R^{15}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}$$R^{10}$, -halogen, —$NO_2$ and —CN, and two $R^{15}$ on the same carbon optionally combine to form oxo; $R^{17}$ is Het or Ar, and all other variables are defined as described above with reference to structural formulae (1-I)-(1-XXXVII). $R^{17}$ can be, for example, an optionally substituted phenyl, an optionally-substituted pyridyl, an optionally substituted pyrazolyl, an optionally substituted imidazolyl, an optionally substituted pyrrolyl, an optionally substituted triazolyl or an optionally substituted thiadiazolyl. In one embodiment, Q is a single bond. In another embodiment, Q is —$CH_2$—. In other embodiments, Q is —C(O)— or —S(O)$_2$—. In certain embodiments, G is —$CH_2$—. In other embodiments, G is —C(O)— or —S(O)$_2$—. In other embodiments, G is —CH($CH_3$)—. For example, in one embodiment, Q i)s a single bond and G is —$CH_2$— or —C(O)—. As described above, in certain embodiments, the ring system denoted by "A" is aryl or heteroaryl. In one embodiment, the ring system denoted by "A" is substituted with one or more electron-withdrawing groups. In another embodiment, $R^{17}$ is substituted with one or more electron-withdrawing groups. In certain embodiments, the ring system denoted by "A", $R^{17}$ or both are not substituted with an aryl, heteroaryl, cycloalkyl or heterocycloalkyl-containing group.

In the presently disclosed compounds of structural formula (1-XXXVIII), v is 0, 1, 2, 3 or 4. In one embodiment, v is 0, 1, 2 or 3. For example, v can be 0, or can be 1 or 2.

In certain embodiments of the presently disclosed compounds of structural formula (1-XXXVIII), two $R^{15}$s combine to form an oxo. The oxo can be bound, for example, at the position alpha to the nitrogen of the azacycloalkyl ring. In other embodiments, no two $R^{15}$s combine to form an oxo.

In certain embodiments of the presently disclosed compounds of structural formula (1-XXXVIII), when v is 4, not all four $R^{15}$ moieties are ($C_1$-$C_6$ alkyl).

In certain embodiments of the presently disclosed compounds of structural formula (1-XXXVIII), each $R^{15}$ is independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}$$R^{10}$, -halogen, —$NO_2$ and —CN and two $R^{15}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{15}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN and two R$^{15}$ on the same carbon optionally combine to form oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In some embodiments, one R$^{15}$ is —C(O)NR$^9$R$^7$, which can be bound, for example, at a position alpha to the piperidine nitrogen, or at the position linked to the —N(R$^1$)—.

In certain embodiments of the presently disclosed compounds of structural formula (1-XXXVIII), R$^{17}$ is an unsubstituted aryl or heteroaryl. In other embodiments, the R$^{17}$ Ar or Het is substituted with 1, 2 or 3 substituents independently selected from —(C$_1$-C$_6$ alkyl), —(C$_1$-C$_6$ haloalkyl) (e.g., trifluoromethyl), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group.

For example, in one embodiment, the R$^{17}$ Ar or Het is substituted with 1, 2 or 3 substituents independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, R$^{17}$ is substituted with 1, 2 or 3 substituents selected from halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca. R$^{17}$ can be substituted with, for example, one such substituent, or two such substituents. In certain embodiments, R$^{17}$ is substituted with a substituent -G$^2$-R$^{34}$, in which G$^2$ is a single bond, —O—, —C(O)—, —S(O)$_2$— or —CH$_2$—, and R$^{34}$ is a chosen from aryl (such as phenyl), heterocycloalkyl (such as morpholinyl, pyrrolidinyl), and heteroaryl (such as), each of which is optionally substituted with 1 or 2 substituents selected from aryl, (C$_1$-C$_4$ haloalkyl), —O—(C$_1$-C$_4$ haloalkyl), (C$_1$-C$_4$ alkyl), —O—(C$_1$-C$_4$ alkyl), halogen, or CN.

In certain embodiments, the presently disclosed compounds have the structural formula (1-XXXIX):

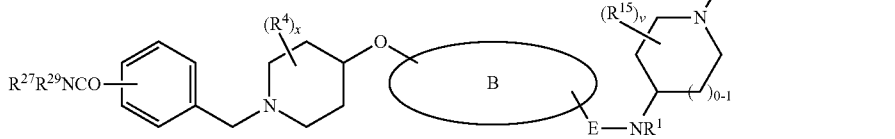

(1-XXXIX)

in which R$^{27}$ is selected from H, —(C$_1$-C$_6$ alkyl), —(C$_1$-C$_6$ haloalkyl) (e.g., trifluoromethyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca, and all other variables are as described above with respect to structural formulae (1-I) and (1-XXXVIII).

In certain embodiments, the presently disclosed compounds have the structural formula (1-XL):

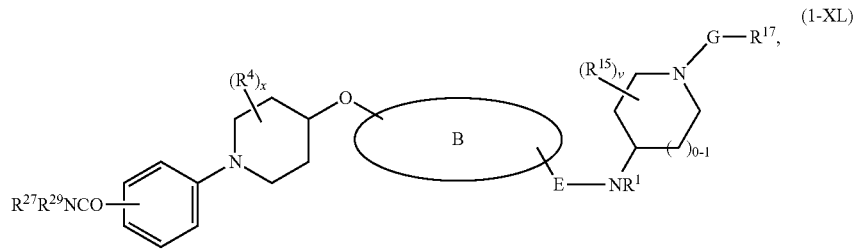

(1-XL)

in which $R^{27}$ is selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with respect to structural formulae (1-I) and (1-XXX-VIII).

In certain embodiments, the presently disclosed compounds have the structural formula (1-XLI):

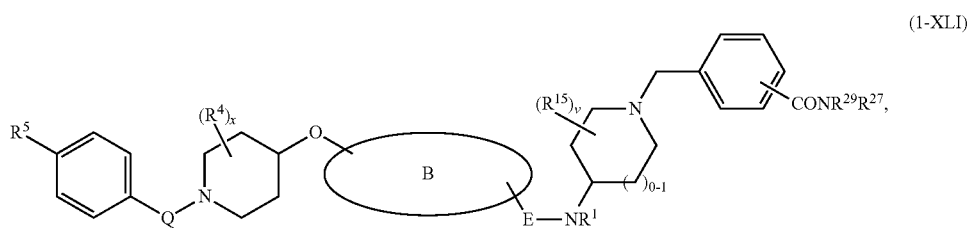

(1-XLI)

in which $R^{27}$ is selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with respect to structural formulae (1-I) and (1-XXX-VIII).

In certain embodiments, the presently disclosed compounds have the structural formula (1-XLII):

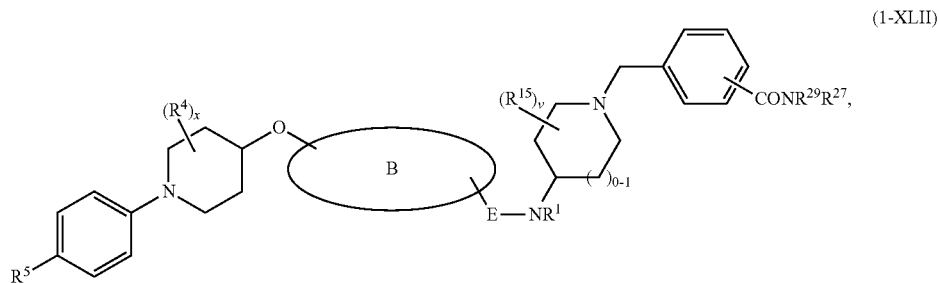

(1-XLII)

in which $R^{27}$ is selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with respect to structural formulae (1-I) and (1-XXXVIII).

In certain embodiments, the presently disclosed compounds have the structural formula (1-XLIII):

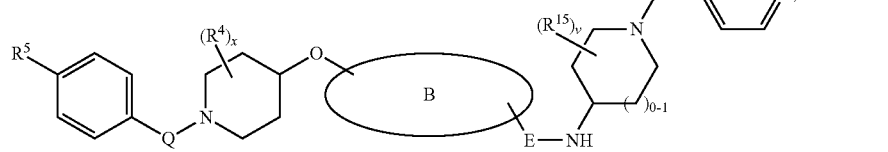

(1-XLIII)

in which all variables are as described above with respect to structural formulae (1-I) and (1-XXXVIII).

In certain embodiments, the presently disclosed compounds have the structural formula (1-XLIV):

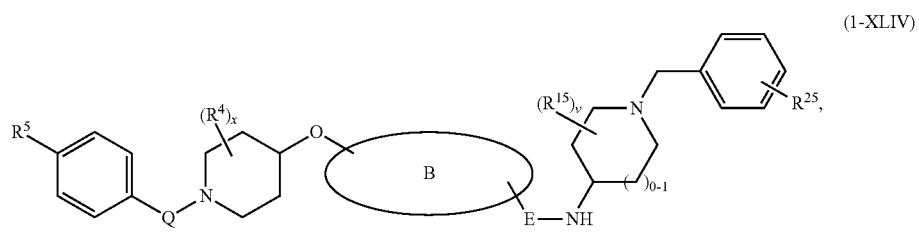

(1-XLIV)

in which $R^{25}$ is selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl or haloalkyl is substituted by an aryl, heteroaryl, cycloalkyl or heterocycloalkyl-containing group; and all other variables are as described above with respect to structural formulae (1-I) and (1-XXXVIII). $R^{25}$ can be, for example, —Cl, —F, cyano, —C(O)CH$_3$, —C(O)OH, —C(O)NH$_2$, trifluoromethyl, difluoromethyl, difluoromethoxy or trifluoromethoxy.

In certain embodiments, the presently disclosed compounds have the structural formula (1-XLV):

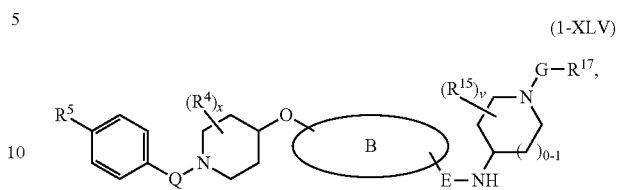

(1-XLV)

in which G is —C(O)— or —S(O)$_2$— and all other variables are as described above with respect to structural formulae (1-I) and (1-XXXVIII).

In certain embodiments, the presently disclosed compounds have the structural formula (1-XLVI):

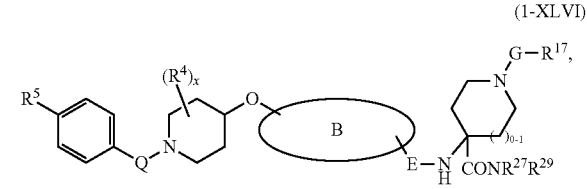

(1-XLVI)

in which $R^{27}$ is selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-

O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with respect to structural formulae (1-I) and (1-XXXVIII). In some embodiments, the compounds of structural formula (1-XLVI) are present as racemic mixtures or scalemic mixtures. In other embodiments, the compounds of structural formula (1-XLVI) are present in an enantiomerically-enriched form, for example as a substantially pure stereoisomer.

In certain embodiments, the presently disclosed compounds have the structural formula (1-XLVII):

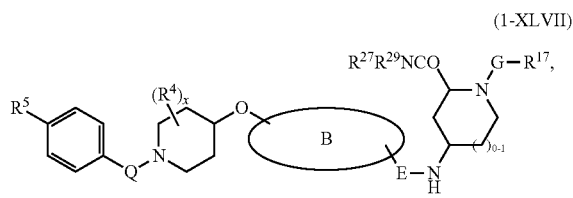

(1-XLVII)

in which $R^{27}$ is selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-NR$^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with respect to structural formulae (1-I) and (1-XXXVIII). In some embodiments, the compounds of structural formula (1-XLVII) are present as racemic mixtures or scalemic mixtures. In other embodiments, the compounds of structural formula (1-XLVII) are present in an enantiomerically-enriched form, for example as a substantially pure stereoisomer.

In certain embodiments, the presently disclosed compounds have the structural formula (1-XLVIII):

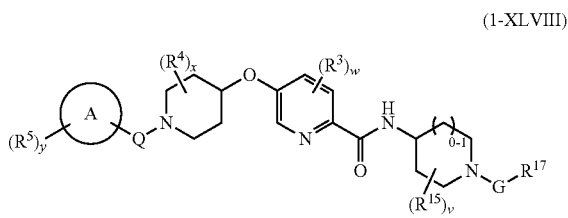

(1-XLVIII)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-XLIX):

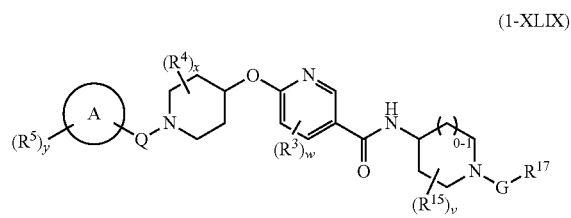

(1-XLIX)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-L):

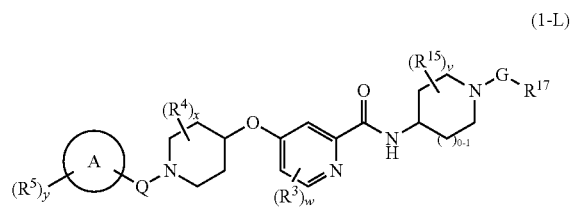

(1-L)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LI):

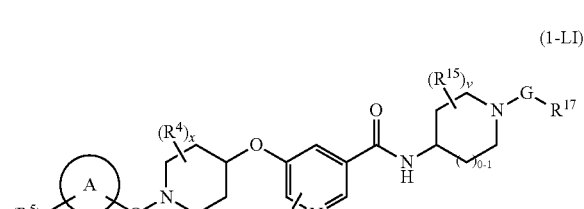

(1-LI)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LII):

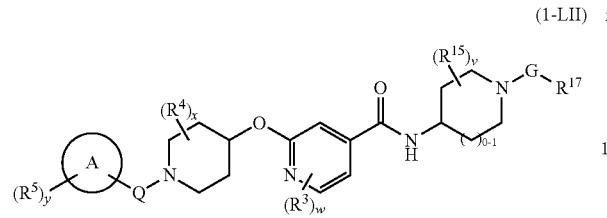
(1-LII)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LIII):

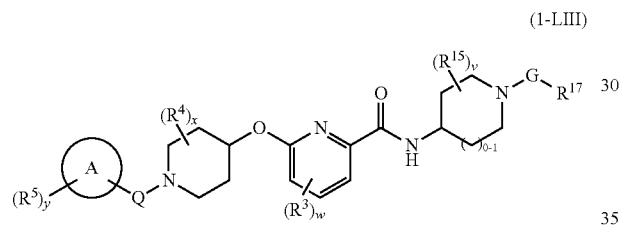
(1-LIII)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LIV):

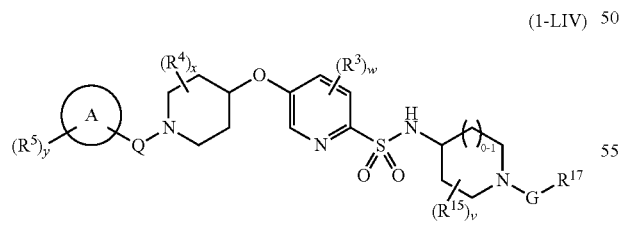
(1-LIV)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LV):

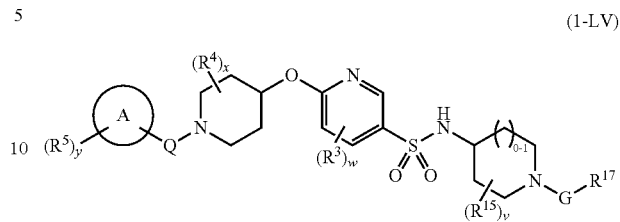
(1-LV)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LVI):

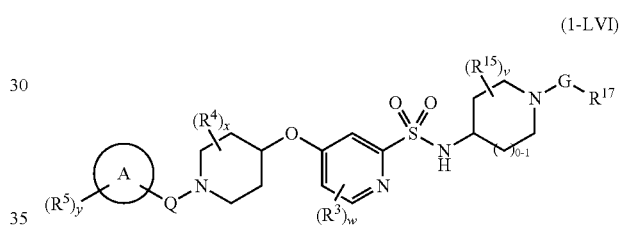
(1-LVI)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LVII):

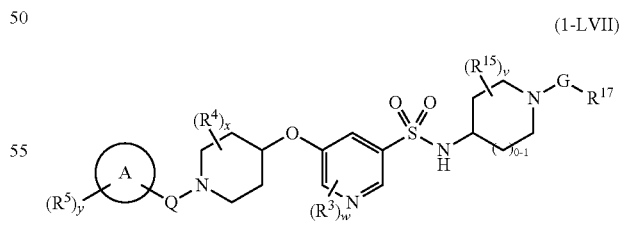
(1-LVII)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LVIII):

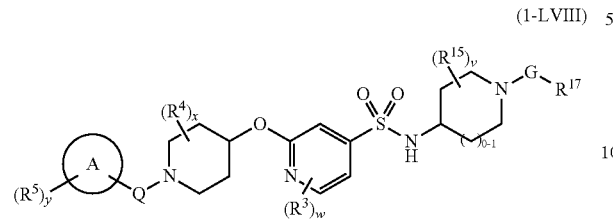

(1-LVIII)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LIX):

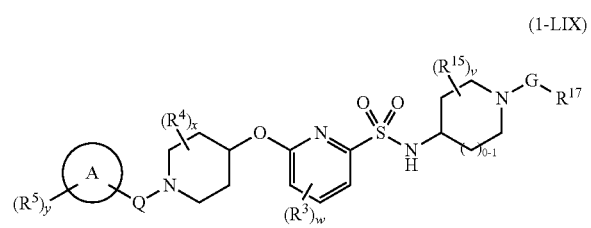

(1-LIX)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LX):

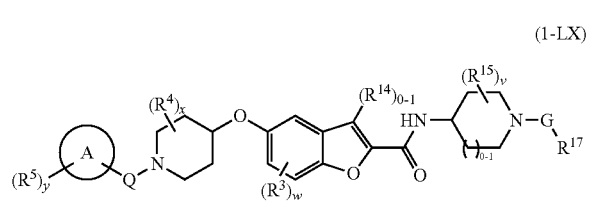

(1-LX)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII). In certain embodiments, one $R^{14}$ is substituted on the furano carbon. $R^{14}$ can be, for example, as described above with reference to structural formula (1-I). For example, in one embodiment $R^{14}$ is halo (e.g., —Cl or —F), cyano unsubstituted —($C_1$-$C_4$ alkyl) (e.g., methyl or ethyl), unsubstituted —($C_1$-$C_4$ haloakyl) (e.g., trifluoromethyl). In other embodiments, no $R^{14}$ is substituted on the furano carbon.

In certain embodiments, the presently disclosed compounds have the structural formula (1-LXI):

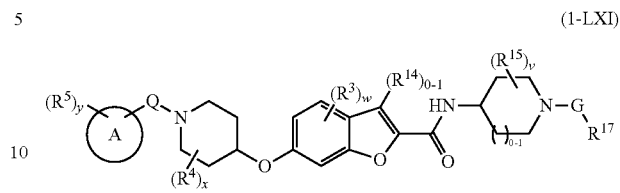

(1-LXI)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII). In certain embodiments, one $R^{14}$ is substituted on the furano carbon. $R^{14}$ can be, for example, as described above with reference to structural formula (1-I). For example, in one embodiment $R^{14}$ is halo (e.g., —Cl or —F), cyano unsubstituted —($C_1$-$C_4$ alkyl) (e.g., methyl or ethyl), unsubstituted —($C_1$-$C_4$ haloakyl) (e.g., trifluoromethyl). In other embodiments, no $R^{14}$ is substituted on the furano carbon.

In certain embodiments, the presently disclosed compounds have the structural formula (1-LXII):

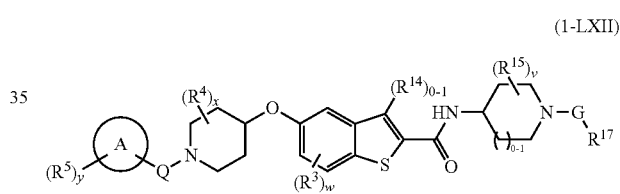

(1-LXII)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII). In certain embodiments, one $R^{14}$ is substituted on the thieno carbon. $R^{14}$ can be, for example, as described above with reference to structural formula (1-I). For example, in one embodiment $R^{14}$ is halo (e.g., —Cl or —F), cyano unsubstituted —($C_1$-$C_4$ alkyl) (e.g., methyl or ethyl), unsubstituted —($C_1$-$C_4$ haloakyl) (e.g., trifluoromethyl). In other embodiments, no $R^{14}$ is substituted on the thieno carbon.

In certain embodiments, the presently disclosed compounds have the structural formula (1-LXIII):


(1-LXIII)

in which G, v, $R^{15}$ and $R^{17}$ are defined as described above with reference to structural formula (1-XXXVIII), and all other variables are defined as described above with reference to structural formulae (1-I) and (1-XXXVIII). $R^5$, v, $R^{15}$, $R^{17}$, Q, G and the ring denoted by "A" can be defined, for example, as described with respect to any of structural formulae (1-XXXIX)-(1-XLVII). In certain embodiments, one $R^{14}$ is substituted on the thieno carbon. $R^{14}$ can be, for example, as described above with reference to structural formula (1-I). For example, in one embodiment $R^{14}$ is halo (e.g., —Cl or —F), cyano unsubstituted —($C_1$-$C_4$ alkyl) (e.g., methyl or ethyl), unsubstituted —($C_1$-$C_4$ haloakyl) (e.g., trifluoromethyl). In other embodiments, no $R^{14}$ is substituted on the thieno carbon.

In certain embodiments, the presently disclosed compounds have the structural formula (1-LXIV):

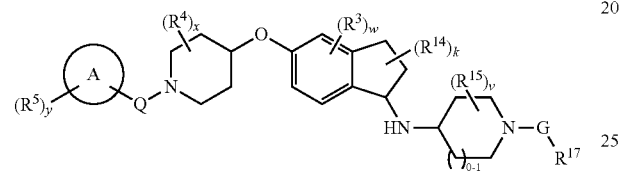
(1-LXIV)

in which Q, G, v, $R^{15}$ and $R^{17}$ are defined as described above with reference to structural formula (1-XXXVIII), and all other variables are defined as described above with reference to structural formula (1-I). $R^5$, $R^{15}$, $R^{17}$, Q, G and the ring denoted by "A" can be defined, for example, as described with respect to any of structural formulae (1-XXXIX)-(1-XLVII).

In certain embodiments, the presently disclosed compounds have the structural formula (1-LXV):

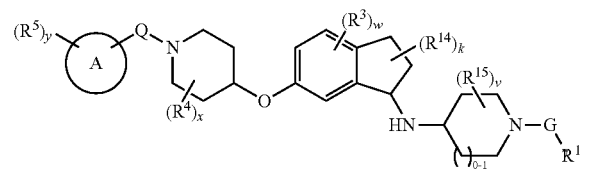
(1-LXV)

in which Q, G, v, $R^{15}$ and $R^{17}$ are defined as described above with reference to structural formula (1-XXXVIII), and all other variables are defined as described above with reference to structural formula (1-I). $R^5$, $R^{15}$, $R^{17}$, Q, G and the ring denoted by "A" can be defined, for example, as described with respect to any of structural formulae (1-XXXIX)-(1-XLVII).

One aspect of the disclosure provides compounds of structural formulae (1-XX)-(I-LXV) in which x is 1 and $R^4$ is F. For example, in certain embodiments of compounds having structural formulae (1-XX)-(I-LXV), the

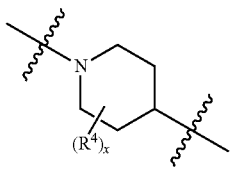

moiety has the structure

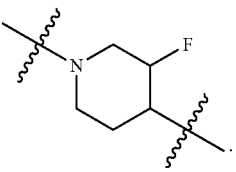 [SMILES: *C1CCN(*)CC1F]

For example, in certain embodiments, the compound has structural formula (1-LXVI):

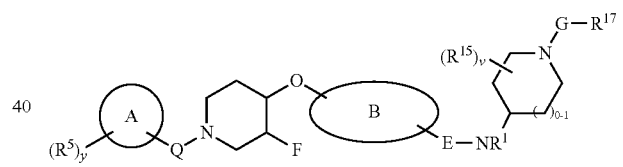
(1-LXVI)

in which the variables are as described above with reference to any of structural formulae (1-XXXVIII)-(I-LXV). In one embodiment, the compound has the structural formula (1-LXVII) or (1-LXVIII):

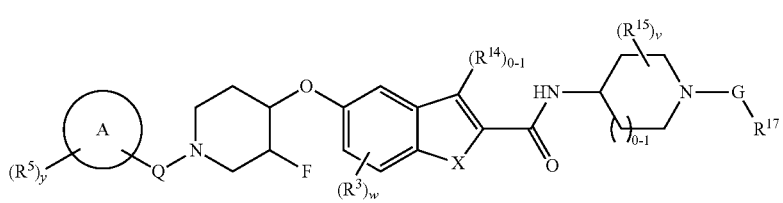
(1-LXVII)

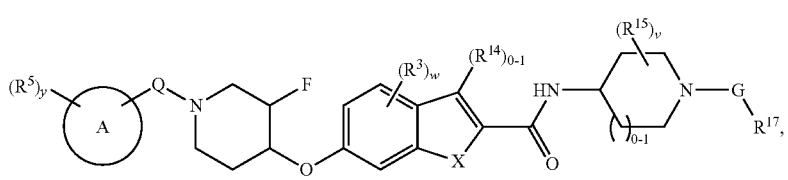
(1-LXVIII)

in which X is O or S, and in which all other variables are as described above with reference to any of structural formulae (1-LX)-(I-LXIII).

In one embodiment, the 3-fluoro and the 4-substituent are substituted in a cis manner on the piperidine. In other embodiments, the 3-fluoro and the 4-substituent are substituted in a trans manner on the piperidine. For example in one embodiment, the piperidine moiety has the structure

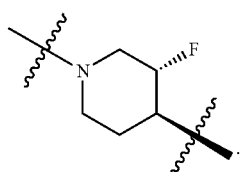 [SMILES: *N1CC[C@H](C)[C@@H](F)C1]

In certain particular embodiments, the compound has structural formula (1-LXIX) or (1-LXX):

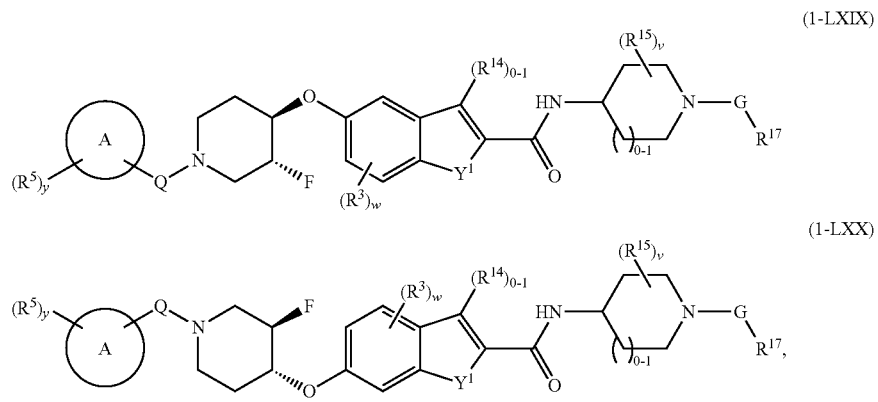

in which the variables are as described above with reference to structural formulae (1-LXVII) and (1-LXVIII). Compounds according to structural formulae (1-LXIX) and (1-LXX) can be provided in racemic form, in enantiomerically enriched form, or in substantially enantiomerically pure form.

In certain embodiments of compounds having structural formulae (1-XXXVIII)-(1-LXX), the

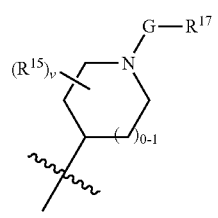

moiety has the structure

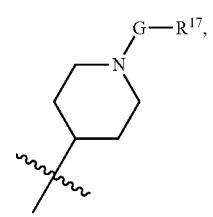

in which G is —CH$_2$—, —CH(CH$_3$)—, —C(O)— or —S(O)$_2$—. For example, in one embodiment, G is —CH$_2$—. In another embodiment, G is —C(O)— or —S(O)$_2$—.

In other embodiments of compounds having structural formulae (1-XXXVIII)-(1-LXX), the

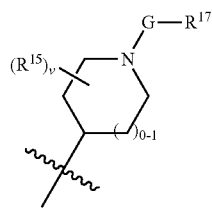

moiety has the structure

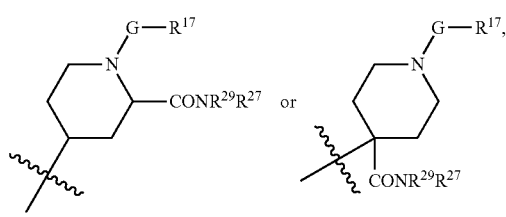

in which G is —CH$_2$—, —C(O)— or —S(O)$_2$—. In such embodiments, the compounds can be present as racemic mixtures or scalemic mixtures, or in an enantiomerically-enriched form, for example as a substantially pure stereoisomer.

In other embodiments of compounds having structural formulae (1-XXXVIII)-(1-LXX), the

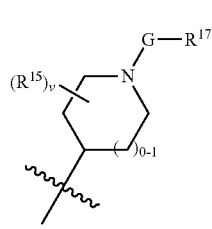

moiety has the structure

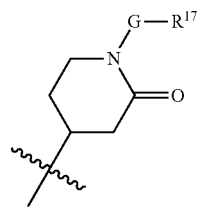

in which G is —CH$_2$—, —C(O)— or —S(O)$_2$—.

In certain embodiments of compounds having structural formulae (1-XXXVIII)-(1-LXX), the

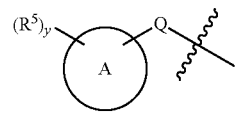

moiety is p-(trifluoromethyl)phenyl.

In one embodiment, the presently disclosed compounds have the structural formula (1-LXXI):

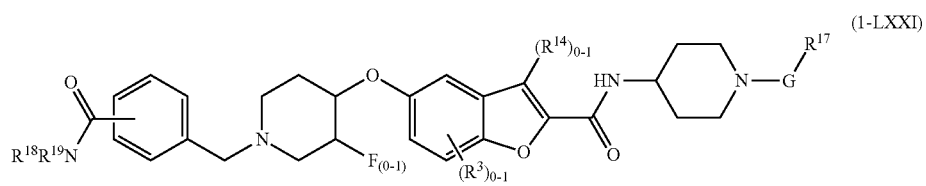
(1-LXXI)

In certain embodiments of compounds having structural formulae (1-XXXVIII)-(1-LXX), the R$^{17}$ moiety has the structure

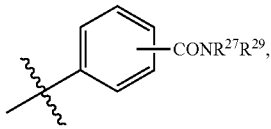

in which R$^{27}$ is selected from H, —(C$_1$-C$_6$ alkyl), —(C$_1$-C$_6$ haloalkyl) (e.g., trifluoromethyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca.

In certain embodiments described above, each R$^{27}$ is selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN and two R$^{21}$ on the same carbon optionally combine to form oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group, and each R$^{29}$ is H, methyl or ethyl, or R$^{27}$ and R$^{29}$ together with the nitrogen to which they are bound form Hca.

in which G, R$^3$ and R$^{17}$ are as described above with respect to structural formula (1-XXXVIII); R$^{18}$ is H, —(C$_1$-C$_6$ alkyl), —(C$_1$-C$_6$ haloalkyl) (e.g., trifluoromethyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), in which no alkyl or haloalkyl is substituted with an aryl-, heteroaryl-, cycloalkyl- or heterocycloalkyl-containing group and R$^{19}$ is —H, —(C$_1$-C$_4$ alkyl) or —CO—O—(C$_1$-C$_4$ alkyl) in which no alkyl is substituted by an aryl, heteroaryl, cycloalkyl or heterocycloalkyl-containing group, or R$^{18}$ and R$^{19}$ together with the nitrogen to which they are bound form Hca; and R$^{20}$ is Ar or Het. In certain embodiments, R$^{18}$ is H or (C$_1$-C$_4$ alkyl), and R$^{19}$ is —H. In certain embodiments, one R$^{14}$ is substituted on the furano carbon. R$^{14}$ can be, for example, as described above with reference to structural formula (1-I). For example, in one embodiment R$^{14}$ is halo (e.g., —Cl or —F), cyano unsubstituted —(C$_1$-C$_4$ alkyl) (e.g., methyl or ethyl), unsubstituted —(C$_1$-C$_4$ haloakyl) (e.g., trifluoromethyl). In other embodiments, no R$^{14}$ is substituted on the furano carbon.

In certain embodiments of compounds of structural formula (1-LXXI), w is 1, and R$^3$ is —NR$^8$R$^9$. In certain such embodiments, R$^3$ is substituted at a benzo or pyrido ring position meta to the alicyclic ethereal oxygen.

In other embodiments of compounds of structural formula (1-LXXI), w is 1, and R$^3$ is —(C$_0$-C$_3$ alkyl)-Y$^1$—(C$_1$-C$_3$ alkyl)-Y$^2$—(C$_0$-C$_3$ alkyl), in which each of Y$^1$ and Y$^2$ is independently L, —O—, —S— or —NR$^9$—. In certain such embodiments, R$^3$ is substituted at a benzo or pyrido ring position meta to the alicyclic ethereal oxygen.

In another embodiment, the presently disclosed compounds have the structural formula (1-LXXII):

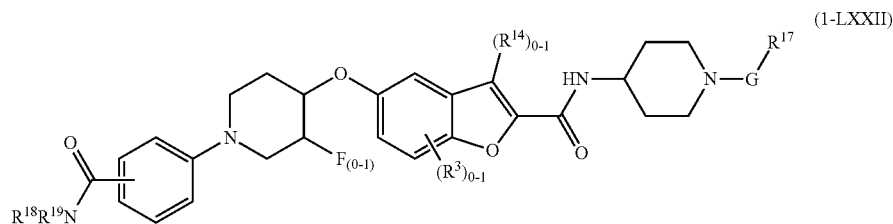

in which $R^3$ and $R^{14}$ are defined as described above with reference to structural formulae (1-I) and (1-XXXVIII); G and $R^{17}$ are defined as described above with reference to structural formula (1-XXXVIII); and $R^{18}$ and $R^{19}$ are defined as described above with reference to structural formula (1-LXXI).

In another embodiment, the presently disclosed compounds have the structural formula (1-LXXIII):

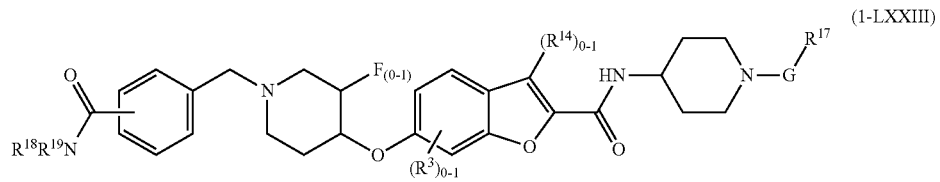

in which $R^3$ and $R^{14}$ are defined as described above with reference to structural formulae (1-I) and (1-XXXVIII); G and $R^{17}$ are defined as described above with reference to structural formula (1-XXXVIII); and $R^{18}$ and $R^{19}$ are defined as described above with reference to structural formula (1-LXXI).

In another embodiment, the presently disclosed compounds have the structural formula (1-LXXIV):

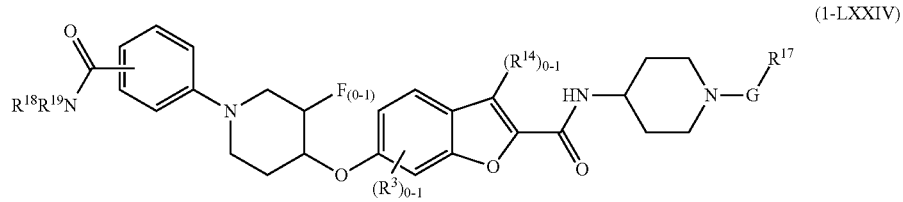

in which $R^3$ and $R^{14}$ are defined as described above with reference to structural formulae (1-I) and (1-XXXVIII); G and $R^{17}$ are defined as described above with reference to structural formula (1-XXXVIII); and $R^{18}$ and $R^{19}$ are defined as described above with reference to structural formula (1-LXXI).

In another embodiment, the presently disclosed compounds have the structural formula (1-LXXV):

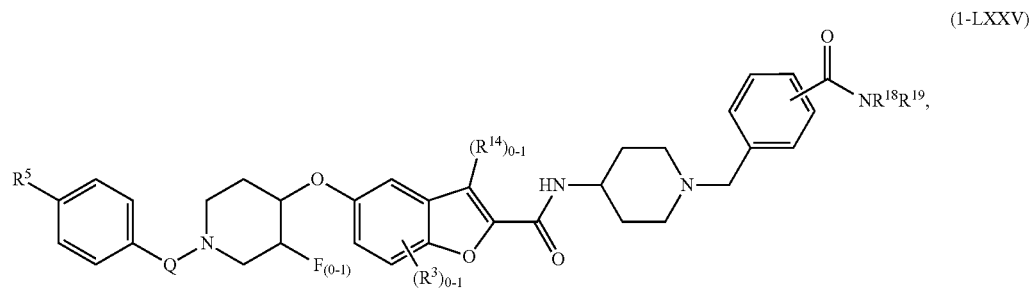

in which Q, $R^3$, $R^5$ and $R^{14}$ are defined as described above with reference to structural formulae (1-I) and (1-XXXVIII); and $R^{18}$ and $R^{19}$ are defined as described above with reference to structural formula (1-LXXI).

In another embodiment, the presently disclosed compounds have the structural formula (1-LXXVI):

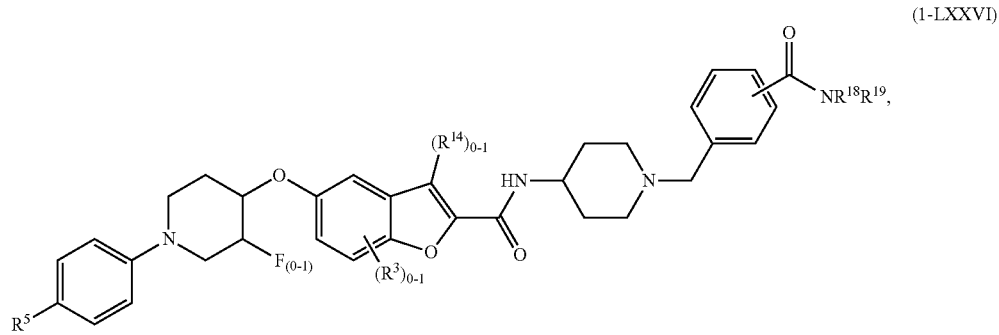
(1-LXXVI)

in which $R^3$, $R^5$ and $R^{14}$ are defined as described above with reference to structural formulae (1-I) and (1-XXXVIII); and $R^{18}$ and $R^{19}$ are defined as described above with reference to structural formula (1-LXXI).

In another embodiment, the presently disclosed compounds have the structural formula (1-LXXVII):

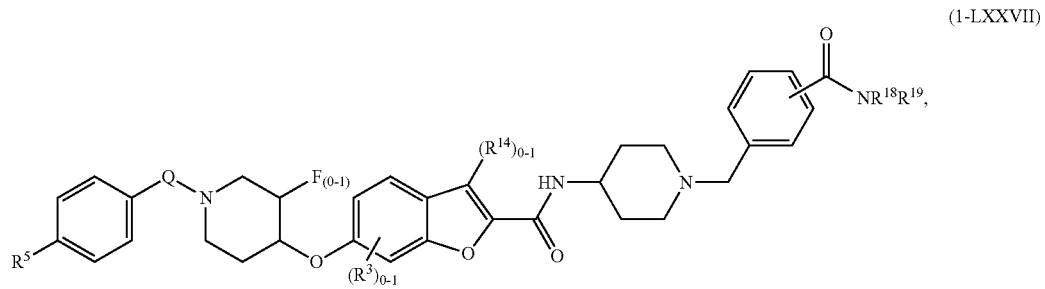
(1-LXXVII)

in which Q, $R^3$, $R^5$ and $R^{14}$ are defined as described above with reference to structural formulae (1-I) and (1-XXXVIII); and $R^{18}$ and $R^{19}$ are defined as described above with reference to structural formula (1-LXXI).

In another embodiment, the presently disclosed compounds have the structural formula (1-LXXVIII):

in which $R^3$, $R^5$ and $R^{14}$ are defined as described above with reference to structural formulae (1-I) and (1-XXXVIII); and $R^{18}$ and $R^{19}$ are defined as described above with reference to structural formula (1-LXXI).

In another embodiment, the presently disclosed compounds have the structural formula (1-LXXIX):

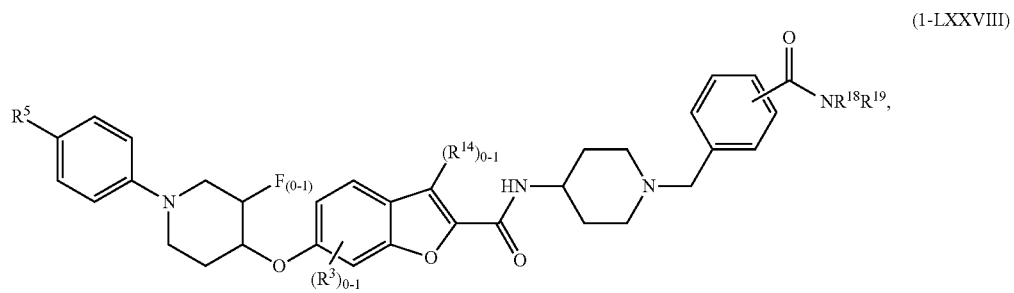
(1-LXXVIII)

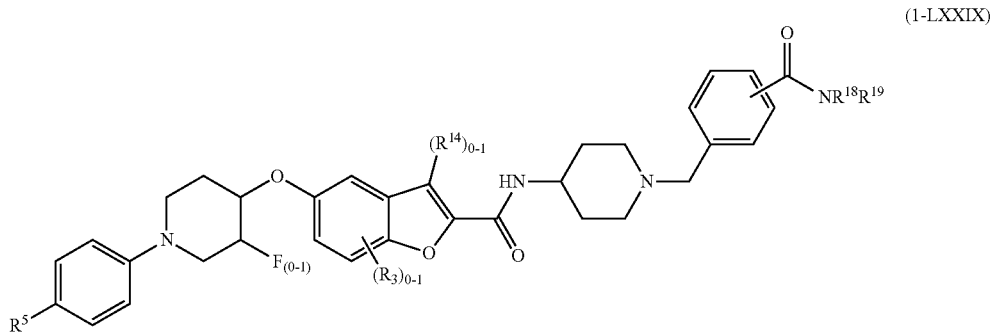

(1-LXXIX)

in which $R^3$, $R^5$ and $R^{14}$ are defined as described above with reference to structural formulae (1-I) and (1-XXXVIII); and $R^{18}$ and $R^{19}$ are defined as described above with reference to structural formula (1-LXXI).

In one embodiment, the presently disclosed compounds have the structural formula (1-LXXX):

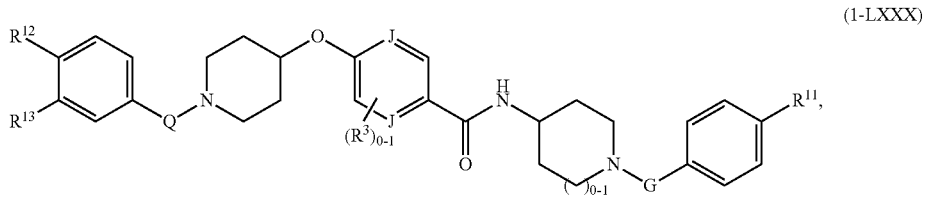

(1-LXXX)

in which one J is N and the other is CH; Q is —CH$_2$— or a single bond; G is CH$_2$ or C(O); $R^3$ is as described above with respect to structural formulae (1-I) and (1-XXXVIII) (e.g., absent or halo); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H.

In certain embodiments, the presently disclosed compounds have the structural formula (1-LXXXI):

in which one J is N and the other is CH; Q is —CH$_2$— or a single bond; G is CH$_2$ or C(O); $R^3$ is as described above with respect to structural formulae (1-I) and (1-XXXVIII) (e.g., absent or halo); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H.

In certain embodiments, the presently disclosed compounds have the structural formula (1-LXXXII):

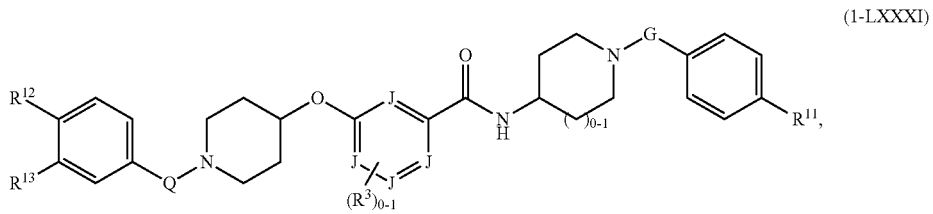

(1-LXXXI)

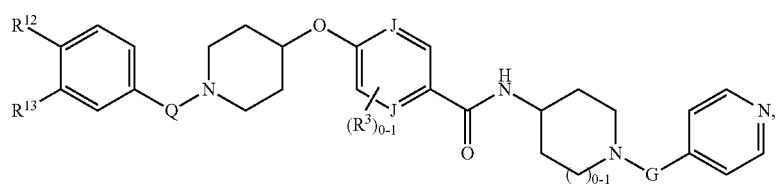

(1-LXXXII)

in which one J is N, and the other is CH; Q is —CH$_2$— or a single bond; G is CH$_2$ or C(O); R$^3$ is as described above with respect to structural formulae (1-I) and (1-XXXVIII) (e.g., absent or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (1-LXXXIII):

in which one J is N and the other is CH; Q is —CH$_2$— or a single bond G is CH$_2$ or C(O); R$^3$ is as described above with respect to structural formulae (1-I) and (1-XXXVIII) (e.g., absent or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (1-LXXXV):

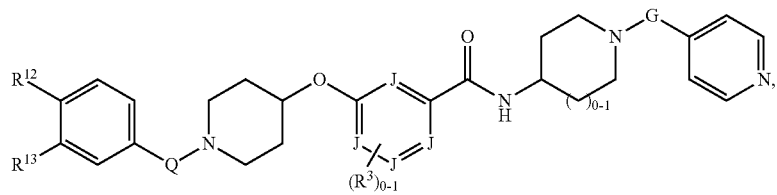

(1-LXXXIII)

in which one J is N, and the other three are CH; Q is —CH$_2$— or a single bond; G G is CH$_2$ or C(O); R$^3$ is as described above with respect to structural formulae (1-I) and (1-XXXVIII) (e.g., absent or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H.

In certain embodiments, the presently disclosed compounds have the structural formula (1-LXXXIV):

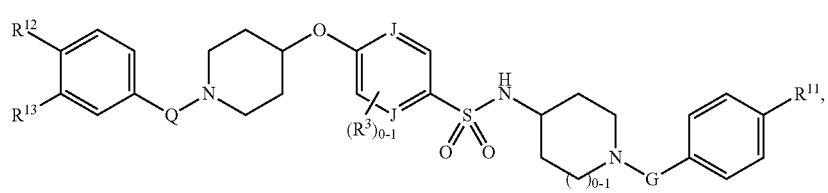

(1-LXXXIV)

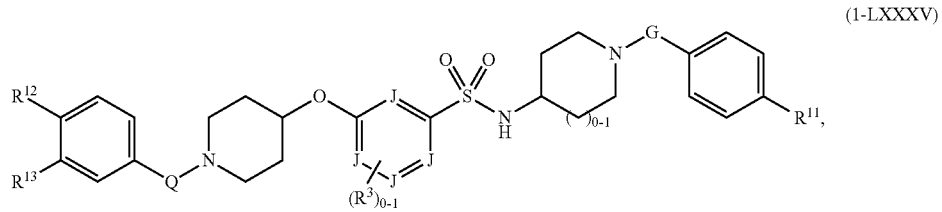

(1-LXXXV)

in which one J is N, and the other three are CH; Q is —$CH_2$— or a single bond; G is $CH_2$ or C(O); $R^3$ is as described above with respect to structural formulae (1-I) and (1-XXXVIII) (e.g., absent or halo); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H.

In certain embodiments, the presently disclosed compounds have the structural formula (1-LXXXVI):

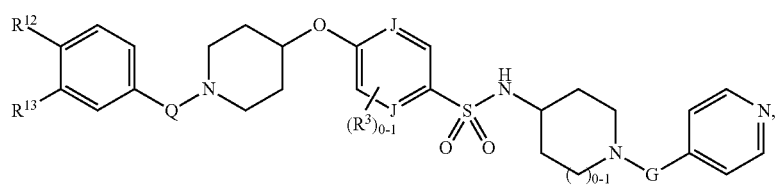

(1-LXXXVI)

in which one J is N, and the other is CH; Q is —$CH_2$— or a single bond; G is $CH_2$ or C(O); $R^3$ is as described above with respect to structural formulae (1-I) and (1-XXXVIII) (e.g., absent or halo); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H.

In certain embodiments, the presently disclosed compounds have the structural formula (1-LXXXVII):

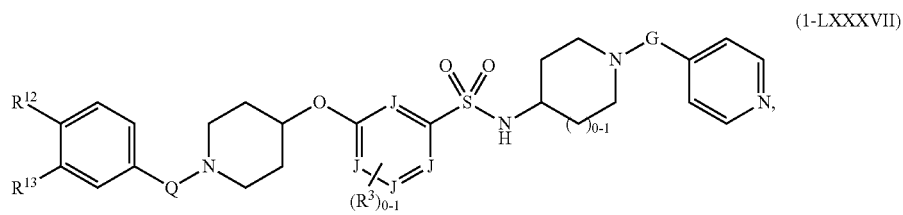

(1-LXXXVII)

in which one J is N, and the other three are CH; Q is —$CH_2$— or a single bond; G is $CH_2$ or C(O); $R^3$ is as described above with respect to structural formulae (1-I) and (1-XXXVIII) (e.g., absent or halo); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H.

In certain embodiments, the presently disclosed compounds have the structural formula (1-LXXXVIII):

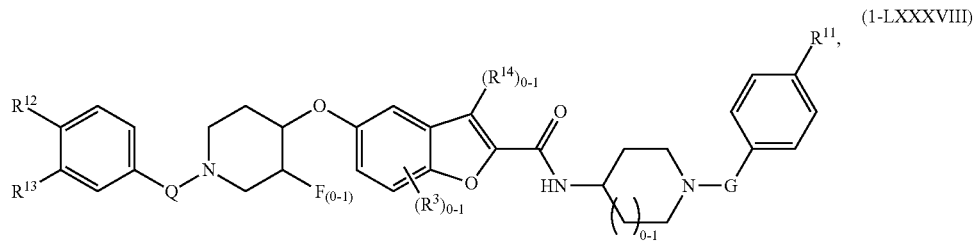

(1-LXXXVIII)

in which Q is —CH$_2$— or a single bond; G is CH$_2$ or C(O); R$^3$ is as described above with respect to structural formulae (1-I) and (1-XXXVIII) (e.g., absent or halo); R$^{14}$ is as described above with respect to structural formulae (1-I) and (1-LX) (e.g., absent, methyl or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (1-LXXXIX):

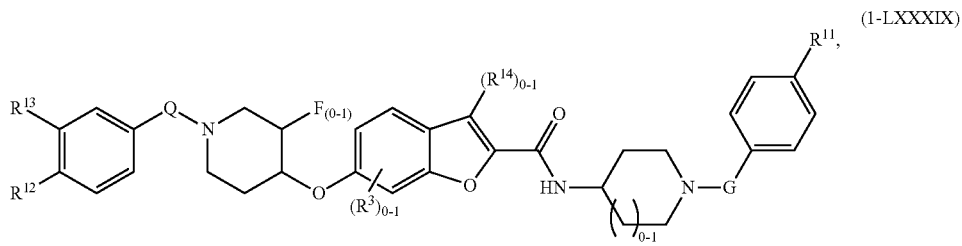

(1-LXXXIX)

in which Q is —CH$_2$— or a single bond; G is CH$_2$ or C(O); R$^3$ is as described above with respect to structural formulae (1-I) and (1-XXXVIII) (e.g., absent or halo); R$^{14}$ is as described above with respect to structural formulae (1-I) and (1-LXI) (e.g., absent, methyl or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (1-XC):

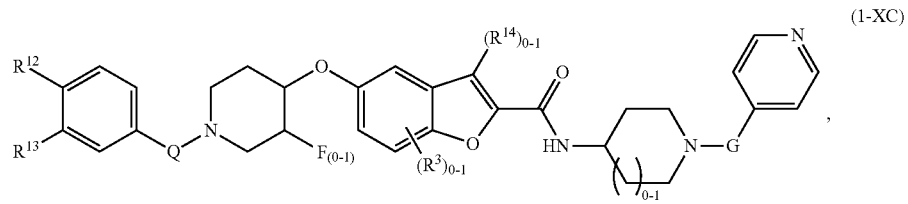

(1-XC)

in which Q is —CH$_2$— or a single bond; G is CH$_2$ or C(O); R$^3$ is as described above with respect to structural formulae (1-I) and (1-XXXVIII) (e.g., absent or halo); R$^{14}$ is as described above with respect to structural formulae (1-I) and (1-LX) (e.g., absent, methyl or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H.

In certain embodiments, the presently disclosed compounds have the structural formula (1-XCI):

in which Q is —CH$_2$— or a single bond; G is CH$_2$ or C(O); R$^3$ is as described above with respect to structural formulae (1-I) and (1-XXXVIII) (e.g., absent or halo); R$^{14}$ is as described above with respect to structural formulae (1-I) and (1-LXII) (e.g., absent, methyl or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (1-XCIII):

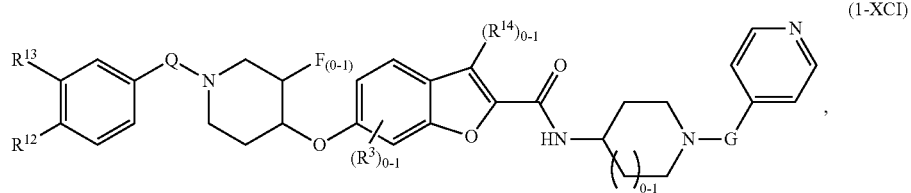

(1-XCI)

in which Q is —CH$_2$— or a single bond; G is CH$_2$ or C(O); R$^3$ is as described above with respect to structural formulae (1-I) and (1-XXXVIII) (e.g., absent or halo); R$^{14}$ is as described above with respect to structural formulae (1-I) and (1-LXI) (e.g., absent, methyl or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H.

In certain embodiments, the presently disclosed compounds have the structural formula (1-XCII):

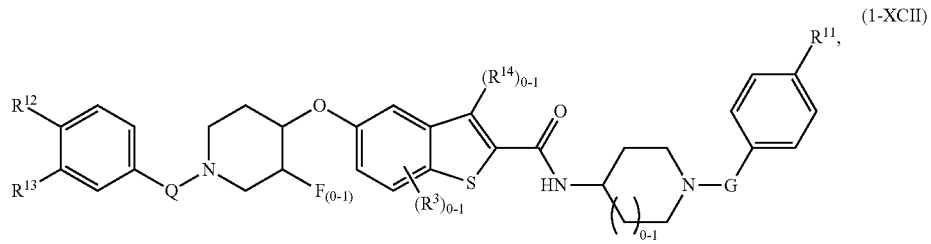

(1-XCII)

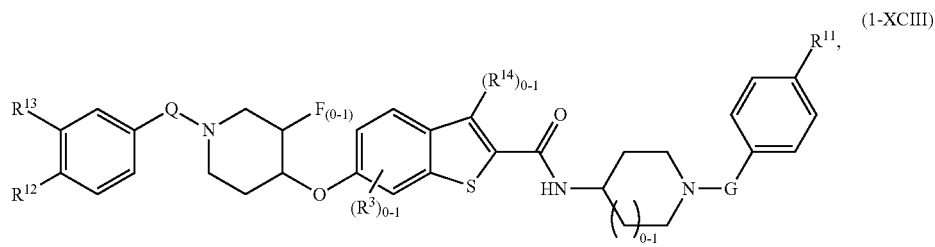

(1-XCIII)

in which Q is —CH$_2$— or a single bond; G is CH$_2$ or C(O); R$^3$ is as described above with respect to structural formulae (1-I) and (1-XXXVIII) (e.g., absent or halo); R$^{14}$ is as described above with respect to structural formulae (1-I) and (1-LXIII) (e.g., absent, methyl or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (1-XCIV):

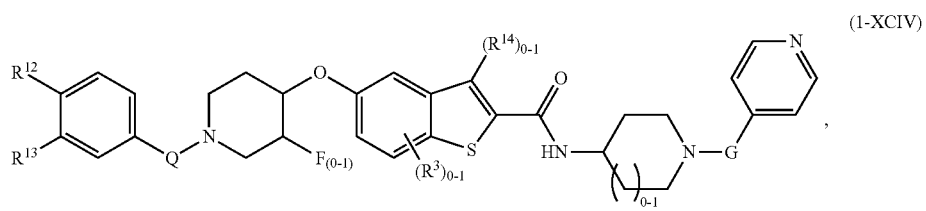

(1-XCIV)

in which Q is —CH$_2$— or a single bond; G is CH$_2$ or C(O); R$^3$ is as described above with respect to structural formulae (1-I) and (1-XXXVIII) (e.g., absent or halo); R$^{14}$ is as described above with respect to structural formulae (1-I) and (1-LXII) (e.g., absent, methyl or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H.

In certain embodiments, the presently disclosed compounds have the structural formula (1-XCV):

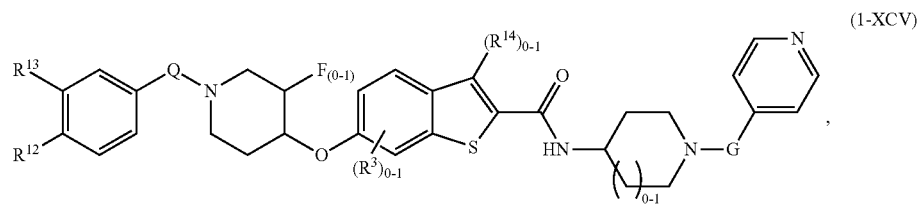

(1-XCV)

in which Q is —CH$_2$— or a single bond; G is CH$_2$ or CO; G is CH$_2$ or C(O); R$^3$ is as described above with respect to structural formulae (1-I) and (1-XXXVIII) (e.g., absent or halo); R$^{14}$ is as described above with respect to structural formulae (1-I) and (1-LXIII) (e.g., absent, methyl or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H.

In certain embodiments, the presently disclosed compounds have the structural formula (1-XCVI):

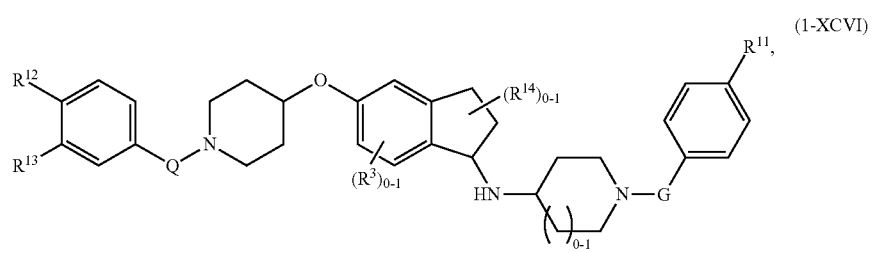

in which Q is —CH$_2$— or a single bond; G is CH$_2$ or C(O); R$^3$ is as described above with respect to structural formulae (1-I) and (1-XXXVIII) (e.g., absent or halo); R$^{14}$ is as described above with respect to structural formula (1-I) (e.g., absent, methyl or halo); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H.

In certain embodiments, the presently disclosed compounds have the structural formula (1-XCVII):

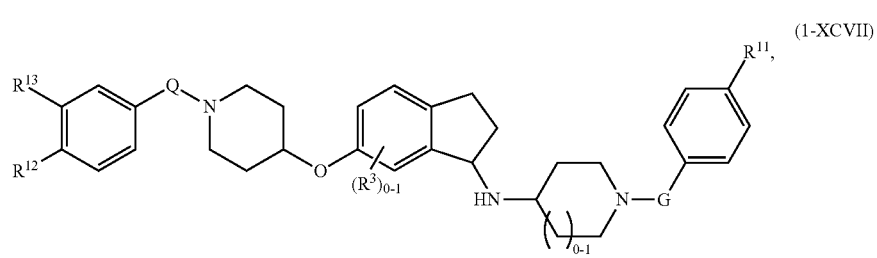

In certain embodiments, the presently disclosed compounds have the structural formula (1-XCVIII):

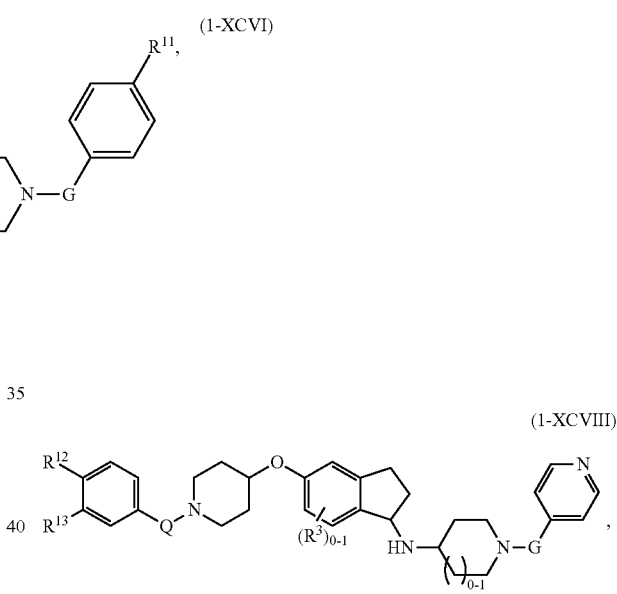

in which Q is —CH$_2$— or a single bond; G is CH$_2$ or C(O); R$^3$ is as described above with respect to structural formulae (1-I) and (1-XXXVIII) (e.g., absent or halo); R$^{14}$ is as described above with respect to structural formula (1-I) (e.g., absent, methyl or halo); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C₀-C₄ alkyl), NO₂ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H.

In certain embodiments, the presently disclosed compounds have the structural formula (1-XCIX):

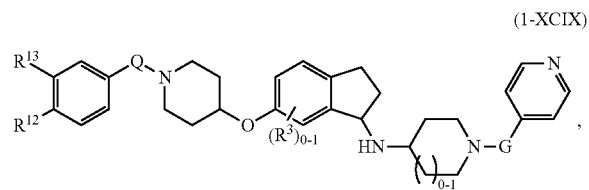

(1-XCIX)

in which Q is —CH₂— or a single bond; G is CH₂ or C(O); $R^3$ is as described above with respect to structural formulae (1-I) and (1-XXXVIII) (e.g., absent or halo); $R^{14}$ is as described above with respect to structural formula (1-I) (e.g., absent, methyl or halo); and $R^{12}$ and $R^{13}$ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H.

Examples of compounds according to structural formula (1-I) include those listed in Table 1. These compounds can be made, for example using a procedure analogous to those described in U.S. Patent Application Publications nos. 2009/0163511, 2009/0170829, 2009/0186894 and 2009/0275609, and in U.S. patent application Ser. Nos. 12/695,861 and 13/194,810, each of which is hereby incorporated by reference in its entirety.

TABLE 1

| No. | Name | Structure |
|---|---|---|
| 1-1 | 5-(1-(4-cyanophenyl)piperidin-4-yloxy)-N-(1-(pyridin-4-ylmethyl)piperidin-4-yl)picolinamide | 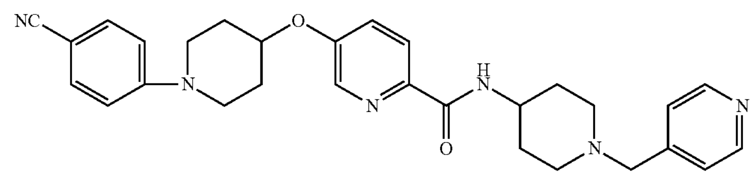 [SMILES: N#Cc1ccc(N2CCC(Oc3ccc(C(=O)NC4CCN(Cc5ccncc5)CC4)nc3)CC2)cc1] |
| 1-2 | N-(1-(4-cyanobenzyl)piperidin-4-yl)-5-(1-(4-cyanophenyl)piperidin-4-yloxy)picolinamide | 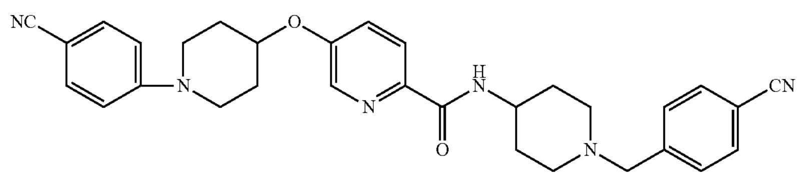 [SMILES: N#Cc1ccc(CN2CCC(NC(=O)c3ccc(OC4CCN(c5ccc(C#N)cc5)CC4)cn3)CC2)cc1] |
| 1-3 | N-(1-(pyridin-4-ylmethyl)piperidin-4-yl)-5-(1-(4-(trifluoromethyl)phenyl)piperidin-4-yloxy)picolinamide | 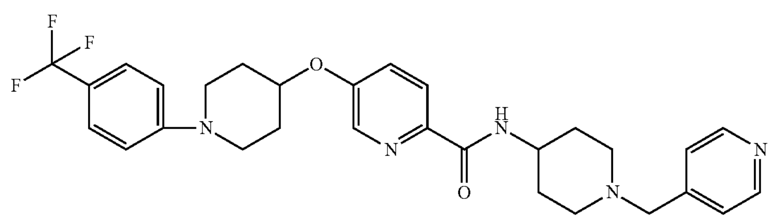 [SMILES: O=C(NC1CCN(Cc2ccncc2)CC1)c1ccc(OC2CCN(c3ccc(C(F)(F)F)cc3)CC2)cn1] |
| 1-4 | N-(1-(4-cyanobenzyl)piperidin-4-yl)-5-(1-(4-(trifluoromethyl)phenyl)piperidin-4-yloxy)picolinamide | 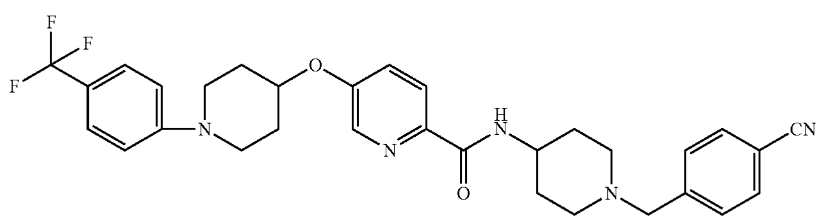 [SMILES: N#Cc1ccc(CN2CCC(NC(=O)c3ccc(OC4CCN(c5ccc(C(F)(F)F)cc5)CC4)cn3)CC2)cc1] |
| 1-5 | N-(1-(pyridin-3-ylmethyl)piperidin-4-yl)-5-(1-(4-(trifluoromethyl)phenyl)piperidin-4-yloxy)picolinamide | 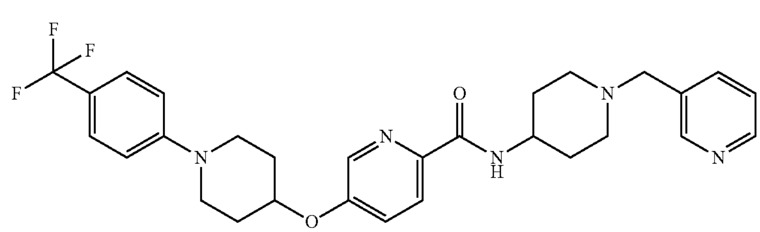 [SMILES: O=C(NC1CCN(Cc2cccnc2)CC1)c1ccc(OC2CCN(c3ccc(C(F)(F)F)cc3)CC2)cn1] |

TABLE 1-continued

| No. | Name | Structure |
|---|---|---|
| 1-6 | N-(1-(pyridin-3-ylmethyl)piperidin-4-yl)-5-(1-(4-cyanophenyl)piperidin-4-yloxy)picolinamide | 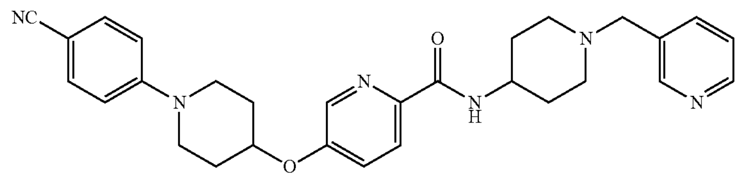 [SMILES: N#Cc1ccc(N2CCC(Oc3ccc(C(=O)NC4CCN(Cc5cccnc5)CC4)nc3)CC2)cc1] |
| 1-7 | methyl 4-((4-(5-(1-(4-cyanophenyl)piperidin-4-yloxy)picolinamido)piperidin-1-yl)methyl)benzoate | 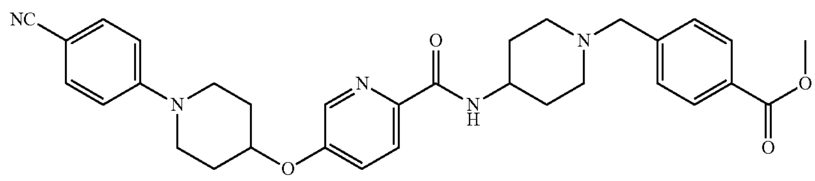 [SMILES: COC(=O)c1ccc(CN2CCC(NC(=O)c3ccc(OC4CCN(c5ccc(C#N)cc5)CC4)cn3)CC2)cc1] |
| 1-8 | methyl 4-((4-(5-(1-(4-(trifluoromethyl)phenyl)piperidin-4-yloxy)picolinamido)piperidin-1-yl)methyl)benzoate | 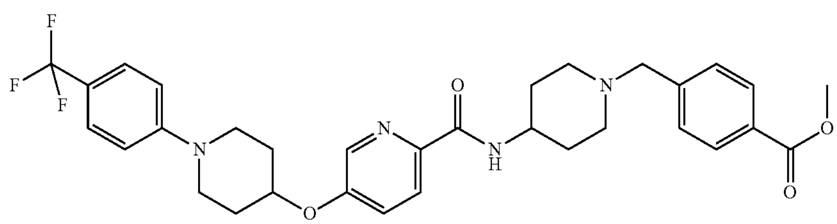 [SMILES: COC(=O)c1ccc(CN2CCC(NC(=O)c3ccc(OC4CCN(c5ccc(C(F)(F)F)cc5)CC4)cn3)CC2)cc1] |
| 1-9 | tert-butyl 4-(6-(1-(4-(trifluoromethyl)phenyl)piperidin-4-yloxy)nicotinamido)piperidine-1-carboxylate | 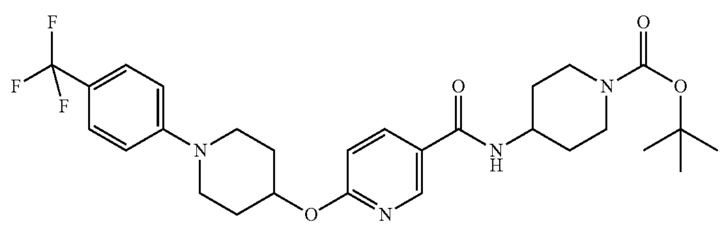 [SMILES: CC(C)(C)OC(=O)N1CCC(NC(=O)c2ccc(OC3CCN(c4ccc(C(F)(F)F)cc4)CC3)nc2)CC1] |
| 1-10 | N-(1-(pyridin-4-ylmethyl)piperidin-4-yl)-6-(1-(4-(trifluoromethyl)phenyl)piperidin-4-yloxy)nicotinamide | 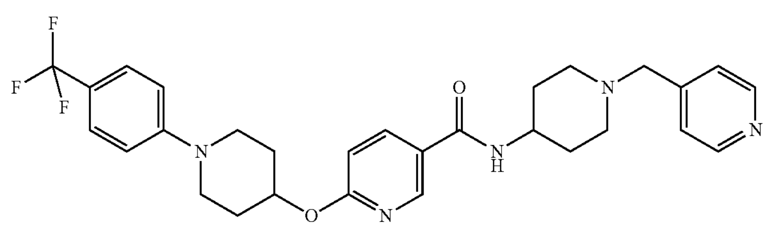 [SMILES: O=C(NC1CCN(Cc2ccncc2)CC1)c1ccc(OC2CCN(c3ccc(C(F)(F)F)cc3)CC2)nc1] |
| 1-11 | N-(1-(4-fluorobenzyl)piperidin-4-yl)-6-(1-(4-(trifluoromethyl)phenyl)piperidin-4-yloxy)nicotinamide | 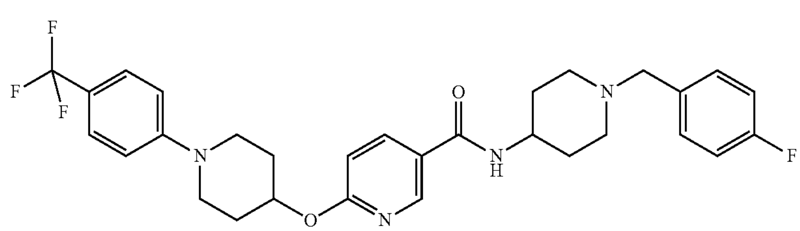 [SMILES: O=C(NC1CCN(Cc2ccc(F)cc2)CC1)c1ccc(OC2CCN(c3ccc(C(F)(F)F)cc3)CC2)nc1] |

TABLE 1-continued
| No. | Name | Structure |
|---|---|---|
| 1-12 | tert-butyl 4-(4-(1-(4-(trifluoromethyl)phenyl)piperidin-4-yloxy)picolinamido)piperidine-1-carboxylate | 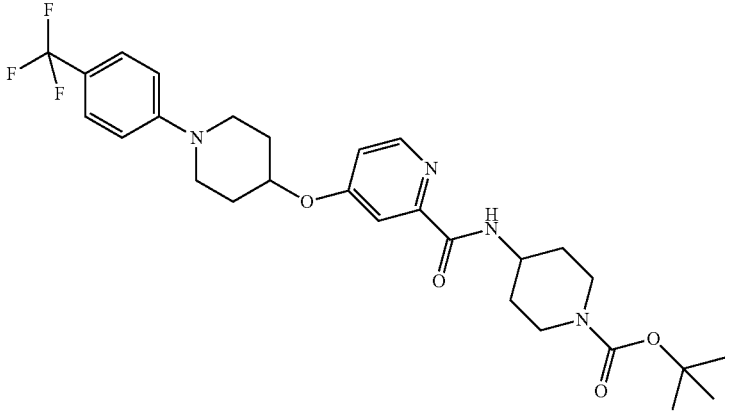 [SMILES: CC(C)(C)OC(=O)N1CCC(NC(=O)c2cc(OC3CCN(c4ccc(C(F)(F)F)cc4)CC3)ccn2)CC1] |
| 1-13 | N-(1-(pyridin-4-ylmethyl)piperidin-4-yl)-4-(1-(4-(trifluoromethyl)phenyl)piperidin-4-yloxy)picolinamide | 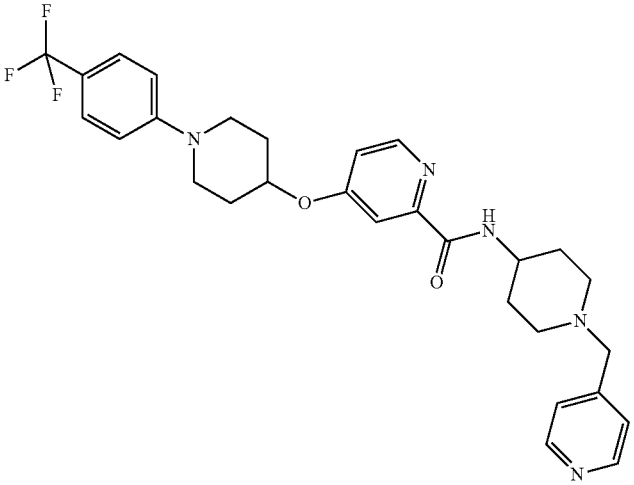 [SMILES: O=C(NC1CCN(Cc2ccncc2)CC1)c1cc(OC2CCN(c3ccc(C(F)(F)F)cc3)CC2)ccn1] |
| 1-14 | N-(1-(pyridin-4-ylmethyl)piperidin-4-yl)-5-(1-(4-(trifluoromethyl)phenyl)piperidin-4-yloxy)nicotinamide | 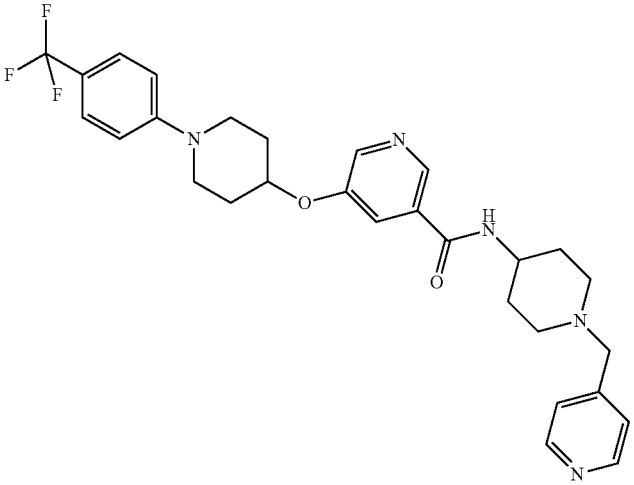 [SMILES: O=C(NC1CCN(Cc2ccncc2)CC1)c1cncc(OC2CCN(c3ccc(C(F)(F)F)cc3)CC2)c1] |

TABLE 1-continued

| No. | Name | Structure |
|---|---|---|
| 1-15 | tert-butyl 4-(2-(1-(4-(trifluoromethyl)phenyl)piperidin-4-yloxy)isonicotinamido)piperidine-1-carboxylate | 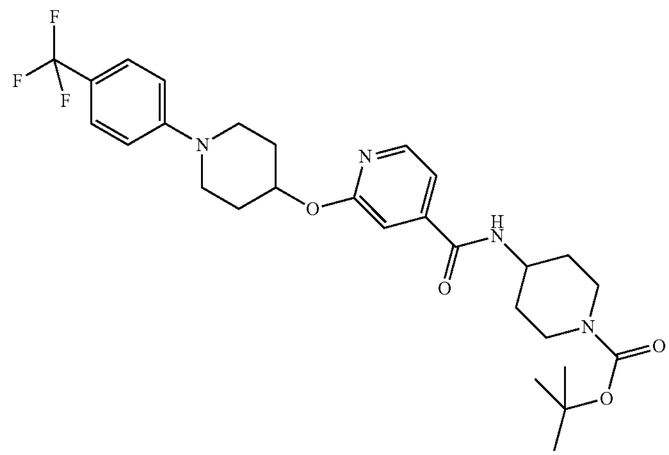 [SMILES: CC(C)(C)OC(=O)N1CCC(NC(=O)c2ccnc(OC3CCN(c4ccc(C(F)(F)F)cc4)CC3)c2)CC1] |
| 1-16 | N-(1-(4-fluorobenzyl)piperidin-4-yl)-5-(1-(4-(trifluoromethyl)phenyl)piperidin-4-yloxy)nicotinamide | 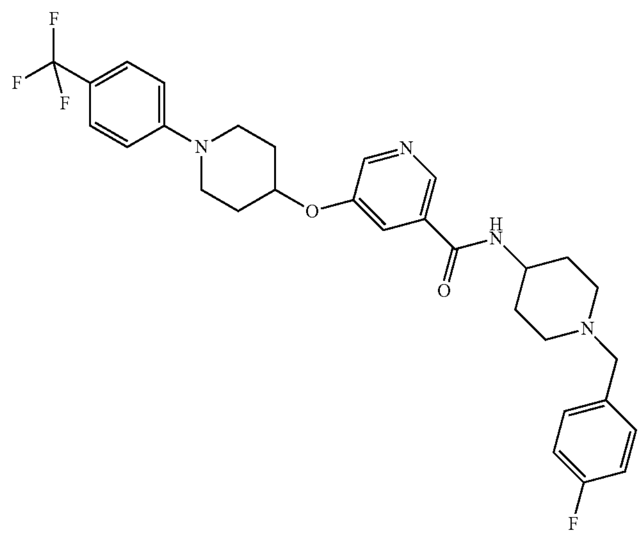 [SMILES: O=C(NC1CCN(Cc2ccc(F)cc2)CC1)c1cncc(OC2CCN(c3ccc(C(F)(F)F)cc3)CC2)c1] |
| 1-17 | N-(1-(4-cyanobenzyl)piperidin-4-yl)-5-(1-(4-(trifluoromethyl)phenyl)piperidin-4-yloxy)nicotinamide | 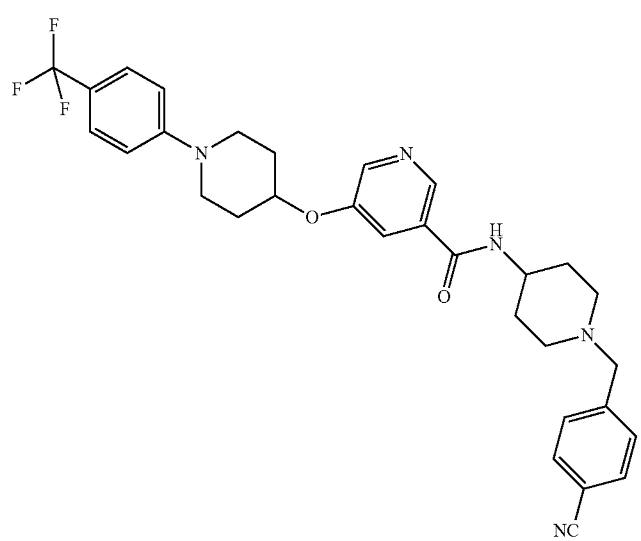 |

TABLE 1-continued
| No. | Name | Structure |
|---|---|---|
| 1-18 | N-(1-(pyridin-3-ylmethyl)piperidin-4-yl)-5-(1-(4-(trifluoromethyl)phenyl)piperidin-4-yloxy)nicotinamide | 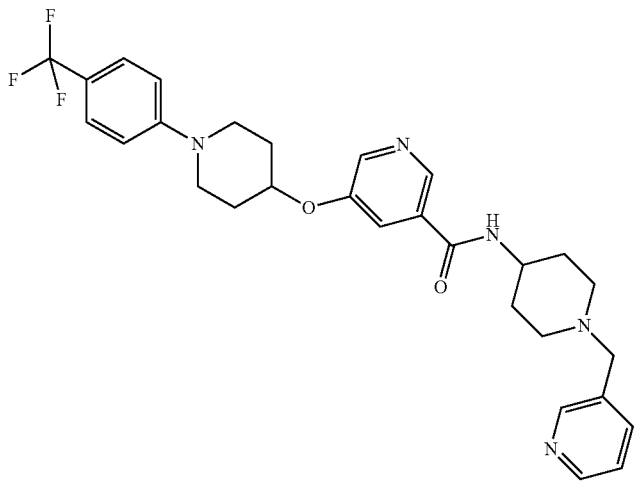 [SMILES: O=C(NC1CCN(Cc2cccnc2)CC1)c1cncc(OC2CCN(c3ccc(C(F)(F)F)cc3)CC2)c1] |
| 1-19 | N-(piperidin-4-yl)-2-(1-(4-(trifluoromethyl)phenyl)piperidin-4-yloxy)isonicotinamide | 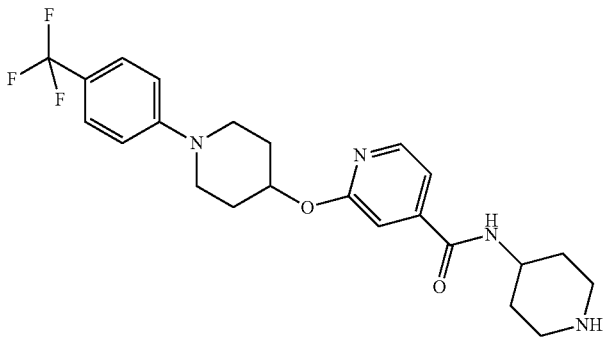 [SMILES: O=C(NC1CCNCC1)c1ccnc(OC2CCN(c3ccc(C(F)(F)F)cc3)CC2)c1] |
| 1-20 | N-(1-(pyridin-4-ylmethyl)piperidin-4-yl)-2-(1-(4-(trifluoromethyl)phenyl)piperidin-4-yloxy)isonicotinamide | 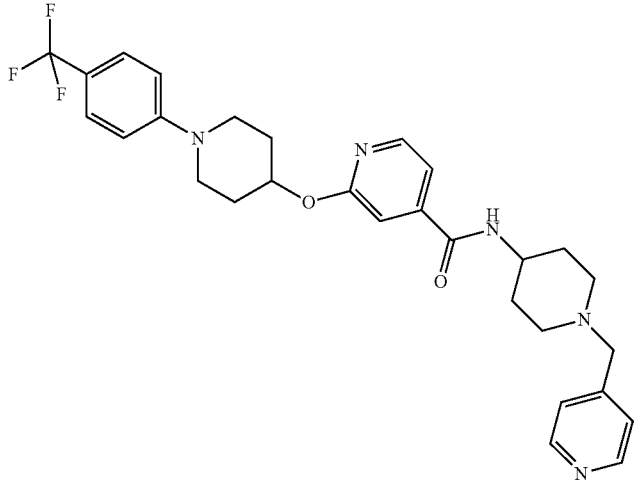 [SMILES: O=C(NC1CCN(Cc2ccncc2)CC1)c1ccnc(OC2CCN(c3ccc(C(F)(F)F)cc3)CC2)c1] |

TABLE 1-continued

| No. | Name | Structure |
|---|---|---|
| 1-21 | N-(1-(4-cyanobenzyl)piperidin-4-yl)-2-(1-(4-(trifluoromethyl)phenyl)piperidin-4-yloxy)isonicotinamide | 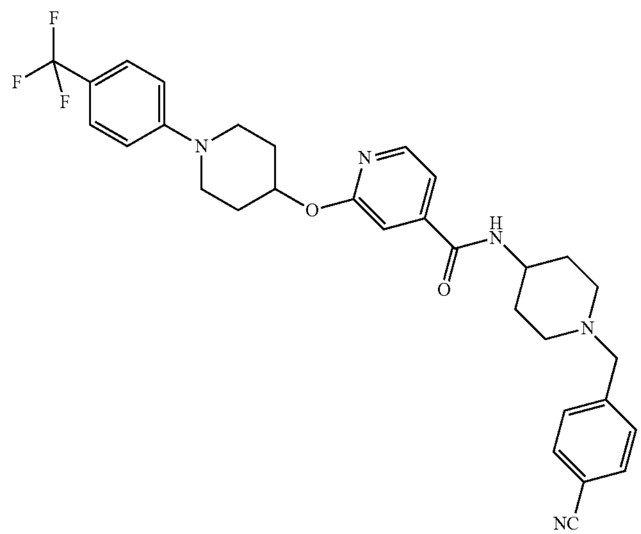 [SMILES: N#Cc1ccc(CN2CCC(NC(=O)c3ccnc(OC4CCN(c5ccc(C(F)(F)F)cc5)CC4)c3)CC2)cc1] |
| 1-22 | N-(1-(4-fluorobenzyl)piperidin-4-yl)-2-(1-(4-(trifluoromethyl)phenyl)piperidin-4-yloxy)isonicotinamide | 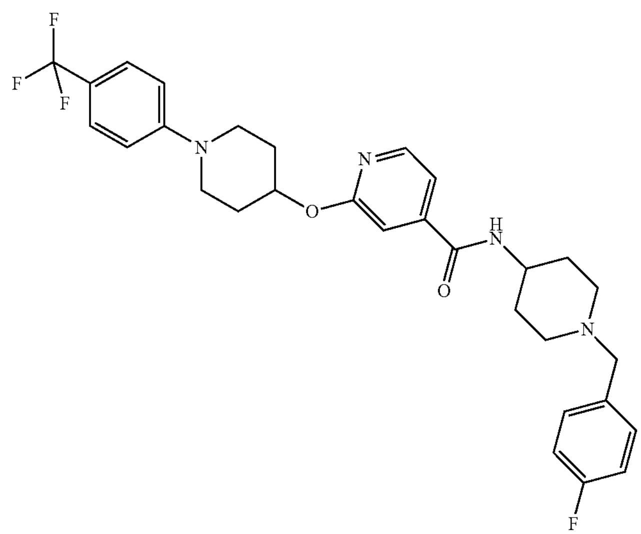 [SMILES: O=C(NC1CCN(Cc2ccc(F)cc2)CC1)c1ccnc(OC2CCN(c3ccc(C(F)(F)F)cc3)CC2)c1] |
| 1-23 | (R)-tert-butyl 3-(5-(1-(4-(trifluoromethyl)phenyl)piperidin-4-yloxy)picolinamido)pyrrolidine-1-carboxylate | 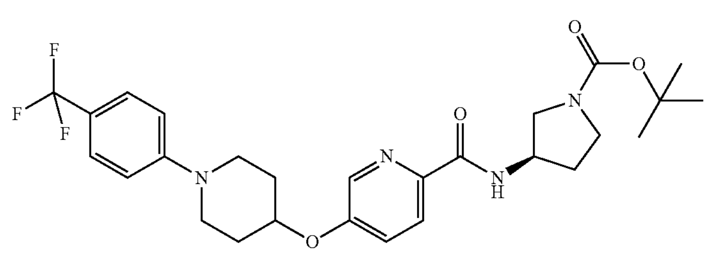 [SMILES: CC(C)(C)OC(=O)N1CC[C@@H](NC(=O)c2ccc(OC3CCN(c4ccc(C(F)(F)F)cc4)CC3)cn2)C1] |
| 1-24 | (R)-N-(pyrrolidin-3-yl)-5-(1-(4-(trifluoromethyl)phenyl)piperidin-4-yloxy)picolinamide | 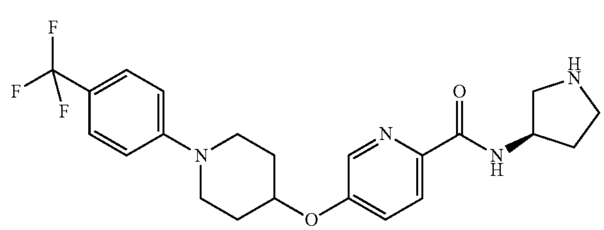 [SMILES: O=C(N[C@@H]1CCNC1)c1ccc(OC2CCN(c3ccc(C(F)(F)F)cc3)CC2)cn1] |

TABLE 1-continued

| No. | Name | Structure |
|---|---|---|
| 1-25 | (R)-N-(1-(pyridin-4-ylmethyl)pyrrolidin-3-yl)-5-(1-(4-(trifluoromethyl)phenyl)piperidin-4-yloxy)picolinamide | 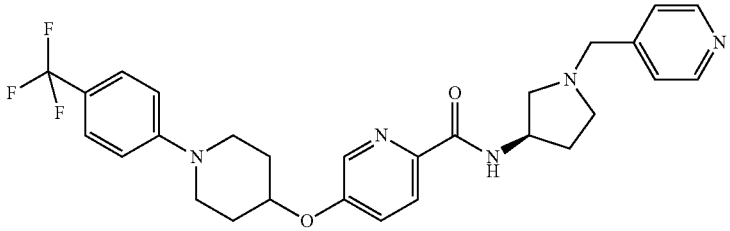 [SMILES: O=C(N[C@@H]1CCN(Cc2ccncc2)C1)c1ccc(OC2CCN(c3ccc(C(F)(F)F)cc3)CC2)cn1] |
| 1-26 | (S)-tert-butyl 3-(5-(1-(4-(trifluoromethyl)phenyl)piperidin-4-yloxy)picolinamido)pyrrolidine-1-carboxylate | 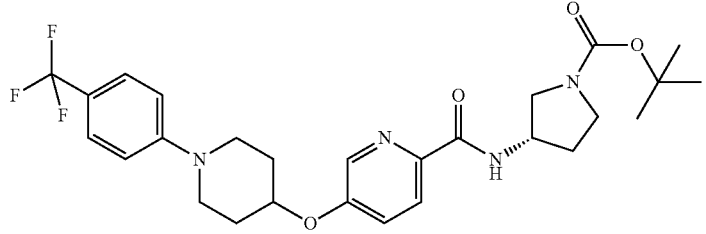 [SMILES: CC(C)(C)OC(=O)N1CC[C@H](NC(=O)c2ccc(OC3CCN(c4ccc(C(F)(F)F)cc4)CC3)cn2)C1] |
| 1-27 | (S)-N-(pyrrolidin-3-yl)-5-(1-(4-(trifluoromethyl)phenyl)piperidin-4-yloxy)picolinamide | 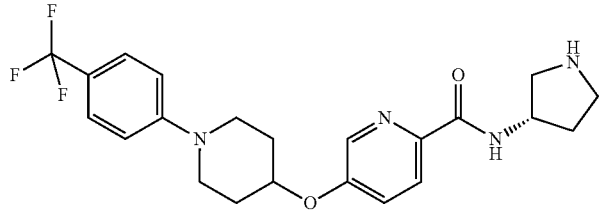 [SMILES: O=C(N[C@H]1CCNC1)c1ccc(OC2CCN(c3ccc(C(F)(F)F)cc3)CC2)cn1] |
| 1-28 | N-(1-(4-cyanobenzyl)piperidin-4-yl)-4-(1-(4-(trifluoromethyl)phenyl)piperidin-4-yloxy)picolinamide | 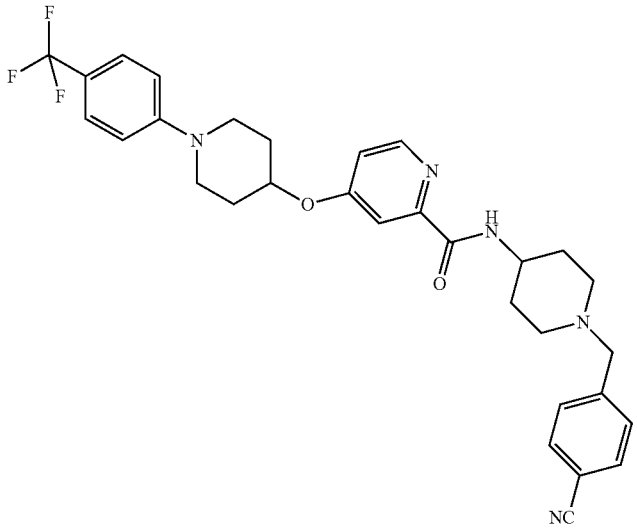 [SMILES: N#Cc1ccc(CN2CCC(NC(=O)c3cc(OC4CCN(c5ccc(C(F)(F)F)cc5)CC4)ccn3)CC2)cc1] |

TABLE 1-continued

| No. | Name | Structure |
|---|---|---|
| 1-29 | N-(1-(4-fluorobenzyl)piperidin-4-yl)-4-(1-(4-(trifluoromethyl)phenyl)piperidin-4-yloxy)picolinamide | 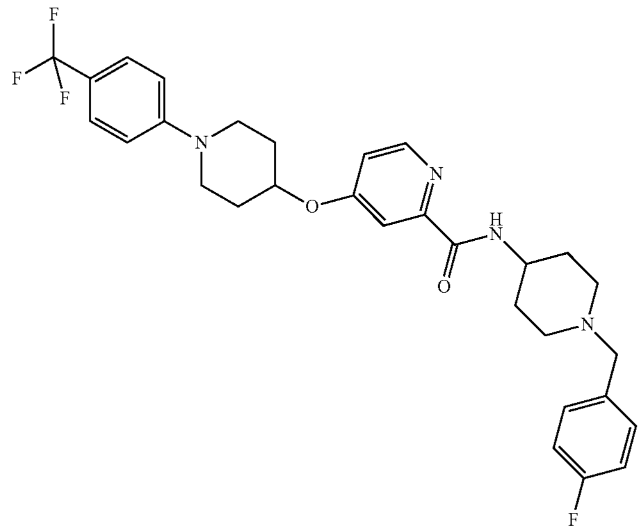 [SMILES: O=C(NC1CCN(Cc2ccc(F)cc2)CC1)c1cc(OC2CCN(c3ccc(C(F)(F)F)cc3)CC2)ccn1] |
| 1-30 | (S)-N-(1-(pyridin-4-ylmethyl)pyrrolidin-3-yl)-5-(1-(4-(trifluoromethyl)phenyl)piperidin-4-yloxy)picolinamide | 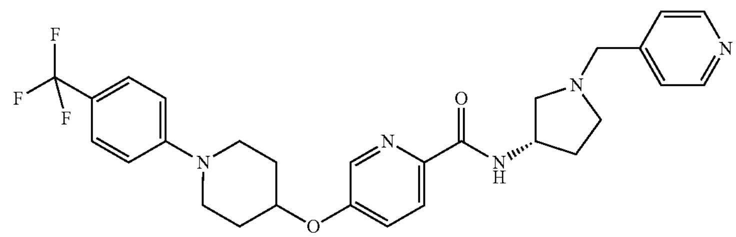 [SMILES: O=C(N[C@H]1CCN(Cc2ccncc2)C1)c1ccc(OC2CCN(c3ccc(C(F)(F)F)cc3)CC2)cn1] |
| 1-31 | (S)-N-(1-(4-cyanobenzyl)pyrrolidin-3-yl)-5-(1-(4-(trifluoromethyl)phenyl)piperidin-4-yloxy)picolinamide | 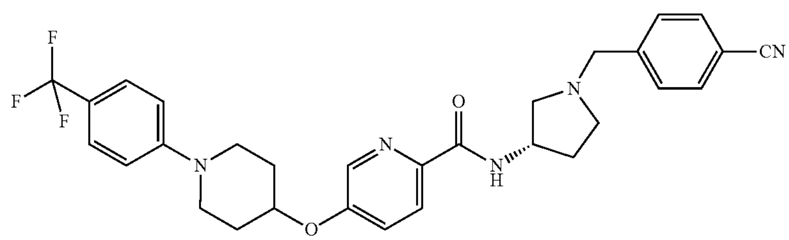 [SMILES: N#Cc1ccc(CN2CC[C@H](NC(=O)c3ccc(OC4CCN(c5ccc(C(F)(F)F)cc5)CC4)cn3)C2)cc1] |
| 1-32 | (S)-N-(1-(4-fluorobenzyl)pyrrolidin-3-yl)-5-(1-(4-(trifluoromethyl)phenyl)piperidin-4-yloxy)picolinamide | 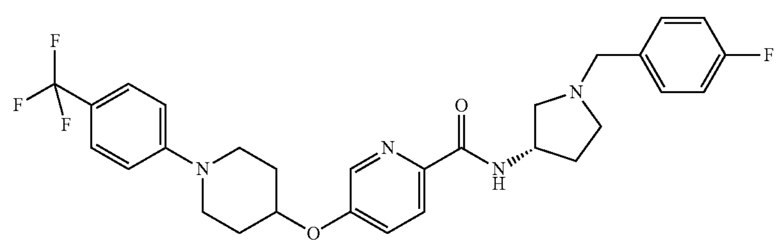 [SMILES: O=C(N[C@H]1CCN(Cc2ccc(F)cc2)C1)c1ccc(OC2CCN(c3ccc(C(F)(F)F)cc3)CC2)cn1] |
| 1-33 | (R)-N-(1-(4-cyanobenzyl)pyrrolidin-3-yl)-5-(1-(4-(trifluoromethyl)phenyl)piperidin-4-yloxy)picolinamide | 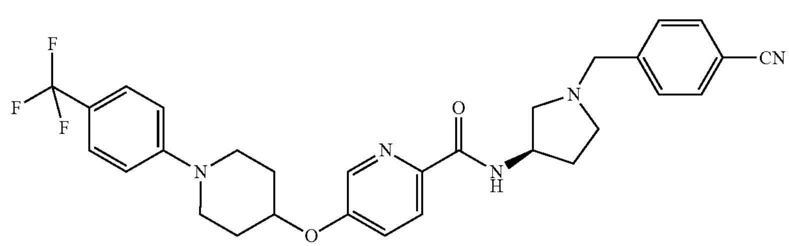 [SMILES: N#Cc1ccc(CN2CC[C@@H](NC(=O)c3ccc(OC4CCN(c5ccc(C(F)(F)F)cc5)CC4)cn3)C2)cc1] |

TABLE 1-continued

| No. | Name | Structure |
|---|---|---|
| 1-34 | (R)-N-(1-(4-fluorobenzyl)pyrrolidin-3-yl)-5-(1-(4-(trifluoromethyl)phenyl)piperidin-4-yloxy)picolinamide | 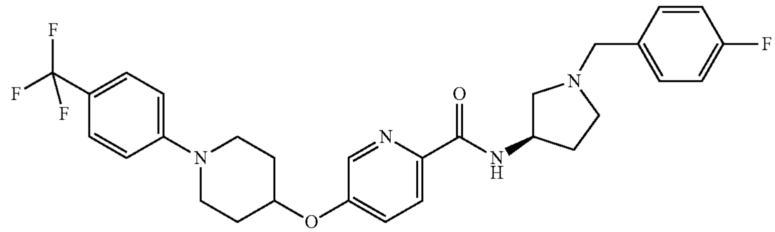 [SMILES: O=C(N[C@@H]1CCN(Cc2ccc(F)cc2)C1)c1ccc(OC2CCN(c3ccc(C(F)(F)F)cc3)CC2)cn1] |
| 1-35 | N-(1-(4-cyanobenzyl)piperidin-4-yl)-6-(1-(4-(trifluoromethyl)phenyl)piperidin-4-yloxy)nicotinamide | 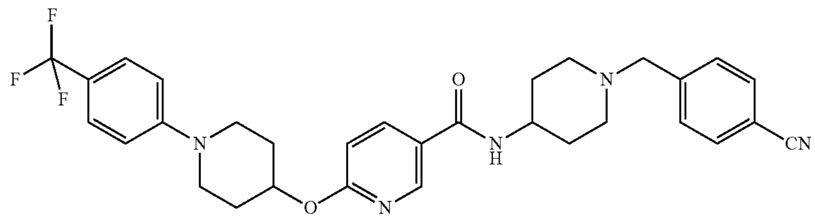 [SMILES: N#Cc1ccc(CN2CCC(NC(=O)c3ccc(OC4CCN(c5ccc(C(F)(F)F)cc5)CC4)nc3)CC2)cc1] |
| 1-36 | N-(1-phenethylpiperidin-4-yl)-5-(1-(4-(trifluoromethyl)phenyl)piperidin-4-yloxy)picolinamide | 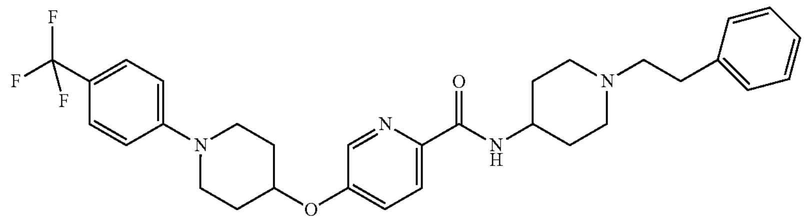 [SMILES: O=C(NC1CCN(CCc2ccccc2)CC1)c1ccc(OC2CCN(c3ccc(C(F)(F)F)cc3)CC2)cn1] |
| 1-37 | N-(1-(naphthalen-2-ylmethyl)piperidin-4-yl)-5-(1-(4-(trifluoromethyl)phenyl)piperidin-4-yloxy)picolinamide | 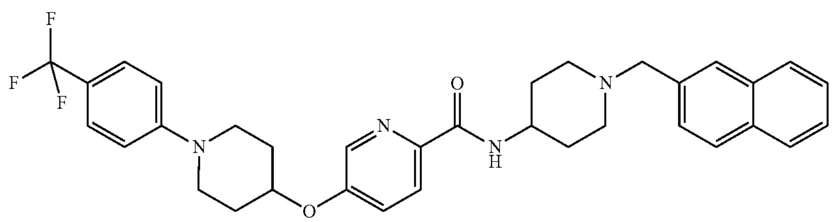 [SMILES: O=C(NC1CCN(Cc2ccc3ccccc3c2)CC1)c1ccc(OC2CCN(c3ccc(C(F)(F)F)cc3)CC2)cn1] |
| 1-38 | N-(1-benzylpiperidin-4-yl)-5-(1-(4-(trifluoromethyl)phenyl)piperidin-4-yloxy)picolinamide | 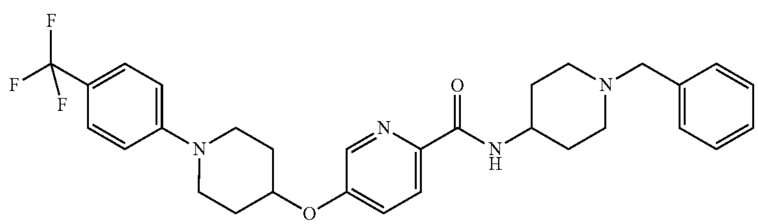 [SMILES: O=C(NC1CCN(Cc2ccccc2)CC1)c1ccc(OC2CCN(c3ccc(C(F)(F)F)cc3)CC2)cn1] |
| 1-39 | N-(1-(4-(dimethylamino)benzyl)piperidin-4-yl)-5-(1-(4-(trifluoromethyl)phenyl)piperidin-4-yloxy)picolinamide | 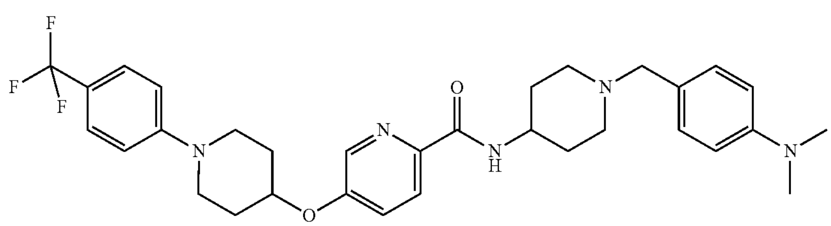 [SMILES: CN(C)c1ccc(CN2CCC(NC(=O)c3ccc(OC4CCN(c5ccc(C(F)(F)F)cc5)CC4)cn3)CC2)cc1] |
| 1-40 | N-(1-(4-morpholinobenzyl)piperidin-4-yl)-5-(1-(4-(trifluoromethyl)phenyl)piperidin-4-yloxy)picolinamide | 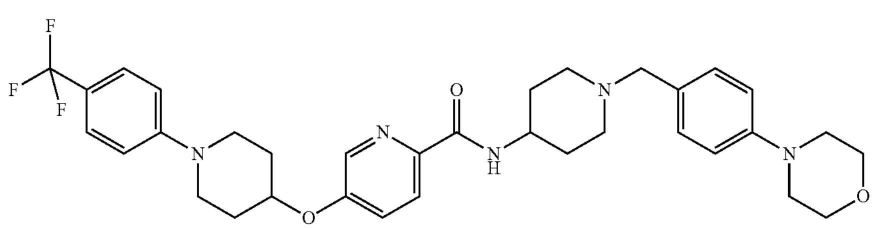 [SMILES: O=C(NC1CCN(Cc2ccc(N3CCOCC3)cc2)CC1)c1ccc(OC2CCN(c3ccc(C(F)(F)F)cc3)CC2)cn1] |

TABLE 1-continued

| No. | Name | Structure |
|---|---|---|
| 1-41 | N-(1-(4-cyanobenzyl)azetidin-3-yl)-5-(1-(4-(trifluoromethyl)phenyl)piperidin-4-yloxy)picolinamide | 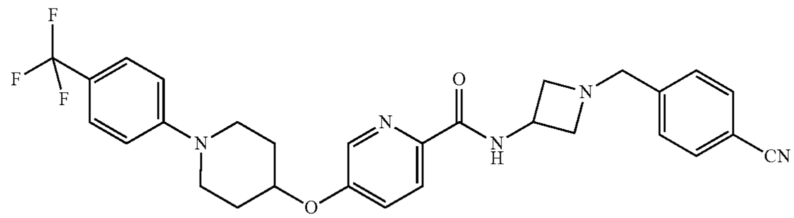 [SMILES: N#Cc1ccc(CN2CC(NC(=O)c3ccc(OC4CCN(c5ccc(C(F)(F)F)cc5)CC4)cn3)C2)cc1] |
| 1-42 | N-(1-(pyridin-4-ylmethyl)azetidin-3-yl)-5-(1-(4-(trifluoromethyl)phenyl)piperidin-4-yloxy)picolinamide | 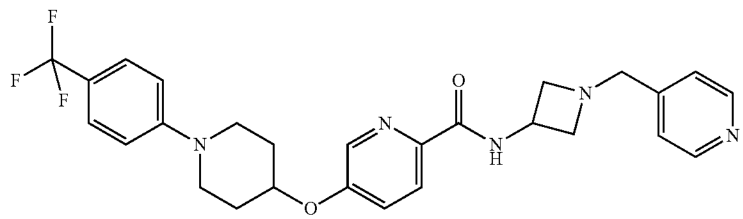 [SMILES: O=C(NC1CN(Cc2ccncc2)C1)c1ccc(OC2CCN(c3ccc(C(F)(F)F)cc3)CC2)cn1] |
| 1-43 | N-(1-(pyridin-4-ylmethyl)piperidin-4-yl)-6-(1-(4-(trifluoromethyl)phenyl)piperidin-4-yloxy)picolinamide | 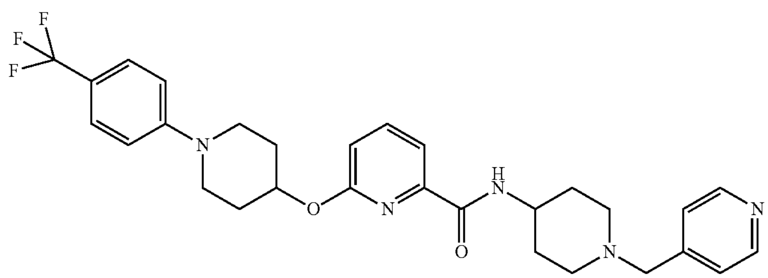 [SMILES: O=C(NC1CCN(Cc2ccncc2)CC1)c1cccc(OC2CCN(c3ccc(C(F)(F)F)cc3)CC2)n1] |
| 1-44 | N-(1-(pyrimidin-5-ylmethyl)piperidin-4-yl)-5-(1-(4-(trifluoromethyl)phenyl)piperidin-4-yloxy)picolinamide | 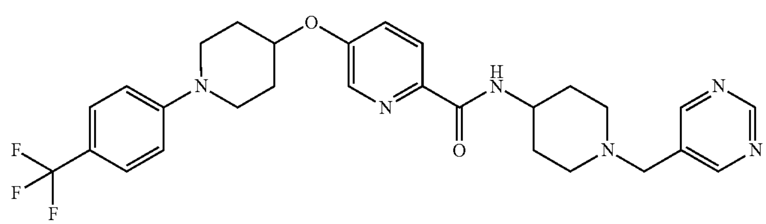 [SMILES: O=C(NC1CCN(Cc2cncnc2)CC1)c1ccc(OC2CCN(c3ccc(C(F)(F)F)cc3)CC2)cn1] |
| 1-45 | methyl 4-((4-(6-(1-(4-(trifluoromethyl)phenyl)piperidin-4-yloxy)nicotinamido)piperidin-1-yl)methyl)benzoate | 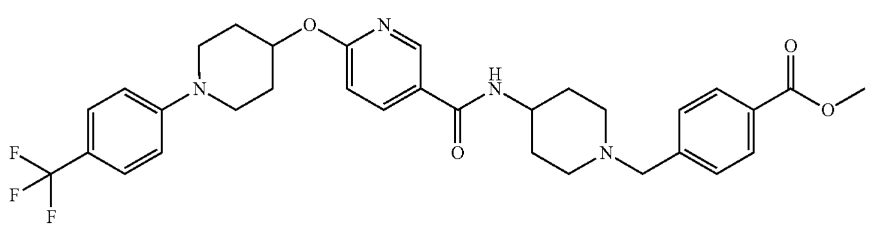 [SMILES: COC(=O)c1ccc(CN2CCC(NC(=O)c3ccc(OC4CCN(c5ccc(C(F)(F)F)cc5)CC4)nc3)CC2)cc1] |
| 1-46 | 4-((4-(6-(1-(4-(trifluoromethyl)phenyl)piperidin-4-yloxy)nicotinamido)piperidin-1-yl)methyl)benzoic acid | 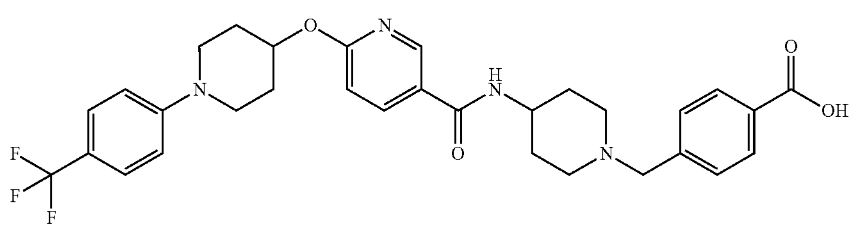 [SMILES: O=C(O)c1ccc(CN2CCC(NC(=O)c3ccc(OC4CCN(c5ccc(C(F)(F)F)cc5)CC4)nc3)CC2)cc1] |

TABLE 1-continued

| No. | Name |
|---|---|
| 1-47 | 5-(1-(4-(trifluoromethyl)phenyl)piperidin-4-yloxy)-N-(1-((1-trityl-1H-imidazol-4-yl)methyl)piperidin-4-yl)picolinamide |
| 1-48 | N-(1-((1H-imidazol-4-yl)methyl)piperidin-4-yl)-5-(1-(4-(trifluoromethyl)phenyl)piperidin-4-yloxy)picolinamide |
| 1-49 | tert-butyl 3-(5-(1-(4-(trifluoromethyl)phenyl)piperidin-4-yloxy)picolinamido)propylcarbamate |
| 1-50 | N-(3-(pyridin-4-ylmethylamino)propyl)-5-(1-(4-(trifluoromethyl)phenyl)piperidin-4-yloxy)picolinamide |
| 1-51 | N-(1-(pyridin-4-ylmethyl)piperidin-4-yl)-6-(1-(4-(trifluoromethyl)phenyl)piperidin-4-yloxy)pyridine-3-sulfonamide |
| 1-52 | N-(1-(pyridin-4-ylmethyl)piperidin-4-yl)-6-(1-(4-cyanophenyl)piperidin-4-yloxy)pyridine-3-sulfonamide |
| 1-53 | 6-(1-(4-cyanobenzyl)piperidin-4-yloxy)-N-(1-(pyridin-4-ylmethyl)piperidin-4-yl)pyridine-3-sulfonamide |

TABLE 1-continued

| No. | Name | Structure |
|---|---|---|
| 1-54 | tert-butyl 4-(6-(1-(4-(trifluoromethyl)phenyl)piperidin-4-yloxy)pyridine-3-sulfonamido)piperidine-1-carboxylate | 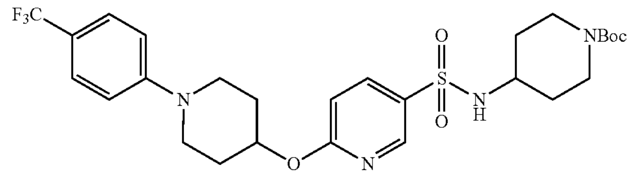 [SMILES: CC(C)(C)OC(=O)N1CCC(NS(=O)(=O)c2ccc(OC3CCN(c4ccc(C(F)(F)F)cc4)CC3)nc2)CC1] |
| 1-55 | N-(piperidin-4-yl)-6-(1-(4-(trifluoromethyl)phenyl)piperidin-4-yloxy)pyridine-3-sulfonamide | 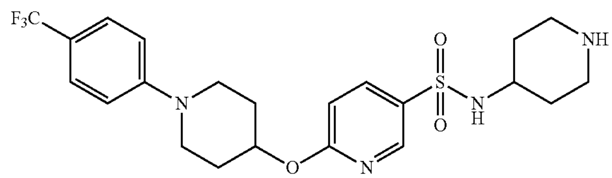 [SMILES: O=S(=O)(NC1CCNCC1)c1ccc(OC2CCN(c3ccc(C(F)(F)F)cc3)CC2)nc1] |
| 1-56 | N-(1-(4-cyanobenzyl)piperidin-4-yl)-6-(1-(4-(trifluoromethyl)phenyl)piperidin-4-yloxy)pyridine-3-sulfonamide | 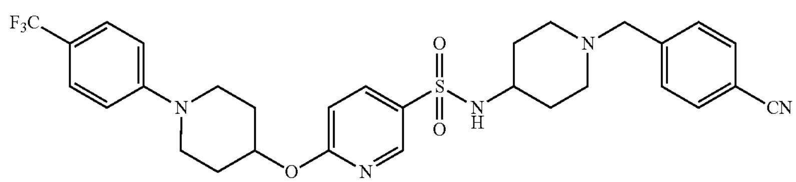 [SMILES: N#Cc1ccc(CN2CCC(NS(=O)(=O)c3ccc(OC4CCN(c5ccc(C(F)(F)F)cc5)CC4)nc3)CC2)cc1] |
| 1-57 | N-(1-(3-cyanobenzyl)piperidin-4-yl)-6-(1-(4-(trifluoromethyl)phenyl)piperidin-4-yloxy)pyridine-3-sulfonamide | 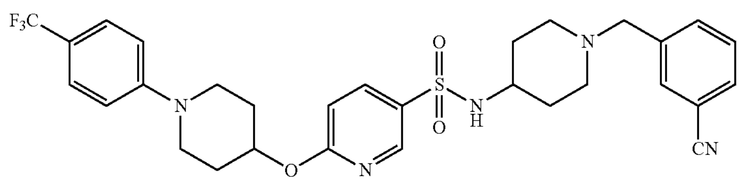 |
| 1-58 | N-(1-(4-(trifluoromethyl)benzyl)piperidin-4-yl)-6-(1-(4-(trifluoromethyl)phenyl)piperidin-4-yloxy)pyridine-3-sulfonamide | 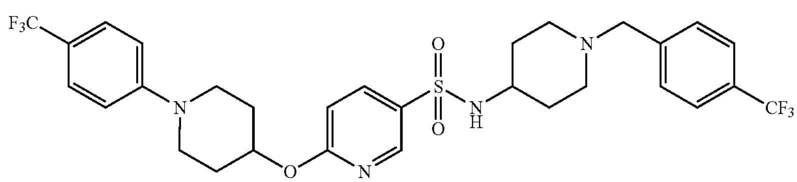 [SMILES: O=S(=O)(NC1CCN(Cc2ccc(C(F)(F)F)cc2)CC1)c1ccc(OC2CCN(c3ccc(C(F)(F)F)cc3)CC2)nc1] |
| 1-59 | N-(1-(3-(trifluoromethyl)benzyl)piperidin-4-yl)-6-(1-(4-(trifluoromethyl)phenyl)piperidin-4-yloxy)pyridine-3-sulfonamide | 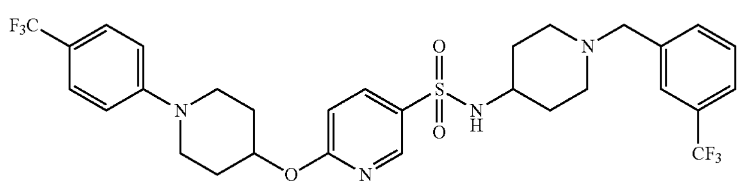 [SMILES: O=S(=O)(NC1CCN(Cc2cccc(C(F)(F)F)c2)CC1)c1ccc(OC2CCN(c3ccc(C(F)(F)F)cc3)CC2)nc1] |
| 1-60 | N-(1-(4-fluorobenzoyl)piperidin-4-yl)-6-(1-(4-(trifluoromethyl)phenyl)piperidin-4-yloxy)pyridine-3-sulfonamide | 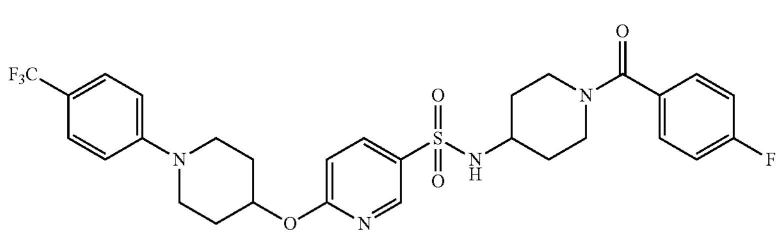 [SMILES: O=C(c1ccc(F)cc1)N1CCC(NS(=O)(=O)c2ccc(OC3CCN(c4ccc(C(F)(F)F)cc4)CC3)nc2)CC1] |

TABLE 1-continued

| No. | Name |
|---|---|
| 1-61 | tert-butyl 4-(3-methyl-6-(1-(4-(trifluoromethyl)phenyl)piperidin-4-yloxy)benzofuran-2-carboxamido)piperidine-1-carboxylate |
| 1-62 | 3-methyl-N-(piperidin-4-yl)-6-(1-(4-(trifluoromethyl)phenyl)piperidin-4-yloxy)benzofuran-2-carboxamide |
| 1-63 | N-(1-(4-fluorobenzyl)piperidin-4-yl)-3-methyl-6-(1-(4-(trifluoromethyl)phenyl)piperidin-4-yloxy)benzofuran-2-carboxamide |
| 1-64 | N-(1-(4-cyanobenzyl)piperidin-4-yl)-3-methyl-6-(1-(4-(trifluoromethyl)phenyl)piperidin-4-yloxy)benzofuran-2-carboxamide |

TABLE 1-continued

| No. | Name | Structure |
|---|---|---|
| 1-65 | 3-methyl-N-(1-(pyridin-4-ylmethyl)piperidin-4-yl)-6-(1-(4-(trifluoromethyl)phenyl)piperidin-4-yloxy)benzofuran-2-carboxamide | 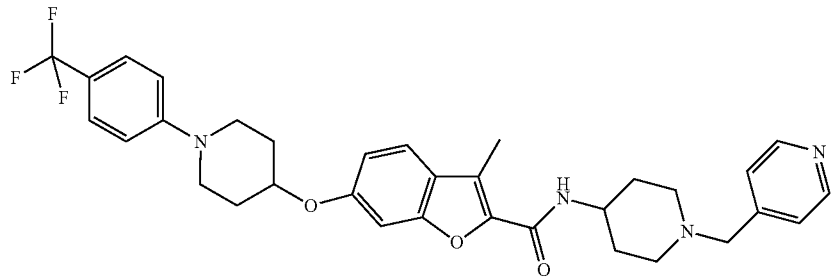 [SMILES: Cc1c(C(=O)NC2CCN(Cc3ccncc3)CC2)oc2cc(OC3CCN(c4ccc(C(F)(F)F)cc4)CC3)ccc12] |
| 1-66 | N-(1-(3-cyanobenzyl)piperidin-4-yl)-3-methyl-6-(1-(4-(trifluoromethyl)phenyl)piperidin-4-yloxy)benzofuran-2-carboxamide | 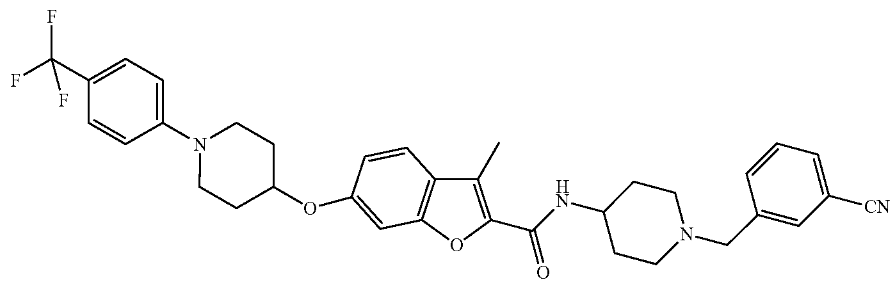 [SMILES: Cc1c(C(=O)NC2CCN(Cc3cccc(C#N)c3)CC2)oc2cc(OC3CCN(c4ccc(C(F)(F)F)cc4)CC3)ccc12] |
| 1-67 | N-(1-(2-cyanobenzyl)piperidin-4-yl)-3-methyl-6-(1-(4-(trifluoromethyl)phenyl)piperidin-4-yloxy)benzofuran-2-carboxamide | 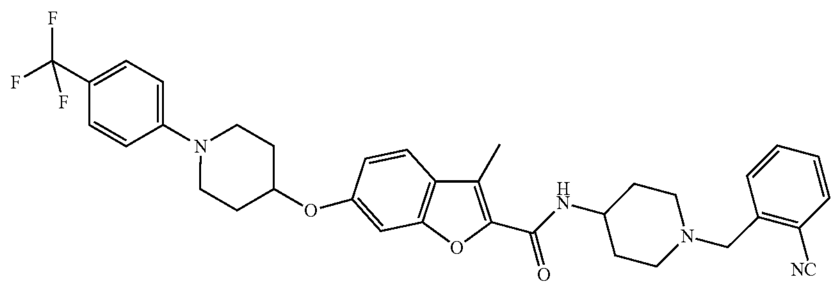 [SMILES: Cc1c(C(=O)NC2CCN(Cc3ccccc3C#N)CC2)oc2cc(OC3CCN(c4ccc(C(F)(F)F)cc4)CC3)ccc12] |
| 1-68 | 3-methyl-N-(1-(pyridin-2-ylmethyl)piperidin-4-yl)-6-(1-(4-(trifluoromethyl)phenyl)piperidin-4-yloxy)benzofuran-2-carboxamide | 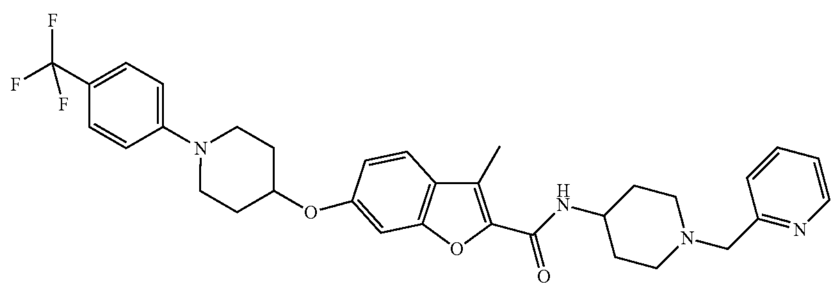 [SMILES: Cc1c(C(=O)NC2CCN(Cc3ccccn3)CC2)oc2cc(OC3CCN(c4ccc(C(F)(F)F)cc4)CC3)ccc12] |
| 1-69 | 3-methyl-N-(1-(pyridin-3-ylmethyl)piperidin-4-yl)-6-(1-(4-(trifluoromethyl)phenyl)piperidin-4-yloxy)benzofuran-2-carboxamide | 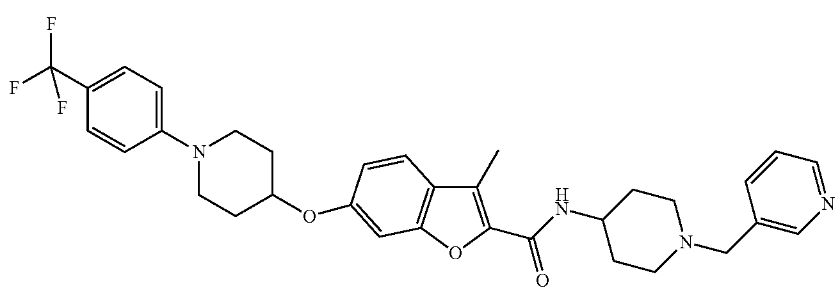 [SMILES: Cc1c(C(=O)NC2CCN(Cc3cccnc3)CC2)oc2cc(OC3CCN(c4ccc(C(F)(F)F)cc4)CC3)ccc12] |
| 1-70 | N-(1-benzylpiperidin-4-yl)-5-(1-(4-cyanobenzyl)piperidin-4-yloxy)benzofuran-2-carboxamide | 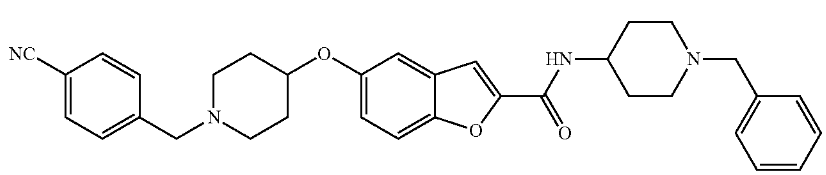 [SMILES: N#Cc1ccc(CN2CCC(Oc3ccc4oc(C(=O)NC5CCN(Cc6ccccc6)CC5)cc4c3)CC2)cc1] |

TABLE 1-continued

| No. | Name | Structure |
|---|---|---|
| 1-71 | N-(1-benzylpiperidin-4-yl)-5-(1-(4-cyanophenyl)piperidin-4-yloxy)benzofuran-2-carboxamide | 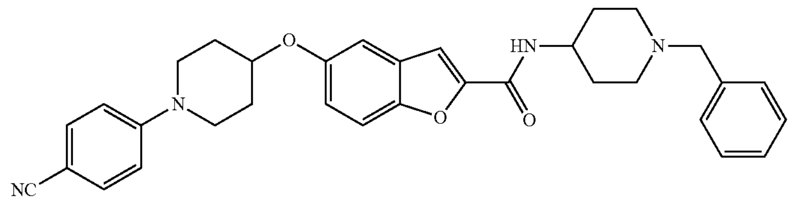 [SMILES: N#Cc1ccc(N2CCC(Oc3ccc4oc(C(=O)NC5CCN(Cc6ccccc6)CC5)cc4c3)CC2)cc1] |
| 1-72 | N-(1-benzylpiperidin-4-yl)-5-(1-(4-chlorobenzyl)piperidin-4-yloxy)benzofuran-2-carboxamide | 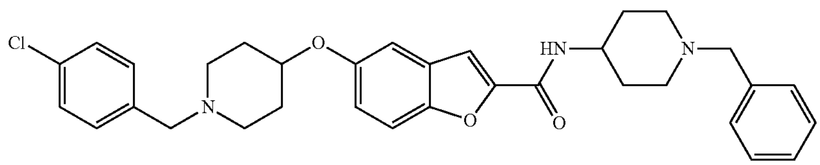 [SMILES: O=C(NC1CCN(Cc2ccccc2)CC1)c1cc2cc(OC3CCN(Cc4ccc(Cl)cc4)CC3)ccc2o1] |
| 1-73 | N-(1-benzylpiperidin-4-yl)-5-(1-(3-(trifluoromethyl)benzyl)piperidin-4-yloxy)benzofuran-2-carboxamide | 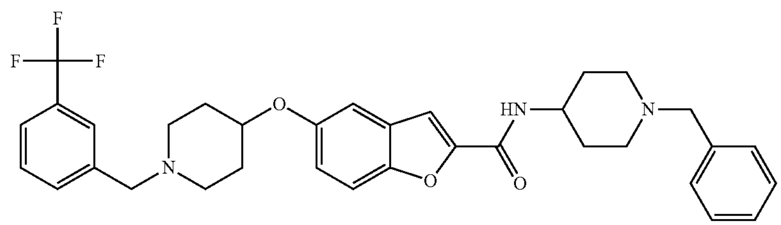 [SMILES: O=C(NC1CCN(Cc2ccccc2)CC1)c1cc2cc(OC3CCN(Cc4cccc(C(F)(F)F)c4)CC3)ccc2o1] |
| 1-74 | N-(1-benzylpiperidin-4-yl)-5-(1-(3,4-difluorobenzyl)piperidin-4-yloxy)benzofuran-2-carboxamide | 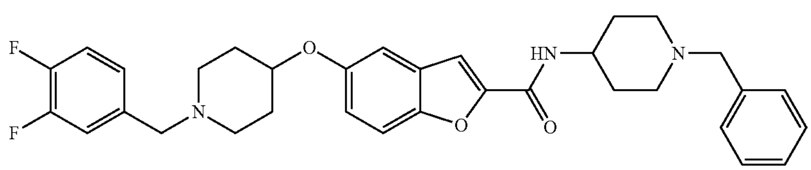 [SMILES: O=C(NC1CCN(Cc2ccccc2)CC1)c1cc2cc(OC3CCN(Cc4ccc(F)c(F)c4)CC3)ccc2o1] |
| 1-75 | N-(1-benzylpiperidin-4-yl)-5-(1-(4-(trifluoromethyl)phenyl)piperidin-4-yloxy)benzofuran-2-carboxamide | 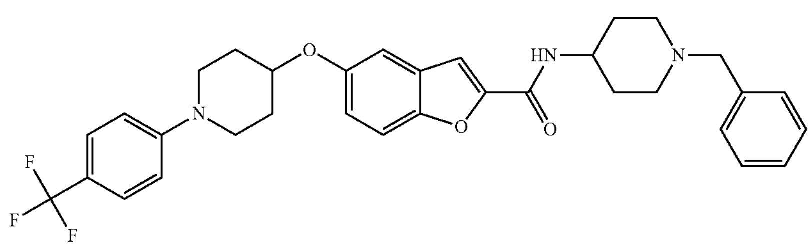 [SMILES: O=C(NC1CCN(Cc2ccccc2)CC1)c1cc2cc(OC3CCN(c4ccc(C(F)(F)F)cc4)CC3)ccc2o1] |
| 1-76 | N-(1-(pyridin-4-ylmethyl)piperidin-4-yl)-5-(1-(4-(trifluoromethyl)phenyl)piperidin-4-yloxy)benzofuran-2-carboxamide | 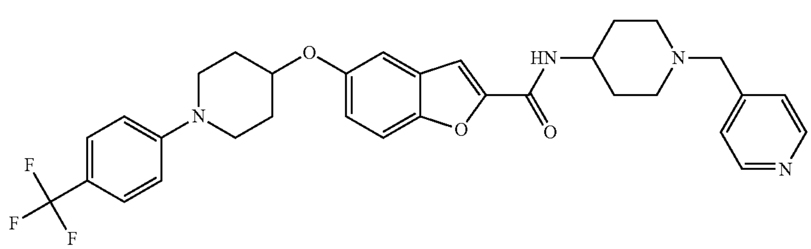 [SMILES: O=C(NC1CCN(Cc2ccncc2)CC1)c1cc2cc(OC3CCN(c4ccc(C(F)(F)F)cc4)CC3)ccc2o1] |
| 1-77 | 5-(1-(4-chlorobenzyl)piperidin-4-yloxy)-N-(1-(pyridin-4-ylmethyl)piperidin-4-yl)benzofuran-2-carboxamide | 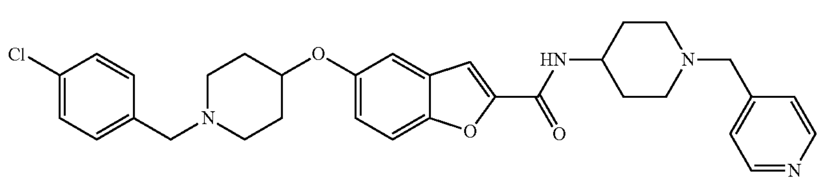 [SMILES: O=C(NC1CCN(Cc2ccncc2)CC1)c1cc2cc(OC3CCN(Cc4ccc(Cl)cc4)CC3)ccc2o1] |

TABLE 1-continued

| No. | Name | Structure |
|---|---|---|
| 1-78 | N-(1-(pyridin-4-ylmethyl)piperidin-4-yl)-5-(1-(4-(trifluoromethoxy)phenyl)piperidin-4-yloxy)benzofuran-2-carboxamide | 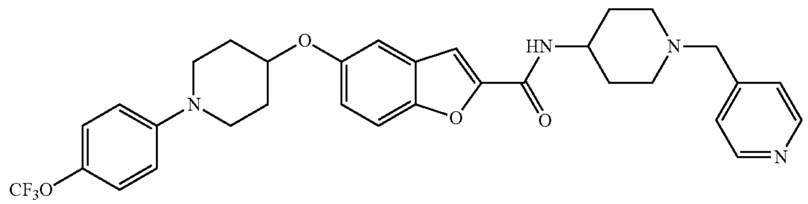 |
| 1-79 | 5-(1-(4-cyanobenzyl)piperidin-4-yloxy)-N-(1-(pyridin-4-ylmethyl)piperidin-4-yl)benzofuran-2-carboxamide | 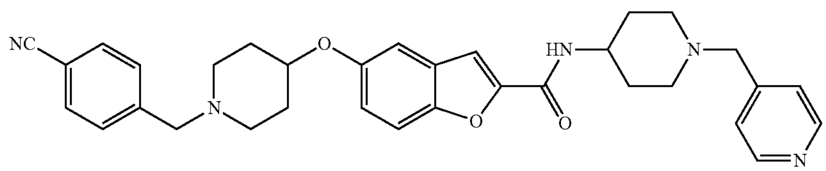 [SMILES: N#Cc1ccc(CN2CCC(Oc3ccc4oc(C(=O)NC5CCN(Cc6ccncc6)CC5)cc4c3)CC2)cc1] |
| 1-80 | N-(1-benzylpiperidin-4-yl)-5-(1-(4-(trifluoromethoxy)phenyl)piperidin-4-yloxy)benzofuran-2-carboxamide | 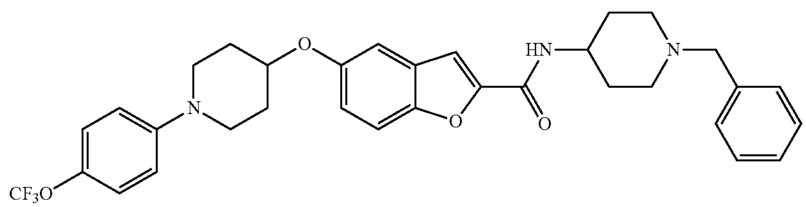 |
| 1-81 | tert-butyl 4-(6-(1-(4-(trifluoromethoxy)phenyl)piperidin-4-yloxy)benzofuran-2-carboxamido)piperidine-1-carboxylate | 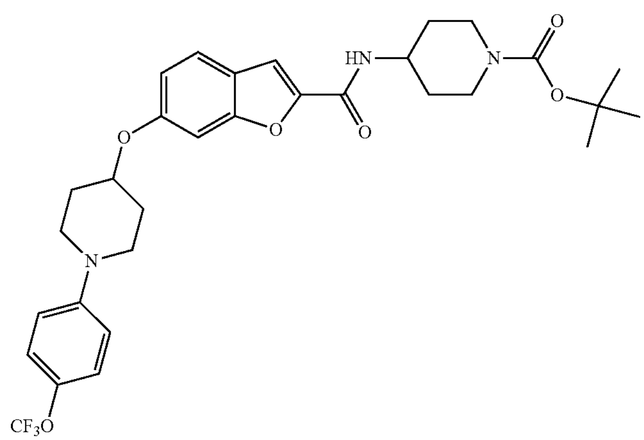 |
| 1-82 | tert-butyl 4-(6-(1-(4-(trifluoromethyl)phenyl)piperidin-4-yloxy)benzofuran-2-carboxamido)piperidine-1-carboxylate | 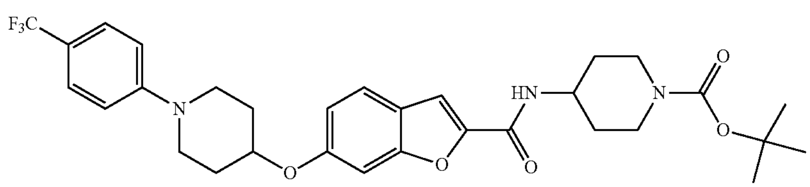 [SMILES: CC(C)(C)OC(=O)N1CCC(NC(=O)c2cc3ccc(OC4CCN(c5ccc(C(F)(F)F)cc5)CC4)cc3o2)CC1] |
| 1-83 | N-(piperidin-4-yl)-6-(1-(4-(trifluoromethoxy)phenyl)piperidin-4-yloxy)benzofuran-2-carboxamide | 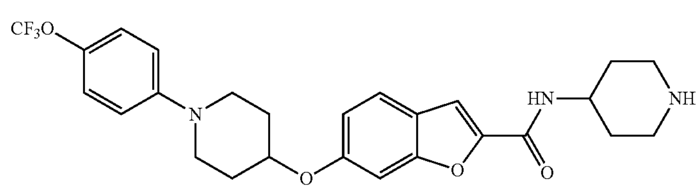 |
| 1-84 | N-(piperidin-4-yl)-6-(1-(4-(trifluoromethyl)phenyl)piperidin-4-yloxy)benzofuran-2-carboxamide | 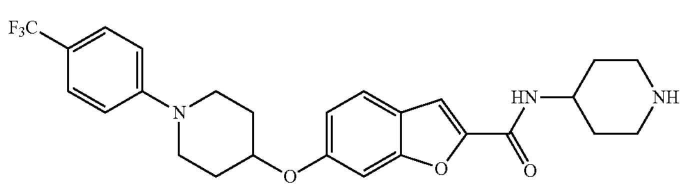 |

TABLE 1-continued

| No. | Name |
|---|---|
| 1-85 | tert-butyl 4-(5-(1-(4-(trifluoromethyl)phenyl)piperidin-4-yloxy)benzofuran-2-carboxamido)piperidine-1-carboxylate |
| 1-86 | N-(piperidin-4-yl)-5-(1-(4-(trifluoromethyl)phenyl)piperidin-4-yloxy)benzofuran-2-carboxamide |
| 1-87 | N-(1-(pyridin-4-ylmethyl)piperidin-4-yl)-6-(1-(4-(trifluoromethyl)phenyl)piperidin-4-yloxy)benzofuran-2-carboxamide |
| 1-88 | N-(1-(pyridin-4-ylmethyl)piperidin-4-yl)-6-(1-(4-(trifluoromethoxy)phenyl)piperidin-4-yloxy)benzofuran-2-carboxamide |
| 1-89 | N-(1-(4-cyanobenzyl)piperidin-4-yl)-6-(1-(4-(trifluoromethoxy)phenyl)piperidin-4-yloxy)benzofuran-2-carboxamide |
| 1-90 | N-(1-(4-cyanobenzyl)piperidin-4-yl)-6-(1-(4-(trifluoromethyl)phenyl)piperidin-4-yloxy)benzofuran-2-carboxamide |

TABLE 1-continued

| No. | Name |
|---|---|
| 1-91 | N-(1-(4-fluorobenzyl)piperidin-4-yl)-6-(1-(4-(trifluoromethyl)phenyl)piperidin-4-yloxy)benzofuran-2-carboxamide |
| 1-92 | N-(1-(pyridin-2-ylmethyl)piperidin-4-yl)-6-(1-(4-(trifluoromethoxy)phenyl)piperidin-4-yloxy)benzofuran-2-carboxamide |
| 1-93 | N-(1-(pyridin-2-ylmethyl)piperidin-4-yl)-6-(1-(4-(trifluoromethyl)phenyl)piperidin-4-yloxy)benzofuran-2-carboxamide |
| 1-94 | N-(1-(4-fluorobenzyl)piperidin-4-yl)-6-(1-(4-(trifluoromethoxy)phenyl)piperidin-4-yloxy)benzofuran-2-carboxamide |
| 1-95 | N-(1-(pyridin-3-ylmethyl)piperidin-4-yl)-6-(1-(4-(trifluoromethoxy)phenyl)piperidin-4-yloxy)benzofuran-2-carboxamide |
| 1-96 | N-(1-(pyridin-3-ylmethyl)piperidin-4-yl)-6-(1-(4-(trifluoromethyl)phenyl)piperidin-4-yloxy)benzofuran-2-carboxamide |
| 1-97 | N-(1-(2-cyanobenzyl)piperidin-4-yl)-6-(1-(4-(trifluoromethoxy)phenyl)piperidin-4-yloxy)benzofuran-2-carboxamide |

TABLE 1-continued

| No. | Name |
|---|---|
| 1-98 | N-(1-(2-cyanobenzyl)piperidin-4-yl)-6-(1-(4-(trifluoromethyl)phenyl)piperidin-4-yloxy)benzofuran-2-carboxamide |
| 1-99 | N-(1-(4-(trifluoromethyl)benzyl)piperidin-4-yl)-6-(1-(4-(trifluoromethyl)phenyl)piperidin-4-yloxy)benzofuran-2-carboxamide |
| 1-100 | N-(1-(4-(trifluoromethyl)benzyl)piperidin-4-yl)-5-(1-(4-(trifluoromethyl)phenyl)piperidin-4-yloxy)benzofuran-2-carboxamide |
| 1-101 | N-(1-(pyridin-3-ylmethyl)piperidin-4-yl)-5-(1-(4-(trifluoromethyl)phenyl)piperidin-4-yloxy)benzofuran-2-carboxamide |
| 1-102 | tert-butyl 4-(N-methyl-5-(1-(4-(trifluoromethyl)phenyl)piperidin-4-yloxy)benzofuran-2-carboxamido)piperidine-1-carboxylate |
| 1-103 | N-methyl-N-(piperidin-4-yl)-5-(1-(4-(trifluoromethyl)phenyl)piperidin-4-yloxy)benzofuran-2-carboxamide |

TABLE 1-continued

| No. | Name | Structure |
|---|---|---|
| 1-104 | N-methyl-N-(1-(pyridin-4-ylmethyl)piperidin-4-yl)-5-(1-(4-(trifluoromethyl)phenyl)piperidin-4-yloxy)benzofuran-2-carboxamide | 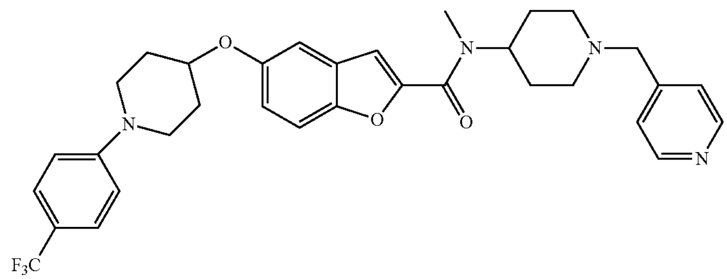 |
| 1-105 | N-(1-(pyridin-4-ylmethyl)piperidin-4-yl)-5-(1-(4-(trifluoromethyl)phenyl)piperidin-4-yloxy)benzofuran-2-carboxamide, formate salt | ·HC(O)OH |
| 1-106 | N-(1-(pyridin-3-ylsulfonyl)piperidin-4-yl)-6-(1-(4-(trifluoromethyl)phenyl)piperidin-4-yloxy)benzofuran-2-carboxamide | 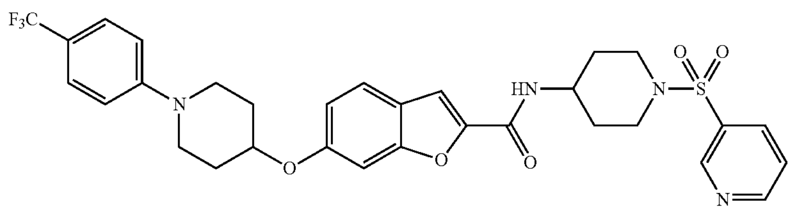 [SMILES: O=C(NC1CCN(S(=O)(=O)c2cccnc2)CC1)c1cc2ccc(OC3CCN(c4ccc(C(F)(F)F)cc4)CC3)cc2o1] |
| 1-107 | N-(1-(4-cyanobenzyl)piperidin-4-yl)-N-methyl-5-(1-(4-(trifluoromethyl)phenyl)piperidin-4-yloxy)benzofuran-2-carboxamide | 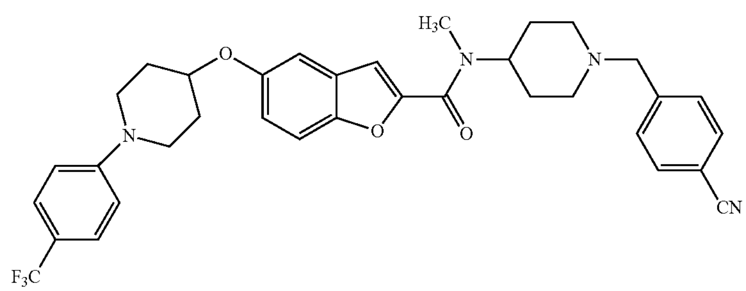 [SMILES: CN(C(=O)c1cc2cc(OC3CCN(c4ccc(C(F)(F)F)cc4)CC3)ccc2o1)C1CCN(Cc2ccc(C#N)cc2)CC1] |
| 1-108 | N-(1-(pyridin-3-ylsulfonyl)piperidin-4-yl)-6-(1-(4-(trifluoromethoxy)phenyl)piperidin-4-yloxy)benzofuran-2-carboxamide | 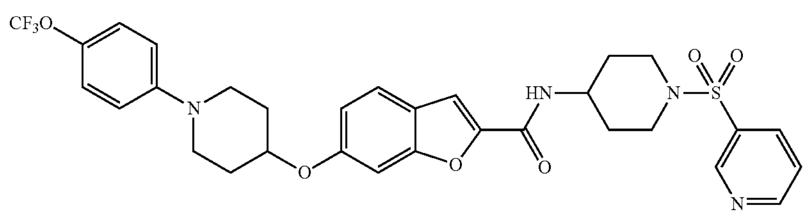 |
| 1-109 | N-methyl-N-(1-(pyridin-3-ylmethyl)piperidin-4-yl)-5-(1-(4-(trifluoromethyl)phenyl)piperidin-4-yloxy)benzofuran-2-carboxamide | 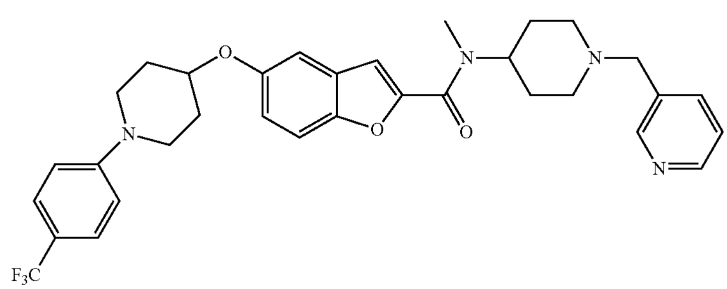 [SMILES: CN(C(=O)c1cc2cc(OC3CCN(c4ccc(C(F)(F)F)cc4)CC3)ccc2o1)C1CCN(Cc2cccnc2)CC1] |

TABLE 1-continued

| No. | Name | Structure |
|---|---|---|
| 1-110 | N-(1-(3-cyanobenzyl)piperidin-4-yl)-N-methyl-5-(1-(4-(trifluoromethyl)phenyl)piperidin-4-yloxy)benzofuran-2-carboxamide | 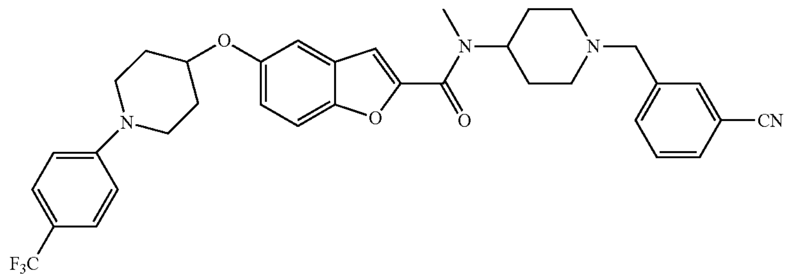 [SMILES: CN(C(=O)c1cc2cc(OC3CCN(c4ccc(C(F)(F)F)cc4)CC3)ccc2o1)C1CCN(Cc2cccc(C#N)c2)CC1] |
| 1-111 | N-(1-(2-cyanobenzyl)piperidin-4-yl)-N-methyl-5-(1-(4-(trifluoromethyl)phenyl)piperidin-4-yloxy)benzofuran-2-carboxamide | 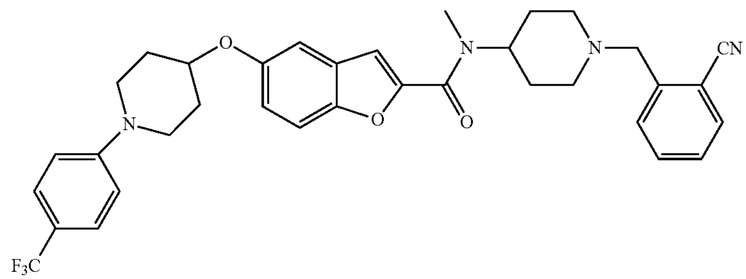 [SMILES: CN(C(=O)c1cc2cc(OC3CCN(c4ccc(C(F)(F)F)cc4)CC3)ccc2o1)C1CCN(Cc2ccccc2C#N)CC1] |
| 1-112 | N-(1-isonicotinoylpiperidin-4-yl)-6-(1-(4-(trifluoromethyl)phenyl)piperidin-4-yloxy)benzofuran-2-carboxamide | 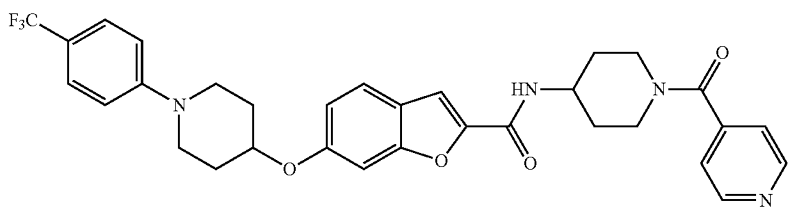 [SMILES: O=C(NC1CCN(C(=O)c2ccncc2)CC1)c1cc2ccc(OC3CCN(c4ccc(C(F)(F)F)cc4)CC3)cc2o1] |
| 1-113 | tert-butyl 4-(5-(1-(4-cyanobenzyl)piperidin-4-yloxy)benzofuran-2-carboxamido)piperidine-1-carboxylate | 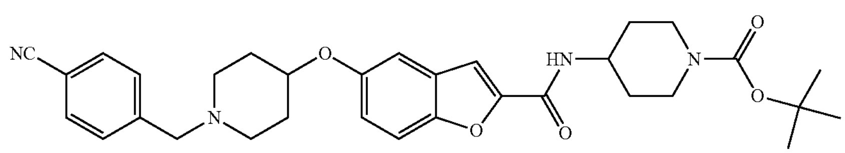 [SMILES: CC(C)(C)OC(=O)N1CCC(NC(=O)c2cc3cc(OC4CCN(Cc5ccc(C#N)cc5)CC4)ccc3o2)CC1] |
| 1-114 | N-(1-benzylpiperidin-4-yl)-5-(1-(4-cyanobenzyl)piperidin-4-yloxy)benzofuran-2-carboxamide | 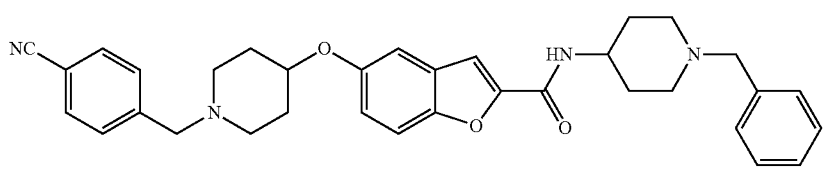 [SMILES: N#Cc1ccc(CN2CCC(Oc3ccc4oc(C(=O)NC5CCN(Cc6ccccc6)CC5)cc4c3)CC2)cc1] |
| 1-115 | N-(1-isonicotinoylpiperidin-4-yl)-5-(1-(4-(trifluoromethyl)phenyl)piperidin-4-yloxy)benzofuran-2-carboxamide | 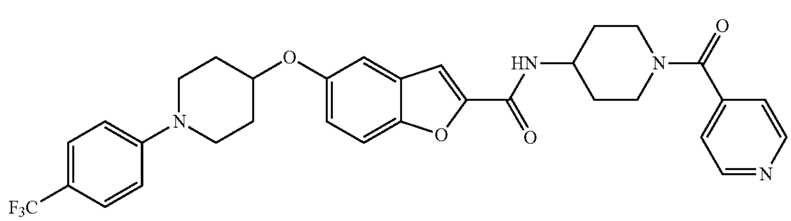 [SMILES: O=C(NC1CCN(C(=O)c2ccncc2)CC1)c1cc2cc(OC3CCN(c4ccc(C(F)(F)F)cc4)CC3)ccc2o1] |
| 1-116 | N-(1-benzylpiperidin-4-yl)-5-(1-(4-carbamoylbenzyl)piperidin-4-yloxy)benzofuran-2-carboxamide | 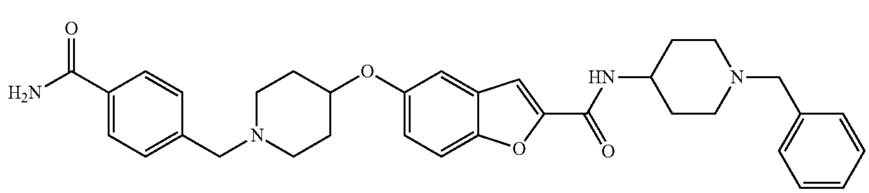 [SMILES: NC(=O)c1ccc(CN2CCC(Oc3ccc4oc(C(=O)NC5CCN(Cc6ccccc6)CC5)cc4c3)CC2)cc1] |

TABLE 1-continued

| No. | Name | Structure |
|---|---|---|
| 1-117 | N-methyl-N-(1-(pyridin-2-ylmethyl)piperidin-4-yl)-5-(1-(4-(trifluoromethyl)phenyl)piperidin-4-yloxy)benzofuran-2-carboxamide | 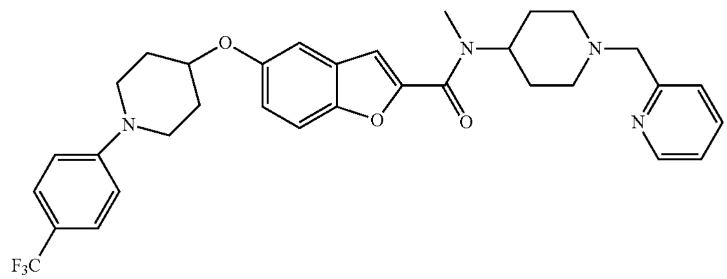 |
| 1-118 | N-(1-isonicotinoylpiperidin-4-yl)-N-methyl-5-(1-(4-(trifluoromethyl)phenyl)piperidin-4-yloxy)benzofuran-2-carboxamide | 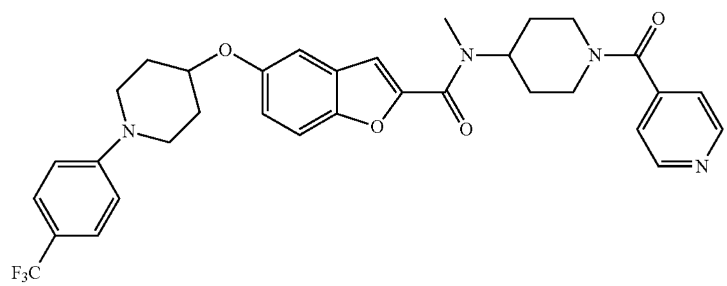 [SMILES: CN(C(=O)c1cc2cc(OC3CCN(c4ccc(C(F)(F)F)cc4)CC3)ccc2o1)C1CCN(C(=O)c2ccncc2)CC1] |
| 1-119 | N-methyl-N-(1-(4-(trifluoromethyl)benzyl)piperidin-4-yl)-5-(1-(4-(trifluoromethyl)phenyl)piperidin-4-yloxy)benzofuran-2-carboxamide | 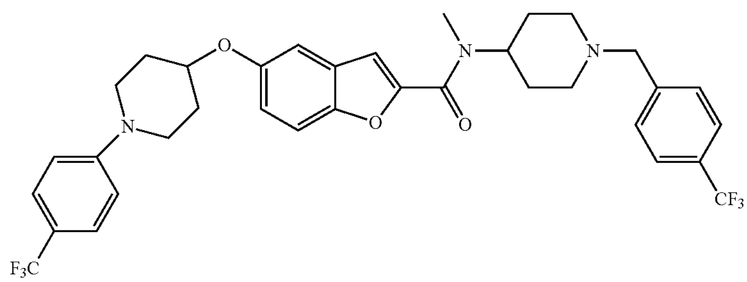 [SMILES: CN(C(=O)c1cc2cc(OC3CCN(c4ccc(C(F)(F)F)cc4)CC3)ccc2o1)C1CCN(Cc2ccc(C(F)(F)F)cc2)CC1] |
| 1-120 | (R)-tert-butyl 3-(5-(1-(4-(trifluoromethyl)phenyl)piperidin-4-yloxy)benzofuran-2-carboxamido)pyrrolidine-1-carboxylate | 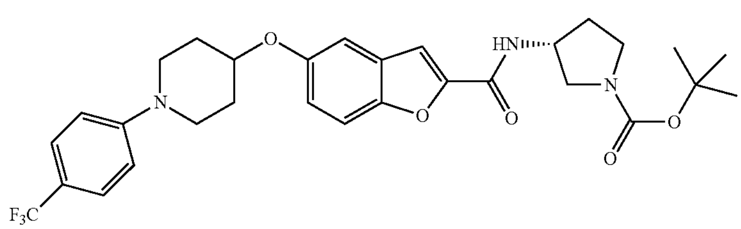 [SMILES: CC(C)(C)OC(=O)N1CC[C@@H](NC(=O)c2cc3cc(OC4CCN(c5ccc(C(F)(F)F)cc5)CC4)ccc3o2)C1] |
| 1-121 | (R)-N-(pyrrolidin-3-yl)-5-(1-(4-(trifluoromethyl)phenyl)piperidin-4-yloxy)benzofuran-2-carboxamide | 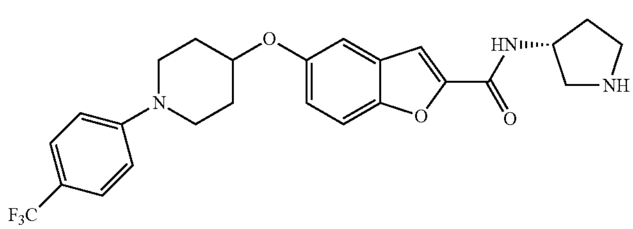 [SMILES: O=C(N[C@@H]1CCNC1)c1cc2cc(OC3CCN(c4ccc(C(F)(F)F)cc4)CC3)ccc2o1] |
| 1-122 | (R)-N-(1-(pyridin-4-ylmethyl)pyrrolidin-3-yl)-5-(1-(4-(trifluoromethyl)phenyl)piperidin-4-yloxy)benzofuran-2-carboxamide | 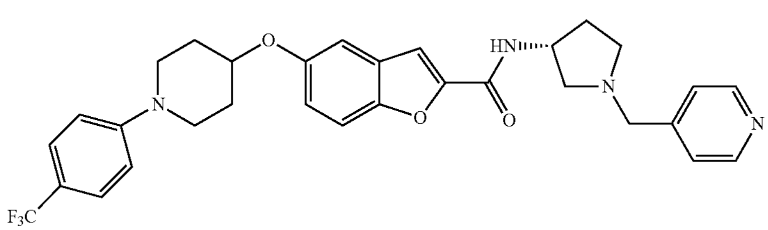 [SMILES: O=C(N[C@@H]1CCN(Cc2ccncc2)C1)c1cc2cc(OC3CCN(c4ccc(C(F)(F)F)cc4)CC3)ccc2o1] |

TABLE 1-continued

| No. | Name |
|---|---|
| 1-123 | (R)-N-(1-(pyridin-3-ylmethyl)pyrrolidin-3-yl)-5-(1-(4-(trifluoromethyl)phenyl)piperidin-4-yloxy)benzofuran-2-carboxamide |
| 1-124 | (R)-N-(1-(pyridin-2-ylmethyl)pyrrolidin-3-yl)-5-(1-(4-(trifluoromethyl)phenyl)piperidin-4-yloxy)benzofuran-2-carboxamide |
| 1-125 | (R)-N-(1-isonicotinoylpyrrolidin-3-yl)-5-(1-(4-(trifluoromethyl)phenyl)piperidin-4-yloxy)benzofuran-2-carboxamide |
| 1-126 | (R)-N-(1-(pyridin-3-ylsulfonyl)pyrrolidin-3-yl)-5-(1-(4-(trifluoromethyl)phenyl)piperidin-4-yloxy)benzofuran-2-carboxamide |
| 1-127 | (S)-tert-butyl 3-(5-(1-(4-chlorobenzyl)piperidin-4-yloxy)benzofuran-2-carboxamido)pyrrolidine-1-carboxylate |
| 1-128 | (S)-5-(1-(4-chlorobenzyl)piperidin-4-yloxy)-N-(pyrrolidin-3-yl)benzofuran-2-carboxamide |
| 1-129 | (S)-5-(1-(4-chlorobenzyl)piperidin-4-yloxy)-N-(1-(pyridin-4-ylmethyl)pyrrolidin-3-yl)benzofuran-2-carboxamide |
| 1-130 | (S)-5-(1-(4-chlorobenzyl)piperidin-4-yloxy)-N-(1-(pyridin-3-ylmethyl)pyrrolidin-3-yl)benzofuran-2-carboxamide |

TABLE 1-continued

| No. | Name | Structure |
|---|---|---|
| 1-131 | 5-(1-(4-carbamoylbenzyl)piperidin-4-yloxy)-N-(1-(pyridin-4-ylmethyl)piperidin-4-yl)benzofuran-2-carboxamide | 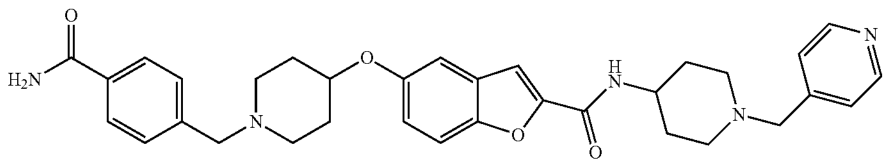 [SMILES: NC(=O)c1ccc(CN2CCC(Oc3ccc4oc(C(=O)NC5CCN(Cc6ccncc6)CC5)cc4c3)CC2)cc1] |
| 1-132 | 5-(1-(4-carbamoylbenzyl)piperidin-4-yloxy)-N-(1-isonicotinoylpiperidin-4-yl)benzofuran-2-carboxamide | 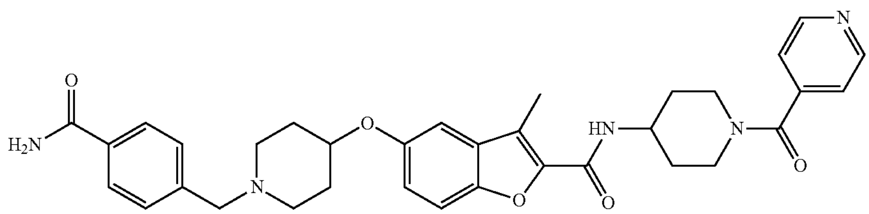 [SMILES: Cc1c(C(=O)NC2CCN(C(=O)c3ccncc3)CC2)oc2ccc(OC3CCN(Cc4ccc(C(N)=O)cc4)CC3)cc12] |
| 1-133 | 5-(1-(4-carbamoylbenzyl)piperidin-4-yloxy)-N-(1-(4-cyanobenzyl)piperidin-4-yl)benzofuran-2-carboxamide | 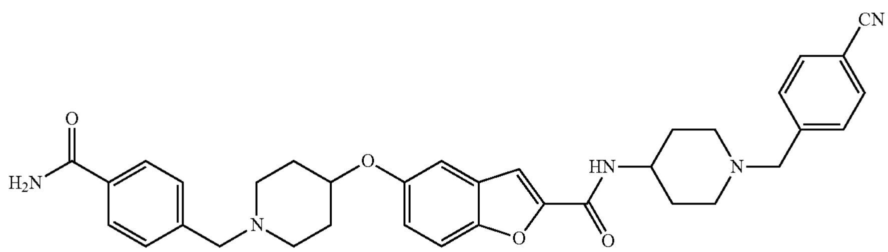 [SMILES: N#Cc1ccc(CN2CCC(NC(=O)c3cc4cc(OC5CCN(Cc6ccc(C(N)=O)cc6)CC5)ccc4o3)CC2)cc1] |
| 1-134 | 5-(1-(4-carbamoylphenyl)piperidin-4-yloxy)-N-(1-(pyridin-4-ylmethyl)piperidin-4-yl)benzofuran-2-carboxamide | 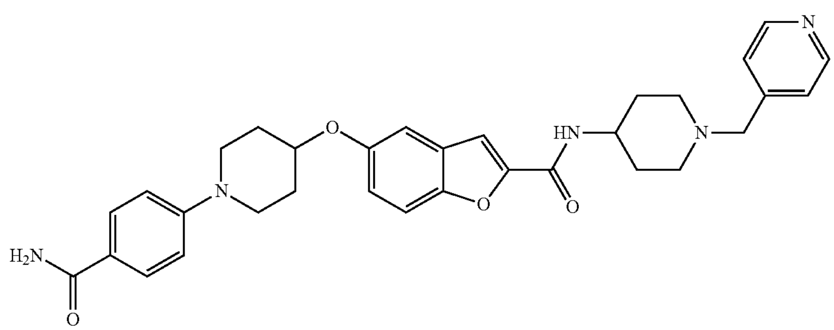 [SMILES: NC(=O)c1ccc(N2CCC(Oc3ccc4oc(C(=O)NC5CCN(Cc6ccncc6)CC5)cc4c3)CC2)cc1] |
| 1-135 | 5-(1-(4-carbamoylphenyl)piperidin-4-yloxy)-N-(1-isonicotinoylpiperidin-4-yl)benzofuran-2-carboxamide | 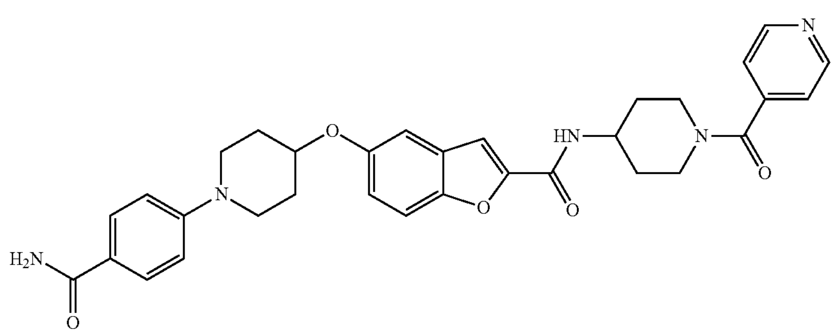 [SMILES: NC(=O)c1ccc(N2CCC(Oc3ccc4oc(C(=O)NC5CCN(C(=O)c6ccncc6)CC5)cc4c3)CC2)cc1] |

TABLE 1-continued

| No. | Name |
|---|---|
| 1-136 | 5-(1-(4-carbamoylphenyl)piperidin-4-yloxy)-N-(1-(4-cyanobenzyl)piperidin-4-yl)benzofuran-2-carboxamide |
| 1-137 | N-(1-(pyridin-4-ylmethyl)piperidin-4-yl)-5-(1-(4-(trifluoromethoxy)phenyl)piperidin-4-yloxy)benzo[b]thiophene-2-carboxamide |
| 1-138 | N-(1-(pyridin-4-ylmethyl)piperidin-4-yl)-5-(1-(4-(trifluoromethyl)phenyl)piperidin-4-yloxy)benzo[b]thiophene-2-carboxamide |
| 1-139 | N-(1-(pyridin-4-ylmethyl)piperidin-4-yl)-5-(1-(4-chlorophenyl)piperidin-4-yloxy)benzo[b]thiophene-2-carboxamide |
| 1-140 | tert-butyl 4-(6-(1-(4-(trifluoromethyl)phenyl)piperidin-4-yloxy)benzo[b]thiophene-2-carboxamido)piperidine-1-carboxylate |
| 1-141 | N-(piperidin-4-yl)-6-(1-(4-(trifluoromethyl)phenyl)piperidin-4-yloxy)benzo[b]thiophene-2-carboxamide |
| 1-142 | N-(1-(pyridin-4-ylmethyl)piperidin-4-yl)-6-(1-(4-(trifluoromethyl)phenyl)piperidin-4-yloxy)benzo[b]thiophene-2-carboxamide |

TABLE 1-continued

| No. | Name | Structure |
|---|---|---|
| 1-143 | N-(1-(pyridin-2-ylmethyl)piperidin-4-yl)-6-(1-(4-(trifluoromethyl)phenyl)piperidin-4-yloxy)benzo[b]thiophene-2-carboxamide | 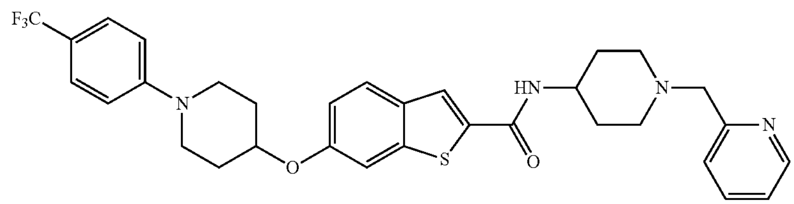 [SMILES: O=C(NC1CCN(Cc2ccccn2)CC1)c1cc2ccc(OC3CCN(c4ccc(C(F)(F)F)cc4)CC3)cc2s1] |
| 1-144 | N-(1-(4-cyanobenzyl)piperidin-4-yl)-6-(1-(4-(trifluoromethyl)phenyl)piperidin-4-yloxy)benzo[b]thiophene-2-carboxamide | 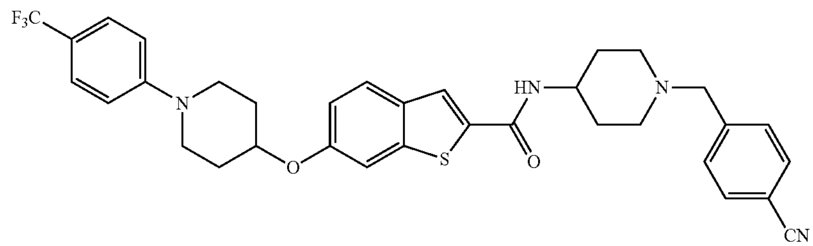 [SMILES: N#Cc1ccc(CN2CCC(NC(=O)c3cc4ccc(OC5CCN(c6ccc(C(F)(F)F)cc6)CC5)cc4s3)CC2)cc1] |
| 1-145 | N-(1-(3-cyanobenzyl)piperidin-4-yl)-6-(1-(4-(trifluoromethyl)phenyl)piperidin-4-yloxy)benzo[b]thiophene-2-carboxamide | 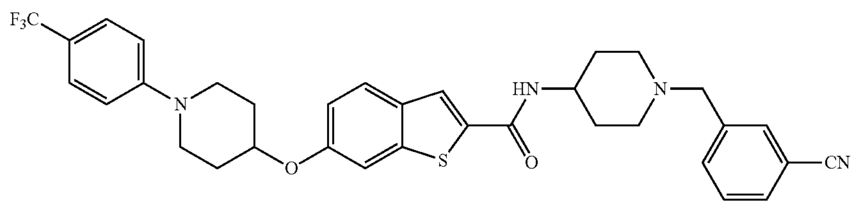 [SMILES: N#Cc1cccc(CN2CCC(NC(=O)c3cc4ccc(OC5CCN(c6ccc(C(F)(F)F)cc6)CC5)cc4s3)CC2)c1] |
| 1-146 | N-(1-(2-cyanobenzyl)piperidin-4-yl)-6-(1-(4-(trifluoromethyl)phenyl)piperidin-4-yloxy)benzo[b]thiophene-2-carboxamide | 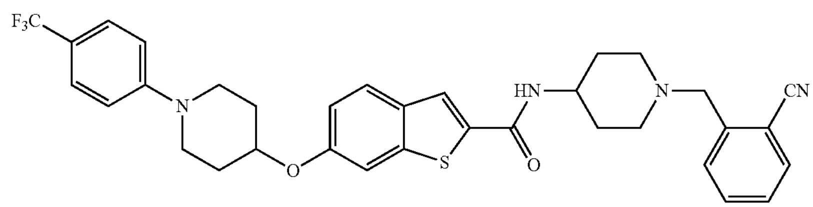 [SMILES: N#Cc1ccccc1CN1CCC(NC(=O)c2cc3ccc(OC4CCN(c5ccc(C(F)(F)F)cc5)CC4)cc3s2)CC1] |
| 1-147 | tert-butyl 4-(3-chloro-6-(1-(4-(trifluoromethyl)phenyl)piperidin-4-yloxy)benzo[b]thiophene-2-carboxamido)piperidine-1-carboxylate | 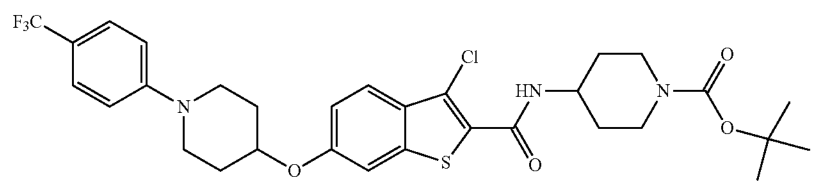 |
| 1-148 | 3-chloro-N-(piperidin-4-yl)-6-(1-(4-(trifluoromethyl)phenyl)piperidin-4-yloxy)benzo[b]thiophene-2-carboxamide | 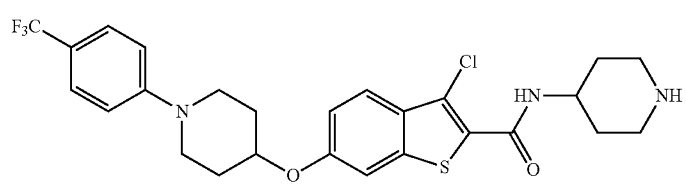 [SMILES: O=C(NC1CCNCC1)c1sc2cc(OC3CCN(c4ccc(C(F)(F)F)cc4)CC3)ccc2c1Cl] |
| 1-149 | tert-butyl 4-(5-(1-(4-(trifluoromethyl)phenyl)piperidin-4-yloxy)benzo[b]thiophene-2-carboxamido)piperidine-1-carboxylate | 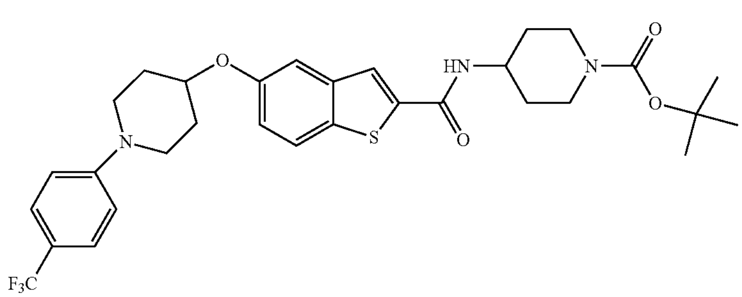 [SMILES: CC(C)(C)OC(=O)N1CCC(NC(=O)c2cc3cc(OC4CCN(c5ccc(C(F)(F)F)cc5)CC4)ccc3s2)CC1] |

TABLE 1-continued

| No. | Name |
|---|---|
| 1-150 | N-(piperidin-4-yl)-5-(1-(4-(trifluoromethyl)phenyl)piperidin-4-yloxy)benzo[b]thiophene-2-carboxamide |
| 1-151 | 3-chloro-N-(1-(pyridin-4-ylmethyl)piperidin-4-yl)-6-(1-(4-(trifluoromethyl)phenyl)piperidin-4-yloxy)benzo[b]thiophene-2-carboxamide |
| 1-152 | 3-chloro-N-(1-(pyridin-3-ylmethyl)piperidin-4-yl)-6-(1-(4-(trifluoromethyl)phenyl)piperidin-4-yloxy)benzo[b]thiophene-2-carboxamide |
| 1-153 | 3-chloro-N-(1-(pyridin-2-ylmethyl)piperidin-4-yl)-6-(1-(4-(trifluoromethyl)phenyl)piperidin-4-yloxy)benzo[b]thiophene-2-carboxamide |
| 1-154 | 3-chloro-N-(1-(4-cyanobenzyl)piperidin-4-yl)-6-(1-(4-(trifluoromethyl)phenyl)piperidin-4-yloxy)benzo[b]thiophene-2-carboxamide |
| 1-155 | 3-chloro-N-(1-isonicotinoylpiperidin-4-yl)-6-(1-(4-(trifluoromethyl)phenyl)piperidin-4-yloxy)benzo[b]thiophene-2-carboxamide |

TABLE 1-continued

| No. | Name | Structure |
|---|---|---|
| 1-156 | tert-butyl 4-(5-(1-(4-(trifluoromethyl)phenyl)piperidin-4-yloxy)-2,3-dihydro-1H-inden-1-ylamino)piperidine-1-carboxylate | 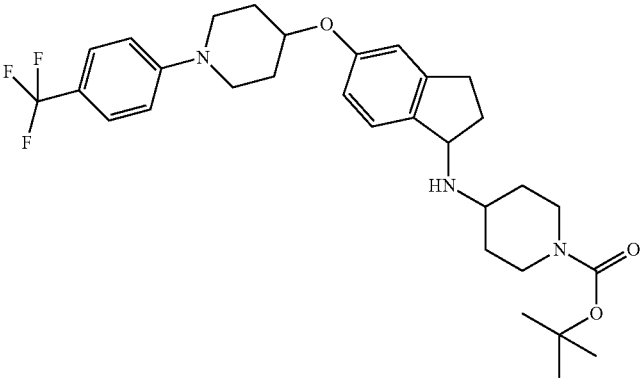 [SMILES: CC(C)(C)OC(=O)N1CCC(NC2CCc3cc(OC4CCN(c5ccc(C(F)(F)F)cc5)CC4)ccc32)CC1] |
| 1-157 | N-(5-(1-(4-(trifluoromethyl)phenyl)piperidin-4-yloxy)-2,3-dihydro-1H-inden-1-yl)piperidin-4-amine | 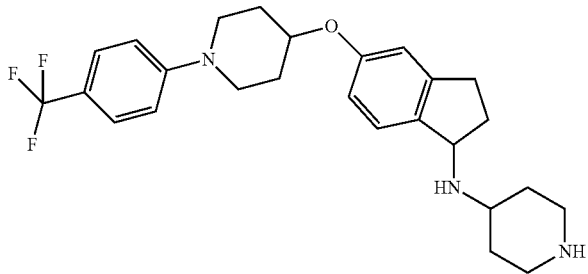 [SMILES: FC(F)(F)c1ccc(N2CCC(Oc3ccc4c(c3)CCC4NC3CCNCC3)CC2)cc1] |
| 1-158 | 1-(pyridin-4-ylmethyl)-N-(5-(1-(4-(trifluoromethyl)phenyl)piperidin-4-yloxy)-2,3-dihydro-1H-inden-1-yl)piperidin-4-amine | 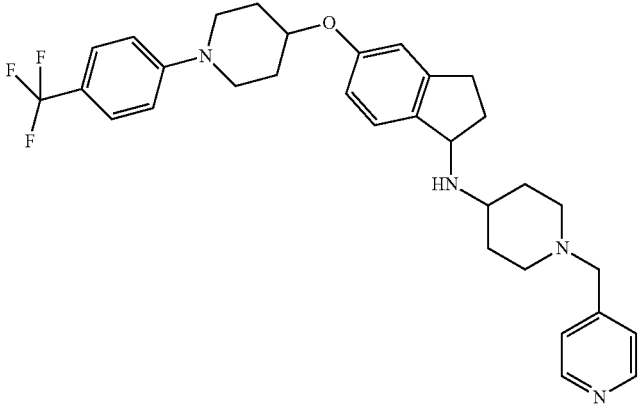 [SMILES: FC(F)(F)c1ccc(N2CCC(Oc3ccc4c(c3)CCC4NC3CCN(Cc4ccncc4)CC3)CC2)cc1] |
| 1-159 | 1-(4-fluorobenzyl)-N-(5-(1-(4-(trifluoromethyl)phenyl)piperidin-4-yloxy)-2,3-dihydro-1H-inden-1-yl)piperidin-4-amine | 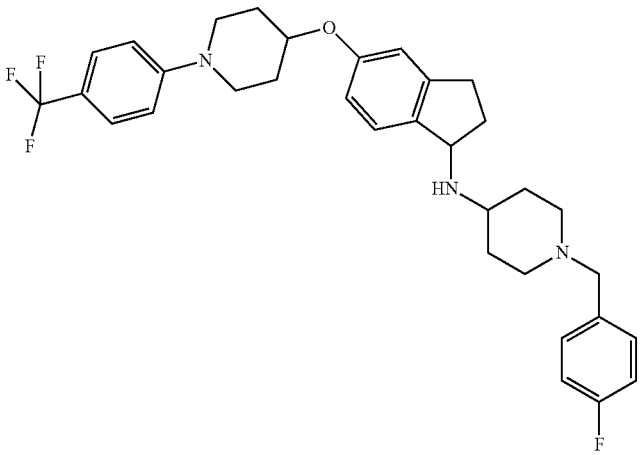 [SMILES: Fc1ccc(CN2CCC(NC3CCc4cc(OC5CCN(c6ccc(C(F)(F)F)cc6)CC5)ccc43)CC2)cc1] |

TABLE 1-continued

| No. | Name |
|---|---|
| 1-160 | 4-((4-(5-(1-(4-(trifluoromethyl)phenyl)piperidin-4-yloxy)-2,3-dihydro-1H-inden-1-ylamino)piperidin-1-yl)methyl)benzonitrile |
| 1-161 | N-(1-(4-cyanobenzyl)piperidin-4-yl)-6-(1-((1-(4-cyanophenyl)-1H-pyrazol-4-yl)methyl)piperidin-4-yloxy)benzofuran-2-carboxamide |
| 1-162 | N-(1-(4-cyanobenzyl)piperidin-4-yl)-5-(1-((1-(4-cyanophenyl)-1H-pyrazol-4-yl)methyl)piperidin-4-yloxy)benzofuran-2-carboxamide |
| 1-163 | 5-(1-(4-(1H-pyrazol-1-yl)benzoyl)piperidin-4-yloxy)-N-(1-(4-cyanobenzyl)piperidin-4-yl)benzofuran-2-carboxamide |
| 1-164 | 5-((3,4-trans)-1-(4-(1H-pyrazol-1-yl)benzyl)-3-fluoropiperidin-4-yloxy)-N-(1-(4-cyanobenzyl)piperidin-4-yl)benzofuran-2-carboxamide |
| 1-165 | N-(1-(4-cyanobenzyl)piperidin-4-yl)-5-((3,4-trans)-3-fluoro-1-(4-(4-fluorophenoxy)benzyl)piperidin-4-yloxy)benzofuran-2-carboxamide |

TABLE 1-continued

| No. | Name | Structure |
|---|---|---|
| 1-166 | N-(1-(4-cyanobenzyl)piperidin-4-yl)-5-((3,4-trans)-1-((1-(4-cyanophenyl)-1H-pyrazol-4-yl)methyl)-3-fluoropiperidin-4-yloxy)benzofuran-2-carboxamide | 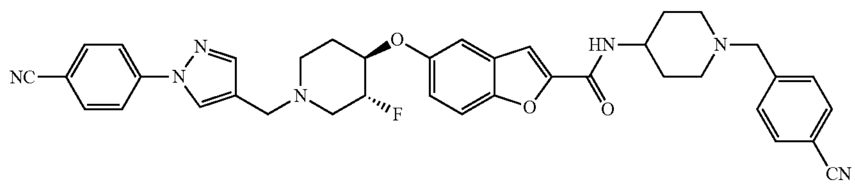 [SMILES: N#Cc1ccc(CN2CCC(NC(=O)c3cc4cc(O[C@@H]5CCN(Cc6cnn(-c7ccc(C#N)cc7)c6)C[C@H]5F)ccc4o3)CC2)cc1] |
| 1-167 | N-(1-(4-cyanobenzyl)piperidin-4-yl)-5-((3,4-trans)-3-fluoro-1-(4-(methylsulfonyl)benzyl)piperidin-4-yloxy)benzofuran-2-carboxamide | 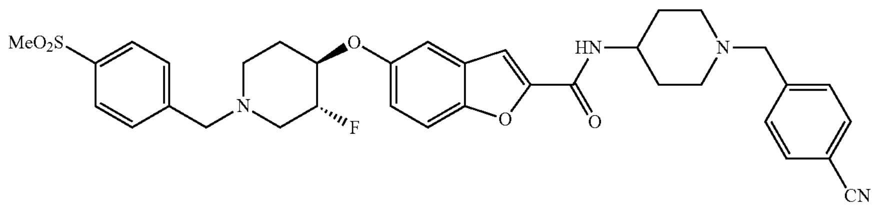 [SMILES: CS(=O)(=O)c1ccc(CN2CC[C@@H](Oc3ccc4oc(C(=O)NC5CCN(Cc6ccc(C#N)cc6)CC5)cc4c3)[C@H](F)C2)cc1] |
| 1-168 | N-(1-(4-cyanobenzyl)piperidin-4-yl)-5-((3,4-trans)-3-fluoro-1-(4-(trifluoromethoxy)benzyl)piperidin-4-yloxy)benzofuran-2-carboxamide | 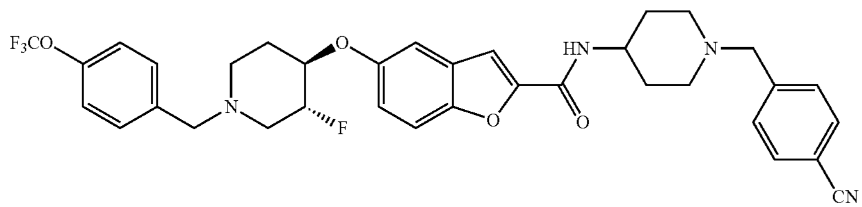 [SMILES: N#Cc1ccc(CN2CCC(NC(=O)c3cc4cc(O[C@@H]5CCN(Cc6ccc(OC(F)(F)F)cc6)C[C@H]5F)ccc4o3)CC2)cc1] |
| 1-169 | 5-((3,4-trans)-1-(4-(1H-pyrazol-1-yl)benzyl)-3-fluoropiperidin-4-yloxy)-N-(1-(4-(trifluoromethoxy)benzyl)piperidin-4-yl)benzofuran-2-carboxamide | 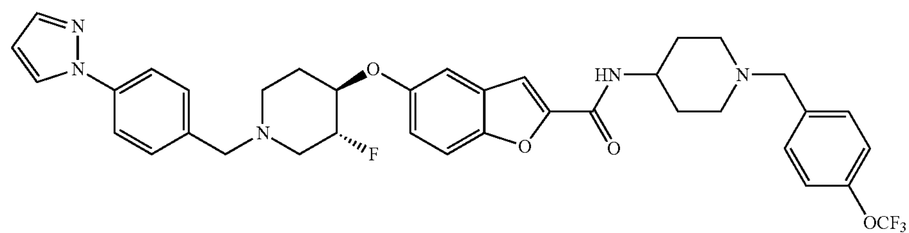 [SMILES: O=C(NC1CCN(Cc2ccc(OC(F)(F)F)cc2)CC1)c1cc2cc(O[C@@H]3CCN(Cc4ccc(-n5cccn5)cc4)C[C@H]3F)ccc2o1] |
| 1-170 | 5-((3,4-trans)-3-fluoro-1-(4-(4-fluorophenoxy)benzyl)piperidin-4-yloxy)-N-(1-(4-(trifluoromethoxy)benzyl)piperidin-4-yl)benzofuran-2-carboxamide | 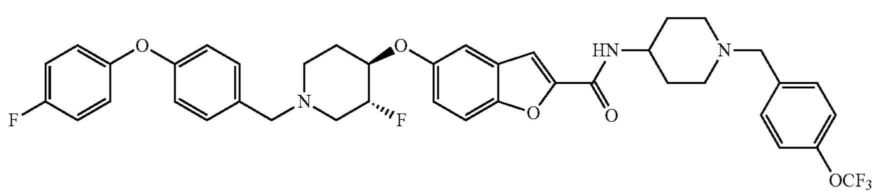 [SMILES: O=C(NC1CCN(Cc2ccc(OC(F)(F)F)cc2)CC1)c1cc2cc(O[C@@H]3CCN(Cc4ccc(Oc5ccc(F)cc5)cc4)C[C@H]3F)ccc2o1] |
| 1-171 | 5-((3,4-trans)-1-((1-(4-cyanophenyl)-1H-pyrazol-4-yl)methyl)-3-fluoropiperidin-4-yloxy)-N-(1-(4-(trifluoromethoxy)benzyl)piperidin-4-yl)benzofuran-2-carboxamide | 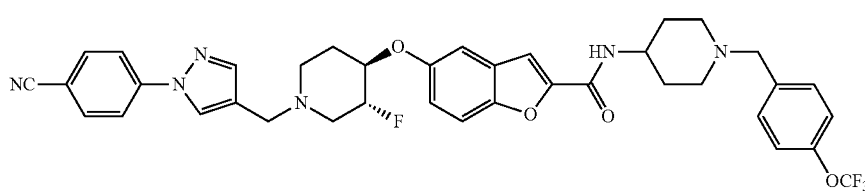 [SMILES: N#Cc1ccc(-n2cc(CN3CC[C@@H](Oc4ccc5oc(C(=O)NC6CCN(Cc7ccc(OC(F)(F)F)cc7)CC6)cc5c4)[C@H](F)C3)cn2)cc1] |
| 1-172 | 5-((3,4-trans)-3-fluoro-1-(4-(methylsulfonyl)benzyl)piperidin-4-yloxy)-N-(1-(4-(trifluoromethoxy)benzyl)piperidin-4-yl)benzofuran-2-carboxamide | 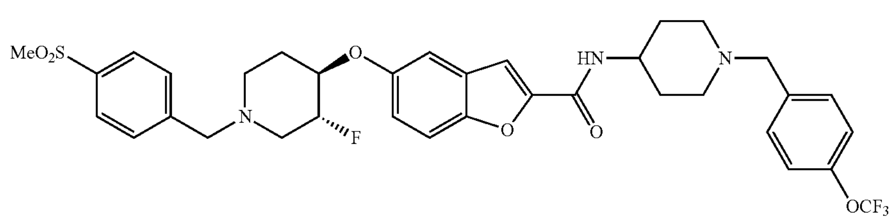 [SMILES: CS(=O)(=O)c1ccc(CN2CC[C@@H](Oc3ccc4oc(C(=O)NC5CCN(Cc6ccc(OC(F)(F)F)cc6)CC5)cc4c3)[C@H](F)C2)cc1] |

TABLE 1-continued

| No. | Name |
|---|---|
| 1-173 | 5-((3,4-trans)-3-fluoro-1-(4-(trifluoromethoxy)benzyl)piperidin-4-yloxy)-N-(1-(4-(trifluoromethoxy)benzyl)piperidin-4-yl)benzofuran-2-carboxamide |
| 1-174 | N-(1-(4-cyanobenzyl)piperidin-4-yl)-5-(1-(4-(trifluoromethyl)benzyl)piperidin-4-yloxy)benzofuran-2-carboxamide |
| 1-175 | N-(1-(4-cyanobenzyl)piperidin-4-yl)-5-(1-(4-(methylsulfonyl)benzyl)piperidin-4-yloxy)benzofuran-2-carboxamide |

Another aspect of the disclosure provides compounds having structural formula (2-I):

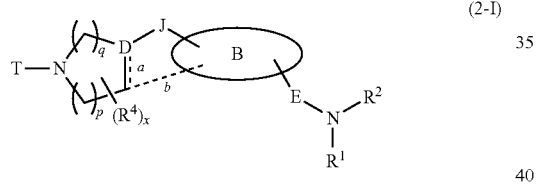

(2-I)

and pharmaceutically acceptable salts, and N-oxides thereof (and solvates and hydrates thereof), wherein "B" represents -(aryl or heteroaryl)- substituted by w $R^3$ and k $R^{14}$;

the dotted line denoted by "b" is absent, a single bond or a double bond;

the dotted line denoted by "a" is a bond or absent, provided that if the dotted line denoted by "b" is a double bond, then the dotted line denoted by "a" is absent;

D is a carbon or N when the dotted line denoted by "a" is absent, and a carbon when the dotted line denoted by "a" is a bond;

J is —O—, —N($R^{38}$)—, —CH$_2$—, —CH($R^{26}$)— or —C($R^{26}$)$_2$—;

E is —C(O)—, —S(O)$_2$— or a single bond, provided that when "B" is phenyl, J is —O— and D is a carbon, E is not —C(O)—;

$R^1$ is H, —(C$_1$-C$_4$ alkyl), —C(O)—(C$_1$-C$_4$ alkyl) or —C(O)O—(C$_1$-C$_4$ alkyl);

$R^2$ is -Hca, -Cak-N($R^9$)-G-$R^{22}$ or —(C$_2$-C$_8$ alkyl)-N($R^9$)—$R^{24}$ in which one or two carbons of the (C$_2$-C$_8$ alkyl) are optionally replaced by —O—, —S— or —N($R^9$)— and $R^{24}$ is —$R^{23}$, -G-$R^{23}$, or —C(O)O—(C$_1$-C$_6$ alkyl), provided that two consecutive carbons of the (C$_2$-C$_8$ alkyl) are not replaced by —O—;

each $R^3$ is substituted on a benzo, pyrido or pyrazino carbon of the ring system denoted by "B" and is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN;

w is 0, 1, 2 or 3;

each $R^{14}$ is substituted on a non-benzo, non-pyrido, non-pyrazino carbon of the ring system denoted by "B", and is independently selected from —(C$_1$-C$_6$ alkyl), —(C$_1$-C$_6$ halooalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN;

k is 0, 1 or 2;

each $R^4$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two $R^4$ on the same carbon optionally combine to form oxo;

x is 0, 1, 2, 3 or 4;

p is 0, 1, 2, 3 or 4;

q is 0, 1, 2, 3 or 4;

the sum of p and q is 1, 2, 3 or 4;

T is —(C$_0$-C$_6$ alkyl)-L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$ or

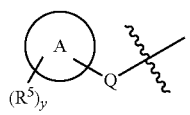

in which
Q is —S(O)$_2$—, L or —(C$_0$-C$_3$ alkyl)-, in which each carbon of the —(C$_0$-C$_3$ alkyl)- is optionally and independently substituted with one or two R$^{16}$;
the ring system denoted by "A" is heteroaryl, aryl, cycloalkyl or heterocycloalkyl;
each R$^5$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, —(C$_0$-C$_6$ alkyl)-C(O)R$^{10}$, -halogen, —NO$_2$ and —CN; and
y is 0, 1, 2, 3 or 4;
in which
each L is independently selected from —NR$^9$C(O)O—, —OC(O)NR$^9$—, —NR$^9$C(O)—NR$^9$—, —NR$^9$C(O)S—, —SC(O)NR$^9$—, —NR$^9$C(O)—, —C(O)—NR$^9$—, —NR$^9$C(S)O—, —OC(S)NR$^9$—, —NR$^9$C(S)—NR$^9$—, —NR$^9$C(S)S—, —SC(S)NR$^9$—, —NR$^9$C(S)—, —C(S)NR$^9$—, —SC(O)NR$^9$—, —NR$^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR$^9$C(NR$^2$)NR$^9$—, —NR$^9$SO$_2$—, —SO$_2$NR$^9$— and —NR$^9$SO$_2$NR$^9$—,
each R$^6$, R$^7$, R$^8$ and R$^{16}$ is independently selected from H, —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-(C$_0$-C$_6$ alkyl), —(C$_0$-C$_6$ alkyl)-NR$^9$—(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl),
each R$^9$ is independently selected from —H, —(C$_1$-C$_4$ alkyl), —C(O)—(C$_1$-C$_4$ alkyl) and —C(O)O—(C$_1$-C$_4$ alkyl),
each G is independently —S(O)$_2$—, L or —(C$_0$-C$_3$ alkyl)-, in which each carbon of the —(C$_0$-C$_3$ alkyl)- is optionally and independently substituted with one or two R$^{16}$, or
each R$^{16}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of R$^{16}$ on the same carbon combine to form oxo,
each R$^{26}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of R$^{26}$ on the same carbon combine to form oxo,
each R$^{38}$ is independently selected from —H, —(C$_1$-C$_4$ alkyl), —C(O)—(C$_1$-C$_4$ alkyl) and —C(O)O—(C$_1$-C$_4$ alkyl),
each R$^{22}$ and R$^{23}$ is independently Ar or Het,
each Ar is an optionally substituted aryl,
each Het is an optionally substituted heteroaryl,
each Cak is an optionally substituted cycloalkyl,
each Hca is an optionally substituted heterocycloalkyl, and
each alkyl is optionally substituted.
Various embodiments of compounds of structural formula (2-I) suitable for use in the methods described herein are described below. Information regarding certain of these compounds can also be found in U.S. Patent Application Publication no. 2009/0163511, which is hereby incorporated by reference in its entirety.

In certain embodiments of the presently disclosed compounds of structural formula (2-I), the compound is not 5-methyl-N,2-bis(tetrahydro-2H-pyran-4-yl)-2,3,4,5-tetrahydro-1H-pyrido[4,3-b]indole-8-carboxamide or 5-methyl-2-(tetrahydro-2H-pyran-4-yl)-N-(tetrahydrothiophen-2-yl)-2,3,4,5-tetrahydro-1H-pyrido[4,3-b]indole-8-carboxamide S,S-dioxide.

In certain embodiments of the presently disclosed compounds of structural formula (2-I), J is —O— or —N(R$^{38}$)—. In certain such embodiments, D can be, for example, a carbon (for example, it is CH or C substituted with one of the x R$^4$ groups when the bond denoted by "a" is absent, or C when the bond denoted by "a" is present). In other embodiments of the presently disclosed compounds of structural formula (2-I), J is —CH$_2$—, —CH(R$^{26}$)— or —C(R$^{26}$)$_2$—, for example, —CH$_2$—. In certain such embodiments, D can be, for example, N.

In certain embodiments of the presently disclosed compounds of structural formula (2-I), R$^{38}$ is —H. In other embodiments, R$^{38}$ is —(C$_1$-C$_4$ alkyl), for example methyl, ethyl or propyl. In other embodiments, R$^{38}$ is —C(O)—(C$_1$-C$_4$ alkyl), for example acetyl. In other embodiments, R$^{38}$ is —C(O)—O—(C$_1$-C$_4$ alkyl)-, for example —C(O)—O-t-butyl. In certain embodiments, no alkyl of R$^{38}$ is substituted with an aryl-, heteroaryl-, cycloalkyl- or heterocycloalkyl-containing group.

In certain embodiments of the presently disclosed compounds of structural formula (2-I), each R$^{26}$ is independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl), and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, each R$^{26}$ is independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, each R$^{26}$ is methyl, ethyl, propyl, or two R$^{26}$ come together to form oxo.

In certain embodiments of the presently disclosed compounds of structural formula (2-I) as described above, the dotted line denoted by "b" is absent. In other embodiments, the dotted line denoted by "b" is a single bond; in one such embodiment, the dotted line denoted by "a" is a bond (thereby forming a double bond between D and the adjacent carbon).

In certain embodiments of the presently disclosed compounds of structural formula (2-I), E is —C(O)—. In other embodiments, E is —S(O)$_2$—

In certain embodiments of the presently disclosed compounds of structural formula (2-I), "B" represents

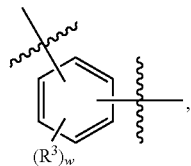

the dotted line denoted by "b" is a single bond, the dotted line denoted by "a" is a bond, k is 0, J is —N($R^{38}$)— and D is a carbon. In one such embodiment, E is —C(O)—.

In other embodiments of the presently disclosed compounds of structural formula (2-I), "B" represents

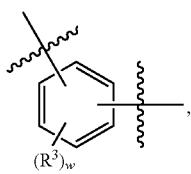

the dotted line denoted by "b" is absent, the dotted line denoted by "a" is absent, k is 0, J is —N($R^{38}$)— and D is a carbon. In one such embodiment, E is —C(O)—.

In other embodiments of the presently disclosed compounds of structural formula (2-I), "B" represents

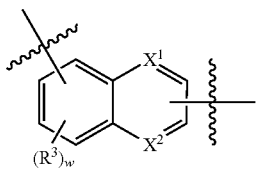

in which $X^1$ and $X^2$ are independently a carbon (for example, CH or C substituted with one of the w $R^3$ groups) or N, and k is 0. In one such embodiment, E is —C(O)—. In certain embodiments, one of $X^1$ and $X^2$ is N and the other is a carbon. In other embodiments, both $X^1$ and $X^2$ are a carbon. Floating bonds indicate attachment on any carbon of the ring system. In some embodiments, for example, the J moiety is on one ring of the ring system, and the E moiety is on the other ring of the naphthalene, and any $R^3$ groups can be on either ring of the fused ring system.

In certain embodiments of the presently disclosed compounds of structural formula (2-I), T is

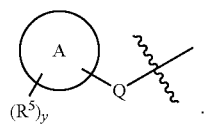

In such embodiments, Q is —S(O)$_2$—, L or —(C$_0$-C$_3$ alkyl)- in which each carbon of the (C$_0$-C$_3$ alkyl) is optionally and independently substituted with one or two $R^{16}$, in which each $R^{16}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)- L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of $R^{16}$ on the same carbon combine to form oxo. In certain embodiments, each $R^{16}$ is independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two $R^{16}$ on the same carbon optionally combine to form an oxo, in which each $R^7$, $R^8$ and $R^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl), and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in particular compounds, each $R^{16}$ is —(C$_1$-C$_3$ alkyl), —(C$_1$-C$_3$ haloalkyl), —(C$_0$-C$_3$ alkyl)-L-$R^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, and two $R^{16}$ on the same carbon optionally combine to form an oxo, in which each $R^7$, $R^8$ and $R^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, Q has at most one $R^{16}$ or an oxo substituted thereon. Q can be, for example, an unsubstituted —(C$_0$-C$_3$ alkyl)-. In other embodiments, Q is a (C$_1$-C$_3$ alkyl) having as its only substitution a single oxo group. For example, in certain embodiments, Q is —CH$_2$—; a single bond; —S(O)$_2$—; —C(O)—; or —CH(CH$_3$)—.

In certain embodiments of the compounds of structural formula (2-I), the

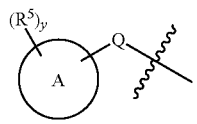

moiety is

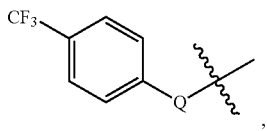

for example, p-(trifluoromethyl)phenyl. In other embodiments, the

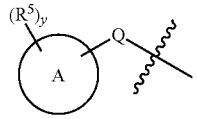

moiety is

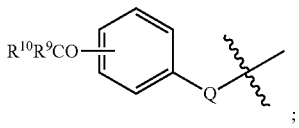

;

in one such embodiment, Q is a single bond.

The number of substituents on the ring system denoted by "A", y, is 0, 1, 2, 3 or 4. For example, in some embodiments of the presently disclosed compounds of structural formula (2-I), y is 0, 1, 2 or 3, such as 1. In one embodiment, y is not zero and at least one $R^5$ is halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ or —C(O)—Hca wherein the Hca contains a ring nitrogen atom through which it is bound to the —C(O)—, and wherein no alkyl, haloalkyl or heterocycloalkyl is substituted by an aryl, heteroaryl, cycloalkyl or heterocycloalkyl-containing group.

In certain embodiments of the presently disclosed compounds of structural formula (2-I), each $R^5$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^5$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group.

In one embodiment of the compounds of structural formula (2-I), y is 0.

In the presently disclosed compounds of structural formula (2-I), the ring system denoted by "A" is heteroaryl, aryl, cycloalkyl or heterocycloalkyl. For example, in one embodiment, the ring system denoted by "A" is an aryl or a heteroaryl. The ring system denoted by "A" can be, for example, a monocyclic aryl or heteroaryl. In one embodiment, when the "A" ring system is aryl, Q is a —($C_0$-$C_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. For example, in certain embodiments, Q is —$CH_2$—; a single bond; —S(O)$_2$—; —C(O)—; or —CH($CH_3$)—.

For example, in certain embodiments of the presently disclosed compounds of structural formula (2-I), the ring system denoted by "A" is a phenyl. In one embodiment, y is 1 and $R^5$ is attached to the phenyl in the para position relative to Q. In another embodiment, y is 1 and $R^5$ is selected from the group consisting of halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, and in which no ($C_0$-$C_4$ alkyl) or ($C_1$-$C_4$ alkyl) is substituted by an aryl, heteroaryl, cycloalkyl or heterocycloalkyl-containing group. $R^5$ can be, for example, —Cl, —F, cyano, —C(O)$CH_3$, —C(O)OH, —C(O)$NH_2$, trifluoromethyl, difluoromethyl, difluoromethoxy or trifluoromethoxy. In another embodiment, the

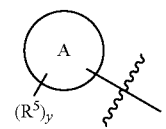

moiety is a 3,4-dihalophenyl.

In another embodiment of the presently disclosed compounds of structural formula (2-I), the ring system denoted by "A" is a heteroaryl. For example, in certain embodiments, the ring system denoted by "A" is a pyridyl, a thienyl, or a furanyl. In other embodiments, the ring system denoted by "A" is a pyrazolyl, imidazolyl, pyrrolyl, triazolyl or thiadiazolyl. In one embodiment, when the "A" ring system is heteroaryl, Q is a —($C_0$-$C_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. In certain embodiments, Q is —$CH_2$—; a single bond; —S(O)$_2$—; —C(O)—; or —CH($CH_3$)—.

In certain embodiments of the presently disclosed compounds of structural formula (2-I), the

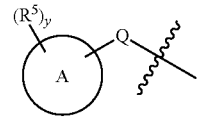

moiety is

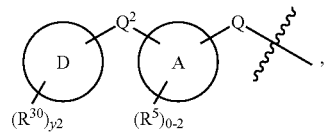

, in which the ring system denoted by "A" is aryl or heteroaryl, the ring system denoted by "D" is cycloalkyl, heterocycloalkyl, aryl or heteroaryl; $Q^2$ is —S(O)$_2$—, —O— or —($C_0$-$C_3$ alkyl)- in which each carbon of the ($C_0$-$C_3$ alkyl) is optionally and independently substituted with one or two $R^{16}$, defined as described above with respect to Q; $y^2$ is 0, 1 or 2; and each $R^{30}$ is independently selected from is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, $Q^2$ has at most one $R^{16}$ or an oxo substituted thereon. Q² can be, for example, an unsubstituted —(C₀-C₃ alkyl)-. In other embodiments, Q² is a (C₁-C₃ alkyl) having as its only substitution a single oxo group. For example, in certain embodiments, Q² is —CH₂—; a single bond; —S(O)₂—; —O—; —C(O)—; or —CH(CH₃)—. In certain embodiments, at least one R³⁰ is halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ or —C(O)—Hca in which the Hca contains a ring nitrogen atom through which it is bound to the —C(O)—, and in which no alkyl, haloalkyl or heterocycloalkyl is substituted by an aryl, heteroaryl, cycloalkyl or heterocycloalkyl-containing group. In certain embodiments, at least one R⁵ is —SO₂(C₁-C₆ alkyl), —SO₂(C₁-C₆ haloalkyl), —SO₂N(C₀-C₆ alkyl)(C₀-C₆ alkyl), —SO₂(C₃-C₈ cycloalkyl), —SO₂(C₃-C₈ heterocycloalkyl), such as —SO₂Me, —SO₂Et, —SO₂Pr, —SO₂Bu, —SO₂cyclopropyl, —SO₂morphylinyl, SO₂pyrrolidinyl, SO₂NHEt, SO₂pyridyl or —SO₂phenyl. The number of substituents on the ring system denoted by "D", y², is 0, 1, or 2. For example, in some embodiments, y² is 0 or 1, for example 1. In other embodiments, y² is 0. R³⁰ can be further defined as described above with respect to R⁵. In certain embodiments, the ring system denoted by "D" is cyclopropyl, morpholinyl, pyrazolyl, pyridyl, imidazolyl or phenyl.

In certain embodiments, at least one R⁵ is —SO₂(C₁-C₆ alkyl), —SO₂(C₁-C₆ haloalkyl), —SO₂N(C₀-C₆ alkyl)₂, —SO₂(C₃-C₈ cycloalkyl), —SO₂(C₃-C₈ heterocycloalkyl), such as —SO₂Me, —SO₂Et, —SO₂Pr, —SO₂Bu, —SO₂cyclopropyl, —SO₂morphylinyl, SO₂pyrrolidinyl, SO₂NHEt, SO₂pyridyl or —SO₂phenyl.

In one embodiment of the presently disclosed compounds, the compound has structural formula (2-II):

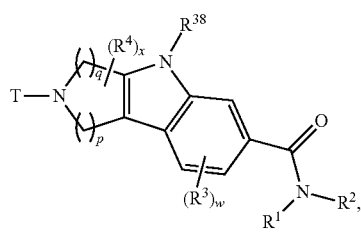

(2-II)

in which the variables are defined as described above with reference to structural formula (2-I). In certain embodiments, $R^{38}$ is not H. For example, $R^{38}$ can in one embodiment be methyl, ethyl or propyl. In another embodiment, $R^{38}$ can be acetyl. In other embodiments, $R^{38}$ is H.

In one embodiment of the presently disclosed compounds, the compound has structural formula (2-III):

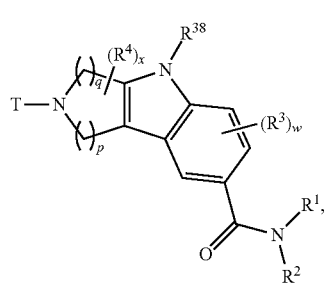

(2-III)

in which the variables are defined as described above with reference to structural formula (2-I). In certain embodiments, $R^{38}$ is not H. For example, $R^{38}$ can in one embodiment be methyl, ethyl or propyl. In another embodiment, $R^{38}$ can be acetyl. In other embodiments, $R^{38}$ is H.

In another embodiment of the presently disclosed compounds, the compound has structural formula (2-IV):

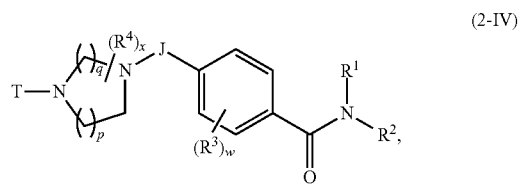

(2-IV)

in which k is 0, q is 1, 2, 3 or 4, J is —CH₂—, —CH(R²⁶)— or —C(R²⁶)₂— (e.g., —CH₂—), and all other variables are defined as described above with reference to structural formula (2-I).

In another embodiment of the presently disclosed compounds, the compound has structural formula (2-V):

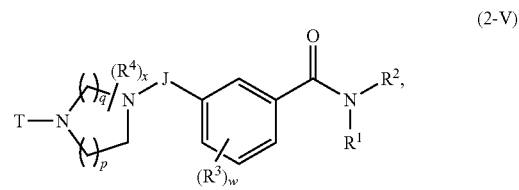

(2-V)

in which k is 0, q is 1, 2, 3 or 4, J is —CH₂—, —CH(R²⁶)— or —C(R²⁶)₂— (e.g., —CH₂—), and all other variables are defined as described above with reference to structural formula (2-I).

In certain embodiments according to structural formulae (2-I)-(2-V), the sum of p and q is 2 or 3. For example, in one embodiment, the sum of p and q is 2 (e.g., p is 1 and q is 1). In another embodiment, the sum of p and q is 3 (e.g., p is 1 and q is 2).

In another embodiment of the presently disclosed compounds, the compound has structural formula (2-VI):

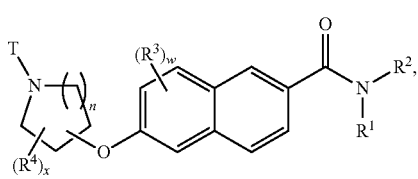

(2-VI)

in which k is 0, n is 0, 1, 2 or 3, and all other variables are defined as described above with reference to structural formula (2-I).

In another embodiment of the presently disclosed compounds, the compound has structural formula (2-VII):

(2-VII)

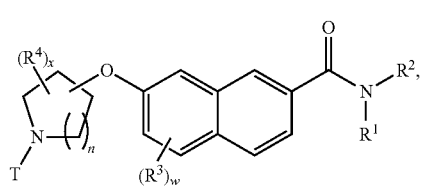

in which k is 0, n is 0, 1, 2 or 3, and all other variables are defined as described above with reference to structural formula (2-I).

In another embodiment of the presently disclosed compounds, the compound has structural formula (2-VIII):

(2-VIII)

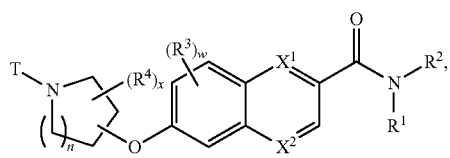

in which k is 0, n is 0, 1, 2 or 3, one of $X^1$ and $X^2$ is N and the other is a carbon, and all other variables are defined as described above with reference to structural formula (2-I). In one embodiment, for example, $X^1$ is N and $X^2$ is a carbon. In another embodiment, $X^1$ is a carbon, and $X^2$ is N.

In another embodiment of the presently disclosed compounds, the compound has structural formula (2-IX):

(2-IX)

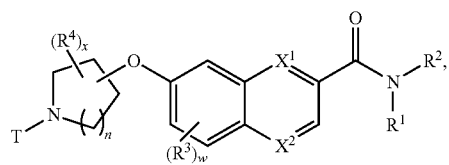

in which k is 0, n is 0, 1, 2 or 3, one of $X^1$ and $X^2$ is N and the other is a carbon, and all other variables are defined as described above with reference to structural formula (2-I). In one embodiment, for example, $X^1$ is N and $X^2$ is a carbon. In another embodiment, $X^1$ is a carbon, and $X^2$ is N.

In one embodiment of the presently disclosed compounds, the compound has the structural formula (2-X):

(2-X)

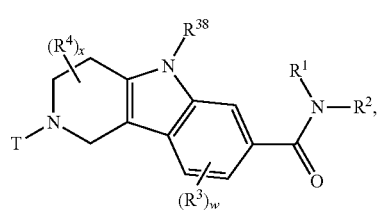

in which the variables are defined as described above with reference to structural formulae (2-I) and (2-II).

In another embodiment of the presently disclosed compounds, the compound has structural formula (2-XI):

(2-XI)

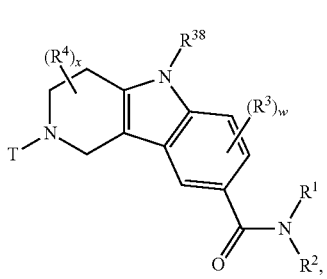

in which the variables are defined as described above with reference to structural formulae (2-I) and (2-III).

In another embodiment of the presently disclosed compounds, the compound has structural formula (2-XII):

(2-XII)

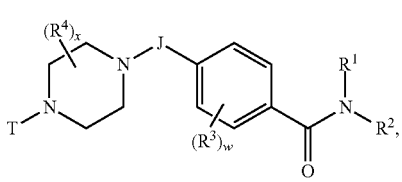

in which J is —$CH_2$—, —$CH(R^{26})$— or —$C(R^{26})_2$— (e.g., —$CH_2$—), and all other variables are defined as described above with reference to structural formulae (2-I) and (2-IV).

In another embodiment of the presently disclosed compounds, the compound has structural formula (2-XIII):

(2-XIII)

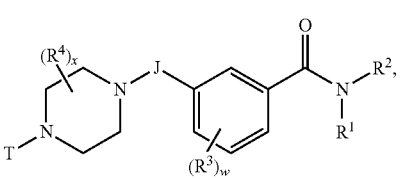

in which J is —$CH_2$—, —$CH(R^{26})$— or —$C(R^{26})_2$— (e.g., —$CH_2$—), and all other variables are defined as described above with reference to structural formulae (2-I) and (2-V).

In another embodiment of the presently disclosed compounds, the compound has structural formula (2-XIV):

(2-XIV)

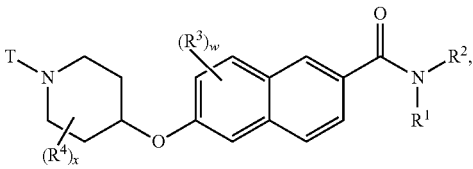

in which the variables are defined as described above with reference to structural formulae (2-I) and (2-VI).

In another embodiment of the presently disclosed compounds, the compound has structural formula (2-XV):

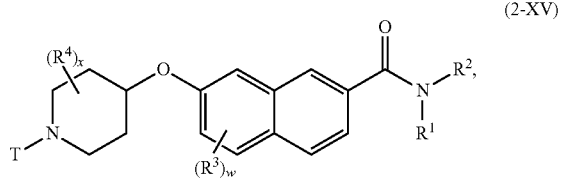

(2-XV)

in which the variables are defined as described above with reference to structural formulae (2-I) and (2-VII).

In one embodiment of the presently disclosed compounds, the compound has structural formula (2-XVI):

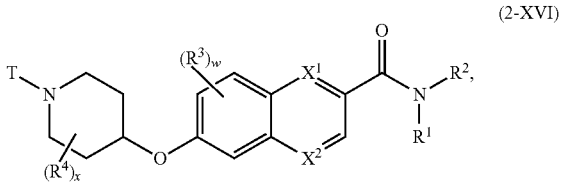

(2-XVI)

in which one of $X^1$ and $X^2$ is N, and the other is a carbon; and the other variables are defined as described above with reference to structural formulae (2-I) and (2-VIII). In one embodiment, for example, $X^1$ is N and $X^2$ is a carbon. In another embodiment, $X^1$ is a carbon, and $X^2$ is N.

In another embodiment of the presently disclosed compounds, the compound has structural formula (2-XVII):

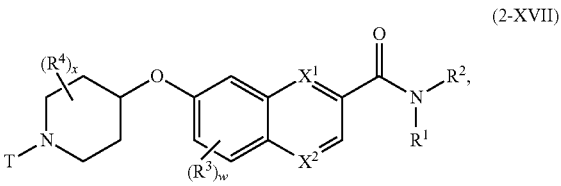

(2-XVII)

in which one of $X^1$ and $X^2$ is N, and the other is a carbon; and the other variables are defined as described above with reference to structural formulae (2-I) and (2-IX). In one embodiment, for example, $X^1$ is N and $X^2$ is a carbon. In another embodiment, $X^1$ is a carbon, and $X^2$ is N.

In certain embodiments of the presently disclosed compounds of any of structural formulae (2-I)-(2-XVII), $R^1$ is —H. In other embodiments, $R^1$ is ($C_1$-$C_4$ alkyl), for example methyl, ethyl, n-propyl or isopropyl.

In certain embodiments of the presently disclosed compounds of any structural formulae (2-I)-(2-XVII), $R^2$ is -Hca. In certain embodiments, $R^2$ is an optionally-substituted monocyclic heterocycloalkyl. In another embodiment, $R^2$ is not an oxo-substituted heterocycloalkyl. In certain embodiments (e.g., when the compound has structural formula (2-II) or (2-III)), $R^2$ is not tetrahydro-2H-pyran-4-yl moiety or a tetrahydrothiophene S,S-dioxide moiety.

In certain of the presently disclosed compounds of any structural formulae (2-I)-(2-XVII), $R^2$ is -(optionally-substituted azetidinyl), -(optionally-substituted pyrrolidinyl), -(optionally-substituted piperidinyl), or -(optionally-substituted azepanyl). For example, $R^2$ can be -(optionally substituted piperidinyl) or -(optionally substituted pyrrolidinyl). In one embodiment, $R^2$ is -(optionally substituted piperidinyl). In another embodiment, $R^2$ is -(optionally substituted pyrrolidinyl).

In certain particular embodiments of the presently disclosed compounds of any of structural formulae (2-I)-(2-XVII), $R^2$ is -(optionally-substituted azetidin-3-yl), -(optionally substituted piperidin-4-yl), -(optionally substituted pyrrolidin-3-yl) or -(optionally-substituted azepan-4-yl). For example, in one embodiment, $R^2$ is -(optionally substituted piperidin-4-yl). In another embodiment, $R^2$ is -(optionally substituted pyrrolidin-3-yl).

In certain embodiments of the presently disclosed compounds of any of structural formulae (2-I)-(2-XVII), the azetidinyl, pyrrolidinyl, piperidinyl and azepanyl $R^2$ moieties described above are substituted at their 1-positions. For example, in one embodiment, $R^2$ is substituted at its 1-position with —($C_0$-$C_3$ alkyl)-Ar or —($C_0$-$C_3$ alkyl)-Het, for example -(unsubstituted $C_0$-$C_3$ alkyl)-Ar or -(unsubstituted $C_0$-$C_3$ alkyl)-Het. For example, in one particular embodiment, the azetidinyl, pyrrolidinyl, piperidinyl or azepanyl $R^2$ moiety is substituted at its 1-position with an optionally substituted benzyl or an optionally substituted phenyl. In another embodiment, the azetidinyl, pyrrolidinyl, piperidinyl or azepanyl $R^2$ moiety is substituted at its 1-position with a benzyl substituted with an electron withdrawing group; or with a pyridinylmethyl optionally substituted with an electron withdrawing group. For example, the benzyl or pyridinylmethyl can be substituted with an electron withdrawing group selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), $NO_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In other embodiments, the azetidinyl, pyrrolidinyl, piperidinyl or azepanyl $R^2$ moiety is substituted at its 1-position with an unsubstituted benzyl or an unsubstituted phenyl.

In other embodiments of the compounds disclosed herein having any of structural formulae (2-I)-(2-XVII), the azetidinyl, pyrrolidinyl, piperidinyl or azepanyl $R^2$ moiety is substituted at its 1-position with an optionally substituted pyridinylmethyl, an optionally substituted furanylmethyl, an optionally substituted thienylmethyl, an optionally substituted oxazolylmethyl, or an optionally substituted imidazolylmethyl. For example, the azetidinyl, pyrrolidinyl, piperidinyl or azepanyl $R^2$ moiety can be substituted with an unsubstituted pyridinylmethyl, an unsubstituted furanylmethyl, an unsubstituted thienylmethyl, an unsubstituted oxazolylmethyl, or an unsubstituted imidazolylmethyl. In other embodiments, the azetidinyl, pyrrolidinyl, piperidinyl or azepanyl $R^2$ moiety can be substituted with an pyridinylmethyl, furanylmethyl, thienylmethyl, oxazolylmethyl or imidazolylmethyl substituted with an electron withdrawing group as described above.

In certain embodiments of the compounds disclosed herein having any of structural formulae (2-I)-(2-XVII), the azetidinyl, pyrrolidinyl, piperidinyl or azepanyl $R^2$ moiety is substituted at its 1-position with -L-Ar or -L-Het, in which Ar and Het can be, for example, as described above with reference to —($C_0$-$C_3$ alkyl)-Ar or —($C_0$-$C_3$ alkyl)-Het. In one such embodiment, L is —C(O)—$NR^9$—, such as —C(O)—NH—.

In other embodiments of the presently disclosed compounds of any structural formulae (2-I)-(2-XVII), the azetidinyl, pyrrolidinyl, piperidinyl or azepanyl $R^2$ moiety is substituted at its 1-position with —C(O)—O($C_0$-$C_6$ alkyl), —C(O)-Het, —C(O)—Ar, —S(O)$_2$-Het, —S(O)$_2$—Ar or —S(O)$_2$—O($C_0$-$C_6$ alkyl), in which Ar and Het can be, for example, as described above with reference to —($C_0$-$C_3$ alkyl)-Ar or —(C$_0$-C$_3$ alkyl)-Het. In one embodiment, the azetidinyl, pyrrolidinyl, piperidinyl or azepanyl R$^2$ moiety is substituted at its 1-position with —C(O)-Het or —C(O)—Ar; in another embodiment, it is substituted at its 1-position with —S(O)$_2$-Het or —S(O)$_2$—Ar. For example, in certain embodiments, the azetidinyl, pyrrolidinyl, piperidinyl or azepanyl R$^2$ moiety is substituted at its 1-position with an optionally-substituted benzoyl (e.g., substituted with an electron withdrawing group as described above); or with an optionally-substituted nicotinyl, isonicotinyl or picolinyl (e.g., optionally substituted with an electron withdrawing group as described above). In other embodiments, the azetidinyl, pyrrolidinyl, piperidinyl or azepanyl R$^2$ moiety is substituted at its 1-position with an unsubstituted benzoyl; or an unsubstituted nicotinoyl, isonicotinoyl or picolinoyl.

In certain embodiments of the compounds of any of structural formulae (2-I)-(2-XVII), R$^2$ is -Cak-N(R$^9$)-G-R$^{22}$, as described above. For example, in one embodiment of the disclosed compounds, R$^2$ has the structure

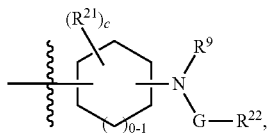

in which c is 0, 1, 2, 3 or 4, and each R$^{21}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two R$^{21}$ on the same carbon optionally combine to form oxo. In certain embodiments of the presently disclosed compounds, each R$^{21}$ is independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN and two R$^{21}$ on the same carbon optionally combine to form oxo, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, each R$^{21}$ is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN and two R$^{21}$ on the same carbon optionally combine to form oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, c is 1 or 2. In other embodiments, c is 0. In certain embodiments, R$^9$ is H. In certain embodiments, G is a single bond. In certain embodiments of the presently disclosed compounds, each R$^{22}$ is not substituted with an aryl-, heteroaryl-, cycloalkyl- or heterocycloalkyl-containing group. In certain embodiments of the presently disclosed compounds, each R$^{23}$ is not substituted with an aryl-, heteroaryl-, cycloalkyl- or heterocycloalkyl-containing group.

In one embodiment of compounds of any of structural formulae (2-I)-(2-XVII), R$^2$ has the structure

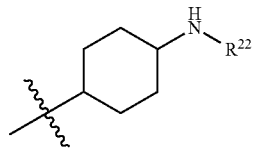

In certain embodiments of the compounds of any of structural formulae (2-I)-(2-XVII), R$^2$ is —(C$_2$-C$_8$ alkyl)-N(R$^9$)—R$^{24}$ in which one or two carbons of the (C$_2$-C$_8$ alkyl) are optionally replaced by —O— or —N(R$^9$)— and R$^{24}$ is —R$^{23}$, -GR$^{23}$ or —C(O)O—(C$_1$-C$_6$ alkyl). In certain embodiments, the (C$_2$-C$_8$ alkyl) is unsubstituted and no carbon is replaced by —O— or —N(R$^9$)—. For example, in one embodiment, R$^2$ is —CH$_2$—CH$_2$—CH$_2$—N(R$^9$)—R$^{24}$ or —CH$_2$—CH$_2$—CH$_2$—CH$_2$—N(R$^9$)—R$^{24}$. In other embodiments, the (C$_2$-C$_8$ alkyl) is substituted and/or one or two carbons are replaced by —O— or —N(R$^9$)—. For example, in one embodiment, R$^2$ is —CH$_2$—CH$_2$—O—CH$_2$—CH$_2$—N(R$^9$)—R$^{24}$; —CH$_2$—CH(CH$_3$)—N(R$^9$)—R$^{24}$; or —CH$_2$—CH$_2$—O—CH$_2$—C(O)—N(R$^9$)—R$^{24}$. In certain embodiments, R$^9$ is H. In certain embodiments, R$^{24}$ is Ar or Het. In certain embodiments, R$^{24}$ is not substituted with an aryl-, heteroaryl- or cycloalkyl- or heterocycloalkyl-containing group. In certain embodiments, the (C$_2$-C$_8$ alkyl) is a (C$_2$-C$_5$ alkyl).

In the compounds of any of structural formulae (2-I)-(2-XVII), the number of substituents on benzo, pyrido or pyrazino carbons of the ring system represented by "B", w, is 0, 1, 2 or 3. For example, in one embodiment, w is 0, 1 or 2. In another embodiment, such as when the ring system represented by "B" does not include a benzo, pyrido or pyrazino moeity, w is 0. In other embodiments, w is at least 1, and at least one R$^3$ is selected from the group consisting of halo, cyano, —(C$_1$-C$_4$ fluoroalkyl), —O—(C$_1$-C$_4$ fluoroalkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), —S(O)$_2$O—(C$_0$-C$_4$ alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. For example, in certain embodiments, at least one R$^3$ is halo (e.g., chloro) or —(C$_1$-C$_4$ alkyl) (e.g., methyl, ethyl or propyl). In certain embodiments, an R$^3$ is substituted on the "B" ring system at a benzo, pyrido or pyrazino ring position in the meta position relative to the J moiety.

In certain embodiments of the compounds of any of structural formulae (2-I)-(2-XVII), each R$^3$ is independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-R$^7$, —(C$_0$-C$_6$ alkyl)-NR$^8$R$^9$, (C$_0$-C$_6$ alkyl)-OR$^{10}$, (C$_0$-C$_6$ alkyl)-C(O)R$^{10}$, —(C$_0$-C$_6$ alkyl)-S(O)$_{0-2}$R$^{10}$, -halogen, —NO$_2$ and —CN, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl), and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, each $R^3$ is —($C_1$-$C_3$ alkyl), —($C_1$-$C_3$ haloalkyl), —($C_0$-$C_3$ alkyl), —($C_0$-$C_3$ alkyl)-$NR^8R^9$, ($C_0$-$C_3$ alkyl)-$OR^{10}$, —($C_0$-$C_3$ alkyl)-C(O)$R^{10}$, —($C_0$-$C_3$ alkyl)-S(O)$_{0-2}$$R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. For example, in certain embodiments, each $R^3$ is halo (e.g., chloro) or —($C_1$-$C_4$ alkyl) (e.g., methyl, ethyl or propyl).

In certain embodiments of the compounds of of any of structural formulae w is at least one, and at least one $R^3$ is —$NR^8R^9$. For example, in one embodiment, w is 1. In certain such embodiments, $R^3$ is substituted on the "B" ring system at a benzo, pyrido or pyrazino ring position in the meta position relative to the J moiety.

In other embodiments of the compounds of of any of structural formulae (2-I)-(2-XVII), w is at least one, and at least one $R^3$ is —($C_0$-$C_3$ alkyl)-$Y^1$—($C_1$-$C_3$ alkyl)-$Y^2$—($C_0$-$C_3$ alkyl), in which each of $Y^1$ and $Y^2$ is independently L, —O—, —S— or —$NR^9$—. For example, in one embodiment, w is 1. In certain such embodiments, $R^3$ is substituted on the "B" ring system at a benzo, pyrido or pyrazino ring position in the meta position relative to the J moiety. In one particular embodiment, $R^3$ is —$CH_2$—N($CH_3$)—$CH_2$—C(O)—$OCH_3$.

In the compounds of structural formula (2-I), the number of substituents on non-benzo, non-pyrido, non-pyrazino carbons, k, is 0, 1 or 2. For example, in one embodiment, k is 1. In other embodiments, such as when the ring system represented by "B" contains only benzo, pyridino and/or piperazino carbons, k is 0. In certain embodiments of the compounds of structural formula (2-I), each $R^{14}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}$$R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{14}$ is independently selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}$$R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. Each $R^{14}$ can be, for example, halo (e.g., —Cl or —F), cyano unsubstituted —($C_1$-$C_4$ alkyl) (e.g., methyl or ethyl) or unsubstituted —($C_1$-$C_4$ haloakyl) (e.g., difluoromethyl, trifluoromethyl and the like).

In the presently disclosed compounds of any of structural formulae (2-I)-(2-XVII), the number of substituents on the azacycloalkyl ring, x, is 0, 1, 2, 3 or 4. In one embodiment, x is 0, 1, 2 or 3. For example, x can be 0, or can be 1 or 2.

In certain embodiments of the presently disclosed compounds of any of structural formula (2-I)-(2-XVII), two $R^4$ groups combine to form an oxo. The oxo can be bound, for example, at the position alpha to the nitrogen of the azacycloalkyl ring. In other embodiments, no two $R^4$ groups combine to form an oxo.

In certain embodiments of the presently disclosed compounds of any of structural formulae (2-I)-(2-XVII), when x is 4, not all four $R^4$ groups are ($C_1$-$C_6$ alkyl).

In certain embodiments of the presently disclosed compounds of any of structural formulae (2-I)-(2-XVII), each $R^4$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}$$R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^4$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}$$R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group.

In certain embodiments, the presently disclosed compounds have the structural formula (2-XVIII):

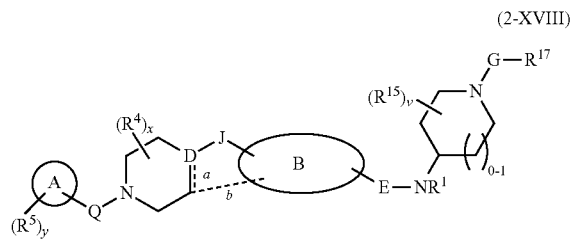

(2-XVIII)

in which Q and G are each independently a bond, —$CH_2$—, —C(H)($R^{16}$)—, —C($R^{16}$)$_2$—, L (e.g., —C(O)—$NR^9$— or —$NR^9$—C(O)—) or —S(O)$_2$—; v is 0, 1, 2, 3 or 4; each $R^{15}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}$$R^{10}$, -halogen, —$NO_2$ and —CN, and two $R^{15}$ on the same carbon optionally combine to form oxo; $R^{17}$ is Het or Ar, and all other variables are defined as described above with reference to any of structural formula (2-I)-(2-XVII). $R^{17}$ can be, for example, an optionally substituted phenyl, an optionally-substituted pyridyl, an optionally substituted pyrazolyl, an optionally substituted imidazolyl, an optionally substituted pyrrolyl, an optionally substituted triazolyl or an optionally substituted thiadiazolyl. In one embodiment, Q is a single bond. In another embodiment, Q is —$CH_2$—. In other embodiments, Q is —C(O)— or —S(O)$_2$—. In certain embodiments, G is —CH$_2$—. In other embodiments, G is —C(O)— or —S(O)$_2$—. In other embodiments, G is —CH(CH$_3$)—. In other embodiments, G is —C(O)—NH—. The above-recited Q and G moieties can be combined in any possible combination. For example, in one embodiment, Q is a single bond and G is —CH$_2$— or —C(O)—. As described above, in certain embodiments, the ring system denoted by "A" is aryl or heteroaryl. In one embodiment, the ring system denoted by "A" is substituted with one or more electron-withdrawing groups as described above. In another embodiment, R$^{17}$ is substituted with one or more electron-withdrawing groups as described above. In certain embodiments, the ring system denoted by "A", R$^{17}$ or both are not substituted with an aryl, heteroaryl, cycloalkyl or heterocycloalkyl-containing group. In certain embodiments, the azacycloalkyl to which -G-R$^{17}$ is bound is a piperidinyl; in other embodiments, it is a pyrrolidinyl.

In the presently disclosed compounds of structural formula (2-XVIII), v is 0, 1, 2, 3 or 4. In one embodiment, v is 0, 1, 2 or 3. For example, v can be 0, or can be 1 or 2.

In certain embodiments of the presently disclosed compounds of structural formula (2-XVIII), two R$^{15}$ groups combine to form an oxo. The oxo can be bound, for example, at the position alpha relative to the nitrogen of the azacycloalkyl ring. In other embodiments, no two R$^{15}$ groups combine to form an oxo.

In certain embodiments of the presently disclosed compounds of structural formula (2-XVIII), when v is 4, not all four R$^{15}$ moieties are (C$_1$-C$_6$ alkyl).

In certain embodiments of the presently disclosed compounds of structural formula (2-XVIII), each R$^{15}$ is independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN and two R$^{15}$ on the same carbon optionally combine to form oxo, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, each R$^{15}$ is —(C$_1$-C$_3$ alkyl), —(C$_1$-C$_3$ haloalkyl), —(C$_0$-C$_3$ alkyl), —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN and two R$^{15}$ on the same carbon optionally combine to form oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In some embodiments, one R$^{15}$ is —C(O)NR$^9$R$^7$, which can be bound, for example, at a position alpha relative to the piperidine nitrogen, or at the position linked to the —N(R$^1$)—.

In certain embodiments of the presently disclosed compounds of structural formula (2-XVIII), R$^{17}$ is an unsubstituted aryl or heteroaryl. In other embodiments, the R$^{17}$ Ar or Het is substituted with 1, 2 or 3 substituents independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, the R$^{17}$ Ar or Het is substituted with 1, 2 or 3 substituents independently selected from —(C$_1$-C$_3$ alkyl), —(C$_1$-C$_3$ haloalkyl), —(C$_0$-C$_3$ alkyl), —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, R$^{17}$ is substituted with 1, 2 or 3 substituents selected from halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca. R$^{17}$ can be substituted with, for example, one such substituent, or two such substituents. In certain embodiments, R$^{17}$ is substituted with a substitutent -G$^2$-R$^{34}$, in which G$^2$ is a single bond, —O—, —C(O)—, —S(O)$_2$— or —CH$_2$—, and R$^{34}$ is a chosen from aryl (such as phenyl), heterocycloalkyl (such as morpholinyl, pyrrolidinyl), and heteroaryl (such as), each of which is optionally substituted with 1 or 2 substituents selected from aryl, (C$_1$-C$_4$ haloalkyl), —O—(C$_1$-C$_4$ haloalkyl), (C$_1$-C$_4$ alkyl), —O—(C$_1$-C$_4$ alkyl), halogen, or CN.

In certain embodiments, the presently disclosed compounds have the structural formula (2-XXIX):

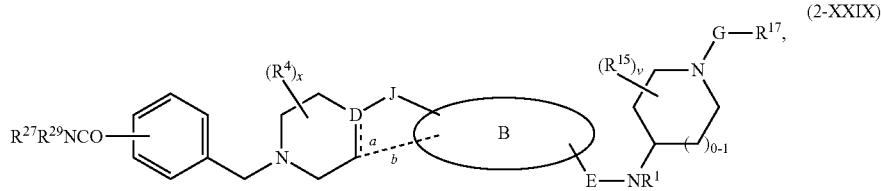

(2-XXIX)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (2-I)-(2-XVIII). In one embodiment, $R^{27}$ and $R^{29}$ are both H.

In certain embodiments, the presently disclosed compounds have the structural formula (2-XX):

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (2-I)-(2-XVIII). In one embodiment, $R^{27}$ and $R^{29}$ are both H.

In certain embodiments, the presently disclosed compounds have the structural formula (2-XXII):

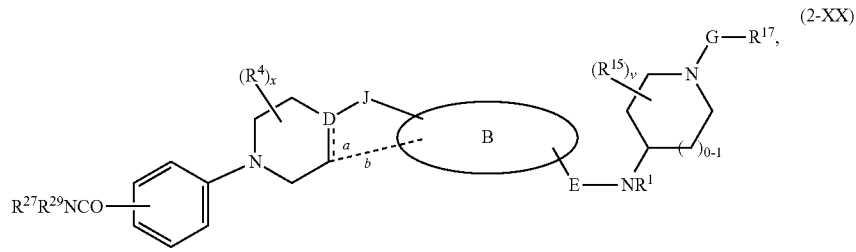

(2-XX)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (2-I)-(2-XVIII). In one embodiment, $R^{27}$ and $R^{29}$ are both H.

In certain embodiments, the presently disclosed compounds have the structural formula (2-XXI):

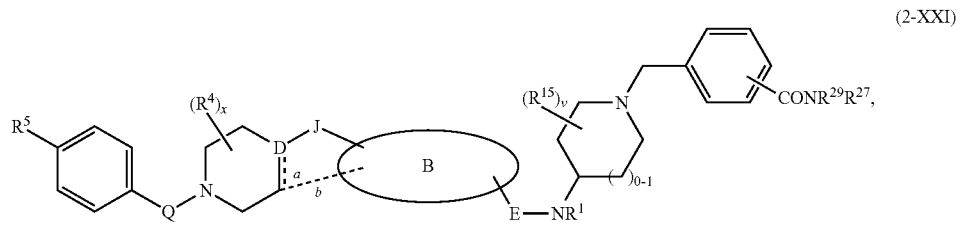

(2-XXI)

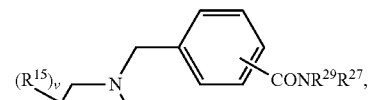
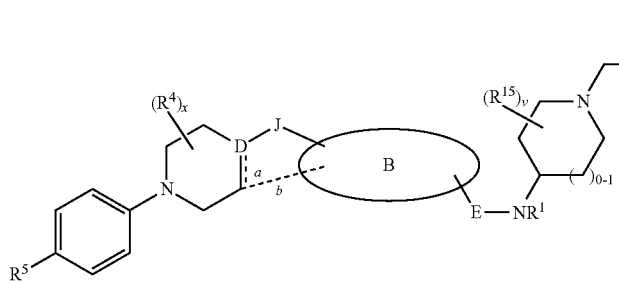

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-$S(O)_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (2-I)-(2-XVIII). In one embodiment, $R^{27}$ and $R^{29}$ are both H.

In certain embodiments, the presently disclosed compounds have the structural formula (2-XXIII):

in which $R^{25}$ is selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl or haloalkyl is substituted by an aryl, heteroaryl, cycloalkyl or heterocycloalkyl-containing group; and all other variables are as described above with reference to any of structural formulae (2-I)-(2-XVIII). $R^{25}$ can be, for example, —Cl, —F, cyano, —C(O)$CH_3$, —C(O)OH, —C(O)$NH_2$, trifluoromethyl, difluoromethyl, difluoromethoxy or trifluoromethoxy.

In certain embodiments, the presently disclosed compounds have the structural formula (2-XXV):

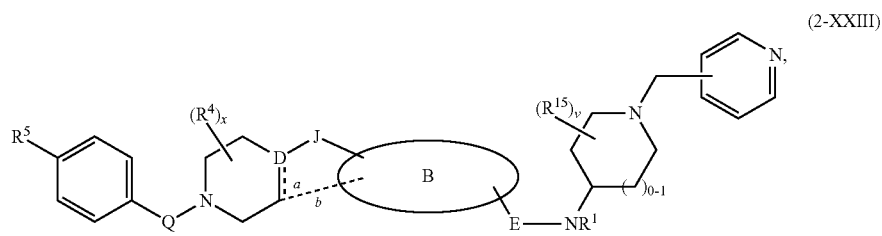

in which all variables are as described above with reference to any of structural formulae (2-I)-(2-XVIII).

In certain embodiments, the presently disclosed compounds have the structural formula (2-XXIV):

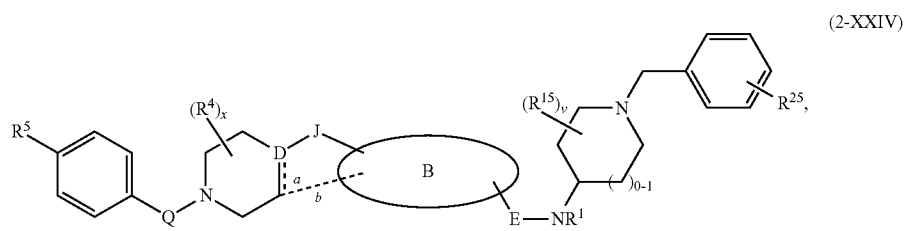

(2-XXV)

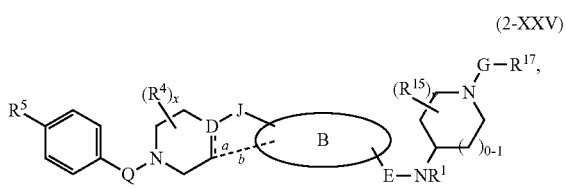

in which G is —C(O)—, —S(O)$_2$— or —C(O)—NH— and all other variables are as described above with reference to any of structural formulae (2-I)-(2-XVIII).

In certain embodiments, the presently disclosed compounds have the structural formula (2-XXVI):

(2-XXVI)

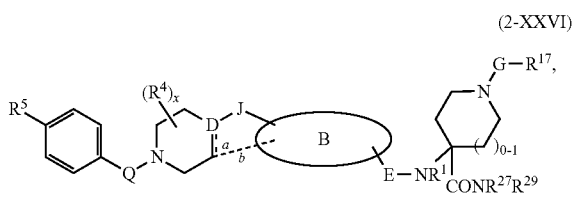

in which $R^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and $R^{29}$ is —H, —(C$_1$-C$_4$ alkyl), —CO—O—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (2-I)-(2-XVIII). In one embodiment, $R^{27}$ and $R^{29}$ are both H. In some embodiments, the compounds of structural formula (2-XXVI) are present as racemic mixtures or scalemic mixtures. In other embodiments, the compounds of structural formula (2-XXVI) are present in an enantiomerically-enriched form, for example as a substantially pure stereoisomer.

In certain embodiments, the presently disclosed compounds have the structural formula (2-XXVII):

(2-XXVII)

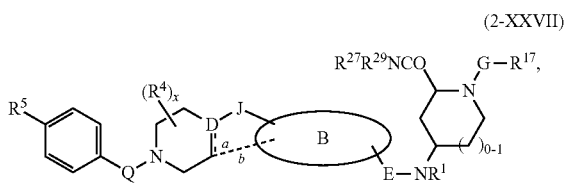

in which $R^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and $R^{29}$ is —H, —(C$_1$-C$_4$ alkyl), —CO—O—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (2-I)-(2-XVIII). In one embodiment, $R^{27}$ and $R^{29}$ are both H. In some embodiments, the compounds of structural formula (2-XXVII) are present as racemic mixtures or scalemic mixtures. In other embodiments, the compounds of structural formula (2-XXVII) are present in an enantiomerically-enriched form, for example as a substantially pure stereoisomer.

In certain embodiments, the presently disclosed compounds have the structural formula (2-XXVIII):

(2-XXVIII)

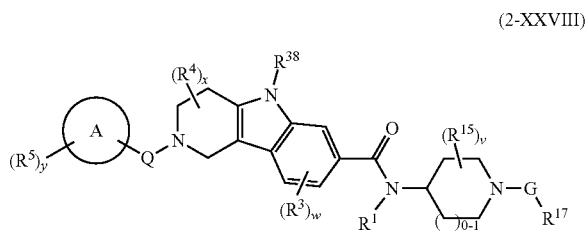

in which G, v, $R^{15}$ and $R^{17}$ are defined as described above with reference to structural formula (2-XVIII), and all other variables are defined as described above with reference to structural formulae (2-I) or (2-II). $R^5$, y, v, $R^{15}$, $R^{17}$, Q, G and the ring denoted by "A" can be defined, for example, as described with reference to any of structural formulae (2-XXIX)-(2-XXVII).

In certain embodiments, the presently disclosed compounds have the structural formula (2-XXIX):

(2-XXIX)

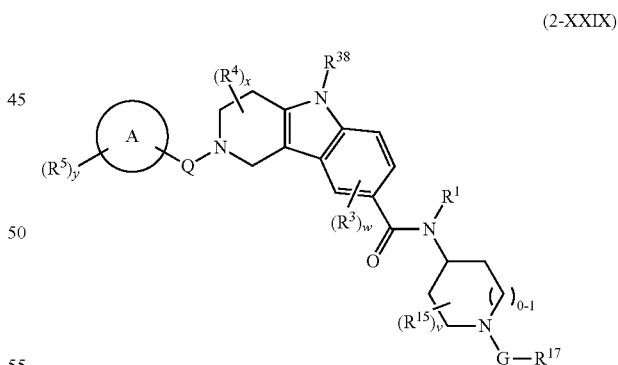

in which G, v, $R^{15}$ and $R^{17}$ are defined as described above with reference to structural formula (2-XVIII), and all other variables are defined as described above with reference to structural formulae (2-I) or (2-III). $R^5$, y, v, $R^{15}$, $R^{17}$, Q, G and the ring denoted by "A" can be defined, for example, as described with reference to any of structural formulae (2-XXIX)-(2-XXVII).

In certain embodiments, the presently disclosed compounds have the structural formula (2-XXX):

(2-XXX)

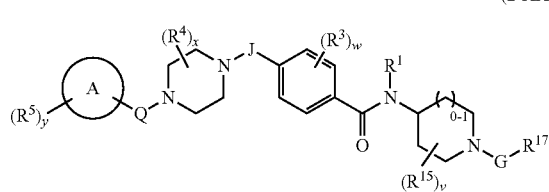

(2-XXXI)

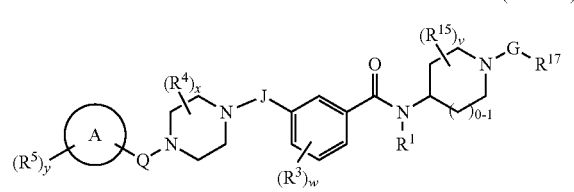

in which J is —CH$_2$—, —CH(R$^{26}$)— or —C(R$^{26}$)$_2$— (e.g., —CH$_2$—), G, v, R$^{15}$ and R$^{17}$ are defined as described above with reference to structural formula (2-XVIII), and all other variables are defined as described above with reference to structural formulae (2-I) or (2-IV). R$^5$, y, v, R$^{15}$, R$^{17}$, Q, G and the ring denoted by "A" can be defined, for example, as described with reference to any of structural formulae (2-XXIX)-(2-XXVII).

In certain embodiments, the presently disclosed compounds have the structural formula (2-XXXI):

in which J is —CH$_2$—, —CH(R$^{26}$)— or —C(R$^{26}$)$_2$— (e.g., —CH$_2$—), G, v, R$^{15}$ and R$^{17}$ are defined as described above with reference to structural formula (2-XVIII), and all other variables are defined as described above with reference to structural formulae (2-I) or (2-V). R$^5$, y, v, R$^{15}$, R$^{17}$, Q, G and the ring denoted by "A" can be defined, for example, as described with reference to any of structural formulae (2-XXIX)-(2-XXVII).

In certain embodiments, the presently disclosed compounds have the structural formula (2-XXXII):

(2-XXXII)

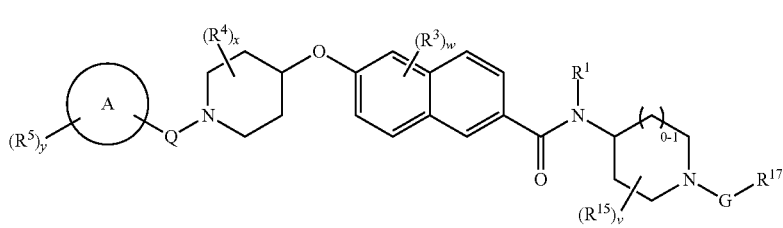

in which G, v, R$^{15}$ and R$^{17}$ are defined as described above with reference to structural formula (2-XVIII), and all other variables are defined as described above with reference to structural formulae (2-I) or (2-VI). R$^5$, y, v, R$^{15}$, R$^{17}$, Q, G and the ring denoted by "A" can be defined, for example, as described with reference to any of structural formulae (2-XXIX)-(2-XXVII).

In certain embodiments, the presently disclosed compounds have the structural formula (2-XXXIII):

(2-XXXIII)

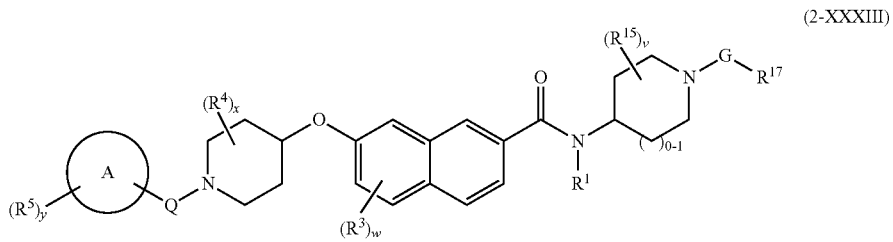

in which G, v, $R^{15}$ and $R^{17}$ are defined as described above with reference to structural formula (2-XVIII), and all other variables are defined as described above with reference to structural formulae (2-I) or (2-VII). $R^5$, y, v, $R^{15}$, $R^{17}$, Q, G and the ring denoted by "A" can be defined, for example, as described with reference to any of structural formulae (2-XXIX)-(2-XXVII).

In certain embodiments, the presently disclosed compounds have the structural formula (2-XXXIV):

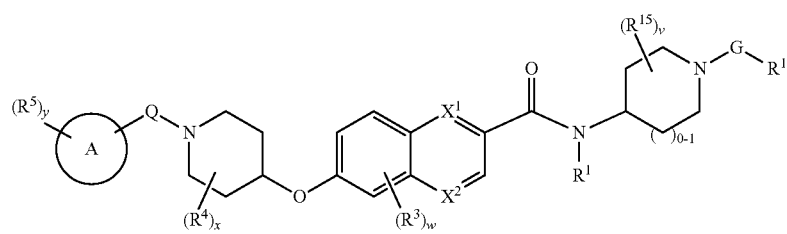

(2-XXXIV)

in which one of $X^1$ and $X^2$ is N, and the other is a carbon; G, v, $R^{15}$ and $R^{17}$ are defined as described above with reference to structural formula (2-XVIII), and all other variables are defined as described above with reference to structural formulae (2-I) or (2-VIII). $R^5$, y, v, $R^{15}$, $R^{17}$, Q, G and the ring denoted by "A" can be defined, for example, as described with reference to any of structural formulae (2-XXIX)-(2-XXVII). In one embodiment, for example, $X^1$ is N and $X^2$ is a carbon. In another embodiment, $X^1$ is a carbon, and $X^2$ is N.

In certain embodiments, the presently disclosed compounds have the structural formula (2-XXXV):

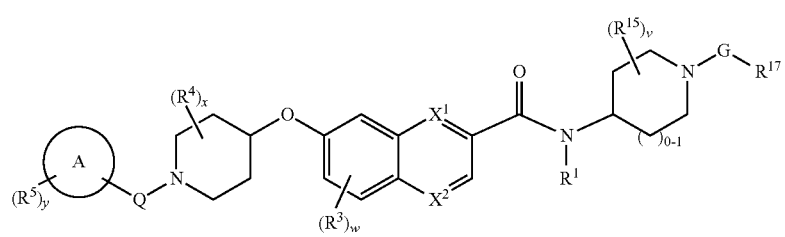

(2-XXXV)

in which in which one of $X^1$ and $X^2$ is N, and the other is a carbon; G, v, $R^{15}$ and $R^{17}$ are defined as described above with reference to structural formula (2-XVIII), and all other variables are defined as described above with reference to structural formulae (2-I) or (2-IX). $R^5$, y, v, $R^{15}$, $R^{17}$, Q, G and the ring denoted by "A" can be defined, for example, as described with reference to any of structural formulae (2-XXIX)-(2-XXVII). In one embodiment, for example, $X^1$ is N and $X^2$ is a carbon. In another embodiment, $X^1$ is a carbon, and $X^2$ is N.

In certain embodiments of compounds having structural formulae (2-XVIII)-(2-XXXV), the

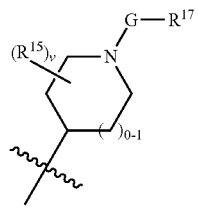

moiety has the structure

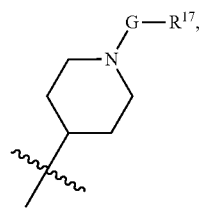

in which G is —$CH_2$—, —$CH(CH_3)$—, —C(O)—, —$S(O)_2$— or —C(O)—NH—. For example, in one embodiment, G is —$CH_2$—. In another embodiment, G is —C(O)— or —$S(O)_2$—. In another embodiment, G is —C(O)—NH—.

In other embodiments of compounds having structural formulae (2-XVIII)-(2-XXXV), the

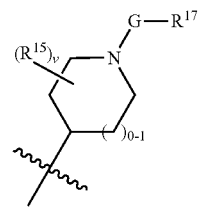

moiety has the structure

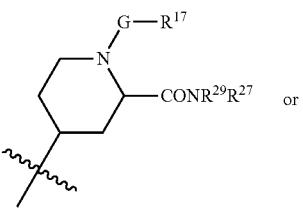

or

-continued

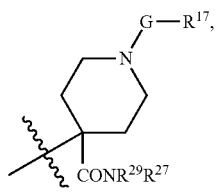

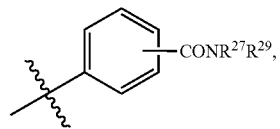

in which G is —CH$_2$—, —C(O)—, —S(O)$_2$— or —C(O)—NH—, R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —CO—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca. In such embodiments, the compounds can be present as racemic mixtures or scalemic mixtures, or in an enantiomerically-enriched form, for example as a substantially pure stereoisomer.

In other embodiments of compounds having structural formulae (2-XVIII)-(2-XXXV), the

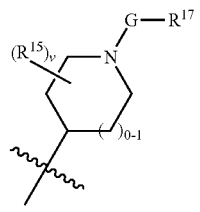

moiety has the structure

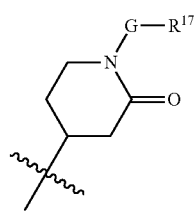

in which G is —CH$_2$—, —C(O)—, —S(O)$_2$— or —C(O)—NH—.

In certain embodiments of compounds having structural formulae (2-XVIII)-(2-XXXV), the R$^{17}$ moiety has the structure in which R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —CO—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca.

In certain embodiments of compounds having structural formulae (2-XVIII)-(2-XXXV), w is 1, and R$^3$ is —NR$^8$R$^9$. In certain such embodiments, R$^3$ is substituted at a benzo, pyrido or pyrazino ring position in the meta position relative to the J moiety.

In other embodiments of compounds having structural formulae (2-XVIII)-(2-XXXV), w is 1, and R$^3$ is —(C$_0$-C$_3$ alkyl)-Y$^1$—(C$_1$-C$_3$ alkyl)-Y$^2$—(C$_0$-C$_3$ alkyl), in which each of Y$^1$ and Y$^2$ is independently L, —O—, —S— or —NR$^9$—. In certain such embodiments, R$^3$ is substituted at a benzo, pyrido or pyrazino ring position in the meta position relative to the J moiety.

In certain embodiments described above, each R$^{27}$ is selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN and two R$^{21}$ on the same carbon optionally combine to form oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group, and each R$^{29}$ is H, methyl or ethyl, or R$^{27}$ and R$^{29}$ together with the nitrogen to which they are bound form Hca.

In certain embodiments of compounds having structural formulae (2-XVIII)-(2-XXXV), at least one R$^5$ moiety is a haloalkyl group, and in exemplary embodiments of these formulae the

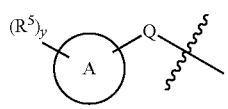

moiety is p-(trifluoromethyl)phenyl. By way of further illustration, certain exemplary compounds including such

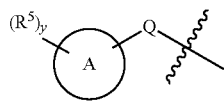

moieties have structural formula (2-XXXVI) or (2-XXXVII):

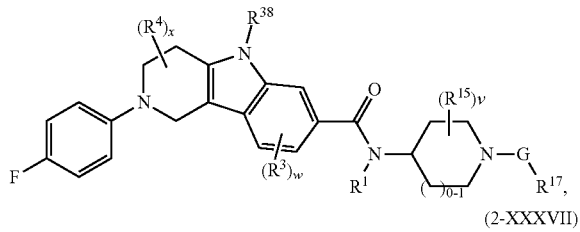

(2-XXXVI)

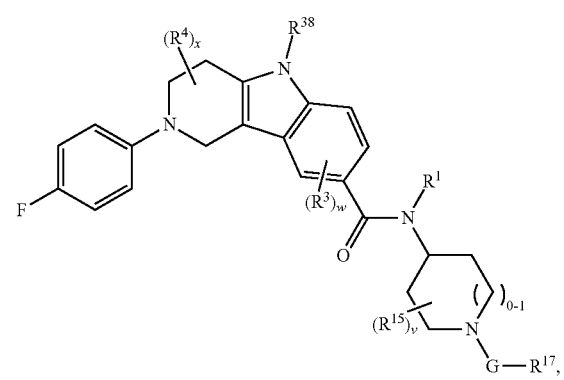

(2-XXXVII)

in which all variables are as described above with reference to structural formulae (2-XXVIII) or (2-XXIX).

In one embodiment, the presently disclosed compounds have the structural formula (2-XXXVIII):

in which G, $R^1$, $R^3$, $R^{17}$ and $R^{38}$ are as described above with reference to any of structural formulae (2-I), (2-II), (2-X) or (2-XVIII), $R^{18}$ is H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), in which no alkyl or haloalkyl is substituted with an aryl-, heteroaryl-, cycloalkyl- or heterocycloalkyl-containing group and $R^{19}$ is —H, —($C_1$-$C_4$ alkyl), —CO—($C_1$-$C_4$ alkyl) or —CO—O—($C_1$-$C_4$ alkyl) in which no alkyl is substituted by an aryl, heteroaryl, cycloalkyl or heterocycloalkyl-containing group, or $R^{18}$ and $R^{19}$ together with the nitrogen to which they are bound form Hca. In one embodiment, $R^{18}$ and $R^{19}$ are both H.

In one embodiment, the presently disclosed compounds have the structural formula (2-XXXIX):

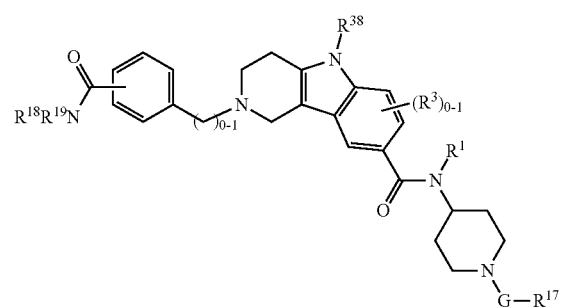

(2-XXXIX)

in which G, $R^1$, $R^3$, $R^{17}$ and $R^{38}$ are as described above with reference to any of structural formulae (2-I), (2-III), (2-XI) and (2-XVIII), and $R^{18}$ and $R^{19}$ are defined as described above with reference to structural formula (2-XXXVIII).

In another embodiment, the presently disclosed compounds have the structural formula (2-XL):

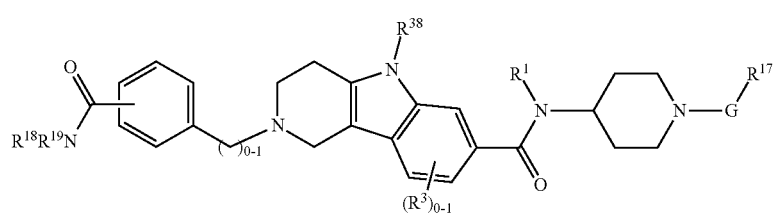

(2-XXXVIII)

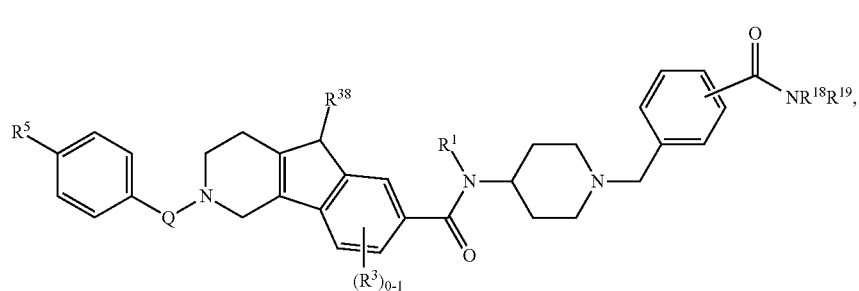
(2-XL)

in which Q, $R^1$, $R^3$, $R^5$ and $R^{38}$ are defined as described above with reference to any of structural formulae (2-I), (2-II), (2-X) and (2-XVIII), and $R^{18}$ and $R^{19}$ are defined as described above with reference to structural formula (2-XXXVIII).

In another embodiment, the presently disclosed compounds have the structural formula (2-XLI):

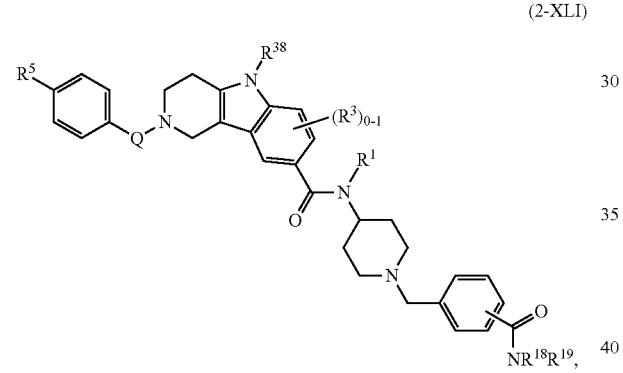
(2-XLI)

in which Q, $R^1$, $R^3$, $R^5$ and $R^{38}$ are defined as described above with reference to any of structural formulae (2-I), (2-III), (2-XI) and (2-XVIII), and $R^{18}$ and $R^{19}$ are defined as described above with reference to structural formula (2-XXXVIII).

In another embodiment, the presently disclosed compounds have the structural formula (2-XLII):

in which $R^1$, $R^3$, $R^5$ and $R^{38}$ are defined as described above with reference to any of structural formulae (2-I), (2-II), (2-X) and (2-XVIII), and $R^{18}$ and $R^{19}$ are defined as described above with reference to structural formula (2-XXXVIII).

In another embodiment, the presently disclosed compounds have the structural formula (2-XLIV):

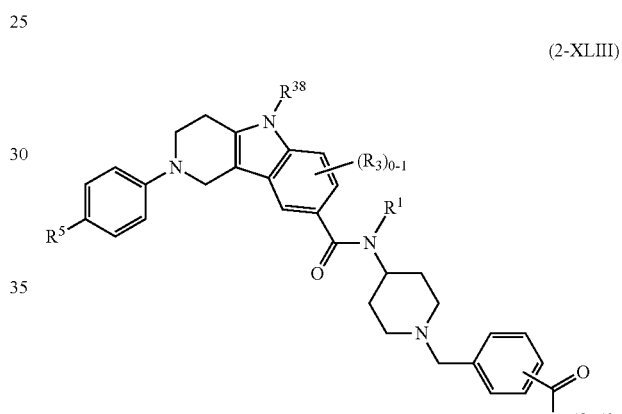
(2-XLIII)

in which $R^1$, $R^3$, $R^5$ and $R^{38}$ are defined as described above with reference to any of structural formulae (2-I), (2-III), (2-XI) and (2-XVIII), and $R^{18}$ and $R^{19}$ are defined as described above with reference to structural formula (2-XXXVIII).

In compounds according to any of structural formulae (2-I), (2-IV)-(2-XI) and (2-XII)-(2-XIX), T and $R^2$ can be defined as described above with reference to structural formulae (2-XVIII)-(2-XLIII).

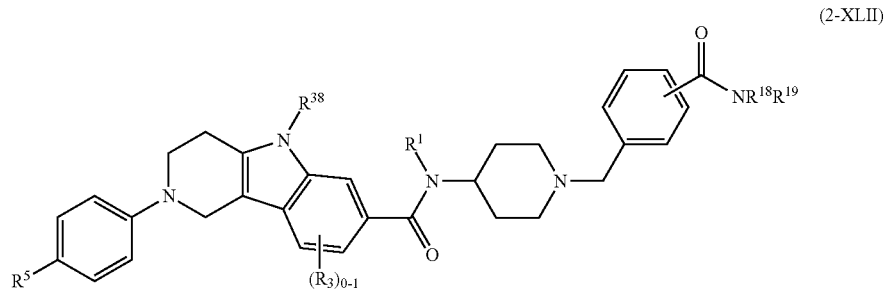
(2-XLII)

In certain embodiments, the presently disclosed compounds have the structural formula (2-XLIV):

(2-XVLIV)

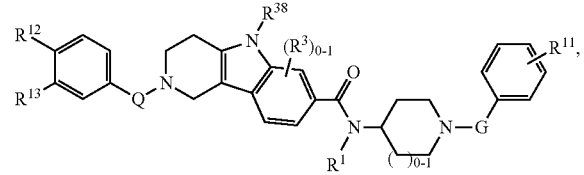

in which Q is —CH$_2$—, —C(O)— or a single bond; G is a single bond, —CH$_2$—, —C(O)—, —S(O)$_2$— or —C(O)—NH—; R$^1$, R$^3$ and R$^{38}$ are as described above with reference to any of structural formulae (2-I), (2-II) (2-X) and (2-XVIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, no R$^3$ is substituted on the benzo moiety. In another embodiment, one R$^3$ (e.g., —Cl, —F, —CH$_3$, —C$_2$H$_5$, —C$_3$H$_7$) is substituted on the benzo moiety.

In certain embodiments, the presently disclosed compounds have the structural formula (2-XLV):

(2-XLV)

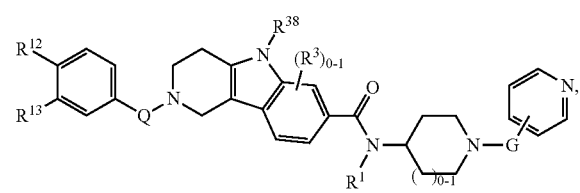

in which Q is —CH$_2$—, —C(O)— or a single bond; G is a single bond, —CH$_2$—, —C(O)—, —S(O)$_2$— or —C(O)—NH—; R$^1$, R$^3$ and R$^{38}$ are as described above with reference to any of structural formulae (2-I), (2-II), (2-X) and (2-XVIII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyrido nitrogen is disposed in the para position relative to the G moiety; in another embodiment, the pyrido nitrogen is disposed in the meta position relative to the G moiety. In one embodiment, no R$^3$ is substituted on the benzo moiety. In another embodiment, one R$^3$ (e.g., —Cl, —F, —CH$_3$, —C$_2$H$_5$, —C$_3$H$_7$) is substituted on the benzo moiety.

In certain embodiments, the presently disclosed compounds have the structural formula (2-XLVI):

(2-XLVI)

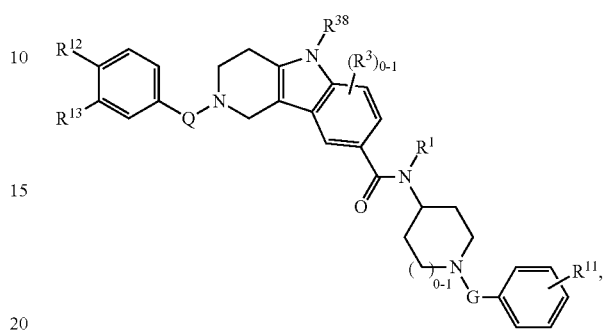

in which Q is —CH$_2$—, —C(O)— or a single bond; G is a single bond, —CH$_2$—, —C(O)—, —S(O)$_2$— or —C(O)—NH—; R$^1$, R$^3$ and R$^{38}$ are as described above with reference to any of structural formulae (2-I), (2 III) (2-XI) and (2-XVIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, no R$^3$ is substituted on the benzo moiety. In another embodiment, one R$^3$ (e.g., —Cl, —F, —CH$_3$, —C$_2$H$_5$, —C$_3$H$_7$) is substituted on the benzo moiety.

In certain embodiments, the presently disclosed compounds have the structural formula (2-XLVII):

(2-XLVII)

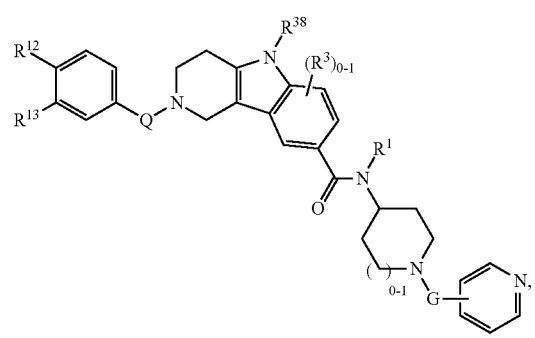

in which Q is —CH$_2$—, —C(O)— or a single bond; G is a single bond, —CH$_2$—, —C(O)—, —S(O)$_2$— or —C(O)—NH—; R$^1$, R$^3$ and R$^{38}$ are as described above with reference to any of structural formulae (2-I), (2-III), (2-XI) and (2-XVIII); $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the benzo moiety. In another embodiment, one $R^3$ (e.g., —Cl, —F, —$CH_3$, —$C_2H_5$, —$C_3H_7$) is substituted on the benzo moiety.

In one embodiment, the presently disclosed compounds have the structural formula (2-XLVIII):

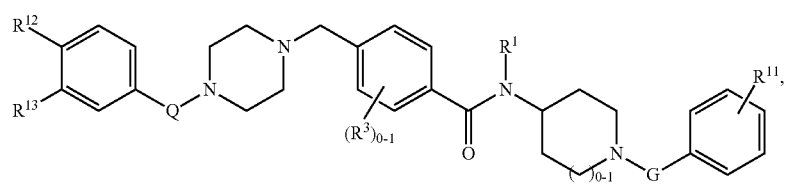

(2-XLVIII)

in which Q is —$CH_2$—, —C(O)— or a single bond; G is a single bond, —$CH_2$—, —C(O)—, —$S(O)_2$— or —C(O)—NH—; $R^1$ and $R^3$ are as described above with respect to any of structural formulae (2-I), (2-IV), (2 XII) and (2 XVIII); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the central phenyl moiety. In another embodiment, one $R^3$ (e.g., —Cl, —F, —$CH_3$, —$C_2H_5$, —$C_3H_7$) is substituted on the central phenyl moiety.

In certain embodiments, the presently disclosed compounds have the structural formula (2-XLIX):

in which Q is —$CH_2$—, —C(O)— or a single bond; G is a single bond, —$CH_2$—, —C(O)—, —$S(O)_2$— or —C(O)—NH—; $R^1$ and $R^3$ are as described above with reference to any of structural formulae (2-I), (2-IV), (2-XII) and (2-XVIII); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the central phenyl moiety. In another embodiment, one $R^3$ (e.g., —Cl, —F, —$CH_3$, —$C_2H_5$, —$C_3H_7$) is substituted on the central phenyl moiety.

In certain embodiments, the presently disclosed compounds have the structural formula (2-L):

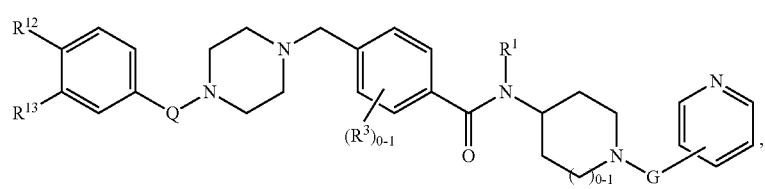

(2-XLIX)

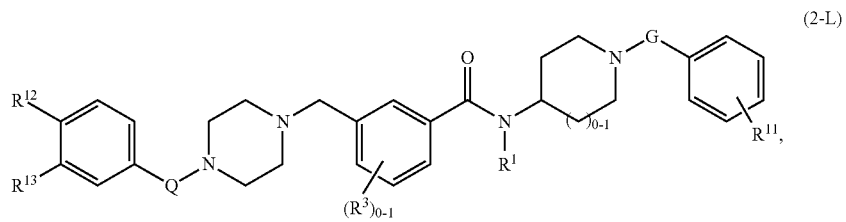

(2-L)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with respect to any of structural formulae (2-I), (2-V), (2-XIII) and (2-XVIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, no R$^3$ is substituted on the central phenyl moiety. In another embodiment, one R$^3$ (e.g., —Cl, —F, —CH$_3$, —C$_2$H$_5$, —C$_3$H$_7$) is substituted on the central phenyl moiety.

In certain embodiments, the presently disclosed compounds have the structural formula (2-LI):

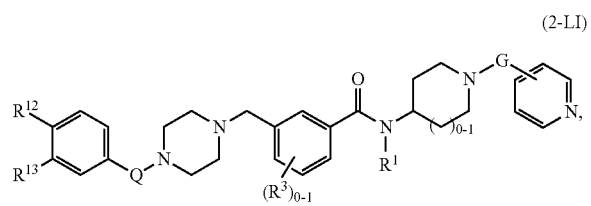

(2-LI)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (2-I), (2-V), (2-XIII) and (2-XVIII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyrido nitrogen is disposed in the para position relative to the G moiety; in another embodiment, the pyrido nitrogen is disposed in the meta position relative to the G moiety. In one embodiment, no R$^3$ is substituted on the central phenyl moiety. In another embodiment, one R$^3$ (e.g., —Cl, —F, —CH$_3$, —C$_2$H$_5$, —C$_3$H$_7$) is substituted on the central phenyl moiety.

In certain embodiments, the presently disclosed compounds have the structural formula (2-LII):

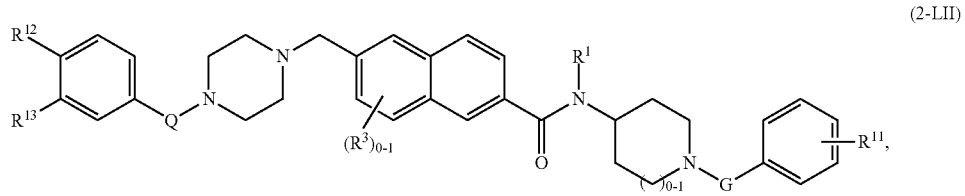

(2-LII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (2-I), (2-VI), (2-XIV) and (2-XVIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, no R$^3$ is substituted on the naphthyl moiety. In another embodiment, one R$^3$ (e.g., —Cl, —F, —CH$_3$, —C$_2$H$_5$, —C$_3$H$_7$) is substituted on the naphthyl moiety.

In certain embodiments, the presently disclosed compounds have the structural formula (2-LIII):

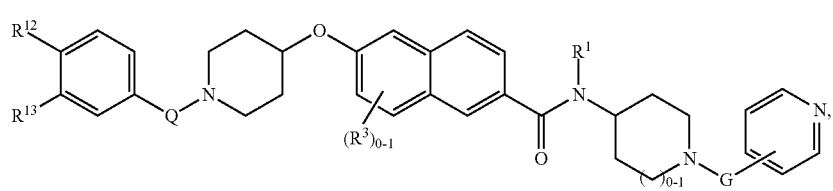

(2-LIII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to structural formulae (2-I), (2-VI), (2-XIV) and (2-XVIII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyrido nitrogen is disposed in the para position relative to the G moiety; in another embodiment, the pyrido nitrogen is disposed in the meta position relative to the G moiety. In one embodiment, no R$^3$ is substituted on the naphthyl moiety. In another embodiment, one R$^3$ (e.g., —Cl, —F, —CH$_3$, —C$_2$H$_5$, —C$_3$H$_7$) is substituted on the naphthyl moiety.

In certain embodiments, the presently disclosed compounds have the structural formula (2-LIV):

and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, no R$^3$ is substituted on the naphthyl moiety. In another embodiment, one R$^3$ (e.g., —Cl, —F, —CH$_3$, —C$_2$H$_5$, —C$_3$H$_7$) is substituted on the naphthyl moiety.

In certain embodiments, the presently disclosed compounds have the structural formula (2-LV):

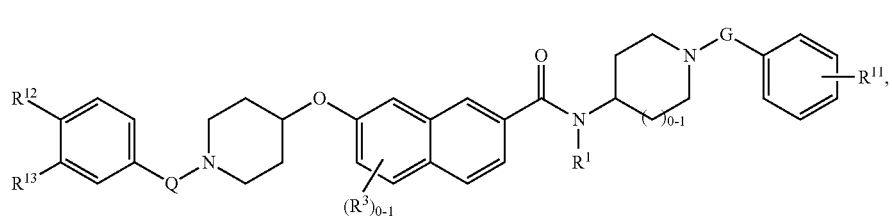

(2-LIV)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (2-I), (2-VII), (2-XV) and (2-XVIII);

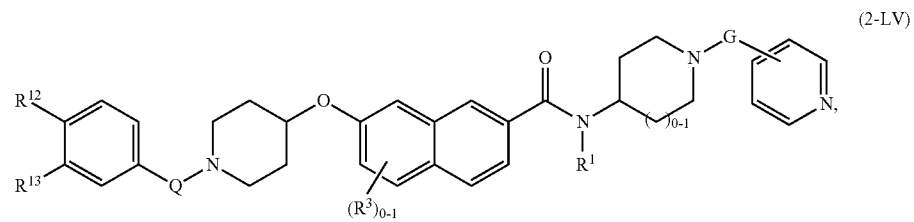

(2-LV)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to structural formulae (2-I), (2-VII), (2-XV) and (2-XVIII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyrido nitrogen is disposed in the para position relative to the G moiety; in another embodiment, the pyrido nitrogen is disposed in the meta position relative to the G moiety. In one embodiment, no R$^3$ is substituted on the naphthyl moiety. In another embodiment, one R$^3$ (e.g., —Cl, —F, —CH$_3$, —C$_2$H$_5$, —C$_3$H$_7$) is substituted on the naphthyl moiety.

In certain embodiments, the presently disclosed compounds have the structural formula (2-LVI):

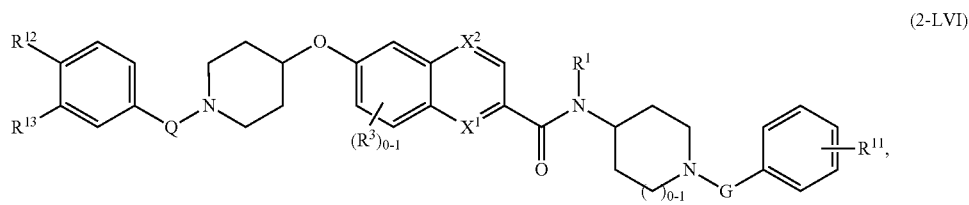

(2-LVI)

in which one of X$^1$ and X$^2$ is N and the other is a carbon; Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (2-I), (2-VIII), (2-XVI) and (2-XVIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, no R$^3$ is substituted on the quinolinyl moiety. In another embodiment, one R$^3$ (e.g., —Cl, —F, —CH$_3$, —C$_2$H$_5$, —C$_3$H$_7$) is substituted on the quinolinyl moiety.

In certain embodiments, the presently disclosed compounds have the structural formula (2-LVII):

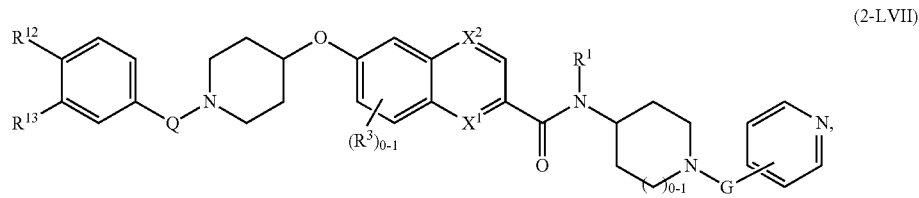

(2-LVII)

in which one of $X^1$ and $X^2$ is N and the other is a carbon; Q is —$CH_2$—, —C(O)— or a single bond; G is a single bond, —$CH_2$—, —C(O)—, —$S(O)_2$— or —C(O)—NH—; $R^1$ and $R^3$ are as described above with reference to structural formulae (2-I), (2-VIII), (2-XVI) and (2-XVIII); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the quinolinyl moiety. In another embodiment, one $R^3$ (e.g., —Cl, —F, —$CH_3$, —$C_2H_5$, —$C_3H_7$) is substituted on the quinolinyl moiety.

In certain embodiments, the presently disclosed compounds have the structural formula (2-LVIII):

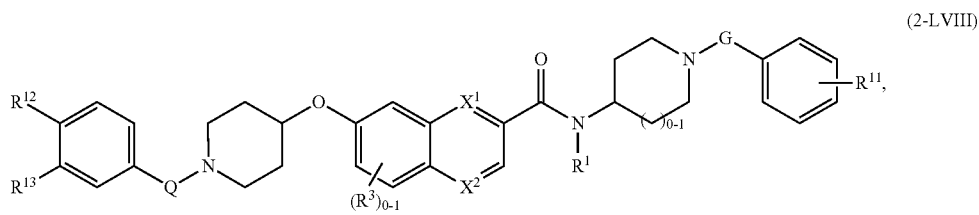

(2-LVIII)

in which one of $X^1$ and $X^2$ is N and the other is a carbon; Q is —$CH_2$—, —C(O)— or a single bond; G is a single bond, —$CH_2$—, —C(O)—, —$S(O)_2$— or —C(O)—NH—; $R^1$ and $R^3$ are as described above with reference to any of structural formulae (2-I), (2-IX), (2-XVII) and (2-XVIII); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the quinolinyl moiety. In another embodiment, one $R^3$ (e.g., —Cl, —F, —$CH_3$, —$C_2H_5$, —$C_3H_7$) is substituted on the quinolinyl moiety.

In certain embodiments, the presently disclosed compounds have the structural formula (2-LIX):

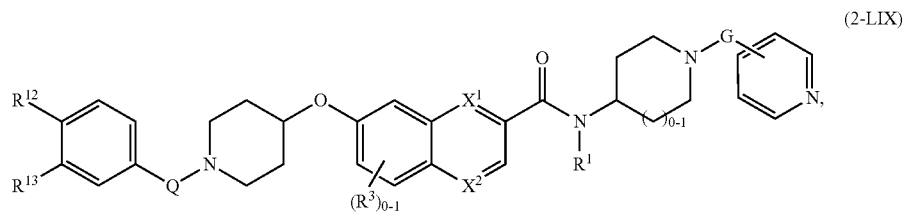

(2-LIX)

in which one of $X^1$ and $X^2$ is N and the other is a carbon; Q is —$CH_2$—, —C(O)— or a single bond; G is a single bond, —$CH_2$—, —C(O)—, —$S(O)_2$— or —C(O)—NH—; $R^1$ and $R^3$ are as described above with reference to structural formulae (2-I), (2-IX), (2-XVII) and (2-XVIII); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the quinolinyl moiety. In another embodiment, one $R^3$ (e.g., —Cl, —F, —$CH_3$, —$C_2H_5$, —$C_3H_7$) is substituted on the quinolinyl moiety.

In certain embodiments, the presently disclosed compounds have the structural formula (2-LX):

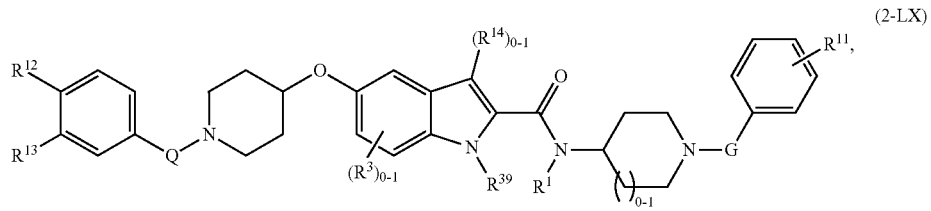

(2-LX)

in which Q is —$CH_2$—, —C(O)— or a single bond; G is a single bond, —$CH_2$—, —C(O)—, —$S(O)_2$— or —C(O)—NH—; $R^1$, $R^3$ and $R^{39}$ are as described above with reference to any of structural formulae (2-I), (2-X) and (2-XVIII); $R^{14}$ is as described above with reference to structural formulae (2-I), (2-X) and (2-XVIII) (e.g., absent, methyl or halo); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the benzo moiety. In another embodiment, one $R^3$ (e.g., —Cl, —F, —$CH_3$, —$C_2H_5$, —$C_3H_7$) is substituted on the benzo moiety.

Examples of compounds according to structural formula (2-I) include those listed in Table 2. These compounds can be made, for example using a procedure analogous to those described in U.S. Patent Application Publications nos. 2009/0163511, 2009/0170829, 2009/0186894 and 2009/0275609, and in U.S. patent application Ser. Nos. 12/695,861 and 13/194,810, each of which is hereby incorporated by reference in its entirety.

TABLE 2

| No. | Name | Structure |
|---|---|---|
| 2-1 | benzyl 8-(1-(4-cyanobenzyl)piperidin-4-ylcarbamoyl)-3,4-dihydro-1H-pyrido[4,3-b]indole-2(5H)-carboxylate | 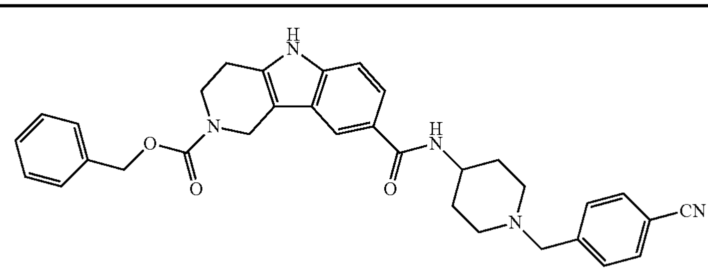 |

TABLE 2-continued

| No. | Name |
|---|---|
| 2-2 | benzyl 8-(1-(4-benzyl)piperidin-4-ylcarbamoyl)-3,4-dihydro-1H-pyrido[4,3-b]indole-2(5H)-carboxylate |
| 2-3 | benzyl 8-(1-(tert-butoxycarbonyl)piperidin-4-ylcarbamoyl)-3,4-dihydro-1H-pyrido[4,3-b]indole-2(5H)-carboxylate |
| 2-4 | 2-benzyl-N-(1-(4-cyanobenzyl)piperidin-4-yl)-2,3,4,5-tetrahydro-1H-pyrido[4,3-b]indole-8-carboxamide |
| 2-5 | 2-benzyl-N-(1-(4-trifluoromethylbenzyl)piperidin-4-yl)-2,3,4,5-tetrahydro-1N-pyrido[4,3-b]indole-8-carboxamide |
| 2-6 | tert-butyl 4-(2-(4-(trifluoromethyl)benzyl)-2,3,4,5-tetrahydro-1H-pyrido[4,3-b]indole-8-carboxamido)piperidine-1-carboxylate |

TABLE 2-continued

| No. | Name | Structure |
|-----|------|-----------|
| 2-7 | 2-benzyl-N-(1-(pyridin-4-ylmethyl)piperidin-4-yl)-2,3,4,5-tetrahydro-1H-pyrido[4,3-b]indole-8-carboxamide | 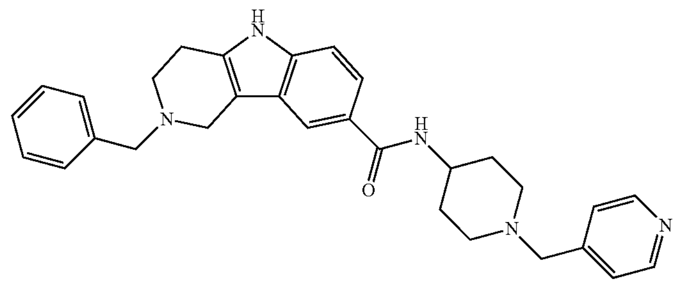 [SMILES: O=C(NC1CCN(Cc2ccncc2)CC1)c1ccc2[nH]c3c(c2c1)CN(Cc1ccccc1)CC3] |
| 2-8 | 2-(4-fluorobenzyl)-N-(1-(pyridin-3-ylmethyl)piperidin-4-yl)-2,3,4,5-tetrahydro-1H-pyrido[4,3-b]indole-8-carboxamide | 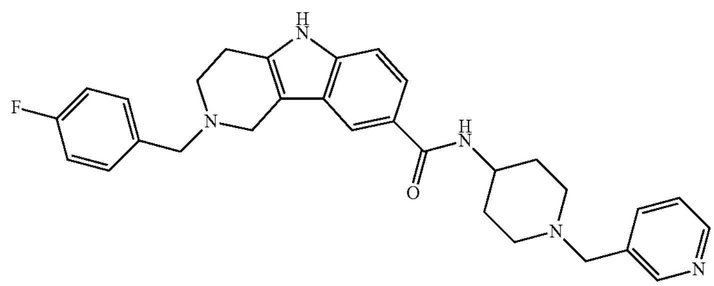 [SMILES: O=C(NC1CCN(Cc2cccnc2)CC1)c1ccc2[nH]c3c(c2c1)CN(Cc1ccc(F)cc1)CC3] |
| 2-9 | N-(1-(4-cyanobenzyl)piperidin-4-yl)-2-(4-fluorobenzyl)-2,3,4,5-tetrahydro-1H-pyrido[4,3-b]indole-8-carboxamide | 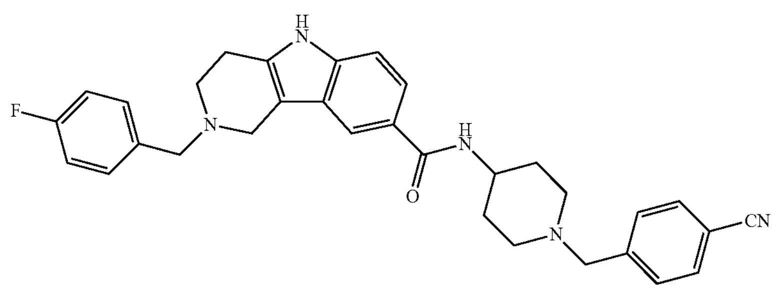 [SMILES: N#Cc1ccc(CN2CCC(NC(=O)c3ccc4[nH]c5c(c4c3)CN(Cc3ccc(F)cc3)CC5)CC2)cc1] |
| 2-10 | N-(1-(4-trifluoromethylbenzyl)piperidin-4-yl)-2-(4-fluorobenzyl)-2,3,4,5-tetrahydro-1H-pyrido[4,3-b]indole-8-carboxamide | 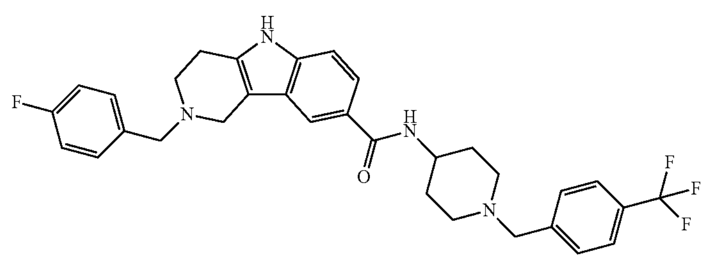 [SMILES: O=C(NC1CCN(Cc2ccc(C(F)(F)F)cc2)CC1)c1ccc2[nH]c3c(c2c1)CN(Cc1ccc(F)cc1)CC3] |
| 2-11 | N-(1-(pyridin-3-ylmethyl)piperidin-4-yl)-2-(4-(trifluoromethyl)benzyl)-2,3,4,5-tetrahydro-1H-pyrido[4,3-b]indole-8-carboxamide | 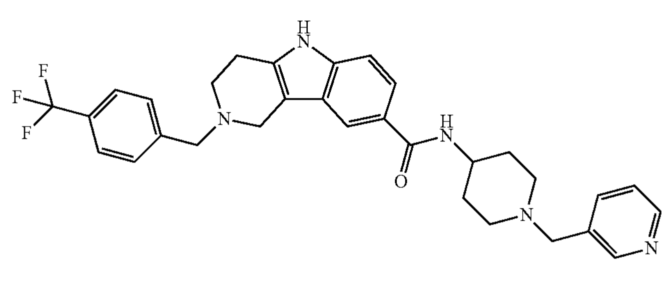 [SMILES: O=C(NC1CCN(Cc2cccnc2)CC1)c1ccc2[nH]c3c(c2c1)CN(Cc1ccc(C(F)(F)F)cc1)CC3] |

TABLE 2-continued

| No. | Name |
|---|---|
| 2-12 | N-(1-(4-cyanobenzyl)piperidin-4-yl)-2-(4-(trifluoromethyl)benzyl)-2,3,4,5-tetrahydro-1H-pyrido[4,3-b]indole-8-carboxamide |
| 2-13 | N-(1-(4-trifluoromethylbenzyl)piperidin-4-yl)-2-(4-(trifluoromethyl)benzyl)-2,3,4,5-tetrahydro-1H-pyrido[4,3-b]indole-8-carboxamide |
| 2-14 | N-(1-phenethylpiperidin-4-yl)-2-(4-(trifluoromethyl)benzyl)-2,3,4,5-tetrahydro-1H-pyrido[4,3-b]indole-8-carboxamide |
| 2-15 | N-(1-(4-fluorophenyl)piperidin-4-yl)-2-(4-(trifluoromethyl)benzyl)-2,3,4,5-tetrahydro-1H-pyrido[4,3-b]indole-8-carboxamide |
| 2-16 | N-(1-(4-cyanobenzyl)piperidin-4-yl)-5-methyl-2-(4-(trifluoromethyl)benzyl)-2,3,4,5-tetrahydro-1H-pyrido[4,3-b]indole-8-carboxamide |

TABLE 2-continued

| No. | Name | Structure |
|---|---|---|
| 2-17 | N-(1-(4-trifluoromethylbenzyl)piperidin-4-yl)-5-methyl-2-(4-(trifluoromethyl)benzyl)-2,3,4,5-tetrahydro-1H-pyrido[4,3-b]indole-8-carboxamide | 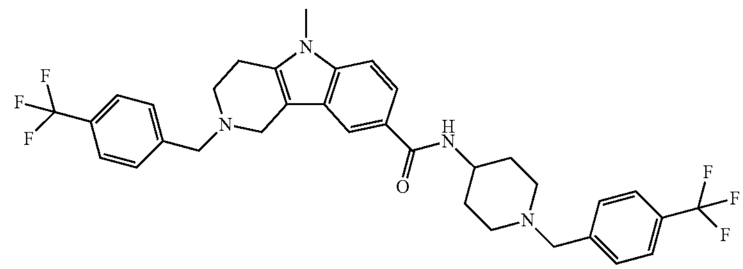 [SMILES: Cn1c2c(c3cc(C(=O)NC4CCN(Cc5ccc(C(F)(F)F)cc5)CC4)ccc31)CN(Cc1ccc(C(F)(F)F)cc1)CC2] |
| 2-18 | 5-methyl-N-(1-(pyridin-3-ylmethyl)piperidin-4-yl)-2-(4-(trifluoromethyl)benzyl)-2,3,4,5-tetrahydro-1H-pyrido[4,3-b]indole-8-carboxamide | 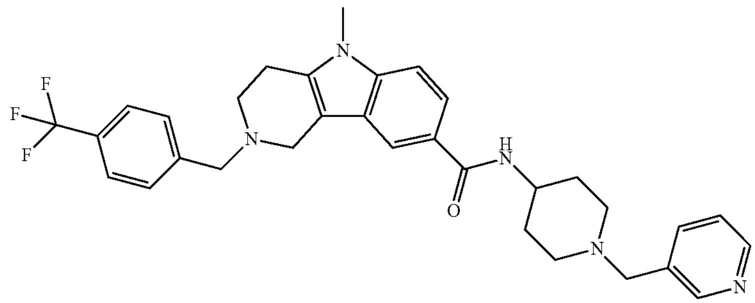 [SMILES: Cn1c2c(c3cc(C(=O)NC4CCN(Cc5cccnc5)CC4)ccc31)CN(Cc1ccc(C(F)(F)F)cc1)CC2] |
| 2-19 | N-(1-benzylpiperidin-4-yl)-2-(4-(trifluoromethyl)phenylsulfonyl)-2,3,4,5-tetrahydro-1H-pyrido[4,3-b]indole-8-carboxamide | 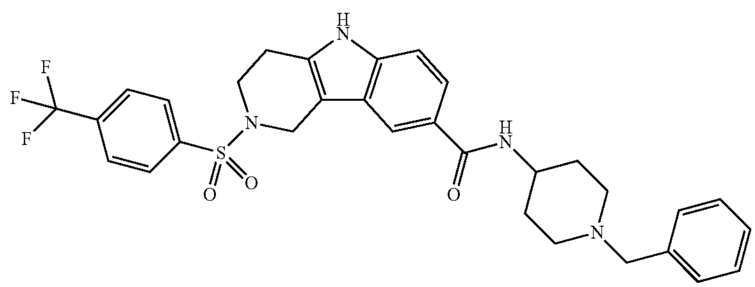 [SMILES: O=C(NC1CCN(Cc2ccccc2)CC1)c1ccc2[nH]c3c(c2c1)CN(S(=O)(=O)c1ccc(C(F)(F)F)cc1)CC3] |
| 2-20 | 5-acetyl-N-(1-(pyridin-3-ylmethyl)piperidin-4-yl)-2-(4-(trifluoromethyl)benzyl)-2,3,4,5-tetrahydro-1H-pyrido[4,3-b]indole-8-carboxamide | 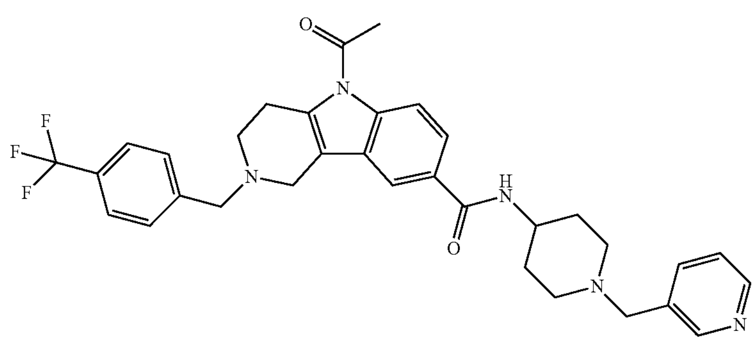 [SMILES: CC(=O)n1c2c(c3cc(C(=O)NC4CCN(Cc5cccnc5)CC4)ccc31)CN(Cc1ccc(C(F)(F)F)cc1)CC2] |
| 2-21 | N-(1-(4-cyanophenylsulfonyl)piperidin-4-yl)-2-(4-(trifluoromethyl)benzyl)-2,3,4,5-tetrahydro-1H-pyrido[4,3-b]indole-8-carboxamide | 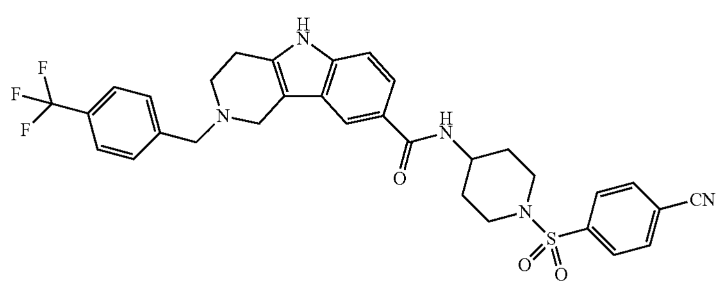 [SMILES: N#Cc1ccc(S(=O)(=O)N2CCC(NC(=O)c3ccc4[nH]c5c(c4c3)CN(Cc3ccc(C(F)(F)F)cc3)CC5)CC2)cc1] |

TABLE 2-continued

| No. | Name | Structure |
|---|---|---|
| 2-22 | N-(1-(pyridin-3-ylsulfonyl)piperidin-4-yl)-2-(4-(trifluoromethyl)benzyl)-2,3,4,5-tetrahydro-1H-pyrido[4,3-b]indole-8-carboxamide | 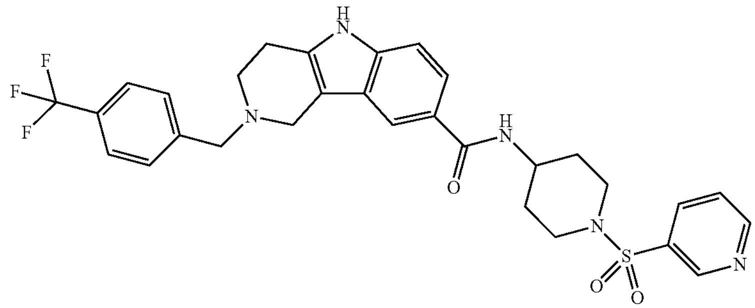 [SMILES: O=C(NC1CCN(S(=O)(=O)c2cccnc2)CC1)c1ccc2[nH]c3c(c2c1)CN(Cc1ccc(C(F)(F)F)cc1)CC3] |
| 2-23 | 2-(4-(trifluoromethyl)benzyl)-N-(1-(4-(trifluoromethyl)phenylsulfonyl)piperidin-4-yl)-2,3,4,5-tetrahydro-1H-pyrido[4,3-b]indole-8-carboxamide | 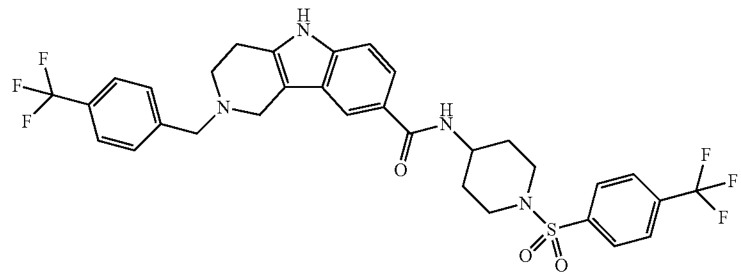 [SMILES: O=C(NC1CCN(S(=O)(=O)c2ccc(C(F)(F)F)cc2)CC1)c1ccc2[nH]c3c(c2c1)CN(Cc1ccc(C(F)(F)F)cc1)CC3] |
| 2-24 | N-(1-(4-cyanobenzyl)piperidin-4-yl)-2-(4-(trifluoromethyl)phenylsulfonyl)-2,3,4,5-tetrahydro-1H-pyrido[4,3-b]indole-8-carboxamide | 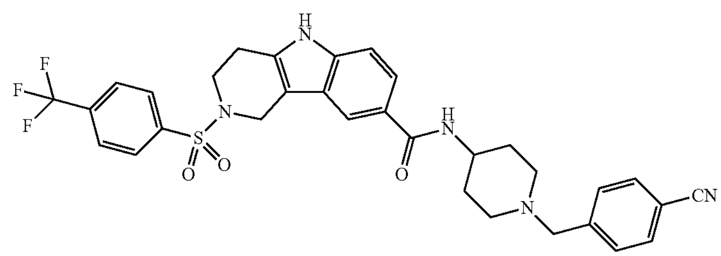 [SMILES: N#Cc1ccc(CN2CCC(NC(=O)c3ccc4[nH]c5c(c4c3)CN(S(=O)(=O)c3ccc(C(F)(F)F)cc3)CC5)CC2)cc1] |
| 2-25 | N-(1-(4-cyanobenzyl)piperidin-4-yl)-2-(4-cyanophenylsulfonyl)-2,3,4,5-tetrahydro-1H-pyrido[4,3-b]indole-8-carboxamide | 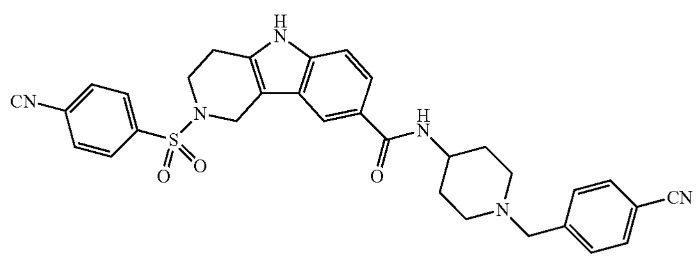 |
| 2-26 | N-(1-(4-cyanobenzyl)piperidin-4-yl)-2-(pyridin-3-ylsulfonyl)-2,3,4,5-tetrahydro-1H-pyrido[4,3-b]indole-8-carboxamide | 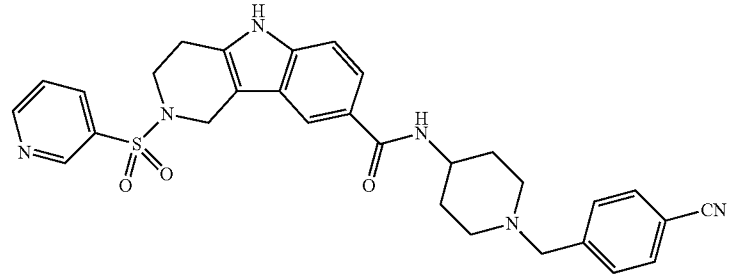 [SMILES: N#Cc1ccc(CN2CCC(NC(=O)c3ccc4[nH]c5c(c4c3)CN(S(=O)(=O)c3cccnc3)CC5)CC2)cc1] |

TABLE 2-continued

| No. | Name |
|---|---|
| 2-27 | N-(1-(4-cyanophenylcarbamoyl)piperidin-4-yl)-2-(4-(trifluoromethyl)benzyl)-2,3,4,5-tetrahydro-1H-pyrido[4,3-b]indole-8-carboxamide |
| 2-28 | N-(1-(4-fluorophenylsulfonyl)piperidin-4-yl)-2-(4-(trifluoromethyl)benzyl)-2,3,4,5-tetrahydro-1H-pyrido[4,3-b]indole-8-carboxamide |
| 2-29 | N-(1-(3-cyanophenylsulfonyl)piperidin-4-yl)-2-(4-(trifluoromethyl)benzyl)-2,3,4,5-tetrahydro-1H-pyrido[4,3-b]indole-8-carboxamide |
| 2-30 | 2-(4-(trifluoromethyl)benzyl)-N-(1-(3-(trifluoromethyl)phenylsulfonyl)piperidin-4-yl)-2,3,4,5-tetrahydro-1H-pyrido[4,3-b]indole-8-carboxamide |
| 2-31 | N-(1-(3-fluorophenylcarbamoyl)piperidin-4-yl)-2-(4-(trifluoromethyl)benzyl)-2,3,4,5-tetrahydro-1H-pyrido[4,3-b]indole-8-carboxamide |

TABLE 2-continued

| No. | Name | Structure |
|---|---|---|
| 2-32 | N-(1-(4-chlorophenylsulfonyl)piperidin-4-yl)-2-(4-(trifluoromethyl)benzyl)-2,3,4,5-tetrahydro-1H-pyrido[4,3-b]indole-8-carboxamide | 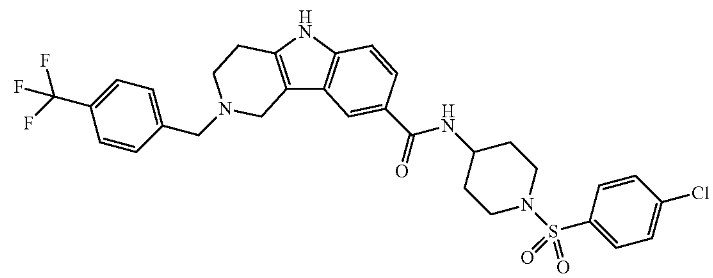 [SMILES: O=C(NC1CCN(S(=O)(=O)c2ccc(Cl)cc2)CC1)c1ccc2[nH]c3c(c2c1)CN(Cc1ccc(C(F)(F)F)cc1)CC3] |
| 2-33 | 2-(4-(trifluoromethyl)benzyl)-N-(1-(4-(trifluoromethyl)phenylcarbamoyl)piperidin-4-yl)-2,3,4,5-tetrahydro-1H-pyrido[4,3-b]indole-8-carboxamide | 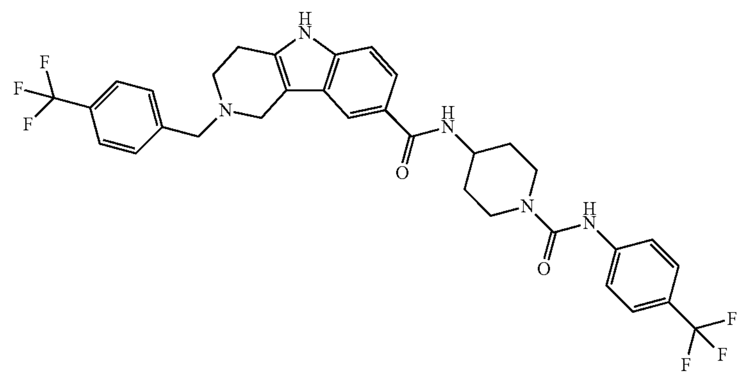 [SMILES: O=C(NC1CCN(C(=O)Nc2ccc(C(F)(F)F)cc2)CC1)c1ccc2[nH]c3c(c2c1)CN(Cc1ccc(C(F)(F)F)cc1)CC3] |
| 2-34 | N-(1-(4-cyanobenzyl)piperidin-4-yl)-2-(4-fluorophenyl)-2,3,4,5-tetrahydro-1H-pyrido[4,3-b]indole-8-carboxamide | 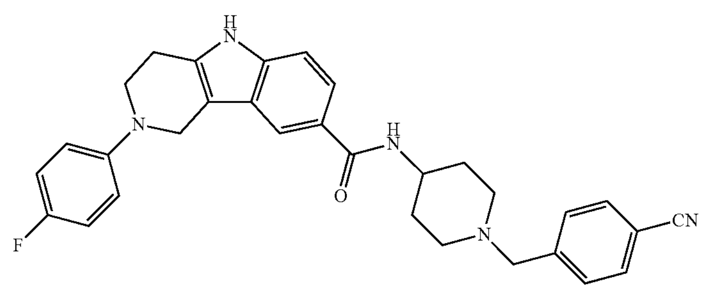 [SMILES: N#Cc1ccc(CN2CCC(NC(=O)c3ccc4[nH]c5c(c4c3)CN(c3ccc(F)cc3)CC5)CC2)cc1] |
| 2-35 | 2-(4-fluorophenyl)-N-(1-(4-fluorophenylsulfonyl)piperidin-4-yl)-2,3,4,5-tetrahydro-1H-pyrido[4,3-b]indole-8-carboxamide | 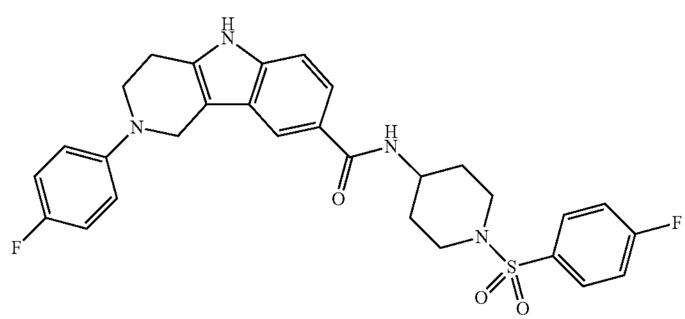 [SMILES: O=C(NC1CCN(S(=O)(=O)c2ccc(F)cc2)CC1)c1ccc2[nH]c3c(c2c1)CN(c1ccc(F)cc1)CC3] |
| 2-36 | 2-(4-fluorophenyl)-N-(1-(pyridin-3-ylmethyl)piperidin-4-yl)-2,3,4,5-tetrahydro-1H-pyrido[4,3-b]indole-8-carboxamide | 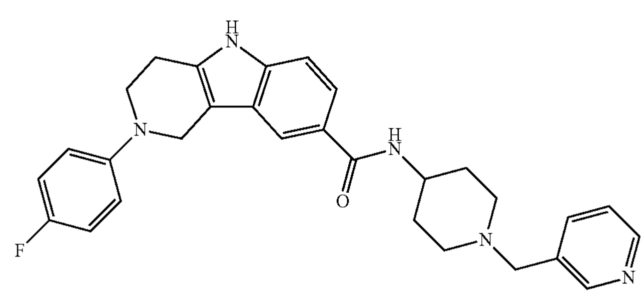 [SMILES: O=C(NC1CCN(Cc2cccnc2)CC1)c1ccc2[nH]c3c(c2c1)CN(c1ccc(F)cc1)CC3] |

TABLE 2-continued

| No. | Name | Structure |
|---|---|---|
| 2-37 | 2-(4-fluorophenyl)-N-(1-(4-(trifluoromethyl)benzyl)piperidin-4-yl)-2,3,4,5-tetrahydro-1H-pyrido[4,3-b]indole-8-carboxamide | 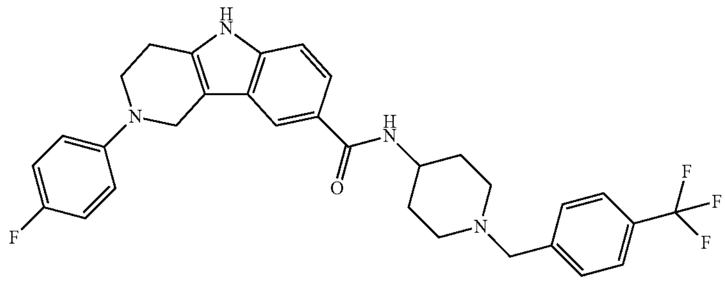 [SMILES: O=C(NC1CCN(Cc2ccc(C(F)(F)F)cc2)CC1)c1ccc2[nH]c3c(c2c1)CN(c1ccc(F)cc1)CC3] |
| 2-38 | tert-butyl 4-(2-(4-fluorophenyl)-2,3,4,5-tetrahydro-1H-pyrido[4,3-b]indole-8-carboxamido)piperidine-1-carboxylate | 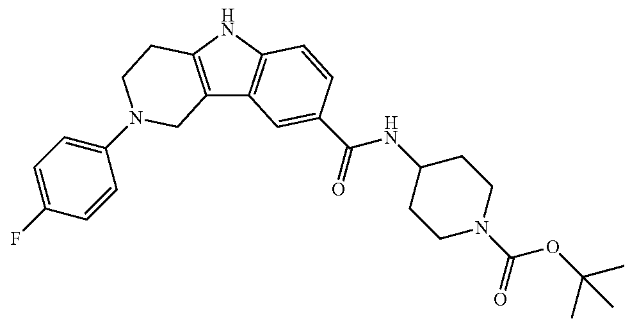 [SMILES: CC(C)(C)OC(=O)N1CCC(NC(=O)c2ccc3[nH]c4c(c3c2)CN(c2ccc(F)cc2)CC4)CC1] |
| 2-39 | N-(1-(4-fluorobenzoyl)piperidin-4-yl)-2-(4-fluorophenyl)-2,3,4,5-tetrahydro-1H-pyrido[4,3-b]indole-8-carboxamide | 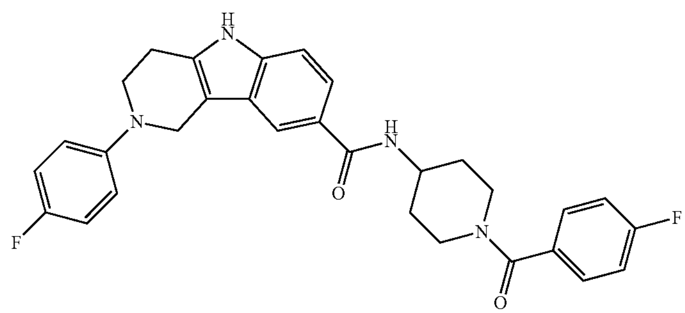 [SMILES: O=C(NC1CCN(C(=O)c2ccc(F)cc2)CC1)c1ccc2[nH]c3c(c2c1)CN(c1ccc(F)cc1)CC3] |
| 2-40 | 2-(4-fluorophenyl)-N-(1-nicotinoylpiperidin-4-yl)-2,3,4,5-tetrahydro-1H-pyrido[4,3-b]indole-8-carboxamide | 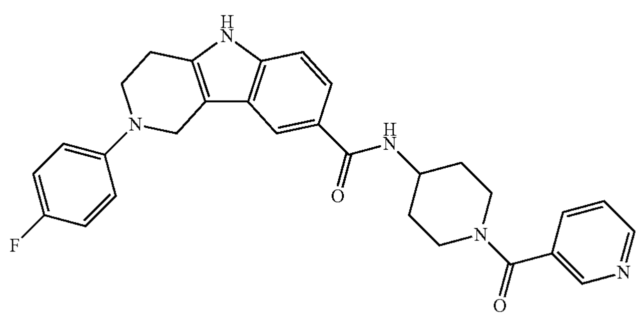 [SMILES: O=C(NC1CCN(C(=O)c2cccnc2)CC1)c1ccc2[nH]c3c(c2c1)CN(c1ccc(F)cc1)CC3] |
| 2-41 | 2-(4-fluorophenyl)-N-(1-(4-(trifluoromethyl)benzoyl)piperidin-4-yl)-2,3,4,5-tetrahydro-1H-pyrido[4,3-b]indole-8-carboxamide | 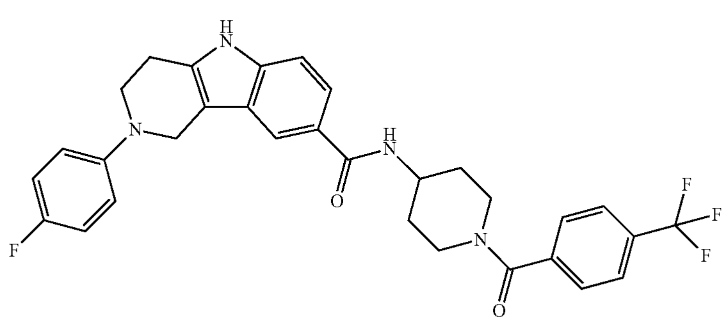 [SMILES: O=C(NC1CCN(C(=O)c2ccc(C(F)(F)F)cc2)CC1)c1ccc2[nH]c3c(c2c1)CN(c1ccc(F)cc1)CC3] |

TABLE 2-continued

| No. | Name |
|---|---|
| 2-42 | N-(1-nicotinoylpiperidin-4-yl)-2-(4-(trifluoromethyl)benzyl)-2,3,4,5-tetrahydro-1H-pyrido[4,3-b]indole-8-carboxamide |
| 2-43 | tert-butyl 4-(2-(4-carbamoylbenzyl)-2,3,4,5-tetrahydro-1H-pyrido[4,3-b]indole-8-carboxamido)piperidine-1-carboxylate |
| 2-44 | 2-(4-carbamoylbenzyl)-N-(1-(4-cyanobenzyl)piperidin-4-yl)-2,3,4,5-tetrahydro-1H-pyrido[4,3-b]indole-8-carboxamide |
| 2-45 | 2-(4-carbamoylbenzyl)-N-(1-(pyridin-4-ylmethyl)piperidin-4-yl)-2,3,4,5-tetrahydro-1H-pyrido[4,3-b]indole-8-carboxamide |
| 2-46 | 2-(4-carbamoylbenzyl)-N-(1-isonicotinoylpiperidin-4-yl)-2,3,4,5-tetrahydro-1H-pyrido[4,3-b]indole-8-carboxamide |

TABLE 2-continued

| No. | Name |
|---|---|
| 2-47 | 2-(4-carbamoylbenzyl)-N-(1-(4-(trifluoromethyl)benzyl)piperidin-4-yl)-2,3,4,5-tetrahydro-1H-pyrido[4,3-b]indole-8-carboxamide |
| 2-48 | 2-(4-carbamoylbenzyl)-N-(1-(4-fluorobenzyl)piperidin-4-yl)-2,3,4,5-tetrahydro-1H-pyrido[4,3-b]indole-8-carboxamide |
| 2-49 | 2-(4-carbamoylbenzyl)-N-(1-(4-carbamoylbenzyl)piperidin-4-yl)-2,3,4,5-tetrahydro-1H-pyrido[4,3-b]indole-8-carboxamide |
| 2-50 | N-(1-(pyridin-4-ylmethyl)piperidin-4-yl)-2-(4-(trifluoromethyl)benzyl)-2,3,4,5-tetrahydro-1H-pyrido[4,3-b]indole-8-carboxamide |
| 2-51 | N-(1-isonicotinoylpiperidin-4-yl)-2-(4-(trifluoromethyl)benzyl)-2,3,4,5-tetrahydro-1H-pyrido[4,3-b]indole-8-carboxamide |
| 2-52 | N-(1-(4-carbamoylbenzyl)piperidin-4-yl)-2-(4-(trifluoromethyl)benzyl)-2,3,4,5-tetrahydro-1H-pyrido[4,3-b]indole-8-carboxamide |

TABLE 2-continued

| No. | Name |
|---|---|
| 2-53 | N-(1-((1-methyl-1H-imidazol-4-yl)methyl)piperidin-4-yl)-2-(4-(trifluoromethyl)benzyl)-2,3,4,5-tetrahydro-1H-pyrido[4,3-b]indole-8-carboxamide |
| 2-54 | N-(1-(oxazol-4-ylmethyl)piperidin-4-yl)-2-(4-(trifluoromethyl)benzyl)-2,3,4,5-tetrahydro-1H-pyrido[4,3-b]indole-8-carboxamide |
| 2-55 | 4-((4-benzylpiperazin-1-yl)methyl)-N-(1-benzylpiperidin-4-yl)benzamide |
| 2-56 | N-(1-benzylpiperidin-4-yl)-4-((4-(cyclohexylmethyl)piperazin-1-yl)methyl)benzamide |
| 2-57 | N-(1-benzylpiperidin-4-yl)-4-((4-(5-(trifluoromethyl)pyridin-2-yl)piperazin-1-yl)methyl)benzamide |
| 2-58 | N-(1-benzylpiperidin-4-yl)-4-((4-(pyridin-2-yl)piperazin-1-yl)methyl)benzamide |
| 2-59 | 4-((4-benzylpiperazin-1-yl)methyl)-N-(1-(pyridin-4-ylmethyl)piperidin-4-yl)benzamide |
| 2-60 | 4-((4-benzylpiperazin-1-yl)methyl)-N-(1-(pyridin-3-ylmethyl)piperidin-4-yl)benzamide |

TABLE 2-continued

| No. | Name | Structure |
|---|---|---|
| 2-61 | 4-((4-benzylpiperazin-1-yl)methyl)-N-(1-(4-cyanobenzyl)piperidin-4-yl)benzamide | 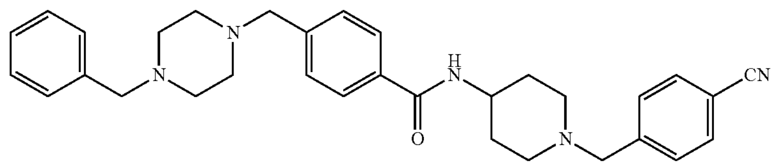 [SMILES: N#Cc1ccc(CN2CCC(NC(=O)c3ccc(CN4CCN(Cc5ccccc5)CC4)cc3)CC2)cc1] |
| 2-62 | 4-((4-benzylpiperazin-1-yl)methyl)-N-(1-(4-trifluoromethylbenzyl)piperidin-4-yl)benzamide | 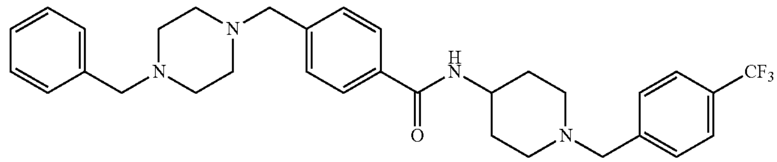 [SMILES: O=C(NC1CCN(Cc2ccc(C(F)(F)F)cc2)CC1)c1ccc(CN2CCN(Cc3ccccc3)CC2)cc1] |
| 2-63 | N-(1-benzylpiperidin-4-yl)-6-(1-(4-(trifluoromethyl)benzyl)piperidin-4-yloxy)-2-naphthamide | 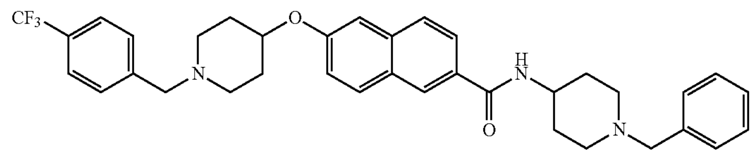 [SMILES: O=C(NC1CCN(Cc2ccccc2)CC1)c1ccc2cc(OC3CCN(Cc4ccc(C(F)(F)F)cc4)CC3)ccc2c1] |
| 2-64 | N-(1-benzylpiperidin-4-yl)-6-(1-(4-cyanobenzyl)piperidin-4-yloxy)-2-naphthamide | 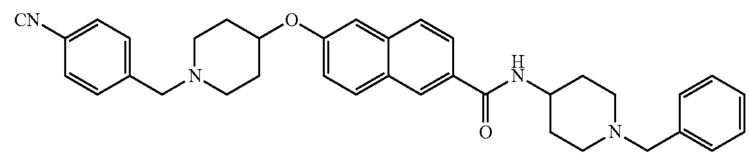 |
| 2-65 | N-(1-benzylpiperidin-4-yl)-6-(1-(4-(trifluoromethyl)phenyl)piperidin-4-yloxy)-2-naphthamide | 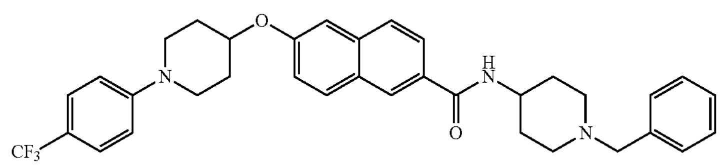 [SMILES: O=C(NC1CCN(Cc2ccccc2)CC1)c1ccc2cc(OC3CCN(c4ccc(C(F)(F)F)cc4)CC3)ccc2c1] |
| 2-66 | tert-butyl 4-(7-(1-(4-(trifluoromethyl)phenyl)piperidin-4-yloxy)-2-naphthamido)piperidine-1-carboxylate | 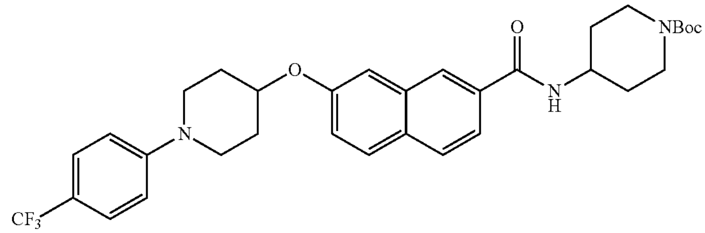 [SMILES: CC(C)(C)OC(=O)N1CCC(NC(=O)c2ccc3ccc(OC4CCN(c5ccc(C(F)(F)F)cc5)CC4)cc3c2)CC1] |
| 2-67 | tert-butyl 4-(6-(1-(4-(trifluoromethyl)phenyl)piperidin-4-yloxy)quinoline-3-carboxamido)piperidine-1-carboxylate | 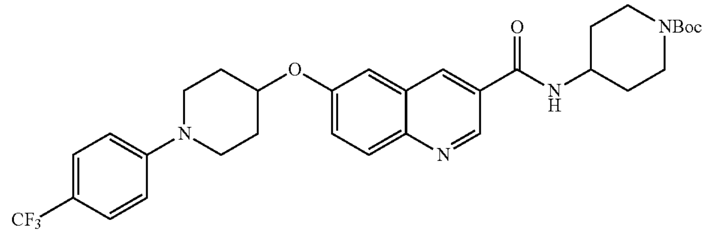 [SMILES: CC(C)(C)OC(=O)N1CCC(NC(=O)c2cnc3ccc(OC4CCN(c5ccc(C(F)(F)F)cc5)CC4)cc3c2)CC1] |
| 2-68 | N-(piperidin-4-yl)-6-(1-(4-(trifluoromethyl)phenyl)piperidin-4-yloxy)quinoline-3-carboxamide | 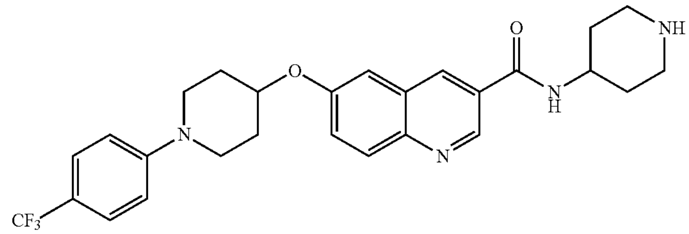 [SMILES: O=C(NC1CCNCC1)c1cnc2ccc(OC3CCN(c4ccc(C(F)(F)F)cc4)CC3)cc2c1] |

TABLE 2-continued

| No. | Name |
|---|---|
| 2-69 | N-(1-(4-cyanobenzyl)piperidin-4-yl)-6-(1-(4-(trifluoromethyl)phenyl)piperidin-4-yloxy)quinoline-3-carboxamide |
| 2-70 | N-(1-(4-(trifluoromethyl)benzyl)piperidin-4-yl)-6-(1-(4-(trifluoromethyl)phenyl)piperidin-4-yloxy)quinoline-3-carboxamide |
| 2-71 | N-(1-benzylpiperidin-4-yl)-6-(1-(4-(trifluoromethyl)phenyl)piperidin-4-yloxy)quinoline-3-carboxamide |
| 2-72 | N-(1-benzylpiperidin-4-yl)-5-(1-(4-(trifluoromethyl)phenyl)piperidin-4-yloxy)-1H-indole-2-carboxamide |

Another aspect of the disclosure provides compounds having structural formula (3-I):

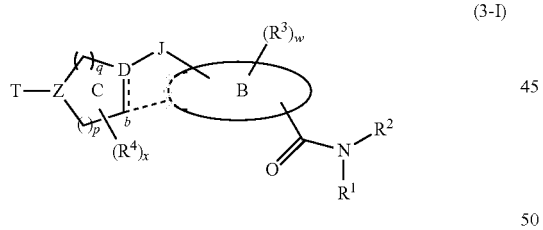

(3-I)

and pharmaceutically acceptable salts, and N-oxides thereof (and solvates and hydrates thereof), wherein ring system "B" is -(aryl or heteroaryl)-;
ring system "C" is an azacycloalkyl ring in which
D is C, CH, CR$^4$, or N,
Z is CH, CR$^4$ or N, provided that at least one of D and Z is N, and the bond between D and the carbon at the position denoted by "b" is a single bond or a double bond;
J is —O—, —N(R$^{38}$)—C(O)—, —C(O)— or absent, provided that:
(a) when J is —O— or —N(R$^{38}$)—C(O)—, D is CH or CR$^4$, Z is N, J links ring systems "B" and "C", the dotted line connecting ring system "B" to the carbon denoted by "b" in ring system "C" is absent, and the bond between D and the carbon atom at the position denoted by "b" is a single bond, (b) when J is —C(O)—, J links ring systems "B" and "C", the dotted line connecting ring "B" to the carbon denoted by "b" in ring system "C" is absent, and the bond between D and the carbon atom at the position denoted by "b" is a single bond,
(c) when J is absent, the dotted line connecting ring system "B" to the carbon denoted by "b" in ring system "C" signifies that ring systems "B" and "C" are fused through the bond connecting D and the carbon atom denoted by "b" in ring system "C", and
(d) when J is —O—, the ring system denoted by "B" is other than phenyl, that is, the compound does not have the formula

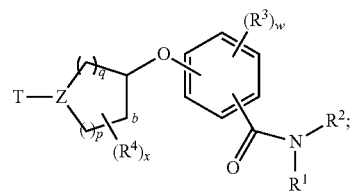

R$^1$ is H, —(C$_1$-C$_4$ alkyl), —C(O)—(C$_1$-C$_4$ alkyl) or —C(O)O—(C$_1$-C$_4$ alkyl), and
R$^2$ is -Hca, -Cak-N(R$^9$)-G-R$^{22}$ or —(C$_2$-C$_8$ alkyl)-N(R$^9$)—R$^{24}$ in which one or two (e.g., non-adjacent) carbons of the (C$_2$-C$_8$ alkyl) are optionally replaced by —O—, —S— or —N(R$^9$)—, and R$^{24}$ is —R$^{23}$, -G-R$^{23}$ or —C(O)O—($C_1$-$C_6$ alkyl), provided that two consecutive carbons of the ($C_2$-$C_8$ alkyl) are not replaced by —O—, or $R^1$ and $R^2$ together with the nitrogen to which they are attached come together to form -Hca;

each $R^3$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN;

w is 0, 1, 2, 3 or 4;

each $R^4$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^4$ on the same carbon optionally combine to form oxo;

p is 0, 1, 2, 3 or 4;

q is 0, 1, 2, 3 or 4, provided that the sum of p and q is 1, 2, 3 or 4;

x is 0 or an integer ≤p+q, wherein when D or Z is $CR^4$, the $R^4$ of D or Z is one of the x $R^4$ groups on ring system "C";

T is —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$ or

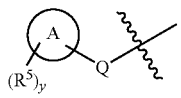

in which

Q is —S(O)$_2$—, L, or ($C_0$-$C_3$ alkyl)-, in which each carbon of the —($C_0$-$C_3$ alkyl)- is optionally and independently substituted with one or two $R^{16}$;

the ring denoted by "A" is heteroaryl, aryl, cycloalkyl or heterocycloalkyl;

each $R^5$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN; and y is 0, 1, 2, 3 or 4;

in which each L is independently selected from —$NR^9$C(O)O—, —OC(O)$NR^9$—, —$NR^9$C(O)—$NR^9$—, —$NR^9$C(O)S—, —SC(O)$NR^9$—, —$NR^9$C(O)—, —C(O)$NR^9$—, —$NR^9$C(S)O—, —OC(S)$NR^9$—, —$NR^9$C(S)—$NR^9$—, —$NR^9$C(S)S—, —SC(S)$NR^9$—, —$NR^9$C(S)—, —C(S)$NR^9$—, —SC(O)$NR^9$—, —$NR^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —$NR^9$C($NR^2$)$NR^9$—, —$NR^9SO_2$—, —$SO_2NR^9$— and —$NR^9SO_2NR^9$—;

each $R^6$, $R^7$, $R^8$ and $R^{10}$ is independently selected from H, —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-($C_0$-$C_6$ alkyl), —($C_0$-$C_6$ alkyl)-$NR^9$—($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), each $R^9$ is independently selected from —H, —($C_1$-$C_4$ alkyl), —C(O)—($C_1$-$C_4$ alkyl) and —C(O)O—($C_1$-$C_4$ alkyl), each G is independently —S(O)$_2$—, L, or —($C_0$-$C_3$ alkyl)-, in which each carbon of the —($C_0$-$C_3$ alkyl)- is optionally and independently substituted with one or two $R^{16}$, each $R^{16}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, or two $R^{16}$ on the same carbon combine to form oxo, $R^{38}$ is independently selected from —H, —($C_1$-$C_4$ alkyl), —C(O)—($C_1$-$C_4$ alkyl) and —C(O)O—($C_1$-$C_4$ alkyl), $R^{22}$ and $R^{23}$ are each independently Ar or Het, each Ar is an optionally substituted aryl, each Het is an optionally substituted heteroaryl, each Cak is an optionally substituted cycloalkyl, each Hca is an optionally substituted heterocycloalkyl, and each alkyl is optionally substituted.

Various embodiments of compounds of structural formula (2-I) suitable for use in the methods described herein are described below. Information regarding certain of these compounds can also be found in U.S. Patent Application Publication no. 2009/0275609, which is hereby incorporated by reference in its entirety.

In certain embodiments of the presently disclosed compounds of structural formula (3-I), J is —O— or —N($R^{38}$)—C(O)— and D is CH or C— substituted with one of the x $R^4$ groups. In other embodiments of the presently disclosed compounds of structural formula (3-I), J is —C(O)—. In certain such embodiments, D is N.

In certain embodiments of the presently disclosed compounds of structural formula (3-I), Z is N and D is C, CH or C— substituted with one of the x $R^4$ groups. In other embodiments, D is N and Z is CH or C— substituted with one of the x $R^4$ groups. In further embodiments, D is N and Z is N.

In certain embodiments of the presently disclosed compounds of structural formula (3-I), $R^{38}$ is —H. In other embodiments, $R^{38}$ is —($C_1$-$C_4$ alkyl), for example methyl, ethyl or propyl. In other embodiments, $R^{38}$ is —C(O)—($C_1$-$C_4$ alkyl), for example acetyl. In other embodiments, $R^{38}$ is —C(O)—O—($C_1$-$C_4$ alkyl)-, for example —C(O)—O-t-butyl. In certain embodiments, no alkyl of $R^{38}$ is substituted with an aryl-, heteroaryl-, cycloalkyl- or heterocycloalkyl-containing group.

In certain embodiments of the presently disclosed compounds of structural formula (3-I) as described above, ring system "B" is not fused to ring system "C" at the position denoted by "b," so that the compounds have structural formula (3-II):

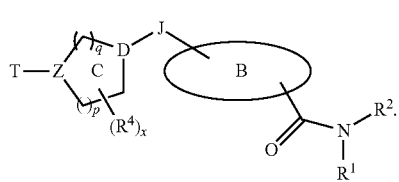

(3-II)

In other embodiments, ring system "B" is fused to ring system "C" at the position denoted by "b"; for example, the compounds can have structural formula (3-III):

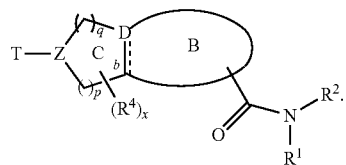

(3-III)

In certain embodiments of the presently disclosed compounds of structural formula (3-I), "B" represents

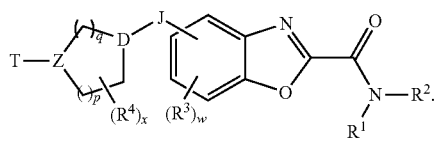

in which the benzo ring is linked or fused to ring system "C" and the dotted line is not a bond but merely indicates that the benzo ring is fused to ring system "C" or not. Examples of such compounds wherein ring system "B" is not fused to ring system "C" are represented by the formula

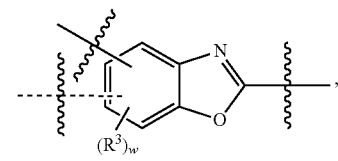

In certain such embodiments, J is —O—, Z is N and D is CH or C— substituted by one of the x $R^4$.

In other embodiments of the presently disclosed compounds of structural formula (3-I), "B" represents

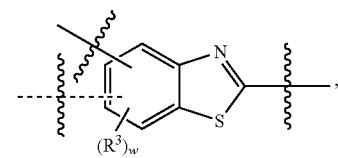

in which the benzo ring is linked or fused to ring system "C" and the dotted line is not a bond but merely indicates that the benzo ring is fused to ring system "C" or not. Examples of such compounds wherein ring system "B" is not fused to ring system "C" are represented by the formula

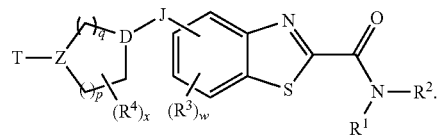

In certain such embodiments, J is —O—, Z is N and D is CH or C— substituted by one of the x $R^4$.

In other embodiments of the presently disclosed compounds of structural formula (3-I), "B" represents

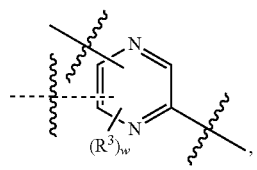

in which the pyrazine ring is linked or fused to ring system "C" and the dotted line is not a bond but merely indicates that the pyrazine ring is fused to ring system "C" or not. Examples of such compounds wherein ring system "B" is not fused to ring system "C" are represented by the formula

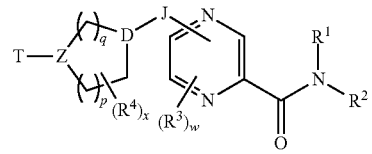

In certain such embodiments, J is —O—, Z is N and D is CH or C— substituted by one of the x $R^4$.

In other embodiments of the presently disclosed compounds of structural formula (3-I), "B" represents

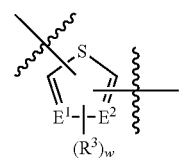

and is not fused to ring system "C", one of $E^1$ and $E^2$ is N and the other is CH, C substituted with the $R^3$, C substituted with the -J-(ring system "C"), or C substituted with the —C(O)—$NR^1R^2$), w is 0 or 1. In certain such embodiments, J is —O—, Z is N and D is CH or C— substituted by one of the x $R^4$.

In other embodiments of the presently disclosed compounds of structural formula (3-I), ring system "B" is

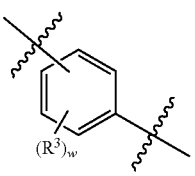

and is not fused to ring system "C". In such embodiments, J is other than O. In certain such embodiments, J is —C(O)—, Z is N, CH or C— substituted by one of the x $R^4$ and D is N. In other such embodiments, J is —N($R^{38}$)—C(O)—, Z is N and D is CH or C— substituted by one of the x $R^4$.

In certain embodiments according to structural formulae (3-I)-(3-III), the sum of p and q is 2 or 3. For example, in one embodiment, the sum of p and q is 2 (e.g., p is 1 and q is 1). In another embodiment, the sum of p and q is 3 (e.g., p is 1 and q is 2).

In other embodiments of the presently disclosed compounds of structural formula (3-I), ring system "B" is a phenyl and is fused to ring system "C" (3-I.e., J is absent), Z is N, D is C, q is 2 and p is 1, such that the compound has structural formula (3-IV):

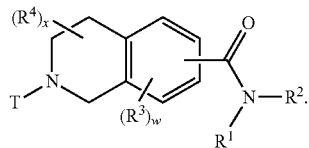

(3-IV)

In certain embodiments of the presently disclosed compounds of structural formulae (3-I)-(3-IV), T is

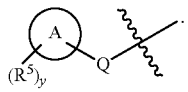

In such embodiments, Q is —S(O)$_2$—, L or —(C$_0$-C$_3$ alkyl)- in which each carbon of the (C$_0$-C$_3$ alkyl) is optionally and independently substituted with one or two $R^{16}$, in which each $R^{16}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of $R^{16}$ on the same carbon combine to form oxo. In certain embodiments, each $R^{16}$ is independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two $R^{16}$ on the same carbon optionally combine to form an oxo, in which each $R^7$, $R^8$ and $R^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl), and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in particular compounds, each $R^{16}$ is —(C$_1$-C$_3$ alkyl), —(C$_1$-C$_3$ haloalkyl), —(C$_0$-C$_3$ alkyl)-L-$R^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, and two $R^{16}$ on the same carbon optionally combine to form an oxo, in which each $R^7$, $R^8$ and $R^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, Q has at most one $R^{16}$ or oxo substituted thereon. Q can be, for example, an unsubstituted —(C$_0$-C$_3$ alkyl)-. In other embodiments, Q is a (C$_1$-C$_3$ alkyl) having as its only substitution a single oxo group. For example, in certain embodiments, Q is —CH$_2$—; a single bond; —S(O)$_2$—; —C(O)—; or —CH(CH$_3$)—.

In certain embodiments of the compounds of structural formulae (3-I)-(3-IV), the

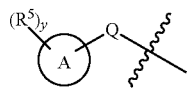

moiety is

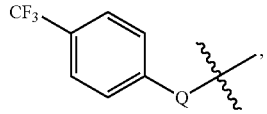

for example, p-(trifluoromethyl)phenyl. In other embodiments, the

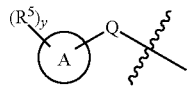

moiety is

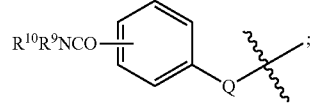

in one such embodiment, Q is a single bond.

The number of substituents on the ring system denoted by "A", y, is 0, 1, 2, 3 or 4. For example, in some embodiments of the presently disclosed compounds of structural formulae (3-I)-(3-IV), y is 0, 1, 2 or 3, such as 1. In one embodiment, y is not zero and at least one $R^5$ is halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ or —C(O)—Hca wherein the Hca contains a ring nitrogen atom through which it is bound to the —C(O)—, and wherein no alkyl, haloalkyl or heterocycloalkyl is substituted by an aryl, heteroaryl, cycloalkyl or heterocycloalkyl-containing group.

In certain embodiments of the presently disclosed compounds of structural formulae (3-I)-(3-IV), each $R^5$ is independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-$R^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, in which each $R^7$, $R^8$ and $R^{10}$ is independently selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, each $R^5$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group.

In one embodiment of the compounds of structural formulae (3-I)-(3-IV), y is 0.

In the presently disclosed compounds of structural formulae (3-I)-(3-IV), the ring system denoted by "A" is heteroaryl, aryl, cycloalkyl or heterocycloalkyl. For example, in one embodiment, the ring system denoted by "A" is an aryl or a heteroaryl. The ring system denoted by "A" can be, for example, a monocyclic aryl or heteroaryl. In one embodiment, when the "A" ring system is aryl, Q is a —($C_0$-$C_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. For example, in certain embodiments, Q is —$CH_2$—; a single bond; —S(O)$_2$—; —C(O)—; or —CH(CH$_3$)—.

For example, in certain embodiments of the presently disclosed compounds of structural formulae (3-I)-(3-IV), the ring system denoted by "A" is a phenyl. In one embodiment, y is 1 and $R^5$ is attached to the phenyl in the para position relative to Q. In another embodiment, y is 1 and $R^5$ is selected from the group consisting of halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, and in which no ($C_0$-$C_4$ alkyl) or ($C_1$-$C_4$ alkyl) is substituted by an aryl, heteroaryl, cycloalkyl or heterocycloalkyl-containing group. $R^5$ can be, for example, —Cl, —F, cyano, —C(O)CH$_3$, —C(O)OH, —C(O)NH$_2$, trifluoromethyl, difluoromethyl, difluoromethoxy or trifluoromethoxy. In another embodiment, the

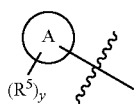

moiety is a 3,4-dihalophenyl.

In another embodiment of the presently disclosed compounds of structural formulae (3-I)-(3-IV), the ring system denoted by "A" is a heteroaryl. For example, in certain embodiments, the ring system denoted by "A" is a pyridyl, a thienyl, or a furanyl. In one embodiment, when the "A" ring system is heteroaryl, Q is a —($C_0$-$C_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. In certain embodiments, Q is —CH—; a single bond; —S(O)$_2$—; —C(O)—; or —CH(CH$_3$)—.

In certain embodiments, at least one $R^5$ is —SO$_2$($C_1$-$C_6$ alkyl), —SO$_2$($C_1$-$C_6$ haloalkyl), —SO$_2$N($C_0$-$C_6$ alkyl)$_2$, —SO$_2$($C_3$-$C_8$ cycloalkyl), —SO$_2$($C_3$-$C_8$ heterocycloalkyl), such as —SO$_2$Me, —SO$_2$Et, —SO$_2$Pr, —SO$_2$Bu, —SO$_2$cyclopropyl, —SO$_2$morphylinyl, SO$_2$pyrrolidinyl, SO$_2$NHEt, SO$_2$pyridyl or —SO$_2$phenyl.

In certain embodiments of the presently disclosed compounds of structural formula (3-I), the

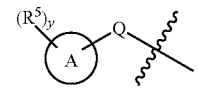

moiety is

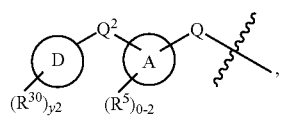

in which the ring system denoted by "A" is aryl or heteroaryl, the ring system denoted by "D" is cycloalkyl, heterocycloalkyl, aryl or heteroaryl; $Q^2$ is —S(O)$_2$—, —O— or —($C_0$-$C_3$ alkyl)- in which each carbon of the ($C_0$-$C_3$ alkyl) is optionally and independently substituted with one or two $R^{16}$, defined as described above with respect to Q; $y^2$ is 0, 1 or 2; and each $R^{30}$ is independently selected from is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, $Q^2$ has at most one $R^{16}$ or an oxo substituted thereon. $Q^2$ can be, for example, an unsubstituted —($C_0$-$C_3$ alkyl)-. In other embodiments, $Q^2$ is a ($C_1$-$C_3$ alkyl) having as its only substitution a single oxo group. For example, in certain embodiments, $Q^2$ is —CH—; a single bond; —S(O)$_2$—; —O—; —C(O)—; or —CH(CH$_3$)—. In certain embodiments, at least one $R^{30}$ is halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ or —C(O)—Hca in which the Hca contains a ring nitrogen atom through which it is bound to the —C(O)—, and in which no alkyl, haloalkyl or heterocycloalkyl is substituted by an aryl, heteroaryl, cycloalkyl or heterocycloalkyl-containing group. In certain embodiments, at least one $R^5$ is —SO$_2$($C_1$-$C_6$ alkyl), —SO$_2$($C_1$-$C_6$ haloalkyl), —SO$_2$N($C_0$-$C_6$ alkyl)($C_0$-$C_6$ alkyl), —SO$_2$($C_3$-$C_8$ cycloalkyl), —SO$_2$($C_3$-$C_8$ heterocycloalkyl), such as —SO$_2$Me, —SO$_2$Et, —SO$_2$Pr, —SO$_2$Bu, —SO$_2$cyclopropyl, —SO$_2$morphylinyl, SO$_2$pyrrolidinyl, SO$_2$NHEt, SO$_2$pyridyl or —SO$_2$phenyl. The number of substituents on the ring system denoted by "D", $y^2$, is 0, 1, or 2. For example, in some embodiments, $y^2$ is 0 or 1, for example 1. In other embodiments, $y^2$ is 0. $R^{30}$ can be further defined as described above with respect to $R^5$. In certain embodiments, the ring system denoted by "D" is cyclopropyl, morpholinyl, pyrazolyl, pyridyl, imidazolyl or phenyl.

In certain embodiments, at least one $R^5$ is —SO$_2$($C_1$-$C_6$ alkyl), —SO$_2$($C_1$-$C_6$ haloalkyl), —SO$_2$N($C_0$-$C_6$ alkyl)$_2$, —SO$_2$($C_3$-$C_8$ cycloalkyl), —SO$_2$($C_3$-$C_8$ heterocycloalkyl), such as —SO₂Me, —SO₂Et, —SO₂Pr, —SO₂Bu, —SO₂cyclopropyl, —SO₂morphylinyl, SO₂pyrrolidinyl, SO₂NHEt, SO₂pyridyl or —SO₂phenyl.

In certain embodiments (e.g., when ring system "B" is a phenyl and is fused to ring system "C", J is absent, Z is N, D is carbon, q is 2 and p is 1), T is not —C(O)O—(C₀-C₆ alkyl).

In certain embodiments (e.g., when ring system "B" is a phenyl and is fused to ring system "C", J is absent, Z is N, D is carbon, q is 2 and p is 1), T is not is not —CH₂C(O)OH; —NH—CH₂—C(O)OH; —O—CH₂—C(O)OH; —CH₂—CH₂—C(O)OH; —CH=CH—C(O)OH; —N(C(O)CH₃)—CH₂—C(O)OH; =CH—C(O)OH or =CH—CH₂—CH₂—C(O)OH.

In one embodiment of the presently disclosed compounds, the compound has structural formula (3-V):

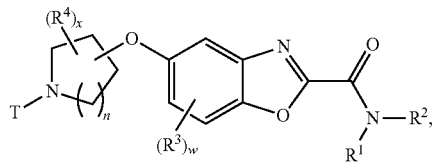

(3-V)

in which n is 1, 2, 3 or 4, and all other variables are defined as described above with reference to structural formulae (3-I)-(3-IV).

In one embodiment of the presently disclosed compounds, the compound has structural formula (3-VI):

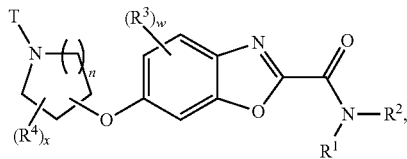

(3-VI)

in which n is 1, 2, 3 or 4, and all other variables are defined as described above with reference to structural formulae (3-I)-(3-IV).

In one embodiment of the presently disclosed compounds, the compound has structural formula (3-VII):

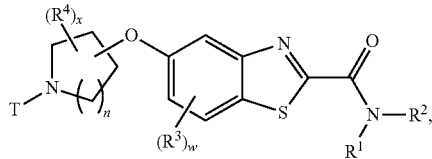

(3-VII)

in which n is 1, 2, 3 or 4, and all other variables are defined as described above with reference to structural formulae (3-I)-(3-IV).

In one embodiment of the presently disclosed compounds, the compound has structural formula (3-VIII):

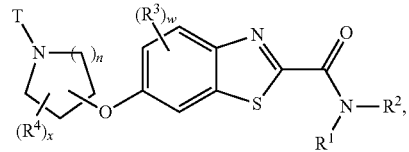

(3-VIII)

in which n is 1, 2, 3 or 4, and all other variables are defined as described above with reference to structural formulae (3-I)-(3-IV).

In one embodiment of the presently disclosed compounds, the compound has structural formula (3-IX):

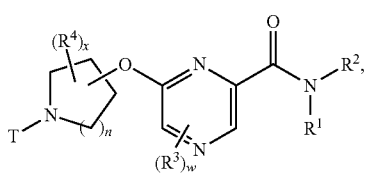

(3-IX)

in which n is 1, 2, 3 or 4, and all other variables are defined as described above with reference to structural formulae (3-I)-(3-IV).

In one embodiment of the presently disclosed compounds, the compound has structural formula (3-X):

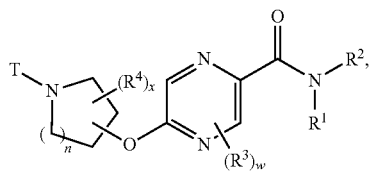

(3-X)

in which n is 1, 2, 3 or 4, and all other variables are defined as described above with reference to structural formulae (3-I)-(3-IV).

In one embodiment of the presently disclosed compounds, the compound has structural formula (3-XI):

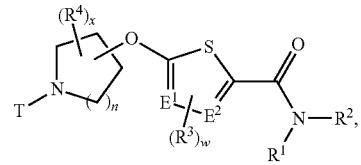

(3-XI)

in which n is 1, 2, 3 or 4, w is 0 or 1, and all other variables are defined as described above with reference to structural formulae (3-I)-(3-IV). For example, in one embodiment, E¹ is N and E² is —CH— or —CR³—. In another embodiment, E¹ is —CH— or —CR³— and E² is N.

In one embodiment of the presently disclosed compounds, the compound has structural formula (3-XII):

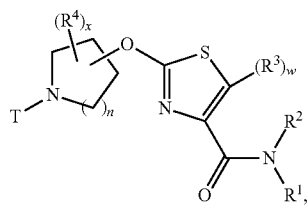
(3-XII)

in which n is 1, 2, 3 or 4, w is 0 or 1, and all other variables are defined as described above with reference to structural formulae (3-I)-(3-IV). When w is 0, the ring position shown occupied by $R^3$ bears a hydrogen atom.

In one embodiment of the presently disclosed compounds, the compound has structural formula (3-XIII):

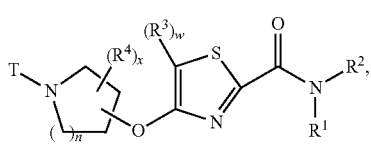
(3-XIII)

in which n is 1, 2, 3 or 4, w is 0 or 1, and all other variables are defined as described above with reference to structural formulae (3-I)-(3-IV). When w is 0, the ring position shown occupied by $R^3$ bears a hydrogen atom.

In certain embodiments of the compounds disclosed with reference to structural formulae (3-V)-(3-XIII), n is 1 or 2. For example, in one embodiment, n is 2. In another embodiment, n is 1.

For example, in one embodiment of the presently disclosed compounds, the compound has structural formula (3-XIV):

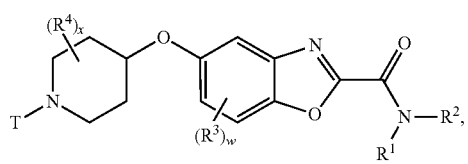
(3-XIV)

in which all variables are defined as described above with reference to structural formulae (3-I)-(3-IV).

In another embodiment of the presently disclosed compounds, the compound has structural formula (3-XV):

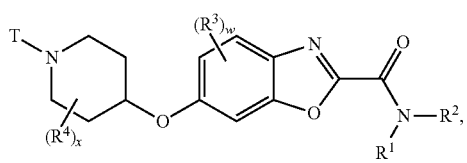
(3-XV)

in which all variables are defined as described above with reference to structural formulae (3-I)-(3-IV).

In another embodiment of the presently disclosed compounds, the compound has structural formula (3-XVI):

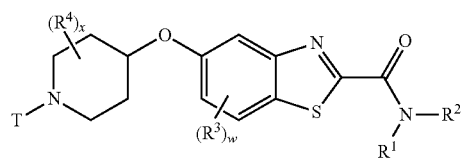
(3-XVI)

in which all variables are defined as described above with reference to structural formulae (3-I)-(3-IV).

In another embodiment of the presently disclosed compounds, the compound has structural formula (3-XVII):

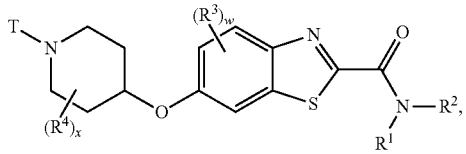
(3-XVII)

in which all variables are defined as described above with reference to structural formulae (3-I)-(3-IV).

In another embodiment of the presently disclosed compounds, the compound has structural formula (3-XVIII):

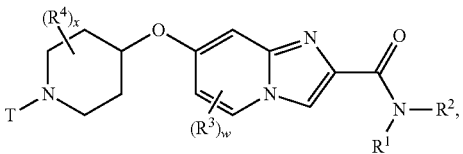
(3-XVIII)

in which all variables are defined as described above with reference to structural formulae (3-I)-(3-IV).

In another embodiment of the presently disclosed compounds, the compound has structural formula (3-XIX):

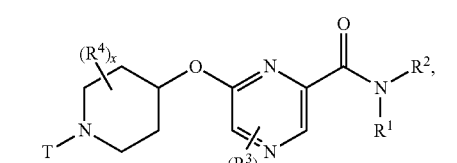
(3-XIX)

in which all variables are defined as described above with reference to structural formulae (3-I)-(3-IV).

In another embodiment of the presently disclosed compounds, the compound has structural formula (3-XX):

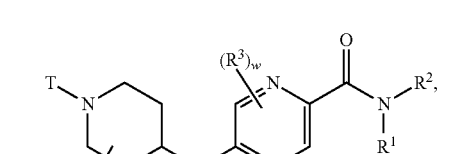
(3-XX)

in which all variables are defined as described above with reference to structural formulae (3-I)-(3-IV).

In another embodiment of the presently disclosed compounds, the compound has structural formula (3-XXI):

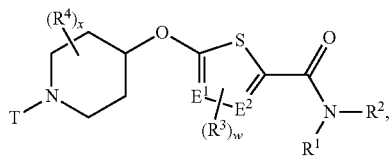

(3-XXI)

in which w is 0 or 1 and all other variables are defined as described above with reference to structural formulae (3-I)-(3-IV). When w is 0, the ring position shown occupied by $R^3$ bears a hydrogen atom. In one embodiment, $E^1$ is —CH— or —$CR^3$— and $E^2$ is N. In another embodiment, $E^1$ is N and $E^2$ is —CH— or —$CR^3$—.

In another embodiment of the presently disclosed compounds, the compound has structural formula (3-XXII):

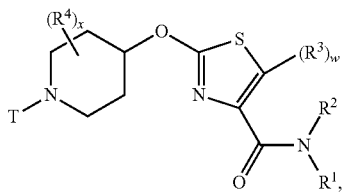

(3-XXII)

in which w is 0 or 1 and all other variables are defined as described above with reference to structural formulae (3-I)-(3-IV). When w is 0, the ring position shown occupied by $R^3$ bears a hydrogen atom.

In another embodiment of the presently disclosed compounds, the compound has structural formula (3-XXIII):

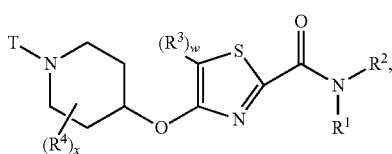

(3-XXIII)

in which w is 0 or 1 and all other variables are defined as described above with reference to structural formulae (3-I)-(3-IV). When w is 0, the ring position shown occupied by $R^3$ bears a hydrogen atom.

In one embodiment of the presently disclosed compounds, the compound has structural formula (3-XXIV):

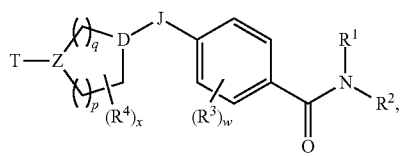

(3-XXIV)

in which all variables are defined as described above with reference to structural formulae (3-I)-(3-IV). In one such embodiment, J is —C(O)—, Z is CH or C substituted with one of the x $R^4$ and D is N. In another such embodiment, J is —C(O)—, Z is N and D is N. In a further such embodiment, J is —N($R^{38}$)—C(O)— (e.g., —NH—C(O)—), Z is N and D is CH or C substituted with one of the x $R^4$.

In another embodiment of the presently disclosed compounds, the compound has structural formula (3-XXV):

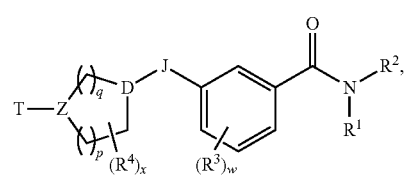

(3-XXV)

in which all variables are defined as described above with reference to structural formulae (3-I)-(3-IV). In one such embodiment, J is —C(O)—, Z is CH or C substituted with one of the x $R^4$ and D is N. In another such embodiment, J is —C(O)—, Z is N and D is N. In a further such embodiment, J is —N($R^{38}$)—C(O)— (e.g., —NH—C(O)—), Z is N and D is CH or C substituted with one of the x $R^4$.

In another embodiment of the presently disclosed compounds, the compound has structural formula (3-XXVI):

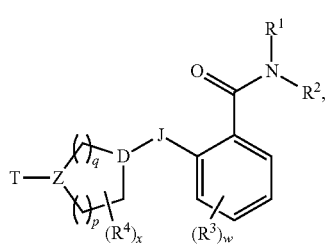

(3-XXVI)

in which all variables are defined as described above with reference to structural formulae (3-I)-(3-IV). In one such embodiment, J is —C(O)—, Z is CH or C substituted with one of the x $R^4$ and D is N. In another such embodiment, J is —C(O)—, Z is N and D is N. In a further such embodiment, J is —N($R^{38}$)—C(O)— (e.g., —NH—C(O)—), Z is N and D is CH or C substituted with one of the x $R^4$.

In certain embodiments according to structural formulae (3-XXIV)-(3-XXVI), the sum of p and q is 2 or 3. For example, in one embodiment, the sum of p and q is 2 (e.g., p is 1 and q is 1). In another embodiment, the sum of p and q is 3 (e.g., p is 1 and q is 2).

For example, in one embodiment of the presently disclosed compounds, the compound has structural formula (3-XXVII):

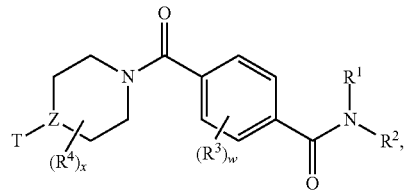

(3-XXVII)

in which all variables are defined as described above with reference to structural formulae (3-I)-(3-IV). In one such embodiment, Z is N. In another such embodiment, Z is CH or C substituted with one of the x $R^4$.

In another embodiment of the presently disclosed compounds, the compound has structural formula (3-XXVIII):

(3-XXVIII)

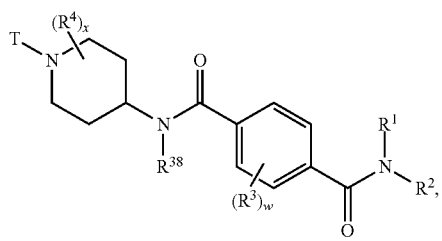

in which all variables are defined as described above with reference to structural formulae (3-I)-(3-IV).

In another embodiment of the presently disclosed compounds, the compound has structural formula (3-XXIX):

(3-XXIX)

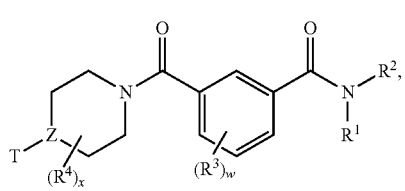

in which all variables are defined as described above with reference to structural formulae (3-I)-(3-IV). In one such embodiment, Z is N. In another such embodiment, Z is CH or C substituted with one of the x $R^4$.

For example, in one embodiment of the presently disclosed compounds, the compound has structural formula (3-XXX):

(3-XXX)

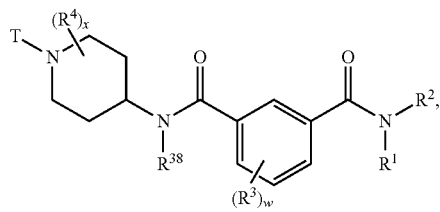

in which all variables are defined as described above with reference to structural formulae (3-I)-(3-IV).

For example, in one embodiment of the presently disclosed compounds, the compound has structural formula (3-XXXI):

(3-XXXI)

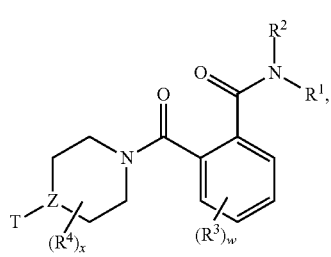

in which all variables are defined as described above with reference to structural formulae (3-I)-(3-IV). In one such embodiment, Z is N. In another such embodiment, Z is CH or C substituted with one of the x $R^4$.

In another embodiment of the presently disclosed compounds, the compound has structural formula (3-XXXII):

(3-XXXII)

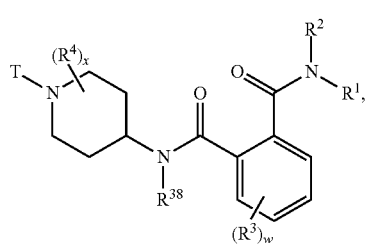

in which all variables are defined as described above with reference to structural formulae (3-I)-(3-IV).

In one embodiment of the presently disclosed compounds, the compound has structural formula (3-XXXIII):

(3-XXXIII)

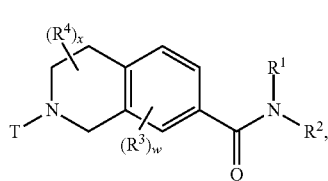

in which all variables are defined as described above with reference to structural formulae (3-I)-(3-IV).

In one embodiment of the presently disclosed compounds, the compound has structural formula (3-XXXIV):

(3-XXXIV)

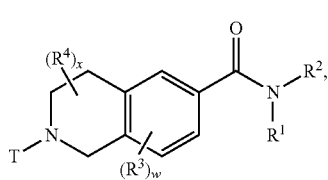

in which all variables are defined as described above with reference to structural formulae (3-I)-(3-IV).

In one embodiment of the presently disclosed compounds, the compound has structural formula (3-XXXV):

(3-XXXV)

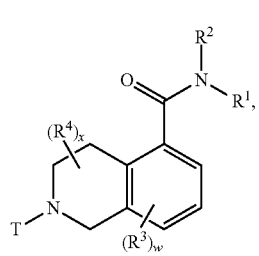

in which all variables are defined as described above with reference to structural formulae (3-I)-(3-IV).

In one embodiment of the presently disclosed compounds, the compound has structural formula (3-XXXVI):

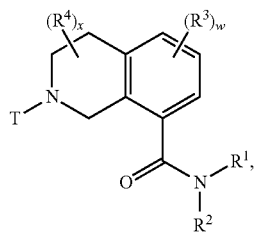

(3-XXXVI)

in which all variables are defined as described above with reference to structural formulae (3-I)-(3-IV).

In certain embodiments of the presently disclosed compounds of structural formulae (3-I)-(3-XXXVI), $R^1$ is H, —($C_1$-$C_4$ alkyl), —C(O)—($C_1$-$C_4$ alkyl) or —C(O)O—($C_1$-$C_4$ alkyl), and $R^2$ is -Hca, -Cak-N($R^9$)-G-$R^{22}$ or —($C_2$-$C_8$ alkyl)-N($R^9$)—$R^{24}$ in which one or two (for example, non-adjacent) carbons of the ($C_2$-$C_8$ alkyl) are optionally replaced by —O—, —S— or —N($R^9$)—, and $R^{24}$ is —$R^{23}$, -G-$R^{23}$ or —C(O)O—($C_1$-$C_6$ alkyl), provided that two consecutive carbons of the ($C_2$-$C_8$ alkyl) are not replaced by —O—. For example, in one embodiment, $R^1$ is H, —($C_1$-$C_4$ alkyl), —C(O)—($C_1$-$C_4$ alkyl) or —C(O)O—($C_1$-$C_4$ alkyl), and $R^2$ is -Hca.

In certain embodiments of the presently disclosed compounds of any of structural formulae (3-I)-(3-XXXVI), $R^1$ is —H. In other embodiments, $R^1$ is ($C_1$-$C_4$ alkyl), for example methyl, ethyl, n-propyl or isopropyl.

In certain embodiments of the presently disclosed compounds of any of structural formulae (3-I)-(3-XXXVI), $R^2$ is -Hca. In certain embodiments, $R^2$ is an optionally-substituted monocyclic heterocycloalkyl.

In certain of the presently disclosed compounds of any structural formulae (3-I)-(3-XXXVI), $R^2$ is -(optionally-substituted azetidinyl), -(optionally-substituted pyrrolidinyl), -(optionally-substituted piperidinyl) or -(optionally-substituted azepanyl). For example, $R^2$ can be -(optionally substituted piperidinyl) or -(optionally substituted pyrrolidinyl). In one embodiment, $R^2$ is -(optionally substituted piperidinyl). In another embodiment, $R^2$ is -(optionally substituted pyrrolidinyl).

In certain particular embodiments of the presently disclosed compounds of any of structural formulae (3-I)-(3-XXXVI), $R^2$ is -(optionally-substituted azetidin-3-yl), -(optionally substituted piperidin-4-yl), -(optionally substituted pyrrolidin-3-yl) or -(optionally-substituted azepan-4-yl). For example, in one embodiment, $R^2$ is -(optionally substituted piperidin-4-yl). In another embodiment, $R^2$ is -(optionally substituted pyrrolidin-3-yl).

In certain embodiments of the presently disclosed compounds of any of structural formulae (3-I)-(3-XXXVI), the azetidinyl, pyrrolidinyl, piperidinyl and azepanyl $R^2$ moieties described above are substituted at their 1-positions. For example, in one embodiment, $R^2$ is substituted at its 1-position with —($C_0$-$C_3$ alkyl)-Ar or —($C_0$-$C_3$ alkyl)-Het, for example -(unsubstituted $C_0$-$C_3$ alkyl)-Ar or -(unsubstituted $C_0$-$C_3$ alkyl)-Het. For example, in one particular embodiment, the azetidinyl, pyrrolidinyl, piperidinyl or azepanyl $R^2$ moiety is substituted at its 1-position with an optionally substituted benzyl or an optionally substituted phenyl. In another embodiment, the azetidinyl, pyrrolidinyl, piperidinyl or azepanyl $R^2$ moiety is substituted at its 1-position with a benzyl substituted with an electron withdrawing group; or with a pyridinylmethyl optionally substituted with an electron withdrawing group. For example, the benzyl or pyridinylmethyl can be substituted with an electron withdrawing group selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In other embodiments, the azetidinyl, pyrrolidinyl, piperidinyl or azepanyl $R^2$ moiety is substituted at its 1-position with an unsubstituted benzyl or an unsubstituted phenyl.

In other embodiments of the compounds disclosed herein having any of structural formulae (3-I)-(3-XXXVI), the azetidinyl, pyrrolidinyl, piperidinyl or azepanyl $R^2$ moiety is substituted at its 1-position with an optionally substituted pyridinylmethyl, an optionally substituted furanylmethyl, an optionally substituted thienylmethyl, an optionally substituted oxazolylmethyl, or an optionally substituted imidazolylmethyl. For example, the azetidinyl, pyrrolidinyl, piperidinyl or azepanyl $R^2$ moiety can be substituted with an unsubstituted pyridinylmethyl, an unsubstituted furanylmethyl, an unsubstituted thienylmethyl, an unsubstituted oxazolylmethyl, or an unsubstituted imidazolylmethyl. In other embodiments, the azetidinyl, pyrrolidinyl, piperidinyl or azepanyl $R^2$ moiety can be substituted with an pyridinylmethyl, furanylmethyl, thienylmethyl, oxazolylmethyl or imidazolylmethyl substituted with an electron withdrawing group as described above.

In certain embodiments of the compounds disclosed herein having any of structural formulae (3-I)-(3-XXXVI), the azetidinyl, pyrrolidinyl, piperidinyl or azepanyl $R^2$ moiety is substituted at its 1-position with -L-Ar or -L-Het, in which Ar and Het can be, for example, as described above with reference to —($C_0$-$C_3$ alkyl)-Ar or —($C_0$-$C_3$ alkyl)-Het. In one such embodiment, L is —C(O)—NR$^9$—, such as —C(O)—NH—.

In other embodiments of the presently disclosed compounds of any of structural formulae (3-I)-(3-XXXVI), the azetidinyl, pyrrolidinyl, piperidinyl or azepanyl $R^2$ moiety is substituted at its 1-position with —C(O)—O($C_0$-$C_6$ alkyl), —C(O)-Het, —C(O)—Ar, —S(O)$_2$-Het, —S(O)$_2$—Ar or —S(O)$_2$—O($C_0$-$C_6$ alkyl), in which Ar and Het can be, for example, as described above with reference to —($C_0$-$C_3$ alkyl)-Ar or —($C_0$-$C_3$ alkyl)-Het. In one embodiment, the azetidinyl, pyrrolidinyl, piperidinyl or azepanyl $R^2$ moiety is substituted at its 1-position with —C(O)-Het or —C(O)—Ar; in another embodiment, it is substituted at its 1-position with —S(O)$_2$-Het or —S(O)$_2$—Ar. For example, in certain embodiments, the azetidinyl, pyrrolidinyl, piperidinyl or azepanyl $R^2$ moiety is substituted at its 1-position with an optionally-substituted benzoyl (e.g., substituted with an electron withdrawing group as described above); or with an optionally-substituted nicotinyl, isonicotinyl or picolinyl (e.g., optionally substituted with an electron withdrawing group as described above). In other embodiments, the azetidinyl, pyrrolidinyl, piperidinyl or azepanyl $R^2$ moiety is substituted at its 1-position with an unsubstituted benzoyl; or an unsubstituted nicotinoyl, isonicotinoyl or picolinoyl.

In certain embodiments, $R^2$ is an optionally-substituted bridged azacycloalkyl or diazacycloalkyl, for example, a bridged azabicyclohexyl, a bridged azabicycloheptyl, a bridged azabicyclooctyl, a bridged diazabicyclohexyl, a bridged diazabicycloheptyl or a bridged diazabicyclooctyl. Particular examples of such $R^2$ moieties include optionally substituted azabicyclo[2.2.2]octyl, optionally substituted azabicyclo[3.2.1]octyl, and optionally substituted 2,5-diazabicyclo[2.2.1]heptyl.

When $R^2$ is a bridged azacycloalkyl or diazacycloalkyl, it can be substituted as described above with reference to the azetidinyl, pyrrolidinyl, piperidinyl and azepanyl $R^2$ moieties. For example, a bridged azacycloalkyl or diazacycloalkyl $R^2$ moiety can be substituted (e.g., at a nitrogen) with —($C_0$-$C_3$ alkyl)-Ar, —($C_0$-$C_3$ alkyl)-Het, -L-Ar, -L-Het, —C(O)—O($C_0$-$C_6$ alkyl), —C(O)-Het, —C(O)—Ar, —S(O)$_2$-Het, —S(O)$_2$—Ar or —S(O)$_2$—O($C_0$-$C_6$ alkyl), as described above.

In certain embodiments of the compounds of any of structural formulae (3-I)-(3-XXXVI), $R^2$ is -Cak-N($R^9$)-G-$R^{22}$, as described above. For example, in one embodiment of the disclosed compounds, $R^2$ has the structure

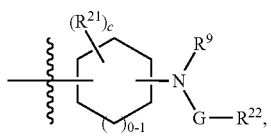

in which c is 0, 1, 2, 3 or 4, and each $R^{21}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-N$R^8R^9$, —($C_0$-$C_6$ alkyl)-O$R^{10}$, —($C_0$-$C_6$ alkyl)-C(O)$R^{10}$, —($C_0$-$C_6$ alkyl)-S(O)$_{0-2}R^{10}$, -halogen, —NO$_2$ and —CN, and two $R^{21}$ on the same carbon optionally combine to form oxo. In certain embodiments of the presently disclosed compounds, each $R^{21}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-N$R^8R^9$, —($C_0$-$C_6$ alkyl)-O$R^{10}$, —($C_0$-$C_6$ alkyl)-C(O)$R^{10}$, —($C_0$-$C_6$ alkyl)-S(O)$_{0-2}R^{10}$, -halogen, —NO$_2$ and —CN and two $R^{21}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-N$R^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{21}$ is —($C_1$-$C_3$ alkyl), —($C_1$-$C_3$ haloalkyl), —($C_0$-$C_3$ alkyl)-L-$R^7$, —($C_0$-$C_3$ alkyl)-N$R^8R^9$, —($C_0$-$C_3$ alkyl)-O$R^{10}$, —($C_0$-$C_3$ alkyl)-C(O)$R^{10}$, —($C_0$-$C_3$ alkyl)-S(O)$_{0-2}R^{10}$, -halogen, —NO$_2$ and —CN and two $R^{21}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-N$R^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, c is 1 or 2. In other embodiments, c is 0. In certain embodiments, $R^9$ is H. In certain embodiments, G is a single bond. In certain embodiments of the presently disclosed compounds, $R^{22}$ is not substituted with an aryl-, heteroaryl-, cycloalkyl- or heterocycloalkyl-containing group. In certain embodiments of the presently disclosed compounds, $R^{23}$ is not substituted with an aryl-, heteroaryl-, cycloalkyl- or heterocycloalkyl-containing group.

In one embodiment of compounds of any of structural formulae (3-I)-(3-XXXVI), $R^2$ has the structure

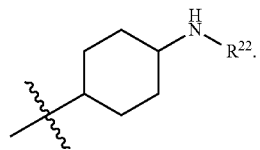

In certain embodiments of the compounds of any of structural formulae (3-I)-(3-XLIII), $R^2$ is —($C_2$-$C_8$ alkyl)-N($R^9$)—$R^{24}$ in which one or two carbons of the ($C_2$-$C_8$ alkyl) are optionally replaced by —O— or —N($R^9$)— and $R^{24}$ is —$R^{23}$, -G$R^{23}$ or —C(O)O—($C_1$-$C_6$ alkyl). In certain embodiments, the ($C_2$-$C_8$ alkyl) is unsubstituted and no carbon is replaced by —O— or —N($R^9$)—. For example, in one embodiment, $R^2$ is —CH$_2$—CH$_2$—CH$_2$—N($R^9$)—$R^{24}$ or —CH$_2$—CH$_2$—CH$_2$—CH$_2$—N($R^9$)—$R^{24}$. In other embodiments, the ($C_2$-$C_8$ alkyl) is substituted and/or one or two carbons are replaced by —O— or —N($R^9$)—. For example, in one embodiment, $R^2$ is —CH$_2$—CH$_2$—O—CH$_2$—CH$_2$—N($R^9$)_$R^{24}$; —CH$_2$—CH(CH$_3$)—N($R^9$)—$R^{24}$; or —CH$_2$—CH$_2$—O—CH$_2$—C(O)—N($R^9$)—$R^{24}$. In certain embodiments, $R^9$ is H. In certain embodiments, $R^{24}$ is Ar or Het. In certain embodiments, $R^{24}$ is not substituted with an aryl-, heteroaryl-, cycloalkyl- or heterocycloalkyl-containing group. In certain embodiments, the ($C_2$-$C_8$ alkyl) is a ($C_2$-$C_5$ alkyl).

In certain embodiments (e.g., when rings system "B" is

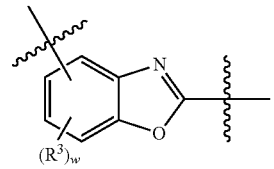

or

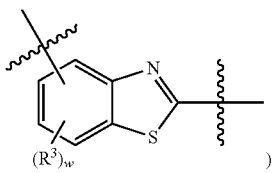

), when $R^2$ is an azabicycloalkyl moiety (e.g., a 1-azabicycloheptyl, a 1-azabicyclooctyl, a 1-azabicyclononyl or a 1-azabicyclodecyl), $R^2$ is not vicinally substituted (3-I.e., at the position next to the amide nitrogen) with —($C_0$-$C_4$)-Het.

In certain embodiments (e.g., when rings system "B" is

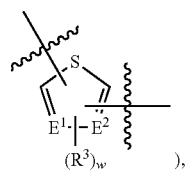

), $R^2$ is not a benzo-, pyrido-, pyrimido-, pyrazino- or pyridazino-fused azacycloalkyl. In other embodiments, $R^2$ is not 7-azabicyclo[2.2.1]hept-2-yl. In other embodiments, $R^2$ is not a quinuclidin-3-yl moiety.

In certain embodiments (e.g., when "B" represents

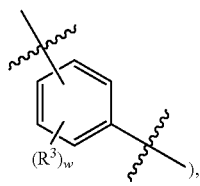

$R^2$ is not a 4,5-dihydroisoxazol-4-yl moiety or an optionally substituted optionally ring-fused azetidin-2-on-3-yl moiety. In one embodiment, $R^2$ is not an oxo-substituted heterocycloalkyl.

In certain embodiments of the presently disclosed compounds, $R^1$ and $R^2$ together with the nitrogen to which they are attached (3-I.e., the carboxamide nitrogen) come together to form Hca. $R^1$, $R^2$ and the nitrogen can come together to form, for example, an optionally-substituted monocyclic azacycloalkyl or monocyclic diazacycloalkyl, such as a piperidine, a pyrrolidine, a piperazine or an imidazolidine. In other embodiments, $R^1$ and $R^2$ come together to form an optionally-substituted bridged azacycloalkyl or diazacycloalkyl, for example, a bridged azabicyclohexyl, a bridged azabicycloheptyl, a bridged azabicyclooctyl, a bridged diazabicyclohexyl, a bridged diazabicycloheptyl or a bridged diazabicyclooctyl. Particular examples of such $R^2$ moieties include azabicyclo[2.2.2]octyl, azabicyclo[3.2.1]octyl, and 2,5-diazabicyclo[2.2.1]heptyl.

When $R^1$, $R^2$ and the nitrogen come together to form Hca, the Hca can be substituted as described above with reference to the azetidinyl, pyrrolidinyl, piperidinyl and azepanyl $R^2$ moieties. For example, the heterocycloalkyl can be substituted with —(C$_0$-C$_3$ alkyl)-Ar, —(C$_0$-C$_3$ alkyl)-Het, -L-Ar, -L-Het, —C(O)—O(C$_0$-C$_6$ alkyl), —C(O)-Het, —C(O)—Ar, —S(O)$_2$-Het, —S(O)$_2$—Ar or —S(O)$_2$—O(C$_0$-C$_6$ alkyl), as described above. When $R^1$ and $R^2$ come together to form a diazacycloalkyl, it can be substituted at a nitrogen atom.

For example, in certain embodiments, the —C(O)—NR$^1$R$^2$ moiety is

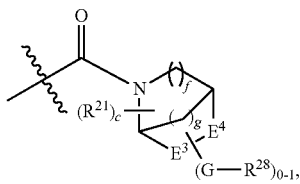

in which f is 0 or 1; g is 0, 1 or 2; c is 0, 1, 2, 3 or 4; $R^{28}$ is Ar or Het; $E^3$ is NH, N substituted by one of the c $R^{21}$, N substituted by the -G-R$^{28}$, CH$_2$, CH substituted by one of the c $R^{21}$, CH substituted by the -G-R$^{28}$, or C substituted by one of the c $R^{21}$ and the -G-R$^{28}$; and $E^4$ is absent, NH, N substituted by one of the c $R^{21}$, N substituted by the -G-R$^{28}$, CH$_2$, CH substituted by one of the c $R^{21}$, CH substituted by the -G-R$^{28}$, or C substituted by one of the c $R^{21}$ and the -G-R$^{28}$, provided that both $E^3$ and $E^4$ are not N. When g is 0, $R^1$, $R^2$ and the nitrogen come together to form a monocyclic azacycloalkyl or diazacycloalkyl. In other embodiments, when g is 1 or 2, $R^1$, $R^2$ and the nitrogen come together to form a bridged bicyclic azacycloalkyl or diazacycloalkyl. The c $R^{21}$ moieties can be disposed anywhere on the azacycloalkyl or diazacycloalkyl ring system. Each $R^{21}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two $R^{21}$ on the same carbon optionally combine to form oxo. In certain embodiments of the presently disclosed compounds, each $R^{21}$ is independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN and two $R^{21}$ on the same carbon optionally combine to form oxo, in which each $R^7$, $R^8$ and $R^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, each $R^{21}$ is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN and two $R^{21}$ on the same carbon optionally combine to form oxo, in which each $R^7$, $R^8$ and $R^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, c is 1 or 2. In other embodiments, c is 0. In certain embodiments, G is a single bond, CH$_2$, or C(O). In certain embodiments of the presently disclosed compounds, $R^{28}$ is not substituted with an aryl-, heteroaryl-, cycloalkyl- or heterocycloalkyl-containing group. In one embodiment, $R^{28}$ is monocyclic aryl or heteroaryl substituted with 0-3 substituents selected from halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl) and NO$_2$, in which each alkyl is not further substituted. The -G-R$^{28}$ moiety, when present, can in some embodiments be as described below for -G-R$^{17}$.

For example, in certain embodiments, the —C(O)—NR$^1$R$^2$ moiety is

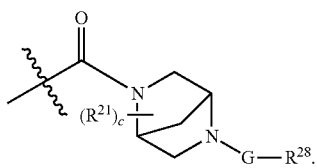

In the compounds of any of structural formulae (3-I)-(3-XLIII), the number of substituents on ring system "B", w, is 0, 1, 2 or 3. For example, in one embodiment, w is 0, 1 or 2. In another embodiment, w is 0. In other embodiments, w is at least 1, and at least one $R^3$ is selected from the group consisting of halo, cyano, —(C$_1$-C$_4$ fluoroalkyl), —O—(C$_1$-C$_4$ fluoroalkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), —S(O)$_2$O—(C$_0$-C$_4$ alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. For example, in certain embodiments, at least one $R^3$ is halo (e.g., chloro) or —($C_1$-$C_4$ alkyl) (e.g., methyl, ethyl or propyl). In certain embodiments, an $R^3$ is substituted on the "B" ring system at a 6-membered aromatic ring position in the meta position relative to the J moiety.

In certain embodiments of the compounds of any of structural formulae (3-I)-(3-XLIII), each $R^3$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^3$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, ($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. For example, in certain embodiments, each $R^3$ is halo (e.g., chloro) or —($C_1$-$C_4$ alkyl) (e.g., methyl, ethyl or propyl).

In certain embodiments of the compounds of of any of structural formulae (3-I)-(3-XXXVI), w is at least one, and at least one $R^3$ is —$NR^8R^9$. For example, in one embodiment, w is 1. In certain such embodiments, $R^3$ is substituted on the "B" ring system at a 6-membered aromatic ring position in the meta position relative to the J moiety.

In other embodiments of the compounds of of any of structural formulae (3-I)-(3-XXXVI), w is at least one, and at least one $R^3$ is —($C_0$-$C_3$ alkyl)-$Y^1$—($C_1$-$C_3$ alkyl)-$Y^2$—($C_0$-$C_3$ alkyl), in which each of $Y^1$ and $Y^2$ is independently L, —O—, —S— or —$NR^9$—. For example, in one embodiment, w is 1. In certain such embodiments, $R^3$ is substituted on the "B" ring system at a 6-membered aromatic ring position in the meta position relative to the J moiety. In one particular embodiment, $R^3$ is —$CH_2$—N($CH_3$)—$CH_2$—C(O)—$OCH_3$.

In certain embodiments in which ring system "B" is

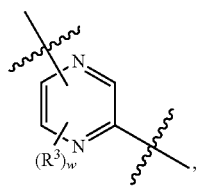

the compound does not have two $R^3$ moieties that include Ar or Het in the moieties' structure. In another embodiment, when an $R^3$ is —$NR^9$—($C_0$-$C_6$ alkyl)-Ar, —$NR^9$—($C_0$-$C_6$ alkyl)-Het, —$NR^9$—Hca, —O—($C_0$-$C_6$ alkyl)-Ar or —O—($C_0$-$C_6$ alkyl)-Het, it is not substituted on the pyrazine core at a position ortho to (3-I.e., on the carbon adjacent to) the amide. In another embodiment, when an $R^3$ is —Ar or -Het, it is substituted on the pyrazine core at a position para to (3-I.e., directly across the ring from) the amide.

In certain embodiments in which ring system "B" is

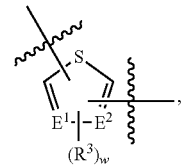

when $R^3$ is ($C_0$-$C_4$ alkyl)-O—($C_0$-$C_4$ alkyl)-(optionally-substituted phenyl); ($C_0$-$C_4$ alkyl)-S(O)$_{0-2}$—($C_0$-$C_4$ alkyl)-(optionally-substituted phenyl) or ($C_0$-$C_4$ alkyl)-S(O)$_{0-2}$—($C_0$-$C_4$ alkyl)-O-(optionally-substituted phenyl), it is not at the 2 position of the thiazole core (3-I.e., not on the carbon between the N and the S of the thiazole). In one embodiment, the compound does not have two $R^3$ moieties that include Ar or Het in the moieties' structure.

In the presently disclosed compounds of any of structural formulae (3-I)-(3-XXXVI), the number of substituents on ring system "C", x, is 0 or an integer less than or equal to the sum of p and q. when D or Z is $CR^4$, the $R^4$ of D or Z is one of the x $R^4$ groups on ring system "C". In one embodiment, x is 0, 1, 2 or 3. For example, x can be 0, or can be 1 or 2.

In certain embodiments of the presently disclosed compounds of any of structural formula (3-I)-(3-XXXVI), two $R^4$ groups combine to form an oxo. The oxo can be bound, for example, at the position alpha to a nitrogen of ring system "C". In other embodiments, no two $R^4$ groups combine to form an oxo.

In certain embodiments of the presently disclosed compounds of any of structural formulae (3-I)-(3-XXXVI), when x is 4, not all four $R^4$ groups are ($C_1$-$C_6$ alkyl).

In certain embodiments of the presently disclosed compounds of any of structural formulae (3-I)-(3-XXXVI), each $R^4$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^4$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group.

In certain embodiments, the presently disclosed compounds have the structural formula (3-XXXVII):

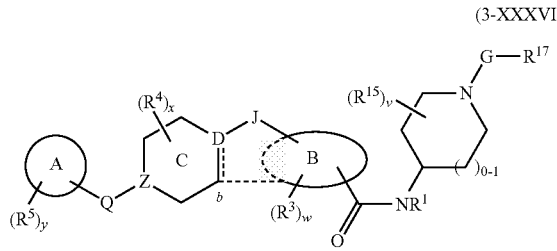

(3-XXXVII)

in which Q and G are each independently a bond, —$CH_2$—, —C(H)($R^{16}$)—, —C($R^{16}$)$_2$—, L (e.g., —C(O)—$NR^9$— or —$NR^9$—C(O)—) or —S(O)$_2$—; v is 0, 1, 2, 3 or 4; each $R^{15}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^{15}$ on the same carbon optionally combine to form oxo; $R^{17}$ is Het or Ar, and all other variables are defined as described above with reference to any of structural formula (3-I)-(3-XXXVI). $R^{17}$ can be, for example, an optionally substituted phenyl, an optionally-substituted pyridyl, an optionally substituted pyrazolyl, an optionally substituted imidazolyl, an optionally substituted pyrrolyl, an optionally substituted triazolyl or an optionally substituted thiadiazolyl. In one embodiment, Q is a single bond. In another embodiment, Q is —$CH_2$—. In other embodiments, Q is —C(O)— or —S(O)$_2$—. In certain embodiments, G is —$CH_2$—. In other embodiments, G is —C(O)— or —S(O)$_2$—. In other embodiments, G is —CH($CH_3$)—. In other embodiments, G is —C(O)—NH—. The above-recited Q and G moieties can be combined in any possible combination. For example, in one embodiment, Q is a single bond and G is —$CH_2$— or —C(O)—. As described above, in certain embodiments, the ring system denoted by "A" is aryl or heteroaryl. In one embodiment, the ring system denoted by "A" is substituted with one or more electron-withdrawing groups as described above. In another embodiment, $R^{17}$ is substituted with one or more electron-withdrawing groups as described above. In certain embodiments, the ring system denoted by "A", $R^{17}$ or both are not substituted with an aryl, heteroaryl, cycloalkyl or heterocycloalkyl-containing group. In certain embodiments, the azacycloalkyl to which -G-$R^{17}$ is bound is a piperidinyl; in other embodiments, it is a pyrrolidinyl.

In the presently disclosed compounds of structural formula (3-XXXVII), v is 0, 1, 2, 3 or 4. In one embodiment, v is 0, 1, 2 or 3. For example, v can be 0, or can be 1 or 2.

In certain embodiments of the presently disclosed compounds of structural formula (3-XXXVII), two $R^{15}$ groups combine to form an oxo. The oxo can be bound, for example, at the position alpha relative to the nitrogen of the azacycloalkyl ring. In other embodiments, no two $R^{15}$ groups combine to form an oxo.

In certain embodiments of the presently disclosed compounds of structural formula (3-XXXVII), when v is 4, not all four $R^{15}$ moieties are ($C_1$-$C_6$ alkyl).

In certain embodiments of the presently disclosed compounds of structural formula (3-XXXVII), each $R^{15}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN and two $R^{15}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{15}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN and two $R^{15}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In some embodiments, one $R^{15}$ is —C(O)$NR^9R^7$, which can be bound, for example, at a position alpha relative to the piperidine nitrogen, or at the position linked to the —N($R^1$)—.

In certain embodiments of the presently disclosed compounds of structural formula (3-XXXVII), $R^{17}$ is an unsubstituted aryl or heteroaryl. In other embodiments, the $R^{17}$ Ar or Het is substituted with 1, 2 or 3 substituents independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, the $R^{17}$ Ar or Het is substituted with 1, 2 or 3 substituents independently selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, $R^{17}$ is substituted with 1, 2 or 3 substituents selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca. $R^{17}$ can be substituted with, for example, one such substituent, or two such substituents. In certain embodiments, $R^{17}$ is substituted with a substituent -$G^2$-$R^{34}$, in which $G^2$ is a single bond, —O—, —C(O)—, —S(O)$_2$— or —$CH_2$—, and $R^{34}$ is chosen from aryl (such as phenyl), heterocycloalkyl (such as morpholinyl, pyrrolidinyl), and heteroaryl (such as), each of which is optionally substituted with 1 or 2 substituents selected from aryl, ($C_1$-$C_4$ haloalkyl), —O—($C_1$-$C_4$ haloalkyl), ($C_1$-$C_4$ alkyl), —O—($C_1$-$C_4$ alkyl), halogen, or CN.

For example, in certain embodiments, the presently disclosed compounds have the structural formula (3-XXXVIII):

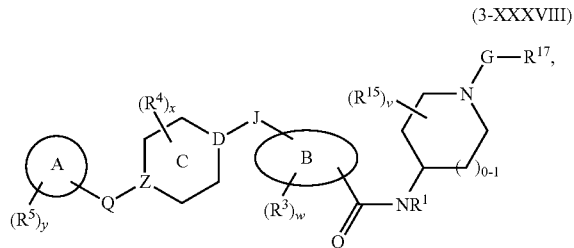

(3-XXXVIII)

in which all variables are as defined above with reference to any of structural formulae (3-I)-(3-XXXVII).

In other embodiments, the presently disclosed compounds have structural formula (3-XXXIX):

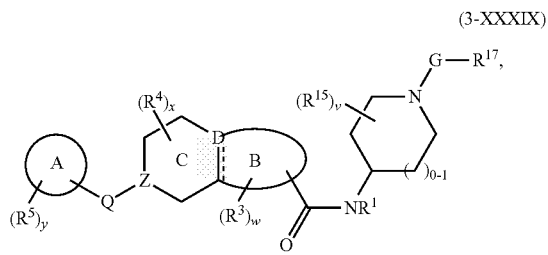

(3-XXXIX)

in which all variables are as defined above with reference to any of structural formulae (3-I)-(3-XXXVII).

In certain embodiments, the presently disclosed compounds have the structural formula (3-XL):

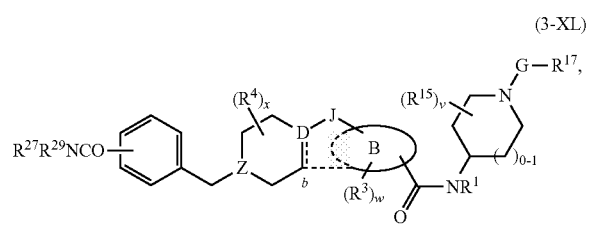

(3-XL)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (3-I)-(3-XXXVII). In one embodiment, $R^{27}$ and $R^{29}$ are both H.

In certain embodiments, the presently disclosed compounds have the structural formula (3-XLI):

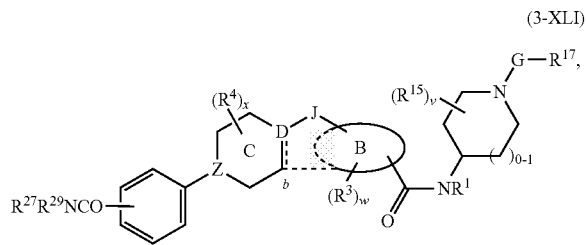

(3-XLI)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (3-I)-(3-XXXVII). In one embodiment, $R^{27}$ and $R^{29}$ are both H.

In certain embodiments, the presently disclosed compounds have the structural formula (3-XLII):

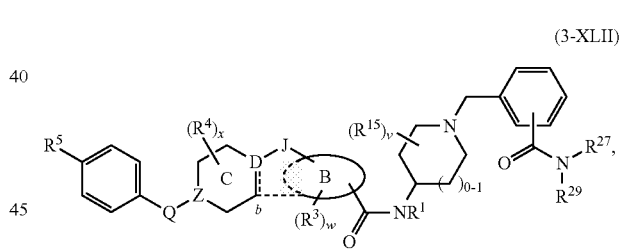

(3-XLII)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (3-I)-(3-XXXVII). In one embodiment, $R^{27}$ and $R^{29}$ are both H.

In certain embodiments, the presently disclosed compounds have the structural formula (3-XLIII):

(3-XLIII)

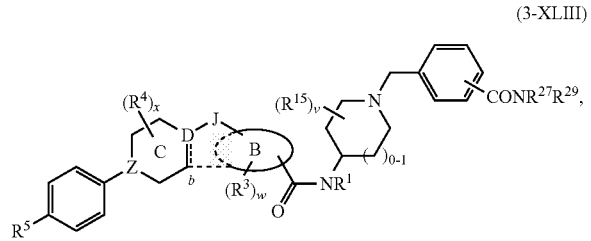

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (3-I)-(3-XXXVII). In one embodiment, $R^{27}$ and $R^{29}$ are both H.

In certain embodiments, the presently disclosed compounds have the structural formula (3-XLIV):

(3-XLIV)

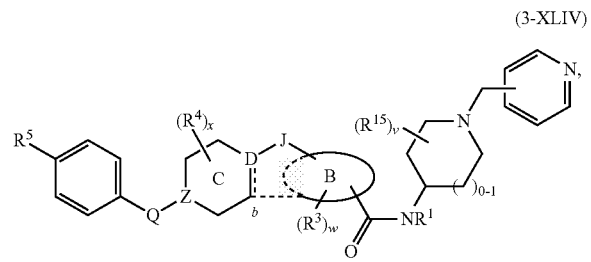

in which all variables are as described above with reference to any of structural formulae (3-I)-(3-XXXVII).

In certain embodiments, the presently disclosed compounds have the structural formula (3-XLV):

(3-XLV)

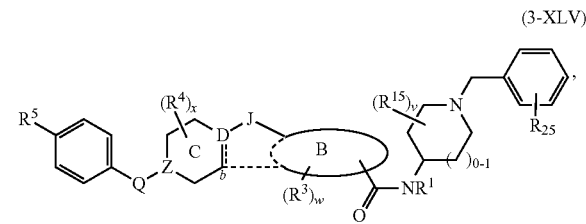

in which $R^{25}$ is selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl or haloalkyl is substituted by an aryl, heteroaryl, cycloalkyl or heterocycloalkyl-containing group; and all other variables are as described above with reference to any of structural formulae (3-I)-(3-XXXIX). $R^{25}$ can be, for example, —Cl, —F, cyano, —C(O)$CH_3$, —C(O)OH, —C(O)$NH_2$, trifluoromethyl, difluoromethyl, difluoromethoxy or trifluoromethoxy.

In certain embodiments, the presently disclosed compounds have the structural formula (3-XLVI):

(3-XLVI)

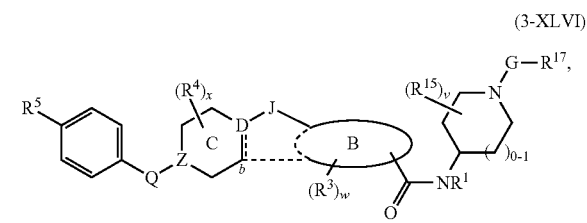

in which G is —C(O)—, —S(O)$_2$— or —C(O)—NH— and all other variables are as described above with reference to any of structural formulae (3-I)-(3-XXXIX).

In certain embodiments, the presently disclosed compounds have the structural formula (3-XLVII):

(3-XLVII)

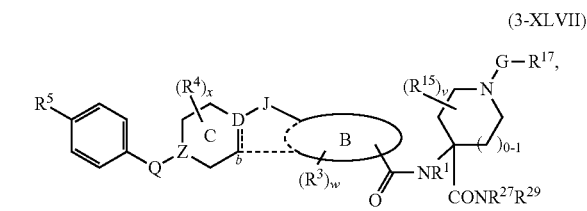

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (3-I)-(3-XXXIX). In one embodiment, $R^{27}$ and $R^{29}$ are both H. In some embodiments, the compounds of structural formula (3-XLVII) are present as racemic mixtures or scalemic mixtures. In other embodiments, the compounds of structural formula (3-XLVII) are present in an enantiomerically-enriched form, for example as a substantially pure stereoisomer.

In certain embodiments, the presently disclosed compounds have the structural formula (3-XLVIII):

(3-XLVIII)

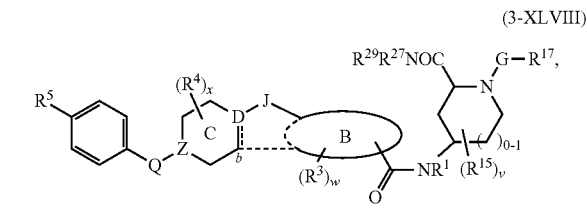

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (3-I)-(3-XXXIX). In one embodiment, $R^{27}$ and $R^{29}$ are both H. In some embodiments, the compounds of structural formula (3-XLVIII) are present as racemic mixtures or scalemic mixtures. In other embodiments, the compounds of structural formula (3-XLVIII) are present in an enantiomerically-enriched form, for example as a substantially pure stereoisomer.

In certain embodiments, the presently disclosed compounds have the structural formula (3-XLIX):

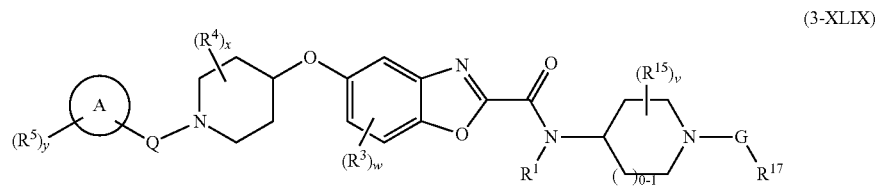

(3-XLIX)

in which G, v, $R^{15}$ and $R^{17}$ are defined as described above with reference to structural formula (3-XXXVII), and all other variables are defined as described above with reference to structural formulae (3-I)-(3-IV) and (3-XIV). $R^5$, y, v, $R^{15}$, $R^{17}$, Q, G and the ring denoted by "A" can be defined, for example, as described with reference to any of structural formulae (3-XL)-(3-XLVIII).

In certain embodiments, the presently disclosed compounds have the structural formula (3-L):

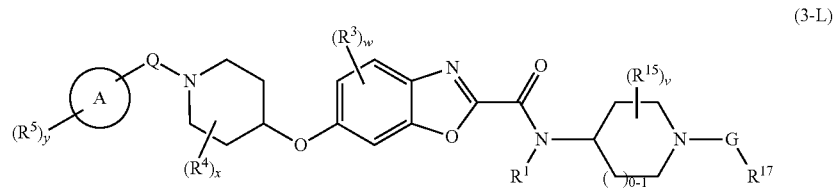

(3-L)

in which G, v, $R^{15}$ and $R^{17}$ are defined as described above with reference to structural formula (3-XXXVII), and all other variables are defined as described above with reference to structural formulae (3-I)-(3-IV) and (3-XV). $R^5$, y, v, $R^{15}$, $R^{17}$, Q, G and the ring denoted by "A" can be defined, for example, as described with reference to any of structural formulae (3-XL)-(3-XLVIII).

In certain embodiments, the presently disclosed compounds have the structural formula (3-LI):

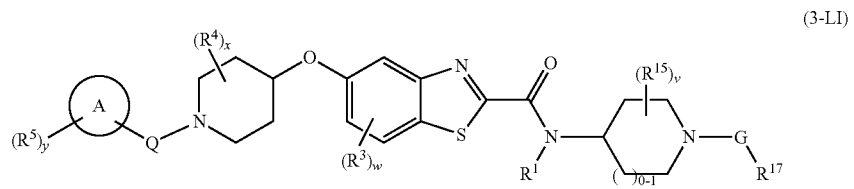

(3-LI)

in which G, v, $R^{15}$ and $R^{17}$ are defined as described above with reference to structural formula (3-XXXVII), and all other variables are defined as described above with reference to structural formulae (3-I)-(3-IV) and (3-XVI). $R^5$, y, v, $R^{15}$, $R^{17}$, Q, G and the ring denoted by "A" can be defined, for example, as described with reference to any of structural formulae (3-XL)-(3-XLVIII).

In certain embodiments, the presently disclosed compounds have the structural formula (3-LII):

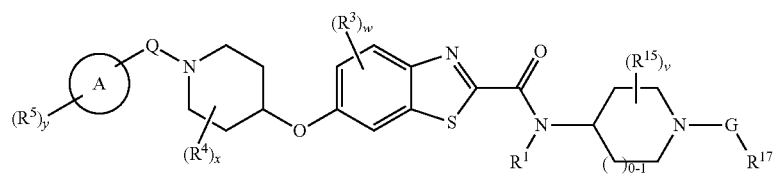

(3-LII)

in which G, v, $R^{15}$ and $R^{17}$ are defined as described above with reference to structural formula (3-XXXVII), and all other variables are defined as described above with reference to structural formulae (3-I)-(3-IV) and (3-XVII). $R^5$, y, v, $R^{15}$, $R^{17}$, Q, G and the ring denoted by "A" can be defined, for example, as described with reference to any of structural formulae (3-XL)-(3-XLVIII).

In certain embodiments, the presently disclosed compounds have the structural formula (3-LIII):

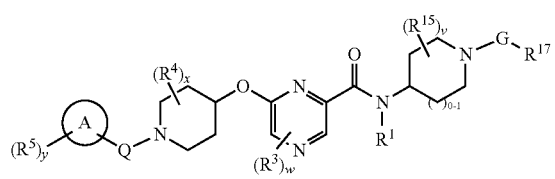

(3-LIII)

in which G, v, $R^{15}$ and $R^{17}$ are defined as described above with reference to structural formula (3-XXXVII), and all other variables are defined as described above with reference to structural formulae (3-I)-(3-IV) and (3-XIX). $R^5$, y, v, $R^{15}$, $R^{17}$, Q, G and the ring denoted by "A" can be defined, for example, as described with reference to any of structural formulae (3-XL)-(3-XLVIII).

In certain embodiments, the presently disclosed compounds have the structural formula (3-LIV):

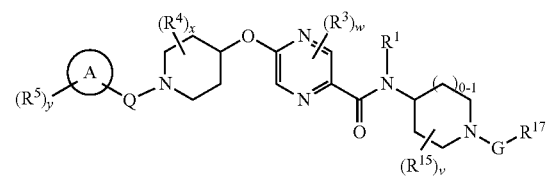

(3-LIV)

in which G, v, $R^{15}$ and $R^{17}$ are defined as described above with reference to structural formula (3-XXXVII), and all other variables are defined as described above with reference to structural formulae (3-I)-(3-IV) and (3-XX). $R^5$, y, v, $R^{15}$, $R^{17}$, Q, G and the ring denoted by "A" can be defined, for example, as described with reference to any of structural formulae (3-XL)-(3-XLVIII).

In certain embodiments, the presently disclosed compounds have the structural formula (3-LV):

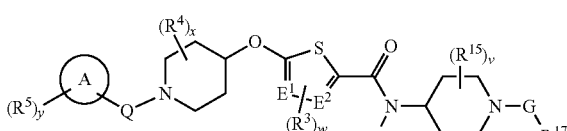

(3-LV)

in which G, v, $R^{15}$ and $R^{17}$ are defined as described above with reference to structural formula (3-XXXVII), and all other variables are defined as described above with reference to structural formulae (3-I)-(3-IV) and (3-XXI). $R^5$, y, v, $R^{15}$, $R^{17}$, Q, G and the ring denoted by "A" can be defined, for example, as described with reference to any of structural formulae (3-XL)-(3-XLVIII). In one embodiment, $E^1$ is carbon and $E^2$ is N. In another embodiment, $E^1$ is N and $E^2$ is carbon.

In certain embodiments, the presently disclosed compounds have the structural formula (3-LVI):

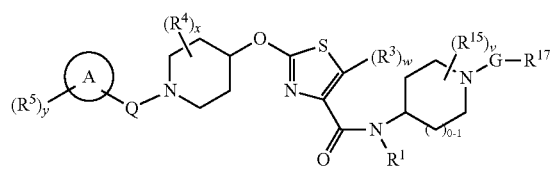

(3-LVI)

in which G, v, $R^{15}$ and $R^{17}$ are defined as described above with reference to structural formula (3-XXXVII), and all other variables are defined as described above with reference to structural formulae (3-I)-(3-IV) or (3-XXII). $R^5$, y, v, $R^{15}$, $R^{17}$, Q, G and the ring denoted by "A" can be defined, for example, as described with reference to any of structural formulae (3-XL)-(3-XLVIII). When w is 0, the ring position shown occupied by $R^3$ bears a hydrogen atom.

In certain embodiments, the presently disclosed compounds have the structural formula (3-LVII):

(3-LVII)

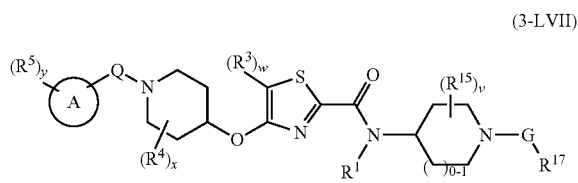

in which G, v, $R^{15}$ and $R^{17}$ are defined as described above with reference to structural formula (3-XXXVII), and all other variables are defined as described above with reference to structural formulae (3-I)-(3-IV) and (3-XXIII). $R^5$, y, v, $R^{15}$, $R^{17}$, Q, G and the ring denoted by "A" can be defined, for example, as described with reference to any of structural formulae (3-XL)-(3-XLVIII). When w is 0, the ring position shown occupied by $R^3$ bears a hydrogen atom.

In certain embodiments, the presently disclosed compounds have the structural formula (3-LVIII):

(3-LVIII)

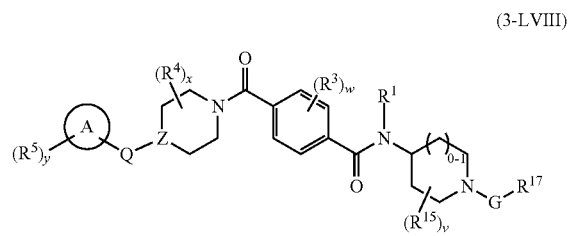

in which G, v, $R^{15}$ and $R^{17}$ are defined as described above with reference to structural formula (3-XXXVII), and all other variables are defined as described above with reference to structural formulae (3-I)-(3-IV) and (3-XXVII). $R^5$, y, v, $R^{15}$, $R^{17}$, Q, G and the ring denoted by "A" can be defined, for example, as described with reference to any of structural formulae (3-XL)-(3-XLVIII). In certain embodiments, Z is N. In other embodiments, Z is CH or C substituted with one of the x $R^4$.

In certain embodiments, the presently disclosed compounds have the structural formula (3-LIX):

(3-LIX)

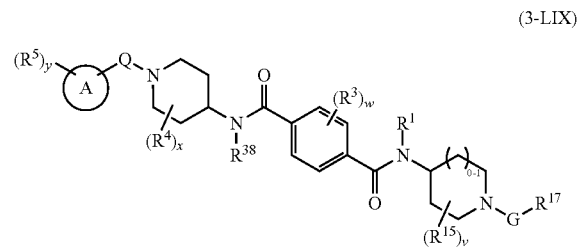

in which G, v, $R^{15}$ and $R^{17}$ are defined as described above with reference to structural formula (3-XXXVII), and all other variables are defined as described above with reference to structural formulae (3-I)-(3-IV) and (3-XXVIII). $R^5$, y, v, $R^{15}$, $R^{17}$, Q, G and the ring denoted by "A" can be defined, for example, as described with reference to any of structural formulae (3-XL)-(3-XLVIII).

In certain embodiments, the presently disclosed compounds have the structural formula (3-LX):

(3-LX)

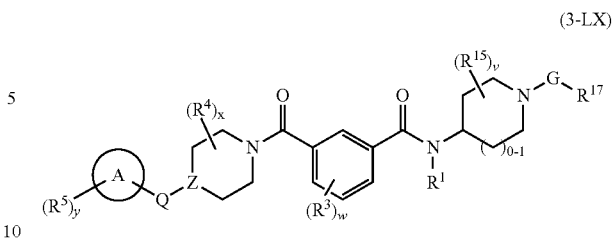

in which G, v, $R^{15}$ and $R^{17}$ are defined as described above with reference to structural formula (3-XXXVII), and all other variables are defined as described above with reference to structural formulae (3-I)-(3-IV) and (3-XXIX). $R^5$, y, v, $R^{15}$, $R^{17}$, Q, G and the ring denoted by "A" can be defined, for example, as described with reference to any of structural formulae (3-XL)-(3-XLVIII). In certain embodiments, Z is N. In other embodiments, Z is CH or C substituted with one of the x $R^4$.

In certain embodiments, the presently disclosed compounds have the structural formula (3-LXI):

(3-LXI)

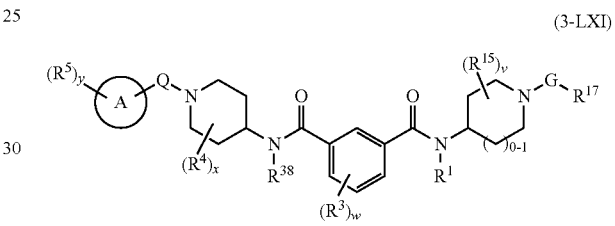

in which G, v, $R^{15}$ and $R^{17}$ are defined as described above with reference to structural formula (3-XXXVII), and all other variables are defined as described above with reference to structural formulae (3-I)-(3-IV) and (3-XXX). $R^5$, y, v, $R^{15}$, $R^{17}$, Q, G and the ring denoted by "A" can be defined, for example, as described with reference to any of structural formulae (3-XL)-(3-XLVIII).

In certain embodiments, the presently disclosed compounds have the structural formula (3-LXII):

(3-LXII)

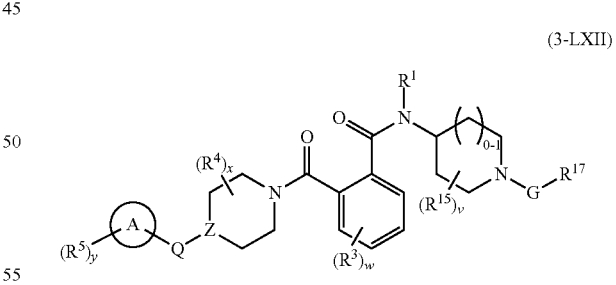

in which G, v, $R^{15}$ and $R^{17}$ are defined as described above with reference to structural formula (3-XXXVII), and all other variables are defined as described above with reference to structural formulae (3-I)-(3-IV) and (3-XXXI). $R^5$, y, v, $R^{15}$, $R^{17}$, Q, G and the ring denoted by "A" can be defined, for example, as described with reference to any of structural formulae (3-XL)-(3-XLVIII). In certain embodiments, Z is N. In other embodiments, Z is carbon (e.g., CH or C substituted with one of the x $R^4$).

In certain embodiments, the presently disclosed compounds have the structural formula (3-LXIII):

(3-LXIII)

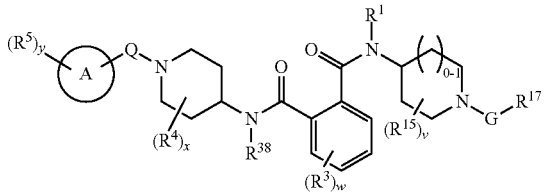

in which G, v, $R^{15}$ and $R^{17}$ are defined as described above with reference to structural formula (3-XXXVII), and all other variables are defined as described above with reference to structural formulae (3-I)-(3-IV) and (3-XXXII). $R^5$, y, v, $R^{15}$, $R^{17}$, Q, G and the ring denoted by "A" can be defined, for example, as described with reference to any of structural formulae (3-XL)-(3-XLVIII).

In certain embodiments of compounds having structural formulae (3-XXXVII)-(3-XLI), (3-XLVI) and (3-XLIX)-(3-LXIII), the

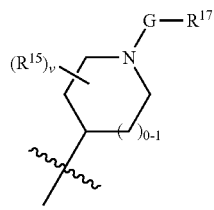

moiety has the structure

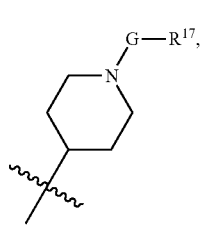

in which G is —CH$_2$—, —CH(CH$_3$)—, —C(O)—, —S(O)$_2$— or —C(O)—NH—. For example, in one embodiment, G is —CH$_2$—. In another embodiment, G is —C(O)— or —S(O)$_2$—. In another embodiment, G is —C(O)—NH—.

In other embodiments of compounds having structural formulae (3-XXXVII)-(3-XLI), (3-XLVI) and (3-XLIX)-(3-LXIII), the

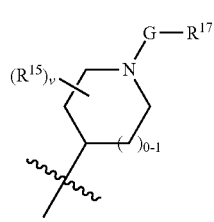

moiety has the structure

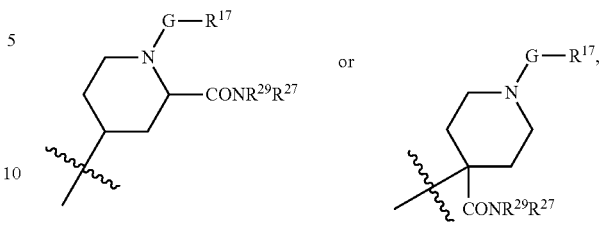

in which G is —CH$_2$—, —C(O)—, —S(O)$_2$— or —C(O)—NH—, $R^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and $R^{29}$ is —H, —(C$_1$-C$_4$ alkyl), —CO—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or $R^{27}$ and $R^{29}$ together with the nitrogen to which they are bound form Hca. In such embodiments, the compounds can be present as racemic mixtures or scalemic mixtures, or in an enantiomerically-enriched form, for example as a substantially pure stereoisomer.

In other embodiments of compounds having structural formulae (3-XXXVII)-(3-XLI), (3-XLVI) and (3-XLIX)-(3-LXIII), the


moiety has the structure

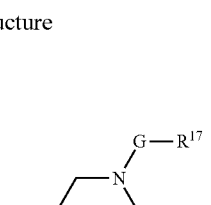

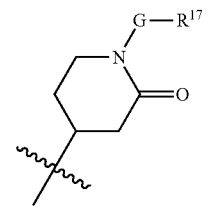

in which G is —CH$_2$—, —C(O)—, —S(O)$_2$— or —C(O)—NH—.

In certain embodiments of compounds having structural formulae (3-XXXVII)-(3-XLI), (3-XLVI) and (3-XLIX)-(3-LXIII), the $R^{17}$ moiety has the structure

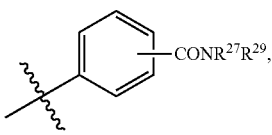

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca.

In certain embodiments of compounds having structural formulae (3-XXXVII)-(3-LXIII), w is 1, and $R^3$ is —$NR^8R^9$. In certain such embodiments, $R^3$ is substituted at a 6-membered aromatic ring position in the meta position relative to the J moiety.

In other embodiments of compounds having structural formulae (3-XXXVII)-(3-LXIII), w is 1, and $R^3$ is —($C_0$-$C_3$ alkyl)-$Y^1$—($C_1$-$C_3$ alkyl)-$Y^2$—($C_0$-$C_3$ alkyl), in which each of $Y^1$ and $Y^2$ is independently L, —O—, —S— or —$NR^9$—. In certain such embodiments, $R^3$ is substituted at a 6-membered aromatic ring position in the meta position relative to the J moiety.

In certain embodiments described above, each $R^{27}$ is selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group, and each $R^{29}$ is H, methyl or ethyl, or $R^{27}$ and $R^{29}$ together with the nitrogen to which they are bound form Hca.

In certain embodiments of compounds having structural formulae (3-XXXVII)-(3-XXXIX) and (3-XLII)-(3-LXIII), at least one $R^5$ moiety is a haloalkyl group, and in exemplary embodiments of these formulae the

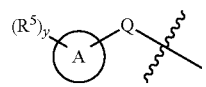

moiety is p-(trifluoromethyl)phenyl.

In one embodiment, the presently disclosed compounds of any of structural formulae (3-I)-(3-XXXVI) have a T moiety having the structural formula

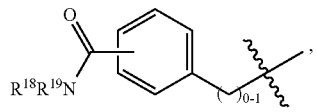

and an $R^2$ moiety having the structural formula

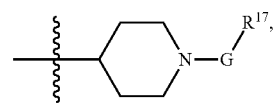

in which G and $R^{17}$ are as described above with reference to any of structural formulae (3-I)-(3-LXVIII), $R^{18}$ is H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), in which no alkyl or haloalkyl is substituted with an aryl-, heteroaryl-, cycloalkyl- or heterocycloalkyl-containing group and $R^{19}$ is —H, —($C_1$-$C_4$ alkyl), —CO—($C_1$-$C_4$ alkyl) or —CO—O—($C_1$-$C_4$ alkyl) in which no alkyl is substituted by an aryl, heteroaryl, cycloalkyl or heterocycloalkyl-containing group, or $R^{18}$ and $R^{19}$ together with the nitrogen to which they are bound form Hca. In one embodiment, $R^{18}$ and $R^{19}$ are both H.

In another embodiment, the presently disclosed compounds of any of structural formulae (3-I)-(3-XXXVII) have a T moiety having the structural formula

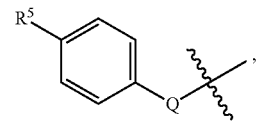

and an $R^2$ moiety having the structural formula

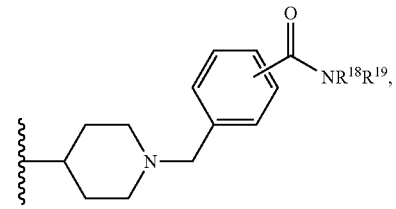

in which Q and $R^5$ are defined as described above with reference to any of structural formulae (3-I)-(3-LXVIII), $R^{18}$ is H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), in which no alkyl or haloalkyl is substituted with an aryl-, heteroaryl-, cycloalkyl- or heterocycloalkyl-containing group and $R^{19}$ is —H, —($C_1$-$C_4$ alkyl), —CO—($C_1$-$C_4$ alkyl) or —CO—O—($C_1$-$C_4$ alkyl) in which no alkyl is substituted by an aryl, heteroaryl, cycloalkyl or heterocycloalkyl-containing group, or $R^{18}$ and $R^{19}$ together with the nitrogen to which they are bound form Hca. In one embodiment, $R^{18}$ and $R^{19}$ are both H.

In another embodiment, the presently disclosed compounds of any of structural formulae (3-I)-(3-XXXVII) have a T moiety having the structural formula

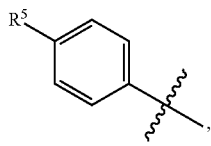

and an R² moiety having the structural formula

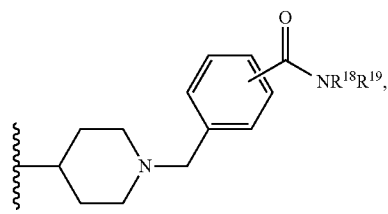

in which Q and $R^5$ are defined as described above with reference to any of structural formulae (3-I)-(3-LXVIII), $R^{18}$ is H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), in which no alkyl or haloalkyl is substituted with an aryl-, heteroaryl-, cycloalkyl- or heterocycloalkyl-containing group and $R^{19}$ is —H, —($C_1$-$C_4$ alkyl), —CO—($C_1$-$C_4$ alkyl) or —CO—O—($C_1$-$C_4$ alkyl) in which no alkyl is substituted by an aryl, heteroaryl, cycloalkyl or heterocycloalkyl-containing group, or $R^{18}$ and $R^{19}$ together with the nitrogen to which they are bound form Hca. In one embodiment, $R^{18}$ and $R^{19}$ are both H.

In certain embodiments, the presently disclosed compounds have the structural formula (3-LXIV):

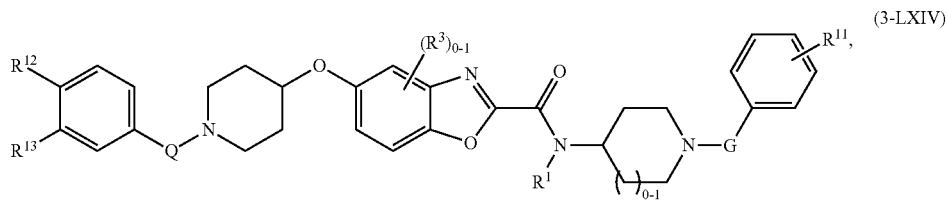

(3-LXIV)

in which Q is —$CH_2$—, —C(O)— or a single bond; G is a single bond, —$CH_2$—, —C(O)—, —S(O)$_2$— or —C(O)—NH—; $R^1$ and $R^3$ are as described above with reference to any of structural formulae (3-I)-(3-IV) and (3-XLIX); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the benzo moiety of the central benzo[d]oxazole. In another embodiment, one $R^3$ (e.g., —Cl, —F, —$CH_3$, —$C_2H_5$, —$C_3H_7$) is substituted on the benzo moiety of the central benzo[d]oxazole.

In certain embodiments, the presently disclosed compounds have the structural formula (3-LXV):

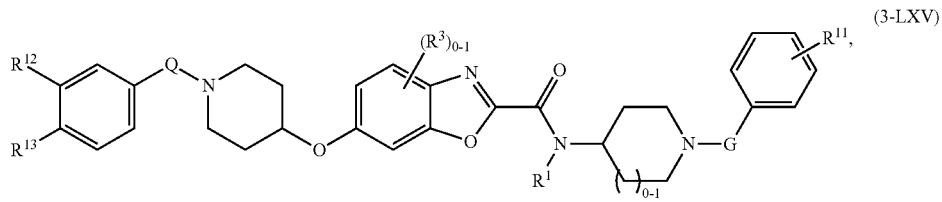

(3-LXV)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-L); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group.

In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]oxazole. In another embodiment, one R$^3$ (e.g., —Cl, —F, —CH$_3$, —C$_2$H$_5$, —C$_3$H$_7$) is substituted on the benzo moiety of the central benzo[d]oxazole.

In certain embodiments, the presently disclosed compounds have the structural formula (3-LXVI):

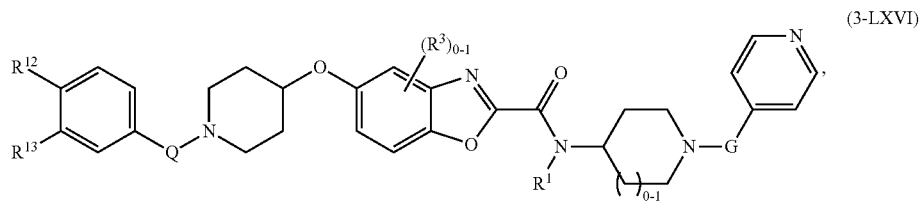

(3-LXVI)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-XLIX); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]oxazole. In another embodiment, one R$^3$ (e.g., —Cl, —F, —CH$_3$, —C$_2$H$_5$, —C$_3$H$_7$) is substituted on the benzo moiety of the central benzo[d]oxazole.

In certain embodiments, the presently disclosed compounds have the structural formula (3-LXVII):

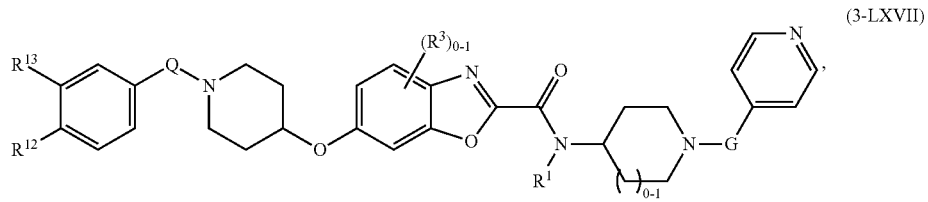

(3-LXVII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-L); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]oxazole. In another embodiment, one R$^3$ (e.g., —Cl, —F, —CH$_3$, —C$_2$H$_5$, —C$_3$H$_7$) is substituted on the benzo moiety of the central benzo[d]oxazole.

In certain embodiments, the presently disclosed compounds have the structural formula (3-LXVIII):

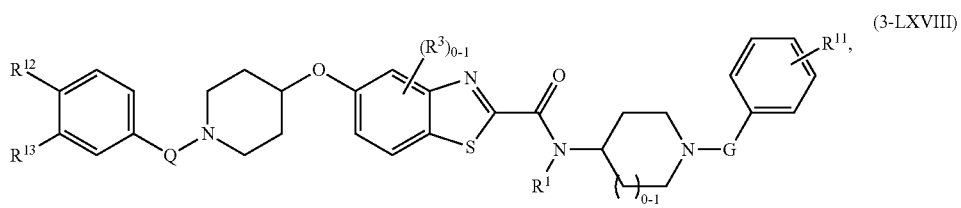

(3-LXVIII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LI); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]thiazole. In another embodiment, one R$^3$ (e.g., —Cl, —F, —CH$_3$, —C$_2$H$_5$, —C$_3$H$_7$) is substituted on the benzo moiety of the central benzo[d]thiazole.

In certain embodiments, the presently disclosed compounds have the structural formula (3-LXIX):

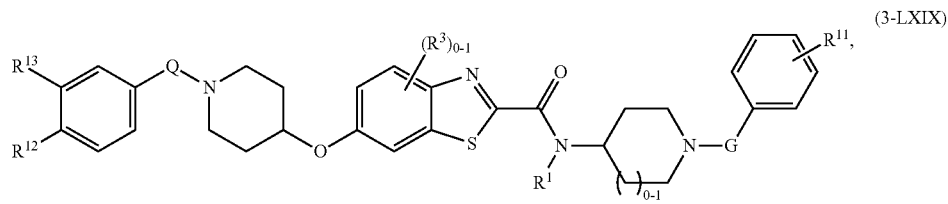

(3-LXIX)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group.

In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]thiazole. In another embodiment, one R$^3$ (e.g., —Cl, —F, —CH$_3$, —C$_2$H$_5$, —C$_3$H$_7$) is substituted on the benzo moiety of the central benzo[d]thiazole.

In certain embodiments, the presently disclosed compounds have the structural formula (3-LXX):

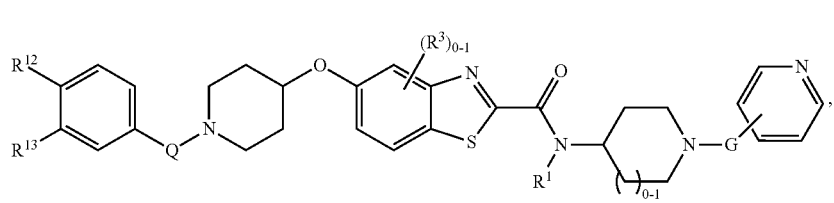

(3-LXX)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LI); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]thiazole. In another embodiment, one R$^3$ (e.g., —Cl, —F, —CH$_3$, —C$_2$H$_5$, —C$_3$H$_7$) is substituted on the benzo moiety of the central benzo[d]thiazole.

In certain embodiments, the presently disclosed compounds have the structural formula (3-LXXI):

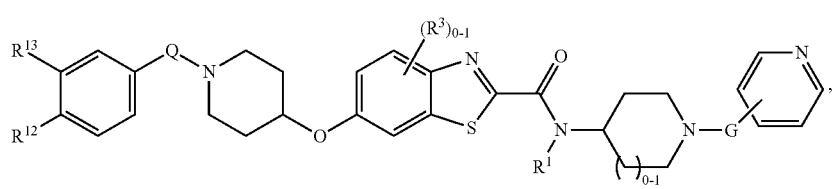

(3-LXXI)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]thiazole. In another embodiment, one R$^3$ (e.g., —Cl, —F, —CH$_3$, —C$_2$H$_5$, —C$_3$H$_7$) is substituted on the benzo moiety of the central benzo[d]thiazole.

In certain embodiments, the presently disclosed compounds have the structural formula (3-LXXII):

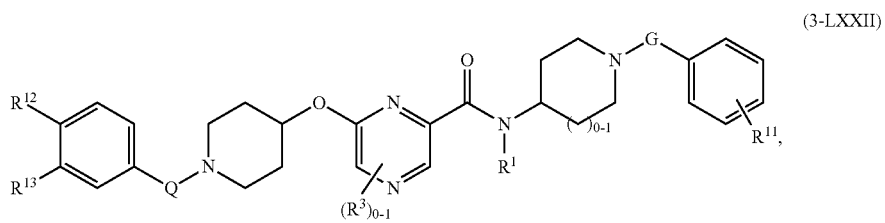

(3-LXXII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central pyrazine. In another embodiment, one R$^3$ (e.g., —Cl, —F, —CH$_3$, —C$_2$H$_5$, —C$_3$H$_7$) is substituted on the central pyrazine.

In certain embodiments, the presently disclosed compounds have the structural formula (3-LXXIII):

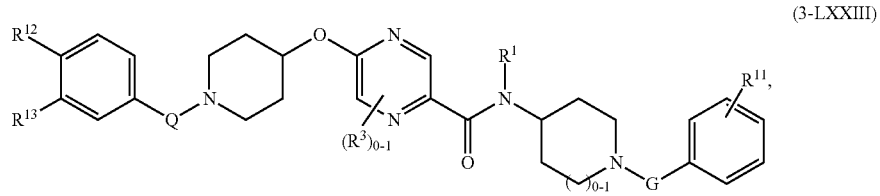

(3-LXXIII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LIV); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central pyrazine. In another embodiment, one R$^3$ (e.g., —Cl, —F, —CH$_3$, —C$_2$H$_5$, —C$_3$H$_7$) is substituted on the central pyrazine.

In certain embodiments, the presently disclosed compounds have the structural formula (3-LXXIV):

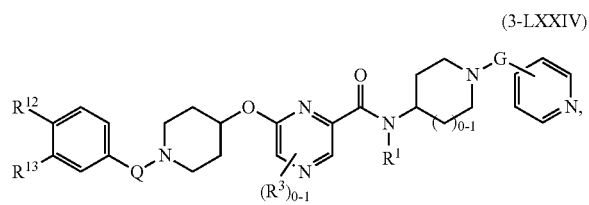

(3-LXXIV)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I) and (3-LIII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central pyrazine. In another embodiment, one R$^3$ (e.g., —Cl, —F, —CH$_3$, —C$_2$H$_5$, —C$_3$H$_7$) is substituted on the central pyrazine.

In certain embodiments, the presently disclosed compounds have the structural formula (3-LXXV):

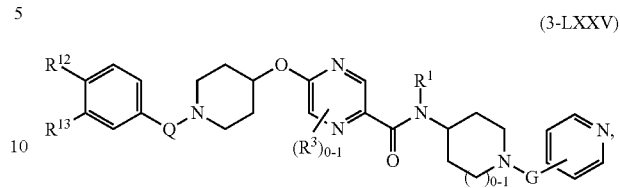

(3-LXXV)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (3-I)-(3-IV) and (3-LIV); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central pyrazine. In another embodiment, one R$^3$ (e.g., —Cl, —F, —CH$_3$, —C$_2$H$_5$, —C$_3$H$_7$) is substituted on the central pyrazine.

In certain embodiments, the presently disclosed compounds have the structural formula (3-LXXVI):

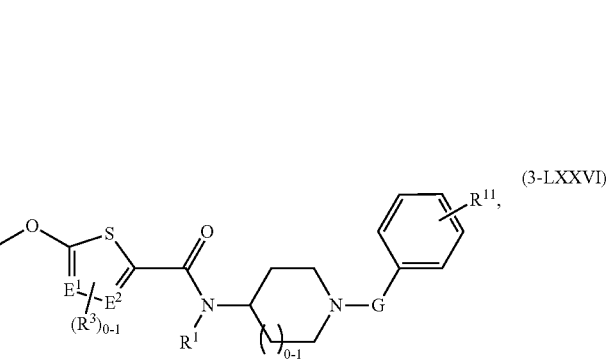

(3-LXXVI)

haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central pyrazine. In another embodiment, one R$^3$ (e.g., —Cl, —F, —CH$_3$, —C$_2$H$_5$, —C$_3$H$_7$) is substituted on the central pyrazine.

in which Q is —CH$_2$—, —C(O)— or a single bond; G is a single bond, —CH$_2$—, —C(O)—, —S(O)$_2$— or —C(O)—NH—; E$^1$, E$^2$, R$^1$ and R$^3$ are as described above with reference to any of structural formulae (3-I)-(3-IV) and (3-LV); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H.

is substituted on the central thiazole (3-I.e., the ring position shown occupied by $R^3$ bears a hydrogen atom). In another embodiment, one $R^3$ (e.g., —Cl, —F, —CH$_3$, —C$_2$H$_5$, —C$_3$H$_7$) is substituted on the central thiazole.

In certain embodiments, the presently disclosed compounds have the structural formula (3-LXXVIII):

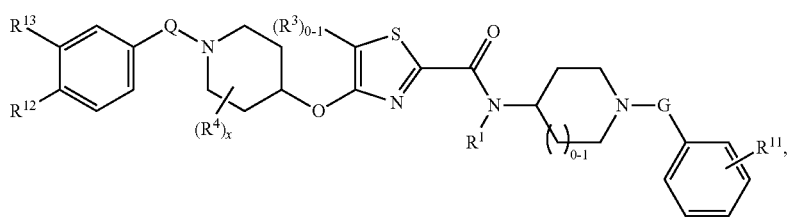

(3-LXXVIII)

In another embodiment, $R^1$ is methyl, ethyl, propyl or butyl. In one embodiment, no $R^3$ is substituted on the central thiazole. In another embodiment, one $R^3$ (e.g., —Cl, —F, —CH$_3$, —C$_2$H$_5$, —C$_3$H$_7$) is substituted on the central thiazole. In one embodiment, $E^1$ is carbon and $E^2$ is N. In another embodiment, $E^1$ is N and $E^2$ is carbon.

In certain embodiments, the presently disclosed compounds have the structural formula (3-LXXVII):

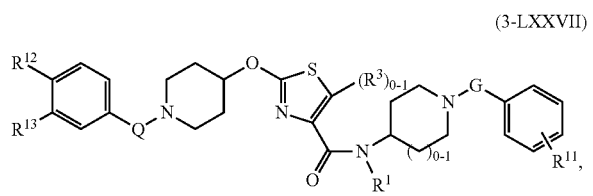

(3-LXXVII)

in which Q is —CH$_2$—, —C(O)— or a single bond; G is a single bond, —CH$_2$—, —C(O)—, —S(O)$_2$— or —C(O)—NH—; $R^1$ and $R^3$ are as described above with reference to any of structural formulae (3-I)-(3-IV) and (3-LVI); and R$_{11}$, R$_{12}$ and R$_{13}$ are independently selected from H, halo, cyano, in which Q is —CH$_2$—, —C(O)— or a single bond; G is a single bond, —CH$_2$—, —C(O)—, —S(O)$_2$— or —C(O)—NH—; $R^1$ and $R^3$ are as described above with reference to any of structural formulae (3-I)-(3-IV) and (3-LVII); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central thiazole (3-I.e., the ring position shown occupied by $R^3$ bears a hydrogen atom). In another embodiment, one $R^3$ (e.g., —Cl, —F, —CH$_3$, —C$_2$H$_5$, —C$_3$H$_7$) is substituted on the central thiazole.

In certain embodiments, the presently disclosed compounds have the structural formula (3-LXXIX):

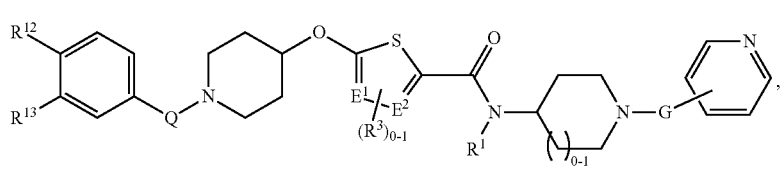

(3-LXXIX)

—(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$_{11}$, R$_{12}$ and R$_{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ in which Q is —CH$_2$—, —C(O)— or a single bond; G is a single bond, —CH$_2$—, —C(O)—, —S(O)$_2$— or —C(O)—NH—; $E^1$, $E^2$, $R^1$ and $R^3$ are as described above with reference to any of structural formulae (3-I)-(3-IV) and (3-LV); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central thiazole. In another embodiment, one $R^3$ (e.g., —Cl, —F, —CH$_3$, —C$_2$H$_5$, —C$_3$H$_7$) is substituted on the central thiazole. In another embodiment, $R^1$ is methyl, ethyl, propyl or butyl. In one embodiment, no $R^3$ is substituted on the central thiazole (3-I.e., the ring position shown occupied by $R^3$ bears a hydrogen atom). In another embodiment, one $R^3$ (e.g., —Cl, —F, —CH$_3$, —C$_2$H$_5$, —C$_3$H$_7$) is substituted on the central thiazole.

In certain embodiments, the presently disclosed compounds have the structural formula (3-LXXXI):

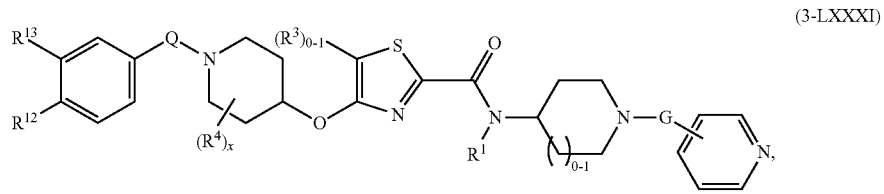

(3-LXXXI)

the central thiazole. In one embodiment, $E^1$ is carbon and $E^2$ is N. In another embodiment, $E^1$ is N and $E^2$ is carbon.

In certain embodiments, the presently disclosed compounds have the structural formula (3-LXXX):

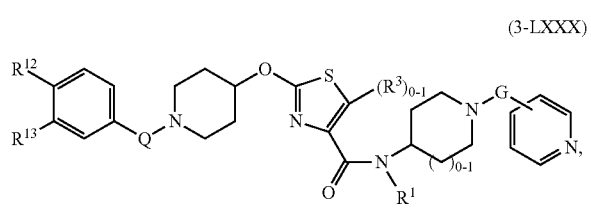

(3-LXXX)

in which Q is —CH$_2$—, —C(O)— or a single bond; G is a single bond, —CH$_2$—, —C(O)—, —S(O)$_2$— or —C(O)—NH—; $R^1$ and $R^3$ are as described above with reference to any of structural formulae (3-I)-(3-IV) and (3-LVI); and $R_{11}$, $R_{12}$ and $R_{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In in which Q is —CH$_2$—, —C(O)— or a single bond; G is a single bond, —CH$_2$—, —C(O)—, —S(O)$_2$— or —C(O)—NH—; $R^1$ and $R^3$ are as described above with reference to any of structural formulae (3-I)-(3-IV) and (3-LVII); and $R_{11}$, $R_{12}$ and $R_{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central thiazole (3-I.e., the ring position shown occupied by $R^3$ bears a hydrogen atom). In another embodiment, one $R^3$ (e.g., —Cl, —F, —CH$_3$, —C$_2$H$_5$, —C$_3$H$_7$) is substituted on the central thiazole.

In certain embodiments, the presently disclosed compounds have the structural formula (3-LXXXII):

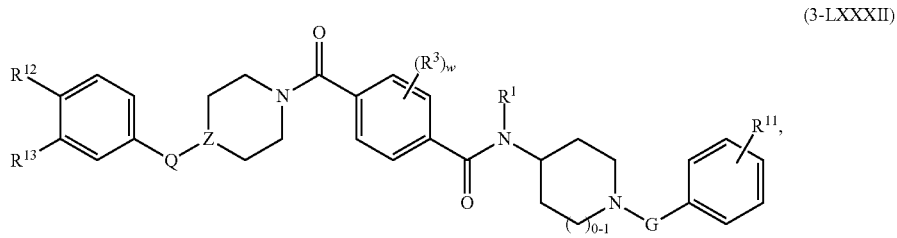

(3-LXXXII)

atom through which it is bound to the —C(O)—, in which no alkyl, haloalkyl or heterocycloalkyl is substituted by an aryl, heteroaryl, cycloalkyl or heterocycloalkyl-containing group. In one embodiment, the pyridine nitrogen is positioned in the para position relative to the G moiety; in another embodiment, the pyridine nitrogen is positioned in the meta position relative to the G moiety. In one embodiment, $R^1$ is H. In in which Q is —CH$_2$—, —C(O)— or a single bond; G is a single bond, —CH$_2$—, —C(O)—, —S(O)$_2$— or —C(O)—NH—; Z, $R^1$ and $R^3$ are as described above with reference to any of structural formulae (3-I)-(3-IV) and (3-LVIII); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-

$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R_{11}$, $R_{12}$ and $R_{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —$CH_3$, —$C_2H_5$, —$C_3H_7$) is substituted on the central phenyl ring. In one embodiment, Z is N. In another embodiment, Z is CH.

In certain embodiments, the presently disclosed compounds have the structural formula (3-LXXXIII):

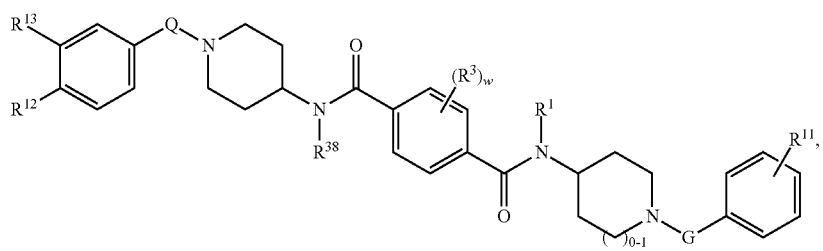

(3-LXXXIII)

in which Q is —$CH_2$—, —C(O)— or a single bond; G is a single bond, —$CH_2$—, —C(O)—, —S(O)$_2$— or —C(O)—NH—; $R^1$, $R^3$ and $R^{38}$ are as described above with reference to any of structural formulae (3-I)-(3-IV) and (3-LIX); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —$CH_3$, —$C_2H_5$, —$C_3H_7$) is substituted on the central phenyl ring. In one embodiment, $R^{38}$ is H. In another embodiment, $R^{38}$ is methyl, ethyl, propyl or butyl.

In certain embodiments, the presently disclosed compounds have the structural formula (3-LXXXIX):

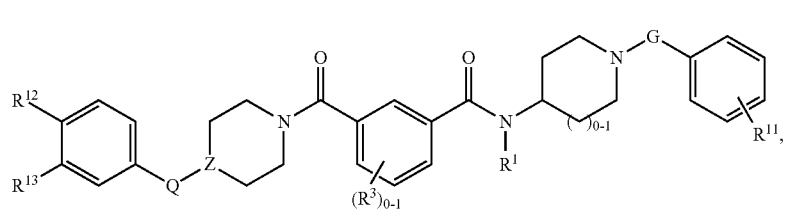

(3-LXXXIX)

in which Q is —CH$_2$—, —C(O)— or a single bond; G is a single bond, —CH$_2$—, —C(O)—, —S(O)$_2$— or —C(O)—NH—; Z, R$^1$ and R$^3$ are as described above with reference to any of structural formulae (3-I)-(3-IV) and (3-LX); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central phenyl ring. In another embodiment, one R$^3$ (e.g., —Cl, —F, —CH$_3$, —C$_2$H$_5$, —C$_3$H$_7$) is substituted on the central phenyl ring. In one embodiment, Z is N. In another embodiment, Z is CH.

In certain embodiments, the presently disclosed compounds have the structural formula (3-XC):

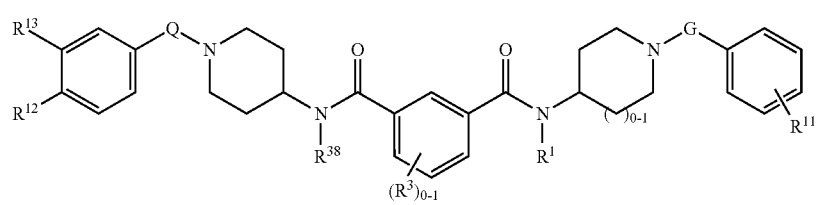

(3-XC)

in which Q is —CH$_2$—, —C(O)— or a single bond; G is a single bond, —CH$_2$—, —C(O)—, —S(O)$_2$— or —C(O)—NH—; R$^1$, R$^3$ and R$^{38}$ are as described above with reference to any of structural formulae (3-I)-(3-IV) and (3-LXI); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central phenyl ring. In another embodiment, one R$^3$ (e.g., —Cl, —F, —CH$_3$, —C$_2$H$_5$, —C$_3$H$_7$) is substituted on the central phenyl ring. In one embodiment, R$^{38}$ is H. In another embodiment, R$^{38}$ is methyl, ethyl, propyl or butyl.

In certain embodiments, the presently disclosed compounds have the structural formula (3-XCI):

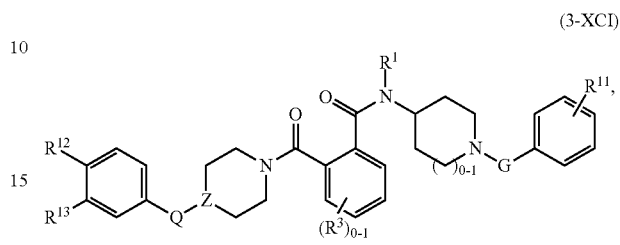

(3-XCI)

in which Q is —CH$_2$—, —C(O)— or a single bond; G is a single bond, —CH$_2$—, —C(O)—, —S(O)$_2$— or —C(O)—NH—; Z, R$^1$ and R$^3$ are as described above with reference to any of structural formulae (3-I)-(3-IV) and (3-LXII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central phenyl ring. In another embodiment, one R$^3$ (e.g., —Cl, —F, —CH$_3$, —C$_2$H$_5$, —C$_3$H$_7$) is substituted on the central phenyl ring. In one embodiment, Z is N. In another embodiment, Z is CH.

In certain embodiments, the presently disclosed compounds have the structural formula (3-XCII):

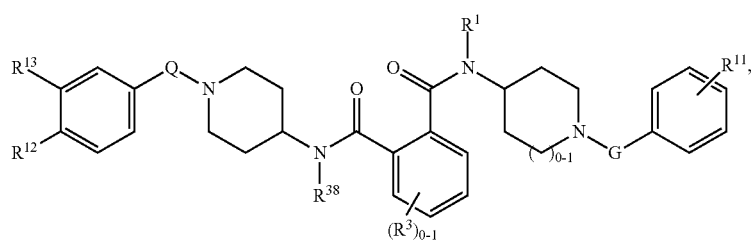

(3-XCII)

in which Q is —CH₂—, —C(O)— or a single bond; G is a single bond, —CH₂—, —C(O)—, —S(O)₂— or —C(O)—NH—; $R^1$, $R^3$ and $R^{38}$ are as described above with reference to any of structural formulae (3-I)-(3-IV) and (3-LXII); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), NO₂ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —CH₃, —C₂H₅, —C₃H₇) is substituted on the central phenyl ring. In one embodiment, $R^{38}$ is H. In another embodiment, $R^{38}$ is methyl, ethyl, propyl or butyl.

In certain embodiments, the presently disclosed compounds have the structural formula (3-XCIII):

in which Q is —CH₂—, —C(O)— or a single bond; G is a single bond, —CH₂—, —C(O)—, —S(O)₂— or —C(O)—NH—; Z, $R^1$ and $R^3$ are as described above with reference to any of structural formulae (3-I)-(3-IV) and (3-LVIII); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), NO₂ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —CH₃, —C₂H₅, —C₃H₇) is substituted on the central phenyl ring. In one embodiment, Z is N. In another embodiment, Z is CH.

In certain embodiments, the presently disclosed compounds have the structural formula (3-XCIV):

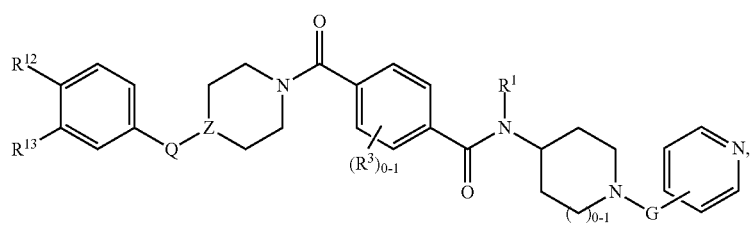

(3-XCIII)

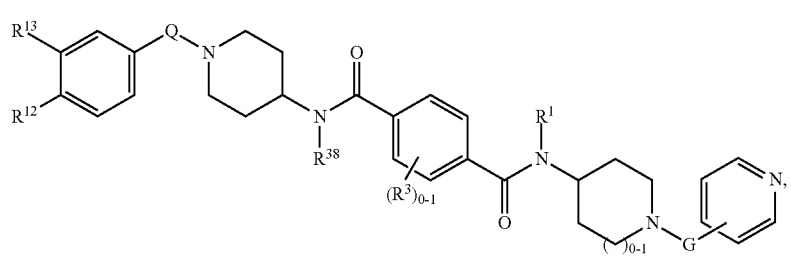

(3-XCIV)

in which Q is —CH$_2$—, —C(O)— or a single bond; G is a single bond, —CH$_2$—, —C(O)—, —S(O)$_2$— or —C(O)—NH—; R$^1$, R$^3$ and R$^{38}$ are as described above with reference to any of structural formulae (3-I)-(3-IV) and (3-LIX); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central phenyl ring. In another embodiment, one R$^3$ (e.g., —Cl, —F, —CH$_3$, —C$_2$H$_5$, —C$_3$H$_7$) is substituted on the central phenyl ring. In one embodiment, R$^{38}$ is H. In another embodiment, R$^{38}$ is methyl, ethyl, propyl or butyl.

In certain embodiments, the presently disclosed compounds have the structural formula (3-XCV):

in which Q is —CH$_2$—, —C(O)— or a single bond; G is a single bond, —CH$_2$—, —C(O)—, —S(O)$_2$— or —C(O)—NH—; Z, R$^1$ and R$^3$ are as described above with reference to any of structural formulae (3-I)-(3-IV) and (3-LX); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central phenyl ring. In another embodiment, one R$^3$ (e.g., —Cl, —F, —CH$_3$, —C$_2$H$_5$, —C$_3$H$_7$) is substituted on the central phenyl ring. In one embodiment, Z is N. In another embodiment, Z is CH.

In certain embodiments, the presently disclosed compounds have the structural formula (3-XCVI):

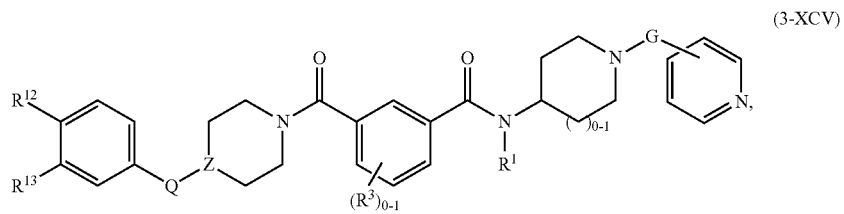

(3-XCV)

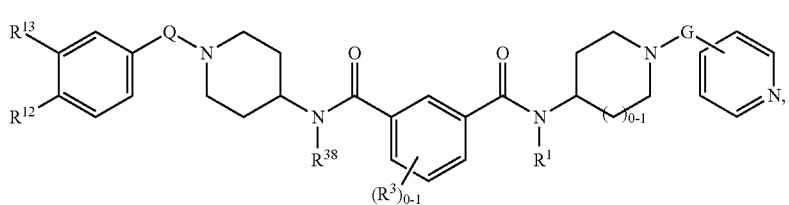

(3-XCVI)

in which Q is —CH$_2$—, —C(O)— or a single bond; G is a single bond, —CH$_2$—, —C(O)—, —S(O)$_2$— or —C(O)—NH—; R$^1$, R$^3$ and R$^{38}$ are as described above with reference to any of structural formulae (3-I)-(3-IV) and (3-LXI); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central phenyl ring. In another embodiment, one R$^3$ (e.g., —Cl, —F, —CH$_3$, —C$_2$H$_5$, —C$_3$H$_7$) is substituted on the central phenyl ring. In one embodiment, R$^{38}$ is H. In another embodiment, R$^{38}$ is methyl, ethyl, propyl or butyl.

In certain embodiments, the presently disclosed compounds have the structural formula (3-XCVII):

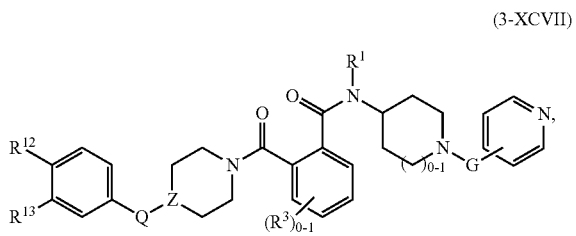

(3-XCVII)

in which Q is —CH$_2$—, —C(O)— or a single bond; G is a single bond, —CH$_2$—, —C(O)—, —S(O)$_2$— or —C(O)—NH—; Z, R$^1$ and R$^3$ are as described above with reference to any of structural formulae (3-I)-(3-IV) and (3-LXII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central phenyl ring. In another embodiment, one R$^3$ (e.g., —Cl, —F, —CH$_3$, —C$_2$H$_5$, —C$_3$H$_7$) is substituted on the central phenyl ring. In one embodiment, Z is N. In another embodiment, Z is CH.

In certain embodiments, the presently disclosed compounds have the structural formula (3-XCVIII):

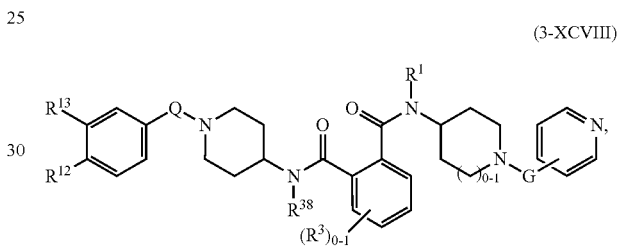

(3-XCVIII)

in which Q is —CH$_2$—, —C(O)— or a single bond; G is a single bond, —CH$_2$—, —C(O)—, —S(O)$_2$— or —C(O)—NH—; R$^1$, R$^3$ and R$^{38}$ are as described above with reference to any of structural formulae (3-I)-(3-IV) and (3-LXIII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central phenyl ring. In another embodiment, one R$^3$ (e.g., —Cl, —F, —CH$_3$, —C$_2$H$_5$, —C$_3$H$_7$) is substituted on the central phenyl ring. In one embodiment, R$^{38}$ is H. In another embodiment, R$^{38}$ is methyl, ethyl, propyl or butyl.

Examples of compounds according to structural formula (3-I) include those listed below in Table 3. These compounds can be made, for example using a procedure analogous to those described in U.S. Patent Application Publications nos. 2009/0163511, 2009/0170829, 2009/0186894 and 2009/0275609, and in U.S. patent application Ser. Nos. 12/695,861 and 13/194,810, each of which is hereby incorporated by reference in its entirety.

TABLE 3

| No. | Name | Structure |
| --- | --- | --- |
| 3-1 | tert-butyl 4-(6-(1-(4-(trifluoromethyl)phenyl)piperidin-4-yloxy)benzo[d]oxazole-2-carboxamido)piperidine-1-carboxylate | 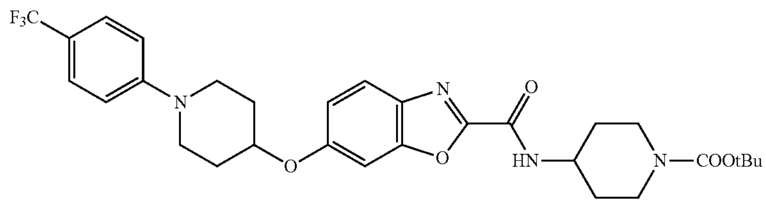 |
| 3-2 | N-(1-(4-cyanobenzyl)piperidin-4-yl)-6-(1-(4-(trifluoromethyl)phenyl)piperidin-4-yloxy)benzo[d]oxazole-2-carboxamide | 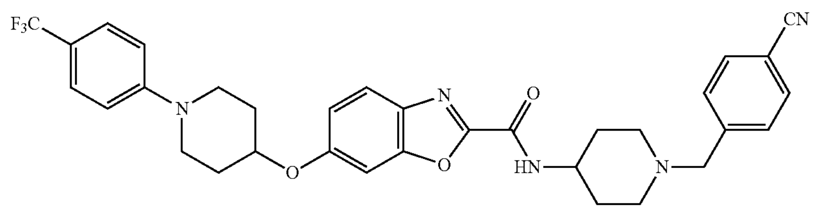 [SMILES: N#Cc1ccc(CN2CCC(NC(=O)c3nc4ccc(OC5CCN(c6ccc(C(F)(F)F)cc6)CC5)cc4o3)CC2)cc1] |
| 3-3 | N-(1-(pyridin-4-ylmethyl)piperidin-4-yl)-6-(1-(4-(trifluoromethyl)phenyl)piperidin-4-yloxy)benzo[d]oxazole-2-carboxamide | 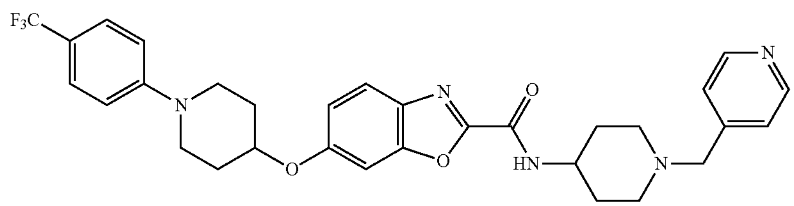 [SMILES: O=C(NC1CCN(Cc2ccncc2)CC1)c1nc2ccc(OC3CCN(c4ccc(C(F)(F)F)cc4)CC3)cc2o1] |
| 3-4 | N-(1-(4-fluorobenzoyl)piperidin-4-yl)-6-(1-(4-(trifluoromethyl)phenyl)piperidin-4-yloxy)benzo[d]oxazole-2-carboxamide | 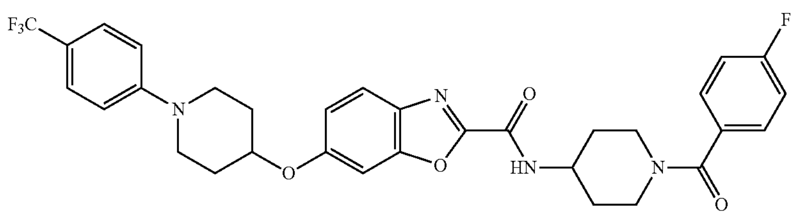 [SMILES: O=C(NC1CCN(C(=O)c2ccc(F)cc2)CC1)c1nc2ccc(OC3CCN(c4ccc(C(F)(F)F)cc4)CC3)cc2o1] |
| 3-5 | N-(piperidin-4-yl)-6-(1-(4-(trifluoromethyl)phenyl)piperidin-4-yloxy)benzo[d]oxazole-2-carboxamide | 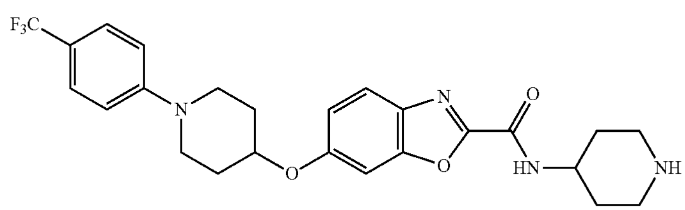 [SMILES: O=C(NC1CCNCC1)c1nc2ccc(OC3CCN(c4ccc(C(F)(F)F)cc4)CC3)cc2o1] |
| 3-6 | N-(1-(4-cyanobenzoyl)piperidin-4-yl)-6-(1-(4-(trifluoromethyl)phenyl)piperidin-4-yloxy)benzo[d]oxazole-2-carboxamide | 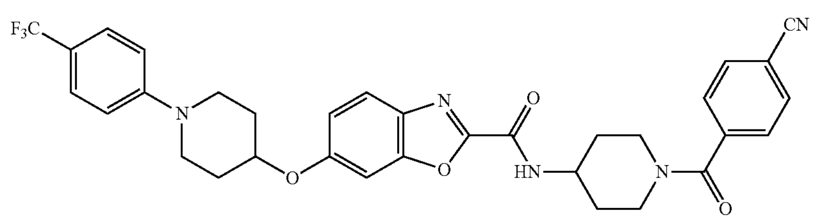 [SMILES: N#Cc1ccc(C(=O)N2CCC(NC(=O)c3nc4ccc(OC5CCN(c6ccc(C(F)(F)F)cc6)CC5)cc4o3)CC2)cc1] |
| 3-7 | N-(4-isonicotinoylcyclohexyl)-6-(1-(4-(trifluoromethyl)phenyl)piperidin-4-yloxy)benzo[d]oxazole-2-carboxamide | 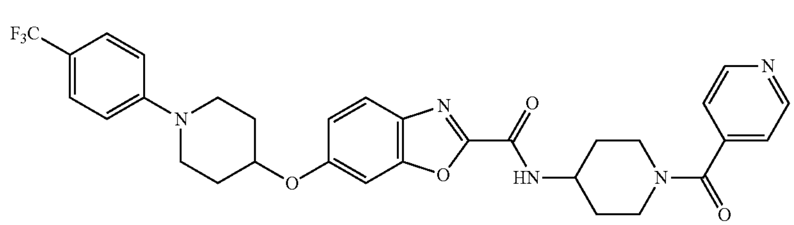 [SMILES: O=C(NC1CCN(C(=O)c2ccncc2)CC1)c1nc2ccc(OC3CCN(c4ccc(C(F)(F)F)cc4)CC3)cc2o1] |

TABLE 3-continued

| No. | Name | Structure |
|---|---|---|
| 3-8 | (5-(pyridin-4-ylmethyl)-2,5-diazabicyclo[2.2.1]heptan-2-yl)(6-(1-(4-(trifluoromethyl)phenyl)piperidin-4-yloxy)benzo[d]oxazol-2-yl)methanone | 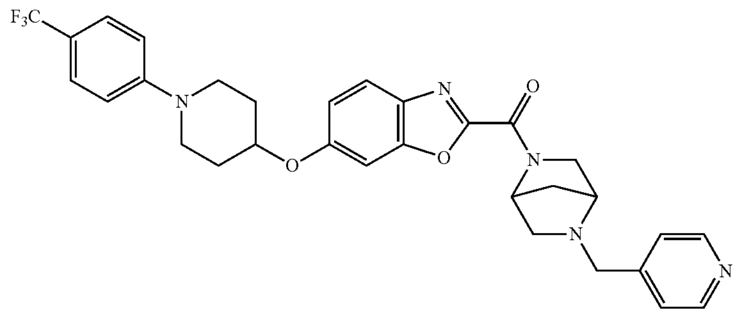 [SMILES: O=C(c1nc2ccc(OC3CCN(c4ccc(C(F)(F)F)cc4)CC3)cc2o1)N1CC2CC1CN2Cc1ccncc1] |
| 3-9 | 4-((5-(6-(1-(4-(trifluoromethyl)phenyl)piperidin-4-yloxy)benzo[d]oxazole-2-carbonyl)-2,5-diazabicyclo[2.2.1]heptan-2-yl)methyl)benzamide | 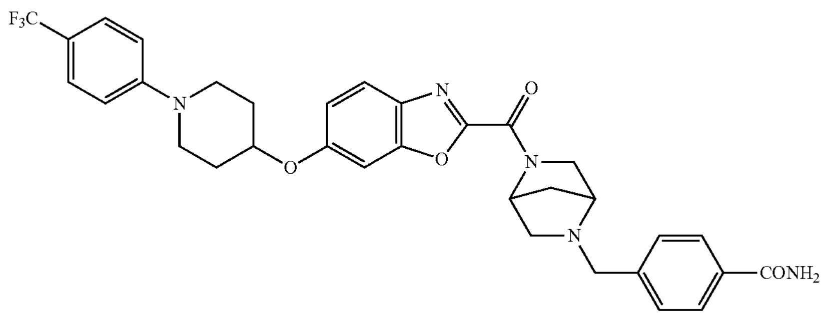 [SMILES: NC(=O)c1ccc(CN2CC3CC2CN3C(=O)c2nc3ccc(OC4CCN(c5ccc(C(F)(F)F)cc5)CC4)cc3o2)cc1] |
| 3-10 | 4-((5-(6-(1-(4-(trifluoromethyl)phenyl)piperidin-4-yloxy)benzo[d]oxazole-2-carbonyl)-2,5-diazabicyclo[2.2.1]heptan-2-yl)methyl)benzonitrile | 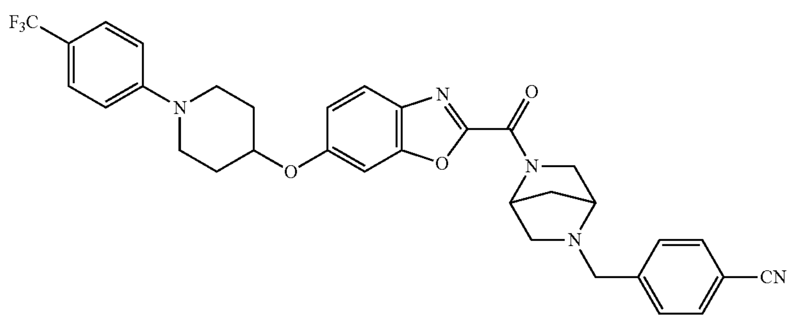 [SMILES: N#Cc1ccc(CN2CC3CC2CN3C(=O)c2nc3ccc(OC4CCN(c5ccc(C(F)(F)F)cc5)CC4)cc3o2)cc1] |
| 3-11 | (5-isonicotinoyl-2,5-diazabicyclo[2.2.1]heptan-2-yl)(6-(1-(4-(trifluoromethyl)phenyl)piperidin-4-yloxy)benzo[d]oxazol-2-yl)methanone | 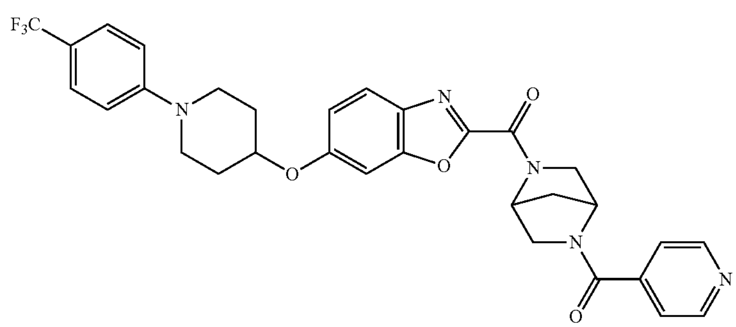 [SMILES: O=C(c1ccncc1)N1CC2CC1CN2C(=O)c1nc2ccc(OC3CCN(c4ccc(C(F)(F)F)cc4)CC3)cc2o1] |
| 3-12 | 4-(5-(6-(1-(4-(trifluoromethyl)phenyl)piperidin-4-yloxy)benzo[d]oxazole-2-carbonyl)-2,5-diazabicyclo[2.2.1]heptane-2-carbonyl)benzonitrile | 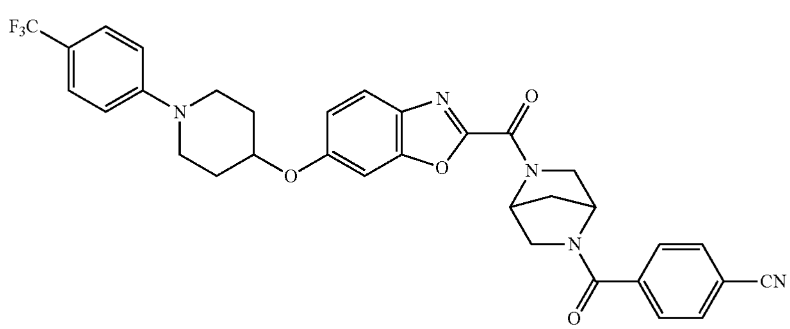 [SMILES: N#Cc1ccc(C(=O)N2CC3CC2CN3C(=O)c2nc3ccc(OC4CCN(c5ccc(C(F)(F)F)cc5)CC4)cc3o2)cc1] |

TABLE 3-continued

| No. | Name | Structure |
|---|---|---|
| 3-13 | (5-(4-fluorobenzoyl)-2,5-diazabicyclo[2.2.1]heptan-2-yl)(6-(1-(4-(trifluoromethyl)phenyl)piperidin-4-yloxy)benzo[d]oxazol-2-yl)methanone | 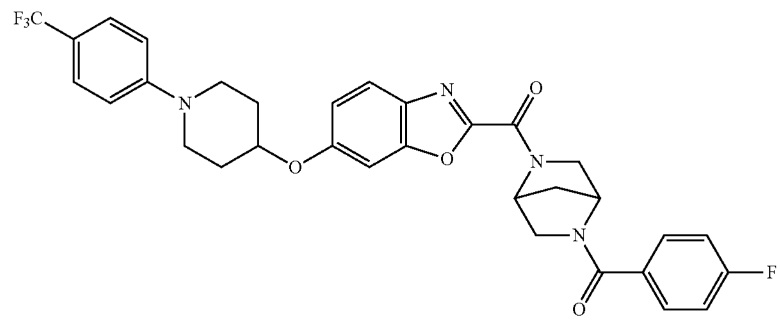 [SMILES: O=C(c1ccc(F)cc1)N1CC2CC1CN2C(=O)c1nc2ccc(OC3CCN(c4ccc(C(F)(F)F)cc4)CC3)cc2o1] |
| 3-14 | tert-butyl 4-(6-(1-(4-(trifluoromethyl)phenyl)piperidin-4-yloxy)benzo[d]thiazole-2-carboxamido)piperidine-1-carboxylate | 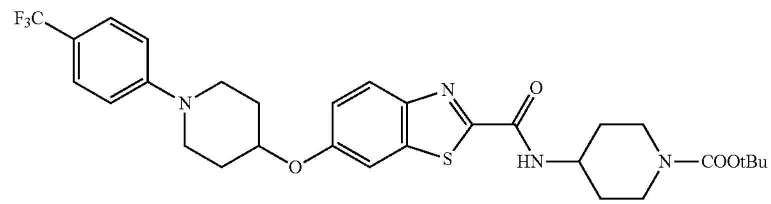 |
| 3-15 | N-(1-(pyridin-4-ylmethyl)piperidin-4-yl)-6-(1-(4-(trifluoromethyl)phenyl)piperidin-4-yloxy)benzo[d]thiazole-2-carboxamide | 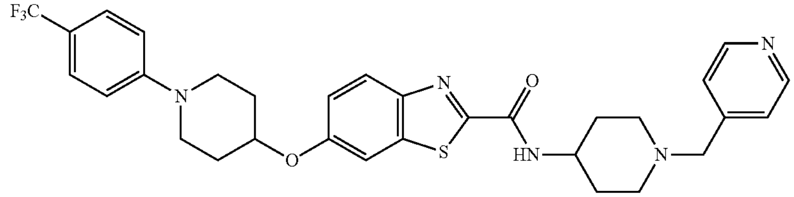 [SMILES: O=C(NC1CCN(Cc2ccncc2)CC1)c1nc2ccc(OC3CCN(c4ccc(C(F)(F)F)cc4)CC3)cc2s1] |
| 3-16 | N-(1-(4-cyanobenzyl)piperidin-4-yl)-6-(1-(4-(trifluoromethyl)phenyl)piperidin-4-yloxy)benzo[d]thiazole-2-carboxamide | 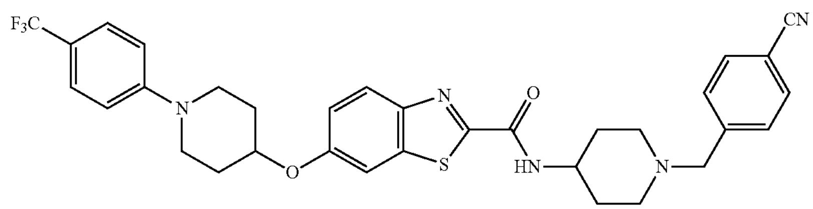 |
| 3-17 | N-(1-(pyridin-4-ylmethyl)piperidin-4-yl)-7-(1-(4-(trifluoromethyl)phenyl)piperidin-4-yloxy)imidazo[1,2-a]pyridine-2-carboxamide | 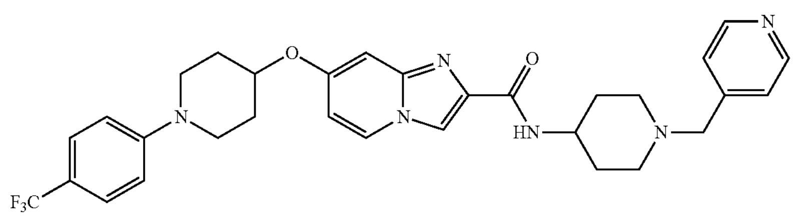 [SMILES: O=C(NC1CCN(Cc2ccncc2)CC1)c1cn2ccc(OC3CCN(c4ccc(C(F)(F)F)cc4)CC3)cc2n1] |
| 3-18 | N-(1-(4-cyanobenzyl)piperidin-4-yl)-7-(1-(4-(trifluoromethyl)phenyl)piperidin-4-yloxy)imidazo[1,2-a]pyridine-2-carboxamide | 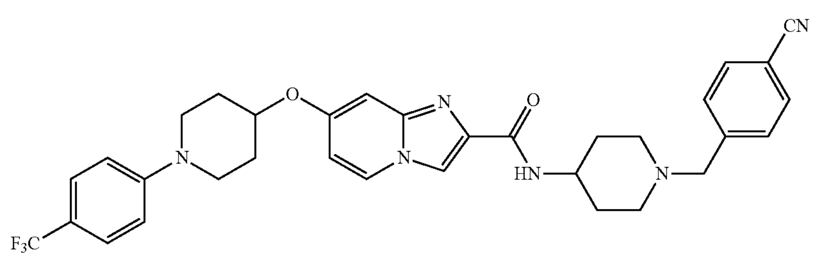 [SMILES: N#Cc1ccc(CN2CCC(NC(=O)c3cn4ccc(OC5CCN(c6ccc(C(F)(F)F)cc6)CC5)cc4n3)CC2)cc1] |
| 3-19 | tert-butyl 4-(5-(1-(4-(trifluoromethyl)phenyl)piperidin-4-yloxy)pyrazine-2-carboxamido)piperidine-1-carboxylate | 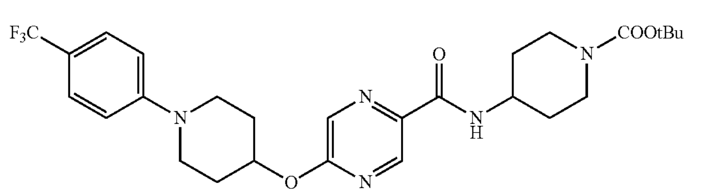 |

TABLE 3-continued

| No. | Name | Structure |
|---|---|---|
| 3-20 | N-(piperidin-4-yl)-5-(1-(4-(trifluoromethyl)phenyl)piperidin-4-yloxy)pyrazine-2-carboxamide | 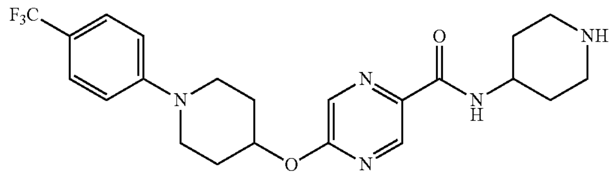 [SMILES: O=C(NC1CCNCC1)c1cnc(OC2CCN(c3ccc(C(F)(F)F)cc3)CC2)cn1] |
| 3-21 | N-(1-(pyridin-4-ylmethyl)piperidin-4-yl)-5-(1-(4-(trifluoromethyl)phenyl)piperidin-4-yloxy)pyrazine-2-carboxamide | 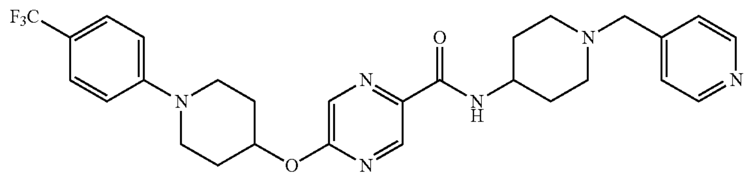 [SMILES: O=C(NC1CCN(Cc2ccncc2)CC1)c1cnc(OC2CCN(c3ccc(C(F)(F)F)cc3)CC2)cn1] |
| 3-22 | N-(1-(4-cyanobenzyl)piperidin-4-yl)-5-(1-(4-(trifluoromethyl)phenyl)piperidin-4-yloxy)pyrazine-2-carboxamide | 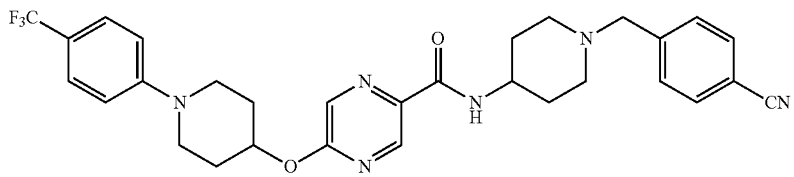 [SMILES: N#Cc1ccc(CN2CCC(NC(=O)c3cnc(OC4CCN(c5ccc(C(F)(F)F)cc5)CC4)cn3)CC2)cc1] |
| 3-23 | N-(1-(4-cyanobenzyl)piperidin-4-yl)-2-(1-(4-(trifluoromethyl)phenyl)piperidin-4-yloxy)thiazole-5-carboxamide | 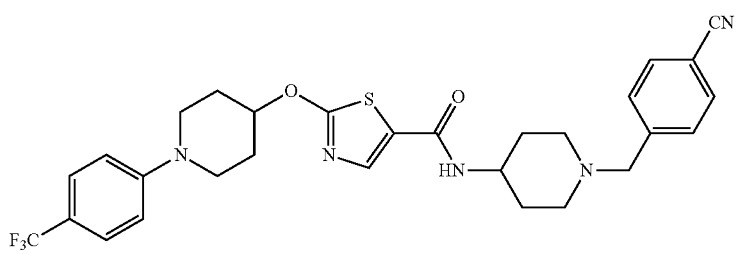 [SMILES: N#Cc1ccc(CN2CCC(NC(=O)c3cnc(OC4CCN(c5ccc(C(F)(F)F)cc5)CC4)s3)CC2)cc1] |
| 3-24 | N-(1-(4-cyanobenzyl)piperidin-4-yl)-2-(1-(4-cyanophenyl)piperidin-4-yloxy)thiazole-5-carboxamide | 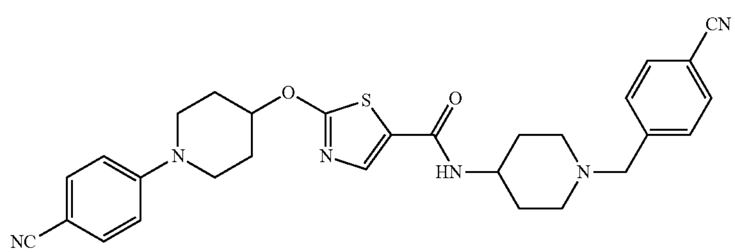 [SMILES: N#Cc1ccc(CN2CCC(NC(=O)c3cnc(OC4CCN(c5ccc(C#N)cc5)CC4)s3)CC2)cc1] |
| 3-25 | N-(1-(4-cyanobenzyl)piperidin-4-yl)-2-(1-(4-(trifluoromethyl)benzyl)piperidin-4-yloxy)thiazole-5-carboxamide | 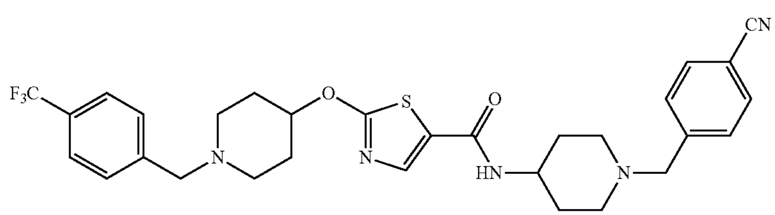 [SMILES: N#Cc1ccc(CN2CCC(NC(=O)c3cnc(OC4CCN(Cc5ccc(C(F)(F)F)cc5)CC4)s3)CC2)cc1] |
| 3-26 | tert-butyl 4-(5-(1-(4-cyanobenzyl)piperidin-4-ylcarbamoyl)thiazol-2-yloxy)piperidine-1-carboxylate | 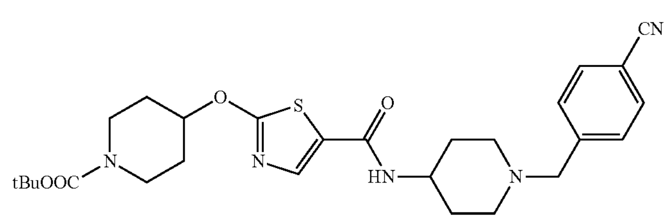 |

TABLE 3-continued

| No. | Name |
|---|---|
| 3-27 | N-(1-(4-cyanobenzyl)piperidin-4-yl)-4-(1-(4-ethoxybenzyl)piperidine-4-carbonyl)benzamide |
| 3-28 | 4-(4-(4-chlorobenzyl)piperazine-1-carbonyl)-N-(1-(4-cyanobenzyl)piperidin-4-yl)benzamide |
| 3-29 | 4-(4-(4-chlorophenyl)piperazine-1-carbonyl)-N-(1-(4-cyanobenzyl)piperidin-4-yl)benzamide |
| 3-30 | N-(1-(4-cyanobenzyl)piperidin-4-yl)-4-(4-(5-(trifluoromethyl)pyridin-2-yl)piperazine-1-carbonyl)benzamide |
| 3-31 | $N^1$-(1-(4-cyanobenzyl)piperidin-4-yl)-$N^4$-(1-(4-(trifluoromethyl)benzyl)piperidin-4-yl)terephthalamide |
| 3-32 | $N^1$-(1-(4-cyanobenzyl)piperidin-4-yl)-$N^4$-(1-phenylpiperidin-4-yl)terephthalamide |

TABLE 3-continued

| No. | Name | Structure |
|---|---|---|
| 3-33 | N¹-(1-benzylpiperidin-4-yl)-N⁴-(1-(4-cyanobenzyl)piperidin-4-yl)terephthalamide | 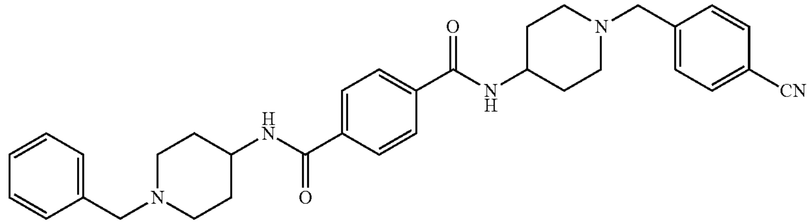 [SMILES: N#Cc1ccc(CN2CCC(NC(=O)c3ccc(C(=O)NC4CCN(Cc5ccccc5)CC4)cc3)CC2)cc1] |
| 3-34 | N-(1-(4-cyanobenzyl)piperidin-4-yl)-2-(4-fluorobenzyl)-1,2,3,4-tetrahydroisoquinoline-7-carboxamide | 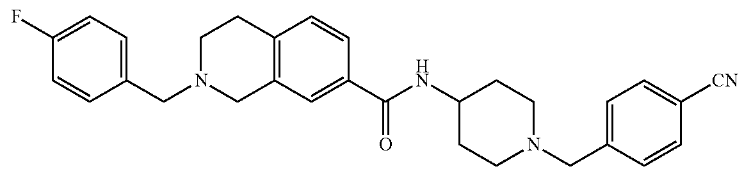 [SMILES: N#Cc1ccc(CN2CCC(NC(=O)c3ccc4c(c3)CN(Cc3ccc(F)cc3)CC4)CC2)cc1] |
| 3-35 | 2-(4-fluorobenzyl)-N-(1-(pyridin-3-ylmethyl)piperidin-4-yl)-1,2,3,4-tetrahydroisoquinoline-7-carboxamide | 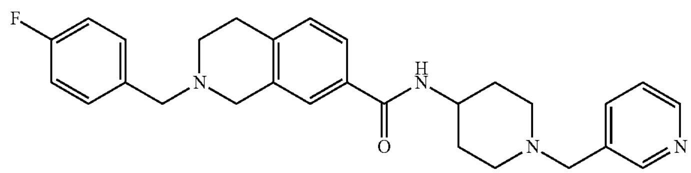 [SMILES: O=C(NC1CCN(Cc2cccnc2)CC1)c1ccc2c(c1)CN(Cc1ccc(F)cc1)CC2] |
| 3-36 | 2-(4-fluorobenzyl)-N-(1-(4-(trifluoromethyl)benzyl)piperidin-4-yl)-1,2,3,4-tetrahydroisoquinoline-7-carboxamide | 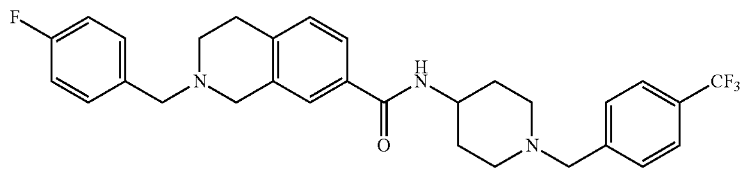 [SMILES: O=C(NC1CCN(Cc2ccc(C(F)(F)F)cc2)CC1)c1ccc2c(c1)CN(Cc1ccc(F)cc1)CC2] |
| 3-37 | 2-(4-cyanobenzyl)-N-(1-(4-cyanobenzyl)piperidin-4-yl)-1,2,3,4-tetrahydroisoquinoline-7-carboxamide | 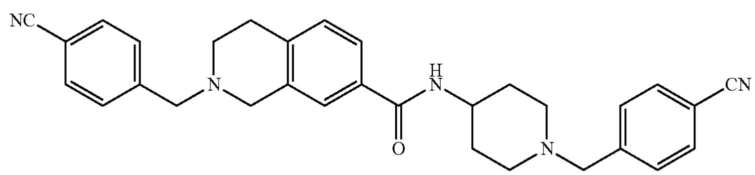 [SMILES: N#Cc1ccc(CN2CCC(NC(=O)c3ccc4c(c3)CN(Cc3ccc(C#N)cc3)CC4)CC2)cc1] |
| 3-38 | 2-(4-cyanobenzyl)-N-(1-(pyridin-3-ylmethyl)piperidin-4-yl)-1,2,3,4-tetrahydroisoquinoline-7-carboxamide | 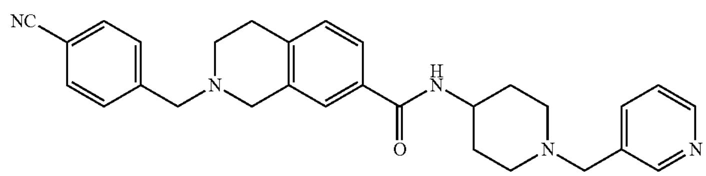 [SMILES: N#Cc1ccc(CN2CCc3ccc(C(=O)NC4CCN(Cc5cccnc5)CC4)cc3C2)cc1] |
| 3-39 | 2-(4-cyanobenzyl)-N-(1-(4-(trifluoromethyl)benzyl)piperidin-4-yl)-1,2,3,4-tetrahydroisoquinoline-7-carboxamide | 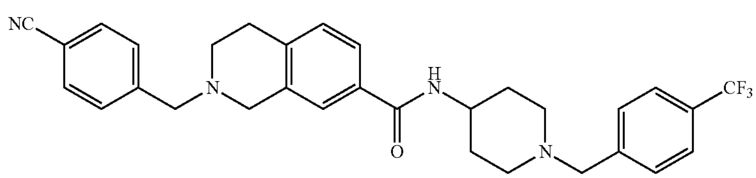 [SMILES: N#Cc1ccc(CN2CCc3ccc(C(=O)NC4CCN(Cc5ccc(C(F)(F)F)cc5)CC4)cc3C2)cc1] |
| 3-40 | N-(1-(4-cyanobenzyl)piperidin-4-yl)-2-(4-fluorobenzyl)-1,2,3,4-tetrahydroisoquinoline-7-carboxamide | 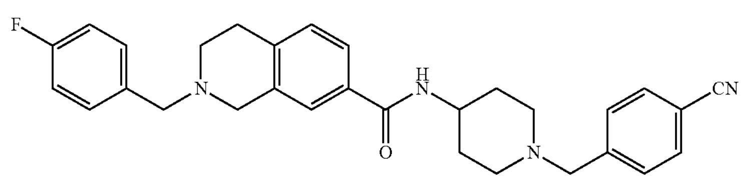 [SMILES: N#Cc1ccc(CN2CCC(NC(=O)c3ccc4c(c3)CN(Cc3ccc(F)cc3)CC4)CC2)cc1] |

TABLE 3-continued

| No. | Name | Structure |
|---|---|---|
| 3-41 | 2-(4-fluorobenzyl)-N-(1-(pyridine-3-ylmethyl)piperidin-4-yl)-1,2,3,4-tetrahydroisoquinoline-7-carboxamide | 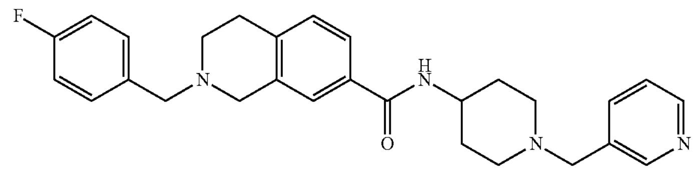 [SMILES: O=C(NC1CCN(Cc2cccnc2)CC1)c1ccc2c(c1)CN(Cc1ccc(F)cc1)CC2] |
| 3-42 | 2-(4-fluorobenzyl)-N-(1-(4-(trifluoromethyl)benzyl)piperidin-4-yl)-1,2,3,4-tetrahydroisoquinoline-7-carboxamide | 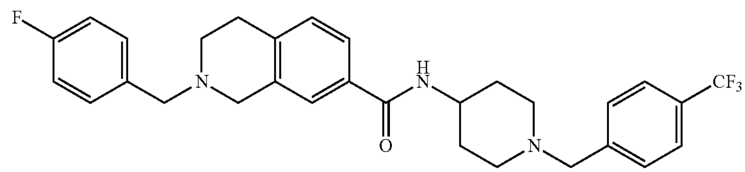 [SMILES: O=C(NC1CCN(Cc2ccc(C(F)(F)F)cc2)CC1)c1ccc2c(c1)CN(Cc1ccc(F)cc1)CC2] |

Another aspect of the disclosure provides compounds having structural formula (4-I):

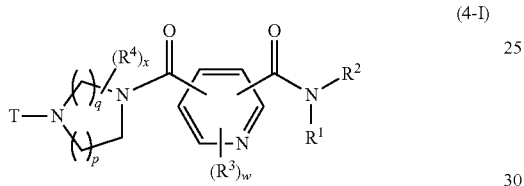

(4-I)

and pharmaceutically acceptable salts, and N-oxides thereof (and solvates and hydrates thereof), in which $R^1$ is H, —($C_1$-$C_4$ alkyl), —C(O)—($C_1$-$C_4$ alkyl) or —C(O)O—($C_1$-$C_4$ alkyl);

$R^2$ is -Hca, -Cak-N($R^9$)-G-$R^{22}$ or —($C_2$-$C_8$ alkyl)-N($R^9$)—$R^{24}$ in which one or two carbons of the ($C_2$-$C_8$ alkyl) are optionally replaced by —O—, —S— or —N($R^9$)— and $R^{24}$ is —$R^{23}$, -G-$R^{23}$ or —C(O)O—($C_1$-$C_6$ alkyl), provided that two consecutive carbons of the ($C_2$-$C_8$ alkyl) are not replaced by —O—;

each $R^3$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN;

w is 0, 1, 2 or 3;

each $R^4$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN, and two $R^4$ on the same carbon optionally combine to form oxo;

x is 0, 1, 2, 3 or 4;

p is 0, 1, 2, 3 or 4;

q is 2, 3 or 4;

the sum of p and q is 2, 3, 4, 5 or 6;

T is —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$ or

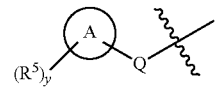

in which

Q is —S(O)$_2$—, L or ($C_0$-$C_3$ alkyl)-, in which each carbon of the —($C_0$-$C_3$ alkyl)- is optionally and independently substituted with one or two $R^{16}$;

the ring system denoted by "A" is heteroaryl, aryl, cycloalkyl or heterocycloalkyl;

each $R^5$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN; and y is 0, 1, 2, 3 or 4;

in which each L is independently selected from —NR$^9$C(O)O—, —OC(O)NR$^9$—, —NR$^9$C(O)—NR$^9$—, —NR$^9$C(O)S—, —SC(O)NR$^9$—, —NR$^9$C(O)—, —C(O)—NR$^9$—, —NR$^9$C(S)O—, —OC(S)NR$^9$—, —NR$^9$C(S)—NR$^9$—, —NR$^9$C(S)S—, —SC(S)NR$^9$—, —NR$^9$C(S)—, —C(S)NR$^9$—, —SC(O)NR$^9$—, —NR$^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR$^9$C(NR$^2$)NR$^9$—, —NR$^9$SO$_2$—, —SO$_2$NR$^9$— and —NR$^9$SO$_2$NR$^9$—, each $R^6$, $R^7$, $R^8$ and $R^{10}$ is independently selected from H, —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-($C_0$-$C_6$ alkyl), —($C_0$-$C_6$ alkyl)-NR$^9$—($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), each $R^9$ is independently selected from —H, —($C_1$-$C_4$ alkyl), —C(O)—($C_1$-$C_4$ alkyl) and —C(O)O—($C_1$-$C_4$ alkyl), each G is independently —S(O)$_2$—, L or —($C_0$-$C_3$ alkyl)-, in which each carbon of the —($C_0$-$C_3$ alkyl)- is optionally and independently substituted with one or two $R^{16}$, each $R^{16}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-$S(O)_{0-2}R^{10}$, -halogen, —$NO_2$ and —CN, and optionally two of $R^{16}$ on the same carbon combine to form oxo, each $R^{22}$ and $R^{23}$ is independently Ar or Het, each Ar is an optionally substituted aryl, each Het is an optionally substituted heteroaryl, each Cak is an optionally substituted cycloalkyl, each Hca is an optionally substituted heterocycloalkyl, and each alkyl is optionally substituted.

Various embodiments of compounds of structural formula (2-I) suitable for use in the methods described herein are described below. Information regarding certain of these compounds can also be found in U.S. patent application Ser. No. 12/695,861, which is hereby incorporated by reference in its entirety.

In certain embodiments of the presently disclosed compounds of structural formula (4-I), T is

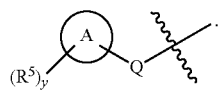

In such embodiments, Q is —$S(O)_2$—, L or —($C_0$-$C_3$ alkyl)- in which each carbon of the ($C_0$-$C_3$ alkyl) is optionally and independently substituted with one or two $R^{16}$, in which each $R^{16}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-$S(O)_{0-2}R^{10}$, -halogen, —$NO_2$ and —CN, and optionally two of $R^{16}$ on the same carbon combine to form oxo. In certain embodiments, each $R^{16}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-$S(O)_{0-2}R^{10}$, -halogen, —$NO_2$ and —CN, and two $R^{16}$ on the same carbon optionally combine to form an oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-$S(O)_{0-2}$—($C_0$-$C_6$ alkyl), and in which no alkyl or haloalkyl is substituted with an aryl-, heteroaryl-, cycloalkyl- or heterocycloalkyl-containing group. For example, in particular compounds, each $R^{16}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-$S(O)_{0-2}R^{10}$, -halogen, —$NO_2$ and —CN, and two $R^{16}$ on the same carbon optionally combine to form an oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-$S(O)_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, Q has at most one $R^{16}$ or an oxo substituted thereon. Q can be, for example, an unsubstituted —($C_0$-$C_3$ alkyl)-. In other embodiments, Q is a ($C_1$-$C_3$ alkyl) having as its only substitution a single oxo group. For example, in certain embodiments, Q is —$CH_2$—; a single bond; —$S(O)_2$—; —C(O)—; or —CH($CH_3$)—.

In certain embodiments of the compounds of structural formula (4-I), the

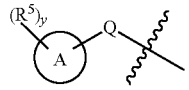

moiety is

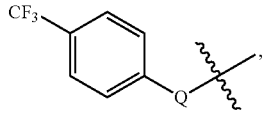

for example, p-(trifluoromethyl)phenyl. In other embodiments, the

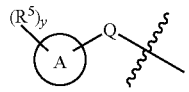

moiety is

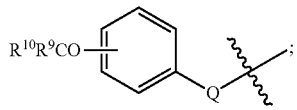

in one such embodiment, Q is a single bond.

The number of substituents on the ring system denoted by "A", y, is 0, 1, 2, 3 or 4. For example, in some embodiments of the presently disclosed compounds of structural formula (4-I), y is 0, 1, 2 or 3, such as 1. In one embodiment, y is not zero and at least one $R^5$ is halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ or —C(O)—Hca wherein the Hca contains a ring nitrogen atom through which it is bound to the —C(O)—, and wherein no alkyl, haloalkyl or heterocycloalkyl is substituted by an aryl, heteroaryl, cycloalkyl or heterocycloalkyl-containing group.

In certain embodiments of the presently disclosed compounds of structural formula (4-I), each $R^5$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-$S(O)_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-$S(O)_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^5$ is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group.

In one embodiment of the compounds of structural formula (4-I), y is 0.

In the presently disclosed compounds of structural formula (4-I), the ring system denoted by "A" is heteroaryl, aryl, cycloalkyl or heterocycloalkyl. For example, in one embodiment, the ring system denoted by "A" is an aryl or a heteroaryl. The ring system denoted by "A" can be, for example, a monocyclic aryl or heteroaryl. In one embodiment, when the "A" ring system is aryl, Q is a —(C$_0$-C$_3$ alkyl)- optionally substituted with oxo, and optionally substituted with one or more R$^{16}$. For example, Q can be a —(C$_1$-C$_3$ alkyl)- having its only substitution a single oxo, or an unsubstituted —(C$_0$-C$_3$ alkyl)-. For example, in certain embodiments, Q is —CH$_2$—; a single bond; —S(O)$_2$—; —C(O)—; or —CH(CH$_3$)—.

For example, in certain embodiments of the presently disclosed compounds of structural formula (4-I), the ring system denoted by "A" is a phenyl. In one embodiment, y is 1 and R$^5$ is attached to the phenyl in the para position relative to Q. In another embodiment, y is 1 and R$^5$ is selected from the group consisting of halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, and in which no (C$_0$-C$_4$ alkyl) or (C$_1$-C$_4$ alkyl) is substituted by an aryl, heteroaryl, cycloalkyl or heterocycloalkyl-containing group. R$^5$ can be, for example, —Cl, —F, cyano, —C(O)CH$_3$, —C(O)OH, —C(O)NH$_2$, trifluoromethyl, difluoromethyl, difluoromethoxy or trifluoromethoxy. In another embodiment, the

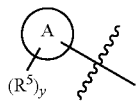

moiety is a 3,4-dihalophenyl.

In another embodiment of the presently disclosed compounds of structural formula (4-I), the ring system denoted by "A" is a heteroaryl. For example, in certain embodiments, the ring system denoted by "A" is a pyridyl, a thienyl, or a furanyl. In other embodiments, the ring system denoted by "A" is a pyrazolyl, imidazolyl, pyrrolyl, triazolyl or thiadiazolyl. In one embodiment, when the "A" ring system is heteroaryl, Q is a —(C$_0$-C$_3$ alkyl)- optionally substituted with oxo, and optionally substituted with one or more R$^{16}$. For example, Q can be a —(C$_1$-C$_3$ alkyl)- having its only substitution a single oxo, or an unsubstituted —(C$_0$-C$_3$ alkyl)-. In certain embodiments, Q is —CH$_2$—; a single bond; —S(O)$_2$—; —C(O)—; or —CH(CH$_3$)—.

In certain embodiments of the presently disclosed compounds of structural formula (1-I), the

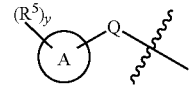

moiety is

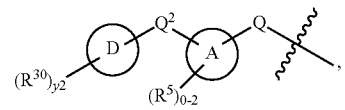

in which the ring system denoted by "A" is aryl or heteroaryl, the ring system denoted by "D" is cycloalkyl, heterocycloalkyl, aryl or heteroaryl; Q$^2$ is —S(O)$_2$—, —O— or —(C$_0$-C$_3$ alkyl)- in which each carbon of the (C$_0$-C$_3$ alkyl) is optionally and independently substituted with one or two R$^{16}$, defined as described above with respect to Q; y$^2$ is 0, 1 or 2; and each R$^{30}$ is independently selected from is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, Q$^2$ has at most one R$^{16}$ or an oxo substituted thereon. Q$^2$ can be, for example, an unsubstituted —(C$_0$-C$_3$ alkyl)-. In other embodiments, Q$^2$ is a (C$_1$-C$_3$ alkyl) having as its only substitution a single oxo group. For example, in certain embodiments, Q$^2$ is —CH$_2$—; a single bond; —S(O)$_2$—; —O—; —C(O)—; or —CH(CH$_3$)—. In certain embodiments, at least one R$^{30}$ is halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ or —C(O)—Hca in which the Hca contains a ring nitrogen atom through which it is bound to the —C(O)—, and in which no alkyl, haloalkyl or heterocycloalkyl is substituted by an aryl, heteroaryl, cycloalkyl or heterocycloalkyl-containing group. In certain embodiments, at least one R$^5$ is —SO$_2$(C$_1$-C$_6$ alkyl), —SO$_2$(C$_1$-C$_6$ haloalkyl), —SO$_2$N(C$_0$-C$_6$ alkyl)(C$_0$-C$_6$ alkyl), —SO$_2$(C$_3$-C$_8$ cycloalkyl), —SO$_2$(C$_3$-C$_8$ heterocycloalkyl), such as —SO$_2$Me, —SO$_2$Et, —SO$_2$Pr, —SO$_2$Bu, —SO$_2$cyclopropyl, —SO$_2$morphylinyl, SO$_2$pyrrolidinyl, SO$_2$NHEt, SO$_2$pyridyl or —SO$_2$phenyl. The number of substituents on the ring system denoted by "D", y$^2$, is 0, 1, or 2. For example, in some embodiments, y$^2$ is 0 or 1, for example 1. In other embodiments, y$^2$ is 0. R$^{30}$ can be further defined as described above with respect to R$^5$. In certain embodiments, the ring system denoted by "D" is cyclopropyl, morpholinyl, pyrazolyl, pyridyl, imidazolyl or phenyl, In certain embodiments, at least one R$^5$ is —SO$_2$(C$_1$-C$_6$ alkyl), —SO$_2$(C$_1$-C$_6$ haloalkyl), —SO$_2$N(C$_0$-C$_6$ alkyl)$_2$, —SO$_2$(C$_3$-C$_8$ cycloalkyl), —SO$_2$(C$_3$-C$_8$ heterocycloalkyl), such as —SO$_2$Me, —SO$_2$Et, —SO$_2$Pr, —SO$_2$Bu, —SO$_2$cyclopropyl, —SO$_2$morphylinyl, SO$_2$pyrrolidinyl, SO$_2$NHEt, SO$_2$pyridyl or —SO$_2$phenyl.

In one embodiment of the presently disclosed compounds, the compound has structural formula (4-II):

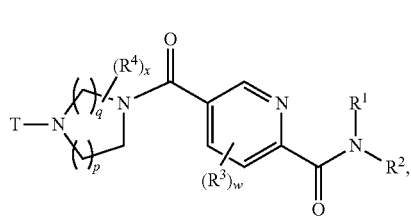

(4-II)

in which the variables are defined as described above with reference to structural formula (4-I).

In one embodiment of the presently disclosed compounds, the compound has structural formula (4-III):

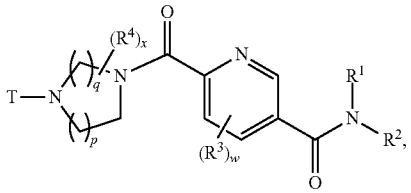

(4-III)

in which the variables are defined as described above with reference to structural formula (4-I).

In another embodiment of the presently disclosed compounds, the compound has structural formula (4-IV):

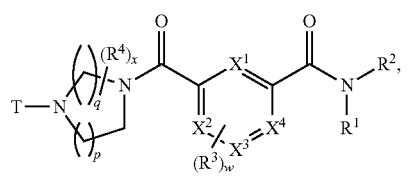

(4-IV)

in which one of $X^1$, $X^2$, $X^3$ and $X^4$ are N, and the others are carbons (for example, independently CH or C substituted with one of the w $R^3$ groups), and all other variables are defined as described above with reference to structural formula (4-I). For example, in one embodiment, $X^1$ is N and $X^2$, $X^3$ and $X^4$ are carbons. In another embodiment, $X^2$ is N and $X^1$, $X^3$ and $X^4$ are carbons. In another embodiment, $X^3$ is N and $X^1$, $X^2$ and $X^4$ are carbons. In another embodiment, $X^4$ is N and $X^1$, $X^2$ and $X^3$ are carbons.

In compounds according to structural formulae (4-I)-(4-IV), p is 0, 1, 2, 3 or 4 and q is 2, 3 or 4. For example, in one embodiment, q is 2. In certain embodiments, p is 1.

In certain embodiments according to structural formulae (4-I)-(4-IV), the sum of p and q is 2 or 3. For example, in one embodiment, the sum of p and q is 2 (e.g., p is 0 and q is 2). In another embodiment, the sum of p and q is 3 (e.g., p is 1 and q is 2). In other embodiments the sum of p and q is 4, 5, or 6. Accordingly the ring containing the p and q carbon atoms can be a 5, 6, 7, 8 or 9-membered ring.

In one embodiment of the presently disclosed compounds, the compound has the structural formula (4-V):

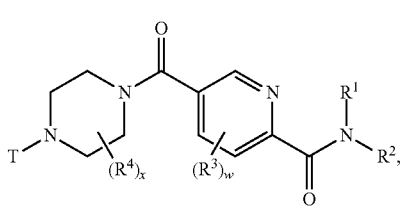

(4-V)

in which the variables are defined as described above with reference to structural formula (4-I).

In another embodiment of the presently disclosed compounds, the compound has structural formula (4-VI):

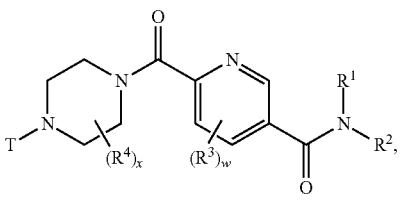

(4-VI)

in which the variables are defined as described above with reference to structural formula (4-I).

In another embodiment of the presently disclosed compounds, the compound has structural formula (4-VII):

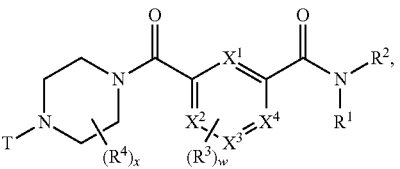

(4-VII)

in which one of $X^1$, $X^2$, $X^3$ and $X^4$ are N, and the others are carbons (for example, independently CH or C substituted with one of the w $R^3$ groups), and all other variables are defined as described above with reference to structural formula (4-I). For example, in one embodiment, $X^1$ is N and $X^2$, $X^3$ and $X^4$ are carbons. In another embodiment, $X^2$ is N and $X^1$, $X^3$ and $X^4$ are carbons. In another embodiment, $X^3$ is N and $X^1$, $X^2$ and $X^4$ are carbons. In another embodiment, $X^4$ is N and $X^1$, $X^2$ and $X^3$ are carbons.

In certain embodiments of the presently disclosed compounds of any of structural formulae (4-I)-(4-VII), $R^1$ is —H. In other embodiments, $R^1$ is ($C_1$-$C_4$ alkyl), for example methyl, ethyl, n-propyl or isopropyl. In still other embodiments, $R^1$ is —C(O)—O—($C_1$-$C_4$ alkyl), for example —C(O)—O-t-butyl. In certain embodiments, no alkyl of $R^1$ is substituted with an aryl-, heteroaryl-, cycloalkyl- or heterocycloalkyl-containing group.

In certain embodiments of the presently disclosed compounds of any structural formulae (4-I)-(4-VII), $R^2$ is -Hca. In certain embodiments, $R^2$ is an optionally-substituted monocyclic heterocycloalkyl. In one embodiment, $R^2$ is not an oxo-substituted heterocycloalkyl.

In certain of the presently disclosed compounds of any structural formulae (4-I)-(4-VII), $R^2$ is -(optionally-substituted azetidinyl), -(optionally-substituted pyrrolidinyl), -(optionally-substituted piperidinyl), or -(optionally-substituted azepanyl). For example, $R^2$ can be -(optionally substituted piperidinyl) or -(optionally substituted pyrrolidinyl). In one embodiment, $R^2$ is -(optionally substituted piperidinyl). In another embodiment, $R^2$ is -(optionally substituted pyrrolidinyl).

In certain particular embodiments of the presently disclosed compounds of any of structural formulae (4-I)-(4-VII), $R^2$ is -(optionally-substituted azetidin-3-yl), -(optionally substituted piperidin-4-yl), -(optionally substituted pyrrolidin-3-yl) or -(optionally-substituted azepan-4-yl). For example, in one embodiment, $R^2$ is -(optionally substituted piperidin-4-yl). In another embodiment, $R^2$ is -(optionally substituted pyrrolidin-3-yl).

In certain embodiments of the presently disclosed compounds of any of structural formulae (4-I)-(4-VII), the azetidinyl, pyrrolidinyl, piperidinyl and azepanyl $R^2$ moieties described above are substituted at their 1-positions. For example, in one embodiment, $R^2$ is substituted at its 1-position with —($C_0$-$C_3$ alkyl)-Ar or —($C_0$-$C_3$ alkyl)-Het, for example -(unsubstituted $C_0$-$C_3$ alkyl)-Ar or -(unsubstituted $C_0$-$C_3$ alkyl)-Het. For example, in one particular embodiment, the azetidinyl, pyrrolidinyl, piperidinyl or azepanyl $R^2$ moiety is substituted at its 1-position with an optionally substituted benzyl or an optionally substituted phenyl. In another embodiment, the azetidinyl, pyrrolidinyl, piperidinyl or azepanyl $R^2$ moiety is substituted at its 1-position with a benzyl substituted with an electron withdrawing group; or with a pyridinylmethyl optionally substituted with an electron withdrawing group. For example, the benzyl or pyridinylmethyl can be substituted with an electron withdrawing group selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), $NO_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In other embodiments, the azetidinyl, pyrrolidinyl, piperidinyl or azepanyl $R^2$ moiety is substituted at its 1-position with an unsubstituted benzyl or an unsubstituted phenyl.

In other embodiments of the compounds disclosed herein having any of structural formulae (4-I)-(4-VII), the azetidinyl, pyrrolidinyl, piperidinyl or azepanyl $R^2$ moiety is substituted at its 1-position with an optionally substituted pyridinylmethyl, an optionally substituted furanylmethyl, an optionally substituted thienylmethyl, an optionally substituted oxazolylmethyl, or an optionally substituted imidazolylmethyl. For example, the azetidinyl, pyrrolidinyl, piperidinyl or azepanyl $R^2$ moiety can be substituted with an unsubstituted pyridinylmethyl, an unsubstituted furanylmethyl, an unsubstituted thienylmethyl, an unsubstituted oxazolylmethyl, or an unsubstituted imidazolylmethyl. In other embodiments, the azetidinyl, pyrrolidinyl, piperidinyl or azepanyl $R^2$ moiety can be substituted with an pyridinylmethyl, furanylmethyl, thienylmethyl, oxazolylmethyl or imidazolylmethyl substituted with an electron withdrawing group as described above.

In certain embodiments of the compounds disclosed herein having any of structural formulae (4-I)-(4-VII), the azetidinyl, pyrrolidinyl, piperidinyl or azepanyl $R^2$ moiety is substituted at its 1-position with -L-Ar or -L-Het, in which Ar and Het can be, for example, as described above with reference to —($C_0$-$C_3$ alkyl)-Ar or —($C_0$-$C_3$ alkyl)-Het. In one such embodiment, L is —C(O)—$NR^9$—, such as —C(O)—NH—.

In other embodiments of the presently disclosed compounds of any of structural formulae (4-I)-(4-VII), the azetidinyl, pyrrolidinyl, piperidinyl or azepanyl $R^2$ moiety is substituted at its 1-position with —C(O)—O($C_0$-$C_6$ alkyl), —C(O)-Het, —C(O)—Ar, —S(O)$_2$-Het, —S(O)$_2$—Ar or —S(O)$_2$—O($C_0$-$C_6$ alkyl), in which Ar and Het can be, for example, as described above with reference to —($C_0$-$C_3$ alkyl)-Ar or —($C_0$-$C_3$ alkyl)-Het. In one embodiment, the azetidinyl, pyrrolidinyl, piperidinyl or azepanyl $R^2$ moiety is substituted at its 1-position with —C(O)-Het or —C(O)—Ar; in another embodiment, it is substituted at its 1-position with —S(O)$_2$-Het or —S(O)$_2$—Ar. For example, in certain embodiments, the azetidinyl, pyrrolidinyl, piperidinyl or azepanyl $R^2$ moiety is substituted at its 1-position with an optionally-substituted benzoyl (e.g., substituted with an electron withdrawing group as described above); or with an optionally-substituted nicotinyl, isonicotinyl or picolinyl (e.g., optionally substituted with an electron withdrawing group as described above). In other embodiments, the azetidinyl, pyrrolidinyl, piperidinyl or azepanyl $R^2$ moiety is substituted at its 1-position with an unsubstituted benzoyl; or an unsubstituted nicotinoyl, isonicotinoyl or picolinoyl.

In certain embodiments of the compounds of any of structural formulae (4-I)-(4-VII), $R^2$ is -Cak-N($R^9$)-G-$R^{22}$, as described above. For example, in one embodiment of the disclosed compounds, $R^2$ has the structure

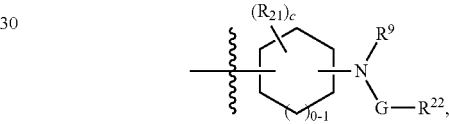

in which c is 0, 1, 2, 3 or 4, and each $R^{21}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, and two $R^{21}$ on the same carbon optionally combine to form oxo. In certain embodiments of the presently disclosed compounds, each $R^{21}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{21}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, c is 1 or 2. In other embodiments, c is 0. In certain embodiments, $R^9$ is H. In certain embodiments, G is a single bond. In certain embodiments of the presently disclosed compounds, each $R^{22}$ is not substituted with an aryl-, heteroaryl-, cycloalkyl- or heterocycloalkyl-containing group. In certain embodiments of the presently disclosed compounds, each $R^{23}$ is not substituted with an aryl-, heteroaryl-, cycloalkyl- or heterocycloalkyl-containing group.

In one embodiment of compounds of any of structural formulae (4-I)-(4-VII), $R^2$ has the structure

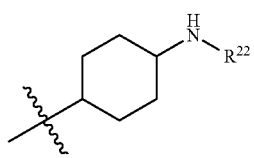

In certain embodiments of the compounds of any of structural formulae (4-I)-(4-VII), $R^2$ is —$(C_2-C_8$ alkyl)-N($R^9$)—$R^{24}$ in which one or two carbons of the ($C_2-C_8$ alkyl) are optionally replaced by —O— or —N($R^9$)— and $R^{24}$ is —$R^{23}$, -$GR^{23}$ or —C(O)O—($C_1-C_6$ alkyl). In certain embodiments, the ($C_2-C_8$ alkyl) is unsubstituted and no carbon is replaced by —O— or —N($R^9$)—. For example, in one embodiment, $R^2$ is —$CH_2$—$CH_2$—$CH_2$—N($R^9$)—$R^{24}$ or —$CH_2$—$CH_2$—$CH_2$—$CH_2$—N($R^9$)—$R^{24}$. In other embodiments, the ($C_2-C_8$ alkyl) is substituted and/or one or two carbons are replaced by —O— or —N($R^9$)—. For example, in one embodiment, $R^2$ is —$CH_2$—$CH_2$—O—$CH_2$—$CH_2$—N($R^9$)—$R^{24}$; —$CH_2$—CH($CH_3$)—N($R^9$)—$R^{24}$; or —$CH_2$—$CH_2$—O—$CH_2$—C(O)—N($R^9$)—$R^{24}$. In certain embodiments, $R^9$ is H. In certain embodiments, $R^{24}$ is Ar or Het. In certain embodiments, $R^{24}$ is not substituted with an aryl-, heteroaryl-, cycloalkyl- or heterocycloalkyl-containing group. In certain embodiments, the ($C_2-C_8$ alkyl) is a ($C_2-C_5$ alkyl).

In the compounds of any of structural formulae (4-I)-(4-VII), the number of substituents on the central pyridine, w, is 0, 1, 2 or 3. For example, in one embodiment, w is 0, 1 or 2. In another embodiment, w is 0. In other embodiments, w is at least 1, and at least one $R^3$ is selected from the group consisting of halo, cyano, —($C_1-C_4$ fluoroalkyl), —O—($C_1-C_4$ fluoroalkyl), —C(O)—($C_0-C_4$ alkyl), —C(O)O—($C_0-C_4$ alkyl), —C(O)N($C_0-C_4$ alkyl)($C_0-C_4$ alkyl), —S(O)$_2$O—($C_0-C_4$ alkyl), $NO_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. For example, in certain embodiments, at least one $R^3$ is halo (e.g., chloro) or —($C_1-C_4$ alkyl) (e.g., methyl, ethyl or propyl). In certain embodiments, an $R^3$ is substituted on the central pyridine in the meta position relative to the carbonyl bearing the diazacycloalkyl moiety.

In certain embodiments of the compounds of any of structural formulae (4-I)-(4-VII), each $R^3$ is independently selected from —($C_1-C_6$ alkyl), —($C_1-C_6$ haloalkyl) (e.g., difluoromethyl, trifluoromethyl and the like), —($C_0-C_6$ alkyl)-L-$R^7$, —($C_0-C_6$ alkyl)-$NR^8R^9$, —($C_0-C_6$ alkyl)-$OR^{10}$, —($C_0-C_6$ alkyl)-C(O)$R^{10}$, —($C_0-C_6$ alkyl)-S(O)$_{0-2}R^{10}$, -halogen, —$NO_2$ and —CN, in which each $R^7$, $R^8$ and $R^{10}$ is independently selected from H, —($C_1-C_6$ alkyl), —($C_1-C_6$ haloalkyl), —($C_0-C_6$ alkyl)-L-($C_0-C_6$ alkyl), —($C_0-C_6$ alkyl)-$NR^9$($C_0-C_6$ alkyl), —($C_0-C_6$ alkyl)-O—($C_0-C_6$ alkyl), —($C_0-C_6$ alkyl)-C(O)—($C_0-C_6$ alkyl), and —($C_0-C_6$ alkyl)-S(O)$_{0-2}$—($C_0-C_6$ alkyl), and in which no alkyl or haloalkyl is substituted with an aryl-, heteroaryl-, cycloalkyl- or heterocycloalkyl-containing group. For example, in one embodiment, each $R^3$ is —($C_1-C_3$ alkyl), —($C_1-C_3$ haloalkyl), —($C_0-C_3$ alkyl)-L-$R^7$, —($C_0-C_3$ alkyl)-$NR^8R^9$, —($C_0-C_3$ alkyl)-$OR^{10}$, —($C_0-C_3$ alkyl)-C(O)$R^{10}$, —($C_0-C_3$ alkyl)-S(O)$_{0-2}R^{10}$, -halogen, —$NO_2$ and —CN, in which each $R^7$, $R^8$ and $R^{10}$ is independently selected from H, —($C_1-C_2$ alkyl), —($C_1-C_2$ haloalkyl), —($C_0-C_2$ alkyl)-L-($C_0-C_2$ alkyl), —($C_0-C_2$ alkyl)-$NR^9$($C_0-C_2$ alkyl), —($C_0-C_2$ alkyl)-O—($C_0-C_2$ alkyl), —($C_0-C_2$ alkyl)-C(O)—($C_0-C_2$ alkyl) and —($C_0-C_2$ alkyl)-S(O)$_{0-2}$—($C_0-C_2$ alkyl), and in which no alkyl or haloalkyl is substituted with an aryl-, heteroaryl-, cycloalkyl- or heterocycloalkyl-containing group. For example, in certain embodiments, each $R^3$ is halo (e.g., chloro) or —($C_1-C_4$ alkyl) (e.g., methyl, ethyl or propyl).

In certain embodiments of the compounds of any of structural formulae (4-I)-(4-VII), w is at least one, and at least one $R^3$ is —$NR^8R^9$. For example, in one embodiment, w is 1. In certain such embodiments, an $R^3$ is substituted on the central pyridine in the meta position relative to the carbonyl bearing the diazacycloalkyl moiety.

In other embodiments of the compounds of any of structural formulae (4-I)-(4-VII), w is at least one, and at least one $R^3$ is —($C_0-C_3$ alkyl)-$Y^1$—($C_1-C_3$ alkyl)-$Y^2$—($C_0-C_3$ alkyl), in which each of $Y^1$ and $Y^2$ is independently L, —O—, —S— or —$NR^9$—. For example, in one embodiment, w is 1. In certain such embodiments, $R^3$ is substituted on the central pyridine in the meta position relative to the carbonyl bearing the diazacycloalkyl moiety. In one particular embodiment, $R^3$ is —$CH_2$—N($CH_3$)—$CH_2$—C(O)—$OCH_3$.

In the presently disclosed compounds of any of structural formulae (4-I)-(4-VII), the number of substituents on the diazacycloalkyl ring, x, is 0, 1, 2, 3 or 4. In one embodiment, x is 0, 1, 2 or 3. For example, x can be 0, or can be 1 or 2.

In certain embodiments of the presently disclosed compounds of any of structural formula (4-I)-(4-VII), two $R^4$ groups combine to form an oxo. The oxo can be bound, for example, at the position alpha to a nitrogen of the diazacycloalkyl ring. In other embodiments, no two $R^4$ groups combine to form an oxo.

In certain embodiments of the presently disclosed compounds of any of structural formulae (4-I)-(4-VII), when x is 4, not all four $R^4$ groups are ($C_1-C_6$ alkyl).

In certain embodiments of the presently disclosed compounds of any of structural formulae (4-I)-(4-VII), each $R^4$ is independently selected from —($C_1-C_6$ alkyl), —($C_1-C_6$ haloalkyl) (e.g., difluoromethyl, trifluoromethyl and the like), —($C_0-C_6$ alkyl)-L-$R^7$, —($C_0-C_6$ alkyl)-$NR^8R^9$, —($C_0-C_6$ alkyl)-$OR^{10}$, —($C_0-C_6$ alkyl)-C(O)$R^{10}$, —($C_0-C_6$ alkyl)-S(O)$_{0-2}R^{10}$, -halogen, —$NO_2$ and —CN, in which each $R^7$, $R^8$ and $R^{10}$ is independently selected from H, —($C_1-C_6$ alkyl), —($C_1-C_6$ haloalkyl), —($C_0-C_6$ alkyl)-L-($C_0-C_6$ alkyl), —($C_0-C_6$ alkyl)-$NR^9$($C_0-C_6$ alkyl), —($C_0-C_6$ alkyl)-O—($C_0-C_6$ alkyl), —($C_0-C_6$ alkyl)-C(O)—($C_0-C_6$ alkyl) and —($C_0-C_6$ alkyl)-S(O)$_{0-2}$—($C_0-C_6$ alkyl), and in which no alkyl or haloalkyl is substituted with an aryl-, heteroaryl-, cycloalkyl- or heterocycloalkyl-containing group. For example, in one embodiment, each $R^4$ is —($C_1-C_3$ alkyl), —($C_1-C_3$ haloalkyl), —($C_0-C_3$ alkyl)-L-$R^7$, —($C_0-C_3$ alkyl)-$NR^8R^9$, —($C_0-C_3$ alkyl)-$OR^{10}$, —($C_0-C_3$ alkyl)-C(O)$R^{10}$, —($C_0-C_3$ alkyl)-S(O)$_{0-2}R^{10}$, -halogen, —$NO_2$ and —CN, in which each $R^7$, $R^8$ and $R^{10}$ is independently selected from H, —($C_1-C_2$ alkyl), —($C_1-C_2$ haloalkyl), —($C_0-C_2$ alkyl)-L-($C_0-C_2$ alkyl), —($C_0-C_2$ alkyl)-$NR^9$($C_0-C_2$ alkyl), —($C_0-C_2$ alkyl)-O—($C_0-C_2$ alkyl), —($C_0-C_2$ alkyl)-C(O)—($C_0-C_2$ alkyl) and —($C_0$-$C_2$ alkyl)-S(O)$_{0\text{-}2}$—($C_0$-$C_2$ alkyl), and in which no alkyl or haloalkyl is substituted with an aryl-, heteroaryl-, cycloalkyl- or heterocycloalkyl-containing group.

In certain embodiments, the presently disclosed compounds have the structural formula (4-VIII):

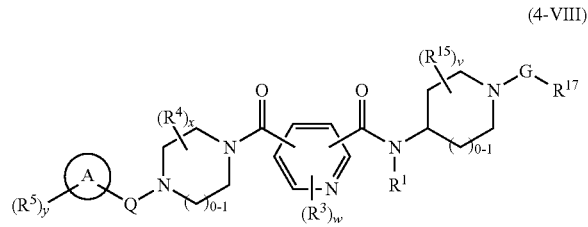

(4-VIII)

in which Q and G are each independently a bond, —CH$_2$—, —C(H)($R^{16}$)—, —C($R^{16}$)$_2$—, L (e.g., —C(O)—NR$^9$— or —NR$^9$—C(O)—) or —S(O)$_2$—; v is 0, 1, 2, 3 or 4; each $R^{15}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0\text{-}2}$R$^{10}$, -halogen, —NO$_2$ and —CN, and two $R^{15}$ on the same carbon optionally combine to form oxo; $R^{17}$ is Het or Ar, and all other variables are defined as described above with reference to any of structural formula (4-I)-(4-VII). $R^{17}$ can be, for example, an optionally substituted phenyl, an optionally-substituted pyridyl, an optionally substituted pyrazolyl, an optionally substituted imidazolyl, an optionally substituted pyrrolyl, an optionally substituted triazolyl or an optionally substituted thiadiazolyl. In one embodiment, Q is a single bond. In another embodiment, Q is —CH$_2$—. In other embodiments, Q is —C(O)— or —S(O)$_2$—. In certain embodiments, G is —CH$_2$—. In other embodiments, G is —C(O)— or —S(O)$_2$—. In other embodiments, G is —CH(CH$_3$)—. In other embodiments, G is —C(O)—NH—. The above-recited Q and G moieties can be combined in any possible combination. For example, in one embodiment, Q is a single bond and G is —CH$_2$— or —C(O)—. As described above, in certain embodiments, the ring system denoted by "A" is aryl or heteroaryl. In one embodiment, the ring system denoted by "A" is substituted with one or more electron-withdrawing groups as described above. In another embodiment, $R^{17}$ is substituted with one or more electron-withdrawing groups as described above. In certain embodiments, the ring system denoted by "A", $R^{17}$ or both are not substituted with an aryl, heteroaryl, cycloalkyl or heterocycloalkyl-containing group. In certain embodiments, the azacycloalkyl to which -G-$R^{17}$ is bound is a piperidinyl; in other embodiments, it is a pyrrolidinyl.

In the presently disclosed compounds of structural formula (4-VIII), v is 0, 1, 2, 3 or 4. In one embodiment, v is 0, 1, 2 or 3. For example, v can be 0, or can be 1 or 2.

In certain embodiments of the presently disclosed compounds of structural formula (4-VIII), two $R^{15}$ groups combine to form an oxo. The oxo can be bound, for example, at the position alpha relative to the nitrogen of the azacycloalkyl ring. In other embodiments, no two $R^{15}$ groups combine to form an oxo.

In certain embodiments of the presently disclosed compounds of structural formula (4-VIII), when v is 4, not all four $R^{15}$ moieties are ($C_1$-$C_6$ alkyl).

In certain embodiments of the presently disclosed compounds of structural formula (4-VIII), each $R^{15}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0\text{-}2}$R$^{10}$, -halogen, —NO$_2$ and —CN and two $R^{15}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-NR$^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0\text{-}2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{15}$ is —($C_1$-$C_3$ alkyl), —($C_1$-$C_3$ haloalkyl), —($C_0$-$C_3$ alkyl)-L-$R^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0\text{-}2}$R$^{10}$, -halogen, —NO$_2$ and —CN and two $R^{15}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-NR$^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0\text{-}2}$—($C_0$-$C_2$ alkyl), and in which no alkyl or haloalkyl is substituted with an aryl-, heteroaryl-, cycloalkyl- or heterocycloalkyl-containing group. In some embodiments, one $R^{15}$ is —C(O)NR$^9$R$^7$, which can be bound, for example, at a position alpha relative to the piperidine nitrogen, or at the position linked to the —N($R^1$)—.

In certain embodiments of the presently disclosed compounds of structural formula (4-VIII), $R^{17}$ is an unsubstituted aryl or heteroaryl. In other embodiments, the $R^{17}$ Ar or Het is substituted with 1, 2 or 3 substituents independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0\text{-}2}$R$^{10}$, -halogen, —NO$_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-NR$^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0\text{-}2}$—($C_0$-$C_6$ alkyl), and in which no alkyl or haloalkyl is substituted with an aryl-, heteroaryl-, cycloalkyl- or heterocycloalkyl-containing group. For example, in one embodiment, the $R^{17}$ Ar or Het is substituted with 1, 2 or 3 substituents independently selected from —($C_1$-$C_3$ alkyl), —($C_1$-$C_3$ haloalkyl), —($C_0$-$C_3$ alkyl)-L-$R^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0\text{-}2}$R$^{10}$, -halogen, —NO$_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-NR$^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0\text{-}2}$—($C_0$-$C_2$ alkyl), and in which no alkyl or haloalkyl is substituted with an aryl-, heteroaryl-, cycloalkyl- or heterocycloalkyl-containing group. In certain embodiments, $R^{17}$ is substituted with 1, 2 or 3 substituents selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca. $R^{17}$ can be substituted with, for example, one such substituent, or two such substituents. In certain embodiments, $R^{17}$ is substituted with a substitutent -$G^2$-$R^{34}$, in which $G^2$ is a single bond, —O—, —C(O)—, —S(O)$_2$— or —$CH_2$—, and $R^{34}$ is a chosen from aryl (such as phenyl), heterocycloalkyl (such as morpholinyl, pyrrolidinyl), and heteroaryl (such as), each of which is optionally substituted with 1 or 2 substituents selected from aryl, ($C_1$-$C_4$ haloalkyl), —O—($C_1$-$C_4$ haloalkyl), ($C_1$-$C_4$ alkyl), —O—($C_1$-$C_4$ alkyl), halogen, or CN.

In certain embodiments, the presently disclosed compounds have the structural formula (4-IX):

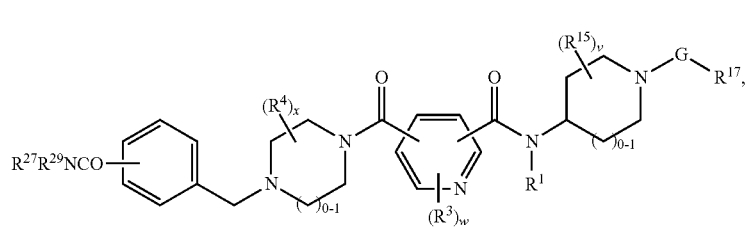

(4-IX)

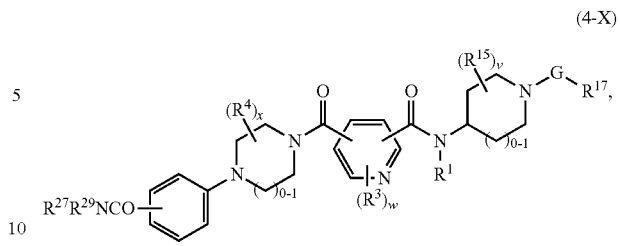

(4-X)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (4-I)-(4-VIII). In one embodiment, $R^{27}$ and $R^{29}$ are both H.

In certain embodiments, the presently disclosed compounds have the structural formula (4-XI):

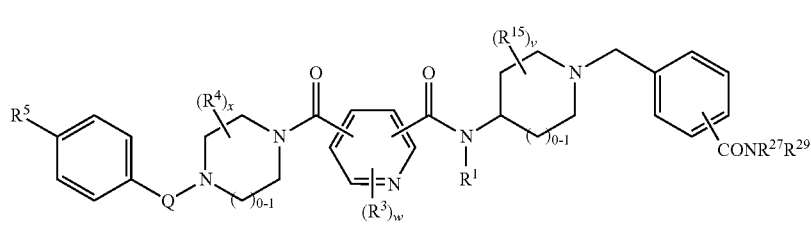

(4-XI)

heteroaryl, cycloalkyl or heterocycloalkyl-containing group, or $R^{27}$ and $R^{29}$ together with the nitrogen to which they are bound form Hca, and all other variables are as described above with reference to any of structural formulae (4-I)-(4-VIII). In one embodiment, $R^{27}$ and $R^{29}$ are both H.

In certain embodiments, the presently disclosed compounds have the structural formula (4-X):

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca, and all other variables are as described above with reference to any of structural formulae (4-I)-(4-VIII). In one embodiment, R$^{27}$ and R$^{29}$ are both H.

In certain embodiments, the presently disclosed compounds have the structural formula (4-XII):

in which R$^{25}$ is selected from halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl or haloalkyl is substituted by an aryl, heteroaryl, cycloalkyl or (4-XII)

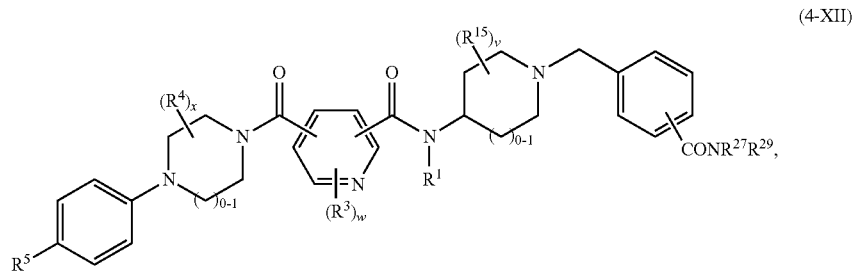

in which R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —CO—O—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca, and all other variables are as described above with reference to any of structural formulae (4-I)-(4-VIII). In one embodiment, R$^{27}$ and R$^{29}$ are both H.

In certain embodiments, the presently disclosed compounds have the structural formula (4-XIII):

(4-XIII)

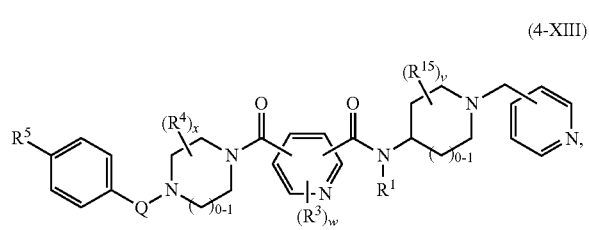

in which all variables are as described above with reference to any of structural formulae (4-I)-(4-VIII).

In certain embodiments, the presently disclosed compounds have the structural formula (4-XIV):

heterocycloalkyl-containing group; and all other variables are as described above with reference to any of structural formulae (4-I)-(4-VIII). R$^{25}$ can be, for example, —Cl, —F, cyano, —C(O)CH$_3$, —C(O)OH, —C(O)NH$_2$, trifluoromethyl, difluoromethyl, difluoromethoxy or trifluoromethoxy.

In certain embodiments, the presently disclosed compounds have the structural formula (4-XV):

(4-XV)

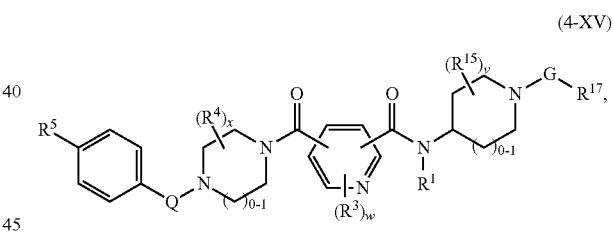

in which G is —C(O)—, —S(O)$_2$— or —C(O)—NH— and all other variables are as described above with reference to any of structural formulae (4-I)-(4-VIII).

In certain embodiments, the presently disclosed compounds have the structural formula (4-XVI):

(4-XIV)

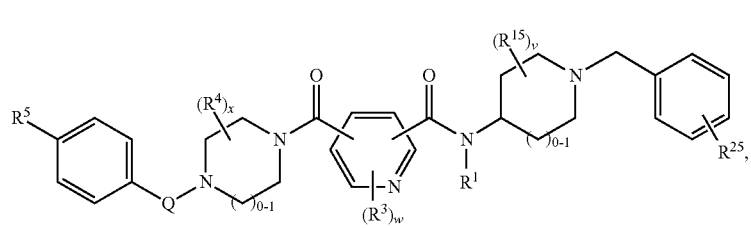 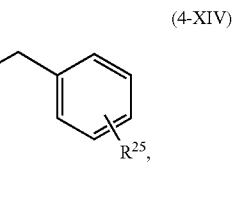

(4-XVI)

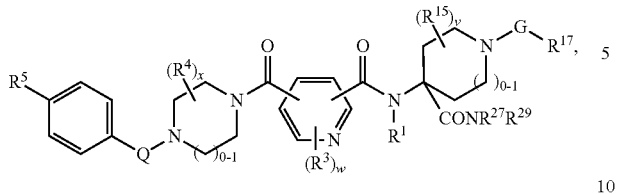

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (4-I)-(4-VIII). In one embodiment, $R^{27}$ and $R^{29}$ are both H. In some embodiments, the compounds of structural formula (4-VIII) are present as racemic mixtures or scalemic mixtures. In other embodiments, the compounds of structural formula (4-XVI) are present in an enantiomerically-enriched form, for example as a substantially pure stereoisomer.

In certain embodiments, the presently disclosed compounds have the structural formula (4-XVII):

(4-XVII)

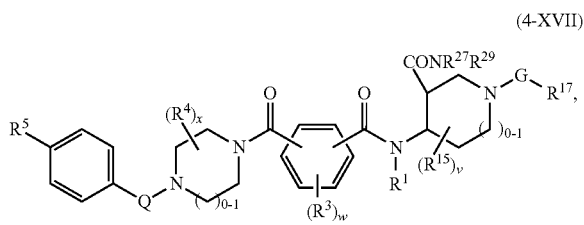

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—O—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (4-I)-(4-VIII). In one embodiment, $R^{27}$ and $R^{29}$ are both H. In some embodiments, the compounds of structural formula (4-VIII) are present as racemic mixtures or scalemic mixtures. In other embodiments, the compounds of structural formula (4-XVII) are present in an enantiomerically-enriched form, for example as a substantially pure stereoisomer.

In certain embodiments, the presently disclosed compounds have the structural formula (4-XVIII):

(4-XVIII)

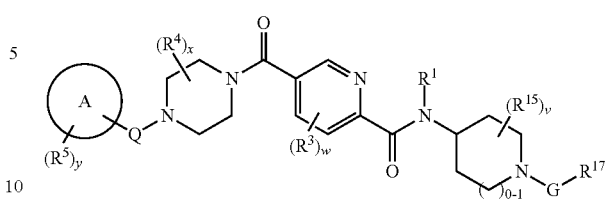

in which G, v, $R^{15}$ and $R^{17}$ are defined as described above with reference to structural formula (4-VIII), and all other variables are defined as described above with reference to structural formulae (4-I) or (4-II). $R^5$, y, v, $R^{15}$, $R^{17}$, Q, G and the ring denoted by "A" can be defined, for example, as described with reference to any of structural formulae (4-IX)-(4-XVII).

In certain embodiments, the presently disclosed compounds have the structural formula (4-XIX):

(4-XIX)

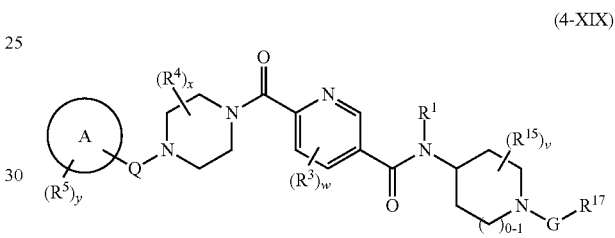

in which G, v, $R^{15}$ and $R^{17}$ are defined as described above with reference to structural formula (4-VIII), and all other variables are defined as described above with reference to structural formulae (4-I) or (4-III). $R^5$, y, v, $R^{15}$, $R^{17}$, Q, G and the ring denoted by "A" can be defined, for example, as described with reference to any of structural formulae (4-IX)-(4-XVII).

In certain embodiments, the presently disclosed compounds have the structural formula (4-XX):

(4-XX)

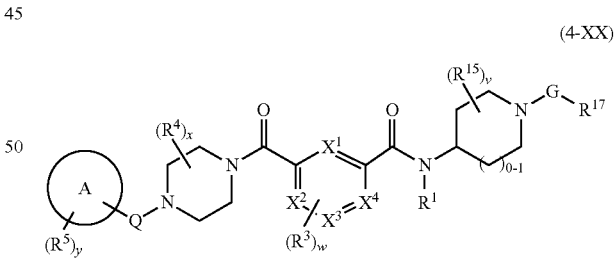

in which one of $X^1$, $X^2$, $X^3$ and $X^4$ are N, and the others are carbons (for example, independently CH or C substituted with one of the w $R^3$ groups), as described above with reference to structural formulae (4-IV) and (4-VII); G, v, $R^{15}$ and $R^{17}$ are defined as described above with reference to structural formula (4-VIII), and all other variables are defined as described above with reference to structural formulae (4-I) or (4-IV). $R^5$, y, v, $R^{15}$, $R^{17}$, Q, G and the ring denoted by "A" can be defined, for example, as described with reference to any of structural formulae (4-IX)-(4-XVII).

In certain embodiments of compounds having structural formulae (4-VIII)-(4-XX), the

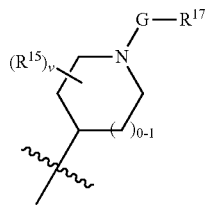

moiety has the structure

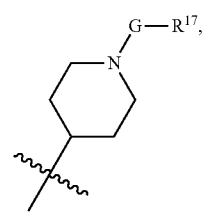

in which G is —CH$_2$—, —CH(CH$_3$)—, —C(O)—, —S(O)$_2$— or —C(O)—NH—. For example, in one embodiment, G is —CH$_2$—. In another embodiment, G is —C(O)— or —S(O)$_2$—. In another embodiment, G is —C(O)—NH—.

In other embodiments of compounds having structural formulae (4-VIII)-(4-XX), the

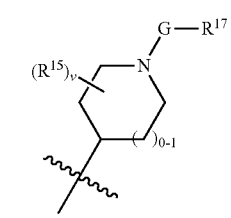

moiety has the structure

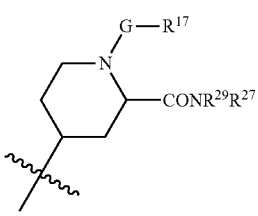

or

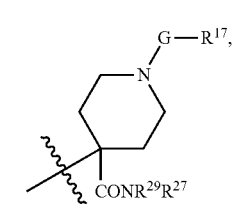

in which G is —CH$_2$—, —C(O)—, —S(O)$_2$— or —C(O)—NH—, R$^{27}$ is selected from H, —(C$_1$-C$_6$ alkyl), —(C$_1$-C$_6$ haloalkyl) (e.g., difluoromethyl, trifluoromethyl and the like), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl)-(C$_0$-C$_6$ alkyl)-S(O)$_{0-2}$—(C$_0$-C$_6$ alkyl), in which no heterocycloalkyl, alkyl or haloalkyl is substituted with an aryl-, heteroaryl-, cycloalkyl- or heterocycloalkyl-containing group, and R$^{29}$ is —H, —(C$_1$-C$_4$ alkyl), —CO—(C$_1$-C$_4$ alkyl) or —CO—O—(C$_1$-C$_4$ alkyl) in which no (C$_1$-C$_4$ alkyl) is substituted by an aryl, heteroaryl, cycloalkyl or heterocycloalkyl-containing group, or R$^{27}$ and R$^{29}$ together with the nitrogen to which they are bound form Hca. In such embodiments, the compounds can be present as racemic mixtures or scalemic mixtures, or in an enantiomerically-enriched form, for example as a substantially pure stereoisomer.

In other embodiments of compounds having structural formulae (4-VIII)-(4-XX), the

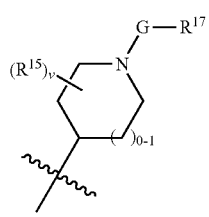

moiety has the structure

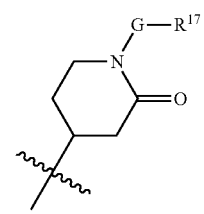

in which G is —CH$_2$—, —C(O)—, —S(O)$_2$— or —C(O)—NH—.

In other embodiments of compounds having structural formulae (4-VIII)-(4-XX), the

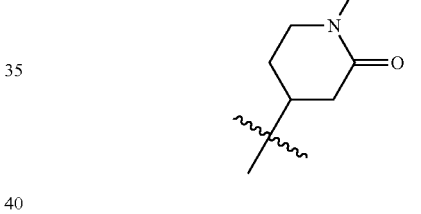

moiety has the structure

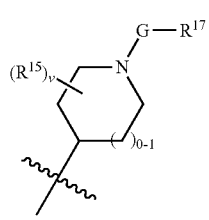

For example, in one embodiment, the 3-fluoro and the 4-substituent of the piperidine are substituted in a cis manner on the piperidine. In other embodiments, the 3-fluoro and the 4-substituent are substituted in a trans manner on the piperidine. For example in one embodiment, the piperidine moiety has the structure

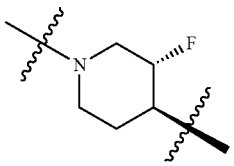

Fluoropiperidine compounds can be provided in racemic form, in enantiomerically enriched form, or in substantially enantiomerically pure form.

In certain embodiments of compounds having structural formulae (4-VIII)-(4-XX), the $R^{17}$ moiety has the structure

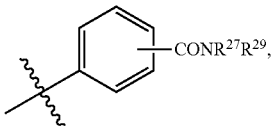

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca.

In certain embodiments of compounds having structural formulae (4-VIII)-(4-XX), w is 1, and $R^3$ is —$NR^8R^9$. In certain such embodiments, $R^3$ is substituted on the central pyridine in a meta position relative to the —C(O)— bearing the diazacycloalkyl moiety.

In other embodiments of compounds having structural formulae (4-VIII)-(4-XX), w is 1, and $R^3$ is —($C_0$-$C_3$ alkyl)-$Y^1$—($C_1$-$C_3$ alkyl)-$Y^2$—($C_0$-$C_3$ alkyl), in which each of $Y^1$ and $Y^2$ is independently L, —O—, —S— or —$NR^9$—. In certain such embodiments, $R^3$ is substituted on the central pyridine in a meta position relative to the —C(O)— bearing the diazacycloalkyl moiety.

In certain embodiments described above, each $R^{27}$ is selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}$$R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group, and each $R^{29}$ is H, methyl or ethyl, or $R^{27}$ and $R^{29}$ together with the nitrogen to which they are bound form Hca.

In certain embodiments of compounds having structural formulae (4-VIII)-(4-XX), at least one $R^5$ moiety is a haloalkyl group, and in exemplary embodiments of these formulae the

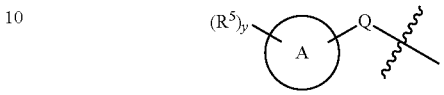

moiety is p-(trifluoromethyl)phenyl, p-fluorophenyl or p-cyanophenyl. By way of further illustration, certain exemplary compounds including such

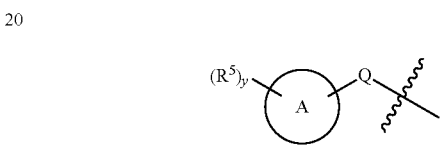

moieties have structural formula (4-XXI), (4-XXII) or (4-XXIII):

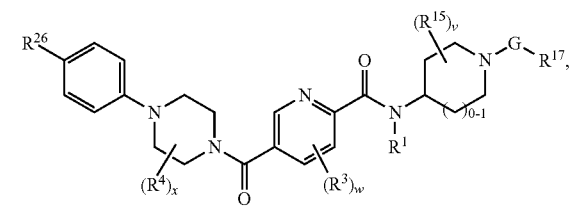
(4-XXI)

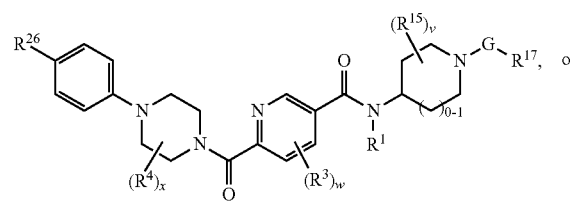
(4-XXII)

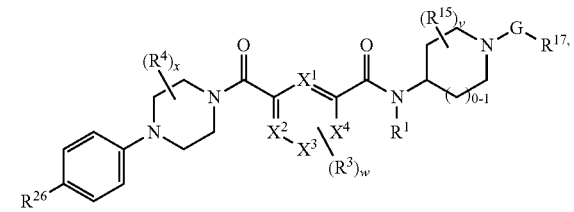
(4-XXIII)

in which $R^{26}$ is trifluoromethyl, chloro, fluoro or cyano and all other variables are as described above with reference to structural formulae (4-XVIII), (4-XIX) and (4-XX).

In certain embodiments, the presently disclosed compounds have the structural formula (4-XXIV):

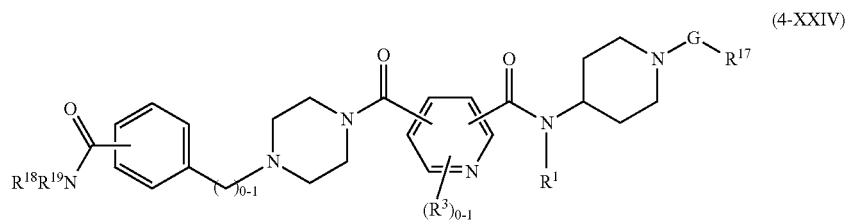

(4-XXIV)

in which G, $R^1$, $R^3$ and $R^{17}$ are as described above with reference to any of structural formulae (4-I)-(4-XXIII), $R^{18}$ is H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), in which no alkyl or haloalkyl is substituted with an aryl-, heteroaryl-, cycloalkyl- or heterocycloalkyl-containing group and $R^{19}$ is —H, —($C_1$-$C_4$ alkyl), —CO—($C_1$-$C_4$ alkyl) or —CO—O—($C_1$-$C_4$ alkyl) in which no alkyl is substituted by an aryl, heteroaryl, cycloalkyl or heterocycloalkyl-containing group, or $R^{18}$ and $R^{19}$ together with the nitrogen to which they are bound form Hca. In one embodiment, $R^{18}$ and $R^{19}$ are both H.

For example, in one embodiment, the presently disclosed compounds have the structural formula (4-XXV):

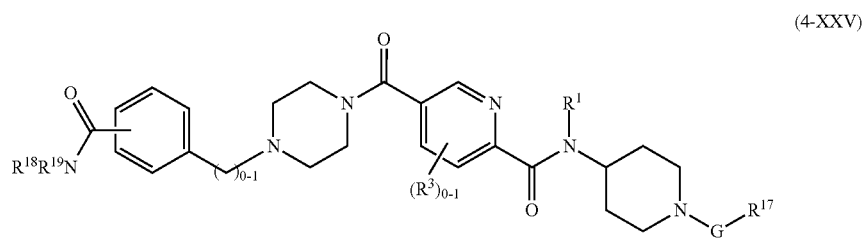

(4-XXV)

in which G, $R^1$, $R^3$ and $R^{17}$ are as described above with reference to any of structural formulae (4-I), (4-VIII), (4-XIII), (4-XIV), (4-XVI) or (4-XXII), and $R^{18}$ and $R^{19}$ are defined as described above with reference to structural formula (4-XXIV).

In certain embodiments, the presently disclosed compounds have the structural formula (4-XXVI):

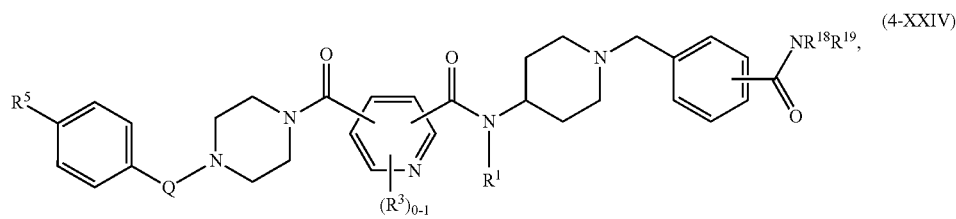

(4-XXIV)

in which Q, $R^1$, $R^3$ and $R^5$ are defined as described above with reference to any of structural formulae (4-I)-(4-XXIII), and $R^{18}$ and $R^{19}$ are defined as described above with reference to structural formula (4-XXIV).

For example, in one embodiment, the presently disclosed compounds have the structural formula (4-XXVII):

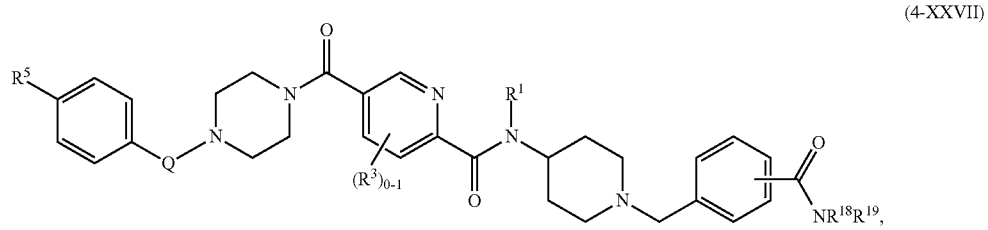

(4-XXVII)

in which Q, $R^1$, $R^3$ and $R^5$ are defined as described above with reference to any of structural formulae (4-I)-(4-XXIII), and $R^{18}$ and $R^{19}$ are defined as described above with reference to structural formula (4-XXIV).

In certain embodiments, the presently disclosed compounds have the structural formula (4-XXVIII):

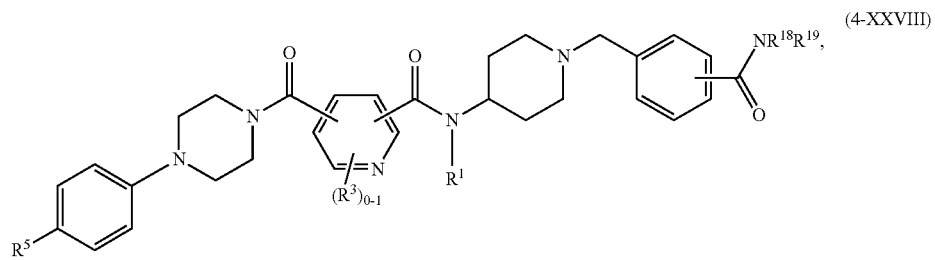

(4-XXVIII)

in which $R^1$, $R^3$ and $R^5$ are defined as described above with reference to any of structural formulae (4-I)-(4-XXIII), and $R^{18}$ and $R^{19}$ are defined as described above with reference to structural formula (4-XXIV).

For example, in one embodiment, the presently disclosed compounds have the structural formula (4-XXIX):

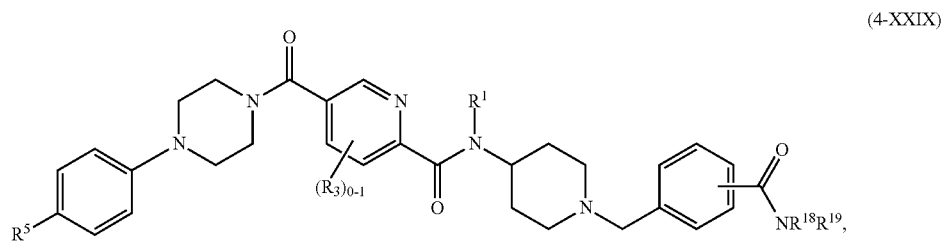

(4-XXIX)

in which $R^1$, $R^3$ and $R^5$ are defined as described above with reference to any of structural formulae (4-I)-(4-XXIII), and $R^{18}$ and $R^{19}$ are defined as described above with reference to structural formula (4-XXIV).

In compounds according to any of structural formulae (4-I)-(4-VII), T and $R^2$ can be defined as described above with reference to structural formulae (4-VIII)-(4-XXIX).

In certain embodiments, the presently disclosed compounds have the structural formula (4-XXX):

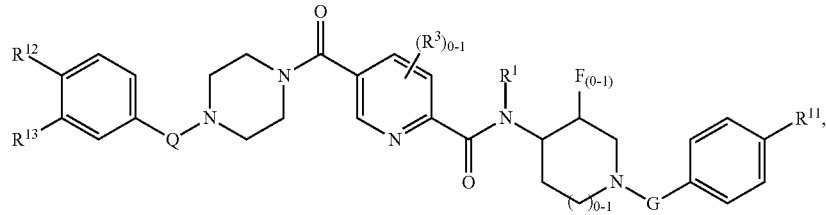

(4-XXX)

in which Q is —$CH_2$—, —C(O)— or a single bond; G is a single bond, —$CH_2$—, —C(O)—, —$S(O)_2$— or —C(O)—NH—; $R^1$ and $R^3$ are as described above with reference to any of structural formulae (4-I), (4-II), and (4-VIII); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the central pyridine. In another embodiment, one $R^3$ (e.g., —Cl, —F, —$CH_3$, —$C_2H_5$, —$C_3H_7$) is substituted on the central pyridine.

In certain embodiments, the presently disclosed compounds have the structural formula (4-XXXI):

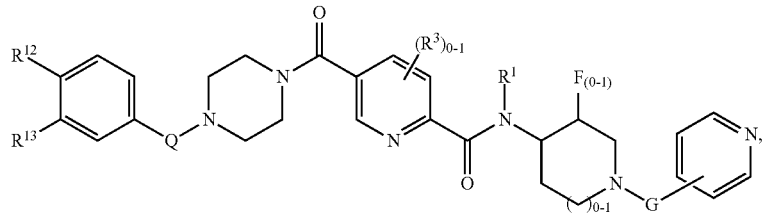

(4-XXXI)

in which Q is —$CH_2$—, —C(O)— or a single bond; G is a single bond, —$CH_2$—, —C(O)—, —$S(O)_2$— or —C(O)—NH—; $R^1$ and $R^3$ are as described above with reference to any of structural formulae (4-I), (4-II) and (4-VIII); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the central pyridine. In another embodiment, one $R^3$ (e.g., —Cl, —F, —$CH_3$, —$C_2H_5$, —$C_3H_7$) is substituted on the central pyridine.

In certain embodiments, the presently disclosed compounds have the structural formula (4-XXXII):

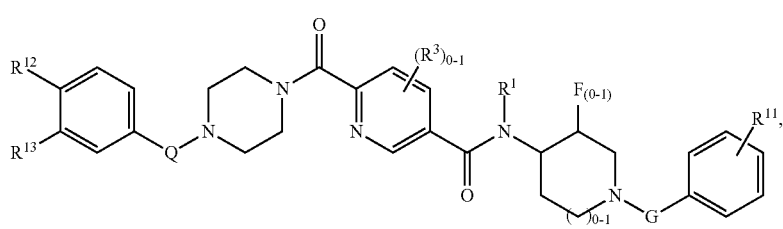

(4-XXXII)

in which Q is —$CH_2$—, —C(O)— or a single bond; G is a single bond, —$CH_2$—, —C(O)—, —$S(O)_2$— or —C(O)—NH—; $R^1$ and $R^3$ are as described above with reference to any of structural formulae (4-I), (4-III), and (4-VIII); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, no $R^3$ is substituted on the central pyridine. In another embodiment, one $R^3$ (e.g., —Cl, —F, —$CH_3$, —$C_2H_5$, —$C_3H_7$) is substituted on the central pyridine.

In certain embodiments, the presently disclosed compounds have the structural formula (4-XXXIII):

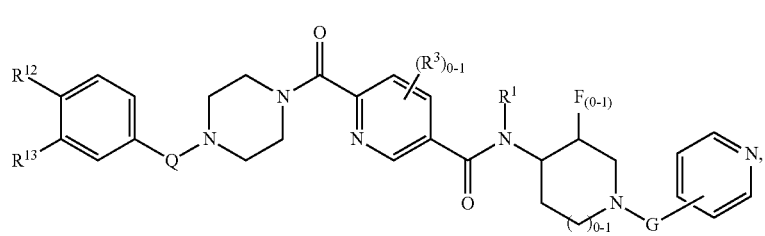

(4-XXXIII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (4-I), (4-III) and (4-VIII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyrido nitrogen is disposed in the para position relative to the G moiety; in another embodiment, the pyrido nitrogen is disposed in the meta position relative to the G moiety. In one embodiment, no R$^3$ is substituted on the central pyridine. In another embodiment, one R$^3$ (e.g., —Cl, —F, —CH$_3$, —C$_2$H$_5$, —C$_3$H$_7$) is substituted on the central pyridine.

In certain embodiments, the presently disclosed compounds have the structural formula (4-XXXIV):

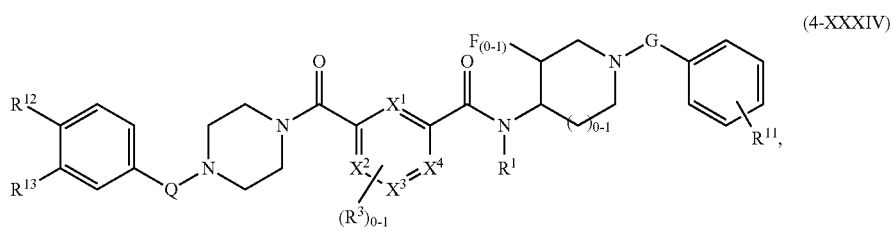

(4-XXXIV)

in which one of X$^1$, X$^2$, X$^3$ and X$^4$ are N, and the others are carbons (for example, independently CH or C substituted with one of the w R$^3$ groups), as described above with reference to structural formulae (4-IV) and (4-VII); Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (4-I), (4-IV), and (4-VIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, no R$^3$ is substituted on the central pyridine. In another embodiment, one R$^3$ (e.g., —Cl, —F, —CH$_3$, —C$_2$H$_5$, —C$_3$H$_7$) is substituted on the central pyridine.

In certain embodiments, the presently disclosed compounds have the structural formula (4-XXXV):

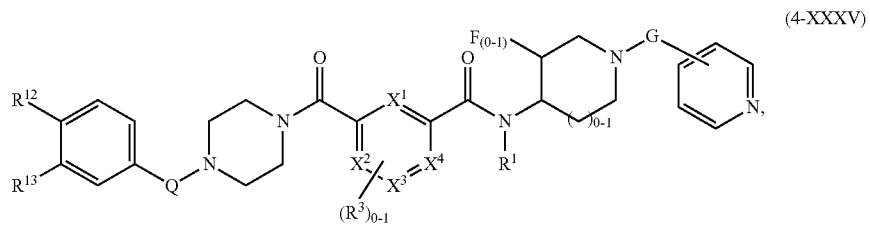

(4-XXXV)

in which one of $X^1$, $X^2$, $X^3$ and $X^4$ are N, and the others are carbons (for example, independently CH or C substituted with one of the w $R^3$ groups), as described above with reference to structural formulae (4-IV) and (4-VII); Q is —$CH_2$—, —C(O)— or a single bond; G is a single bond, —$CH_2$—, —C(O)—, —$S(O)_2$— or —C(O)—NH—; $R^1$ and $R^3$ are as described above with reference to any of structural formulae (4-I), (4-IV) and (4-VIII); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyrido nitrogen is disposed in the para position relative to the G moiety; in another embodiment, the pyrido nitrogen is disposed in the meta position relative to the G moiety. In one embodiment, no $R^3$ is substituted on the central pyridine. In another embodiment, one $R^3$ (e.g., —Cl, —F, —$CH_3$, —$C_2H_5$, —$C_3H_7$) is substituted on the central pyridine.

As the person of skill in the art will recognize, the various embodiments described above can be combined to form other embodiments of the disclosure. For example, in one embodiment, Q is —$CH_2$—, as described above, and G is —$CH_2$—, as described above.

Examples of compounds according to structural formula (4-I) include those listed in Table 4. These compounds can be made, for example using a procedure analogous to those described in U.S. Patent Application Publications nos. 2009/0163511, 2009/0170829, 2009/0186894 and 2009/0275609, and in U.S. patent application Ser. No. 12/695,861, each of which is hereby incorporated by reference in its entirety.

TABLE 4

| No. | Name | Structure |
|---|---|---|
| 4-1 | 5-(4-(4-cyanobenzyl)piperazine-1-carbonyl)-N-(1-(4-cyanobenzyl)piperidin-4-yl)picolinamide | 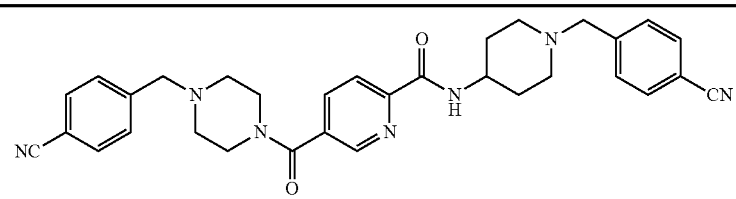 |
| 4-2 | N-(1-(4-cyanobenzyl)piperidin-4-yl)-5-(4-(4-fluorobenzyl)piperazine-1-carbonyl)picolinamide | 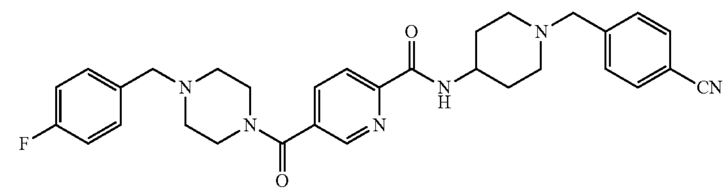 [SMILES: N#Cc1ccc(CN2CCC(NC(=O)c3ccc(C(=O)N4CCN(Cc5ccc(F)cc5)CC4)cn3)CC2)cc1] |
| 4-3 | N-(1-(4-cyanobenzyl)piperidin-4-yl)-5-(4-(4-(trifluoromethyl)benzyl)piperazine-1-carbonyl)picolinamide | 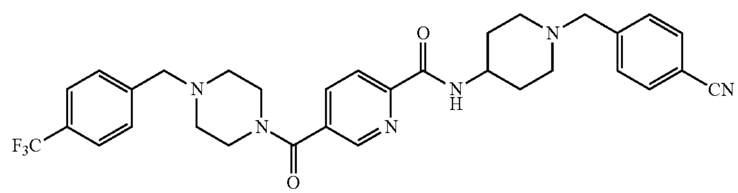 [SMILES: N#Cc1ccc(CN2CCC(NC(=O)c3ccc(C(=O)N4CCN(Cc5ccc(C(F)(F)F)cc5)CC4)cn3)CC2)cc1] |
| 4-4 | (S)-5-(4-(4-chlorophenyl)piperazine-1-carbonyl)-N-(1-(4-fluorobenzyl)pyrrolidin-3-yl)picolinamide | 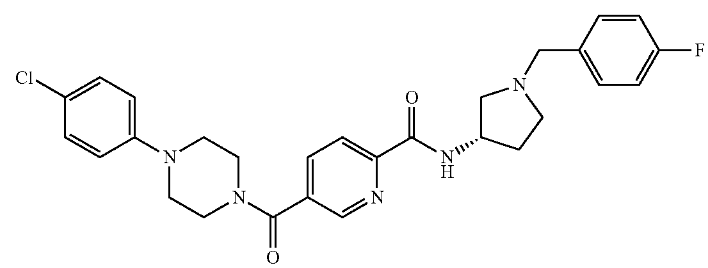 [SMILES: O=C(N[C@H]1CCN(Cc2ccc(F)cc2)C1)c1ccc(C(=O)N2CCN(c3ccc(Cl)cc3)CC2)cn1] |
| 4-5 | (S)-5-(4-(4-chlorophenyl)piperazine-1-carbonyl)-N-(1-(pyridin-4-ylmethyl)pyrrolidin-3-yl)picolinamide | 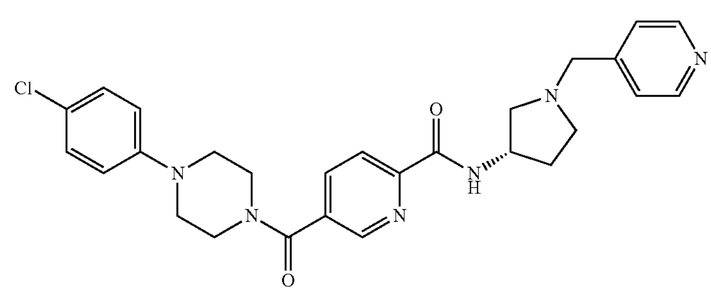 [SMILES: O=C(N[C@H]1CCN(Cc2ccncc2)C1)c1ccc(C(=O)N2CCN(c3ccc(Cl)cc3)CC2)cn1] |

TABLE 4-continued

| No. | Name | Structure |
|---|---|---|
| 4-6 | (S)-5-(4-(4-chlorophenyl)piperazine-1-carbonyl)-N-(1-(4-cyanobenzyl)pyrrolidin-3-yl)picolinamide | 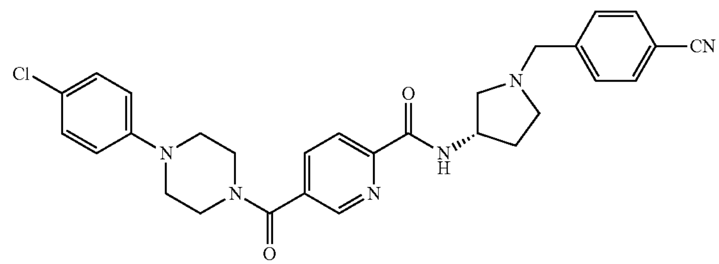 [SMILES: N#Cc1ccc(CN2CC[C@H](NC(=O)c3ccc(C(=O)N4CCN(c5ccc(Cl)cc5)CC4)cn3)C2)cc1] |
| 4-7 | N-(1-(4-chlorobenzyl)pyrrolidin-3-yl)-5-(4-(4-chlorophenyl)piperazine-1-carbonyl)picolinamide | 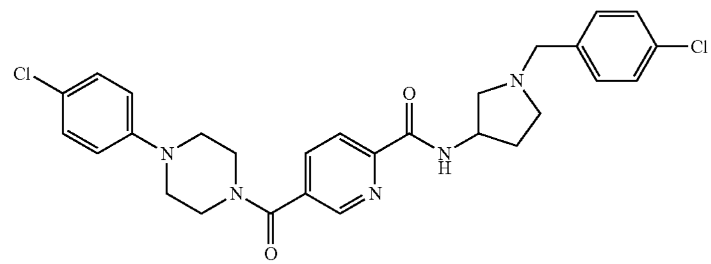 [SMILES: O=C(NC1CCN(Cc2ccc(Cl)cc2)C1)c1ccc(C(=O)N2CCN(c3ccc(Cl)cc3)CC2)cn1] |
| 4-8 | 5-(4-(4-chlorophenyl)piperazine-1-carbonyl)-N-(1-(4-(trifluoromethyl)benzyl)pyrrolidin-3-yl)picolinamide | 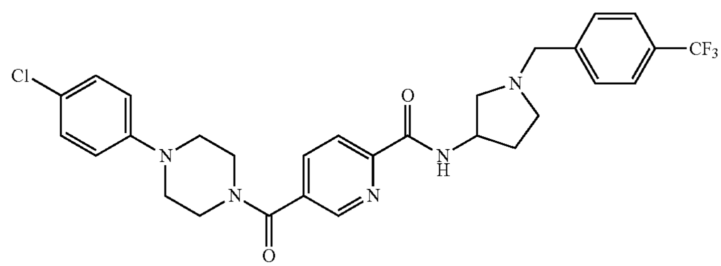 [SMILES: O=C(NC1CCN(Cc2ccc(C(F)(F)F)cc2)C1)c1ccc(C(=O)N2CCN(c3ccc(Cl)cc3)CC2)cn1] |
| 4-9 | N-(1-(4-cyanobenzyl)piperidin-4-yl)-6-(4-(4-(pyrrolidin-1-ylsulfonyl)phenyl)piperazine-1-carbonyl)nicotinamide | 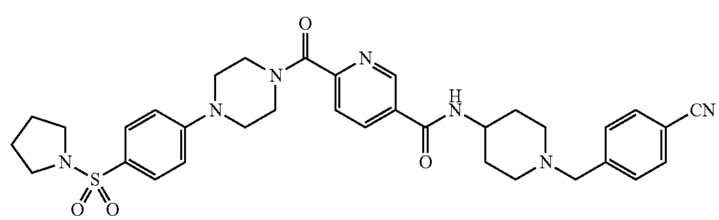 [SMILES: N#Cc1ccc(CN2CCC(NC(=O)c3ccc(C(=O)N4CCN(c5ccc(S(=O)(=O)N6CCCC6)cc5)CC4)nc3)CC2)cc1] |
| 4-10 | 6-(4-(4-(cyclopropanecarbonyl)phenyl)piperazine-1-carbonyl)-N-((3,4-trans)-3-fluoro-1-(4-(trifluoromethoxy)benzyl)piperidin-4-yl)nicotinamide | 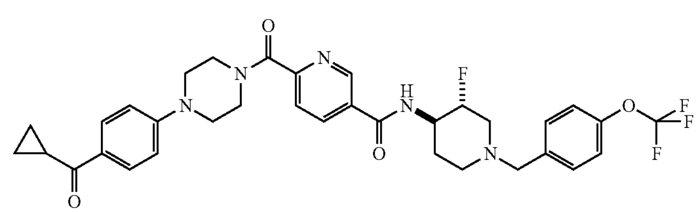 |
| 4-11 | N-((3,4-trans)-3-fluoro-1-(4-(trifluoromethoxy)benzyl)piperidin-4-yl)-6-(4-(4-(isopropylsulfonyl)phenyl)piperazine-1-carbonyl)nicotinamide | 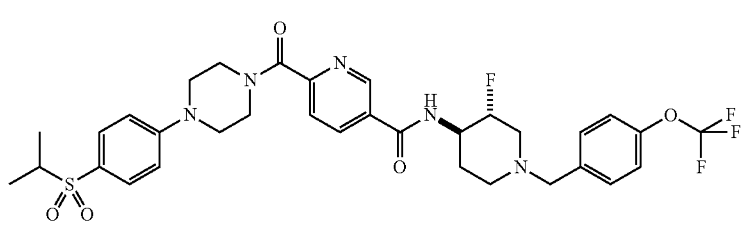 |

TABLE 4-continued

| No. | Name | Structure |
|---|---|---|
| 4-12 | N-((3,4-trans)-1-(4-cyanobenzyl)-3-fluoropiperidin-4-yl)-6-(4-(4-(cyclopropanecarbonyl)phenyl)piperazine-1-carbonyl)nicotinamide | 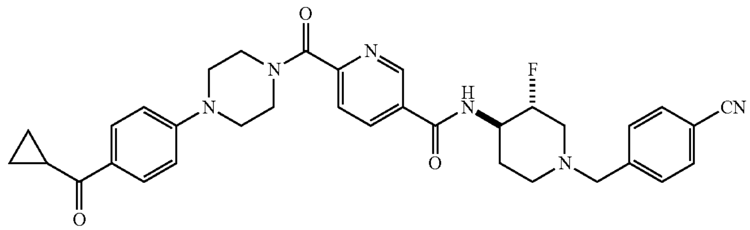 |
| 4-13 | N-((3,4-trans)-1-(4-cyanobenzyl)-3-fluoropiperidin-4-yl)-6-(4-(4-(methylsulfonyl)benzyl)piperazine-1-carbonyl)nicotinamide | 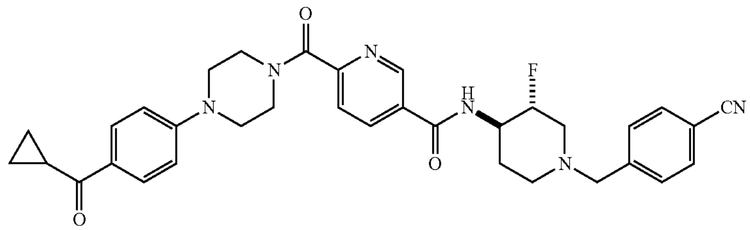 |
| 4-14 | N-((3,4-trans)-3-fluoro-1-(4-(trifluoromethoxy)benzyl)piperidin-4-yl)-6-(4-(4-(pyrrolidin-1-ylsulfonyl)phenyl)piperazine-1-carbonyl)nicotinamide | 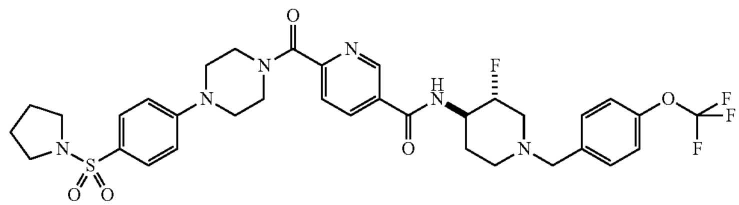 |
| 4-15 | N-((3,4-trans)-3-fluoro-1-(4-(trifluoromethoxy)benzyl)piperidin-4-yl)-6-(4-(4-(pyrrolidin-1-ylsulfonyl)benzyl)piperazine-1-carbonyl)nicotinamide | 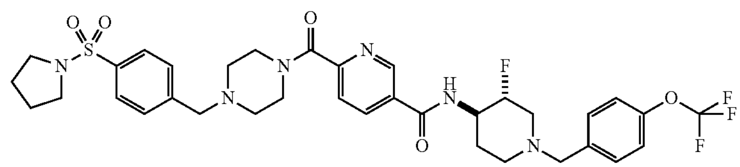 |
| 4-16 | N-(1-(4-cyanobenzyl)piperidin-4-yl)-6-(4-(4-(pyrrolidin-1-ylsulfonyl)benzyl)piperazine-1-carbonyl)nicotinamide | 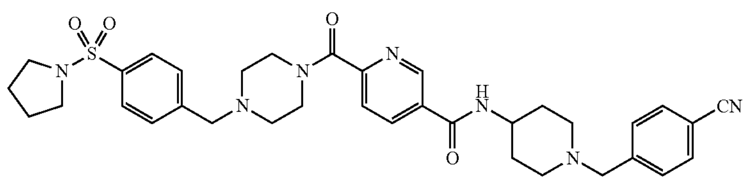 [SMILES: N#Cc1ccc(CN2CCC(NC(=O)c3ccc(C(=O)N4CCN(Cc5ccc(S(=O)(=O)N6CCCC6)cc5)CC4)nc3)CC2)cc1] |
| 4-17 | N-(1-(4-cyanobenzyl)piperidin-4-yl)-6-(4-(4-(N-ethylsulfamoyl)benzyl)piperazine-1-carbonyl)nicotinamide | 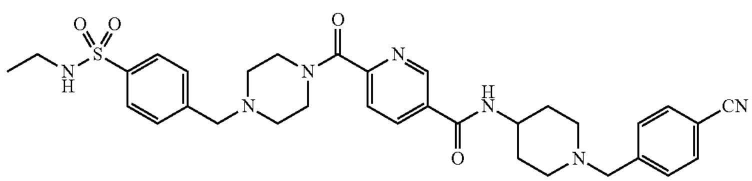 [SMILES: CCNS(=O)(=O)c1ccc(CN2CCN(C(=O)c3ccc(C(=O)NC4CCN(Cc5ccc(C#N)cc5)CC4)cn3)CC2)cc1] |

Another aspect of the disclosure provides compounds having structural formula (5-I):

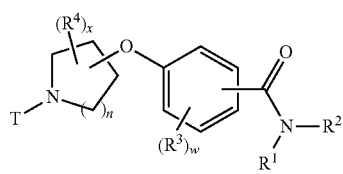

(5-I)

and pharmaceutically acceptable salts, and N-oxides thereof (and solvates and hydrates thereof), in which
$R^1$ is H;
$R^2$ is -Hca;
each $R^3$ is independently selected from —($C_1$-$C_6$ alkyl), —($C_1$-$C_6$ fluoroalkyl), —($C_0$-$C_6$ alkyl)-Ar; —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-$S(O)_{0-2}R^{10}$, -halogen, —$NO_2$ and —CN;

w is 0, 1, 2, or 3;

n is 0, 1 2 or 3;

each $R^4$ is independently selected from —($C_1$-$C_6$ alkyl), —($C_1$-$C_6$ fluoroalkyl), —($C_0$-$C_6$ alkyl)-Ar; —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-$S(O)_{0-2}R^{10}$, -halogen, —NO$_2$ and —CN, and two R$^4$ on the same carbon optionally combine to form oxo;

x is 0, 1, 2, 3 or 4;

T is —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$; or

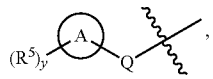

in which

Q is —(C$_0$-C$_3$ alkyl)-, in which each carbon of the —(C$_0$-C$_3$ alkyl)- is optionally and independently substituted with one or two R$^{16}$;

each R$^{16}$ is independently selected from —(C$_1$-C$_6$ alkyl), —(C$_1$-C$_6$ fluoroalkyl), —(C$_0$-C$_6$ alkyl)-Ar; —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$, -halogen, —NO$_2$ and —CN, and two R$^{16}$ on the same carbon optionally combine to form oxo;

the ring system denoted by "A" is heteroaryl, aryl, cycloalkyl or heterocycloalkyl;

each R$^5$ is independently selected from —(C$_1$-C$_6$ alkyl), —(C$_1$-C$_6$ fluoroalkyl), —(C$_0$-C$_6$ alkyl)-Ar; —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$, -halogen, —NO$_2$ and —CN; and y is 0, 1, 2, 3 or 4;

in which each L is independently selected from —NR$^9$C(O)O—, —NR$^9$C(O)—NR$^9$—, —NR$^9$C(O)S—, —NR$^9$C(O)—, —NR$^9$C(S)O—, —NR$^9$C(S)—NR$^9$—, —NR$^9$C(S)S—, —NR$^9$C(S)—, —OC(O)NR$^9$—, —SC(O)NR$^9$—, —C(S)NR$^9$—, —OC(S)NR$^9$—, —SC(S)NR$^9$—, —C(S)NR$^9$—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR$^9$C(NR$^2$)NR$^9$—, —NR$^9$SO$_2$—, —SO$_2$NR$^9$— and —NR$^9$SO$_2$NR$^9$—, each R$^6$, R$^7$, R$^8$ and R$^{10}$ is independently selected from H, —(C$_1$-C$_6$ alkyl), —(C$_1$-C$_6$ fluoroalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl) and —(C$_0$-C$_6$ alkyl)-S(O)$_{0-2}$—(C$_0$-C$_6$ alkyl), each R$^9$ is independently selected from —H, —(C$_1$-C$_4$ alkyl) and —C(O)—(C$_1$-C$_4$ alkyl), each Ar is an optionally substituted aryl, each Het is an optionally substituted heteroaryl, each Cak is an optionally substituted cycloalkyl, each Hca is an optionally substituted heterocycloalkyl, and each alkyl is optionally substituted.

Various embodiments of compounds of structural formula (5-I) suitable for use in the methods described herein are described below. Information regarding certain of these compounds can also be found in U.S. Patent Application Publication no. 2009/0186894, which is hereby incorporated by reference in its entirety.

R$^1$, R$^2$, R$^3$, R$^4$, T, w, x and n may alternatively be as described above with respect to structural formulae (3-I)-(3-CXX).

In one embodiment of compounds of structural formula (5-I), two R$^4$s combine to form an oxo. The oxo can be bound, for example, at the position alpha to the nitrogen of the azacycloalkyl.

In certain embodiments of the compounds of formula (5-I), T is

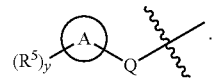

In these embodiments, Q is —(C$_0$-C$_3$ alkyl)-, in which each carbon of the (C$_0$-C$_3$ alkyl) is optionally and independently substituted with one or two R$^{16}$, in which each R$^{16}$ is independently selected from —(C$_1$-C$_6$ alkyl), —(C$_1$-C$_6$ fluoroalkyl), —(C$_0$-C$_6$ alkyl)-Ar; —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$, -halogen, —NO$_2$ and —CN, and two R$^{16}$ on the same carbon optionally combine to form an oxo. Q can be, for example, an unsubstituted (C$_1$-C$_3$ alkyl). In other embodiments, Q is a (C$_1$-C$_3$ alkyl) having as its only substitution a single oxo group. For example, in certain embodiments, Q is —CH$_2$—; a single bond; or —C(O)— or —CH(CH$_3$)—.

The number of substituents on the ring system denoted by "A", y, in these embodiments is 0, 1, 2, 3 or 4. For example, in some embodiments, y is 0, 1, 2 or 3, for example 0, or 1. In one embodiment, y is not zero and at least one R$^5$ is halo, cyano, trifluoromethyl or trifluoromethoxy.

The ring system denoted by "A" is heteroaryl, aryl, cycloalkyl or heterocycloalkyl. For example, of the compounds of structural formula (5-I), the ring system denoted by "A" is an aryl or a heteroaryl. In one embodiment of the compounds of structural formula (5-I), the ring system denoted by "A" is an aryl. The ring system denoted by "A" can be, for example, a monocyclic aryl or heteroaryl.

For example, in one embodiment of the compounds of structural formula (5-I), the ring system denoted by "A" is an aryl, such as a phenyl. In one embodiment of the compounds of structural formula (5-I), y is 1 and R$^5$ is attached to the phenyl para to Q. In another embodiment of the compounds of structural formula (5-I), y is 1 and R$^5$ is selected from the group consisting of halo, cyano, —(C$_1$-C$_4$ fluoroalkyl), —O—(C$_1$-C$_4$ fluoroalkyl), acyl, carboxylate, carboxamide and nitro. R$^5$ can be, for example, —Cl, —F, cyano, trifluoromethyl or trifluoromethoxy. In another embodiment of the compounds of structural formula (5-I), the

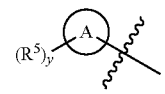

moiety is a 3,4-dihalophenyl.

In another embodiment of the compounds of structural formula (5-I), the ring system denoted by "A" is a heteroaryl. For example, in certain embodiments of the compounds of structural formula (5-I), the ring system denoted by "A" is a pyridyl, a thienyl, or a furanyl. In other embodiments, the ring system denoted by "A" is a pyrazolyl, imidazolyl, pyrrolyl, triazolyl or thiadiazolyl.

In certain embodiments of the presently disclosed compounds of structural formula (1-I), the

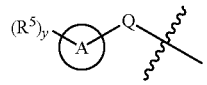

moiety is

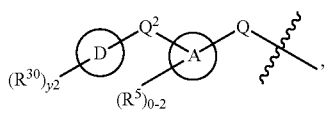

in which the ring system denoted by "A" is aryl or heteroaryl, the ring system denoted by "D" is cycloalkyl, heterocycloalkyl, aryl or heteroaryl; $Q^2$ is —S(O)$_2$—, —O— or —(C$_0$-C$_3$ alkyl)- in which each carbon of the (C$_0$-C$_3$ alkyl) is optionally and independently substituted with one or two R$^{16}$, defined as described above with respect to Q; $y^2$ is 0, 1 or 2; and each R$^{30}$ is independently selected from is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, $Q^2$ has at most one R$^{16}$ or an oxo substituted thereon. $Q^2$ can be, for example, an unsubstituted —(C$_0$-C$_3$ alkyl)-. In other embodiments, $Q^2$ is a (C$_1$-C$_3$ alkyl) having as its only substitution a single oxo group. For example, in certain embodiments, $Q^2$ is —CH—; a single bond; —S(O)$_2$—; —O—; —C(O)—; or —CH(CH$_3$)—. In certain embodiments, at least one R$^{30}$ is halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ or —C(O)—Hca in which the Hca contains a ring nitrogen atom through which it is bound to the —C(O)—, and in which no alkyl, haloalkyl or heterocycloalkyl is substituted by an aryl, heteroaryl, cycloalkyl or heterocycloalkyl-containing group. In certain embodiments, at least one R$^5$ is —SO$_2$(C$_1$-C$_6$ alkyl), —SO$_2$(C$_1$-C$_6$ haloalkyl), —SO$_2$N(C$_0$-C$_6$ alkyl)(C$_0$-C$_6$ alkyl), —SO$_2$(C$_3$-C$_8$ cycloalkyl), —SO$_2$(C$_3$-C$_8$ heterocycloalkyl), such as —SO$_2$Me, —SO$_2$Et, —SO$_2$Pr, —SO$_2$Bu, —SO$_2$cyclopropyl, —SO$_2$morphylinyl, SO$_2$pyrrolidinyl, SO$_2$NHEt, SO$_2$pyridyl or —SO$_2$phenyl. The number of substituents on the ring system denoted by "D", $y^2$, is 0, 1, or 2. For example, in some embodiments, $y^2$ is 0 or 1, for example 1. In other embodiments, $y^2$ is 0. R$^{30}$ can be further defined as described above with respect to R$^5$. In certain embodiments, the ring system denoted by "D" is cyclopropyl, morpholinyl, pyrazolyl, pyridyl, imidazolyl or phenyl.

In certain embodiments, at least one R$^5$ is —SO$_2$(C$_1$-C$_6$ alkyl), —SO$_2$(C$_1$-C$_6$ haloalkyl), —SO$_2$N(C$_0$-C$_6$ alkyl)$_2$, —SO$_2$(C$_3$-C$_8$ cycloalkyl), —SO$_2$(C$_3$-C$_8$ heterocycloalkyl), such as —SO$_2$Me, —SO$_2$Et, —SO$_2$Pr, —SO$_2$Bu, —SO$_2$cyclopropyl, —SO$_2$morphylinyl, SO$_2$pyrrolidinyl, SO$_2$NHEt, SO$_2$pyridyl or —SO$_2$phenyl.

In one embodiment of the compounds of structural formula (5-I), the compound has structural formula (5-II):

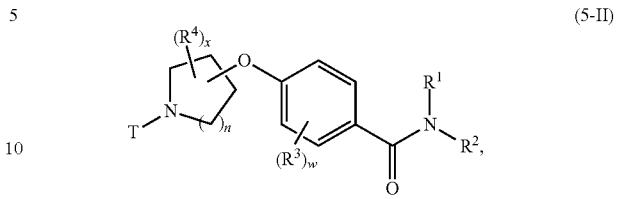

(5-II)

in which the variables are defined as described above with reference to formula (5-I).

In another embodiment of the compounds of structural formula (5-I), the compound has the structural formula (5-III):

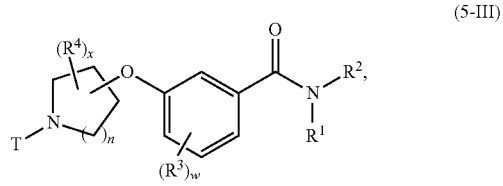

(5-III)

in which the variables are defined as described above with reference to formula (5-I).

For example, compounds according to certain embodiments of the compounds of structural formula (5-I) have structural formula (5-IV):

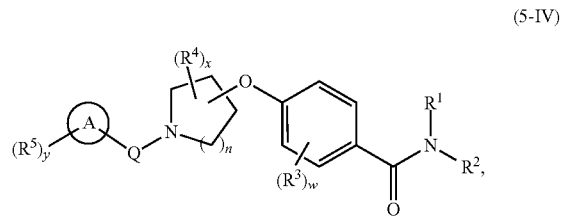

(5-IV)

in which the variables are defined as described above with reference to formula (5-I).

In other embodiments of the compounds of structural formula (5-I) have structural formula (5-V):

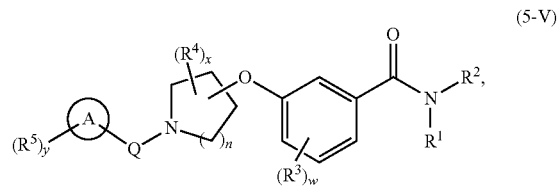

(5-V)

in which the variables are defined as described above with reference to formula (5-I).

In certain embodiments of the compounds of structural formula (5-I), n is 1 or 2. For example, in one embodiment of the compounds of structural formula (5-I), n is 2.

In one embodiment of the compounds of structural formula (5-I), the compound has structural formula (5-VI):

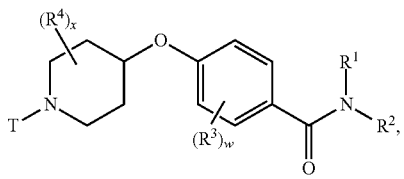

(5-VI)

in which the variables are defined as described above with reference to formula (5-I).

In another embodiment, the compound has the structural formula (5-VII):

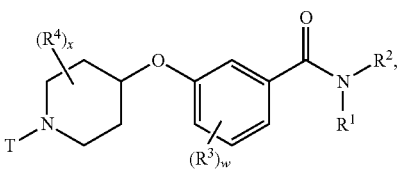

(5-VII)

in which the variables are defined as described above with reference to formula (5-I).

For example, compounds of structural formula (5-I) can have structural formula (5-VIII):

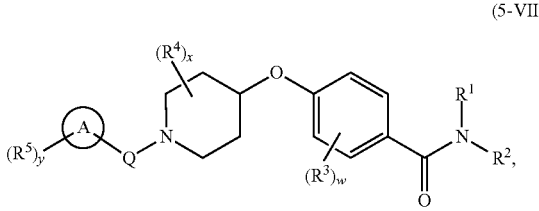

(5-VIII)

in which the variables are defined as described above with reference to formula (5-I).

In other embodiments of the compounds of structural formula (5-I), compounds of have structural formula (5-IX):

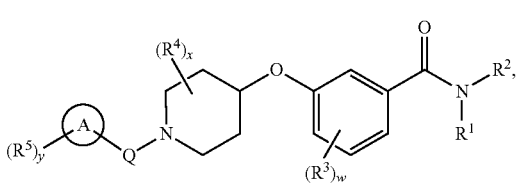

(5-IX)

in which the variables are defined as described above with reference to formula (5-I).

According to structural formula (5-I), $R^1$ is —H and $R^2$ is -Hca. In certain embodiments of the compounds of structural formula (5-I), $R^2$ is substituted with ($C_0$-$C_3$ alkyl)-Het or ($C_0$-$C_3$ alkyl)-Ar. In one embodiment of the compounds of structural formula (5-I), $R^2$ is -(optionally-substituted azetidinyl), -(optionally-substituted pyrrolidinyl), -(optionally-substituted piperidinyl), or -(optionally-substituted azepanyl). For example, $R^2$ can be -(optionally substituted piperidinyl) or -(optionally substituted pyrrolidinyl).

In one embodiment of the compounds of structural formula (5-I), $R^1$ is —H and $R^2$ is -(optionally-substituted azetidin-3-yl), -(optionally substituted piperidin-4-yl), -(optionally substituted pyrrolidin-3-yl) or -(optionally-substituted azepan-4-yl). For example, in one embodiment of the compounds of structural formula (5-I), $R^2$ is -(optionally substituted piperidin-4-yl). In another embodiment of the compounds of structural formula (5-I), $R^2$ is -(optionally substituted pyrrolidin-3-yl).

In certain embodiments of of the compounds of structural formula (5-I), the azetidinyl, pyrrolidinyl, piperidinyl and azepanyl $R^2$ moieties described above are substituted at their 1-positions. For example, in one embodiment of the compounds of structural formula (5-I), $R^2$ is substituted at its 1-position with ($C_0$-$C_3$ alkyl)-Ar or ($C_0$-$C_3$ alkyl)-Het. For example, in one embodiment of the compounds of structural formula (5-I), the azetidinyl, pyrrolidinyl, piperidinyl or azepanyl $R^2$ moiety is substituted at its 1-position with an optionally substituted benzyl or an optionally substituted phenyl. In another embodiment of the compounds of structural formula (5-I), the azetidinyl, pyrrolidinyl, piperidinyl or azepanyl $R^2$ moiety is substituted at its 1-position with a benzyl substituted with an electron withdrawing group; or with a pyridinylmethyl substituted with an electron withdrawing group. For example, the benzyl or pyridinylmethyl can be substituted with an electron withdrawing group selected from the group consisting of halo, cyano, —($C_1$-$C_4$ fluoroalkyl), —O—($C_1$-$C_4$ fluoroalkyl), acyl groups, carboxylate groups, carboxamide groups, cyano groups, sulfonate groups, and nitro groups. In other embodiments of the compounds of structural formula (5-I), the the azetidinyl, pyrrolidinyl, piperidinyl or azepanyl $R^2$ moiety is substituted at its 1-position with an unsubstituted benzyl or an unsubstituted phenyl.

In other embodiments of the compounds of structural formula (5-I), the azetidinyl, pyrrolidinyl, piperidinyl or azepanyl $R^2$ moiety is substituted at its 1-position with an optionally substituted pyridinylmethyl, an optionally substituted furanylmethyl or an optionally substituted thienylmethyl. For example, the the azetidinyl, pyrrolidinyl, piperidinyl or azepanyl $R^2$ moiety can be substituted with an unsubstituted pyridinylmethyl, an unsubstituted furanylmethyl, or an unsubstituted thienylmethyl.

In other embodiments of the compounds of structural formula (5-I), the azetidinyl, pyrrolidinyl, piperidinyl or azepanyl $R^2$ moiety is substituted at its 1-position with —CO—O—($C_0$-$C_6$ alkyl), —CO-Het, —CO—Ar or —$SO_2$—($C_0$-$C_6$ alkyl).

According to structural formula (5-I), the number of substituents on the central phenyl ring, w, is 0, 1, 2, 3 or 4. For example, in one embodiment of the compounds of structural formula (5-I), w is 0, 1 or 2. In another embodiment of the compounds of structural formula (5-I), w is 0. In other embodiments of the compounds of structural formula (5-I), w is at least 1, and at least one $R^3$ is selected from the group consisting of halo, cyano, —($C_1$-$C_4$ fluoroalkyl), —O—($C_1$-$C_4$ fluoroalkyl), acyl, carboxylate, carboxamide and nitro.

In certain embodiments of the compounds of structural formula (5-I), $R^3$ is selected from the group consisting of halo, cyano, —($C_1$-$C_4$ fluoroalkyl), —O—($C_1$-$C_4$ fluoroalkyl), acyl, carboxylate, carboxamide and nitro. $R^3$ can be, for example, —Cl or —F. For example, compounds according to these embodiments can have structural formula (5-X):

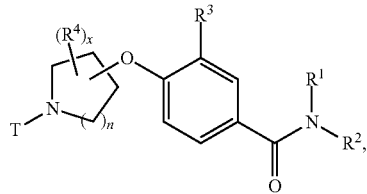
(5-X)

in which the remaining variables are defined as described above with reference to formula (5-I).

Certain other compounds according to these embodiments have structural formula (5-XI):

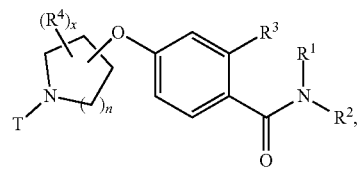
(5-XI)

in which the remaining variables are defined as described above with reference to formula (5-I).

According to the compounds of structural formula (5-I), the number of substituents on the ethereal azacycloalkane ring, x, is 0, 1, 2, 3 or 4. In one embodiment of the compounds of structural formula (5-I), x is 0, 1, 2 or 3. For example, x can be 0, or can be 1 or 2.

Compounds according to one embodiment of the compounds of structural formula (5-I) have the structural formula (5-XII):

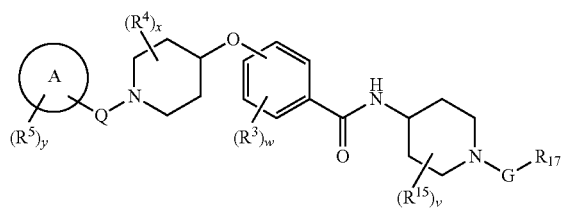
(5-XII)

in which Q and G are each independently a bond, —CH$_2$—, —C(H)(R$^{16}$)— or —C(R$^{16}$)$_2$—; v is 0, 1, 2, 3 or 4; each R$^{15}$ is independently selected from —(C$_1$-C$_6$ alkyl), —(C$_1$-C$_6$ fluoroalkyl), —(C$_0$-C$_6$ alkyl)-Ar; —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-S(O)$_{0-2}$R$^{10}$, -halogen, —NO$_2$ and —CN, and two R$^{15}$ on the same carbon optionally combine to form oxo; R$^{17}$ is Het or Ar, and all other variables are defined as described above with reference to formula (5-I). R$^{17}$ can be, for example, an optionally substituted phenyl, an optionally-substituted pyridyl, an optionally substituted pyrazolyl, an optionally substituted imidazolyl, an optionally substituted pyrrolyl, an optionally substituted triazolyl or an optionally substituted thiadiazolyl. In one embodiment of the compounds of structural formula (5-XII), v is 0. In one embodiment of the compounds of structural formula (5-XII), Q is a single bond. In another embodiment, G is —CH$_2$— or —CO—. For example, in one embodiment of the compounds of structural formula (5-XII), Q is a single bond and G is —CH$_2$— or —CO—. The ethereal linkage of the piperidine to the benzamide can be at any aryl carbon. For example, the ether can be substituted at the 3-position or the 4-position of the benzamide. In one embodiment of the compounds of structural formula (5-I), two R$^{15}$s combine to form an oxo, which can be bound, for example, at a position alpha to the piperidine nitrogen. As described above, in certain embodiments of the compounds of structural formula (5-I), the ring system denoted by "A" is aryl or heteroaryl. In one embodiment of the compounds of structural formula (5-I), the ring system denoted by "A" is substituted with one or more electron-withdrawing groups. In another embodiment, R$^{17}$ is substituted with one or more electron-withdrawing groups.

One aspect of the disclosure provides compounds of structural formulae (5-I)-(5-XII) in which x is 1 and R$^4$ is F. For example, in certain embodiments of compounds having structural formulae (5-I)-(5-XII), the

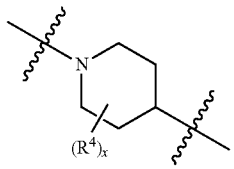

moiety has the structure

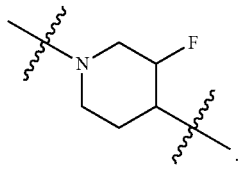 [SMILES: *C1CCN(*)CC1F]

For example, in certain embodiments, the compound has structural formula (5-XIII):

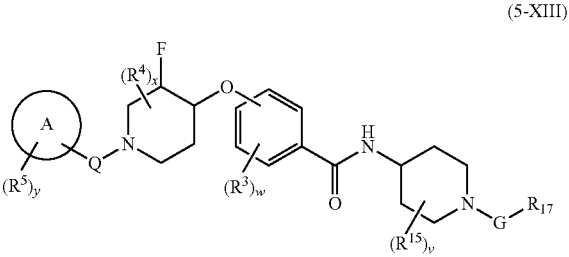
(5-XIII)

in which the variables are as described above with reference to any of structural formulae (5-I)-(5-XII). In one embodiment, the compound has the structural formula (5-XIII) or (5-XIV):

(5-XIII)

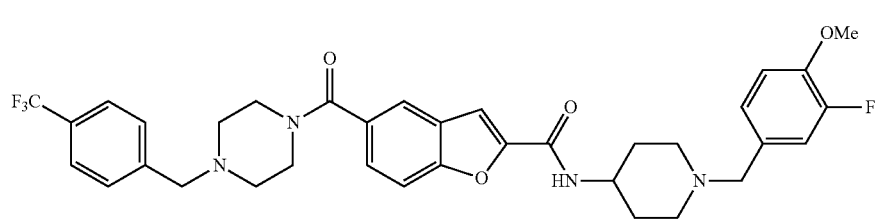

(5-XIV)

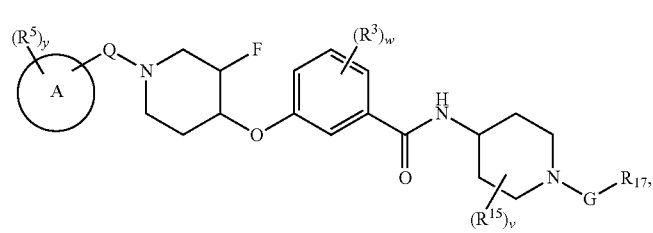

in which all variables are as described above with reference to any of structural formulae (5-I)-(5-XII).

In one embodiment, the 3-fluoro and the 4-substituent are substituted in a cis manner on the piperidine. In other embodiments, the 3-fluoro and the 4-substituent are substituted in a trans manner on the piperidine. For example in one embodiment, the piperidine moiety has the structure

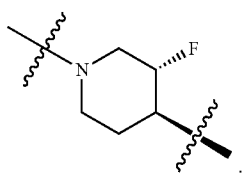

In certain particular embodiments, the compound has structural formula (5-XV) or (5-XVI):

(5-XV)

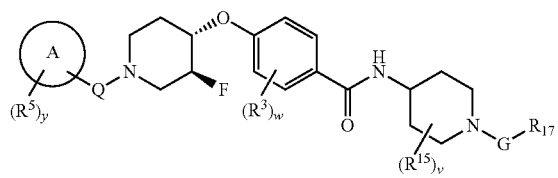

-continued (5-XVI)

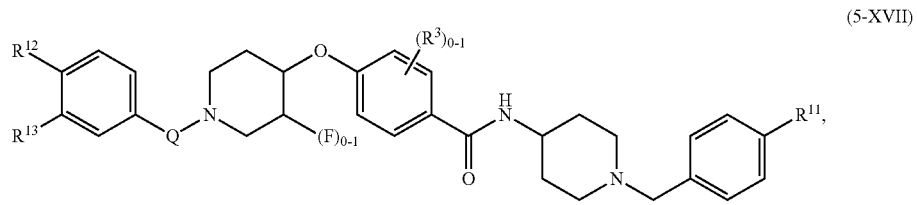

in which the variables are as described above with reference to structural formula (5-XII). according to structural formulae (5-XV) and (5-XVI) can be provided in racemic form, in enantiomerically enriched form, or in substantially enantiomerically pure form.

Compounds according to certain embodiments have the structural formula (5-XVII):

(5-XVII)

in which Q is —CH$_2$— or a single bond; R$^3$ is halo; R$^{11}$ is H, halo, cyano, or a carboxylate; and R$^{12}$ and R$^{13}$ are independently H, trifluoromethyl, trifluoromethoxy, halo or cyano.

Compounds according to other embodiments have structural formula (5-XVIII):

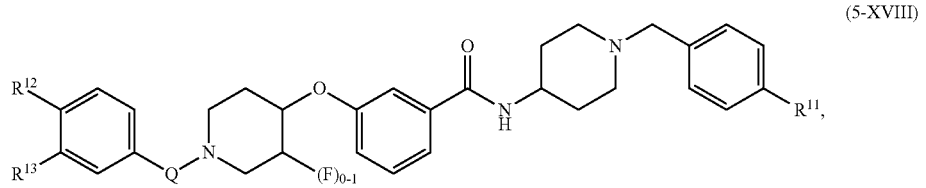

(5-XVIII)

in which Q is —CH$_2$— or a single bond; R$^{11}$ is H, halo, cyano, or a carboxylate; and R$^{12}$ and R$^{13}$ are independently H, trifluoromethyl, trifluoromethoxy, halo or cyano.

Compounds according to certain embodiments have the structural formula (5-XIX):

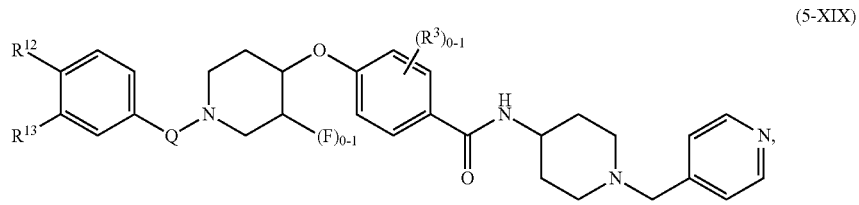

(5-XIX)

in which Q is —CH$_2$— or a single bond; R$^3$ is halo; and R$^{12}$ and R$^{13}$ are independently H, trifluoromethyl, trifluoromethoxy, halo or cyano.

Compounds according to other embodiments have the structural formula (5-XX):

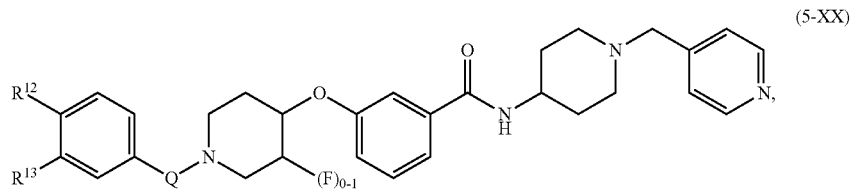

(5-XX)

in which Q is —CH$_2$— or a single bond; and R$^{12}$ and R$^{13}$ are independently H, trifluoromethyl, trifluoromethoxy, halo or cyano.

Another aspect of the disclosure provides compounds having structural formula (5-XXI):

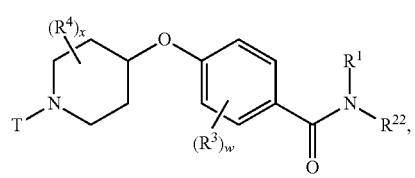

(5-XXI)

or a pharmaceutically acceptable salt, solvate, hydrate, or N-oxide thereof (or a solvate or hydrate thereof), wherein R$^1$ and R$^{22}$, together with the nitrogen to which they are attached, form an optionally substituted monocyclic heterocycloalkyl; or R$^1$ is H and R$^{22}$ is selected from —(C$_2$-C$_4$ alkyl)-(morpholin-4-yl) and —(C$_2$-C$_4$ alkyl)-NH—C(O)O—(C$_1$-C$_6$ alkyl), and all other variables are as described above with reference to structural formulae (5-I)-(5-XX).

In one embodiment of the compounds according to structural formula (5-XXI), R$^1$ and R$^{22}$, together with the nitrogen to which they are attached, form an optionally substituted monocyclic heterocycloalkyl. The heterocycloalkyl can be, for example, piperidine or piperazine. In certain embodiments of the compounds of structural formula (5-XXI), the heterocycloalkyl is piperazine substituted at its 4-position with —C(O)O—(C$_1$-C$_6$ alkyl), —(C$_0$-C$_4$)-Het or —(C$_0$-C$_4$)—Ar. For example, the piperazine may be substituted at its 4-position with —C(O)O-tBu, -optionally-substituted pyridinylmethyl, optionally-substituted phenyl or optionally-substituted pyridinyl.

In another embodiment of the compounds according to structural formula (5-XXI), R$^1$ is H and R$^{22}$ is selected from —(C$_2$-C$_4$ alkyl)-(morpholin-4-yl) and —(C$_2$-C$_4$ alkyl)-NH—C(O)O—(C$_1$-C$_6$ alkyl). However, in certain embodiments, when w and x are zero, y is 1 and R$^5$ is methoxy substituted para to the benzyl methylene, R$^{22}$ is not —(C$_2$-C$_4$ alkyl)-(morpholin-4-yl); and when w is 1, x and y are zero, and R$^3$ is methoxy substituted ortho to the ether oxygen, R$^{22}$ is not —(C$_2$-C$_4$ alkyl)-(morpholin-4-yl). In certain embodiments, R$^{22}$ is —(C$_2$-C$_4$ alkyl)-NH—C(O)O—(C$_1$-C$_6$ alkyl). The C$_1$-C$_6$ alkyl can be, for example, a tert-butyl group.

Examples of compounds according to structural formulae (5-I) and (5-XXI) include those listed in Table 5. These compounds can be made, for example using a procedure analogous to those described in U.S. Patent Application Publications nos. 2009/0163511, 2009/0170829, 2009/0186894 and 2009/0275609, and in U.S. patent application Ser. Nos. 12/695,861 and 13/194,810, each of which is hereby incorporated by reference in its entirety.

TABLE 5

| Cpd | Name | Structure |
| --- | --- | --- |
| 5-1 | N-(1-benzylpiperidin-4-yl)-3-chloro-4-(1-(4-methoxybenzyl)piperidin-4-yloxy)benzamide | 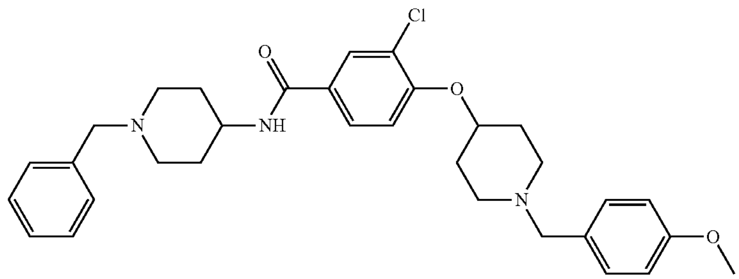 [SMILES: COc1ccc(CN2CCC(Oc3ccc(C(=O)NC4CCN(Cc5ccccc5)CC4)cc3Cl)CC2)cc1] |
| 5-2 | N-(1-benzylpiperidin-4-yl)-4-(1-benzylpiperidin-4-yloxy)-3-methoxybenzamide | 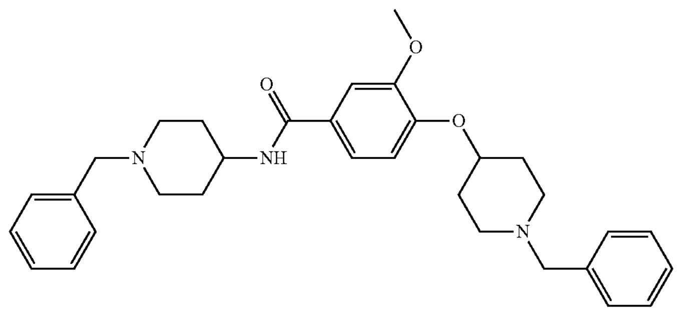 [SMILES: COc1cc(C(=O)NC2CCN(Cc3ccccc3)CC2)ccc1OC1CCN(Cc2ccccc2)CC1] |
| 5-3 | N-(1-benzylpiperidin-4-yl)-4-(1-(furan-2-ylmethyl)piperidin-4-yloxy)benzamide | 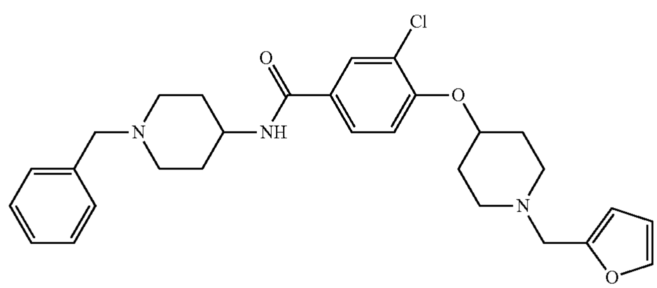 [SMILES: O=C(NC1CCN(Cc2ccccc2)CC1)c1ccc(OC2CCN(Cc3ccco3)CC2)c(Cl)c1] |
| 5-4 | N-(1-benzylpiperidin-4-yl)-4-(1-((1-methyl-1H-imidazol-5-yl)methyl)piperidin-4-yloxy)benzamide | 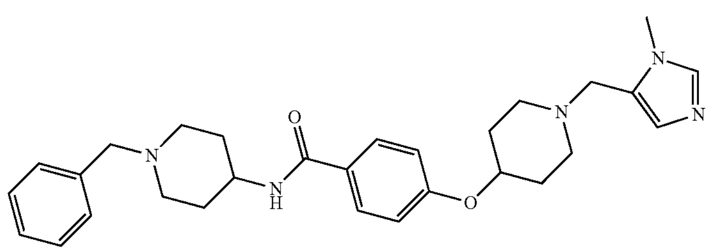 [SMILES: Cn1cncc1CN1CCC(Oc2ccc(C(=O)NC3CCN(Cc4ccccc4)CC3)cc2)CC1] |
| 5-5 | N-(1-benzylpiperidin-4-yl)-3-chloro-4-(1-((1-methyl-1H-imidazol-5-yl)methyl)piperidin-4-yloxy)benzamide | 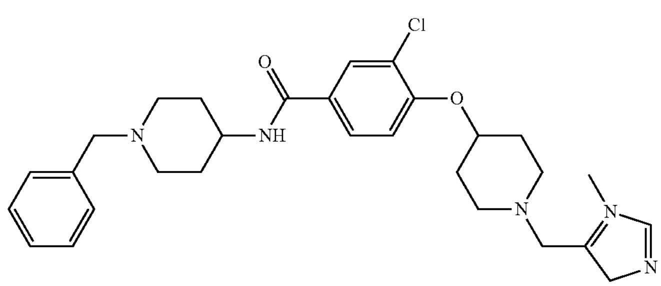 |

TABLE 5-continued

| Cpd | Name | Structure |
|---|---|---|
| 5-6 | N-(1-benzylpiperidin-4-yl)-3-chloro-4-(1-(pyridin-4-ylmethyl)piperidin-4-yloxy)benzamide | 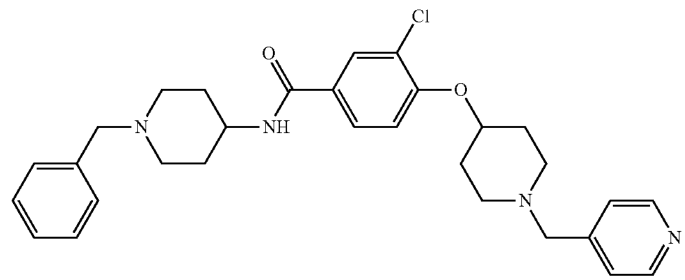 |
| 5-7 | N-(1-benzylpiperidin-4-yl)-3-methoxy-4-(1-(3-phenylpropyl)piperidin-4-yloxy)benzamide | 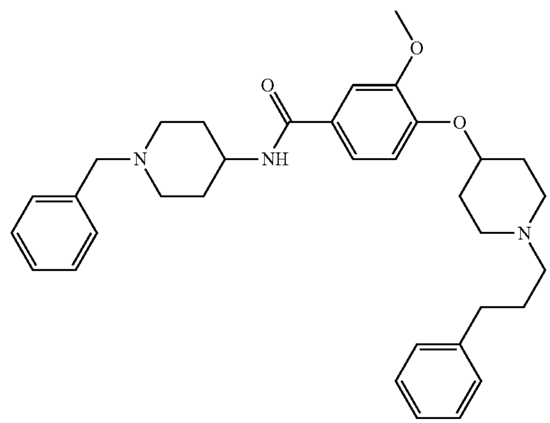 [SMILES: COc1cc(C(=O)NC2CCN(Cc3ccccc3)CC2)ccc1OC1CCN(CCCc2ccccc2)CC1] |
| 5-8 | N-(1-benzylpiperidin-4-yl)-3-methoxy-4-(1-(thiophen-2-yl)piperidin-4-yloxy)benzamide | 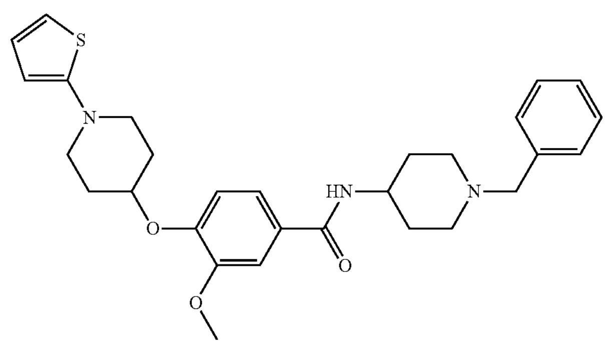 [SMILES: COc1cc(C(=O)NC2CCN(Cc3ccccc3)CC2)ccc1OC1CCN(c2cccs2)CC1] |
| 5-9 | N-(1-benzylpiperidin-4-yl)-3-methoxy-4-(1-(methylsulfonyl)piperidin-4-yloxy)benzamide | 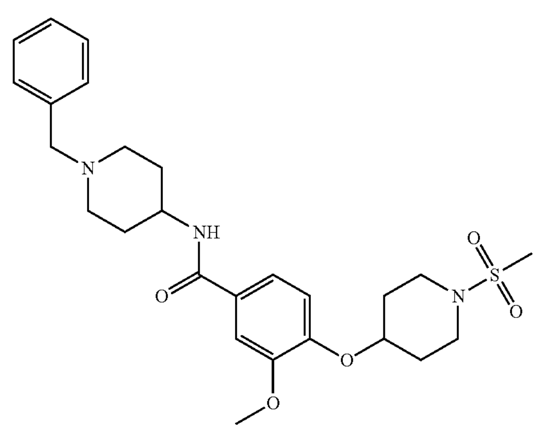 [SMILES: COc1cc(C(=O)NC2CCN(Cc3ccccc3)CC2)ccc1OC1CCN(S(C)(=O)=O)CC1] |

TABLE 5-continued

| Cpd | Name | Structure |
|---|---|---|
| 5-10 | N-(1-benzylpiperidin-4-yl)-3-chloro-4-(1-(thiophen-2-yl)piperidin-4-yloxy)benzamide | 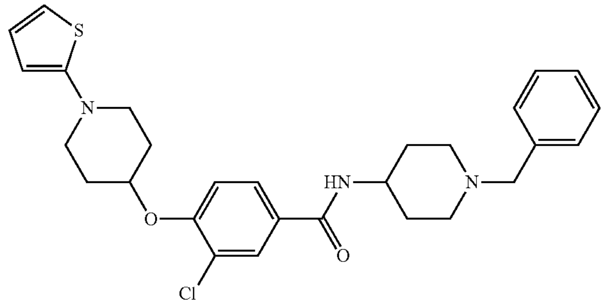 [SMILES: O=C(NC1CCN(Cc2ccccc2)CC1)c1ccc(OC2CCN(c3cccs3)CC2)c(Cl)c1] |
| 5-11 | N-(1-benzylpiperidin-4-yl)-3-chloro-4-(1-(furan-2-yl)piperidin-4-yloxy)benzamide | 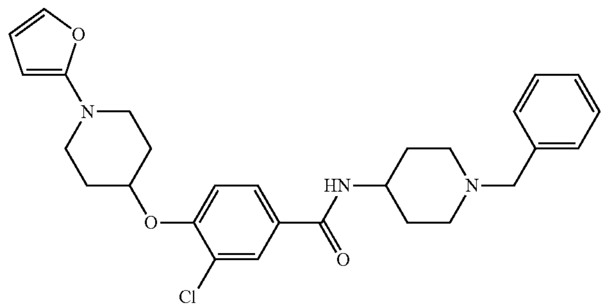 [SMILES: O=C(NC1CCN(Cc2ccccc2)CC1)c1ccc(OC2CCN(c3ccco3)CC2)c(Cl)c1] |
| 5-12 | N-(1-benzylpiperidin-4-yl)-3-methoxy-4-(1-(furan-2-yl)piperidin-4-yloxy)benzamide | 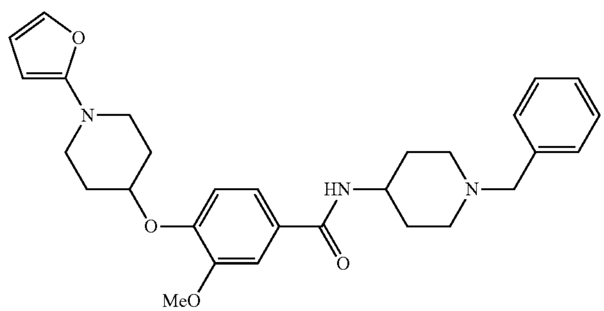 [SMILES: COc1cc(C(=O)NC2CCN(Cc3ccccc3)CC2)ccc1OC1CCN(c2ccco2)CC1] |
| 5-13 | N-(1-benzylpiperidin-4-yl)-3-(1-benzylpiperidin-4-yloxy)benzamide | 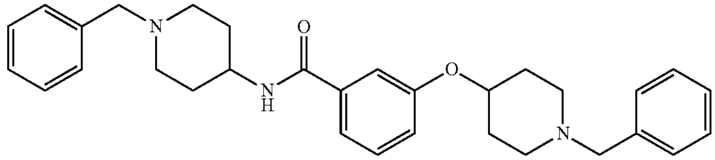 [SMILES: O=C(NC1CCN(Cc2ccccc2)CC1)c1cccc(OC2CCN(Cc3ccccc3)CC2)c1] |
| 5-14 | N-(1-benzylpiperidin-4-yl)-4-(1-benzylpiperidin-4-yloxy)-3-chlorobenzamide | 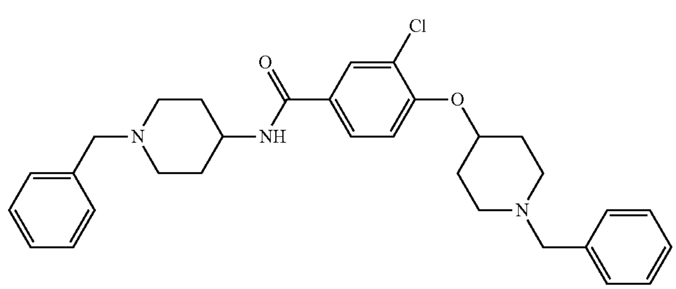 [SMILES: O=C(NC1CCN(Cc2ccccc2)CC1)c1ccc(OC2CCN(Cc3ccccc3)CC2)c(Cl)c1] |

TABLE 5-continued

| Cpd | Name | Structure |
|---|---|---|
| 5-15 | 1-benzylpiperidin-4-yl)-3-chloro-4-(1-((2,3-dihydrobenzo[b][1,4]dioxin-6-yl)methyl)piperidin-4-yloxy)benzamide | 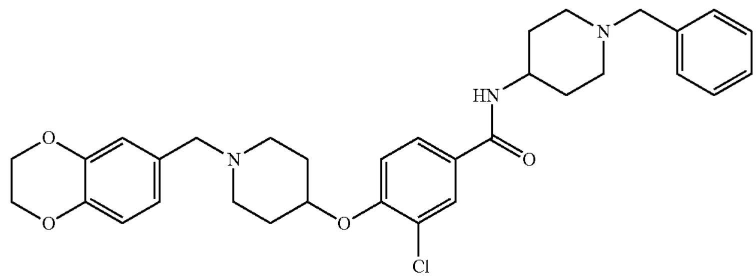 [SMILES: O=C(NC1CCN(Cc2ccccc2)CC1)c1ccc(OC2CCN(Cc3ccc4c(c3)OCCO4)CC2)c(Cl)c1] |
| 5-16 | N-(1-benzylpiperidin-4-yl)-4-(1-(4-tert-butylbenzyl)piperidin-4-yloxy)-3-chlorobenzamide | 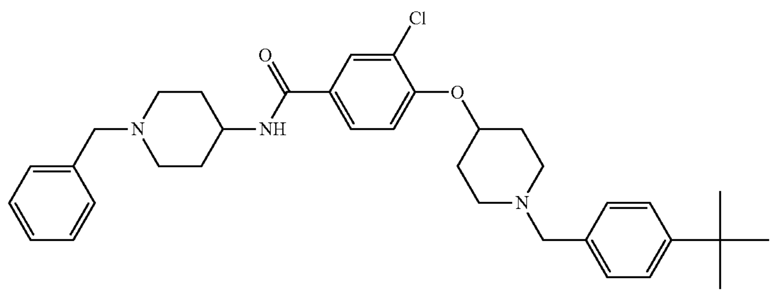 [SMILES: CC(C)(C)c1ccc(CN2CCC(Oc3ccc(C(=O)NC4CCN(Cc5ccccc5)CC4)cc3Cl)CC2)cc1] |
| 5-17 | N-(1-benzylpiperidin-4-yl)-3-chloro-4-(1-(4-(trifluoromethyl)phenyl(piperidin-4-yloxy)benzamide | 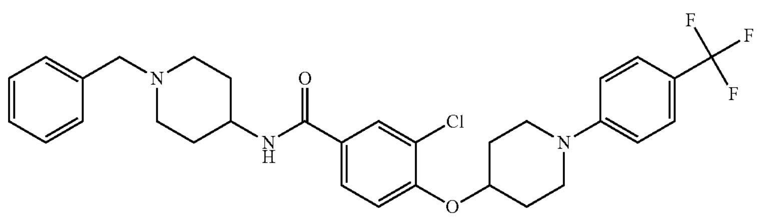 [SMILES: O=C(NC1CCN(Cc2ccccc2)CC1)c1ccc(OC2CCN(c3ccc(C(F)(F)F)cc3)CC2)c(Cl)c1] |
| 5-18 | N-(1-benzylpiperidin-4-yl)-3-chloro-4-(1-(4-(trifluoromethyl)benzoyl)piperidin-4-yloxy)benzamide | 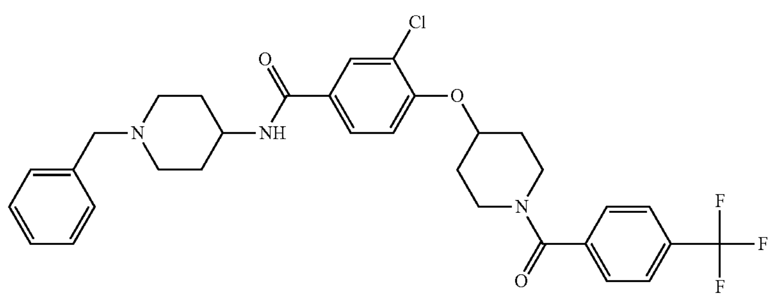 [SMILES: O=C(NC1CCN(Cc2ccccc2)CC1)c1ccc(OC2CCN(C(=O)c3ccc(C(F)(F)F)cc3)CC2)c(Cl)c1] |
| 5-19 | N-(1-benzylpiperidin-4-yl)-3-chloro-4-(1-(4-fluorobenzyl)piperidin-4-yloxy)benzamide | 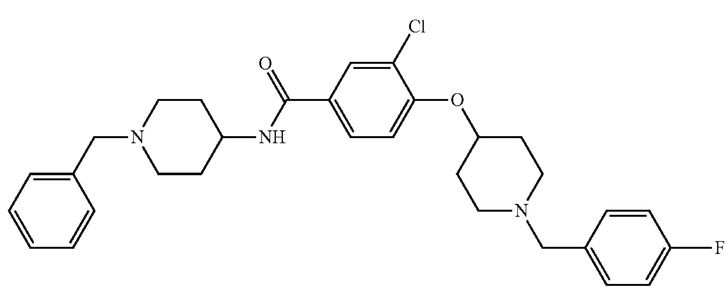 [SMILES: O=C(NC1CCN(Cc2ccccc2)CC1)c1ccc(OC2CCN(Cc3ccc(F)cc3)CC2)c(Cl)c1] |

TABLE 5-continued

| Cpd | Name | Structure |
|---|---|---|
| 5-20 | N-(1-benzylpiperidin-4-yl)-3-fluoro-4-(1-(4-tert-butylbenzyl)piperidin-4-yloxy)benzamide | 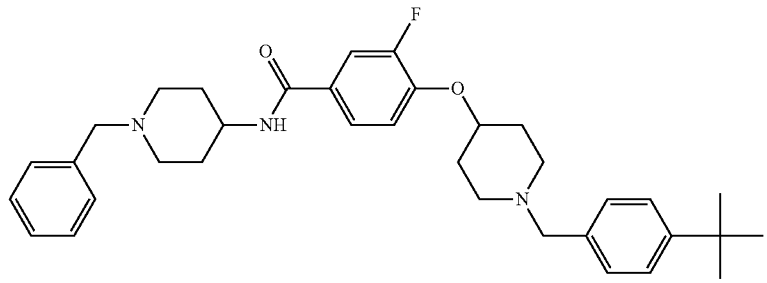 [SMILES: CC(C)(C)c1ccc(CN2CCC(Oc3ccc(C(=O)NC4CCN(Cc5ccccc5)CC4)cc3F)CC2)cc1] |
| 5-21 | N-(1-benzylpiperidin-4-yl)-3-fluoro-4-(1-(1-phenylethyl)piperidin-4-yloxy)benzamide | 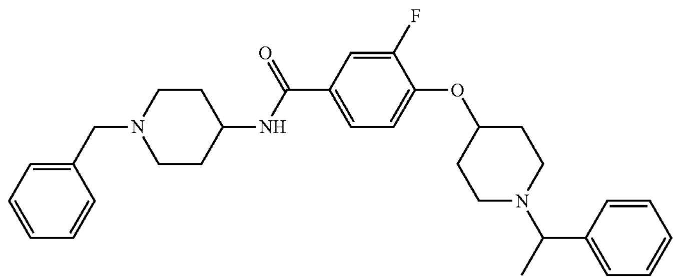 [SMILES: CC(c1ccccc1)N1CCC(Oc2ccc(C(=O)NC3CCN(Cc4ccccc4)CC3)cc2F)CC1] |
| 5-22 | N-(1-benzylpiperidin-4-yl)-3-chloro-4-(1-(4-fluorobenzoyl)piperidin-4-yloxy)benzamide | 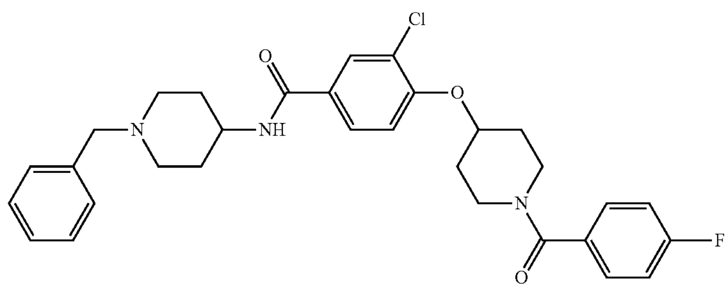 [SMILES: O=C(NC1CCN(Cc2ccccc2)CC1)c1ccc(OC2CCN(C(=O)c3ccc(F)cc3)CC2)c(Cl)c1] |
| 5-23 | N-(1-benzylpiperidin-4-yl)-3-fluoro-4-(1-(4-(trifluoromethyl)phenyl)piperidin-4-yloxy)benzamide | 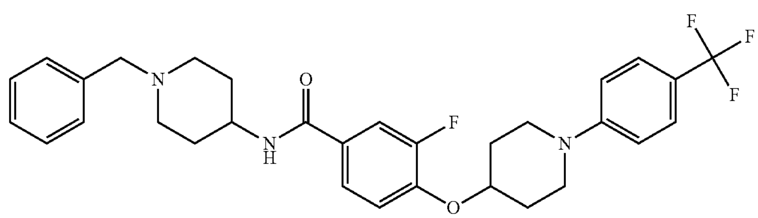 [SMILES: O=C(NC1CCN(Cc2ccccc2)CC1)c1ccc(OC2CCN(c3ccc(C(F)(F)F)cc3)CC2)c(F)c1] |
| 5-24 | N-(1-benzylpiperidin-4-yl)-3-chloro-4-(1-(2-(trifluoromethyl)benzyl)piperidin-4-yloxy)benzamide | 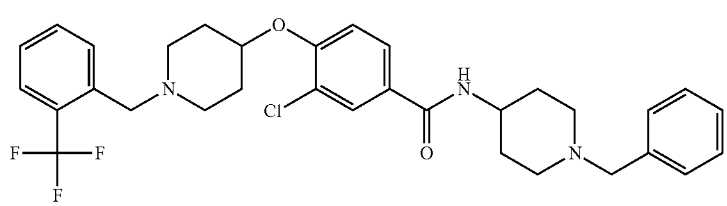 [SMILES: O=C(NC1CCN(Cc2ccccc2)CC1)c1ccc(OC2CCN(Cc3ccccc3C(F)(F)F)CC2)c(Cl)c1] |
| 5-25 | 3-fluoro-N-(1-phenylpiperidin-4-yl)-4-(1-(4-(trifluoromethyl)phenyl)piperidin-4-yloxy)benzamide | 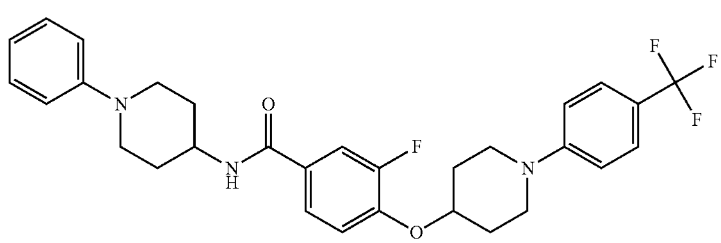 [SMILES: O=C(NC1CCN(c2ccccc2)CC1)c1ccc(OC2CCN(c3ccc(C(F)(F)F)cc3)CC2)c(F)c1] |

TABLE 5-continued

| Cpd | Name | Structure |
|---|---|---|
| 5-26 | tert-butyl 4-(3-fluoro-4-(1-(4-(trifluoromethyl)phenyl)piperidin-4-yloxy)benzamido)piperidine-1-carboxylate | 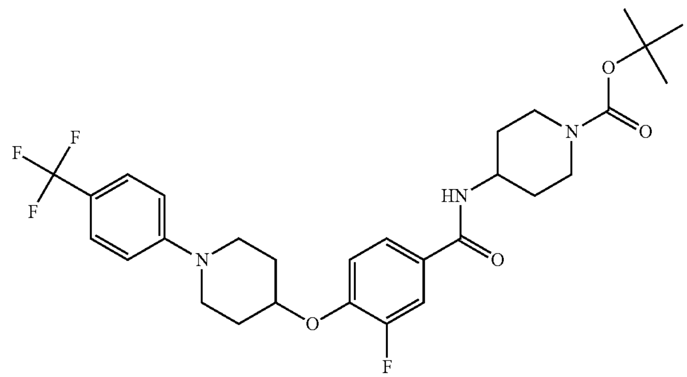 [SMILES: CC(C)(C)OC(=O)N1CCC(NC(=O)c2ccc(OC3CCN(c4ccc(C(F)(F)F)cc4)CC3)c(F)c2)CC1] |
| 5-27 | 3-fluoro-N-(1-(4-fluorobenzyl)piperidin-4-yl)-4-(1-(4-(trifluoromethyl)phenyl)piperidin-4-yloxy)benzamide | 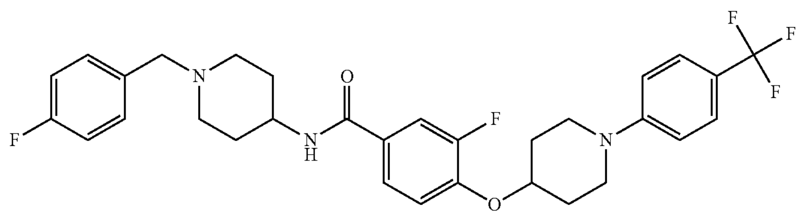 [SMILES: O=C(NC1CCN(Cc2ccc(F)cc2)CC1)c1ccc(OC2CCN(c3ccc(C(F)(F)F)cc3)CC2)c(F)c1] |
| 5-28 | 3-fluoro-N-(1-(pyridin-4-ylmethyl)piperidin-4-yl)-4-(1-(4-(trifluoromethyl)phenyl)piperidin-4-yloxy)benzamide | 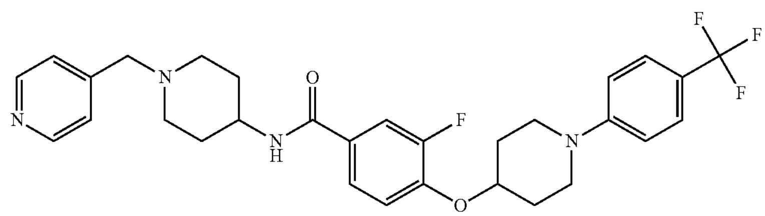 [SMILES: O=C(NC1CCN(Cc2ccncc2)CC1)c1ccc(OC2CCN(c3ccc(C(F)(F)F)cc3)CC2)c(F)c1] |
| 5-29 | 3-fluoro-N-(1-(pyridin-3-ylmethyl)piperidin-4-yl)-4-(1-(4-(trifluoromethyl)phenyl)piperidin-4-yloxy)benzamide | 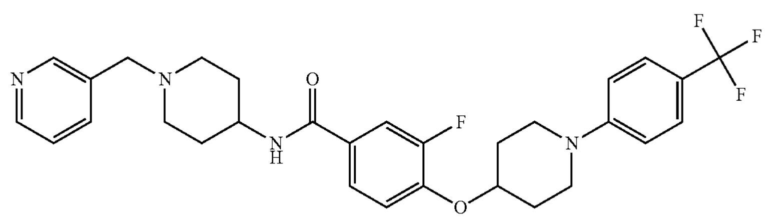 [SMILES: O=C(NC1CCN(Cc2cccnc2)CC1)c1ccc(OC2CCN(c3ccc(C(F)(F)F)cc3)CC2)c(F)c1] |
| 5-30 | 3-fluoro-N-(1-pivaloylpiperidin-4-yl)-4-(1-(4-(trifluoromethyl)phenyl)piperidin-4-yloxy)benzamide | 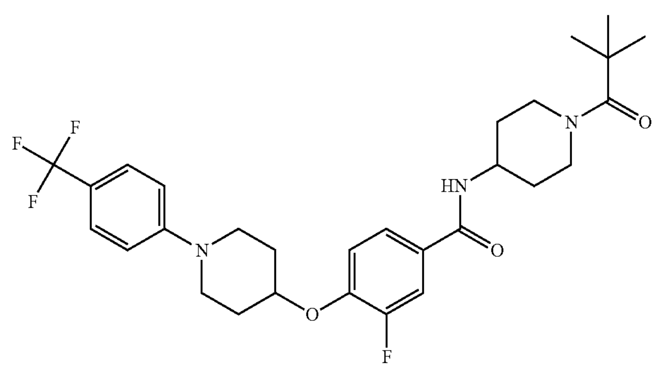 [SMILES: CC(C)(C)C(=O)N1CCC(NC(=O)c2ccc(OC3CCN(c4ccc(C(F)(F)F)cc4)CC3)c(F)c2)CC1] |
| 5-31 | 3-fluoro-N-(1-(4-fluorobenzoyl)piperidin-4-yl)-4-(1-(4-(trifluoromethyl)phenyl)piperidin-4-yloxy)benzamide | 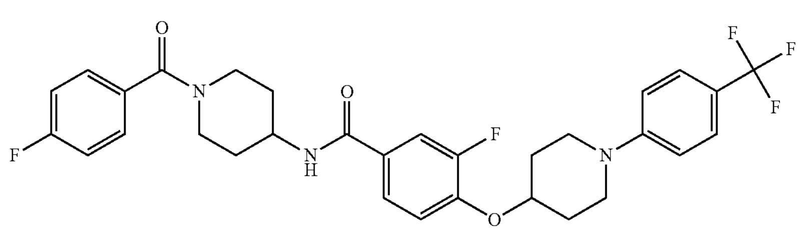 [SMILES: O=C(NC1CCN(C(=O)c2ccc(F)cc2)CC1)c1ccc(OC2CCN(c3ccc(C(F)(F)F)cc3)CC2)c(F)c1] |

TABLE 5-continued

| Cpd | Name | Structure |
|---|---|---|
| 5-32 | 3-fluoro-N-(1-(pyridin-2-ylmethyl)piperidin-4-yl)-4-(1-(4-(trifluoromethyl)phenyl)piperidin-4-yloxy)benzamide | 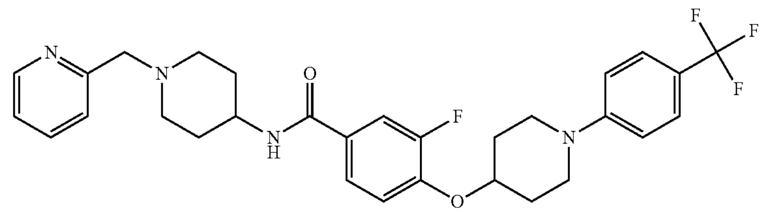 [SMILES: O=C(NC1CCN(Cc2ccccn2)CC1)c1ccc(OC2CCN(c3ccc(C(F)(F)F)cc3)CC2)c(F)c1] |
| 5-33 | methyl 4-((4-(3-fluoro-4-(1-(4-(trifluoromethyl)phenyl)piperidin-4-yloxy)benzamido)piperidin-1-yl)methyl)benzoate | 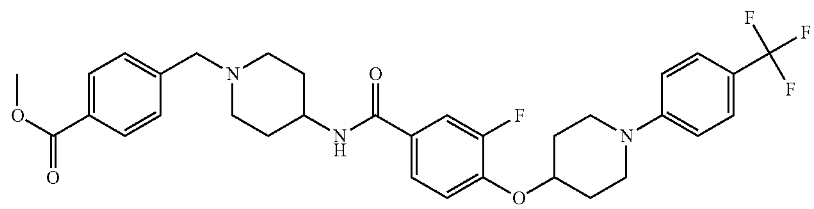 [SMILES: COC(=O)c1ccc(CN2CCC(NC(=O)c3ccc(OC4CCN(c5ccc(C(F)(F)F)cc5)CC4)c(F)c3)CC2)cc1] |
| 5-34 | 3-fluoro-N-(1-(isopropylsulfonyl)piperidin-4-yl)-4-(1-(4-(trifluoromethyl)phenyl)piperidin-4-yloxy)benzamide | 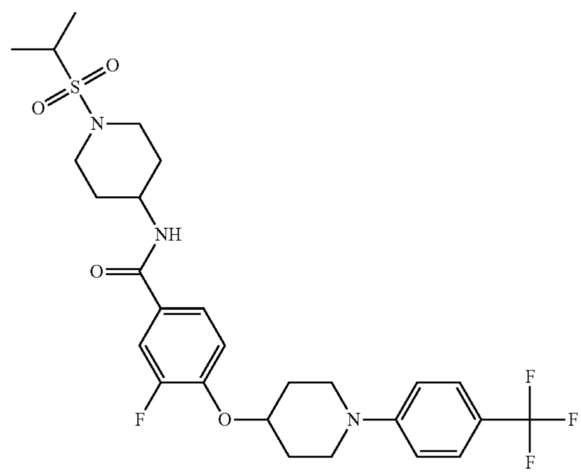 [SMILES: CC(C)S(=O)(=O)N1CCC(NC(=O)c2ccc(OC3CCN(c4ccc(C(F)(F)F)cc4)CC3)c(F)c2)CC1] |
| 5-35 | 4-((4-(3-fluoro-4-(1-(4-(trifluoromethyl)phenyl)piperidin-4-yloxy)benzamido)piperidin-1-yl)methyl)benzoic acid | 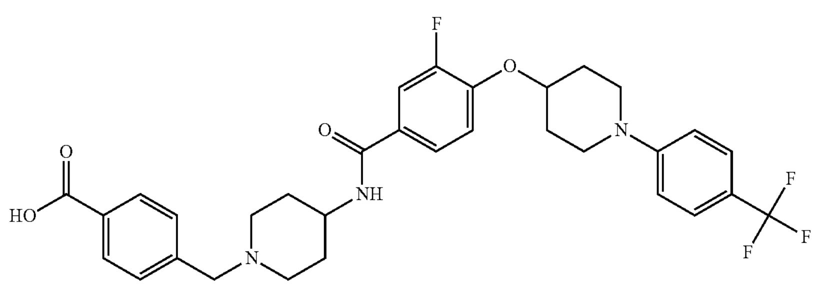 [SMILES: O=C(O)c1ccc(CN2CCC(NC(=O)c3ccc(OC4CCN(c5ccc(C(F)(F)F)cc5)CC4)c(F)c3)CC2)cc1] |
| 5-36 | 4-(1-(4-tert-butylbenzyl)piperidin-4-yloxy)-3-fluoro-N-(1-phenylpiperidin-4-yl)benzamide | 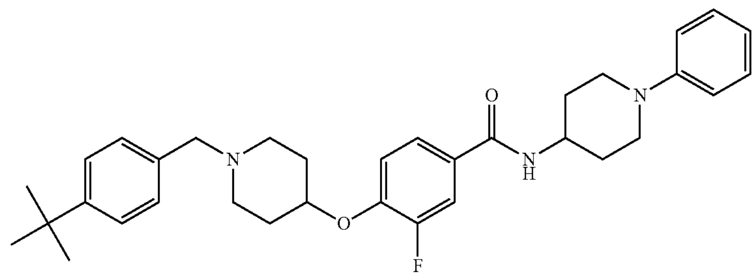 [SMILES: CC(C)(C)c1ccc(CN2CCC(Oc3ccc(C(=O)NC4CCN(c5ccccc5)CC4)cc3F)CC2)cc1] |

//

TABLE 5-continued

| Cpd | Name | Structure |
|---|---|---|
| 5-37 | N-(1-benzylpiperidin-4-yl)-3-fluoro-4-(1-(pyridin-4-ylmethyl)piperidin-4-yloxy)benzamide | 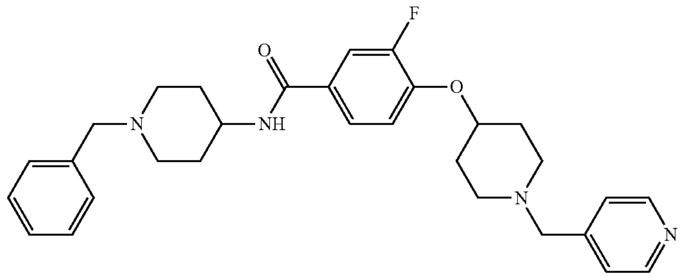 [SMILES: O=C(NC1CCN(Cc2ccccc2)CC1)c1ccc(OC2CCN(Cc3ccncc3)CC2)c(F)c1] |
| 5-38 | N-(1-benzylpiperidin-4-yl)-3-fluoro-4-(1-(pyridin-3-ylmethyl)piperidin-4-yloxy)benzamide | 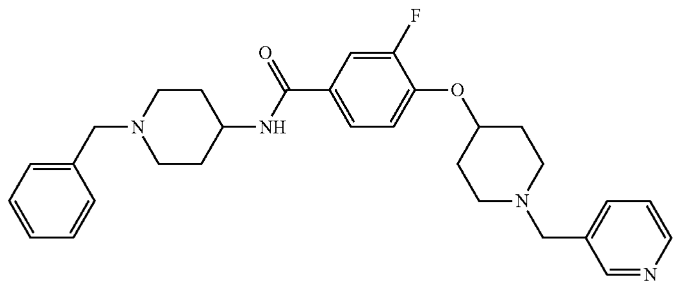 [SMILES: O=C(NC1CCN(Cc2ccccc2)CC1)c1ccc(OC2CCN(Cc3cccnc3)CC2)c(F)c1] |
| 5-39 | N-(1-benzylpiperidin-4-yl)-3-fluoro-4-(1-(pyridin-2-ylmethyl)piperidin-4-yloxy)benzamide | 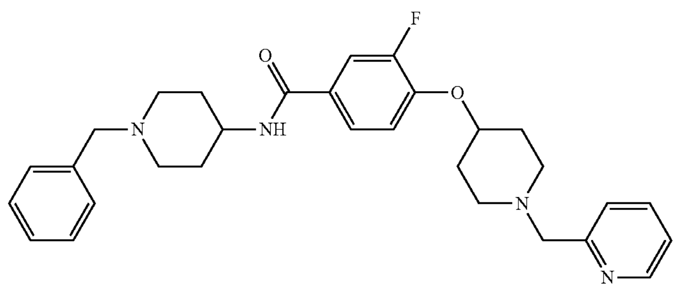 [SMILES: O=C(NC1CCN(Cc2ccccc2)CC1)c1ccc(OC2CCN(Cc3ccccn3)CC2)c(F)c1] |
| 5-40 | 3-fluoro-N-(1-isonicotinoylpiperidin-4-yl)-4-(1-(4-(trifluoromethyl)phenyl)piperidin-4-yloxy)benzamide | 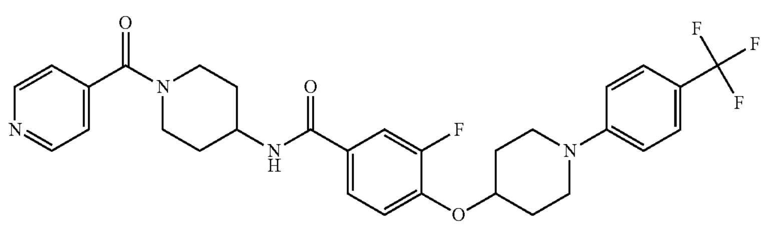 [SMILES: O=C(NC1CCN(C(=O)c2ccncc2)CC1)c1ccc(OC2CCN(c3ccc(C(F)(F)F)cc3)CC2)c(F)c1] |
| 5-41 | N-(1-benzylpiperidin-4-yl)-4-(1-(4-cyanobenzyl)piperidin-4-yloxy)-3-fluorobenzamide | 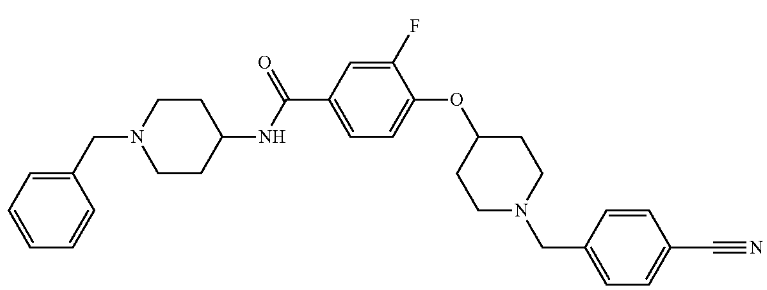 [SMILES: N#Cc1ccc(CN2CCC(Oc3ccc(C(=O)NC4CCN(Cc5ccccc5)CC4)cc3F)CC2)cc1] |

TABLE 5-continued

| Cpd | Name | Structure |
|---|---|---|
| 5-42 | N-(1-benzylpiperidin-4-yl)-3-fluoro-4-(1-(4-methylbenzyl)piperidin-4-yloxy)benzamide | 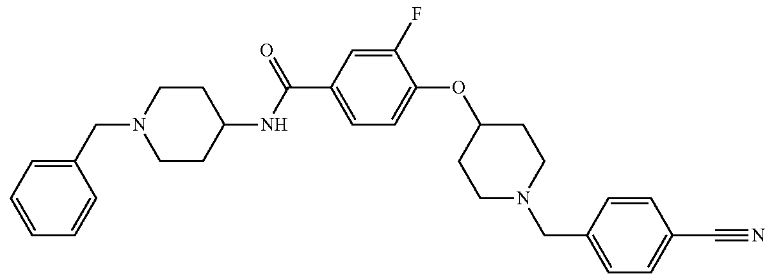 [SMILES: N#Cc1ccc(CN2CCC(Oc3ccc(C(=O)NC4CCN(Cc5ccccc5)CC4)cc3F)CC2)cc1] |
| 5-43 | N-(1-(4-cyanobenzyl)piperidin-4-yl)-3-fluoro-4-(1-(4-(trifluoromethyl)phenyl)piperidin-4-yloxy)benzamide | 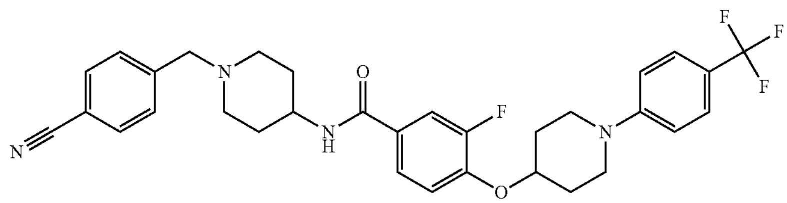 [SMILES: N#Cc1ccc(CN2CCC(NC(=O)c3ccc(OC4CCN(c5ccc(C(F)(F)F)cc5)CC4)c(F)c3)CC2)cc1] |
| 5-44 | 4-(1-(4-cyanophenyl)piperidin-4-yloxy)-3-fluoro-N-(1-(pyridin-4-ylmethyl)piperidin-4-yl)benzamide | 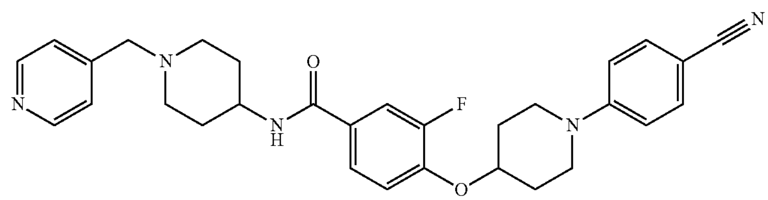 [SMILES: N#Cc1ccc(N2CCC(Oc3ccc(C(=O)NC4CCN(Cc5ccncc5)CC4)cc3F)CC2)cc1] |
| 5-45 | N-(1-(4-cyanobenzyl)piperidin-4-yl)-4-(1-(4-cyanophenyl)piperidin-4-yloxy)-3-fluorobenzamide | 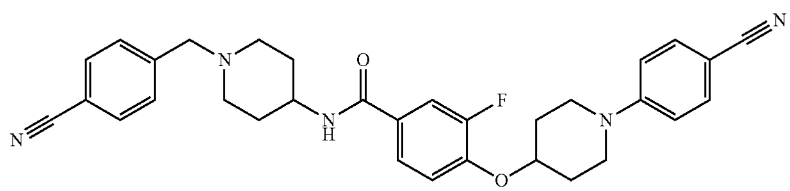 [SMILES: N#Cc1ccc(CN2CCC(NC(=O)c3ccc(OC4CCN(c5ccc(C#N)cc5)CC4)c(F)c3)CC2)cc1] |
| 5-46 | N-(1-benzylpiperidin-4-yl)-3-(1-(4-(trifluoromethyl)phenyl)piperidin-4-yloxy)benzamide | 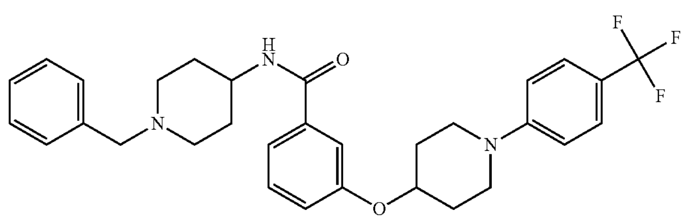 [SMILES: O=C(NC1CCN(Cc2ccccc2)CC1)c1cccc(OC2CCN(c3ccc(C(F)(F)F)cc3)CC2)c1] |
| 5-47 | N-(1-benzylpiperidin-4-yl)-2-chloro-4-(1-(4-(trifluoromethyl)phenyl)piperidin-4-yloxy)benzamide | 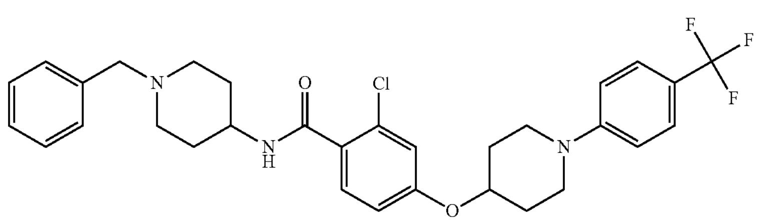 [SMILES: O=C(NC1CCN(Cc2ccccc2)CC1)c1ccc(OC2CCN(c3ccc(C(F)(F)F)cc3)CC2)cc1Cl] |
| 5-48 | N-(1-benzylpiperidin-4-yl)-3-(1-(4-cyanophenyl)piperidin-4-yloxy)benzamide | 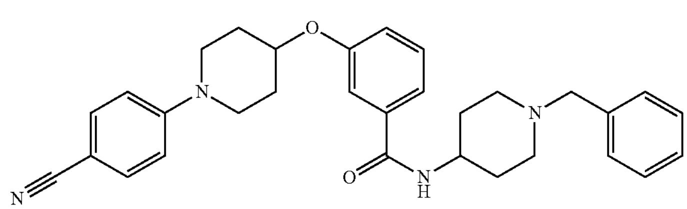 [SMILES: N#Cc1ccc(N2CCC(Oc3cccc(C(=O)NC4CCN(Cc5ccccc5)CC4)c3)CC2)cc1] |

TABLE 5-continued

| Cpd | Name | Structure |
|---|---|---|
| 5-49 | N-(1-benzylpiperidin-4-yl)-2-chloro-4-(1-(4-cyanophenyl)piperidin-4-yloxy)benzamide | 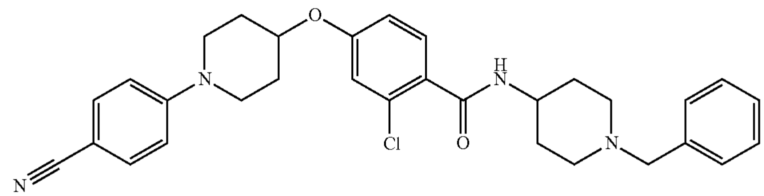 [SMILES: N#Cc1ccc(N2CCC(Oc3ccc(C(=O)NC4CCN(Cc5ccccc5)CC4)c(Cl)c3)CC2)cc1] |
| 5-50 | N-(1-benzylpiperidin-4-yl)-3-(1-(4-cyanobenzyl)piperidin-4-yloxy)benzamide | 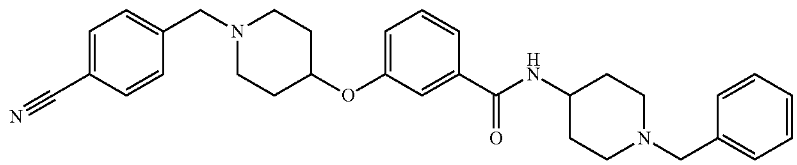 [SMILES: N#Cc1ccc(CN2CCC(Oc3cccc(C(=O)NC4CCN(Cc5ccccc5)CC4)c3)CC2)cc1] |
| 5-51 | N-(1-benzylpiperidin-4-yl)-2-chloro-4-(1-(4-cyanobenzyl)piperidin-4-yloxy)benzamide | 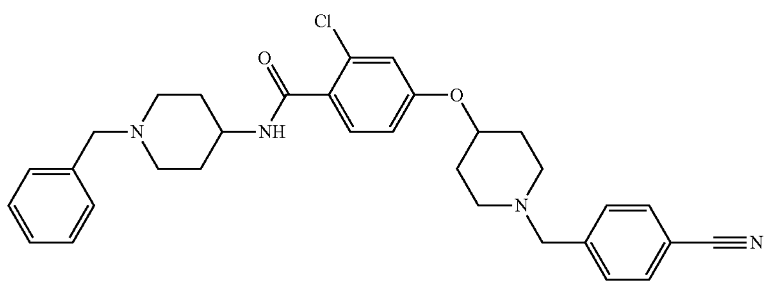 [SMILES: N#Cc1ccc(CN2CCC(Oc3ccc(C(=O)NC4CCN(Cc5ccccc5)CC4)c(Cl)c3)CC2)cc1] |
| 5-52 | N-(1-benzylpiperidin-4-yl)-3-(1-(4-(trifluoromethyl)benzyl)piperidin-4-yloxy)benzamide | 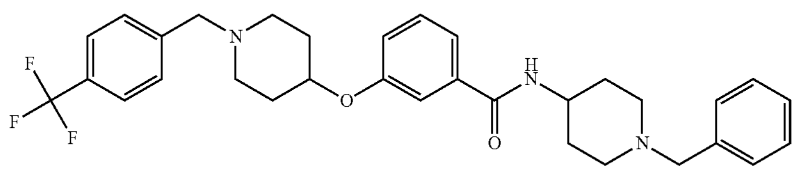 [SMILES: O=C(NC1CCN(Cc2ccccc2)CC1)c1cccc(OC2CCN(Cc3ccc(C(F)(F)F)cc3)CC2)c1] |
| 5-53 | N-(1-benzylpiperidin-4-yl)-3-(1-(pyridin-4-yl)piperidin-4-yloxy)benzamide | 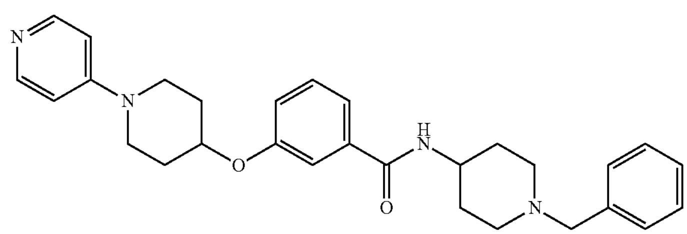 [SMILES: O=C(NC1CCN(Cc2ccccc2)CC1)c1cccc(OC2CCN(c3ccncc3)CC2)c1] |
| 5-54 | N-(1-benzylpiperidin-4-yl)-3-chloro-4-(1-(4-(trifluoromethoxy)benzyl)piperidin-4-yloxy)benzamide | 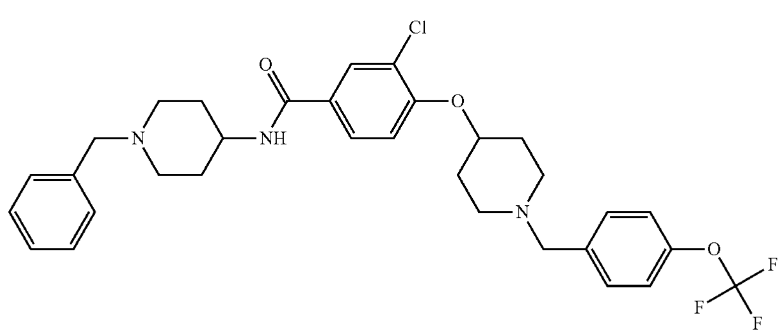 [SMILES: O=C(NC1CCN(Cc2ccccc2)CC1)c1ccc(OC2CCN(Cc3ccc(OC(F)(F)F)cc3)CC2)c(Cl)c1] |

TABLE 5-continued

| Cpd | Name | Structure |
|---|---|---|
| 5-55 | N-(1-benzylpiperidin-4-yl)-3-fluoro-4-(1-(4-(trifluoromethyl)benzyl)piperidin-4-yloxy)benzamide | 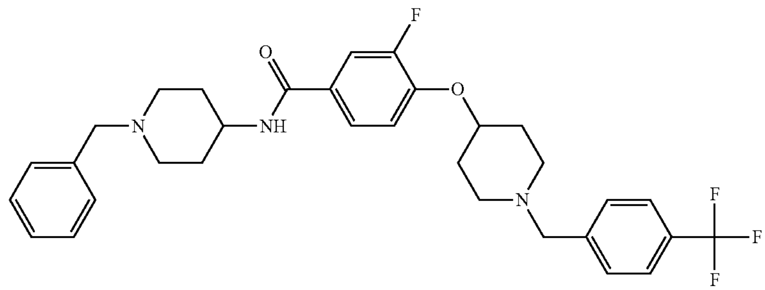 |
| 5-56 | N-(1-benzylpiperidin-4-yl)-3-chloro-4-(1-(4-(trifluoromethyl)benzyl)piperidin-4-yloxy)benzamide | 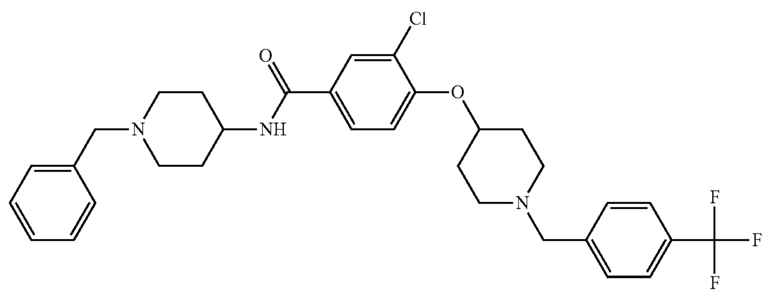 [SMILES: O=C(NC1CCN(Cc2ccccc2)CC1)c1ccc(OC2CCN(Cc3ccc(C(F)(F)F)cc3)CC2)c(F)c1] |
| 5-57 | N-(1-benzylpiperidin-4-yl)-3-fluoro-4-(1-(4-(trifluoromethoxy)benzyl)piperidin-4-yloxy)benzamide | 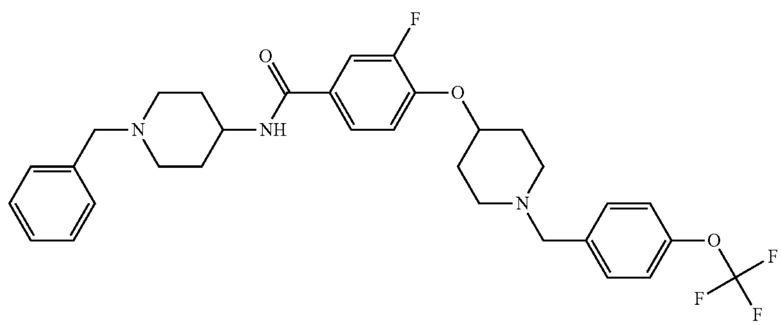 [SMILES: O=C(NC1CCN(Cc2ccccc2)CC1)c1ccc(OC2CCN(Cc3ccc(OC(F)(F)F)cc3)CC2)c(F)c1] |
| 5-58 | 3-chloro-N-(1-methylpiperidin-4-yl)-4-(1-(4-(trifluoromethyl)benzyl)piperidin-4-yloxy)benzamide | 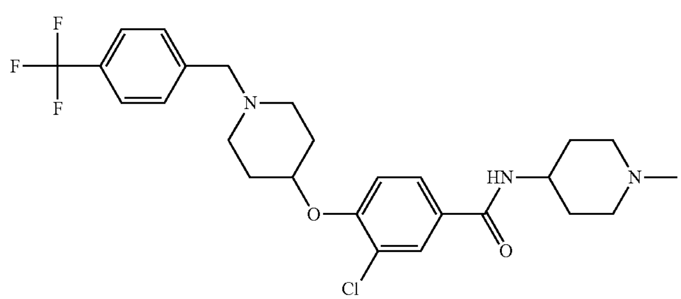 [SMILES: CN1CCC(NC(=O)c2ccc(OC3CCN(Cc4ccc(C(F)(F)F)cc4)CC3)c(Cl)c2)CC1] |
| 5-59 | N-(1-benzylpiperidin-4-yl)-3-fluoro-4-(1-(3-(trifluoromethyl)benzyl)piperidin-4-yloxy)benzamide | 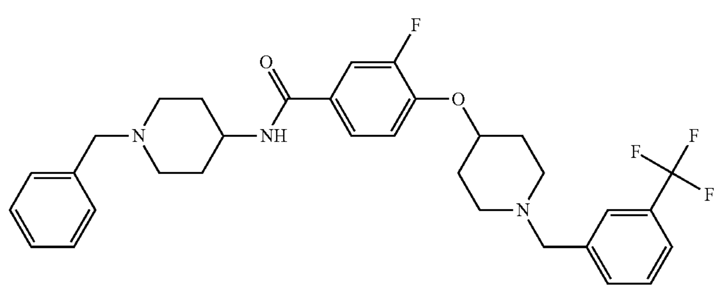 [SMILES: O=C(NC1CCN(Cc2ccccc2)CC1)c1ccc(OC2CCN(Cc3cccc(C(F)(F)F)c3)CC2)c(F)c1] |

TABLE 5-continued

| Cpd | Name | Structure |
|---|---|---|
| 5-60 | N-(1-benzylpiperidin-4-yl)-3-chloro-4-(1-(3-(trifluoromethyl)benzyl)piperidin-4-yloxy)benzamide | 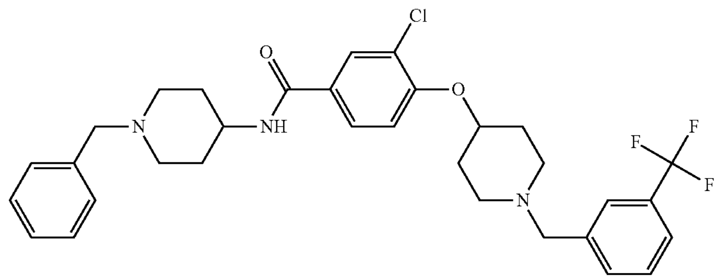 [SMILES: O=C(NC1CCN(Cc2ccccc2)CC1)c1ccc(OC2CCN(Cc3cccc(C(F)(F)F)c3)CC2)c(Cl)c1] |
| 5-61 | N-(1-benzylpiperidin-4-yl)-3-fluoro-4-(1-(4-fluorobenzyl)piperidin-4-yloxy)benzamide | 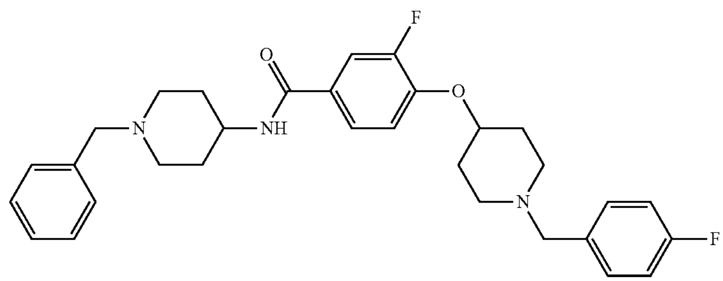 [SMILES: O=C(NC1CCN(Cc2ccccc2)CC1)c1ccc(OC2CCN(Cc3ccc(F)cc3)CC2)c(F)c1] |
| 5-62 | N-(1-benzylpiperidin-4-yl)-3,5-dichloro-4-(1-(3-(trifluoromethyl)benzyl)piperidin-4-yloxy)benzamide | 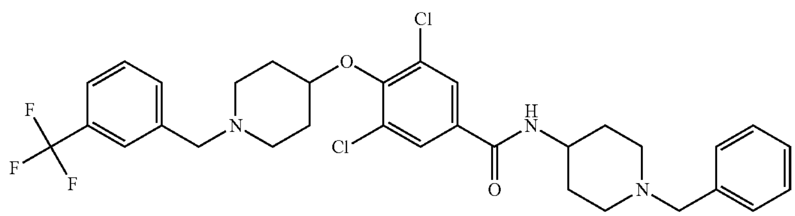 [SMILES: O=C(NC1CCN(Cc2ccccc2)CC1)c1cc(Cl)c(OC2CCN(Cc3cccc(C(F)(F)F)c3)CC2)c(Cl)c1] |
| 5-63 | N-(1-benzylpiperidin-4-yl)-4-(1-(4-(trifluoromethoxy)benzyl)piperidin-4-yloxy)benzamide | 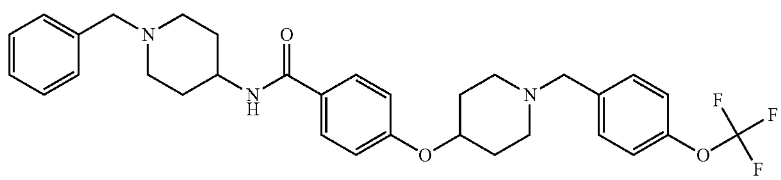 [SMILES: O=C(NC1CCN(Cc2ccccc2)CC1)c1ccc(OC2CCN(Cc3ccc(OC(F)(F)F)cc3)CC2)cc1] |
| 5-64 | N-(1-benzylpiperidin-4-yl)-4-(1-(4-chlorobenzyl)piperidin-4-yloxy)-3-fluorobenzamide | 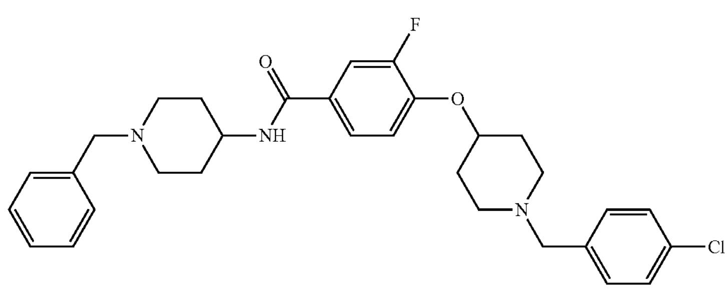 |
| 5-65 | N-(1-benzylpiperidin-4-yl)-3-chloro-4-(1-(4-chlorobenzyl)piperidin-4-yloxy)benzamide | 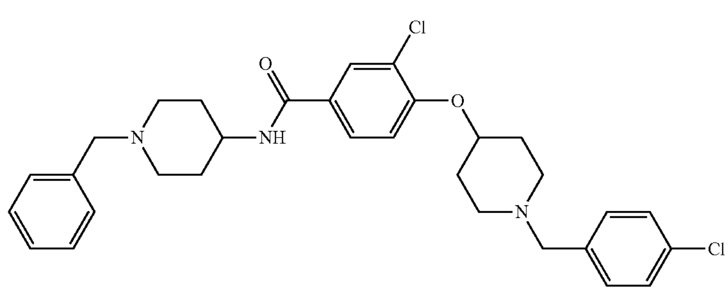 |

TABLE 5-continued

| Cpd | Name | Structure |
|---|---|---|
| 5-66 | 3-chloro-4-(1-(4-chlorobenzyl)piperidin-4-yloxy)-N-(1-(4-fluorobenzyl)piperidin-4-yl)benzamide | 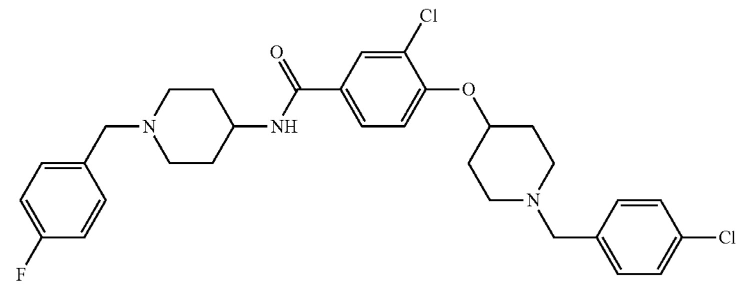 [SMILES: O=C(NC1CCN(Cc2ccc(F)cc2)CC1)c1ccc(OC2CCN(Cc3ccc(Cl)cc3)CC2)c(Cl)c1] |
| 5-67 | N-(1-benzylpiperidin-4-yl)-3-chloro-4-(1-(4-cyanobenzyl)piperidin-4-yloxy)benzamide | 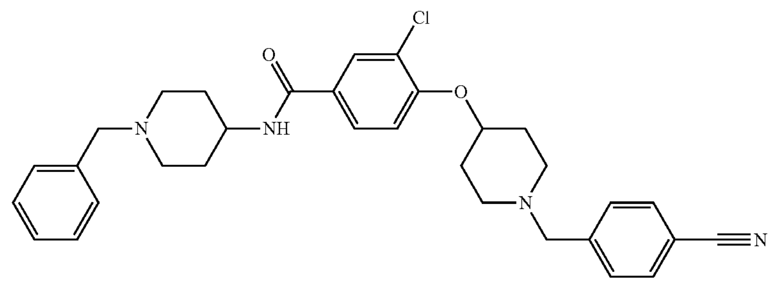 |
| 5-68 | 3-chloro-N-(1-(4-fluorobenzyl)piperidin-4-yl)-4-(1-(4-methylbenzyl)piperidin-4-yloxy)benzamide | 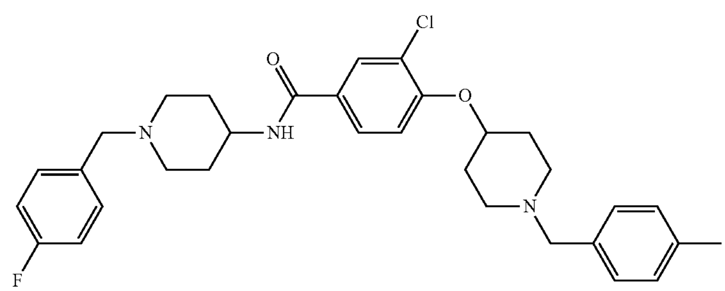 [SMILES: Cc1ccc(CN2CCC(Oc3ccc(C(=O)NC4CCN(Cc5ccc(F)cc5)CC4)cc3Cl)CC2)cc1] |
| 5-69 | N-(1-benzylpiperidin-4-yl)-4-(1-(3,4-difluorobenzyl)piperidin-4-yloxy)-3-fluorobenzamide | 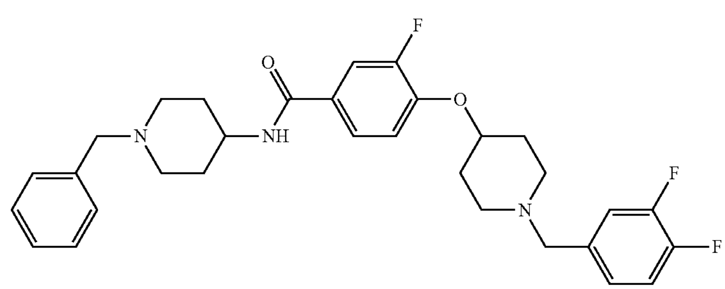 [SMILES: O=C(NC1CCN(Cc2ccccc2)CC1)c1ccc(OC2CCN(Cc3ccc(F)c(F)c3)CC2)c(F)c1] |
| 5-70 | N-(1-(4-chlorobenzyl)piperidin-4-yl)-4-(1-(4-cyanobenzyl)piperidin-4-yloxy)-3-fluorobenzamide | 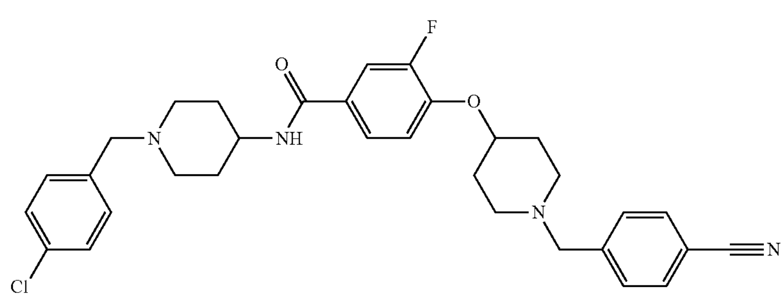 [SMILES: N#Cc1ccc(CN2CCC(Oc3ccc(C(=O)NC4CCN(Cc5ccc(Cl)cc5)CC4)cc3F)CC2)cc1] |

TABLE 5-continued

| Cpd | Name | Structure |
|---|---|---|
| 5-71 | N-(1-(4-chlorobenzyl)piperidin-4-yl)-4-(1-(3,4-difluorobenzyl)piperidin-4-yloxy)-3-fluorobenzamide | 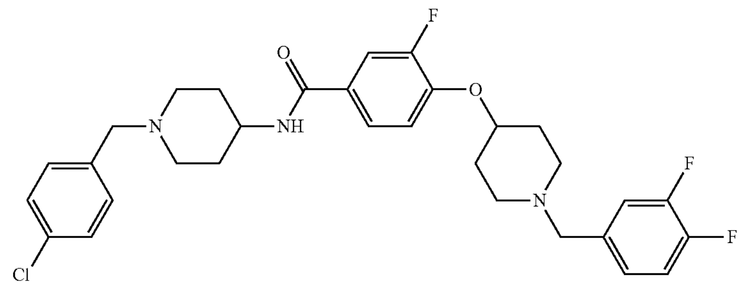 [SMILES: O=C(NC1CCN(Cc2ccc(Cl)cc2)CC1)c1ccc(OC2CCN(Cc3ccc(F)c(F)c3)CC2)c(F)c1] |
| 5-72 | N-(1-(4-chlorobenzyl)piperidin-4-yl)-4-(1-(4-chlorobenzyl)piperidin-4-yloxy)-3-fluorobenzamide | 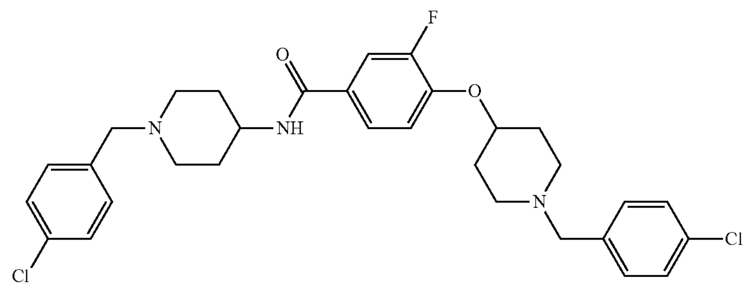 [SMILES: O=C(NC1CCN(Cc2ccc(Cl)cc2)CC1)c1ccc(OC2CCN(Cc3ccc(Cl)cc3)CC2)c(F)c1] |
| 5-73 | N-(1-(4-chlorobenzyl)piperidin-4-yl)-3-fluoro-4-(1-(4-methylbenzyl)piperidin-4-yloxy)benzamide | 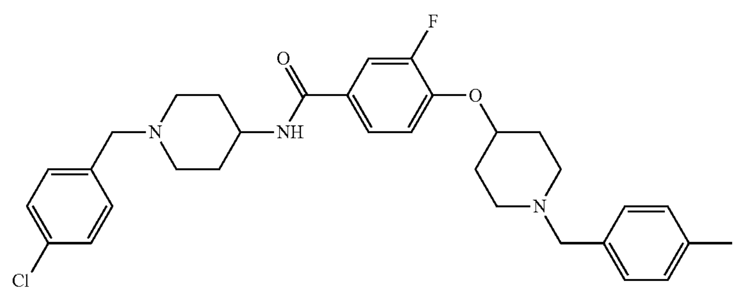 [SMILES: Cc1ccc(CN2CCC(Oc3ccc(C(=O)NC4CCN(Cc5ccc(Cl)cc5)CC4)cc3F)CC2)cc1] |
| 5-74 | N-(1-benzylpiperidin-4-yl)-3-chloro-4-(1-(3,4-difluorobenzyl)piperidin-4-yloxy)benzamide | 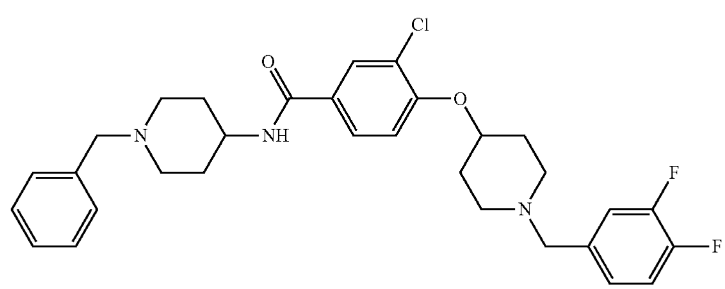 |
| 5-75 | N-(1-benzylpiperidin-4-yl)-3,5-dichloro-4-(1-(4-chlorobenzyl)piperidin-4-yloxy)benzamide | 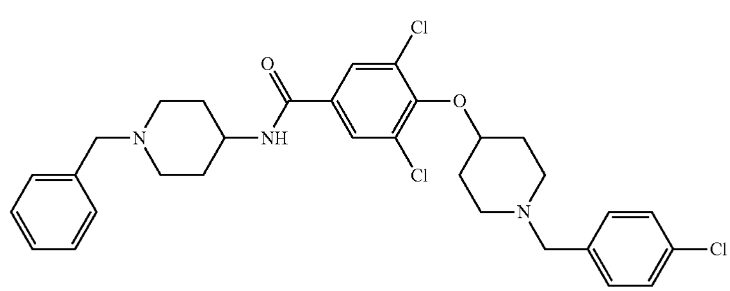 [SMILES: O=C(NC1CCN(Cc2ccccc2)CC1)c1cc(Cl)c(OC2CCN(Cc3ccc(Cl)cc3)CC2)c(Cl)c1] |

TABLE 5-continued

| Cpd | Name | Structure |
|---|---|---|
| 5-76 | N-(1-benzylpiperidin-4-yl)-3,5-dichloro-4-(1-(3,4-difluorobenzyl)piperidin-4-yloxy)benzamide | 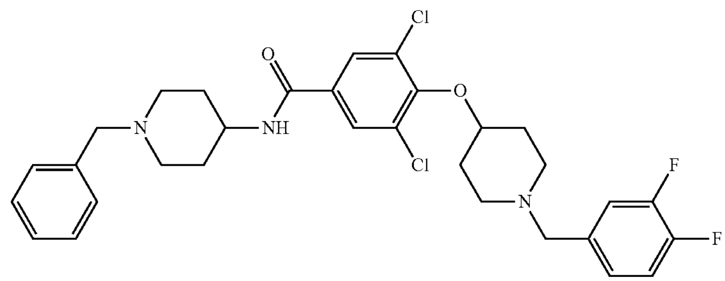 |
| 5-77 | N-(1-benzylpiperidin-4-yl)-3,5-dichloro-4-(1-(4-cyanobenzyl)piperidin-4-yloxy)benzamide | 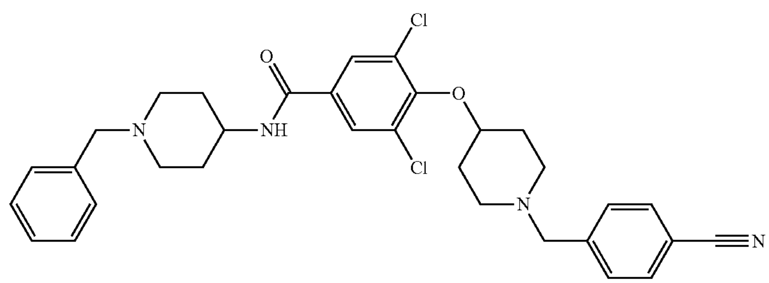 [SMILES: N#Cc1ccc(CN2CCC(Oc3c(Cl)cc(C(=O)NC4CCN(Cc5ccccc5)CC4)cc3Cl)CC2)cc1] |
| 5-78 | tert-butyl 4-(4-(1-(4-cyanobenzyl)piperidin-4-yloxy)benzamido)piperidine-1-carboxylate | 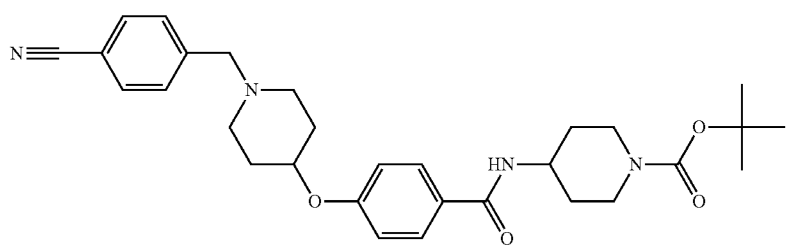 [SMILES: CC(C)(C)OC(=O)N1CCC(NC(=O)c2ccc(OC3CCN(Cc4ccc(C#N)cc4)CC3)cc2)CC1] |
| 5-79 | 4-(1-(4-cyanobenzyl)piperidin-4-yloxy)-N-(piperidin-4-yl)benzamide | 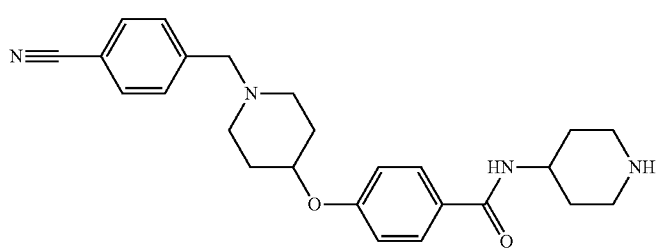 [SMILES: N#Cc1ccc(CN2CCC(Oc3ccc(C(=O)NC4CCNCC4)cc3)CC2)cc1] |
| 5-80 | N-(1-(4-chlorobenzyl)piperidin-4-yl)-4-(1-(3,4-dichlorobenzyl)piperidin-4-yloxy)-3-fluorobenzamide | 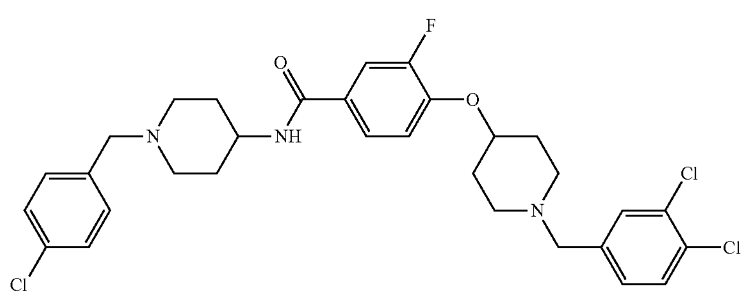 [SMILES: O=C(NC1CCN(Cc2ccc(Cl)cc2)CC1)c1ccc(OC2CCN(Cc3ccc(Cl)c(Cl)c3)CC2)c(F)c1] |

TABLE 5-continued

| Cpd | Name | Structure |
|---|---|---|
| 5-81 | N-(1-(4-chlorobenzyl)piperidin-4-yl)-4-(1-(4-cyanophenyl)piperidin-4-yloxy)-3-fluorobenzamide | 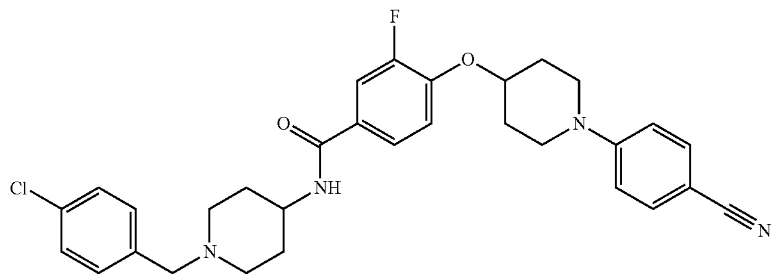 [SMILES: N#Cc1ccc(N2CCC(Oc3ccc(C(=O)NC4CCN(Cc5ccc(Cl)cc5)CC4)cc3F)CC2)cc1] |
| 5-82 | N-(1-benzylpiperidin-4-yl)-4-(1-(3,4-dichlorobenzyl)piperidin-4-yloxy)-3-fluorobenzamide | 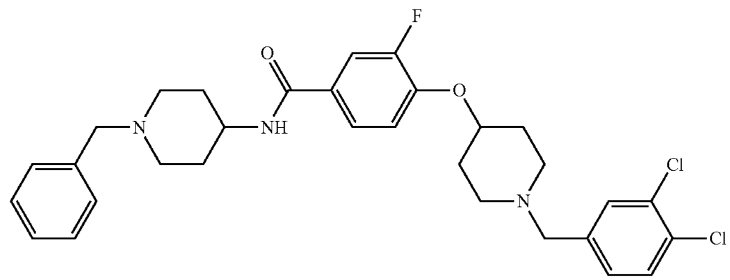 [SMILES: O=C(NC1CCN(Cc2ccccc2)CC1)c1ccc(OC2CCN(Cc3ccc(Cl)c(Cl)c3)CC2)c(F)c1] |
| 5-83 | 4-(1-(4-cyanobenzyl)piperidin-4-yloxy)-N-(1-(pyridin-4-ylmethyl)piperidin-4-yl)benzamide | 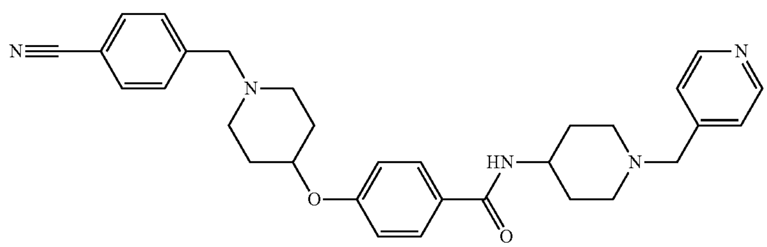 [SMILES: N#Cc1ccc(CN2CCC(Oc3ccc(C(=O)NC4CCN(Cc5ccncc5)CC4)cc3)CC2)cc1] |
| 5-84 | N-(1-benzylpiperidin-4-yl)-3-chloro-4-(1-(3,4-dichlorobenzyl)piperidin-4-yloxy)benzamide | 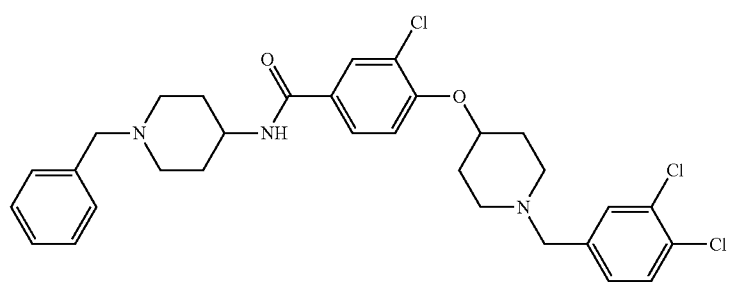 [SMILES: O=C(NC1CCN(Cc2ccccc2)CC1)c1ccc(OC2CCN(Cc3ccc(Cl)c(Cl)c3)CC2)c(Cl)c1] |
| 5-85 | 4-(1-(4-cyanobenzyl)piperidin-4-yloxy)-N-(1-(pyridin-2-ylmethyl)piperidin-4-yl)benzamide | 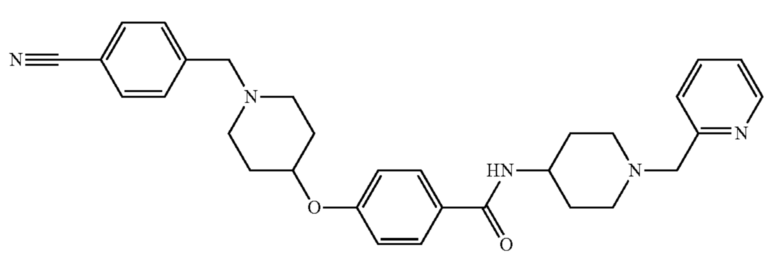 [SMILES: N#Cc1ccc(CN2CCC(Oc3ccc(C(=O)NC4CCN(Cc5ccccn5)CC4)cc3)CC2)cc1] |
| 5-86 | N-(1-benzylpiperidin-4-yl)-3-(1-(pyridin-2-yl)piperidin-4-yloxy)benzamide | 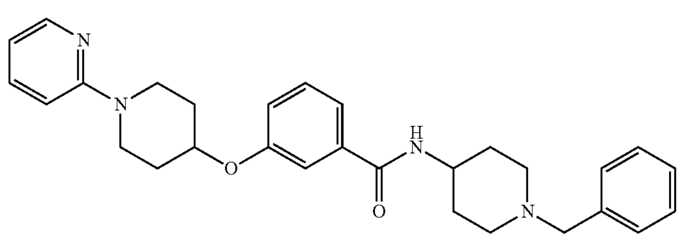 [SMILES: O=C(NC1CCN(Cc2ccccc2)CC1)c1cccc(OC2CCN(c3ccccn3)CC2)c1] |

TABLE 5-continued

| Cpd | Name | Structure |
|---|---|---|
| 5-87 | N-(1-(pyridin-4-ylmethyl)piperidin-4-yl)-3-(1-(4-(trifluoromethyl)phenyl)piperidin-4-yloxy)benzamide | 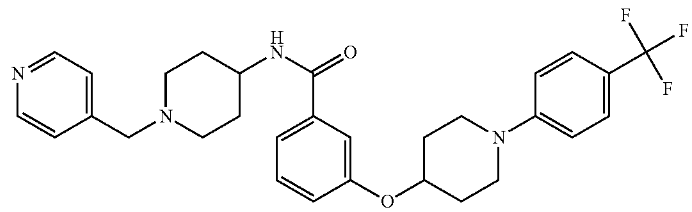 [SMILES: O=C(NC1CCN(Cc2ccncc2)CC1)c1cccc(OC2CCN(c3ccc(C(F)(F)F)cc3)CC2)c1] |
| 5-88 | N-(1-(pyridin-4-ylmethyl)piperidin-4-yl)-3-(1-(4-cyanophenyl)piperidin-4-yloxy)benzamide | 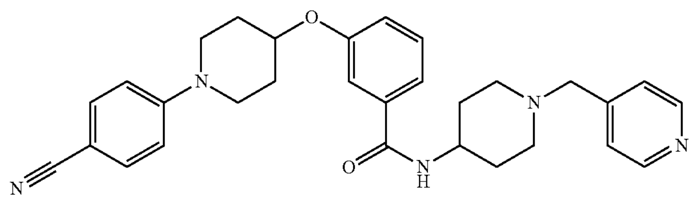 [SMILES: N#Cc1ccc(N2CCC(Oc3cccc(C(=O)NC4CCN(Cc5ccncc5)CC4)c3)CC2)cc1] |
| 5-89 | N-(1-benzylpiperidin-4-yl)-3-(1-(3-cyanobenzyl)piperidin-4-yloxy)benzamide | 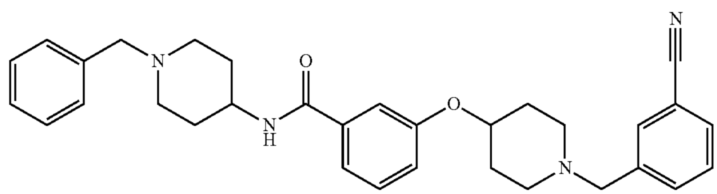 [SMILES: N#Cc1cccc(CN2CCC(Oc3cccc(C(=O)NC4CCN(Cc5ccccc5)CC4)c3)CC2)c1] |
| 5-90 | tert-butyl 4-(4-(1-benzylpiperidin-4-ylcarbamoyl)-2-chlorophenoxy)piperidine-1-carboxylate | 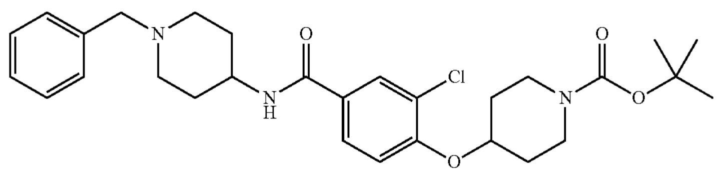 [SMILES: CC(C)(C)OC(=O)N1CCC(Oc2ccc(C(=O)NC3CCN(Cc4ccccc4)CC3)cc2Cl)CC1] |
| 5-91 | N-(1-benzylpiperidin-4-yl)-3-chloro-4-(1-pivaloylpiperidin-4-yloxy)benzamide | 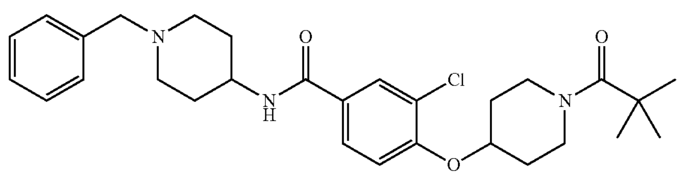 [SMILES: CC(C)(C)C(=O)N1CCC(Oc2ccc(C(=O)NC3CCN(Cc4ccccc4)CC3)cc2Cl)CC1] |
| 5-92 | tert-butyl 4-(4-(1-benzylpiperidin-4-ylcarbamoyl)-2-fluorophenoxy)piperidine-1-carboxylate | 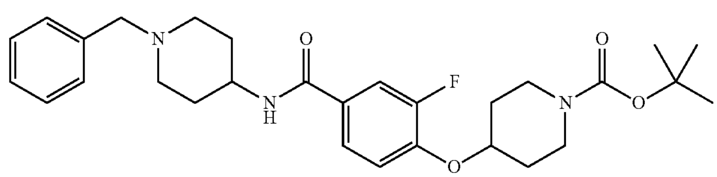 [SMILES: CC(C)(C)OC(=O)N1CCC(Oc2ccc(C(=O)NC3CCN(Cc4ccccc4)CC3)cc2F)CC1] |
| 5-93 | N-(1-benzylpiperidin-4-yl)-3-chloro-4-(piperidin-4-yloxy)benzamide | 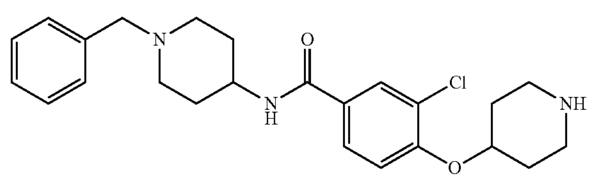 [SMILES: O=C(NC1CCN(Cc2ccccc2)CC1)c1ccc(OC2CCNCC2)c(Cl)c1] |
| 5-94 | tert-butyl 3-(3-methoxy-4-(1-(4-(trifluoromethyl)benzyl)piperidin-4-yloxy)benzamido)propylcarbamate | 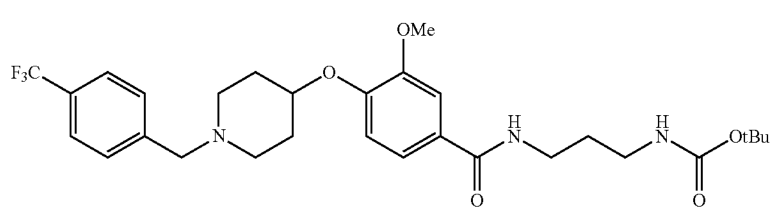 [SMILES: COc1cc(C(=O)NCCCNC(=O)OC(C)(C)C)ccc1OC1CCN(Cc2ccc(C(F)(F)F)cc2)CC1] |

TABLE 5-continued

| Cpd | Name | Structure |
|---|---|---|
| 5-95 | tert-butyl 3-(4-(1-(4-(trifluoromethyl)benzyl)piperidin-4-yloxy)benzamido)propylcarbamate | 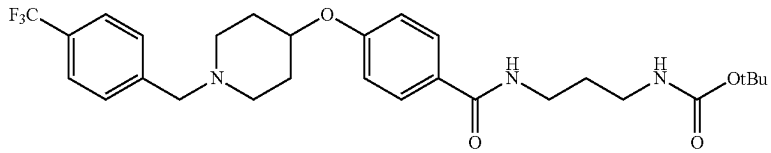 [SMILES: CC(C)(C)OC(=O)NCCCNC(=O)c1ccc(OC2CCN(Cc3ccc(C(F)(F)F)cc3)CC2)cc1] |
| 5-96 | tert-butyl 4-(4-(1-(4-methoxybenzyl)piperidin-4-yloxy)benzoyl)piperazine-1-carboxylate | 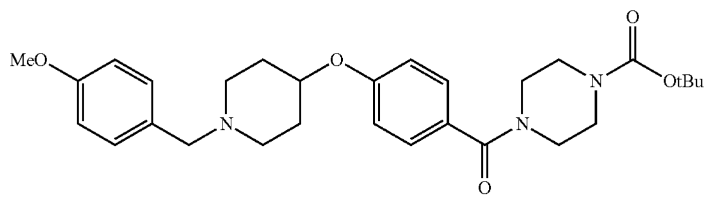 [SMILES: COc1ccc(CN2CCC(Oc3ccc(C(=O)N4CCN(C(=O)OC(C)(C)C)CC4)cc3)CC2)cc1] |
| 5-97 | tert-butyl 3-(3-chloro-4-(1-(4-methoxybenzyl)piperidin-4-yloxy)benzamido)propylcarbamate | 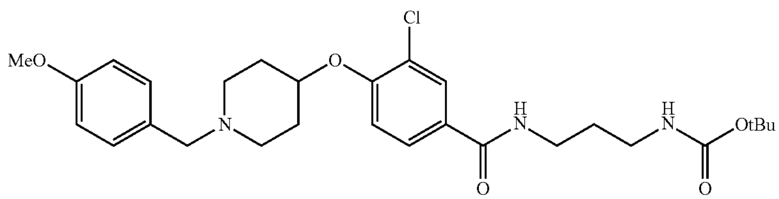 [SMILES: COc1ccc(CN2CCC(Oc3ccc(C(=O)NCCCNC(=O)OC(C)(C)C)cc3Cl)CC2)cc1] |
| 5-98 | 4-(1-(4-chlorobenzyl)piperidin-4-yloxy)-4-methoxy-N-(3-morpholinopropyl)benzamide | 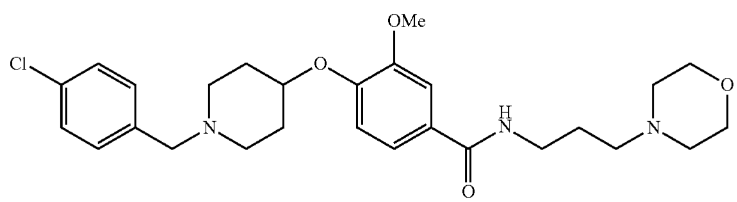 [SMILES: COc1cc(C(=O)NCCCN2CCOCC2)ccc1OC1CCN(Cc2ccc(Cl)cc2)CC1] |
| 5-99 | tert-butyl 4-(4-(1-benzylpiperidin-4-yloxy)benzoyl)piperazine-1-carboxylate | 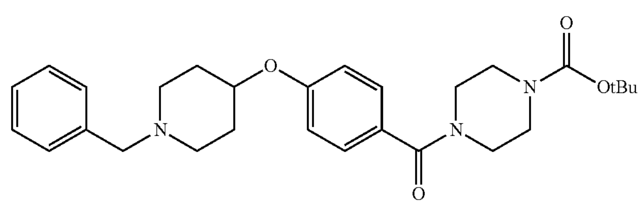 [SMILES: CC(C)(C)OC(=O)N1CCN(C(=O)c2ccc(OC3CCN(Cc4ccccc4)CC3)cc2)CC1] |
| 5-100 | 4-(1-(4-chlorobenzyl)piperidin-4-yloxy)-N-(3-morpholinopropyl)benzamide | 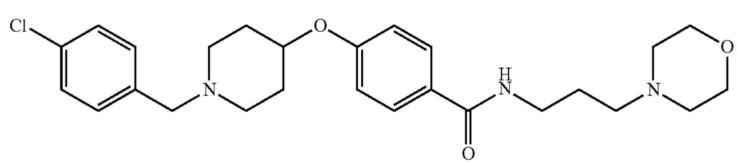 [SMILES: O=C(NCCCN1CCOCC1)c1ccc(OC2CCN(Cc3ccc(Cl)cc3)CC2)cc1] |
| 5-101 | 3-chloro-4-(1-(4-methoxybenzyl)piperidin-4-yloxy)-N-(3-morpholinopropyl)benzamide | 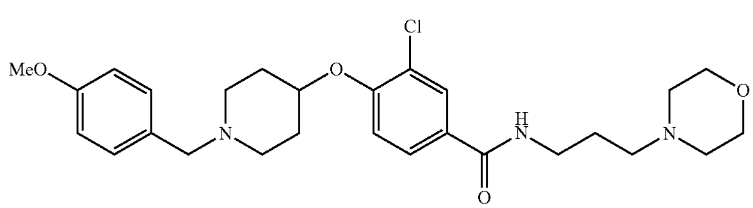 [SMILES: COc1ccc(CN2CCC(Oc3ccc(C(=O)NCCCN4CCOCC4)cc3Cl)CC2)cc1] |
| 5-102 | tert-butyl 3-(4-(1-benzylpiperidin-4-yloxy)-3-chlorobenzamido)propylcarbamate | 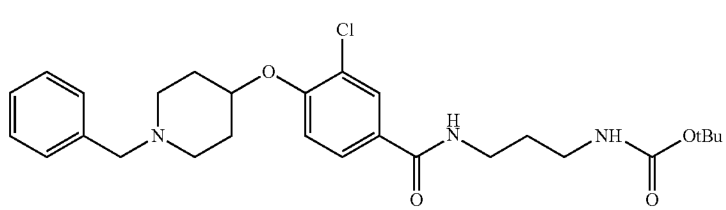 [SMILES: CC(C)(C)OC(=O)NCCCNC(=O)c1ccc(OC2CCN(Cc3ccccc3)CC2)c(Cl)c1] |

TABLE 5-continued

| Cpd | Name | Structure |
|---|---|---|
| 5-103 | (4-(1-benzylpiperidin-4-yloxy)phenyl)(4-phenylpiperazin-1-yl)methanone | 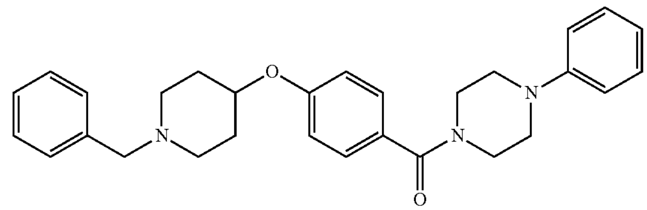 [SMILES: O=C(c1ccc(OC2CCN(Cc3ccccc3)CC2)cc1)N1CCN(c2ccccc2)CC1] |
| 5-104 | 4-(1-(4-methylbenzyl)piperidin-4-yloxy)-N-(3-morpholinopropyl)benzamide | 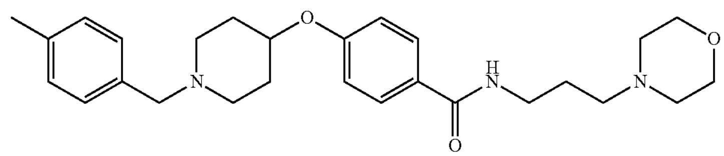 [SMILES: Cc1ccc(CN2CCC(Oc3ccc(C(=O)NCCCN4CCOCC4)cc3)CC2)cc1] |
| 5-105 | (4-(1-benzylpiperidin-4-yloxy)phenyl)(4-(pyridin-2-ylmethyl)piperazin-1-yl)methanone | 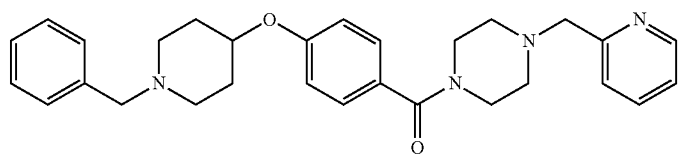 [SMILES: O=C(c1ccc(OC2CCN(Cc3ccccc3)CC2)cc1)N1CCN(Cc2ccccn2)CC1] |
| 5-106 | N-(1-(4-methoxybenzyl)piperidin-4-yl)-3-(1-(4-(pyridin-2-yl)benzyl)piperidin-4-yloxy)benzamide | 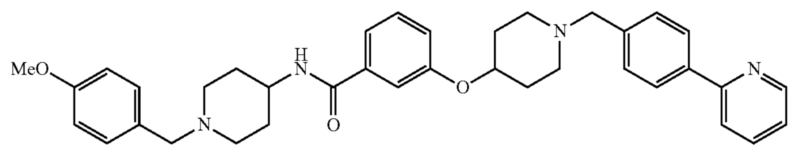 [SMILES: COc1ccc(CN2CCC(NC(=O)c3cccc(OC4CCN(Cc5ccc(-c6ccccn6)cc5)CC4)c3)CC2)cc1] |
| 5-107 | N-(1-(4-methoxybenzyl)piperidin-4-yl)-3-(1-(4-methoxybenzyl)piperidin-4-yloxy)benzamide | 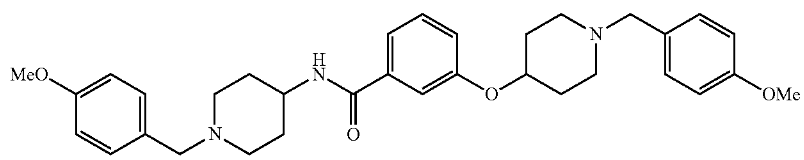 [SMILES: COc1ccc(CN2CCC(NC(=O)c3cccc(OC4CCN(Cc5ccc(OC)cc5)CC4)c3)CC2)cc1] |
| 5-108 | N-(1-(4-methoxybenzyl)piperidin-4-yl)-3-(1-(4-(trifluoromethyl)benzyl)piperidin-4-yloxy)benzamide | 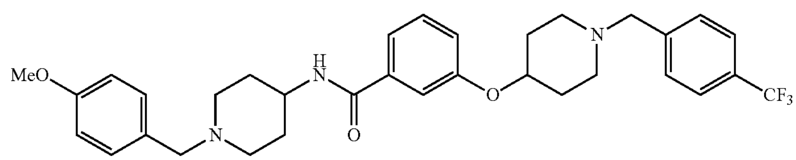 [SMILES: COc1ccc(CN2CCC(NC(=O)c3cccc(OC4CCN(Cc5ccc(C(F)(F)F)cc5)CC4)c3)CC2)cc1] |
| 5-109 | N-(1-(4-methoxybenzyl)piperidin-4-yl)-3-(1-(4-morpholinobenzyl)piperidin-4-yloxy)benzamide | 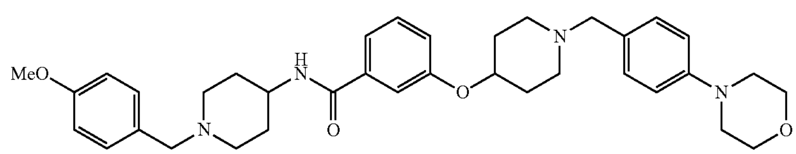 [SMILES: COc1ccc(CN2CCC(NC(=O)c3cccc(OC4CCN(Cc5ccc(N6CCOCC6)cc5)CC4)c3)CC2)cc1] |
| 5-110 | N-(1-(4-methoxybenzyl)piperidin-4-yl)-3-(1-((1-phenylpiperidin-4-yl)methyl)piperidin-4-yloxy)benzamide | 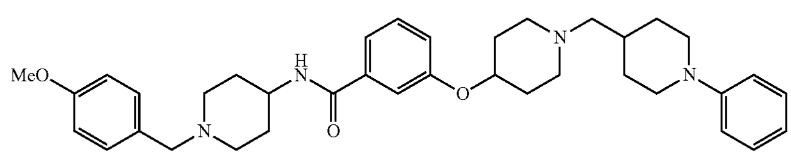 [SMILES: COc1ccc(CN2CCC(NC(=O)c3cccc(OC4CCN(CC5CCN(c6ccccc6)CC5)CC4)c3)CC2)cc1] |
| 5-111 | 3-(1-((1-(4-fluorophenyl)-1H-pyrazol-4-yl)methyl)piperidin-4-yloxy)-N-(1-(4-methoxybenzyl)piperidin-4-yl)benzamide | 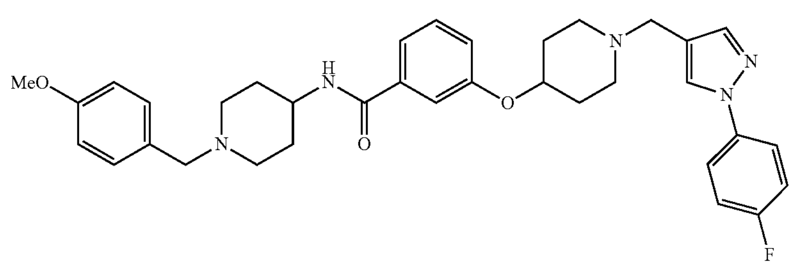 [SMILES: COc1ccc(CN2CCC(NC(=O)c3cccc(OC4CCN(Cc5cnn(-c6ccc(F)cc6)c5)CC4)c3)CC2)cc1] |

TABLE 5-continued

| Cpd | Name | Structure |
|---|---|---|
| 5-112 | methyl 4-((4-(3-(l-(4-methoxybenzyl)piperidin-4-ylcarbamoyl)phenoxy)piperidin-1-yl)methyl)benzoate | 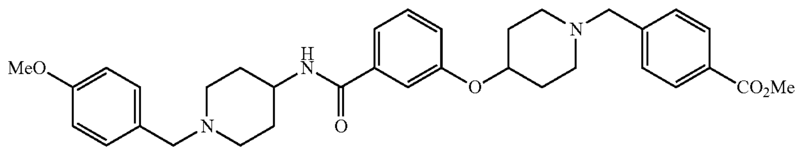 [SMILES: COC(=O)c1ccc(CN2CCC(Oc3cccc(C(=O)NC4CCN(Cc5ccc(OC)cc5)CC4)c3)CC2)cc1] |
| 5-113 | 3-(1-(4-(4-cyanophenoxy)benzyl)piperidin-4-yloxy)-N-(1-(4-methoxybenzyl)piperidin-4-yl)benzamide | 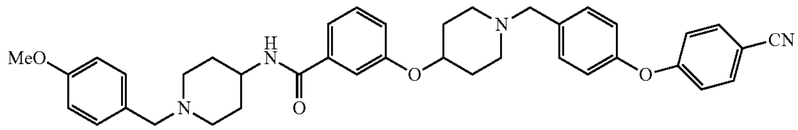 [SMILES: COc1ccc(CN2CCC(NC(=O)c3cccc(OC4CCN(Cc5ccc(Oc6ccc(C#N)cc6)cc5)CC4)c3)CC2)cc1] |
| 5-114 | N-(1-(4-methoxybenzyl)piperidin-4-yl)-3-(1-((1-(pyridin-2-yl)-1H-pyrazol-4-yl)methyl)piperidin-4-yloxy)benzamide | 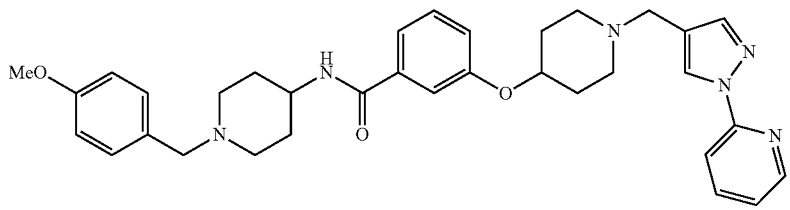 [SMILES: COc1ccc(CN2CCC(NC(=O)c3cccc(OC4CCN(Cc5cnn(-c6ccccn6)c5)CC4)c3)CC2)cc1] |
| 5-115 | N-(1-(4-cyanobenzyl)piperidin-4-yl)-3-(1-(4-cyanophenyl)piperidin-4-yloxy)benzamide | 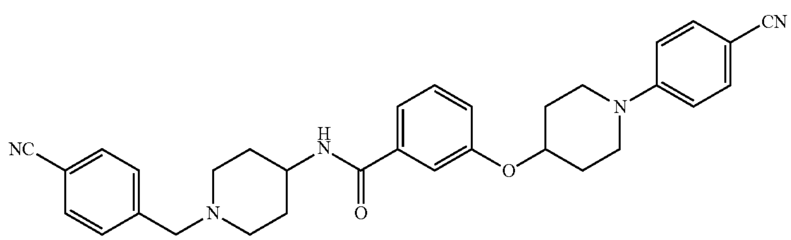 [SMILES: N#Cc1ccc(CN2CCC(NC(=O)c3cccc(OC4CCN(c5ccc(C#N)cc5)CC4)c3)CC2)cc1] |
| 5-116 | N-(1-(4-cyanobenzyl)piperidin-4-yl)-3-(1-(4-(pyrrolidin-1-yl)benzyl)piperidin-4-yloxy)benzamide | 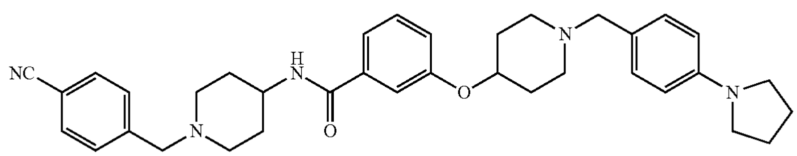 [SMILES: N#Cc1ccc(CN2CCC(NC(=O)c3cccc(OC4CCN(Cc5ccc(N6CCCC6)cc5)CC4)c3)CC2)cc1] |
| 5-117 | N-(1-(4-cyanobenzyl)piperidin-4-yl)-3-(1-(4-phenoxybenzyl)piperidin-4-yloxy)benzamide | 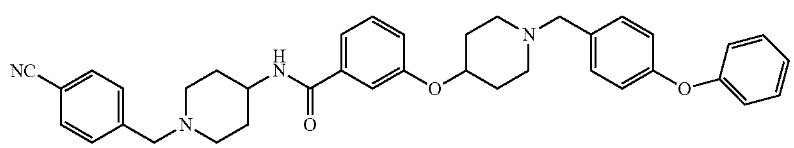 [SMILES: N#Cc1ccc(CN2CCC(NC(=O)c3cccc(OC4CCN(Cc5ccc(Oc6ccccc6)cc5)CC4)c3)CC2)cc1] |
| 5-118 | N-(1-(4-cyanobenzyl)piperidin-4-yl)-3-(1-(4-(pyridin-2-yl)benzyl)piperidin-4-yloxy)benzamide | 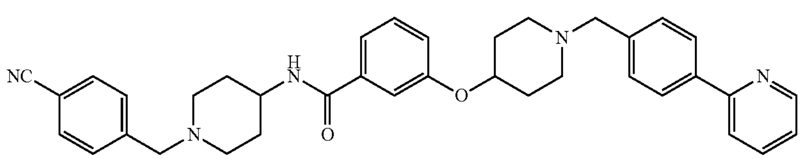 [SMILES: N#Cc1ccc(CN2CCC(NC(=O)c3cccc(OC4CCN(Cc5ccc(-c6ccccn6)cc5)CC4)c3)CC2)cc1] |
| 5-119 | 3-(l-(4-(1H-pyrazol-1-yl)benzyl)piperidin-4-yloxy)-N-(1-(4-cyanobenzyl)piperidin-4-yl)benzamide | 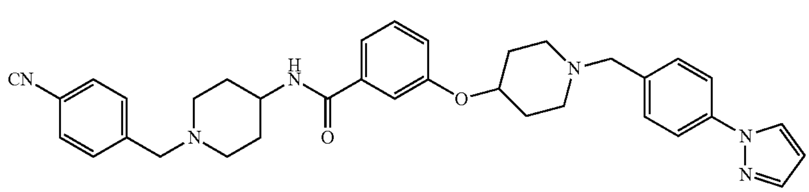 |
| 5-120 | 3-(1-(4-cyano-3-fluorobenzyl)piperidin-4-yloxy)-N-(1-(4-cyanobenzyl)piperidin-4-yl)benzamide | 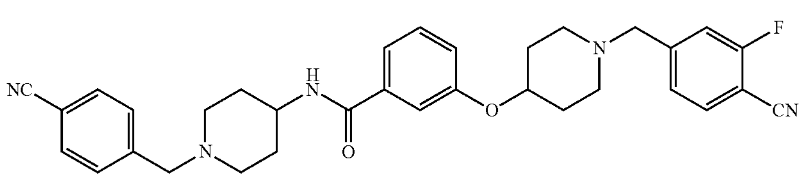 [SMILES: N#Cc1ccc(CN2CCC(NC(=O)c3cccc(OC4CCN(Cc5ccc(C#N)c(F)c5)CC4)c3)CC2)cc1] |

TABLE 5-continued

| Cpd | Name | Structure |
|---|---|---|
| 5-121 | N-(1-(4-cyanobenzyl)piperidin-4-yl)-3-(1-(4-isopropoxybenzyl)piperidin-4-yloxy)benzamide | 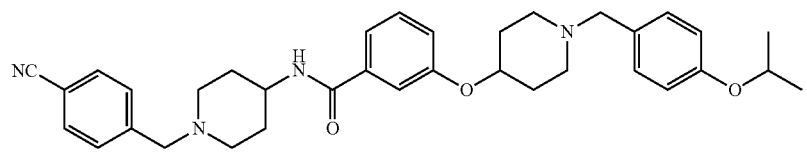 [SMILES: CC(C)Oc1ccc(CN2CCC(Oc3cccc(C(=O)NC4CCN(Cc5ccc(C#N)cc5)CC4)c3)CC2)cc1] |
| 5-122 | N-(1-(4-cyanobenzyl)piperidin-4-yl)-3-(1-((1-(4-fluorophenyl)-1H-pyrazol-4-yl)methyl)piperidin-4-yloxy)benzamide | 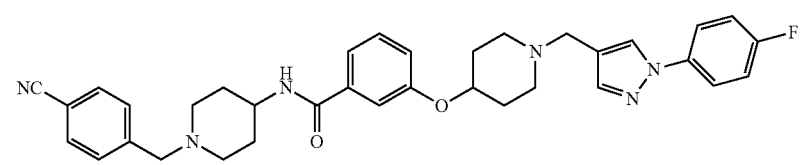 [SMILES: N#Cc1ccc(CN2CCC(NC(=O)c3cccc(OC4CCN(Cc5cnn(-c6ccc(F)cc6)c5)CC4)c3)CC2)cc1] |
| 5-123 | N-(1-(4-cyanobenzyl)piperidin-4-yl)-3-(1-(4-(trifluoromethoxy)benzyl)piperidin-4-yloxy)benzamide | 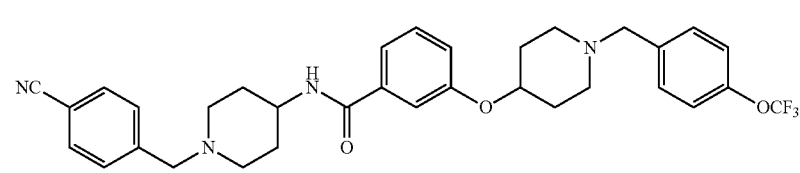 [SMILES: N#Cc1ccc(CN2CCC(NC(=O)c3cccc(OC4CCN(Cc5ccc(OC(F)(F)F)cc5)CC4)c3)CC2)cc1] |
| 5-124 | N-(1-(4-cyanobenzyl)piperidin-4-yl)-3-(1-(4-cyanobenzyl)piperidin-4-yloxy)benzamide | 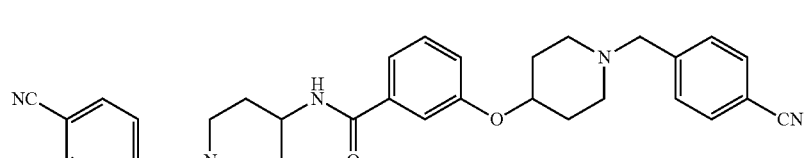 |
| 5-125 | N-(1-(4-cyanobenzyl)piperidin-4-yl)-3-(1-(4-(trifluoromethyl)benzyl)piperidin-4-yloxy)benzamide | 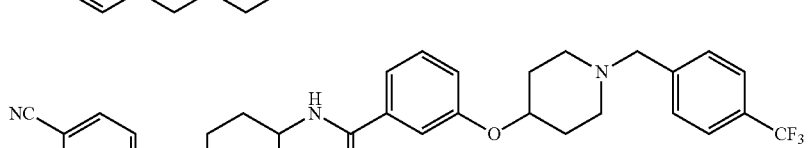 |
| 5-126 | N-(1-(4-cyanobenzyl)piperidin-4-yl)-3-((3,4-trans)-3-fluoro-1-(4-(trifluoromethyl)benzyl)piperidin-4-yloxy)benzamide | 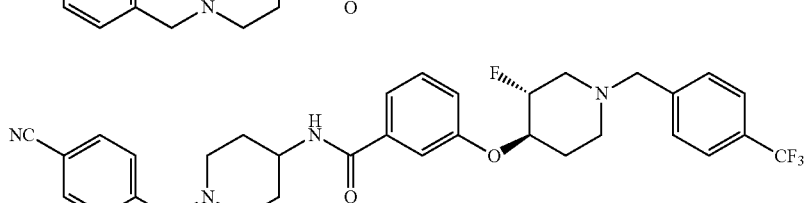 |
| 5-127 | N-(1-(4-cyanobenzyl)piperidin-4-yl)-3-((3,4-trans)-3-fluoro-1-(4-isopropoxybenzyl)piperidin-4-yloxy)benzamide | 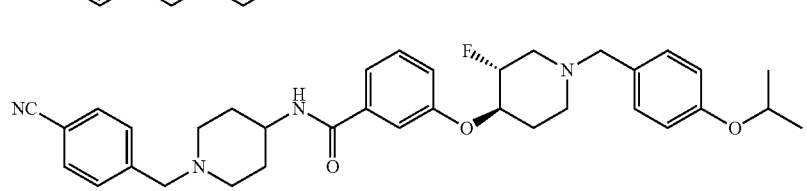 |
| 5-128 | N-(1-(4-cyanobenzyl)piperidin-4-yl)-3-((3,4-trans)-3-fluoro-1-(4-(methylsulfonyl)benzyl)piperidin-4-yloxy)benzamide | 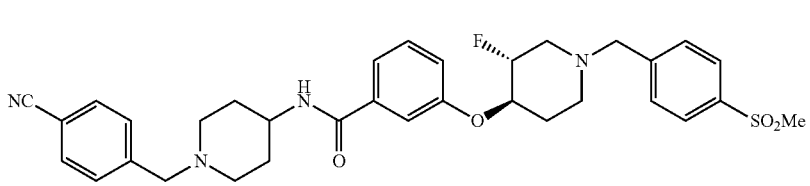 [SMILES: CS(=O)(=O)c1ccc(CN2CC[C@@H](Oc3cccc(C(=O)NC4CCN(Cc5ccc(C#N)cc5)CC4)c3)[C@H](F)C2)cc1] |
| 5-129 | 3-((3,4-trans)-1-(4-cyano-3-fluorobenzyl)-3-fluoropiperidin-4-yloxy)-N-(1-(4-cyanobenzyl)piperidin-4-yl)benzamide | 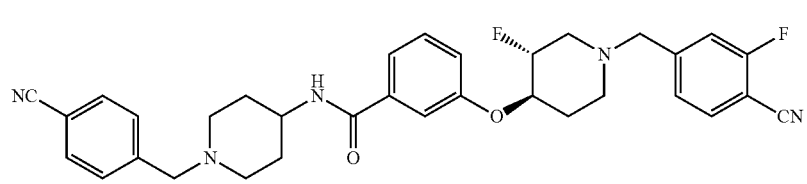 [SMILES: N#Cc1ccc(CN2CCC(NC(=O)c3cccc(O[C@@H]4CCN(Cc5ccc(C#N)c(F)c5)C[C@H]4F)c3)CC2)cc1] |

One aspect of the disclosure provides compounds having structural formula (6-I):

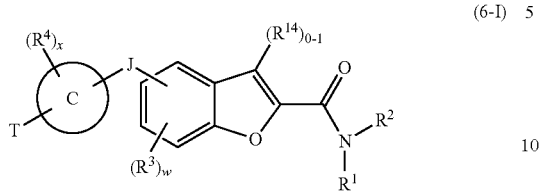

and a pharmaceutically acceptable salts and N-oxides thereof (and solvates and hydrates thereof), wherein
$R^1$ is H, —($C_1$-$C_4$ alkyl), —C(O)—($C_1$-$C_4$ alkyl) or —C(O)O—($C_1$-$C_4$ alkyl);
$R^2$ is —H or

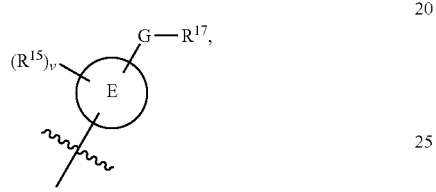

in which
the ring system denoted by "E" is cycloalkyl, heterocycloalkyl, aryl or heteroaryl;
G is a bond, —$CH_2$—, —C(H)($R^{16}$)—, —C($R^{16}$)$_2$—, —O— or —S(O)$_2$—;
v is 0, 1, 2, 3 or 4;
each $R^{15}$ is independently selected from —($C_1$-$C_6$ alkyl), —($C_1$-$C_6$ haloalkyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}$$R^{10}$, -halogen, —$NO_2$ and —CN, and two $R^{15}$ on the same carbon optionally combine to form oxo; and
$R^{17}$ is Het or Ar; or
$R^1$ and $R^2$ come together with the nitrogen to which they are attached to form

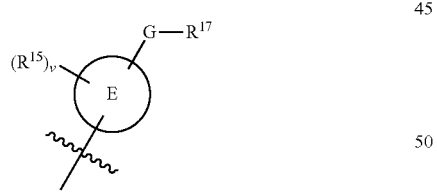

in which E is heterocycloalkyl;
each $R^3$ is substituted on a benzo or pyrido carbon of the ring system denoted by "B" and is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}$$R^{10}$, -halogen, —$NO_2$ and —CN;
w is 0, 1, 2 or 3;
$R^{14}$ is selected from —($C_1$-$C_6$ alkyl), —($C_1$-$C_6$ halooalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}$$R^{10}$, -halogen, —$NO_2$ and —CN;
J is a single bond, —C(O)—, —$CH_2$—, —C(O)—NH—, —$CH_2$—C(O)—NH—, —NH—C(O)—$CH_2$— or —NH—C(O)—
each $R^4$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}$$R^{10}$, -halogen, —$NO_2$ and —CN, and two $R^4$ on the same carbon optionally combine to form oxo;
x is 0, 1, 2, 3 or 4;
the ring system denoted by "C" is aryl, heteroaryl, or

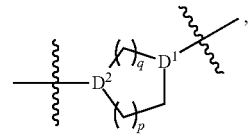

in which each of $D^1$ and $D^2$ is independently N, CH, or C substituted by one of the x $R^4$; p is 0, 1, 2, 3 or 4; q is 0, 1, 2, 3 or 4 and the sum of p and q is 1, 2, 3 or 4;
T is —H, —($C_0$-$C_6$ alkyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}$$R^{10}$, —CN or

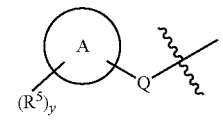

in which
Q is —($C_0$-$C_3$ alkyl)-, in which each carbon of the —($C_0$-$C_3$ alkyl)- is optionally and independently substituted with one or two $R^{16}$, —O—, or —S(O)$_2$—;
the ring system denoted by "A" is heteroaryl, aryl, cycloalkyl or heterocycloalkyl;
each $R^5$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}$$R^{10}$ alkyl)-C(O)$R^{10}$, -halogen, —$NO_2$ and —CN; and
y is 0, 1, 2, 3 or 4;
in which
each L is independently selected from —$NR^9$C(O)O—, —OC(O)$NR^9$—, —$NR^9$C(O)—$NR^9$—, —$NR^9$C(O)S—, —SC(O)$NR^9$—, —$NR^9$C(O)—, —C(O)—$NR^9$—, —$NR^9$C(S)O—, —OC(S)$NR^9$—, —$NR^9$C(S)—$NR^9$—, —$NR^9$C(S)S—, —SC(S)$NR^9$—, —$NR^9$C(S)—, —C(S)$NR^9$—, —SC(O)$NR^9$—, —$NR^9$C(S)—, —S(O)$_{0-2}$—, —C(O)O—, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —$NR^9$C($NR^2$)$NR^9$—, —$NR^9$$SO_2$—, —$SO_2$$NR^9$— and —$NR^9$$SO_2$$NR^9$—,
each $R^6$, $R^7$, $R^8$ and $R^{10}$ is independently selected from H, —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —(C₀-C₆ alkyl)-Hca, —(C₀-C₆ alkyl)-L-(C₀-C₆ alkyl), —(C₀-C₆ alkyl)-NR⁹—(C₀-C₆ alkyl), —(C₀-C₆ alkyl)-O—(C₀-C₆ alkyl), —(C₀-C₆ alkyl)-C(O)—(C₀-C₆ alkyl) and —(C₀-C₆ alkyl)-S(O)₀₋₂—(C₀-C₆ alkyl), each R⁹ is independently selected from —H, —(C₁-C₄ alkyl) and —C(O)O—(C₁-C₄ alkyl), each G is independently —(C₀-C₃ alkyl)-, in which each carbon of the —(C₀-C₃ alkyl)- is optionally and independently substituted with one or two R¹⁶, or —S(O)₂—, each R¹⁶ is independently selected from —(C₁-C₆ alkyl), —(C₁-C₆ haloalkyl), —(C₀-C₆ alkyl)-Ar, —(C₀-C₆ alkyl)-Het, —(C₀-C₆ alkyl)-Cak, —(C₀-C₆ alkyl)-Hca, —(C₀-C₆ alkyl)-L-R⁷, —(C₀-C₆ alkyl)-NR⁸R⁹, —(C₀-C₆ alkyl)-OR¹⁰, —(C₀-C₆ alkyl)-C(O)R¹⁰, —(C₀-C₆ alkyl)-S(O)₀₋₂R¹⁰, -halogen, —NO₂ and —CN, and optionally two of R¹⁶ on the same carbon combine to form oxo, each R²⁰, R²² and R²³ is independently Ar or Het, each Ar is an optionally substituted aryl, each Het is an optionally substituted heteroaryl, each Cak is an optionally substituted cycloalkyl, each Hca is an optionally substituted heterocycloalkyl, and each alkyl is optionally substituted.

In certain embodiments of the presently disclosed compounds of structural formula (6-I), In one such embodiment, R¹⁴ is selected from —(C₁-C₆ alkyl), —(C₁-C₆ haloalkyl) (e.g., trifluoromethyl), —(C₀-C₆ alkyl)-L-R⁷, —(C₀-C₆ alkyl)-NR⁸R⁹, —(C₀-C₆ alkyl)-OR¹⁰, —(C₀-C₆ alkyl)-C(O)R¹⁰, —(C₀-C₆ alkyl)-S(O)₀₋₂R¹⁰, -halogen, —NO₂ and —CN, in which each R⁷, R⁸ and R¹⁰ is independently selected from H, —(C₁-C₆ alkyl), —(C₁-C₆ haloalkyl), —(C₀-C₆ alkyl)-L-(C₀-C₆ alkyl), —(C₀-C₆ alkyl)-NR⁹(C₀-C₆ alkyl), —(C₀-C₆ alkyl)-O—(C₀-C₆ alkyl), —(C₀-C₆ alkyl)-C(O)—(C₀-C₆ alkyl), and —(C₀-C₆ alkyl)-S(O)₀₋₂—(C₀-C₆ alkyl), and in which no alkyl or haloalkyl is substituted with an aryl-, heteroaryl-, cycloalkyl- or heterocycloalkyl-containing group. For example, in one embodiment, R¹⁴ is selected from —(C₁-C₃ alkyl), —(C₁-C₃ haloalkyl), —(C₀-C₃ alkyl)-L-R⁷, —(C₀-C₃ alkyl)-NR⁸R⁹, —(C₀-C₃ alkyl)-OR¹⁰, —(C₀-C₃ alkyl)-C(O)R¹⁰, —(C₀-C₃ alkyl)-S(O)₀₋₂R¹⁰, -halogen, —NO₂ and —CN, in which each R⁷, R⁸ and R¹⁰ is independently selected from H, —(C₁-C₂ alkyl), —(C₁-C₂ haloalkyl), —(C₀-C₂ alkyl)-L-(C₀-C₂ alkyl), —(C₀-C₂ alkyl)-NR⁹(C₀-C₂ alkyl), —(C₀-C₂ alkyl)-O—(C₀-C₂ alkyl), —(C₀-C₂ alkyl)-C(O)—(C₀-C₂ alkyl) and —(C₀-C₂ alkyl)-S(O)₀₋₂—(C₀-C₂ alkyl), and in which no alkyl or haloalkyl is substituted with an aryl-, heteroaryl-, cycloalkyl- or heterocycloalkyl-containing group. R¹⁴ can be, for example, halo (e.g., —Cl or —F), cyano, or unsubstituted —(C₁-C₄ alkyl) (e.g., methyl or ethyl), unsubstituted —(C₁-C₄ haloalkyl) (e.g., trifluoromethyl). In other embodiments, no R¹⁴ is substituted on the furano carbon. In certain embodiments, R¹⁴ is H or methyl; in others, R¹⁴ is halo (e.g., Cl).

In certain embodiments of the presently disclosed compounds of structural formula (6-I), T is

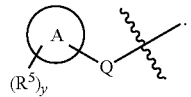

In such embodiments, Q is —O—, —S(O)₂— or —(C₀-C₃ alkyl)- in which each carbon of the (C₀-C₃ alkyl) is optionally and independently substituted with one or two R¹⁶, in which each R¹⁶ is independently selected from —(C₁-C₆ alkyl), —(C₁-C₆ haloalkyl), —(C₀-C₆ alkyl)-Ar, —(C₀-C₆ alkyl)-Het, —(C₀-C₆ alkyl)-Cak, —(C₀-C₆ alkyl)-Hca, —(C₀-C₆ alkyl)-L-R⁷, —(C₀-C₆ alkyl)-NR⁸R⁹, —(C₀-C₆ alkyl)-OR¹⁰, —(C₀-C₆ alkyl)-C(O)R¹⁰, —(C₀-C₆ alkyl)-S(O)₀₋₂R¹⁰, -halogen, —NO₂ and —CN, and optionally two of R¹⁶ on the same carbon combine to form oxo. In certain embodiments, each R¹⁶ is independently selected from —(C₁-C₆ alkyl), —(C₁-C₆ haloalkyl) (e.g., trifluoromethyl), —(C₀-C₆ alkyl)-L-R⁷, —(C₀-C₆ alkyl)-NR⁸R⁹, —(C₀-C₆ alkyl)-OR¹⁰, —(C₀-C₆ alkyl)-C(O)R¹⁰, —(C₀-C₆ alkyl)-S(O)₀₋₂R¹⁰, -halogen, —NO₂ and —CN, and two R¹⁶ on the same carbon optionally combine to form an oxo, in which each R⁷, R⁸ and R¹⁰ is independently selected from H, —(C₁-C₆ alkyl), —(C₁-C₆ haloalkyl), —(C₀-C₆ alkyl)-L-(C₀-C₆ alkyl), —(C₀-C₆ alkyl)-NR⁹(C₀-C₆ alkyl), —(C₀-C₆ alkyl)-O—(C₀-C₆ alkyl), —(C₀-C₆ alkyl)-C(O)—(C₀-C₆ alkyl), and —(C₀-C₆ alkyl)-S(O)₀₋₂—(C₀-C₆ alkyl), and in which no alkyl or haloalkyl is substituted with an aryl-, heteroaryl-, cycloalkyl- or heterocycloalkyl-containing group. For example, in particular compounds, each R¹⁶ is —(C₁-C₃ alkyl), —(C₁-C₃ haloalkyl), —(C₀-C₃ alkyl)-L-R⁷, —(C₀-C₃ alkyl)-NR⁸R⁹, —(C₀-C₃ alkyl)-OR¹⁰, —(C₀-C₃ alkyl)-C(O)R¹⁰, —(C₀-C₃ alkyl)-S(O)₀₋₂R¹⁰, -halogen, —NO₂ and —CN, and two R¹⁶ on the same carbon optionally combine to form an oxo, in which each R⁷, R⁸ and R¹⁰ is independently selected from H, —(C₁-C₂ alkyl), —(C₁-C₂ haloalkyl), —(C₀-C₂ alkyl)-L-(C₀-C₂ alkyl), —(C₀-C₂ alkyl)-NR⁹(C₀-C₂ alkyl), —(C₀-C₂ alkyl)-O—(C₀-C₂ alkyl), —(C₀-C₂ alkyl)-C(O)—(C₀-C₂ alkyl) and —(C₀-C₂ alkyl)-S(O)₀₋₂—(C₀-C₂ alkyl), and in which no alkyl or haloalkyl is substituted with an aryl-, heteroaryl-, cycloalkyl- or heterocycloalkyl-containing group. In certain embodiments, Q has at most one R¹⁶ or an oxo substituted thereon. Q can be, for example, an unsubstituted —(C₀-C₃ alkyl)-. In other embodiments, Q is a (C₁-C₃ alkyl) having as its only substitution a single oxo group. For example, in certain embodiments, Q is —CH₂—; a single bond; —S(O)₂—; —C(O)—; —O—; or —CH(CH₃)—.

In certain embodiments of the presently disclosed compounds of structural formula (6-I), the

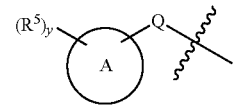

moiety is

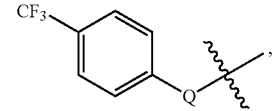

for example, p-(trifluoromethyl)phenyl. In other embodiments, the

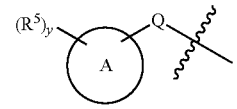

moiety is

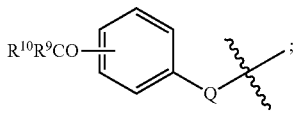

in one such embodiment, Q is a single bond.

The number of substituents on the ring system denoted by "A", y, is 0, 1, 2, 3 or 4. For example, in some embodiments, y is 0, 1, 2 or 3, for example 1. In one embodiment, y is not zero and at least one $R^5$ is halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ or —C(O)—Hca in which the Hca contains a ring nitrogen atom through which it is bound to the —C(O)—, and in which no alkyl, haloalkyl or heterocycloalkyl is substituted by an aryl, heteroaryl, cycloalkyl or heterocycloalkyl-containing group.

In certain embodiments of the presently disclosed compounds of structural formula (6-I), each $R^5$ is independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-S(O)$_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl) (e.g., trifluoromethyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^5$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group.

In one embodiment of the compounds of structural formula (6-I), y is 0.

In the presently disclosed compounds, the ring system denoted by "A" is heteroaryl, aryl, cycloalkyl or heterocycloalkyl. For example, in one embodiment, the ring system denoted by "A" is an aryl or a heteroaryl. The ring system denoted by "A" can be, for example, a monocyclic aryl or heteroaryl. In one embodiment, when the "A" ring system is aryl, Q is a —($C_0$-$C_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. For example, in certain embodiments, Q is —$CH_2$—; a single bond; —S(O)$_2$—; —C(O)—; or —CH($CH_3$)—. In another embodiment, when the "A" ring system is aryl, Q is —O—.

For example, in certain embodiments of the presently disclosed compounds, the ring system denoted by "A" is a phenyl. In one embodiment, y is 1 and $R^5$ is attached to the phenyl para to Q. In another embodiment, y is 1 and $R^5$ is selected from the group consisting of halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, and in which no ($C_0$-$C_4$ alkyl) or ($C_1$-$C_4$ alkyl) is substituted by an aryl, heteroaryl, cycloalkyl or heterocycloalkyl-containing group. $R^5$ can be, for example, —Cl, —F, cyano, —C(O)$CH_3$, —C(O) OH, —C(O)$NH_2$, trifluoromethyl, difluoromethyl, difluoromethoxy or trifluoromethoxy. In another embodiment, the

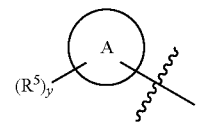

moiety is a 3,4-dihalophenyl.

In another embodiment of the presently disclosed compounds of structural formula (6-I), the ring system denoted by "A" is a heteroaryl. For example, in certain embodiments, the ring system denoted by "A" is a pyridyl, a thienyl, or a furanyl. In other embodiments, the ring system denoted by "A" is a pyrazolyl, imidazolyl, pyrrolyl, triazolyl or thiadiazolyl. In one embodiment, when the "A" ring system is heteroaryl, Q is a —($C_0$-$C_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. In certain embodiments, Q is —$CH_2$—; a single bond; —S(O)$_2$—; —C(O)—; or —CH($CH_3$)—. In another embodiment, when the "A" ring system is heteroaryl, Q is —O—.

In certain embodiments of the presently disclosed compounds of structural formula (6-I), the

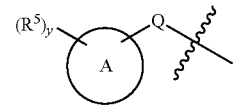

moiety is

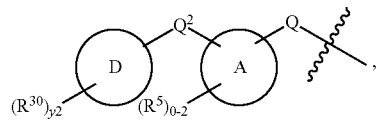

in which the ring system denoted by "A" is aryl or heteroaryl, the ring system denoted by "D" is cycloalkyl, heterocycloalkyl, aryl or heteroaryl; $Q^2$ is —S(O)$_2$—, —O— or —($C_0$-$C_3$ alkyl)- in which each carbon of the ($C_0$-$C_3$ alkyl) is optionally and independently substituted with one or two $R^{16}$, defined as described above with respect to Q; $y^2$ is 0, 1 or 2; and each $R^{30}$ is independently selected from is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O) $R^{10}$, —($C_0$-$C_3$ alkyl)-S(O)$_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, $Q^2$ has at most one $R^{16}$ or an oxo substituted thereon. $Q^2$ can be, for example, an unsubstituted —($C_0$-$C_3$ alkyl)-. In other embodiments, $Q^2$ is a ($C_1$-$C_3$ alkyl) having as its only substitution a single oxo group. For example, in certain embodiments, $Q^2$ is —$CH_2$—; a single bond; —$S(O)_2$—; —O—; —C(O)—; or —$CH(CH_3)$—. In certain embodiments, at least one $R^{30}$ is halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ or —C(O)—Hca in which the Hca contains a ring nitrogen atom through which it is bound to the —C(O)—, and in which no alkyl, haloalkyl or heterocycloalkyl is substituted by an aryl, heteroaryl, cycloalkyl or heterocycloalkyl-containing group. In certain embodiments, at least one $R^5$ is —$SO_2$($C_1$-$C_6$ alkyl), —$SO_2$($C_1$-$C_6$ haloalkyl), —$SO_2N$($C_0$-$C_6$ alkyl)($C_0$-$C_6$ alkyl), —$SO_2$($C_3$-$C_8$ cycloalkyl), —$SO_2$($C_3$-$C_8$ heterocycloalkyl), such as —$SO_2$Me, —$SO_2$Et, —$SO_2$Pr, —$SO_2$Bu, —$SO_2$cyclopropyl, —$SO_2$morphylinyl, $SO_2$pyrrolidinyl, $SO_2$NHEt, $SO_2$pyridyl or —$SO_2$phenyl. The number of substituents on the ring system denoted by "D", $y^2$, is 0, 1, or 2. For example, in some embodiments, $y^2$ is 0 or 1, for example 1. In other embodiments, $y^2$ is 0. $R^{30}$ can be further defined as described above with respect to $R^5$. In certain embodiments, the ring system denoted by "D" is cyclopropyl, morpholinyl, pyrazolyl, pyridyl, imidazolyl or phenyl, In certain embodiments, at least one $R^5$ is —$SO_2$($C_1$-$C_6$ alkyl), —$SO_2$($C_1$-$C_6$ haloalkyl), —$SO_2N$($C_0$-$C_6$ alkyl)$_2$, —$SO_2$($C_3$-$C_8$ cycloalkyl), —$SO_2$($C_3$-$C_8$ heterocycloalkyl), such as —$SO_2$Me, —$SO_2$Et, —$SO_2$Pr, —$SO_2$Bu, —$SO_2$cyclopropyl, —$SO_2$morphylinyl, $SO_2$pyrrolidinyl, $SO_2$NHEt, $SO_2$pyridyl or —$SO_2$phenyl.

In one embodiment of the presently disclosed compounds, the compound has structural formula (6-II):

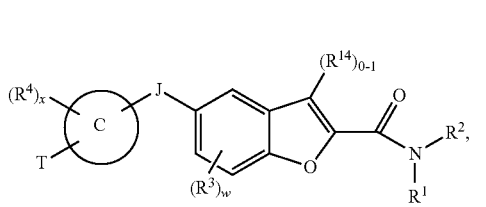

(6-II)

in which the variables are defined as described above with reference to structural formula (6-I). In certain embodiments, one $R^{14}$ is substituted on the furano carbon. In other embodiments, no $R^{14}$ is substituted on the furano carbon.

In another embodiment of the presently disclosed compounds, the compound has structural formula (6-III):

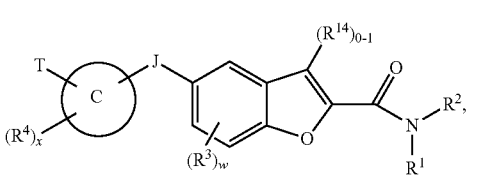

(6-III)

in which the variables are defined as described above with reference to structural formula (6-I). In certain embodiments, one $R^{14}$ is substituted on the furano carbon. In other embodiments, no $R^{14}$ is substituted on the furano carbon.

In one embodiment of the presently disclosed compounds, the compound has structural formula (6-IV):

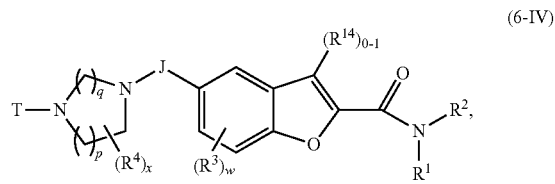

(6-IV)

in which the variables are defined as described above with reference to structural formula (6-I). In certain embodiments, J is a single bond, —C(O)— or —$CH_2$—. In certain embodiments, p is 1 and q is 2. In other embodiments, p is 1 and q is 1. In still other embodiments, q is 1 and p is 0.

In another embodiment of the presently disclosed compounds, the compound has structural formula (6-V):

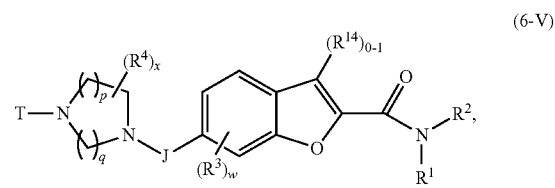

(6-V)

in which the variables are defined as described above with reference to structural formula (6-I). In certain embodiments, J is a single bond, —C(O)— or —$CH_2$—. In certain embodiments, p is 1 and q is 2. In other embodiments, p is 1 and q is 1. In still other embodiments, q is 1 and p is 0.

In one embodiment of the presently disclosed compounds, the compound has structural formula (6-VI):

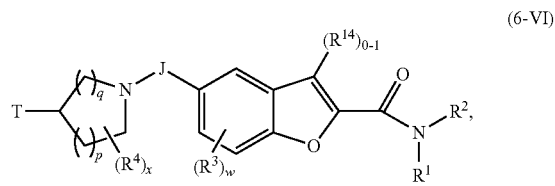

(6-VI)

in which the variables are defined as described above with reference to structural formula (6-I). In certain embodiments, J is —C(O)— or —$CH_2$—. In certain embodiments, p is 1 and q is 2. In other embodiments, p is 1 and q is 1. In still other embodiments, q is 1 and p is 0.

In another embodiment of the presently disclosed compounds, the compound has structural formula (6-VII):

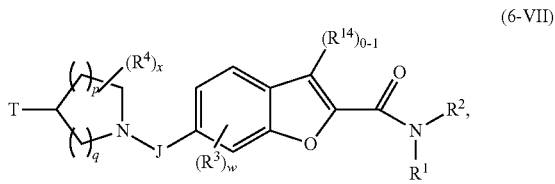

(6-VII)

in which the variables are defined as described above with reference to structural formula (6-I). In certain embodiments, J is —C(O)— or —$CH_2$—. In certain embodiments, p is 1 and q is 2. In other embodiments, p is 1 and q is 1. In still other embodiments, q is 1 and p is 0.

In one embodiment of the presently disclosed compounds, the compound has structural formula (6-VIII):

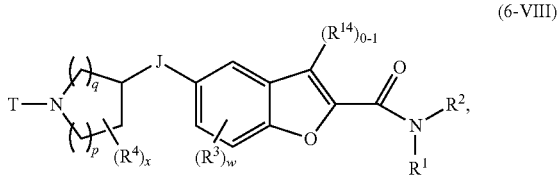

(6-VIII)

in which the variables are defined as described above with reference to structural formula (6-I). In certain embodiments, J is —C(O)—NH—, —NH—C(O)— or —CH₂—C(O)—NH—. In certain embodiments, p is 1 and q is 2. In other embodiments, p is 1 and q is 1. In still other embodiments, q is 1 and p is 0.

In another embodiment of the presently disclosed compounds, the compound has structural formula (6-IX):

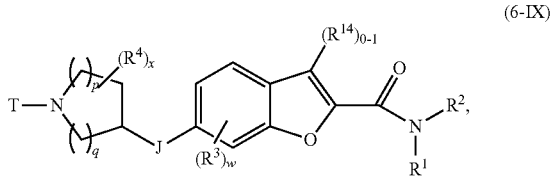

(6-IX)

in which the variables are defined as described above with reference to structural formula (6-I). In certain embodiments, J is —C(O)—NH—, or —NH—C(O)— or —CH₂—C(O)—NH—. In certain embodiments, p is 1 and q is 2. In other embodiments, p is 1 and q is 1. In still other embodiments, q is 1 and p is 0.

In certain embodiments of the presently disclosed compounds, the compound has structural formula (6-II) or (6-III), and the ring system denoted by "C" is heteroaryl, such as phenyl. For example, in one embodiment, the ring system denoted by "C" is a 1,4-phenylene. In certain such embodiments, J is —C(O)—NH—.

In certain embodiments of the presently disclosed compounds, the compound has structural formula (6-II) or (6-III), and the ring system denoted by "C" is heteroaryl, such as thiadiazole, pyrazole, isoxazole, pyridyl. For example, in one embodiment, the ring system denoted by "C" is a 1,2,3-thiadiazol-4,5-ylene, a 1H-pyrazol-1,4-ylene, a 4H-1,2,4-triazol-3,5-ylene, a isoxazol-3,5-ylene, a pyrid-2,5-ylene. In certain such embodiments, J is —C(O)—NH—.

In certain embodiments of the presently disclosed compounds, the compound has structural formula (6-II) or (6-III), and the ring system denoted by "C" is cycloalkyl, such as cyclohexyl, cyclopentyl, or cyclobutyl. For example, in one embodiment, the ring system denoted by "C" is a 1,4-cyclohexylene, a 1,3-cyclopentylene, or a 1,3-cyclobutylene. In certain embodiments, the cycloalkyl is substituted in a cis configuration. In other embodiments, the cycloalkyl is substituted in a trans configuration. In certain such embodiments, J is —C(O)—NH—.

In certain embodiments of the presently disclosed compounds of any of structural formulae (6-I)-(6-IX), $R^1$ is —H. In other embodiments, $R^1$ is ($C_1$-$C_4$ alkyl), for example methyl, ethyl, n-propyl or isopropyl. In still other embodiments, $R^1$ is —C(O)—($C_1$-$C_4$ alkyl), for example, acetyl or t-butylcarbonyl.

In certain embodiments of the presently disclosed compounds of any structural formulae (6-I)-(6-IX), $R^2$ is -Hca. In certain embodiments, $R^2$ is an optionally-substituted monocyclic heterocycloalkyl. In another embodiment, $R^2$ is not an oxo-substituted heterocycloalkyl.

In certain particular compounds disclosed herein having any of structural formulae (6-I)-(6-IX), $R^2$ is H.

In other particular compound disclosed herein of any of structural formulae (6-I)-(6-IX), $R^2$ is

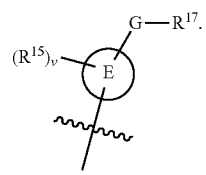

In certain such embodiments, the ring system denoted by "E" is heterocycloalkyl, such as azacycloalkyl. For example, in certain embodiments, the ring system denoted by "E" is azetidinyl, pyrrolidinyl, piperidinyl, or azepanyl. For example, the ring system denoted by "E" can be piperidinyl or pyrrolidinyl. In one embodiment, the ring system denoted by "E" is piperidinyl. In another embodiment, the ring system denoted by "E" is pyrrolidinyl.

In particular embodiments of the presently disclosed compounds of any of structural formulae (6-I)-(6-IX), the ring system denoted by "E" is azetidin-3-yl, piperidin-4-yl, pyrrolidin-3-yl or azepan-4-yl. For example, in one embodiment, the ring system denoted by "E" is piperidin-4-yl. In another embodiment, the ring system denoted by "E" is pyrrolidin-3-yl.

In certain embodiments of the presently disclosed compounds of any of structural formulae (6-I)-(6-IX), the azetidinyl, pyrrolidinyl, piperidinyl and azepanyl "E" ring systems described above are substituted at their 1-positions with the G-$R^{17}$.

In other embodiments of the presently disclosed compounds of any of structural formulae (6-I)-(6-IX), the ring system denoted by "E" is a phenyl, for example, a 1,4-phenylene.

In other embodiments of the presently disclosed compounds of any of structural formula (6-I)-(6-IX), the ring system denoted by "E" is a pyridyl, for example, a 2,5-pyridylene or a 3,6-pyridylene.

In certain embodiments, G is —CH₂—. In other embodiments, G is —C(O)— or —S(O)₂—. In other embodiments, G is —CH(CH₃)—. In other embodiments, G is —O—.

As described above, in certain embodiments, the ring system denoted by "A" is aryl or heteroaryl. In one embodiment, the ring system denoted by "A" is substituted with one or more electron-withdrawing groups. In another embodiment, $R^{17}$ is substituted with one or more electron-withdrawing groups. In certain embodiments, the ring system denoted by "A", $R^{17}$ or both are not substituted with an aryl, heteroaryl, cycloalkyl or heterocycloalkyl-containing group.

For example, in one embodiment, the G-$R^{17}$ moiety is —($C_0$-$C_3$ alkyl)-Ar or —($C_0$-$C_3$ alkyl)-Het, for example -(unsubstituted $C_0$-$C_3$ alkyl)-Ar or -(unsubstituted $C_0$-$C_3$ alkyl)-Het. For example, in one particular embodiment, the G-$R^{17}$ moiety is an optionally substituted benzyl or an optionally substituted phenyl. In another embodiment, the G-$R^{17}$ moiety is a benzyl substituted with an electron withdrawing group; or a pyridinylmethyl optionally substituted with an electron withdrawing group. For example, the benzyl or pyridinylmethyl can be substituted with an electron withdrawing group selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In other embodiments, the G-$R^{17}$ moiety is an unsubstituted benzyl or an unsubstituted phenyl.

In other embodiments of the compounds disclosed herein having any of structural formulae (6-I)-(6-IX), the G-$R^{17}$ moiety is an optionally substituted pyridinylmethyl, an optionally substituted furanylmethyl or an optionally substituted thienylmethyl. For example, the G-$R^{17}$ moiety can be an unsubstituted pyridinylmethyl, an unsubstituted furanylmethyl, or an unsubstituted thienylmethyl.

In other embodiments of the presently disclosed compounds of any of structural formulae (6-I)-(6-IX), the G-$R^{17}$ moiety is —C(O)—O($C_0$-$C_6$ alkyl), —C(O)-Het, —C(O)—Ar, —S(O)$_2$-Het, —S(O)$_2$—Ar or —S(O)$_2$—O($C_0$-$C_6$ alkyl).

In certain embodiments, Q and G are each independently a bond, —CH$_2$—, —C(H)($R^{16}$)—, —C($R^{16}$)$_2$)— or —S(O)$_2$—; v is 0, 1, 2, 3 or 4; each $R^{15}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —(($C_0$-$C_6$ alkyl)-S(O)$_{0-2}$R$^{10}$, -halogen, —NO$_2$ and —CN, and two $R^{15}$ on the same carbon optionally combine to form oxo; $R^{17}$ is Het or Ar, and all other variables are defined as described above with reference to structural formulae (6-I)-(6-IX). $R^{17}$ can be, for example, an optionally substituted phenyl, an optionally-substituted pyridyl, an optionally substituted pyrazolyl, an optionally substituted imidazolyl, an optionally substituted pyrrolyl, an optionally substituted triazolyl or an optionally substituted thiadiazolyl. In one embodiment, Q is a single bond. In another embodiment, Q is —CH$_2$—. In other embodiments, Q is —C(O)— or —S(O)$_2$—. In certain embodiments, G is —CH$_2$—. In other embodiments, G is —C(O)— or —S(O)$_2$—. In other embodiments, G is —CH(CH$_3$)—. For example, in one embodiment, Q i)s a single bond and G is —CH$_2$— or —C(O)—. As described above, in certain embodiments, the ring system denoted by "A" is aryl or heteroaryl. In one embodiment, the ring system denoted by "A" is substituted with one or more electron-withdrawing groups. In another embodiment, $R^{17}$ is substituted with one or more electron-withdrawing groups. In certain embodiments, the ring system denoted by "A", $R^{17}$ or both are not substituted with an aryl, heteroaryl, cycloalkyl or heterocycloalkyl-containing group.

In the presently disclosed compounds of structural formulae (6-I)-(6-IX), v is 0, 1, 2, 3 or 4. In one embodiment, v is 0, 1, 2 or 3. For example, v can be 0, or can be 1 or 2.

In certain embodiments of the presently disclosed compounds of structural formulae (6-I)-(6-IX), two $R^{15}$s combine to form an oxo. The oxo can be bound, for example, at the position alpha to the nitrogen of the azacycloalkyl ring. In other embodiments, no two $R^{15}$s combine to form an oxo.

In certain embodiments of the presently disclosed compounds of structural formulae (6-I)-(6-IX), when v is 4, not all four $R^{15}$ moieties are ($C_1$-$C_6$ alkyl).

In certain embodiments of the presently disclosed compounds of structural formulae (6-I)-(6-IX), each $R^{15}$ is independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN and two $R^{15}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-NR$^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{15}$ is —($C_1$-$C_3$ alkyl), —($C_1$-$C_3$ haloalkyl), —($C_0$-$C_3$ alkyl)-L-$R^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN and two $R^{15}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-NR$^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In some embodiments, one $R^{15}$ is —C(O)NR$^9$R$^7$, which can be bound, for example, at a position alpha to the piperidine nitrogen, or at the position linked to the —N(R$^1$)—.

In certain embodiments of the presently disclosed compounds of structural formulae (6-I)-(6-IX), $R^{17}$ is an unsubstituted aryl or heteroaryl. In other embodiments, the $R^{17}$ Ar or Het is substituted with 1, 2 or 3 substituents independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-NR$^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, the $R^{17}$ Ar or Het is substituted with 1, 2 or 3 substituents independently selected from —($C_1$-$C_3$ alkyl), —($C_1$-$C_3$ haloalkyl), —($C_0$-$C_3$ alkyl)-L-$R^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-NR$^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, $R^{17}$ is substituted with 1, 2 or 3 substituents selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), NO$_2$ and —C(O)—Hca. $R^{17}$ can be substituted with, for example, one such substituent, or two such substituents. In certain embodiments, $R^{12}$ is substituted with a substitutent -G$^2$-R$^{34}$, in which G$^2$ is a single bond, —O—, —C(O)—, —S(O)$_2$— or —CH$_2$—, and R$^{34}$ is a chosen from aryl (such as phenyl), heterocycloalkyl (such as morpholinyl, pyrrolidinyl), and heteroaryl (such as), each of which is optionally substituted with 1 or 2 substituents selected from aryl, ($C_1$-$C_4$ haloalkyl), —O—($C_1$-$C_4$ haloalkyl), ($C_1$-$C_4$ alkyl), —O—($C_1$-$C_4$ alkyl), halogen, or CN.

In the compounds of any of structural formulae (6-I)-(6-IX), w is 0, 1, 2 or 3. For example, in one embodiment, w is 0, 1 or 2. In another embodiment, w is 0. In other embodiments, w is at least 1, and at least one $R^3$ is selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In certain embodiments, an $R^3$ is substituted on the benzofuran at a ring position meta to the J moiety.

In certain embodiments of the compounds of any of structural formulae (6-I)-(6-IX), each $R^3$ is independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-NR$^9$($C_0$-$C_6$ alkyl), —($C_0$-$C_6$ alkyl)-O—($C_0$-$C_6$alkyl), —($C_0$-$C_6$alkyl)-C(O)—($C_0$-$C_6$alkyl), and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^3$ is —($C_1$-$C_3$ alkyl), —($C_1$-$C_3$ haloalkyl), —($C_0$-$C_3$ alkyl)-L-$R^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-NR$^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group.

In certain embodiments of the compounds of any of structural formulae (6-I)-(6-IX), w is at least one, and at least one $R^3$ is —NR$^8$R$^9$. For example, in one embodiment, w is 1. In certain such embodiments, $R^3$ is substituted on the benzofuran at a ring position meta to the J moiety.

In other embodiments of the compounds of any of structural formulae (6-I)-(6-IX), w is at least one, and at least one $R^3$ is —($C_0$-$C_3$ alkyl)-$Y^1$—($C_1$-$C_3$ alkyl)-$Y^2$—($C_0$-$C_3$ alkyl), in which each of $Y^1$ and $Y^2$ is independently L, —O—, —S— or —NR$^9$—. For example, in one embodiment, w is 1. In certain such embodiments, $R^3$ is substituted on the benzofuran at a ring position meta to the J moiety. In one particular embodiment, $R^3$ is —CH$_2$—N(CH$_3$)—CH$_2$—C(O)—OCH$_3$.

In the presently disclosed compounds of any of structural formulae (6-I)-(6-IX), the number of substituents on the "C" ring system, x, is 0, 1, 2, 3 or 4. In one embodiment, x is 0, 1, 2 or 3. For example, x can be 0, or can be 1 or 2.

In certain embodiments of the presently disclosed compounds of any of structural formula (6-I)-(6-IX), two $R^4$s combine to form an oxo. The oxo can be bound, for example, at the position alpha to the nitrogen of an azacycloalkyl "C" ring system. In other embodiments, no two $R^4$s combine to form an oxo.

In certain embodiments of the presently disclosed compounds of any of structural formulae (6-I)-(6-IX), when x is 4, not all four $R^4$ moieties are ($C_1$-$C_6$ alkyl).

In certain embodiments of the presently disclosed compounds of any of structural formulae (6-I)-(6-IX), each $R^4$ is independently selected from —($C_1$-$C_6$ alkyl), —($C_1$-$C_6$ haloalkyl) (e.g., trifluoromethyl), —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}$R$^{10}$, -halogen, —NO$_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-NR$^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^4$ is —($C_1$-$C_3$ alkyl), —($C_1$-$C_3$ haloalkyl), —($C_0$-$C_3$ alkyl)-L-$R^7$, —($C_0$-$C_3$ alkyl)-NR$^8$R$^9$, —($C_0$-$C_3$ alkyl)-OR$^{10}$, —($C_0$-$C_3$ alkyl)-C(O)R$^{10}$, —($C_0$-$C_3$ alkyl)-S(O)$_{0-2}$R$^{10}$, -halogen, —NO$_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-NR$^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group.

In certain embodiments, the presently disclosed compounds have the structural formula (6-X):

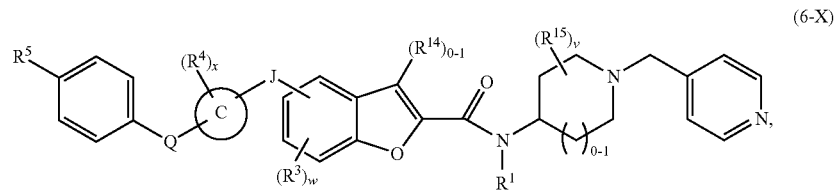

(6-X)

in which all variables are as described above with respect to structural formulae (6-I)-(6-IX)

In certain embodiments, the presently disclosed compounds have the structural formula (6-XI):

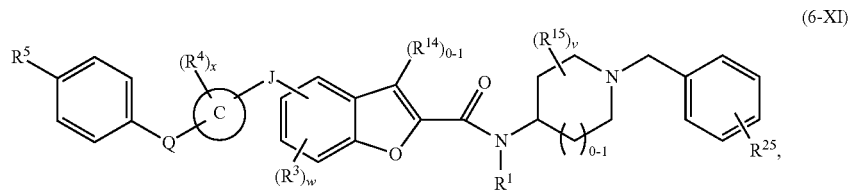

(6-XI)

in which $R^{25}$ is selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)—Hca in which the Hca contains a ring nitrogen atom through which it is bound to the —C(O)—, in which no alkyl or haloalkyl is substituted by an aryl, heteroaryl, cycloalkyl or heterocycloalkyl-containing group; and all other variables are as described above with respect to structural formulae (6-I)-(6-IX). $R^{25}$ can be, for example, —Cl, —F, cyano, —C(O)$CH_3$, —C(O)OH, —C(O)$NH_2$, trifluoromethyl, difluoromethyl, difluoromethoxy or trifluoromethoxy.

One aspect of the disclosure provides compounds of structural formulae (6-I)-(6-IX) in which x is 1 and $R^4$ is F. For example, in certain embodiments of compounds having structural formulae (6-VI)-(6-IX), the azacycloalkyl ring between the J moiety and the T moiety has a. The fluorine can be, for example, at a position beta to the azacycloalkyl nitrogen. For example, the azacycloalkyl can be a 3-fluoropiperidin-1,4-yl. In one embodiment, the 3-fluoro and the 4-substituent (i.e., the T moiety in compounds of structural formulae (6-VI) and (6-VII), or the J moiety in compounds of structural formulae (6-VI) and (6-VII)) are substituted in a cis manner on the piperidine. In other embodiments, the 3-fluoro and the 4-substituent are substituted in a trans manner on the piperidine. For example in one embodiment, the piperidine moiety has the structure

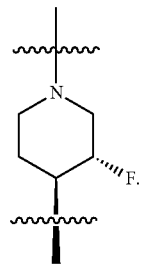

Such compounds can be provided in racemic form, in enantiomerically enriched form, or in substantially enantiomerically pure form.

In certain embodiments of compounds having structural formula (6-I), the $R^2$ moiety has the structure

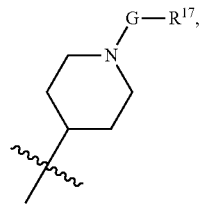

in which G is —$CH_2$—, —CH($CH_3$)—, —C(O)— or —S($O)_2$—. For example, in one embodiment, G is —$CH_2$—. In another embodiment, G is —C(O)— or —S$(O)_2$—.

In certain embodiments, the presently disclosed compounds have the structural formula (6-XII) or (6-XIII):

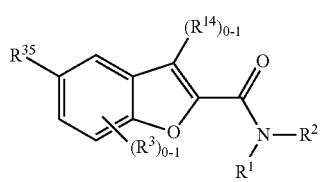
(6-XII)

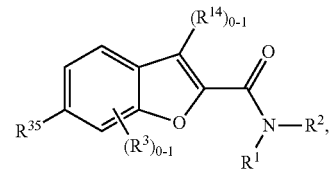
(6-XIII)

in which $R^{35}$ is selected from any of structural formulae (6-XIV)-(6-XXIII)

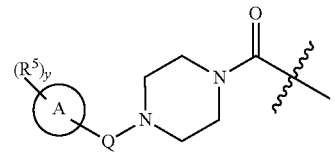
(6-XIV)

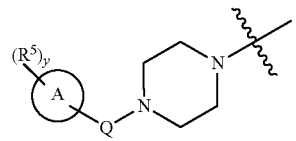
(6-XV)

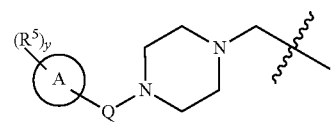
(6-XVI)

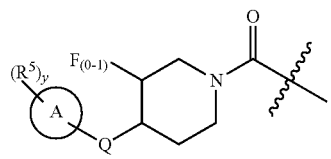
(6-XVII)

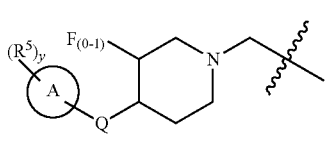
(6-XVIII)

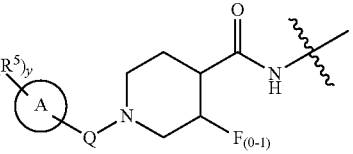
(6-XIX)

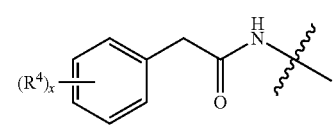
(6-XX)

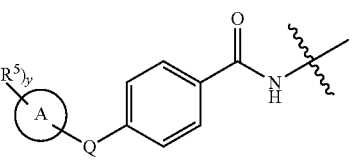
(6-XXI)

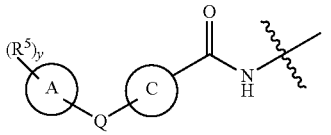

(in which the ring system denoted by "C" is heteroaryl or cycloalkyl) (6-XXII)

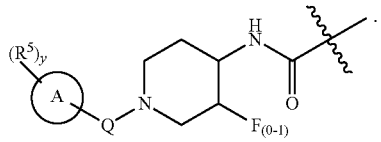
(6-XXIII)

In certain such embodiments, $R^2$ is selected from any of structural formulae (6-XXIV)-(6-XXIX).

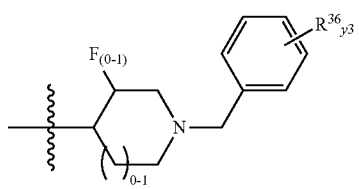
(6-XXIV)

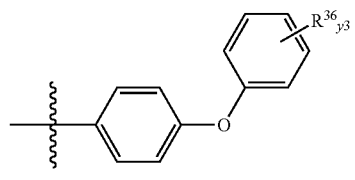
(6-XXV)

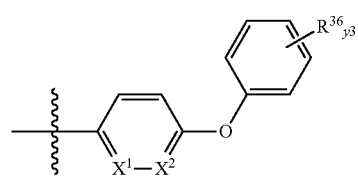
XXVI)

in which one of $X^1$ and $X^2$ is N and the other is CH (6

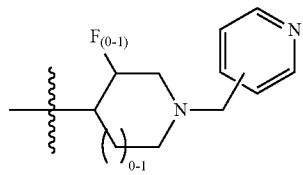
(6-XXVIII)

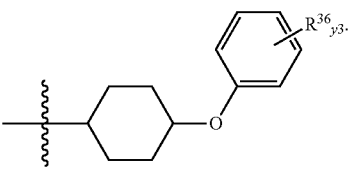
(6-XXIX)

In other such embodiments, $R^1$ and $R^2$ together with the N to which they are bound together form structure (6-XXX)

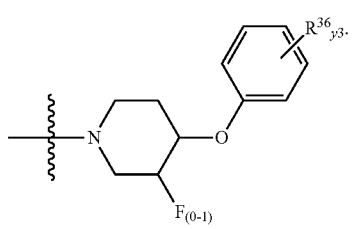
(6-XXX)

In the above-described embodiments, y3 is 0, 1, 2 or 3 (for example, 0, or 1), and each $R^{36}$ is independently selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$($C_1$-$C_4$ alkyl), —S(O)$_2$Hca, —O-aryl, —O-heteroaryl, —C(O)-aryl, —C(O)-heteroaryl, -aryl, -heteroaryl, —SF$_5$, NO$_2$ and —C(O)—Hca in which the Hca contains a ring nitrogen atom through which it is bound to the —C(O)—, in which no alkyl or haloalkyl is substituted by an aryl, heteroaryl, cycloalkyl or heterocycloalkyl-containing group; and all other variables are as described above with respect to structural formulae (6-I)-(6-IX). Each $R^{36}$ can be, for example, —Cl, —F, cyano, —C(O)CH$_3$, —C(O)OH, —C(O)NH$_2$, trifluoromethyl, difluoromethyl, difluoromethoxy, trifluoromethoxy, pentafluoroethoxy, tetrafluoroethoxy, methoxy, S(O)$_2$Me, S(O)$_2$-(1-pyrrolidinyl), 1-pyrazolyl, methyl, or —SF$_5$.

Examples of compounds according to structural formula (6-I) include those listed below in Table 6. These compounds can be made, for example using a procedure analogous to those described in U.S. Patent Application Publications nos. 2009/0163511, 2009/0170829, 2009/0186894 and 2009/0275609, and in U.S. patent application Ser. Nos. 12/695,861 and 13/194,810, each of which is hereby incorporated by reference in its entirety.

TABLE 6

| No. | Name | Structure |
|---|---|---|
| 6-1 | N-(1-(4-cyanobenzyl)piperidin-4-yl)-5-(4-(4-(methylsulfonyl)benzyl)piperazin-1-yl)benzofuran-2-carboxamide | 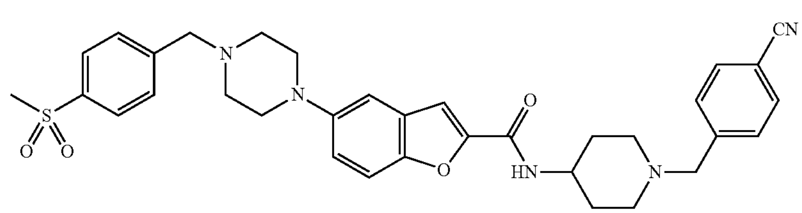 [SMILES: CS(=O)(=O)c1ccc(CN2CCN(c3ccc4oc(C(=O)NC5CCN(Cc6ccc(C#N)cc6)CC5)cc4c3)CC2)cc1] |

TABLE 6-continued

| No. | Name | Structure |
|---|---|---|
| 6-2 | N-(1-(4-cyanobenzyl)piperidin-4-yl)-6-(4-(4-(methylsulfonyl)benzyl)piperazine-1-carbonyl)benzofuran-2-carboxamide | 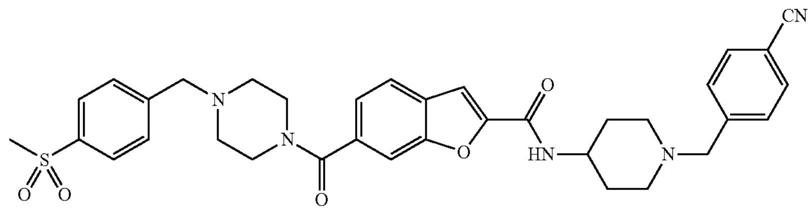 [SMILES: CS(=O)(=O)c1ccc(CN2CCN(C(=O)c3ccc4cc(C(=O)NC5CCN(Cc6ccc(C#N)cc6)CC5)oc4c3)CC2)cc1] |
| 6-3 | N-(1-(4-methoxybenzyl)piperidin-4-yl)-6-(4-(4-(methylsulfonyl)benzyl)piperazine-1-carbonyl)benzofuran-2-carboxamide | 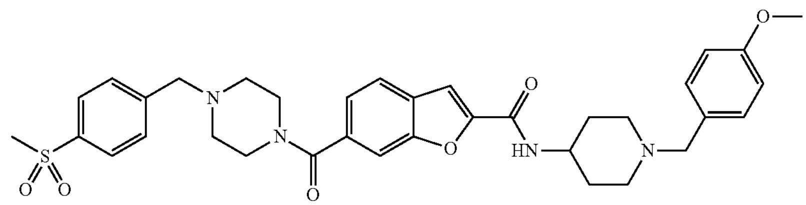 |
| 6-4 | 6-(4-(4-(methylsulfonyl)benzyl)piperazine-1-carbonyl)-N-(1-(4-(trifluoromethoxy)benzyl)piperidin-4-yl)benzofuran-2-carboxamide | 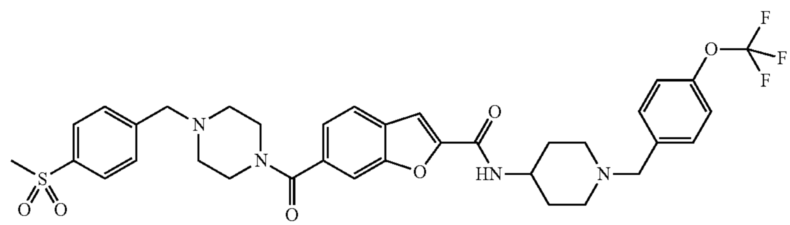 [SMILES: CS(=O)(=O)c1ccc(CN2CCN(C(=O)c3ccc4cc(C(=O)NC5CCN(Cc6ccc(OC(F)(F)F)cc6)CC5)oc4c3)CC2)cc1] |
| 6-5 | N-(1-(3-fluoro-4-methoxybenzyl)piperidin-4-yl)-6-(4-(4-(methylsulfonyl)benzyl)piperazine-1-carbonyl)benzofuran-2-carboxamide | 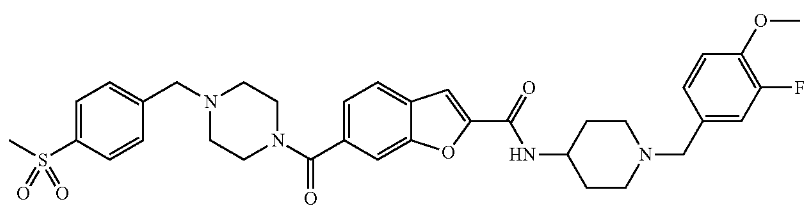 [SMILES: COc1ccc(CN2CCC(NC(=O)c3cc4ccc(C(=O)N5CCN(Cc6ccc(S(C)(=O)=O)cc6)CC5)cc4o3)CC2)cc1F] |
| 6-6 | N-(6-(4-acetylphenoxy)pyridin-3-yl)-6-(4-(4-(methylsulfonyl)benzyl)piperazine-1-carbonyl)benzofuran-2-carboxamide | 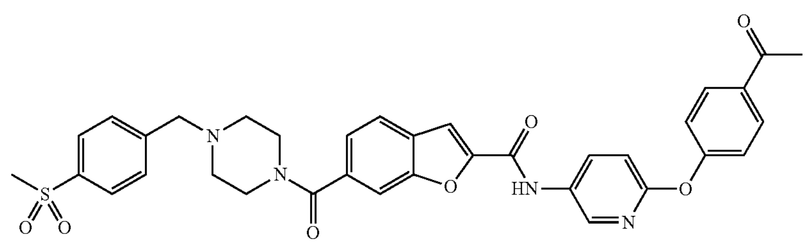 [SMILES: CC(=O)c1ccc(Oc2ccc(NC(=O)c3cc4ccc(C(=O)N5CCN(Cc6ccc(S(C)(=O)=O)cc6)CC5)cc4o3)cn2)cc1] |
| 6-7 | 6-(4-(4-(methylsulfonyl)benzyl)piperazine-1-carbonyl)-N-(1-(4-(1,1,2,2-tetrafluoroethoxy)benzyl)piperidin-4-yl)benzofuran-2-carboxamide | 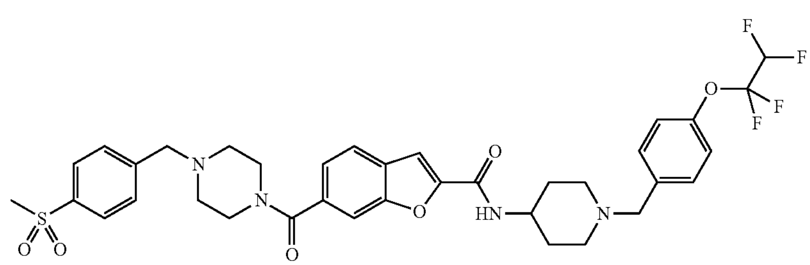 [SMILES: CS(=O)(=O)c1ccc(CN2CCN(C(=O)c3ccc4cc(C(=O)NC5CCN(Cc6ccc(OC(F)(F)C(F)F)cc6)CC5)oc4c3)CC2)cc1] |
| 6-8 | N-(6-(4-cyanophenoxy)pyridin-3-yl)-6-(4-(4-(methylsulfonyl)benzyl)piperazine-1-carbonyl)benzofuran-2-carboxamide | 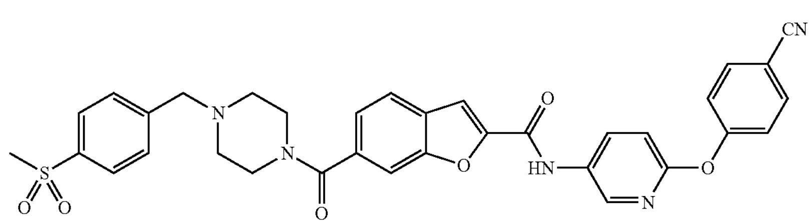 [SMILES: CS(=O)(=O)c1ccc(CN2CCN(C(=O)c3ccc4cc(C(=O)Nc5ccc(Oc6ccc(C#N)cc6)nc5)oc4c3)CC2)cc1] |

TABLE 6-continued

| No. | Name | Structure |
| --- | --- | --- |
| 6-9 | N-(1-(4-cyanobenzyl)piperidin-4-yl)-5-(4-(4-(methylsulfonyl)phenyl)piperazin-1-yl)benzofuran-2-carboxamide | 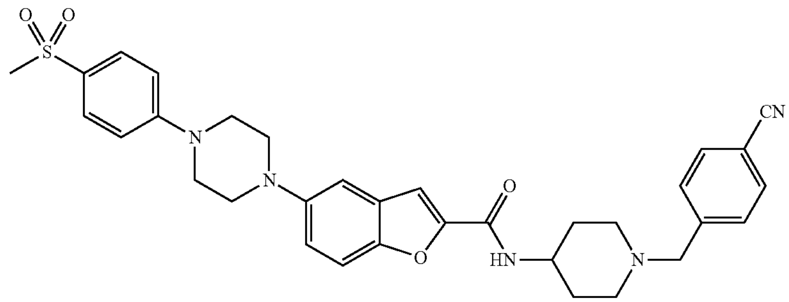 [SMILES: CS(=O)(=O)c1ccc(N2CCN(c3ccc4oc(C(=O)NC5CCN(Cc6ccc(C#N)cc6)CC5)cc4c3)CC2)cc1] |
| 6-10 | N-(1-(4-cyanobenzyl)piperidin-4-yl)-5-(4-(4-(methylsulfonyl)benzyl)piperazin-1-yl)benzofuran-2-carboxamide | 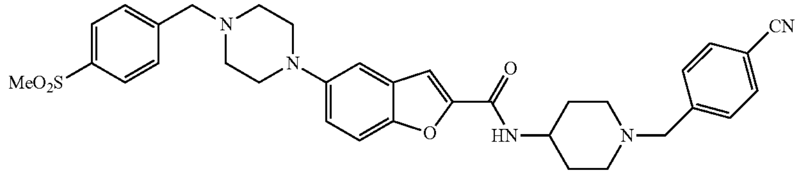 [SMILES: CS(=O)(=O)c1ccc(CN2CCN(c3ccc4oc(C(=O)NC5CCN(Cc6ccc(C#N)cc6)CC5)cc4c3)CC2)cc1] |
| 6-11 | N-(1-(4-cyanobenzyl)piperidin-4-yl)-5-(4-(4-fluorobenzyl)piperazine-1-carbonyl)benzofuran-2-carboxamide | 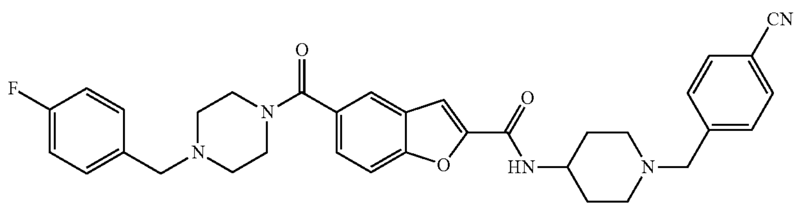 [SMILES: N#Cc1ccc(CN2CCC(NC(=O)c3cc4cc(C(=O)N5CCN(Cc6ccc(F)cc6)CC5)ccc4o3)CC2)cc1] |
| 6-12 | 5-(4-(4-fluorobenzyl)piperazine-1-carbonyl)-N-(4-phenoxyphenyl)benzofuran-2-carboxamide | 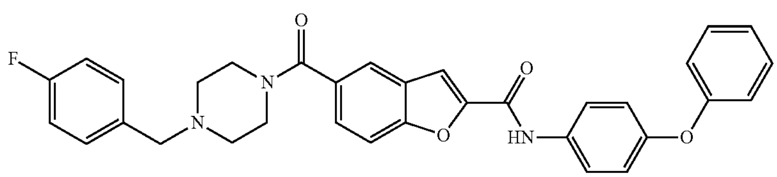 [SMILES: O=C(Nc1ccc(Oc2ccccc2)cc1)c1cc2cc(C(=O)N3CCN(Cc4ccc(F)cc4)CC3)ccc2o1] |
| 6-13 | N-(1-(4-cyanobenzyl)piperidin-4-yl)-5-((4-(4-fluorobenzyl)piperazin-1-yl)methyl)benzofuran-2-carboxamide | 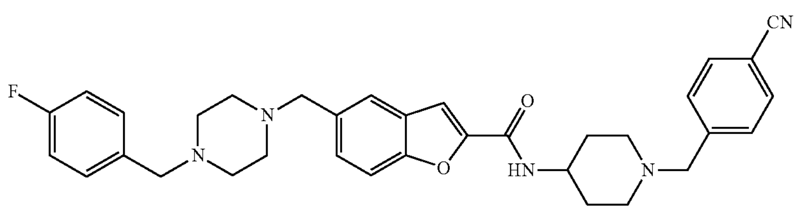 [SMILES: N#Cc1ccc(CN2CCC(NC(=O)c3cc4cc(CN5CCN(Cc6ccc(F)cc6)CC5)ccc4o3)CC2)cc1] |
| 6-14 | N-(1-(4-cyanobenzyl)piperidin-4-yl)-5-((4-(4-cyanophenoxy)piperidin-1-yl)methyl)benzofuran-2-carboxamide | 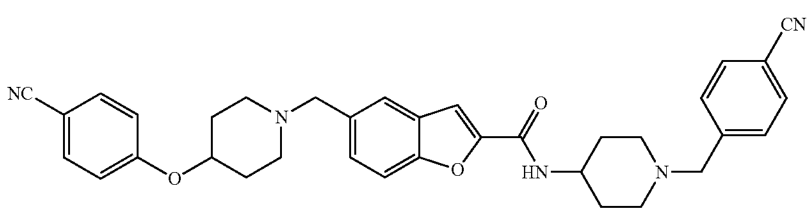 [SMILES: N#Cc1ccc(CN2CCC(NC(=O)c3cc4cc(CN5CCC(Oc6ccc(C#N)cc6)CC5)ccc4o3)CC2)cc1] |
| 6-15 | 5-(4-(4-fluorobenzoyl)piperidine-1-carbonyl)-N-(1-(pyridin-4-ylmethyl)piperidin-4-yl)benzofuran-2-carboxamide | 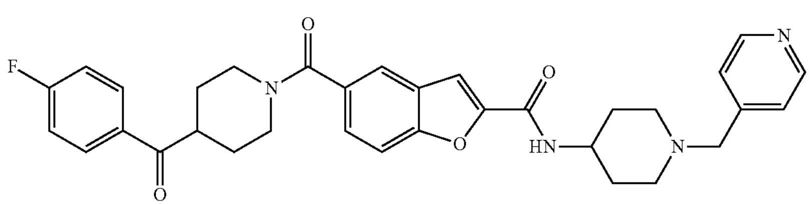 [SMILES: O=C(NC1CCN(Cc2ccncc2)CC1)c1cc2cc(C(=O)N3CCC(C(=O)c4ccc(F)cc4)CC3)ccc2o1] |

TABLE 6-continued

| No. | Name | Structure |
|---|---|---|
| 6-16 | N-(1-(4-cyanobenzyl)piperidin-4-yl)-5-(4-(4-fluorobenzoyl)piperidine-1-carbonyl)benzofuran-2-carboxamide | 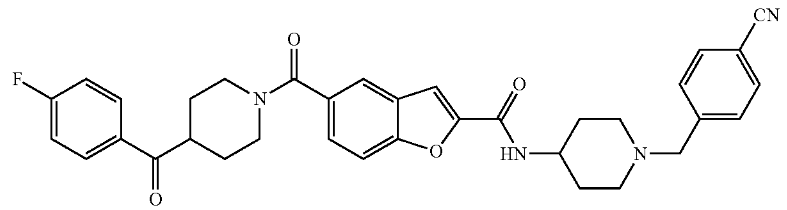 [SMILES: N#Cc1ccc(CN2CCC(NC(=O)c3cc4cc(C(=O)N5CCC(C(=O)c6ccc(F)cc6)CC5)ccc4o3)CC2)cc1] |
| 6-17 | N-(6-(4-cyanophenoxy)pyridin-3-yl)-5-(4-(4-fluorobenzoyl)piperidine-1-carbonyl)benzofuran-2-carboxamide | 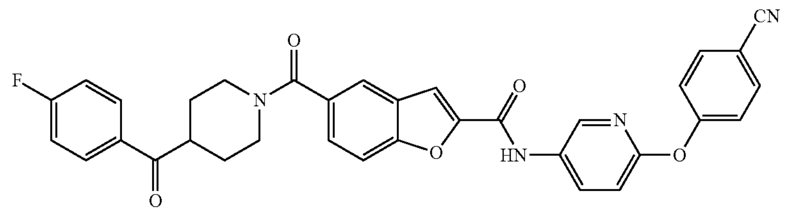 [SMILES: N#Cc1ccc(Oc2ccc(NC(=O)c3cc4cc(C(=O)N5CCC(C(=O)c6ccc(F)cc6)CC5)ccc4o3)cn2)cc1] |
| 6-18 | 5-(4-(4-fluorophenoxy)piperidine-1-carbonyl)-N-(1-(pyridin-4-ylmethyl)piperidin-4-yl)benzofuran-2-carboxamide | 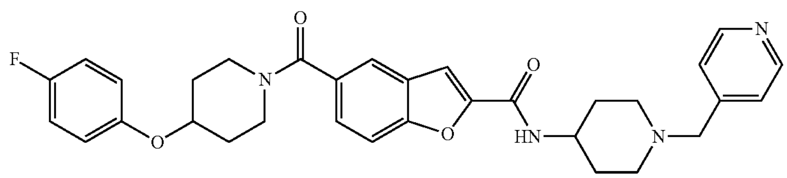 [SMILES: O=C(NC1CCN(Cc2ccncc2)CC1)c1cc2cc(C(=O)N3CCC(Oc4ccc(F)cc4)CC3)ccc2o1] |
| 6-19 | N-(1-(4-cyanobenzyl)piperidin-4-yl)-5-(4-(4-fluorophenoxy)piperidine-1-carbonyl)benzofuran-2-carboxamide | 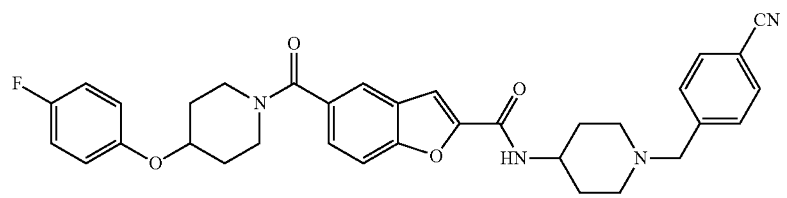 [SMILES: N#Cc1ccc(CN2CCC(NC(=O)c3cc4cc(C(=O)N5CCC(Oc6ccc(F)cc6)CC5)ccc4o3)CC2)cc1] |
| 6-20 | 5-(4-(4-fluorophenoxy)piperidine-1-carbonyl)-N-(6-(4-fluorophenoxy)pyridin-3-yl)benzofuran-2-carboxamide | 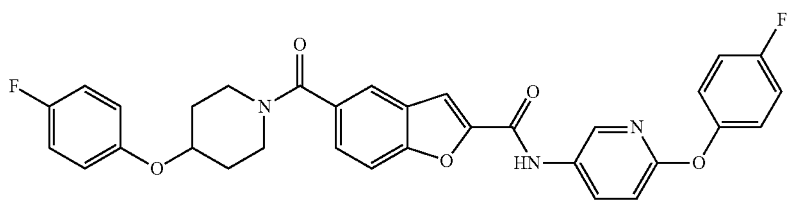 [SMILES: O=C(Nc1ccc(Oc2ccc(F)cc2)nc1)c1cc2cc(C(=O)N3CCC(Oc4ccc(F)cc4)CC3)ccc2o1] |
| 6-21 | 1-(4-cyanophenyl)-N-(2-(1-(4-methoxybenzyl)piperidin-4-ylcarbamoyl)benzofuran-5-yl)piperidine-4-carboxamide | 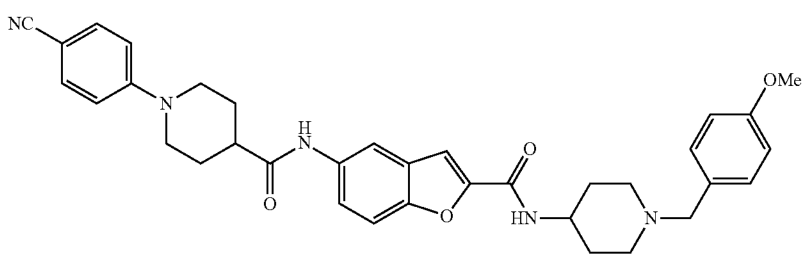 [SMILES: COc1ccc(CN2CCC(NC(=O)c3cc4cc(NC(=O)C5CCN(c6ccc(C#N)cc6)CC5)ccc4o3)CC2)cc1] |
| 6-22 | 1-(4-cyanophenyl)-N-(2-(4-(4-(trifluoromethyl)phenoxy)piperidine-1-carbonyl)benzofuran-5-yl)piperidine-4-carboxamide | 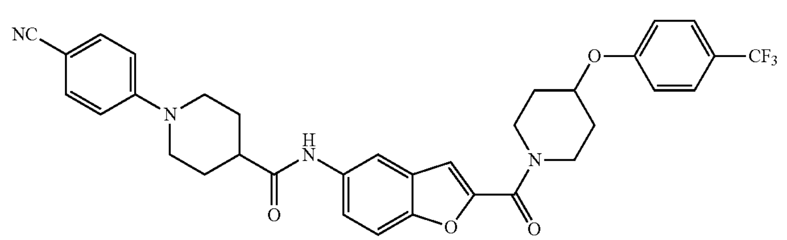 [SMILES: N#Cc1ccc(N2CCC(C(=O)Nc3ccc4oc(C(=O)N5CCC(Oc6ccc(C(F)(F)F)cc6)CC5)cc4c3)CC2)cc1] |

TABLE 6-continued

| No. | Name | Structure |
|---|---|---|
| 6-23 | 5-(4-(4-fluorophenoxy)benzamido)-N-(1-(4-methoxybenzyl)piperidin-4-yl)benzofuran-2-carboxamide | 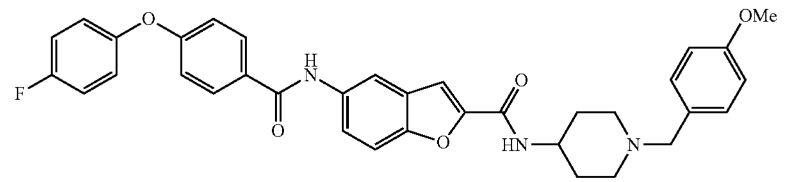 [SMILES: COc1ccc(CN2CCC(NC(=O)c3cc4cc(NC(=O)c5ccc(Oc6ccc(F)cc6)cc5)ccc4o3)CC2)cc1] |
| 6-24 | 4-(4-fluorophenoxy)-N-(2-(4-(4-(trifluoromethyl)phenoxy)piperidine-1-carbonyl)benzofuran-5-yl)benzamide | 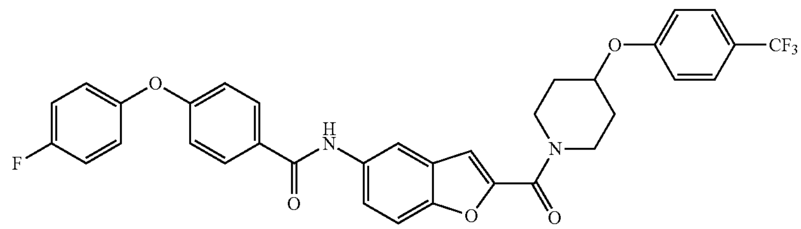 [SMILES: O=C(Nc1ccc2oc(C(=O)N3CCC(Oc4ccc(C(F)(F)F)cc4)CC3)cc2c1)c1ccc(Oc2ccc(F)cc2)cc1] |
| 6-25 | N-(1-(4-methoxybenzyl)piperidin-4-yl)-5-(4-(4-(trifluoromethyl)phenoxy)piperidine-1-carbonyl)benzofuran-2-carboxamide | 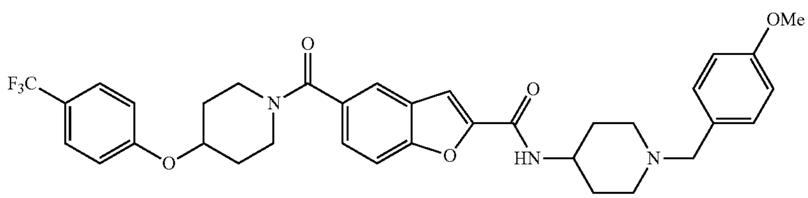 [SMILES: COc1ccc(CN2CCC(NC(=O)c3cc4cc(C(=O)N5CCC(Oc6ccc(C(F)(F)F)cc6)CC5)ccc4o3)CC2)cc1] |
| 6-26 | N-(6-(4-fluorophenoxy)pyridin-3-yl)-5-(4-(4-(trifluoromethyl)phenoxy)piperidine-1-carbonyl)benzofuran-2-carboxamide | 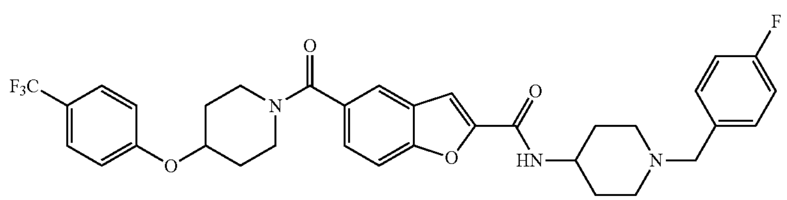 [SMILES: O=C(NC1CCN(Cc2ccc(F)cc2)CC1)c1cc2cc(C(=O)N3CCC(Oc4ccc(C(F)(F)F)cc4)CC3)ccc2o1] |
| 6-27 | N-(1-(4-cyanobenzyl)piperidin-4-yl)-5-((4-(4-(trifluoromethyl)phenoxy)piperidin-1-yl)methyl)benzofuran-2-carboxamide | 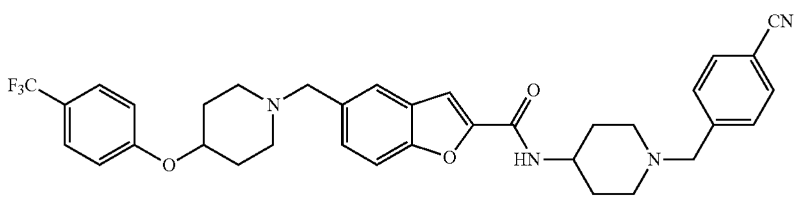 [SMILES: N#Cc1ccc(CN2CCC(NC(=O)c3cc4cc(CN5CCC(Oc6ccc(C(F)(F)F)cc6)CC5)ccc4o3)CC2)cc1] |
| 6-28 | N-(1-(3,5-difluorobenzyl)piperidin-4-yl)-5-((4-(4-(trifluoromethyl)phenoxy)piperidin-1-yl)methyl)benzofuran-2-carboxamide | 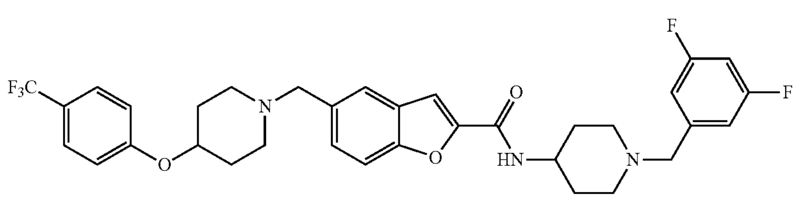 [SMILES: O=C(NC1CCN(Cc2cc(F)cc(F)c2)CC1)c1cc2cc(CN3CCC(Oc4ccc(C(F)(F)F)cc4)CC3)ccc2o1] |
| 6-29 | N-(6-(4-fluorophenoxy)pyridin-3-yl)-5-((4-(4-(trifluoromethyl)phenoxy)piperidin-1-yl)methyl)benzofuran-2-carboxamide | 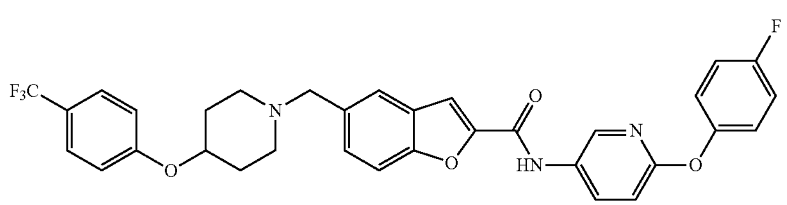 [SMILES: O=C(Nc1ccc(Oc2ccc(F)cc2)nc1)c1cc2cc(CN3CCC(Oc4ccc(C(F)(F)F)cc4)CC3)ccc2o1] |
| 6-30 | N-(1-(4-cyanobenzyl)piperidin-4-yl)-5-(4-(4-(trifluoromethyl)phenoxy)piperidine-1-carbonyl)benzofuran-2-carboxamide | 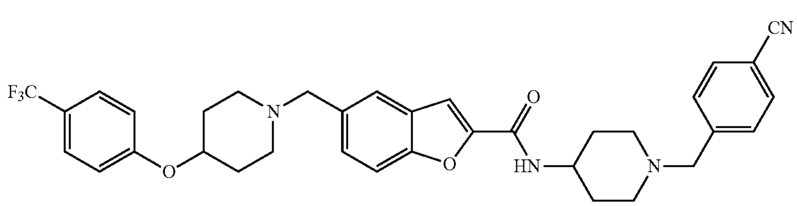 [SMILES: N#Cc1ccc(CN2CCC(NC(=O)c3cc4cc(CN5CCC(Oc6ccc(C(F)(F)F)cc6)CC5)ccc4o3)CC2)cc1] |

TABLE 6-continued

| No. | Name |
|---|---|
| 6-31 | N-((1s,4s)-4-(4-cyanophenoxy)cyclohexyl)-5-(4-(4-(trifluoromethyl)phenoxy)piperidine-1-carbonyl)benzofuran-2-carboxamide |
| 6-32 | N-(2-(1-(4-cyanobenzyl)piperidin-4-ylcarbamoyl)benzofuran-5-yl)piperidine-4-carboxamide |
| 6-33 | N-(2-(1-(4-cyanobenzyl)piperidin-4-ylcarbamoyl)benzofuran-5-yl)-1-(pyridin-2-yl)piperidine-4-carboxamide |
| 6-34 | N-(2-(1-(4-cyanobenzyl)piperidin-4-ylcarbamoyl)benzofuran-5-yl)-1-(pyridin-2-ylmethyl)piperidine-4-carboxamide |
| 6-35 | N-(2-(1-(4-cyanobenzyl)piperidin-4-ylcarbamoyl)benzofuran-5-yl)-1-(pyridin-3-ylmethyl)piperidine-4-carboxamide |
| 6-36 | N-(2-(1-(4-cyanobenzyl)piperidin-4-ylcarbamoyl)benzofuran-5-yl)-1-(cyclopropylmethyl)piperidine-4-carboxamide |
| 6-37 | N-(2-(1-(4-cyanobenzyl)piperidin-4-ylcarbamoyl)benzofuran-5-yl)-1-((1-methyl-1H-pyrrol-2-yl)methyl)piperidine-4-carboxamide |

TABLE 6-continued

| No. | Name |
|---|---|
| 6-38 | N-(2-(1-(4-cyanobenzyl)piperidin-4-ylcarbamoyl)benzofuran-5-yl)-1-((1-methyl-1H-imidazol-2-yl)methyl)piperidine-4-carboxamide |
| 6-39 | N-(2-(1-(4-cyanobenzyl)piperidin-4-ylcarbamoyl)benzofuran-5-yl)-1-(4-(pyrrolidin-1-yl)benzyl)piperidine-4-carboxamide |
| 6-40 | N-(2-(1-(4-cyanobenzyl)piperidin-4-ylcarbamoyl)benzofuran-5-yl)-1-(4-methoxybenzyl)piperidine-4-carboxamide |
| 6-41 | N-(2-(1-(4-cyanobenzyl)piperidin-4-ylcarbamoyl)benzofuran-5-yl)-1-((1-(pyridin-2-yl)-1H-pyrazol-4-yl)methyl)piperidine-4-carboxamide |
| 6-42 | N-(2-(1-(4-cyanobenzyl)piperidin-4-ylcarbamoyl)benzofuran-5-yl)-1-((1-(4-cyanophenyl)-1H-pyrazol-4-yl)methyl)piperidine-4-carboxamide |
| 6-43 | N-(2-(1-(4-cyanobenzyl)piperidin-4-ylcarbamoyl)benzofuran-5-yl)-1-(3,4-difluorobenzyl)piperidine-4-carboxamide |
| 6-44 | N-(2-(1-(4-cyanobenzyl)piperidin-4-ylcarbamoyl)benzofuran-5-yl)-1-(4-phenoxybenzyl)piperidine-4-carboxamide |

TABLE 6-continued

| No. | Name |
|---|---|
| 6-45 | N-(2-(1-(4-cyanobenzyl)piperidin-4-ylcarbamoyl)benzofuran-5-yl)-1-((1-methyl-1H-pyrazol-4-yl)methyl)piperidine-4-carboxamide |
| 6-46 | N-(2-(1-(4-cyanobenzyl)piperidin-4-ylcarbamoyl)benzofuran-5-yl)-1-(4-(trifluoromethoxy)benzyl)piperidine-4-carboxamide |
| 6-47 | 1-((1H-pyrazol-5-yl)methyl)-N-(2-(1-(4-cyanobenzyl)piperidin-4-ylcarbamoyl)benzofuran-5-yl)piperidine-4-carboxamide |
| 6-48 | 1-(4-cyano-3-fluorobenzyl)-N-(2-(1-(4-cyanobenzyl)piperidin-4-ylcarbamoyl)benzofuran-5-yl)piperidine-4-carboxamide |
| 6-49 | 1-(4-cyanobenzyl)-N-(2-(1-(4-cyanobenzyl)piperidin-4-ylcarbamoyl)benzofuran-5-yl)piperidine-4-carboxamide |
| 6-50 | N-(2-(1-(4-cyanobenzyl)piperidin-4-ylcarbamoyl)benzofuran-5-yl)-1-(4-(trifluoromethyl)benzyl)piperidine-4-carboxamide |
| 6-51 | N-(2-(1-(4-cyanobenzyl)piperidin-4-ylcarbamoyl)benzofuran-5-yl)-1-(methylsulfonyl)piperidine-4-carboxamide |

TABLE 6-continued

| No. | Name | Structure |
|---|---|---|
| 6-52 | 1-acetyl-N-(2-(1-(4-cyanobenzyl)piperidin-4-ylcarbamoyl)benzofuran-5-yl)piperidine-4-carboxamide | 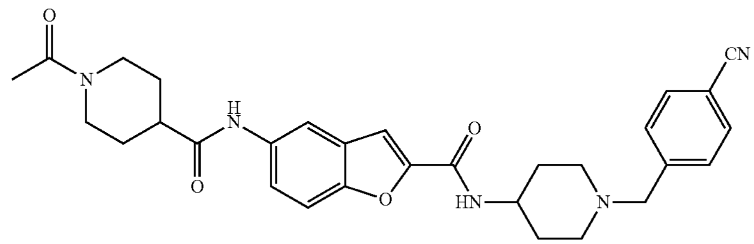 [SMILES: CC(=O)N1CCC(C(=O)Nc2ccc3oc(C(=O)NC4CCN(Cc5ccc(C#N)cc5)CC4)cc3c2)CC1] |
| 6-53 | N-(1-(4-cyanobenzyl)piperidin-4-yl)-5-(2-(pyridin-4-yl)acetamido)benzofuran-2-carboxamide | 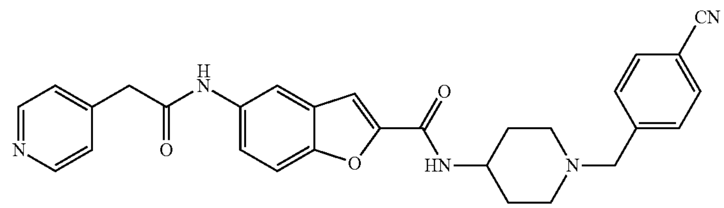 [SMILES: N#Cc1ccc(CN2CCC(NC(=O)c3cc4cc(NC(=O)Cc5ccncc5)ccc4o3)CC2)cc1] |
| 6-54 | N-(1-(4-cyanobenzyl)piperidin-4-yl)-5-(2-(4-(trifluoromethyl)phenyl)acetamido)benzofuran-2-carboxamide | 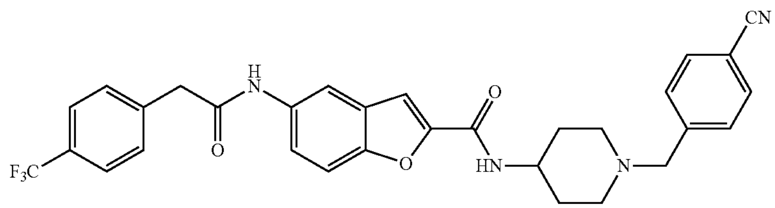 [SMILES: N#Cc1ccc(CN2CCC(NC(=O)c3cc4cc(NC(=O)Cc5ccc(C(F)(F)F)cc5)ccc4o3)CC2)cc1] |
| 6-55 | N-(2-(1-(4-cyanobenzyl)piperidin-4-ylcarbamoyl)benzofuran-5-yl)-1H-imidazole-1-carboxamide | 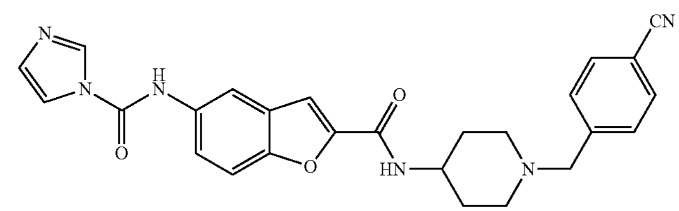 [SMILES: N#Cc1ccc(CN2CCC(NC(=O)c3cc4cc(NC(=O)n5ccnc5)ccc4o3)CC2)cc1] |
| 6-56 | N-(2-(1-(4-cyanobenzyl)piperidin-4-ylcarbamoyl)benzofuran-5-yl)-4-methyl-1,2,3-thiadiazole-5-carboxamide | 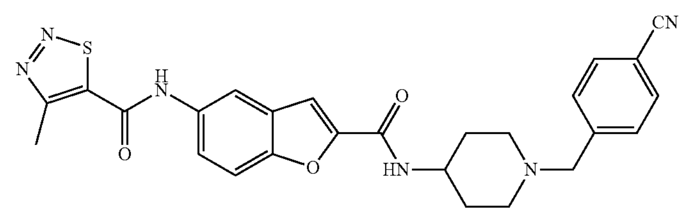 [SMILES: Cc1nnsc1C(=O)Nc1ccc2oc(C(=O)NC3CCN(Cc4ccc(C#N)cc4)CC3)cc2c1] |
| 6-57 | N-(2-(1-(4-cyanobenzyl)piperidin-4-ylcarbamoyl)benzofuran-5-yl)-1-methylpiperidine-4-carboxamide | 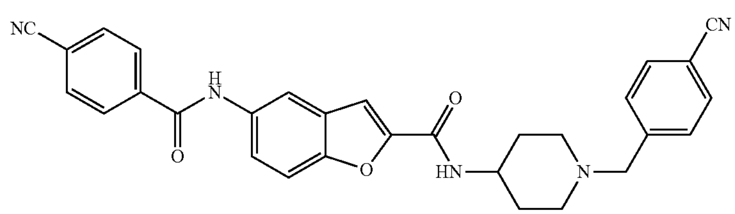 [SMILES: N#Cc1ccc(CN2CCC(NC(=O)c3cc4cc(NC(=O)c5ccc(C#N)cc5)ccc4o3)CC2)cc1] |
| 6-58 | N-(2-(1-(4-cyanobenzyl)piperidin-4-ylcarbamoyl)benzofuran-5-yl)-1-methylpiperidine-4-carboxamide | 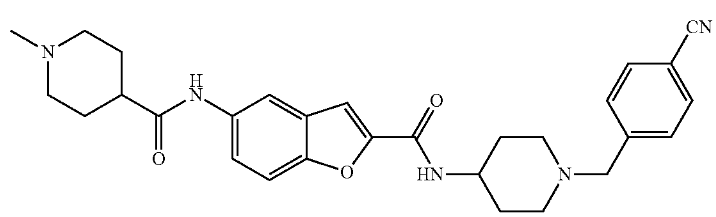 [SMILES: CN1CCC(C(=O)Nc2ccc3oc(C(=O)NC4CCN(Cc5ccc(C#N)cc5)CC4)cc3c2)CC1] |

TABLE 6-continued

| No. | Name | Structure |
|---|---|---|
| 6-59 | N-(2-(1-(4-cyanobenzyl)piperidin-4-ylcarbamoyl)benzofuran-5-yl)-1-(4-methoxyphenyl)-1H-pyrazole-4-carboxamide | 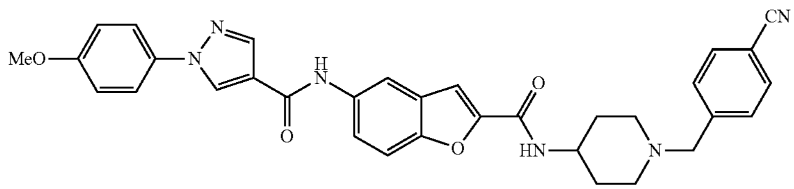 [SMILES: COc1ccc(-n2cc(C(=O)Nc3ccc4oc(C(=O)NC5CCN(Cc6ccc(C#N)cc6)CC5)cc4c3)cn2)cc1] |
| 6-60 | 5-(4-(4H-1,2,4-triazol-3-yl)benzamido)-N-(1-(4-cyanobenzyl)piperidin-4-yl)benzofuran-2-carboxamide | 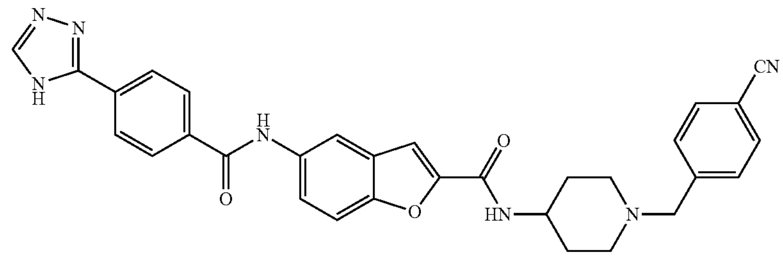 [SMILES: N#Cc1ccc(CN2CCC(NC(=O)c3cc4cc(NC(=O)c5ccc(-c6nnc[nH]6)cc5)ccc4o3)CC2)cc1] |
| 6-61 | N-(2-(1-(4-cyanobenzyl)piperidin-4-ylcarbamoyl)benzofuran-5-yl)-5-methylisoxazole-3-carboxamide | 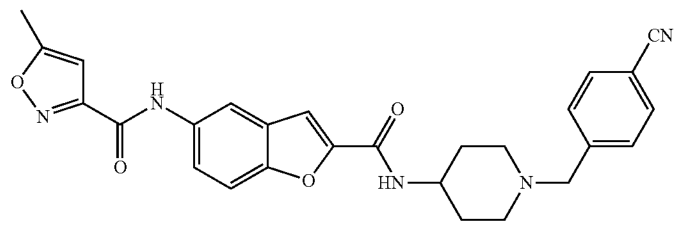 [SMILES: Cc1cc(C(=O)Nc2ccc3oc(C(=O)NC4CCN(Cc5ccc(C#N)cc5)CC4)cc3c2)no1] |
| 6-62 | N-(2-(1-(4-cyanobenzyl)piperidin-4-ylcarbamoyl)benzofuran-5-yl)-3-methyl-1H-pyrazole-4-carboxamide | 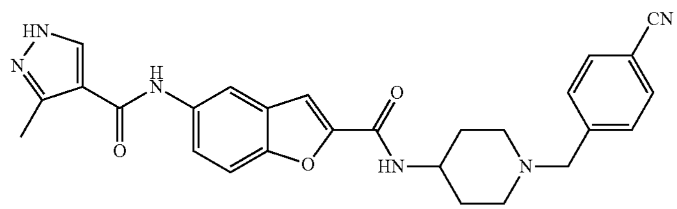 [SMILES: Cc1n[nH]cc1C(=O)Nc1ccc2oc(C(=O)NC3CCN(Cc4ccc(C#N)cc4)CC3)cc2c1] |
| 6-63 | N-(1-(4-cyanobenzyl)piperidin-4-yl)-5-(4-morpholinobenzamido)benzofuran-2-carboxamide | 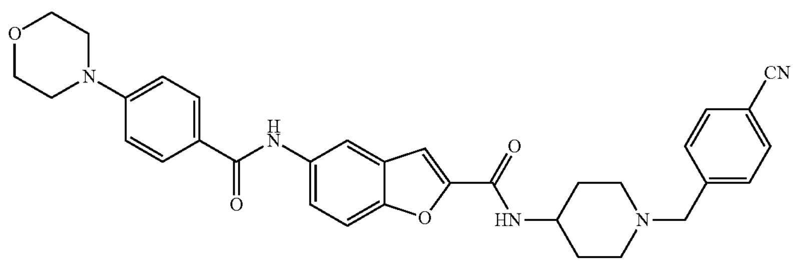 [SMILES: N#Cc1ccc(CN2CCC(NC(=O)c3cc4cc(NC(=O)c5ccc(N6CCOCC6)cc5)ccc4o3)CC2)cc1] |
| 6-64 | N-(2-(1-(4-cyanobenzyl)piperidin-4-ylcarbamoyl)benzofuran-5-yl)-6-(4-fluorophenoxy)nicotinamide | 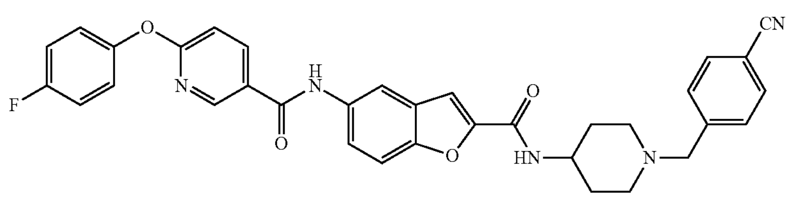 [SMILES: N#Cc1ccc(CN2CCC(NC(=O)c3cc4cc(NC(=O)c5ccc(Oc6ccc(F)cc6)nc5)ccc4o3)CC2)cc1] |
| 6-65 | 5-(4-(1H-pyrazol-1-yl)benzamido)-N-(1-(4-cyanobenzyl)piperidin-4-yl)benzofuran-2-carboxamide | 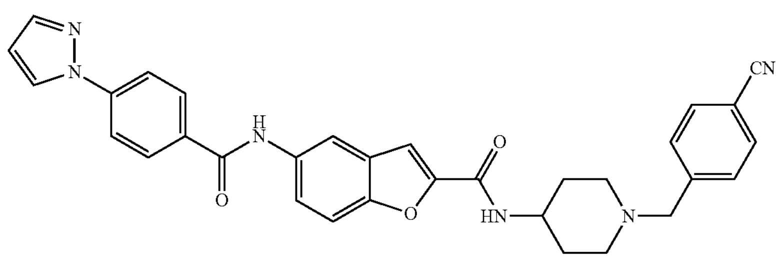 [SMILES: N#Cc1ccc(CN2CCC(NC(=O)c3cc4cc(NC(=O)c5ccc(-n6cccn6)cc5)ccc4o3)CC2)cc1] |

TABLE 6-continued

| No. | Name | Structure |
|---|---|---|
| 6-66 | N-(2-(1-(4-cyanobenzyl)piperidin-4-ylcarbamoyl)benzofuran-5-yl)-1-(4-fluorophenyl)-1H-pyrazole-4-carboxamide | 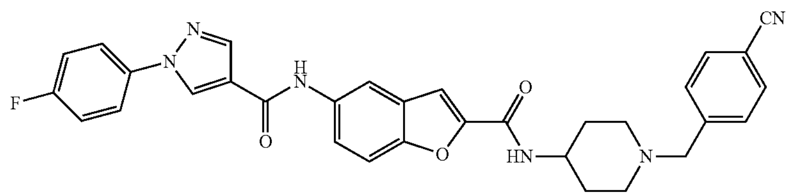 [SMILES: N#Cc1ccc(CN2CCC(NC(=O)c3cc4cc(NC(=O)c5cnn(-c6ccc(F)cc6)c5)ccc4o3)CC2)cc1] |
| 6-67 | N-(1-(4-cyanobenzyl)piperidin-4-yl)-5-(2-(4-cyanophenyl)acetamido)benzofuran-2-carboxamide | 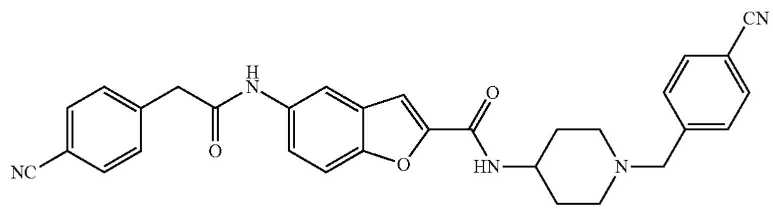 |
| 6-68 | N-(1-(4-cyanobenzyl)piperidin-4-yl)-5-(4-(pyrrolidin-1-yl)benzamido)benzofuran-2-carboxamide | 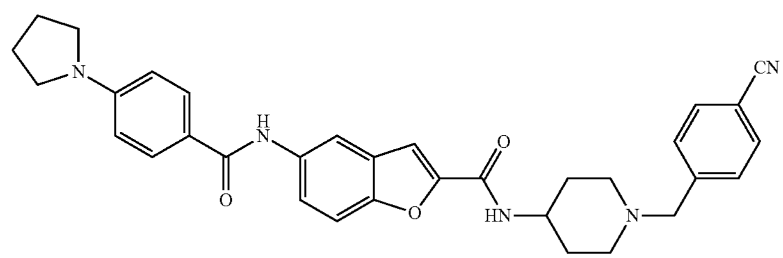 [SMILES: N#Cc1ccc(CN2CCC(NC(=O)c3cc4cc(NC(=O)c5ccc(N6CCCC6)cc5)ccc4o3)CC2)cc1] |
| 6-69 | N-(1-(4-cyanobenzyl)piperidin-4-yl)-5-((1s,4s)-4-(4-cyanophenoxy)cyclohexanecarboxamido)benzofuran-2-carboxamide | 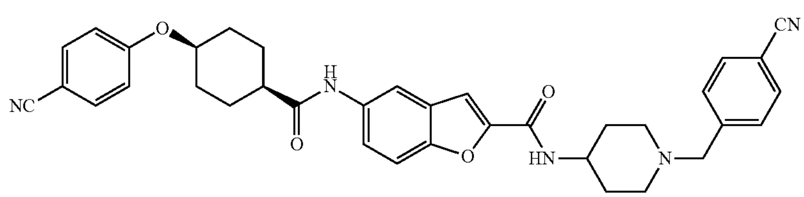 [SMILES: N#Cc1ccc(CN2CCC(NC(=O)c3cc4cc(NC(=O)[C@H]5CC[C@@H](Oc6ccc(C#N)cc6)CC5)ccc4o3)CC2)cc1] |
| 6-70 | N-(2-(1-(4-cyanobenzyl)piperidin-4-ylcarbamoyl)benzofuran-5-yl)-1-(5-cyanopyridin-2-yl)piperidine-4-carboxamide | 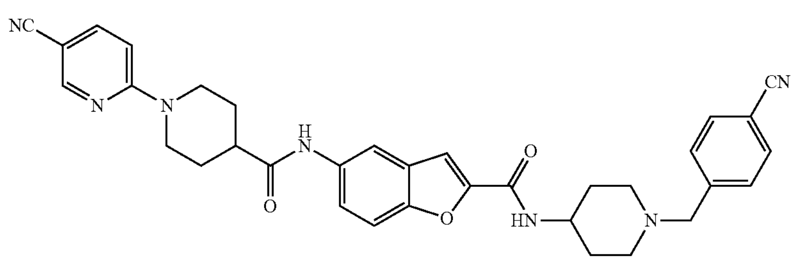 [SMILES: N#Cc1ccc(CN2CCC(NC(=O)c3cc4cc(NC(=O)C5CCN(c6ccc(C#N)cn6)CC5)ccc4o3)CC2)cc1] |
| 6-71 | N-(1-(4-cyanobenzyl)piperidin-4-yl)-5-(4-(5-cyanopyridin-2-yloxy)benzamido)benzofuran-2-carboxamide | 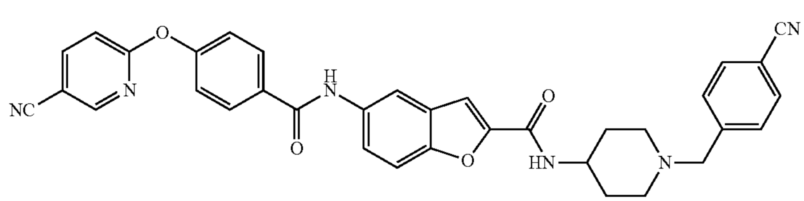 [SMILES: N#Cc1ccc(CN2CCC(NC(=O)c3cc4cc(NC(=O)c5ccc(Oc6ccc(C#N)cn6)cc5)ccc4o3)CC2)cc1] |
| 6-72 | N-(2-(1-(4-cyanobenzyl)piperidin-4-ylcarbamoyl)benzofuran-5-yl)-1-(4-(trifluoromethyl)benzyl)-1H-pyrazole-4-carboxamide | 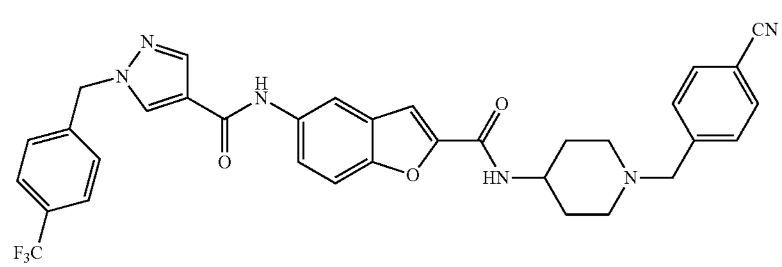 [SMILES: N#Cc1ccc(CN2CCC(NC(=O)c3cc4cc(NC(=O)c5cnn(Cc6ccc(C(F)(F)F)cc6)c5)ccc4o3)CC2)cc1] |

TABLE 6-continued

| No. | Name | Structure |
|---|---|---|
| 6-73 | 1-(4-cyanobenzyl)-N-(2-(1-(4-cyanobenzyl)piperidin-4-ylcarbamoyl)benzofuran-5-yl)-1H-pyrazole-4-carboxamide | 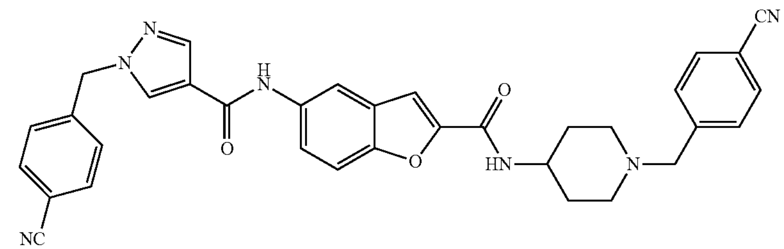 [SMILES: N#Cc1ccc(CN2CCC(NC(=O)c3cc4cc(NC(=O)c5cnn(Cc6ccc(C#N)cc6)c5)ccc4o3)CC2)cc1] |
| 6-74 | N-(2-(1-(4-cyanobenzyl)piperidin-4-ylcarbamoyl)benzofuran-5-yl)-1-(4-cyanophenyl)azetidine-3-carboxamide | 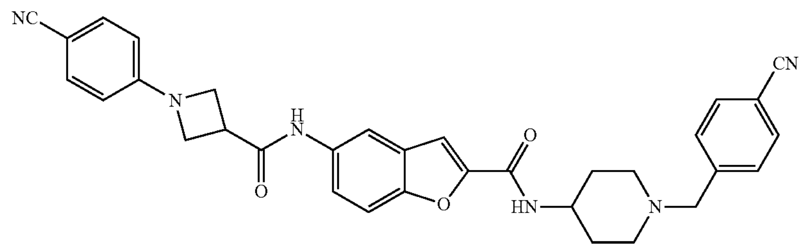 [SMILES: N#Cc1ccc(CN2CCC(NC(=O)c3cc4cc(NC(=O)C5CN(c6ccc(C#N)cc6)C5)ccc4o3)CC2)cc1] |
| 6-75 | N-(1-(4-cyanobenzyl)piperidin-4-yl)-5-(4-(4-(methylsulfonyl)phenoxy)piperidine-1-carbonyl)benzofuran-2-carboxamide | 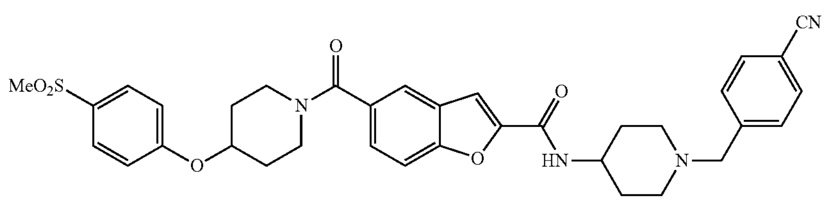 [SMILES: CS(=O)(=O)c1ccc(OC2CCN(C(=O)c3ccc4oc(C(=O)NC5CCN(Cc6ccc(C#N)cc6)CC5)cc4c3)CC2)cc1] |
| 6-76 | N-(2-(1-(4-cyanobenzyl)piperidin-4-ylcarbamoyl)benzofuran-5-yl)-1-(4-cyanophenyl)piperidine-4-carboxamide | 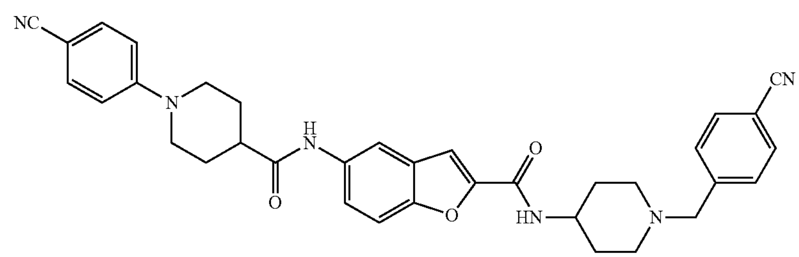 [SMILES: N#Cc1ccc(CN2CCC(NC(=O)c3cc4cc(NC(=O)C5CCN(c6ccc(C#N)cc6)CC5)ccc4o3)CC2)cc1] |
| 6-77 | N-(1-(4-cyanobenzyl)piperidin-4-yl)-5-(4-((1-(4-cyanophenyl)-1H-pyrazol-4-yl)methyl)piperazine-1-carbonyl)benzofuran-2-carboxamide | 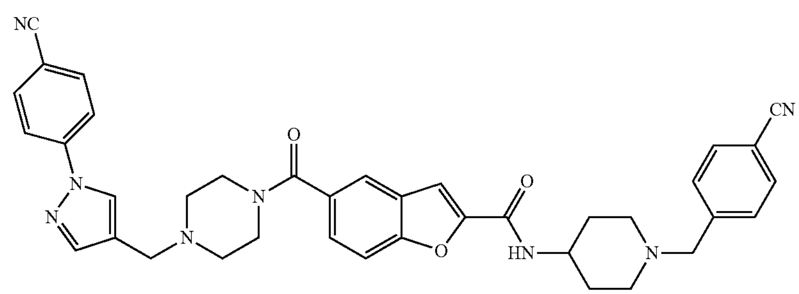 [SMILES: N#Cc1ccc(CN2CCC(NC(=O)c3cc4cc(C(=O)N5CCN(Cc6cnn(-c7ccc(C#N)cc7)c6)CC5)ccc4o3)CC2)cc1] |
| 6-78 | N-(1-(4-cyanobenzyl)piperidin-4-yl)-5-(4-(4-(methylsulfonyl)benzyl)piperazine-1-carbonyl)benzofuran-2-carboxamide | 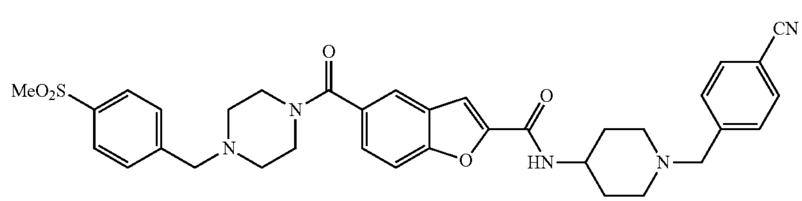 |

TABLE 6-continued

| No. | Name |
|---|---|
| 6-79 | 5-(4-(4-(1H-pyrazol-1-yl)benzyl)piperazine-1-carbonyl)-N-(1-(4-cyanobenzyl)piperidin-4-yl)benzofuran-2-carboxamide |
| 6-80 | N-(1-(4-cyanobenzyl)piperidin-4-yl)-5-(4-(4-(pyrrolidin-1-yl)benzyl)piperazine-1-carbonyl)benzofuran-2-carboxamide |
| 6-81 | N-(1-(4-cyanobenzyl)piperidin-4-yl)-5-(4-(4-(trifluoromethoxy)benzyl)piperazine-1-carbonyl)benzofuran-2-carboxamide |
| 6-82 | N-(1-(4-cyanobenzyl)piperidin-4-yl)-5-(4-(4-(pyridin-2-yl)benzyl)piperazine-1-carbonyl)benzofuran-2-carboxamide |
| 6-83 | N-(2-(1-(4-cyanobenzyl)piperidin-4-ylcarbamoyl)benzofuran-5-yl)-1-(4-(trifluoromethyl)phenyl)piperidine-4-carboxamide |
| 6-84 | N-(2-(1-(4-cyanobenzyl)piperidin-4-ylcarbamoyl)benzofuran-5-yl)-1-(4-(methylsulfonyl)phenyl)piperidine-4-carboxamide |
| 6-85 | N-(1-(4-cyanobenzyl)piperidin-4-yl)-5-(4-(methylsulfonyl)benzamido)benzofuran-2-carboxamide |

TABLE 6-continued

| No. | Name | Structure |
|---|---|---|
| 6-86 | N-(1-(4-cyanobenzyl)piperidin-4-yl)-5-(4-(4-fluorophenyl)piperazine-1-carbonyl)benzofuran-2-carboxamide | 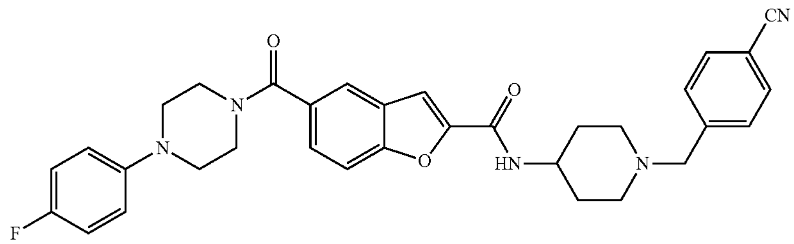 [SMILES: N#Cc1ccc(CN2CCC(NC(=O)c3cc4cc(C(=O)N5CCN(c6ccc(F)cc6)CC5)ccc4o3)CC2)cc1] |
| 6-87 | N-(1-(4-cyanobenzyl)piperidin-4-yl)-5-(4-(4-(methylsulfonyl)phenyl)piperazine-1-carbonyl)benzofuran-2-carboxamide | 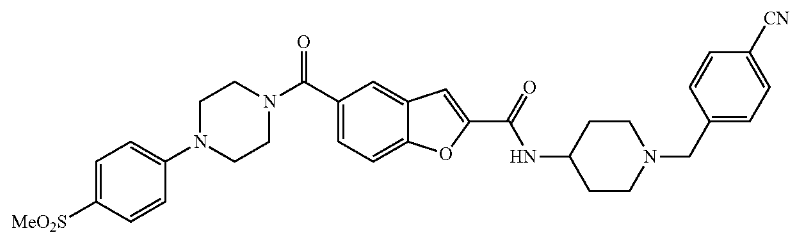 [SMILES: CS(=O)(=O)c1ccc(N2CCN(C(=O)c3ccc4oc(C(=O)NC5CCN(Cc6ccc(C#N)cc6)CC5)cc4c3)CC2)cc1] |
| 6-88 | N-(1-(4-methoxybenzyl)piperidin-4-yl)-5-(4-(4-(methylsulfonyl)phenoxy)piperidine-1-carbonyl)benzofuran-2-carboxamide | 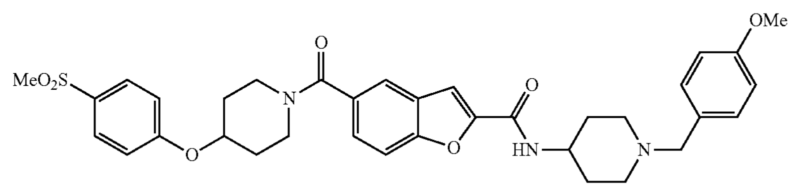 [SMILES: COc1ccc(CN2CCC(NC(=O)c3cc4cc(C(=O)N5CCC(Oc6ccc(S(C)(=O)=O)cc6)CC5)ccc4o3)CC2)cc1] |
| 6-89 | 5-(4-(4-(methylsulfonyl)phenoxy)piperidine-1-carbonyl)-N-(1-(4-(trifluoromethoxy)benzyl)piperidin-4-yl)benzofuran-2-carboxamide | 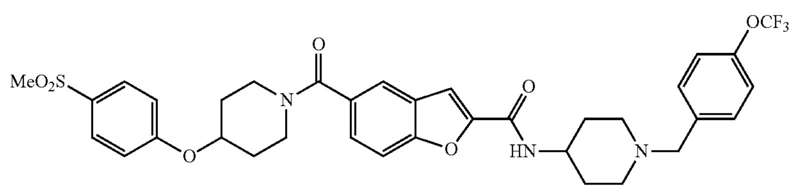 [SMILES: CS(=O)(=O)c1ccc(OC2CCN(C(=O)c3ccc4oc(C(=O)NC5CCN(Cc6ccc(OC(F)(F)F)cc6)CC5)cc4c3)CC2)cc1] |
| 6-90 | N2-(1-(4-cyanobenzyl)piperidin-4-yl)-N5-(1-(4-cyanophenyl)piperidin-4-yl)benzofuran-2,5-dicarboxamide | 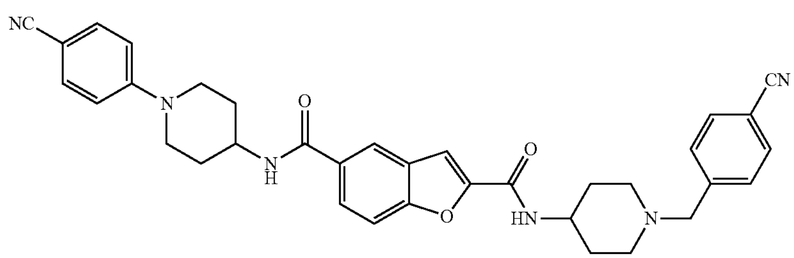 [SMILES: N#Cc1ccc(CN2CCC(NC(=O)c3cc4cc(C(=O)NC5CCN(c6ccc(C#N)cc6)CC5)ccc4o3)CC2)cc1] |
| 6-91 | N2-(1-(4-cyanobenzyl)piperidin-4-yl)-N5-(1-((1-(4-cyanophenyl)-1H-pyrazol-3-yl)methyl)piperidin-4-yl)benzofuran-2,5-dicarboxamide | 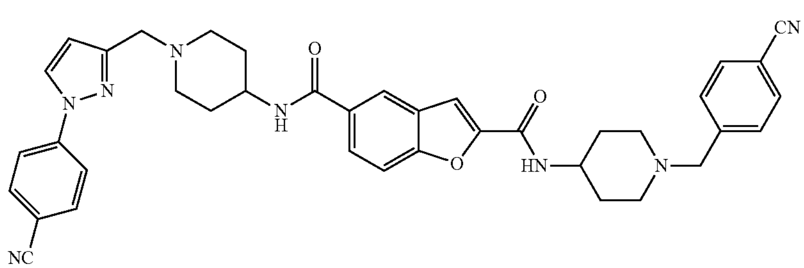 [SMILES: N#Cc1ccc(CN2CCC(NC(=O)c3cc4cc(C(=O)NC5CCN(Cc6ccn(-c7ccc(C#N)cc7)n6)CC5)ccc4o3)CC2)cc1] |
| 6-92 | N5-(1-(4-(1H-pyrazol-1-yl)benzyl)piperidin-4-yl)-N2-(1-(4-cyanobenzyl)piperidin-4-yl)benzofuran-2,5-dicarboxamide | 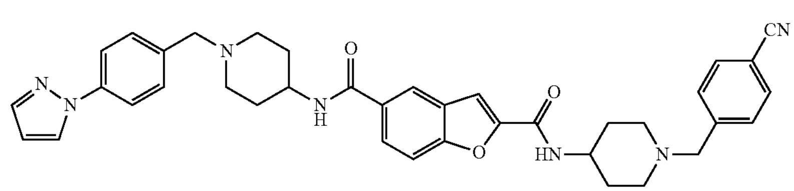 [SMILES: N#Cc1ccc(CN2CCC(NC(=O)c3cc4cc(C(=O)NC5CCN(Cc6ccc(-n7cccn7)cc6)CC5)ccc4o3)CC2)cc1] |

TABLE 6-continued

| No. | Name | Structure |
|---|---|---|
| 6-93 | N2-(1-(4-cyanobenzyl)piperidin-4-yl)-N5-(1-(4-(trifluoromethoxy)benzyl)piperidin-4-yl)benzofuran-2,5-dicarboxamide | 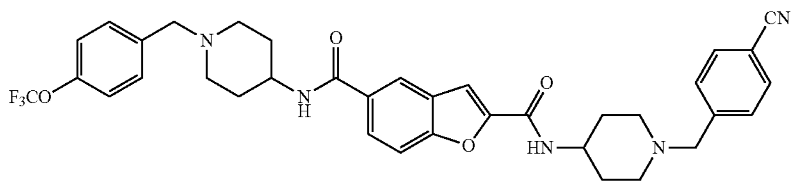 [SMILES: N#Cc1ccc(CN2CCC(NC(=O)c3cc4cc(C(=O)NC5CCN(Cc6ccc(OC(F)(F)F)cc6)CC5)ccc4o3)CC2)cc1] |
| 6-94 | N-(1-(4-methoxybenzyl)piperidin-4-yl)-5-(4-(4-(methylsulfonyl)benzyl)piperazine-1-carbonyl)benzofuran-2-carboxamide | 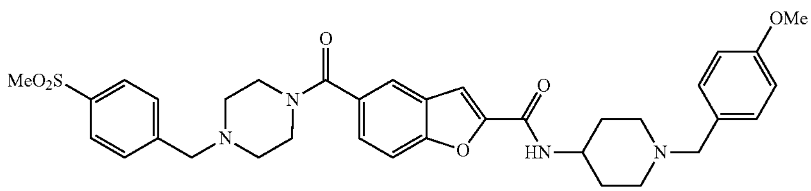 [SMILES: COc1ccc(CN2CCC(NC(=O)c3cc4cc(C(=O)N5CCN(Cc6ccc(S(C)(=O)=O)cc6)CC5)ccc4o3)CC2)cc1] |
| 6-95 | 5-(4-(4-(methylsulfonyl)benzyl)piperazine-1-carbonyl)-N-(1-(4-(trifluoromethoxy)benzyl)piperidin-4-yl)benzofuran-2-carboxamide | 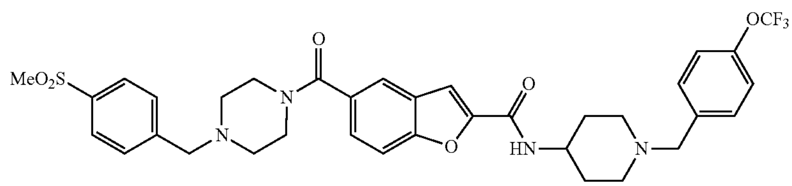 [SMILES: CS(=O)(=O)c1ccc(CN2CCN(C(=O)c3ccc4oc(C(=O)NC5CCN(Cc6ccc(OC(F)(F)F)cc6)CC5)cc4c3)CC2)cc1] |
| 6-96 | 5-(4-(4-(1H-pyrazol-1-yl)benzyl)piperazine-1-carbonyl)-N-(1-(4-methoxybenzyl)piperidin-4-yl)benzofuran-2-carboxamide | 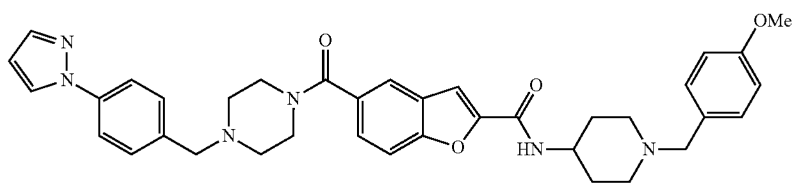 [SMILES: COc1ccc(CN2CCC(NC(=O)c3cc4cc(C(=O)N5CCN(Cc6ccc(-n7cccn7)cc6)CC5)ccc4o3)CC2)cc1] |
| 6-97 | 5-(4-(4-(1H-pyrazol-1-yl)benzyl)piperazine-1-carbonyl)-N-(1-(4-(trifluoromethoxy)benzyl)piperidin-4-yl)benzofuran-2-carboxamide | 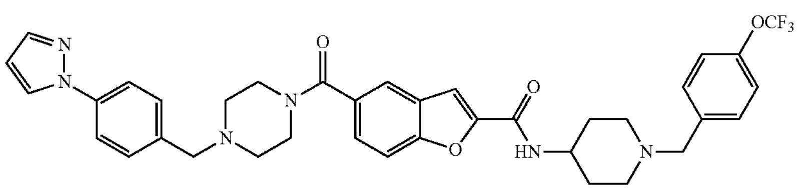 [SMILES: O=C(NC1CCN(Cc2ccc(OC(F)(F)F)cc2)CC1)c1cc2cc(C(=O)N3CCN(Cc4ccc(-n5cccn5)cc4)CC3)ccc2o1] |
| 6-98 | N-(1-(4-fluoro-3-methoxybenzyl)piperidin-4-yl)-5-(4-(4-(methylsulfonyl)benzyl)piperazine-1-carbonyl)benzofuran-2-carboxamide | 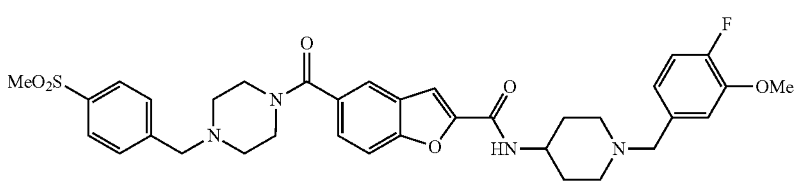 [SMILES: COc1cc(CN2CCC(NC(=O)c3cc4cc(C(=O)N5CCN(Cc6ccc(S(C)(=O)=O)cc6)CC5)ccc4o3)CC2)ccc1F] |
| 6-99 | N-(1-(3-methoxybenzyl)piperidin-4-yl)-5-(4-(4-(methylsulfonyl)benzyl)piperazine-1-carbonyl)benzofuran-2-carboxamide | 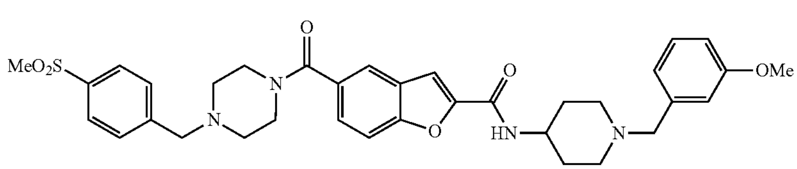 [SMILES: COc1cccc(CN2CCC(NC(=O)c3cc4cc(C(=O)N5CCN(Cc6ccc(S(C)(=O)=O)cc6)CC5)ccc4o3)CC2)c1] |
| 6-100 | N-(1-(3-fluoro-4-methoxybenzyl)piperidin-4-yl)-5-(4-(4-(methylsulfonyl)benzyl)piperazine-1-carbonyl)benzofuran-2-carboxamide | 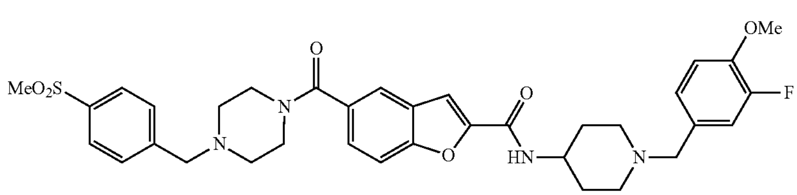 |

TABLE 6-continued

| No. | Name |
|---|---|
| 6-101 | N-(1-(4-(difluoromethoxy)benzyl)piperidin-4-yl)-5-(4-(4-(methylsulfonyl)benzyl)piperazine-1-carbonyl)benzofuran-2-carboxamide |
| 6-102 | N-(1-(4-cyanobenzyl)piperidin-4-yl)-5-(4-(3-fluoro-4-(methylsulfonyl(benzyl(piperazine-1-carbonyl)benzofuran-2-carboxamide |
| 6-103 | N-(1-(4-cyanobenzyl)piperidin-4-yl)-5-(4-(3-methyl-4-(methylsulfonyl)benzyl)piperazine-1-carbonyl)benzofuran-2-carboxamide |
| 6-104 | N-(1-(4-cyanobenzyl)piperidin-4-yl)-5-(4-(4-(cyclopropylsulfonyl)benzyl)piperazine-1-carbonyl)benzofuran-2-carboxamide |
| 6-105 | N-(1-(4-cyanobenzyl)piperidin-4-yl)-5-(4-(4-(methylsulfonyl)-3-(trifluoromethyl)benzyl)piperazine-1-carbonyl)benzofuran-2-carboxamide |
| 6-106 | N-(1-(4-cyanobenzyl)piperidin-4-yl)-5-(4-(4-methoxyphenyl)piperazine-1-carbonyl)benzofuran-2-carboxamide |
| 6-107 | N-(1-(4-cyanobenzyl)piperidin-4-yl)-5-(4-(4-cyanophenyl)piperazine-1-carbonyl)benzofuran-2-carboxamide |

TABLE 6-continued

| No. | Name | Structure |
|---|---|---|
| 6-108 | N-(1-(4-cyanobenzyl)piperidin-4-yl)-5-(4-(4-(isopropylsulfonyl)phenyl)piperazine-1-carbonyl)benzofuran-2-carboxamide | 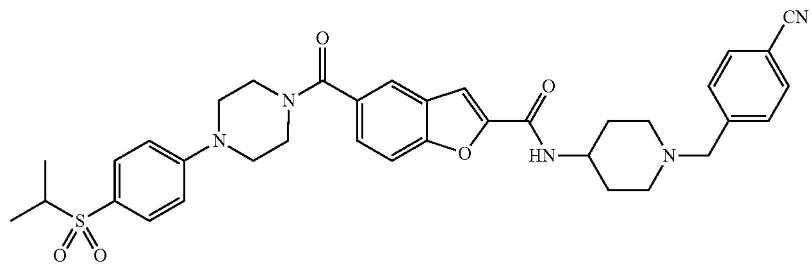 [SMILES: CC(C)S(=O)(=O)c1ccc(N2CCN(C(=O)c3ccc4oc(C(=O)NC5CCN(Cc6ccc(C#N)cc6)CC5)cc4c3)CC2)cc1] |
| 6-109 | N-(1-(4-cyanobenzyl)piperidin-4-yl)-5-(4-(4-(cyclopropanecarbonyl)phenyl)piperazine-1-carbonyl)benzofuran-2-carboxamide | 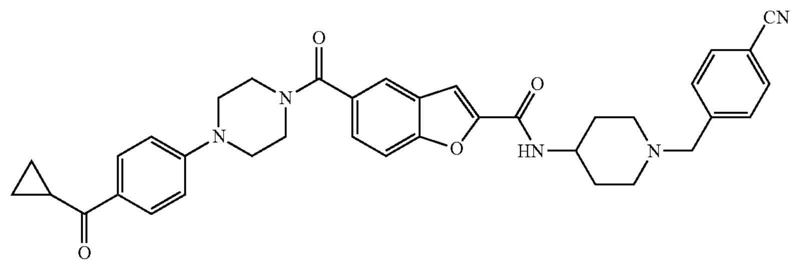 [SMILES: N#Cc1ccc(CN2CCC(NC(=O)c3cc4cc(C(=O)N5CCN(c6ccc(C(=O)C7CC7)cc6)CC5)ccc4o3)CC2)cc1] |
| 6-110 | N-(1-(4-cyanobenzyl)piperidin-4-yl)-5-(4-(4-(dimethylcarbamoyl)phenyl)piperazine-1-carbonyl)benzofuran-2-carboxamide | 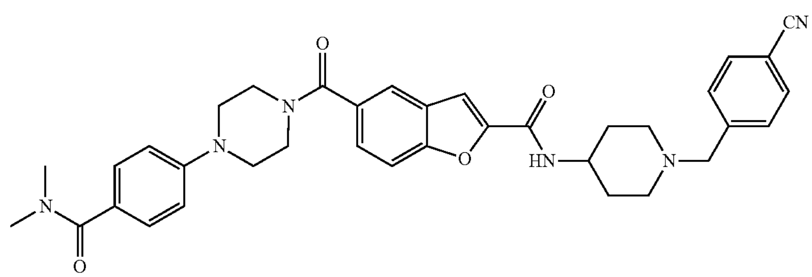 [SMILES: CN(C)C(=O)c1ccc(N2CCN(C(=O)c3ccc4oc(C(=O)NC5CCN(Cc6ccc(C#N)cc6)CC5)cc4c3)CC2)cc1] |
| 6-111 | N-(1-(4-cyanobenzyl)piperidin-4-yl)-5-(4-(4-(methylsulfonyl)-3-(trifluoromethoxy)benzyl)piperazine-1-carbonyl)benzofuran-2-carboxamide | 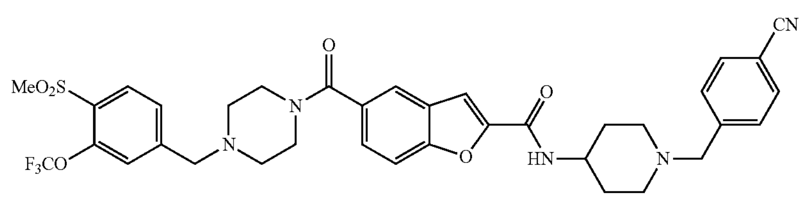 [SMILES: CS(=O)(=O)c1ccc(CN2CCN(C(=O)c3ccc4oc(C(=O)NC5CCN(Cc6ccc(C#N)cc6)CC5)cc4c3)CC2)cc1OC(F)(F)F] |
| 6-112 | 5-(4-(3-chloro-4-(methylsulfonyl)benzyl)piperazine-1-carbonyl)-N-(1-(4-cyanobenzyl)piperidin-4-yl)benzofuran-2-carboxamide | 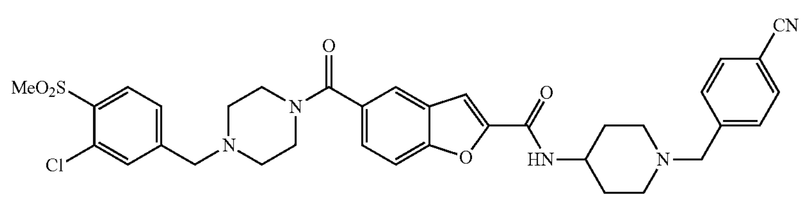 [SMILES: CS(=O)(=O)c1ccc(CN2CCN(C(=O)c3ccc4oc(C(=O)NC5CCN(Cc6ccc(C#N)cc6)CC5)cc4c3)CC2)cc1Cl] |
| 6-113 | N-(1-(4-cyanobenzyl)piperidin-4-yl)-5-((3,4-trans)-3-fluoro-4-(4-(methylsulfonyl)phenoxy)piperidine-1-carbonyl)benzofuran-2-carboxamide | 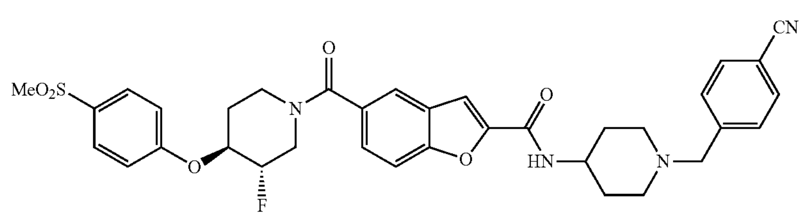 [SMILES: CS(=O)(=O)c1ccc(O[C@H]2CCN(C(=O)c3ccc4oc(C(=O)NC5CCN(Cc6ccc(C#N)cc6)CC5)cc4c3)C[C@@H]2F)cc1] |
| 6-114 | 5-((3,4-trans)-3-fluoro-4-(4-(methylsulfonyl)phenoxy)piperidine-1-carbonyl)-N-(1-(4-methoxybenzyl)piperidin-4-yl)benzofuran-2-carboxamide | 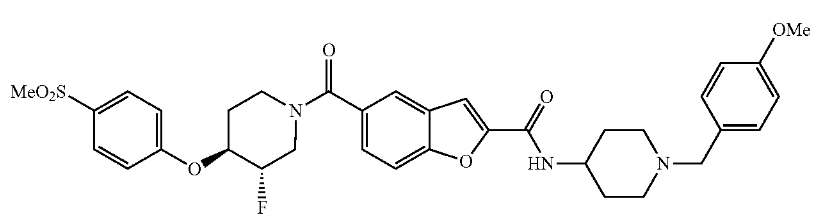 [SMILES: COc1ccc(CN2CCC(NC(=O)c3cc4cc(C(=O)N5CC[C@H](Oc6ccc(S(C)(=O)=O)cc6)[C@@H](F)C5)ccc4o3)CC2)cc1] |

TABLE 6-continued

| No. | Name | Structure |
|---|---|---|
| 6-115 | 5-((3,4-trans)-3-fluoro-4-(4-(methylsulfonyl)phenoxy)piperidine-1-carbonyl)-N-(1-(4-(trifluoromethoxy)benzyl)piperidin-4-yl)benzofuran-2-carboxamide | 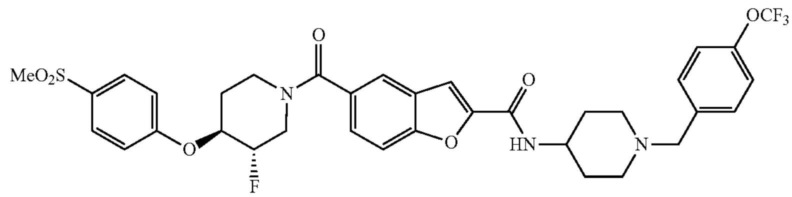 [SMILES: CS(=O)(=O)c1ccc(O[C@H]2CCN(C(=O)c3ccc4oc(C(=O)NC5CCN(Cc6ccc(OC(F)(F)F)cc6)CC5)cc4c3)C[C@@H]2F)cc1] |
| 6-116 | N-(1-(4-cyanobenzyl)piperidin-4-yl)-5-(4-(4-(trifluoromethyl)phenyl)piperazine-1-carbonyl)benzofuran-2-carboxamide | 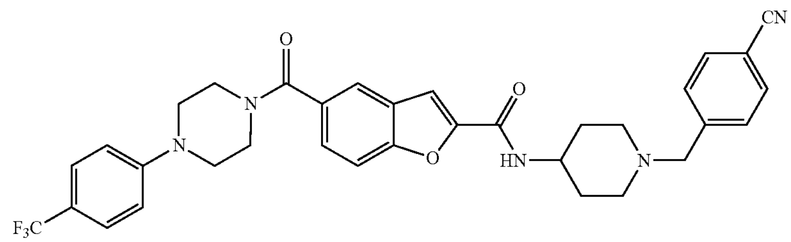 [SMILES: N#Cc1ccc(CN2CCC(NC(=O)c3cc4cc(C(=O)N5CCN(c6ccc(C(F)(F)F)cc6)CC5)ccc4o3)CC2)cc1] |
| 6-117 | 5-(4-(3,5-bis(trifluoromethyl)phenyl)piperazine-1-carbonyl)-N-(1-(4-cyanobenzyl)piperidin-4-yl)benzofuran-2-carboxamide | 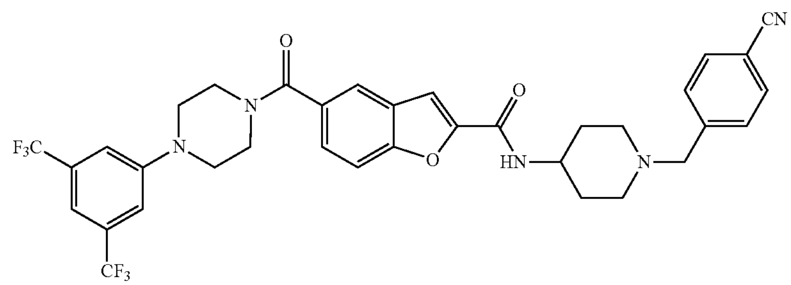 [SMILES: N#Cc1ccc(CN2CCC(NC(=O)c3cc4cc(C(=O)N5CCN(c6cc(C(F)(F)F)cc(C(F)(F)F)c6)CC5)ccc4o3)CC2)cc1] |
| 6-118 | N-(1-(4-cyanobenzyl)piperidin-4-yl)-5-(4-(2,4-dichlorophenyl)piperazine-1-carbonyl)benzofuran-2-carboxamide | 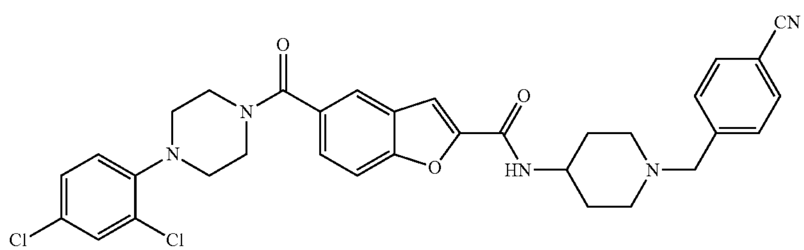 [SMILES: N#Cc1ccc(CN2CCC(NC(=O)c3cc4cc(C(=O)N5CCN(c6ccc(Cl)cc6Cl)CC5)ccc4o3)CC2)cc1] |
| 6-119 | N-(1-(4-methoxybenzyl)piperidin-4-yl)-5-(4-(4-(trifluoromethyl)phenyl)piperazine-1-carbonyl)benzofuran-2-carboxamide | 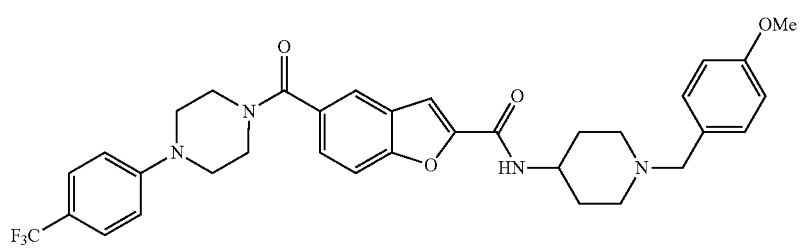 [SMILES: COc1ccc(CN2CCC(NC(=O)c3cc4cc(C(=O)N5CCN(c6ccc(C(F)(F)F)cc6)CC5)ccc4o3)CC2)cc1] |
| 6-120 | 5-(4-(3,5-bis(trifluoromethyl)phenyl)piperazine-1-carbonyl)-N-(1-(4-methoxybenzyl)piperidin-4-yl)benzofuran-2-carboxamide | 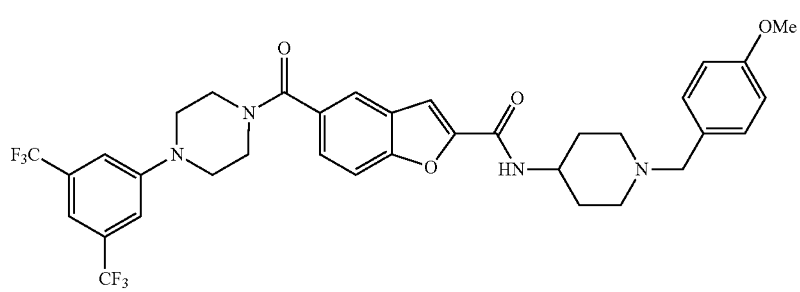 [SMILES: COc1ccc(CN2CCC(NC(=O)c3cc4cc(C(=O)N5CCN(c6cc(C(F)(F)F)cc(C(F)(F)F)c6)CC5)ccc4o3)CC2)cc1] |

TABLE 6-continued

| No. | Name |
|---|---|
| 6-121 | 5-(4-(2,4-dichlorophenyl)piperazine-1-carbonyl)-N-(1-(4-methoxybenzyl)piperidin-4-yl)benzofuran-2-carboxamide |
| 6-122 | N-(1-(4-cyanobenzyl)piperidin-4-yl)-5-(4-(4-fluorophenylsulfonyl)piperidine-1-carbonyl)benzofuran-2-carboxamide |
| 6-123 | N-(1-(4-cyanobenzyl)piperidin-4-yl)-5-(4-(4-(methylsulfonyl)benzyl)piperazine-1-carbonyl)benzofuran-2-carboxamide |
| 6-124 | N-(1-(4-cyanobenzyl)piperidin-4-yl)-5-(4-(4-(trifluoromethylsulfonyl)phenoxy)piperidine-1-carbonyl)benzofuran-2-carboxamide |
| 6-125 | N-(1-(4-cyanobenzyl)piperidin-4-yl)-5-(4-(4-(4-methoxyphenyl)-1H-pyrazol-1-yl)piperidine-1-carbonyl)benzofuran-2-carboxamide |
| 6-126 | N-(2-(1-(4-cyanobenzyl)piperidin-4-ylcarbamoyl)-6-methylbenzofuran-5-yl)-1-(4-cyanophenyl)piperidine-4-carboxamide |
| 6-127 | N-(1-(4-cyanobenzyl)piperidin-4-yl)-5-(4-(4-(trifluoromethyl)benzyl)piperazine-1-carbonyl)benzofuran-2-carboxamide |

TABLE 6-continued

| No. | Name | Structure |
|---|---|---|
| 6-128 | N-(1-(4-cyanobenzyl)piperidin-4-yl)-5-(4-(4-(trifluoromethylsulfonyl)benzyl)piperazine-1-carbonyl)benzofuran-2-carboxamide | 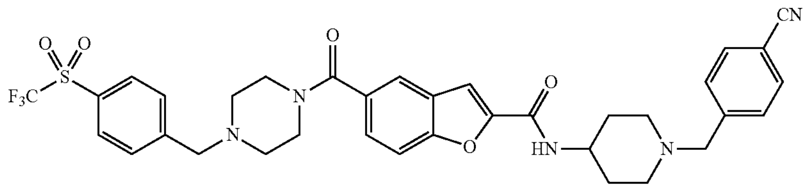 [SMILES: N#Cc1ccc(CN2CCC(NC(=O)c3cc4cc(C(=O)N5CCN(Cc6ccc(S(=O)(=O)C(F)(F)F)cc6)CC5)ccc4o3)CC2)cc1] |
| 6-129 | N-(1-(3-fluoro-4-methoxybenzyl)piperidin-4-yl)-5-(4-(4-(trifluoromethyl)benzyl)piperazine-1-carbonyl)benzofuran-2-carboxamide | 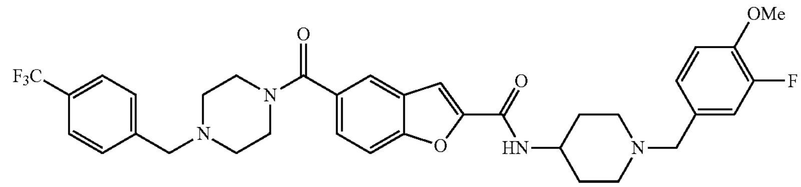 [SMILES: COc1ccc(CN2CCC(NC(=O)c3cc4cc(C(=O)N5CCN(Cc6ccc(C(F)(F)F)cc6)CC5)ccc4o3)CC2)cc1F] |
| 6-130 | N-(1-(3-fluoro-4-methoxybenzyl)piperidin-4-yl)-5-(4-(3-methyl-4-(methylsulfonyl)benzyl)piperazine-1-carbonyl)benzofuran-2-carboxamide | 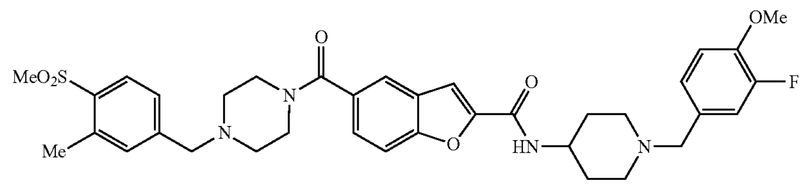 [SMILES: COc1ccc(CN2CCC(NC(=O)c3cc4cc(C(=O)N5CCN(Cc6ccc(S(C)(=O)=O)c(C)c6)CC5)ccc4o3)CC2)cc1F] |
| 6-131 | 5-(4-(4-(cyclopropylsulfonyl)benzyl)piperazine-1-carbonyl)-N-(1-(3-fluoro-4-methoxybenzyl)piperidin-4-yl)benzofuran-2-carboxamide | 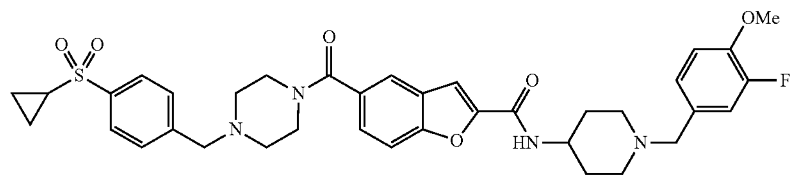 [SMILES: COc1ccc(CN2CCC(NC(=O)c3cc4cc(C(=O)N5CCN(Cc6ccc(S(=O)(=O)C7CC7)cc6)CC5)ccc4o3)CC2)cc1F] |
| 6-132 | N-(1-(3-fluoro-4-methoxybenzyl)piperidin-4-yl)-5-(4-(4-(methylsulfonyl)-3-(trifluoromethyl)benzyl)piperazine-1-carbonyl)benzofuran-2-carboxamide | 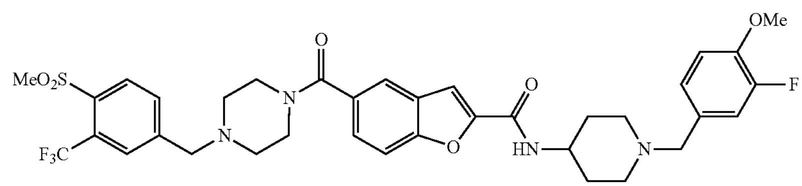 [SMILES: COc1ccc(CN2CCC(NC(=O)c3cc4cc(C(=O)N5CCN(Cc6ccc(S(C)(=O)=O)c(C(F)(F)F)c6)CC5)ccc4o3)CC2)cc1F] |
| 6-133 | 5-(4-(3-chloro-4-(methylsulfonyl)benzyl)piperazine-1-carbonyl)-N-(1-(3-fluoro-4-methoxybenzyl)piperidin-4-yl)benzofuran-2-carboxamide | 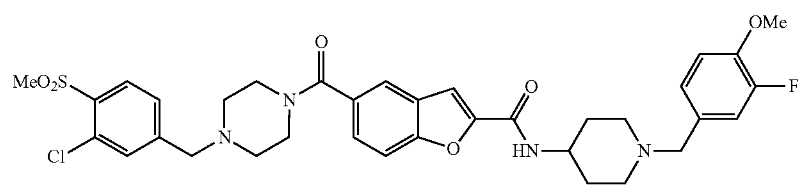 [SMILES: COc1ccc(CN2CCC(NC(=O)c3cc4cc(C(=O)N5CCN(Cc6ccc(S(C)(=O)=O)c(Cl)c6)CC5)ccc4o3)CC2)cc1F] |
| 6-134 | N-(1-(3-fluoro-4-methoxybenzyl)piperidin-4-yl)-5-(4-(4-(trifluoromethylsulfonyl)benzyl)piperazine-1-carbonyl)benzofuran-2-carboxamide | 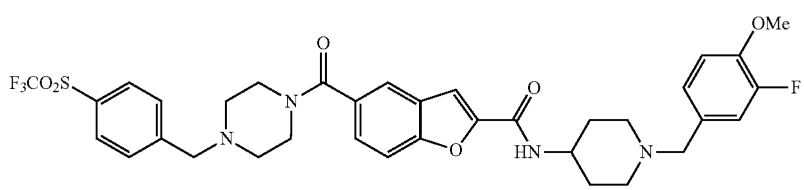 |
| 6-135 | 5-(4-(4-(methylsulfonyl)phenoxy)piperidine-1-carbonyl)-N-(1-(4-(trifluoromethoxy)benzyl)piperidin-4-yl)benzofuran-2-carboxamide | 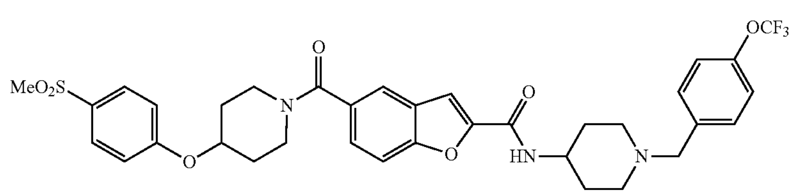 [SMILES: CS(=O)(=O)c1ccc(OC2CCN(C(=O)c3ccc4oc(C(=O)NC5CCN(Cc6ccc(OC(F)(F)F)cc6)CC5)cc4c3)CC2)cc1] |

TABLE 6-continued

| No. | Name |
|---|---|
| 6-136 | N-(1-(4-(trifluoromethoxy)benzyl)piperidin-4-yl)-5-(4-(4-(trifluoromethylsulfonyl)phenoxy)piperidine-1-carbonyl)benzofuran-2-carboxamide |
| 6-137 | N-(1-(3-fluoro-4-methoxybenzyl)piperidin-4-yl)-5-(4-(4-(trifluoromethylsulfonyl)phenoxy)piperidine-1-carbonyl)benzofuran-2-carboxamide |
| 6-138 | N-(1-(3-fluoro-4-(trifluoromethoxy)benzyl)piperidin-4-yl)-5-(4-(4-(methylsulfonyl)benzyl)piperazine-1-carbonyl)benzofuran-2-carboxamide |
| 6-139 | N-(1-(3-fluoro-4-(trifluoromethoxy)benzyl)piperidin-4-yl)-5-(4-(3-(trifluoromethyl)phenyl)piperazine-1-carbonyl)benzofuran-2-carboxamide |
| 6-140 | N-(1-(4-(trifluoromethoxy)benzyl)piperidin-4-yl)-5-(4-(3-(trifluoromethyl)phenyl)piperazine-1-carbonyl)benzofuran-2-carboxamide |
| 6-141 | N-(1-(3-fluoro-4-methoxybenzyl)piperidin-4-yl)-5-(4-(3-(methylsulfonyl)benzyl)piperazine-1-carbonyl)benzofuran-2-carboxamide |
| 6-142 | N-(1-(3-fluoro-4-methoxybenzyl)piperidin-4-yl)-1-methyl-5-(4-(3-(methylsulfonyl)benzyl)piperazine-1-carbonyl)-1H-indole-2-carboxamide |

TABLE 6-continued

| No. | Name | Structure |
|---|---|---|
| 6-143 | 5-(4-(4-bromo-3-(methylsulfonyl)benzyl)piperazine-1-carbonyl)-N-(1-(3-fluoro-4-methoxybenzyl)piperidin-4-yl)benzofuran-2-carboxamide | 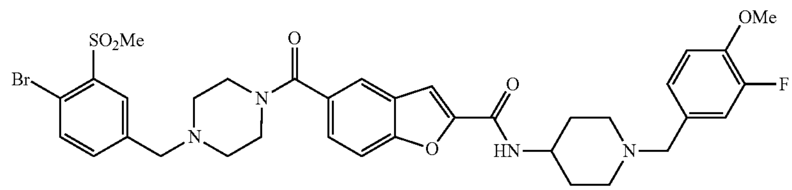 [SMILES: COc1ccc(CN2CCC(NC(=O)c3cc4cc(C(=O)N5CCN(Cc6ccc(Br)c(S(C)(=O)=O)c6)CC5)ccc4o3)CC2)cc1F] |
| 6-144 | 5-(4-(4-(methylsulfonyl)benzyl)piperazine-1-carbonyl)-N-(1-(4-(trifluoromethyl)benzyl)piperidin-4-yl)benzofuran-2-carboxamide | 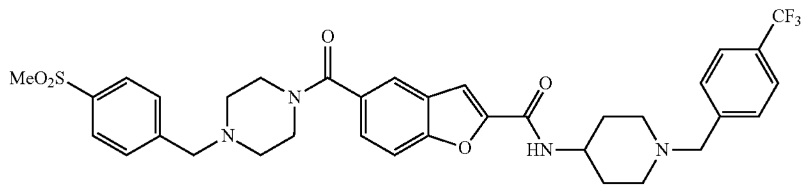 [SMILES: CS(=O)(=O)c1ccc(CN2CCN(C(=O)c3ccc4oc(C(=O)NC5CCN(Cc6ccc(C(F)(F)F)cc6)CC5)cc4c3)CC2)cc1] |
| 6-145 | N-(1-(4-cyano-3-fluorobenzyl)piperidin-4-yl)-5-(4-(4-(methylsulfonyl)benzyl)piperazine-1-carbonyl)benzofuran-2-carboxamide | 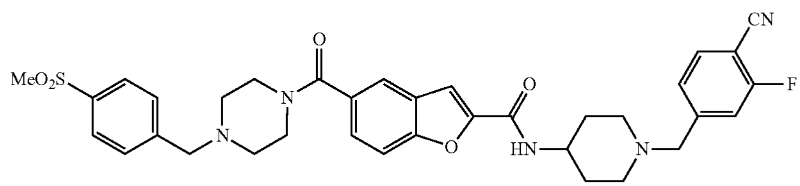 [SMILES: CS(=O)(=O)c1ccc(CN2CCN(C(=O)c3ccc4oc(C(=O)NC5CCN(Cc6ccc(C#N)c(F)c6)CC5)cc4c3)CC2)cc1] |
| 6-146 | 5-(4-(4-(methylsulfonyl)benzyl)piperazine-1-carbonyl)-N-(1-(3-(trifluoromethoxy)benzyl)piperidin-4-yl)benzofuran-2-carboxamide | 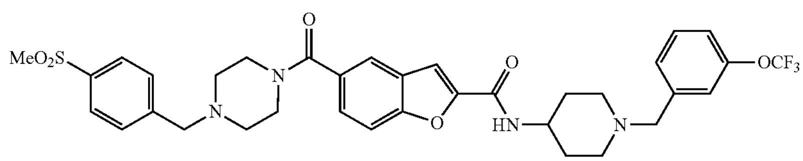 [SMILES: CS(=O)(=O)c1ccc(CN2CCN(C(=O)c3ccc4oc(C(=O)NC5CCN(Cc6cccc(OC(F)(F)F)c6)CC5)cc4c3)CC2)cc1] |
| 6-147 | 5-(4-(4-(methylsulfonyl)benzyl)piperazine-1-carbonyl)-N-(1-(3-(trifluoromethyl)benzyl)piperidin-4-yl)benzofuran-2-carboxamide | 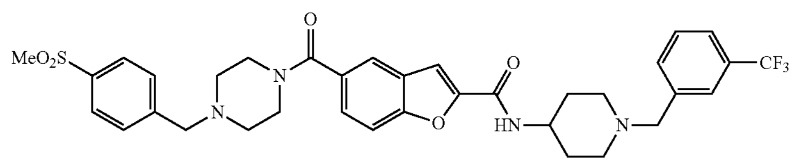 [SMILES: CS(=O)(=O)c1ccc(CN2CCN(C(=O)c3ccc4oc(C(=O)NC5CCN(Cc6cccc(C(F)(F)F)c6)CC5)cc4c3)CC2)cc1] |
| 6-148 | N-(1-(4-(1H-pyrazol-1-yl)benzyl)piperidin-4-yl)-5-(4-(4-(methylsulfonyl)benzyl)piperazine-1-carbonyl)benzofuran-2-carboxamide | 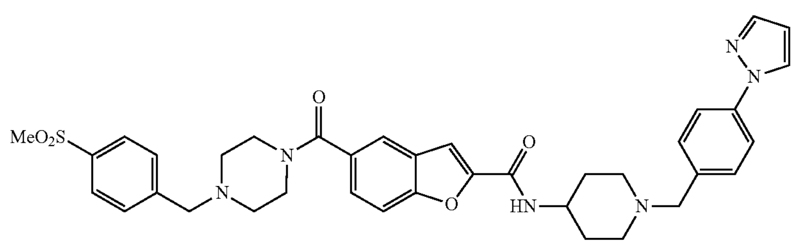 [SMILES: CS(=O)(=O)c1ccc(CN2CCN(C(=O)c3ccc4oc(C(=O)NC5CCN(Cc6ccc(-n7cccn7)cc6)CC5)cc4c3)CC2)cc1] |
| 6-149 | 5-(4-(3-(methylsulfonyl)benzyl)piperazine-1-carbonyl)-N-(1-(4-(trifluoromethyl)benzyl)piperidin-4-yl)benzofuran-2-carboxamide | 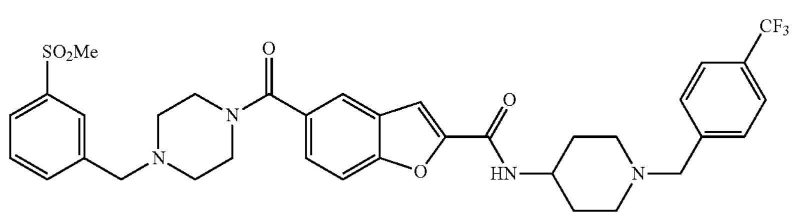 [SMILES: CS(=O)(=O)c1cccc(CN2CCN(C(=O)c3ccc4oc(C(=O)NC5CCN(Cc6ccc(C(F)(F)F)cc6)CC5)cc4c3)CC2)c1] |
| 6-150 | N-(1-(4-cyano-3-fluorobenzyl)piperidin-4-yl)-5-(4-(3-(methylsulfonyl)benzyl)piperazine-1-carbonyl)benzofuran-2-carboxamide | 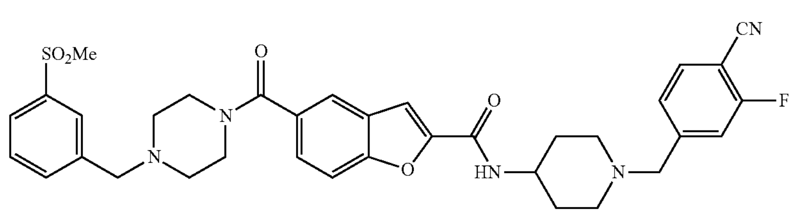 [SMILES: CS(=O)(=O)c1cccc(CN2CCN(C(=O)c3ccc4oc(C(=O)NC5CCN(Cc6ccc(C#N)c(F)c6)CC5)cc4c3)CC2)c1] |

TABLE 6-continued

| No. | Name |
|---|---|
| 6-151 | 5-(4-(3-(methylsulfonyl)benzyl)piperazine-1-carbonyl)-N-(1-(3-(trifluoromethoxy)benzyl)piperidin-4-yl)benzofuran-2-carboxamide |
| 6-152 | 5-(4-(3-(methylsulfonyl)benzyl)piperazine-1-carbonyl)-N-(1-(3-(trifluoromethyl)benzyl)piperidin-4-yl)benzofuran-2-carboxamide |
| 6-153 | N-(1-(4-(1H-pyrazol-1-yl)benzyl)piperidin-4-yl)-5-(4-(3-(methylsulfonyl)benzyl)piperazine-1-carbonyl)benzofuran-2-carboxamide |
| 6-154 | N-(1-(3-fluoro-4-methoxybenzyl)piperidin-4-yl)-5-(4-(4-(methylsulfonyl)benzyl)piperazine-1-carbonyl)benzofuran-2-carboxamide |
| 6-155 | N-((3,4-trans)-3-fluoro-1-(4-(trifluoromethoxy)benzyl)piperidin-4-yl)-5-(4-(4-(methylsulfonyl)phenoxy)piperidine-1-carbonyl)benzofuran-2-carboxamide |
| 6-156 | 5-(4-(4-(methylsulfonyl)benzyl)piperazine-1-carbonyl)-N-(1-(4-(1,1,2,2-tetrafluoroethoxy)benzyl)piperidin-4-yl)benzofuran-2-carboxamide |
| 6-157 | 5-(4-(4-(methylsulfonyl)benzyl)piperazine-1-carbonyl)-N-(1-(3-(1,1,2,2-tetrafluoroethoxy)benzyl)piperidin-4-yl)benzofuran-2-carboxamide |
| 6-158 | N-(1-(3-chloro-4-(trifluoromethoxy)benzyl)piperidin-4-yl)-5-(4-(4-(methylsulfonyl)benzyl)piperazine-1-carbonyl)benzofuran-2-carboxamide |

TABLE 6-continued

| No. | Name | Structure |
|---|---|---|
| 6-159 | 5-(4-(4-(methylsulfonyl)benzyl)piperazine-1-carbonyl)-N-(1-(4-(pyrrolidin-1-ylsulfonyl)benzyl)piperidin-4-yl)benzofuran-2-carboxamide | 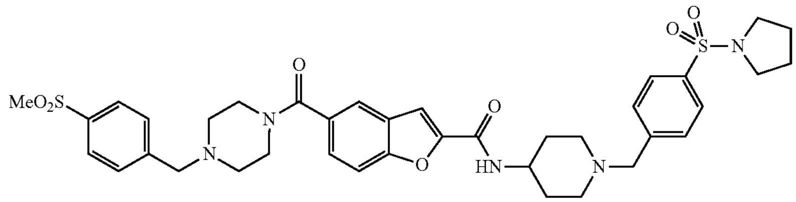 [SMILES: CS(=O)(=O)c1ccc(CN2CCN(C(=O)c3ccc4oc(C(=O)NC5CCN(Cc6ccc(S(=O)(=O)N7CCCC7)cc6)CC5)cc4c3)CC2)cc1] |
| 6-160 | N-(1-(3-fluoro-4-methoxybenzyl)piperidin-4-yl)-5-(4-(4-(pyrrolidin-1-ylsulfonyl)benzyl)piperazine-1-carbonyl)benzofuran-2-carboxamide | 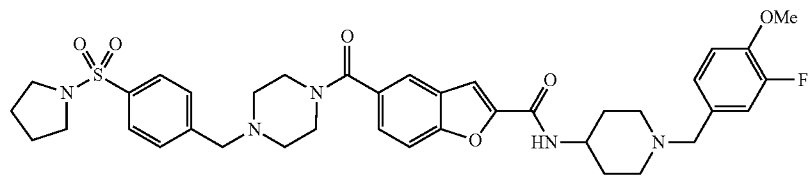 [SMILES: COc1ccc(CN2CCC(NC(=O)c3cc4cc(C(=O)N5CCN(Cc6ccc(S(=O)(=O)N7CCCC7)cc6)CC5)ccc4o3)CC2)cc1F] |
| 6-161 | 5-(4-(4-(N-ethylsulfamoyl)benzyl)piperazine-1-carbonyl)-N-(1-(3-fluoro-4-methoxybenzyl)piperidin-4-yl)benzofuran-2-carboxamide | 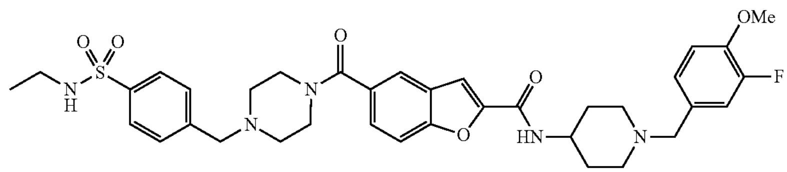 [SMILES: CCNS(=O)(=O)c1ccc(CN2CCN(C(=O)c3ccc4oc(C(=O)NC5CCN(Cc6ccc(OC)c(F)c6)CC5)cc4c3)CC2)cc1] |
| 6-162 | N-(1-(3-fluoro-4-methoxybenzyl)piperidin-4-yl)-5-(4-(4-(morpholinosulfonyl)benzyl)piperazine-1-carbonyl)benzofuran-2-carboxamide | 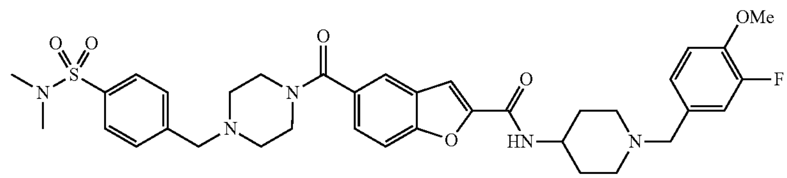 [SMILES: COc1ccc(CN2CCC(NC(=O)c3cc4cc(C(=O)N5CCN(Cc6ccc(S(=O)(=O)N(C)C)cc6)CC5)ccc4o3)CC2)cc1F] |
| 6-163 | N-(1-(3-fluoro-4-methoxybenzyl)piperidin-4-yl)-5-(4-(4-(morpholinosulfonyl)benzyl)piperazine-1-arbonyl)benzofuran-2-carboxamide | 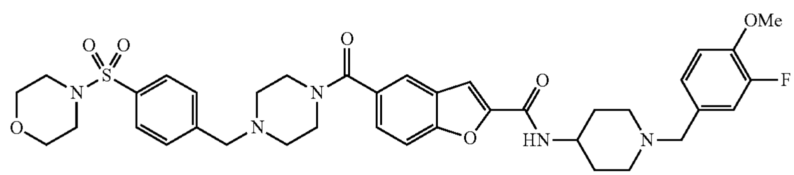 [SMILES: COc1ccc(CN2CCC(NC(=O)c3cc4cc(C(=O)N5CCN(Cc6ccc(S(=O)(=O)N7CCOCC7)cc6)CC5)ccc4o3)CC2)cc1F] |
| 6-164 | N-(1-(4-methoxybenzyl)piperidin-4-yl)-5-(4-(4-(methylsulfonyl)phenoxy)piperidine-1-carbonyl)benzofuran-2-carboxamide | 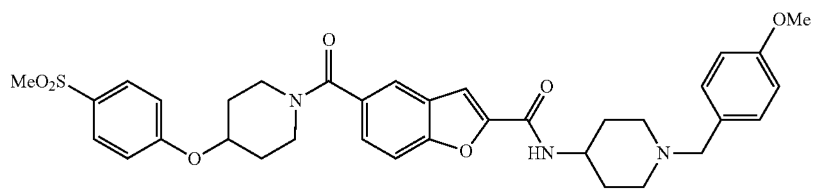 [SMILES: COc1ccc(CN2CCC(NC(=O)c3cc4cc(C(=O)N5CCC(Oc6ccc(S(C)(=O)=O)cc6)CC5)ccc4o3)CC2)cc1] |

Another aspect of the disclosure provides compounds having structural formula (7-I):

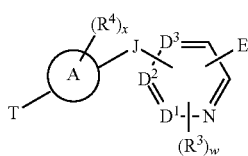

(7-I)

and pharmaceutically acceptable salts, prodrugs and N-oxides thereof (and solvates and hydrates thereof), in which 0 or 1 of $D^1$, $D^2$ and $D^3$ is N, with the others independently being CH or C substituted by one of the w $R^3$;

E is —$R^2$, —C(O)NR$^1$R$^2$, —NR$^1$R$^2$ or —NR$^1$C(O)R$^2$, in which R$^1$ and R$^2$ together with the nitrogen to which they are bound form Hca, or R$^1$ is H, —(C$_1$-C$_4$ alkyl), —C(O)—(C$_1$-C$_4$ alkyl) or —C(O)O—(C$_1$-C$_4$ alkyl), and R$^2$ is —C(O)Hca, —(C$_0$-C$_3$ alkyl)-Ar, —(C$_0$-C$_3$ alkyl)-Het, —(C$_0$-C$_3$ alkyl)-Cak or —(C$_0$-C$_3$ alkyl)-Hca;

J is absent, —C(O)—, —NR$^{13}$—, —NR$^{13}$C(O)— or —C(O)NR$^{13}$—, in which R$^{13}$ is selected from —H, —(C$_1$-C$_4$ alkyl), —C(O)—(C$_1$-C$_4$ alkyl) and —C(O)O—(C$_1$-C$_4$ alkyl);

the ring system denoted by "B" is absent, arylene, heteroarylene,

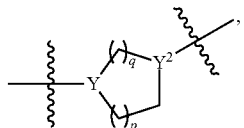

wherein each of $Y^1$ and $Y^2$ is N, C or CH, provided that at least one of $Y^1$ and $Y^2$ is N, p is 0, 1, 2, 3 or 4, q is 1, 2, 3 or 4, and the sum of p and q is 1, 2, 3, 4, 5 or 6, or

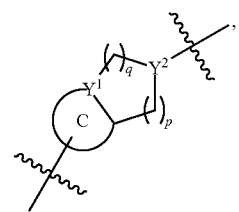

wherein $Y^1$ is N or C and $Y^2$ is N, C or CH, provided that at least one of $Y^1$ and $Y^2$ is N, the ring system denoted by "C" is an arylene or a heteroarylene, p is 0, 1, 2, 3 or 4, q is 1, 2, 3 or 4, and the sum of p and q is 1, 2, 3, 4, 5 or 6;
and all other variables are as described herein, for example, with respect to structural formula (3-I).

In another aspect, the present disclosure provides certain compounds of structural formula (7-I) in which x is 1 and $R^3$ is methyl. For example, in one embodiment, a compound of the disclosure has structural formula (7-II)

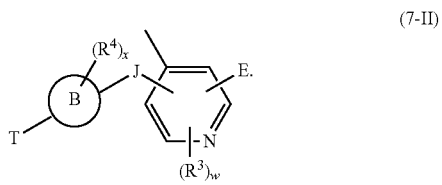

(7-II)

In various embodiments according to this aspect of the disclosure, the other variables can be defined as disclosed U.S. patent application Ser. No. 13/194,810 and in International Patent Application no. PCT/US11/46019, each of which is hereby incorporated by reference in its entirety.

Various embodiments of compounds of structural formula (7-I) suitable for use in the methods described herein are described below. Information regarding certain additional embodiments can be found in U.S. patent application Ser. No. 13/194,810 and in International Patent Application no. PCT/US11/46019, each of which is hereby incorporated by reference in its entirety.

In another aspect, the present disclosure provides certain compounds of structural formula (7-I) described in Table 7, below. These compounds can be made, for example using a procedure analogous to those described in U.S. Patent Application Publications nos. 2009/0163511, 2009/0170829, 2009/0186894 and 2009/0275609, and in U.S. patent application Ser. Nos. 12/695,861 and 13/194,810, each of which is hereby incorporated by reference in its entirety.

TABLE 7

| No. | Name | Structure |
|---|---|---|
| 7-1 | 6-(4-(4-(methylsulfonyl)phenoxy)piperidine-1-carbonyl)-N-(6-(4-(pentafluorosulfanyl)phenoxy)pyridin-3-yl)nicotinamide | 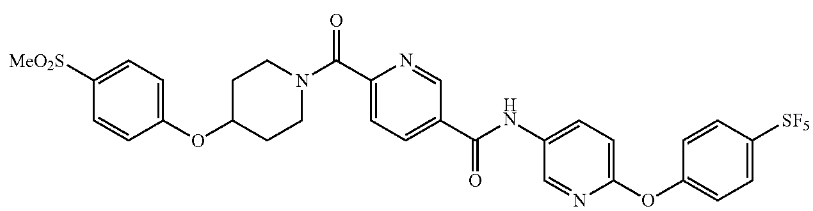 |
| 7-2 | 5-(4-(4-(methylsulfonyl)phenoxy)piperidine-1-carbonyl)-N-(6-(4-(pentafluorosulfanyl)phenoxy)pyridin-3-yl)picolinamide | 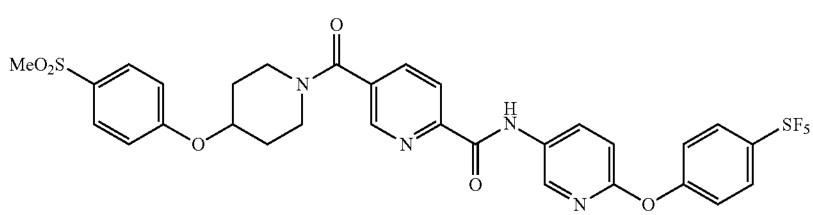 |
| 7-3 | 5-(4-(4-methoxybenzoyl)piperidine-1-carbonyl)-N-(6-(4-(pentafluorosulfanyl)phenoxy)pyridin-3-yl)picolinamide | 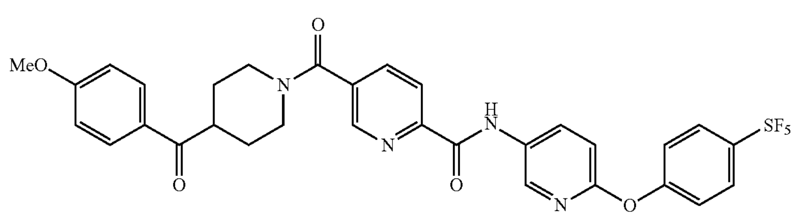 |

TABLE 7-continued

| No. | Name | Structure |
|---|---|---|
| 7-4 | 5-(4-(4-(pyrrolidin-1-yl)benzoyl)piperidine-1-carbonyl)-N-(6-(4-(pentafluorosulfanyl)phenoxy)pyridin-3-yl)picolinamide | 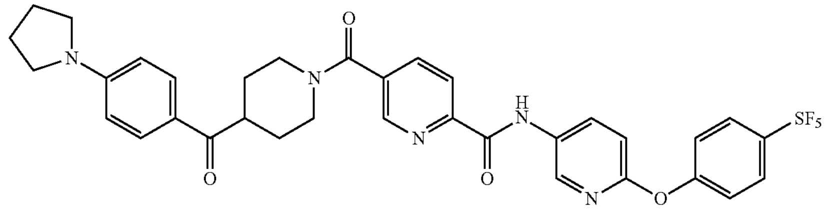 |
| 7-5 | 5-(4-(4-cyanophenoxy)piperidine-1-carbonyl)-N-(6-(4-(pentafluorosulfanyl)phenoxy)pyridin-3-yl)picolinamide | 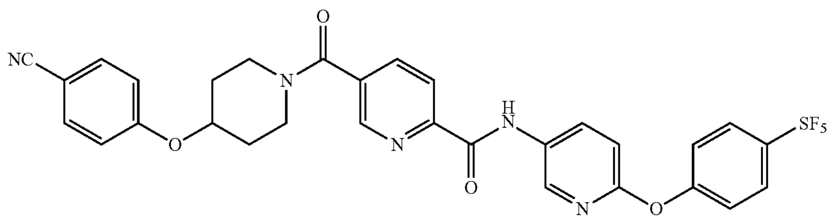 |
| 7-6 | 5-(4-(4-(isopropylsulfonyl)phenyl)piperazine-1-carbonyl)-N-(6-(4-(pentafluorosulfanyl)phenoxy)pyridin-3-yl)picolinamide | 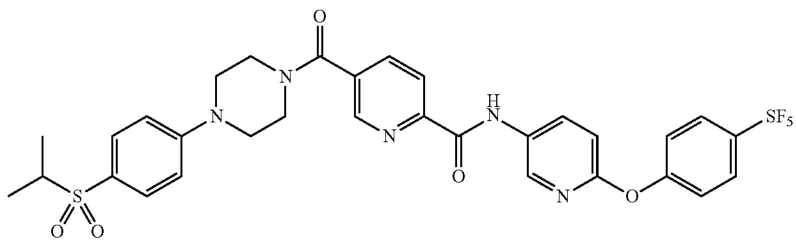 |
| 7-7 | N-(1-(4-cyanobenzyl)piperidin-4-yl)-6-(3-(4-methoxybenzoyl)piperidine-1-carbonyl)nicotinamide | 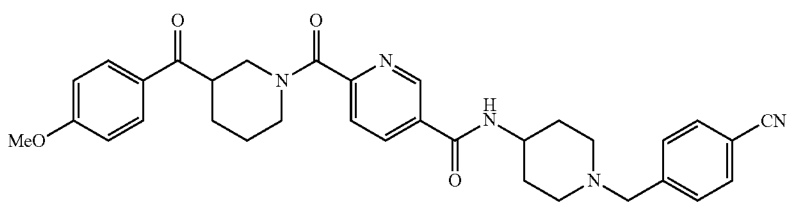 [SMILES: COc1ccc(C(=O)C2CCCN(C(=O)c3ccc(C(=O)NC4CCN(Cc5ccc(C#N)cc5)CC4)cn3)C2)cc1] |
| 7-8 | 6-(3-(4-methoxybenzoyl)piperidine-1-carbonyl)-N-(1-(4-methoxybenzyl)piperidin-4-yl)nicotinamide | 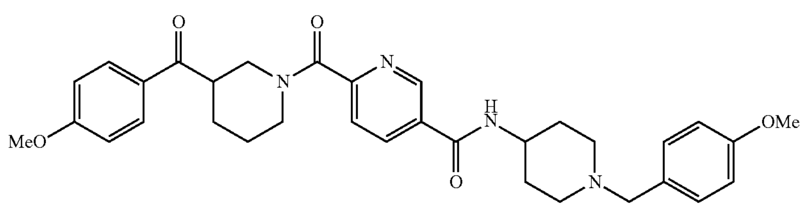 [SMILES: COc1ccc(CN2CCC(NC(=O)c3ccc(C(=O)N4CCCC(C(=O)c5ccc(OC)cc5)C4)nc3)CC2)cc1] |
| 7-9 | N-(1-(4-fluorobenzyl)piperidin-4-yl)-6-(3-(4-methoxybenzoyl)piperidine-1-carbonyl)nicotinamide | 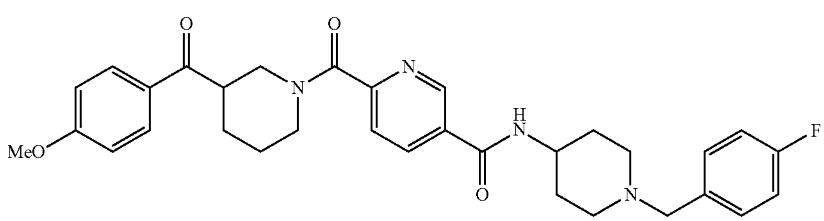 [SMILES: COc1ccc(C(=O)C2CCCN(C(=O)c3ccc(C(=O)NC4CCN(Cc5ccc(F)cc5)CC4)cn3)C2)cc1] |
| 7-10 | N-(6-(4-fluorophenoxy)pyridin-3-yl)-6-(3-(4-methoxybenzoyl)piperidine-1-carbonyl)nicotinamide | 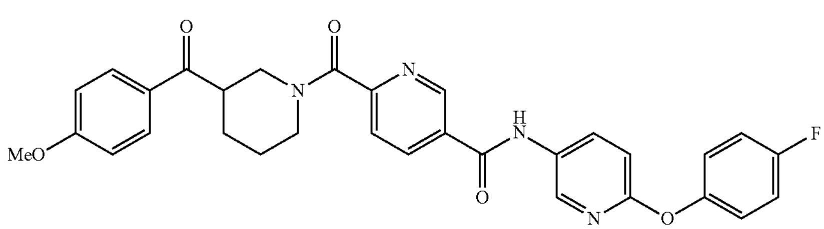 [SMILES: COc1ccc(C(=O)C2CCCN(C(=O)c3ccc(C(=O)Nc4ccc(Oc5ccc(F)cc5)nc4)cn3)C2)cc1] |

TABLE 7-continued

| No. | Name | Structure |
|---|---|---|
| 7-11 | N-(6-(4-acetylphenoxy)pyridin-3-yl)-6-(3-(4-methoxybenzoyl)piperidine-1-carbonyl)nicotinamide | 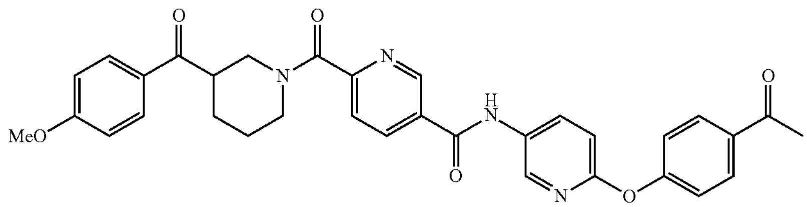 [SMILES: COc1ccc(C(=O)C2CCCN(C(=O)c3ccc(C(=O)Nc4ccc(Oc5ccc(C(C)=O)cc5)nc4)cn3)C2)cc1] |
| 7-12 | N-(6-(4-cyanophenoxy)-4-methylpyridin-3-yl)-6-(4-(4-methoxybenzoyl)piperidine-1-carbonyl)nicotinamide | 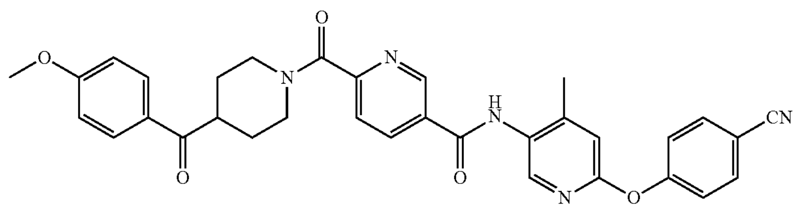 [SMILES: COc1ccc(C(=O)C2CCN(C(=O)c3ccc(C(=O)Nc4cnc(Oc5ccc(C#N)cc5)cc4C)cn3)CC2)cc1] |
| 7-13 | N-(1-(4-cyanobenzyl)piperidin-4-yl)-6-(4-(3-methyl-4-(methylsulfonyl)phenoxy)piperidine-1-carbonyl)nicotinamide | 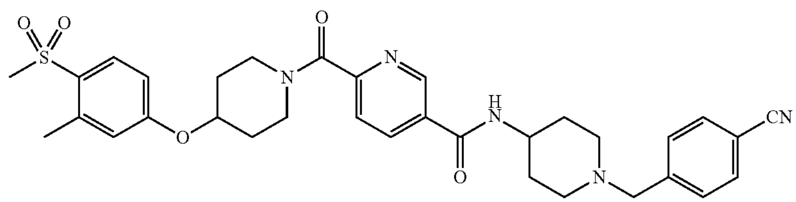 [SMILES: Cc1cc(OC2CCN(C(=O)c3ccc(C(=O)NC4CCN(Cc5ccc(C#N)cc5)CC4)cn3)CC2)ccc1S(C)(=O)=O] |
| 7-14 | 6-(4-(3-methyl-4-(methylsulfonyl)phenoxy)piperidine-1-carbonyl)-N-(1-(4-(trifluoromethoxy)benzyl)piperidin-4-yl)nicotinamide | 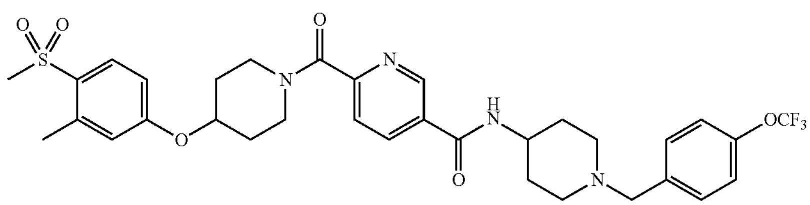 [SMILES: Cc1cc(OC2CCN(C(=O)c3ccc(C(=O)NC4CCN(Cc5ccc(OC(F)(F)F)cc5)CC4)cn3)CC2)ccc1S(C)(=O)=O] |
| 7-15 | N-(6-(4-cyanophenoxy)pyridin-3-yl)-6-(4-(3-methyl-4-(methylsulfonyl)phenoxy)piperidine-1-carbonyl)nicotinamide | 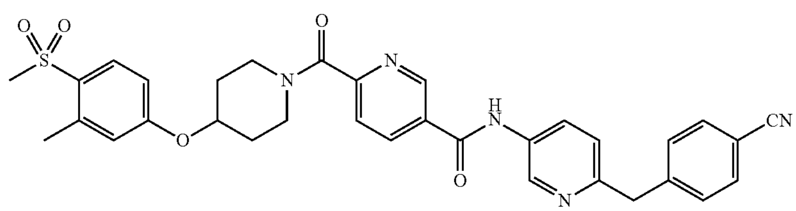 [SMILES: Cc1cc(OC2CCN(C(=O)c3ccc(C(=O)Nc4ccc(Cc5ccc(C#N)cc5)nc4)cn3)CC2)ccc1S(C)(=O)=O] |
| 7-16 | N-(1-(4-methoxybenzyl)piperidin-4-yl)-6-(4-(3-methyl-4-(methylsulfonyl)phenoxy)piperidine-1-carbonyl)nicotinamide | 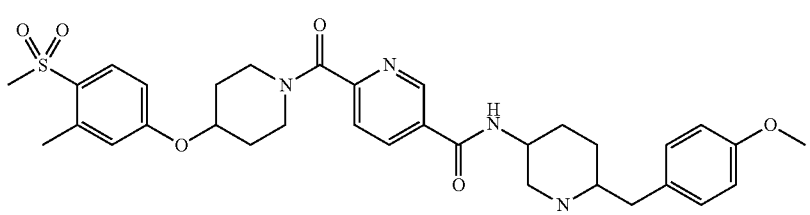 |
| 7-17 | N-(1-(4-cyanobenzyl)piperidin-4-yl)-6-(4-(4-methoxybenzoyl)piperidine-1-carbonyl)-N-(2-methoxyethyl)nicotinamide | 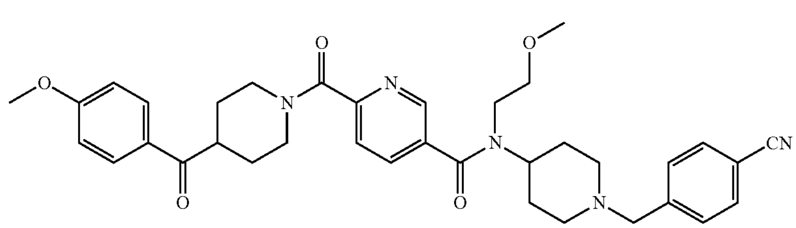 [SMILES: COCCN(C(=O)c1ccc(C(=O)N2CCC(C(=O)c3ccc(OC)cc3)CC2)nc1)C1CCN(Cc2ccc(C#N)cc2)CC1] |

TABLE 7-continued

| No. | Name | Structure |
|---|---|---|
| 7-18 | 6-(4-(4-methoxybenzoyl)piperidine-1-carbonyl)-N-(2-methoxyethyl)-N-(1-(4-(trifluoromethoxy)benzyl)piperidin-4-yl)nicotinamide | 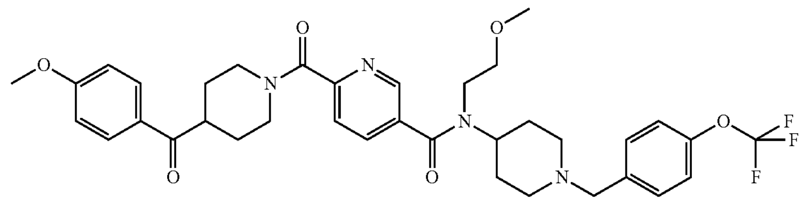 [SMILES: COCCN(C(=O)c1ccc(C(=O)N2CCC(C(=O)c3ccc(OC)cc3)CC2)nc1)C1CCN(Cc2ccc(OC(F)(F)F)cc2)CC1] |
| 7-19 | N-(1-(4-cyanobenzyl)piperidin-4-yl)-5-(5,21-dioxo-25-((3aS,4S,6aR)-2-oxohexahydro-1H-thieno[3,4-d]imidazol-4-yl)-8,11,14,17-tetraoxa-4,20-diazapentacosyl)-6-(4-(4-methoxybenzoyl)piperidine-1-carbonyl)nicotinamide | 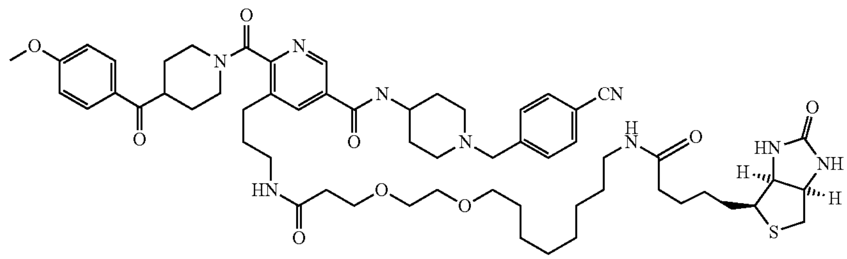 |
| 7-20 | N-(6-(4-acetylphenoxy)pyridin-3-yl)-6-(4-(2-methylbenzo[d]thiazol-5-yloxy)piperidine-1-carbonyl)nicotinamide | 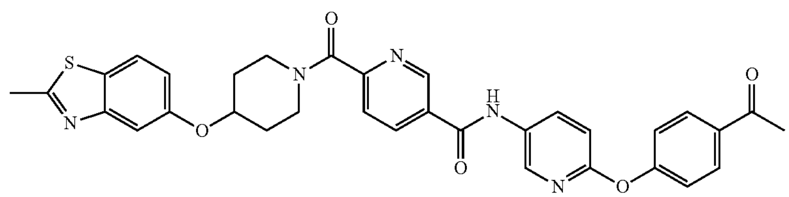 [SMILES: CC(=O)c1ccc(Oc2ccc(NC(=O)c3ccc(C(=O)N4CCC(Oc5ccc6sc(C)nc6c5)CC4)nc3)cn2)cc1] |
| 7-21 | N-((3,4-trans)-3-fluoro-1-(4-methoxybenzyl)piperidin-4-yl)-6-(4-(4-methoxybenzoyl)piperidine-1-carbonyl)nicotinamide | 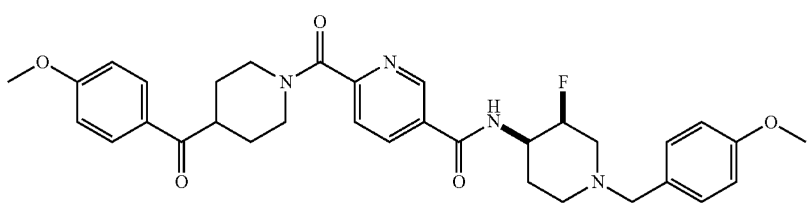 |
| 7-22 | N-(1-(4-cyanobenzyl)piperidin-4-yl)-6-(4-(2-methylbenzo[d]thiazol-5-yloxy)piperidine-1-carbonyl)nicotinamide | 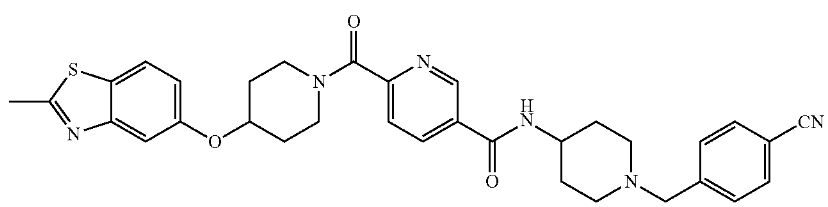 [SMILES: Cc1nc2cc(OC3CCN(C(=O)c4ccc(C(=O)NC5CCN(Cc6ccc(C#N)cc6)CC5)cn4)CC3)ccc2s1] |
| 7-23 | 6-(4-(2-methylbenzo[d]thiazol-5-yloxy)piperidine-1-carbonyl)-N-(1-(4-(trifluoromethoxy)benzyl)piperidin-4-yl)nicotinamide | 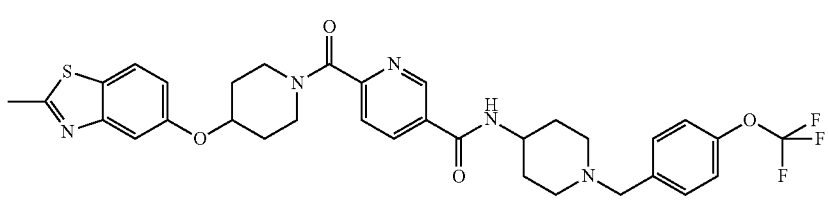 [SMILES: Cc1nc2cc(OC3CCN(C(=O)c4ccc(C(=O)NC5CCN(Cc6ccc(OC(F)(F)F)cc6)CC5)cn4)CC3)ccc2s1] |
| 7-24 | N-(1-(4-methoxybenzyl)piperidin-4-yl)-6-(4-(2-methylbenzo[d]thiazol-5-yloxy)piperidine-1-carbonyl)nicotinamide | 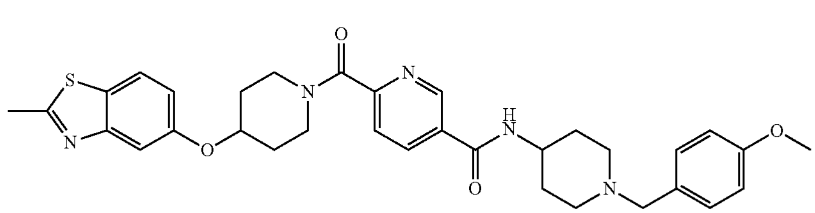 |

TABLE 7-continued

| No. | Name |
|---|---|
| 7-25 | N-(6-(4-cyanophenoxy)pyridin-3-yl)-6-(4-(2-methylbenzo[d]thiazol-5-yloxy)piperidine-1-carbonyl)nicotinamide |
| 7-26 | N-((3,4-trans)-3-fluoro-1-(4-methoxybenzyl)piperidin-4-yl)-6-(4-(4-methoxybenzoyl)piperidine-1-carbonyl)nicotinamide |
| 7-27 | N-((3,4-trans)-1-(3-cyanobenzyl)-3-fluoropiperidin-4-yl)-6-(4-(4-methoxybenzoyl)piperidine-1-carbonyl)nicotinamide |
| 7-28 | N-((3,4-trans)-3-fluoro-1-(4-(trifluoromethyl)benzyl)piperidin-4-yl)-6-(4-(4-methoxybenzoyl)piperidine-1-carbonyl)nicotinamide |
| 7-29 | N-((3,4-trans)-1-(3-cyanobenzyl)-3-fluoropiperidin-4-yl)-6-(4-(4-methoxybenzoyl)piperidine-1-carbonyl)nicotinamide |
| 7-30 | N-((3,4-trans)-3-fluoro-1-(3-methoxybenzyl)piperidin-4-yl)-6-(4-(4-methoxybenzoyl)piperidine-1-carbonyl)nicotinamide |
| 7-31 | N-((3,4-trans)-3-fluoro-1-(4-(trifluoromethyl)benzyl)piperidin-4-yl)-6-(4-(4-methoxybenzoyl)piperidine-1-carbonyl)nicotinamide |

TABLE 7-continued

| No. | Name | Structure |
|---|---|---|
| 7-32 | N-((3,4-trans)-3-fluoro-1-(3-(trifluoromethyl)benzyl)piperidin-4-yl)-6-(4-(4-methoxybenzoyl)piperidine-1-carbonyl)nicotinamide | 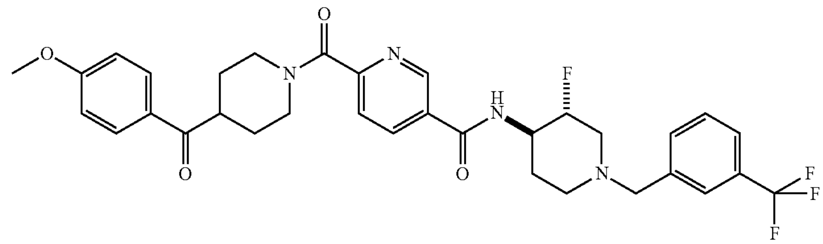 |
| 7-33 | (3,4-trans)-3-fluoro-4-(6-(4-(4-methoxybenzoyl)piperidine-1-carbonyl)nicotinamido)-1-(4-(trifluoromethoxy)benzyl)piperidinium | 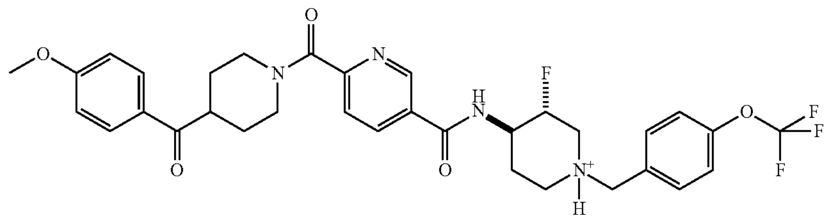 |
| 7-34 | N-((3,4-trans)-3-fluoro-1-(3-(trifluoromethyl)benzyl)piperidin-4-yl)-6-(4-(4-methoxybenzoyl)piperidine-1-carbonyl)nicotinamide | 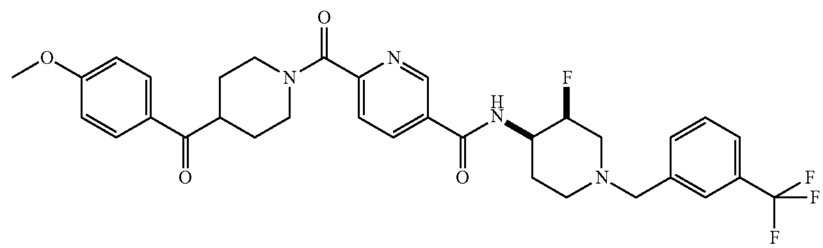 |
| 7-35 | N-((3,4-trans)-3-fluoro-1-(4-(trifluoromethyl)benzyl)piperidin-4-yl)-6-(4-(4-methoxybenzoyl)piperidine-1-carbonyl)nicotinamide - later eluting single enantiomer | 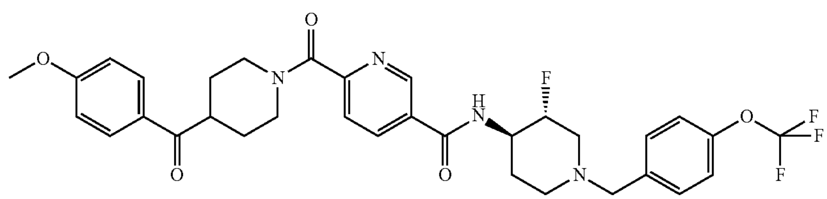 [SMILES: COc1ccc(C(=O)C2CCN(C(=O)c3ccc(C(=O)N[C@@H]4CCN(Cc5ccc(OC(F)(F)F)cc5)C[C@H]4F)cn3)CC2)cc1] |
| 7-36 | N-((3,4-trans)-3-fluoro-1-(4-(trifluoromethyl)benzyl)piperidin-4-yl)-6-(4-(4-methoxybenzoyl)piperidine-1-carbonyl)nicotinamide - earlier eluting single enantiomer | 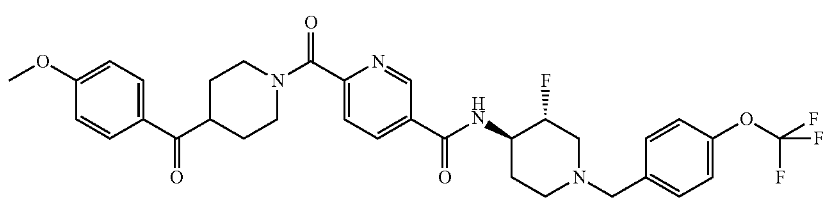 [SMILES: COc1ccc(C(=O)C2CCN(C(=O)c3ccc(C(=O)N[C@@H]4CCN(Cc5ccc(OC(F)(F)F)cc5)C[C@H]4F)cn3)CC2)cc1] |
| 7-37 | N-((3,4-trans)-3-fluoro-1-(4-fluoro-3-methylbenzyl)piperidin-4-yl)-6-(4-(4-methoxybenzoyl)piperidine-1-carbonyl)nicotinamide | 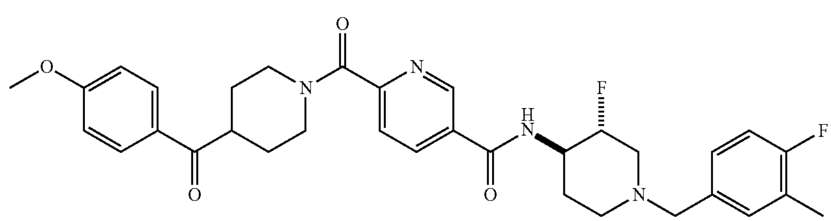 |
| 7-38 | N-(1-(4-cyanobenzyl)piperidin-4-yl)-6-(4-(1-methyl-1H-benzo[d]imidazol-5-yloxy)piperidine-1-carbonyl)nicotinamide | 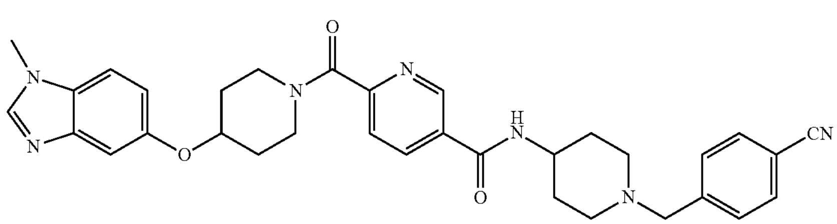 [SMILES: Cn1cnc2cc(OC3CCN(C(=O)c4ccc(C(=O)NC5CCN(Cc6ccc(C#N)cc6)CC5)cn4)CC3)ccc21] |

TABLE 7-continued

| No. | Name | Structure |
|---|---|---|
| 7-39 | 6-(4-(1-methyl-1H-benzo[d]imidazol-5-yloxy)piperidine-1-carbonyl)-N-(1-(4-(trifluoromethoxy)benzyl)piperidin-4-yl)nicotinamide | 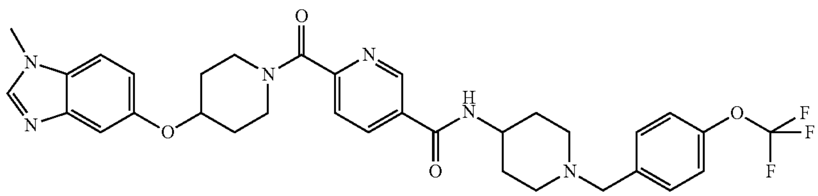 [SMILES: Cn1cnc2cc(OC3CCN(C(=O)c4ccc(C(=O)NC5CCN(Cc6ccc(OC(F)(F)F)cc6)CC5)cn4)CC3)ccc21] |
| 7-40 | N-(1-(4-methoxybenzyl)piperidin-4-yl)-6-(4-(1-methyl-1H-benzo[d]imidazol-5-yloxy)piperidine-1-carbonyl)nicotinamide | 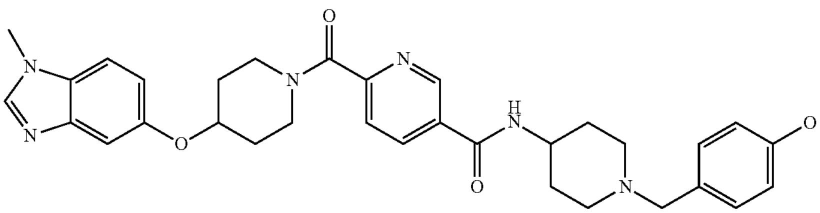 [SMILES: Cn1cnc2cc(OC3CCN(C(=O)c4ccc(C(=O)NC5CCN(Cc6ccc(O)cc6)CC5)cn4)CC3)ccc21] |
| 7-41 | N-((3,4-trans)-1-(4-(1H-pyrazol-1-yl)benzyl)-3-fluoropiperidin-4-yl)-6-(4-(4-methoxybenzoyl)piperidine-1-carbonyl)nicotinamide | 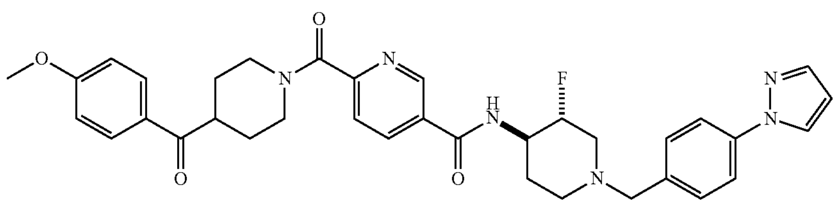 |
| 7-42 | N-((3,4-trans)-1-(4-(1H-imidazol-1-yl)benzyl)-3-fluoropiperidin-4-yl)-6-(4-(4-methoxybenzoyl)piperidine-1-carbonyl)nicotinamide | 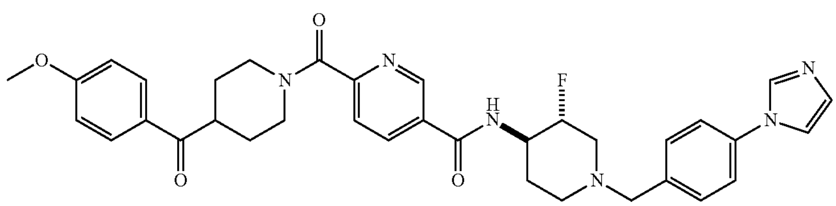 |
| 7-43 | N-((3,4-trans)-3-fluoro-1-(4-fluoro-3-methoxybenzyl)piperidin-4-yl)-6-(4-(4-methoxybenzoyl)piperidine-1-carbonyl)nicotinamide | 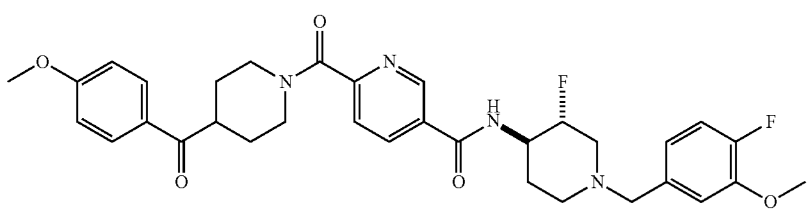 |
| 7-44 | N-((3,4-trans)-3-fluoro-1-(3-fluoro-4-methoxybenzyl)piperidin-4-yl)-6-(4-(4-methoxybenzoyl)piperidine-1-carbonyl)nicotinamide | 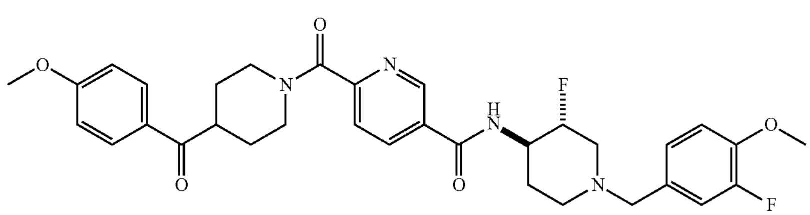 |
| 7-45 | N-((3,4-trans)-3-fluoro-1-(4-fluoro-3-(trifluoromethyl)benzyl)piperidin-4-yl)-6-(4-(4-methoxybenzoyl)piperidine-1-carbonyl)nicotinamide | 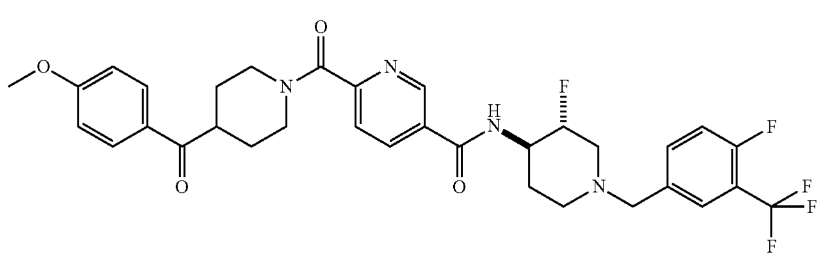 |

TABLE 7-continued

| No. | Name | Structure |
|---|---|---|
| 7-46 | N-(6-(4-acetylphenoxy)pyridin-3-yl)-6-(4-(1-methyl-1H-benzo[d]imidazol-5-yloxy)piperidine-1-carbonyl)nicotinamide | 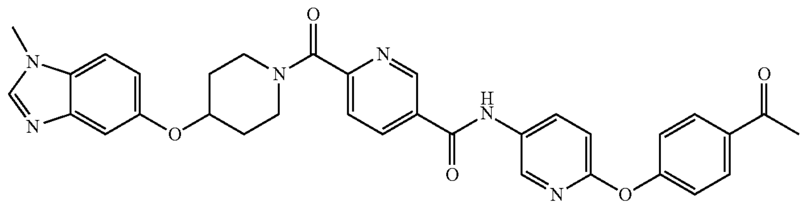 [SMILES: CC(=O)c1ccc(Oc2ccc(NC(=O)c3ccc(C(=O)N4CCC(Oc5ccc6c(c5)ncn6C)CC4)nc3)cn2)cc1] |
| 7-47 | N-((3,4-trans)-3-fluoro-1-(4-(trifluoromethoxy)benzyl)piperidin-4-yl)-6-(4-(3-methyl-4-(methylsulfonyl)phenoxy)piperidine-1-carbonyl)nicotinamide | 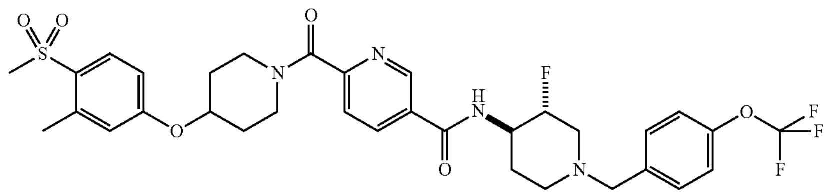 |
| 7-48 | 6-(4-(4-(cyclopropylsulfonyl)phenoxy)piperidine-1-carbonyl)-N-((3,4-trans)-3-fluoro-1-(4-(trifluoromethoxy)benzyl)piperidin-4-yl)nicotinamide | 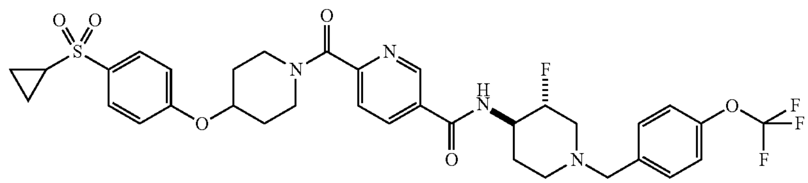 |
| 7-49 | N-((3,4-trans)-3-fluoro-1-(4-(trifluoromethoxy)benzyl)piperidin-4-yl)-6-(4-(4-(methylsulfonyl)phenoxy)piperidine-1-carbonyl)nicotmamide | 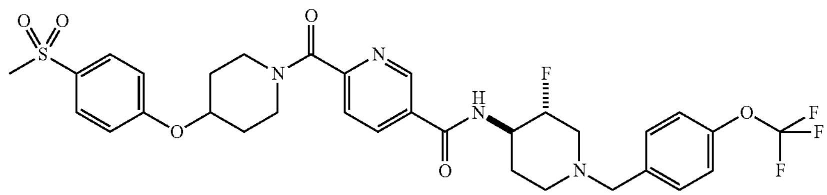 |
| 7-50 | N-((3,4-trans)-3-fluoro-1-(4-(trifluoromethoxy)benzyl)piperidin-4-yl)-6-(4-(4-(trifluoromethylsulfonyl)phenoxy)piperidine-1-carbonyl)nicotinamide | 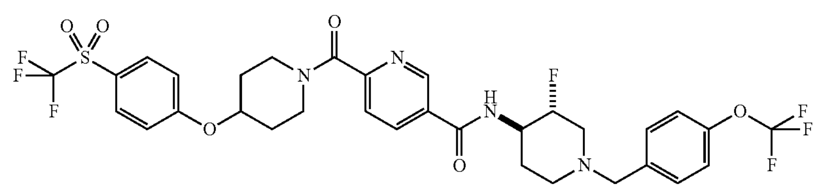 |
| 7-51 | N-((3,4-trans)-3-fluoro-1-(4-(trifluoromethoxy)benzyl)piperidin-4-yl)-6-(4-(2-methylbenzo[d]thiazol-5-yloxy)piperidine-1-carbonyl)nicotinamide | 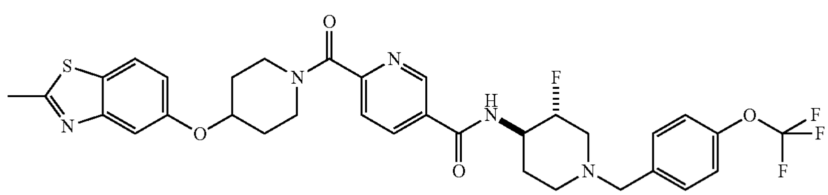 |
| 7-52 | 6-(4-(4-acetylphenoxy)piperidine-1-carbonyl)-N-((3,4-trans)-3-fluoro-1-(4-(trifluoromethoxy)benzyl)piperidin-4-yl)nicotinamide | 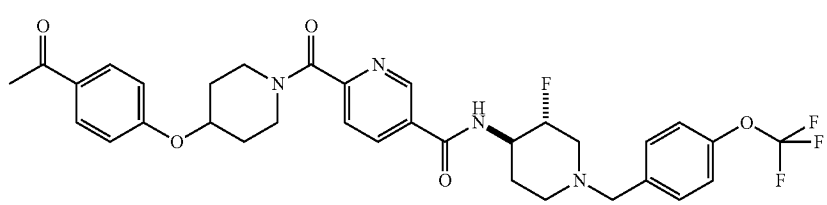 |
| 7-53 | N-((3,4-trans)-3-fluoro-1-(4-(trifluoromethoxy)benzyl)piperidin-4-yl)-6-(4-(4-morpholinobenzoyl)piperidine-1-carbonyl)nicotinamide | 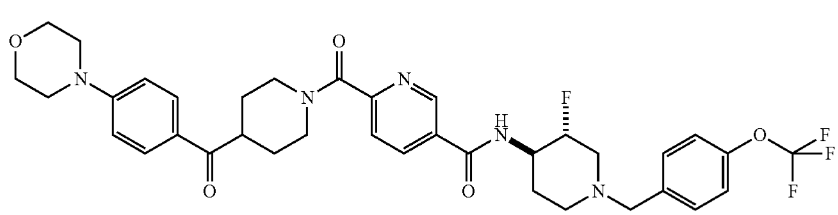 |

TABLE 7-continued

| No. | Name |
|---|---|
| 7-54 | 6-(4-(4-(1H-pyrazol-1-yl)benzoyl)piperidine-1-carbonyl)-N-((3,4-trans)-3-fluoro-1-(4-(trifluoromethoxy)benzyl)piperidin-4-yl)nicotinamide |
| 7-55 | N-((3,4-trans)-1-(3-cyano-4-methoxybenzyl)-3-fluoropiperidin-4-yl)-6-(4-(4-methoxybenzoyl)piperidine-1-carbonyl)nicotinamide |
| 7-56 | N-((3,4-trans)-1-(4-cyano-2-methylbenzyl)-3-fluoropiperidin-4-yl)-6-(4-(4-methoxybenzoyl)piperidine-1-carbonyl)nicotinamide |
| 7-57 | N-((3,4-trans)-3-fluoro-1-(4-(trifluoromethoxy)benzyl)piperidin-4-yl)-6-(4-(4-(pyrrolidin-1-yl)benzoyl)piperidine-1-carbonyl)nicotinamide |
| 7-58 | N-((3,4-trans)-1-(3-cyano-4-methylbenzyl)-3-fluoropiperidin-4-yl)-6-(4-(4-methoxybenzoyl)piperidine-1-carbonyl)nicotinamide |
| 7-59 | N-((3,4-trans)-1-(4-cyano-3-methylbenzyl)-3-fluoropiperidin-4-yl)-6-(4-(4-methoxybenzoyl)piperidine-1-carbonyl)nicotinamide |
| 7-60 | N-((3,4-trans)-1-(5-cyano-2-methoxybenzyl)-3-fluoropiperidin-4-yl)-6-(4-(4-methoxybenzoyl)piperidine-1-carbonyl)nicotinamide |

TABLE 7-continued

| No. | Name | Structure |
|---|---|---|
| 7-61 | N-((3,4-trans)-3-fluoro-1-(4-(trifluoromethoxy)benzyl)piperidin-4-yl)-6-(4-(4-(methylsulfonyl)benzoyl)piperidine-1-carbonyl)nicotinamide | 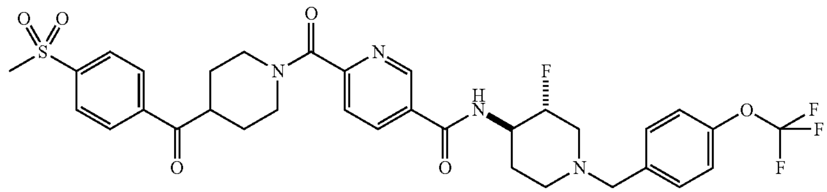 |
| 7-62 | 6-(4-(4-cyanophenoxy)piperidine-1-carbonyl)-N-((3,4-trans)-3-fluoro-1-(4-(trifluoromethoxy)benzyl)piperidin-4-yl)nicotinamide | 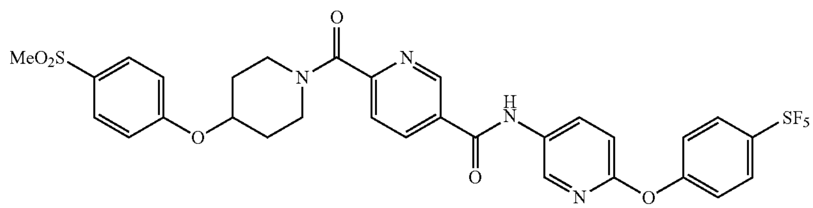 |
| 7-63 | N-((3,4-trans)-3-fluoro-1-((1-methyl-1H-pyrazol-4-yl)methyl)piperidin-4-yl)-6-(4-(4-methoxybenzoyl)piperidine-1-carbonyl)nicotinamide | 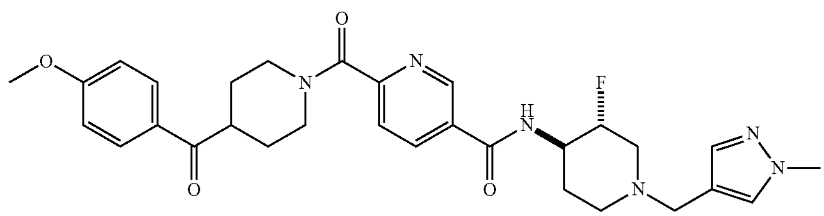 |
| 7-64 | 6-(4-(3-methyl-4-(methylsulfonyl)phenoxy)piperidine-1-carbonyl)-N-(1-(4-(1,1,2,2-tetrafluoroethoxy)benzyl)piperidin-4-yl)nicotinamide | 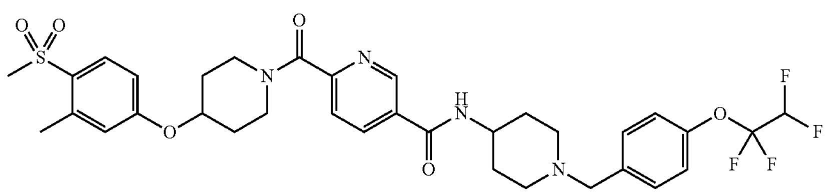 [SMILES: Cc1cc(OC2CCN(C(=O)c3ccc(C(=O)NC4CCN(Cc5ccc(OC(F)(F)C(F)F)cc5)CC4)cn3)CC2)ccc1S(C)(=O)=O] |
| 7-65 | 6-(4-(4-methoxybenzoyl)piperidine-1-carbonyl)-N-(1-(4-(1,1,2,2-tetrafluoroethoxy)benzyl)piperidin-4-yl)nicotinamide | 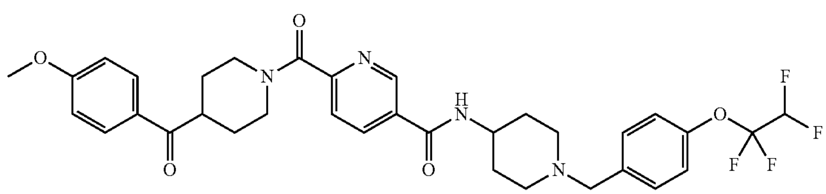 [SMILES: COc1ccc(C(=O)C2CCN(C(=O)c3ccc(C(=O)NC4CCN(Cc5ccc(OC(F)(F)C(F)F)cc5)CC4)cn3)CC2)cc1] |
| 7-66 | N-((3,4-trans)-1-(4-cyano-3-methoxybenzyl)-3-fluoropiperidin-4-yl)-6-(4-(4-methoxybenzoyl)piperidine-1-carbonyl)nicotinamide | 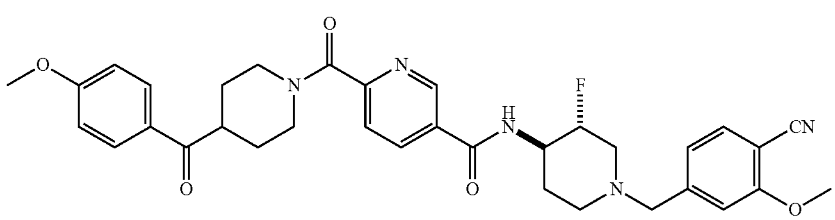 |
| 7-67 | N-((3,4-trans)-1-(4-cyanobenzyl)-3-fluoropiperidin-4-yl)-6-(4-(4-cyanophenoxy)piperidine-1-carbonyl)nicotinamide | 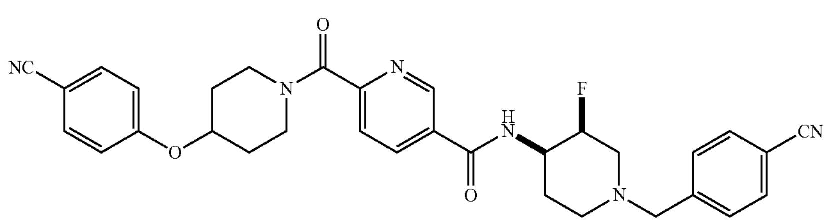 |

TABLE 7-continued

| No. | Name | Structure |
|---|---|---|
| 7-68 | 6-(4-(4-(1H-pyrazol-1-yl)benzoyl)piperidine-1-carbonyl)-N-((3,4-trans)-1-(4-cyanobenzyl)-3-fluoropiperidin-4-yl)nicotinamide | 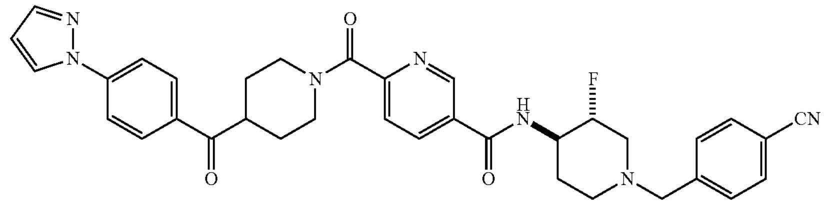 |
| 7-69 | N-((3,4-trans)-3-fluoro-1-(4-(trifluoromethoxy)benzyl)piperidin-4-yl)-6-(4-(4-(trifluoromethoxy)benzoyl)piperidine-1-carbonyl)nicotinamide | 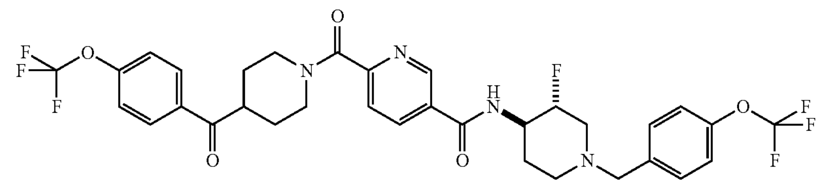 |
| 7-70 | N-(6-(4-acetylphenoxy)pyridin-3-yl)-6-(4-(4-(trifluoromethoxy)benzoyl)piperidine-1-carbonyl)nicotinamide | 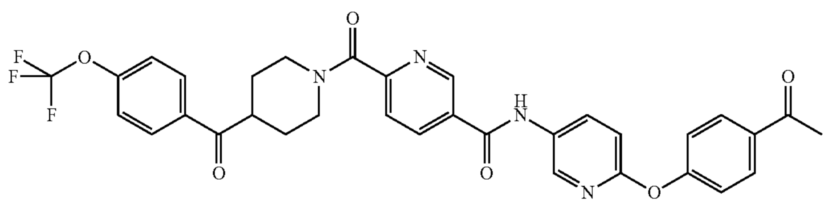 [SMILES: CC(=O)c1ccc(Oc2ccc(NC(=O)c3ccc(C(=O)N4CCC(C(=O)c5ccc(OC(F)(F)F)cc5)CC4)nc3)cn2)cc1] |
| 7-71 | N-((3,4-trans)-1-(4-cyanobenzyl)-3-fluoropiperidin-4-yl)-6-(4-(4-(trifluoromethoxy)benzoyl)piperidine-1-carbonyl)nicotinamide | 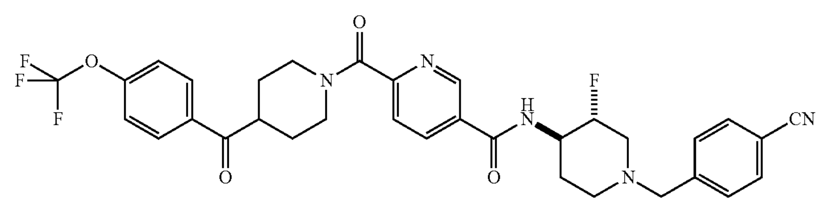 |
| 7-72 | N-((3,4-trans)-1-(4-cyanobenzyl)-3-fluoropiperidin-4-yl)-6-(4-(4-(pyrrolidin-1-yl)benzoyl)piperidine-1-carbonyl)nicotinamide | 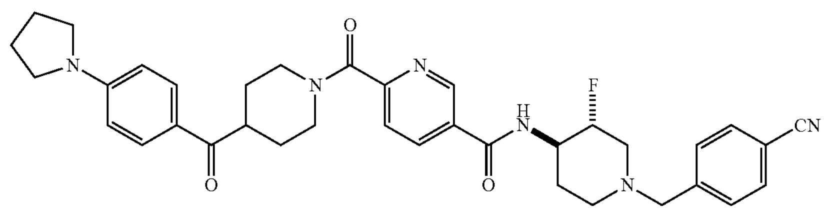 |
| 7-73 | N-((3,4-trans)-1-(4-cyanobenzyl)-3-fluoropiperidin-4-yl)-6-(4-(4-(cyclopropylsulfonyl)phenoxy)piperidine-1-carbonyl)nicotinamide | 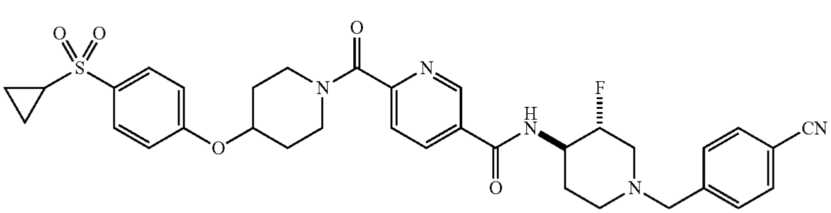 |
| 7-74 | 6-(4-(4-acetylphenoxy)piperidine-1-carbonyl)-N-((3,4-trans)-1-(4-cyanobenzyl)-3-fluoropiperidin-4-yl)nicotinamide | 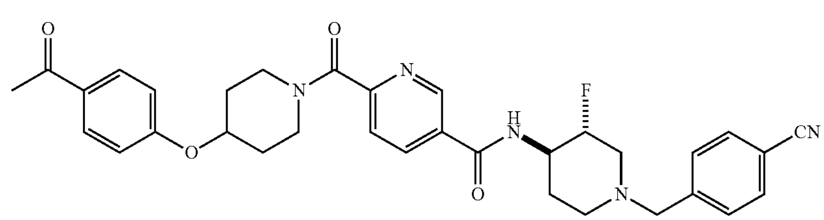 |

TABLE 7-continued

| No. | Name | Structure |
|---|---|---|
| 7-75 | N-((3,4-trans)-1-(4-cyanobenzyl)-3-fluoropiperidin-4-yl)-6-(4-(4-morpholinobenzoyl)piperidine-1-carbonyl)nicotinamide | 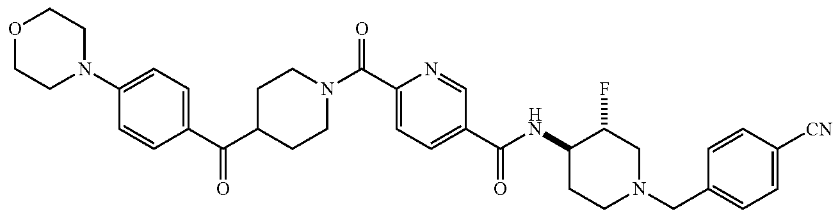 |
| 7-76 | N-(6-(4-acetylphenoxy)pyridin-3-yl)-6-(4-(4-(methylsulfonyl)benzyl)piperazine-1-carbonyl)nicotinamide | 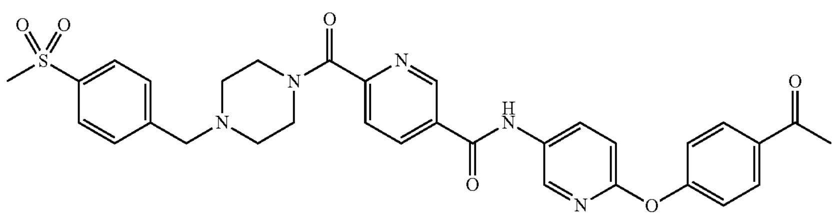 [SMILES: CC(=O)c1ccc(Oc2ccc(NC(=O)c3ccc(C(=O)N4CCN(Cc5ccc(S(C)(=O)=O)cc5)CC4)nc3)cn2)cc1] |
| 7-77 | N-(1-(4-cyanobenzyl)piperidin-4-yl)-6-(4-(4-(methylsulfonyl)phenyl)piperazin-1-yl)nicotinamide | 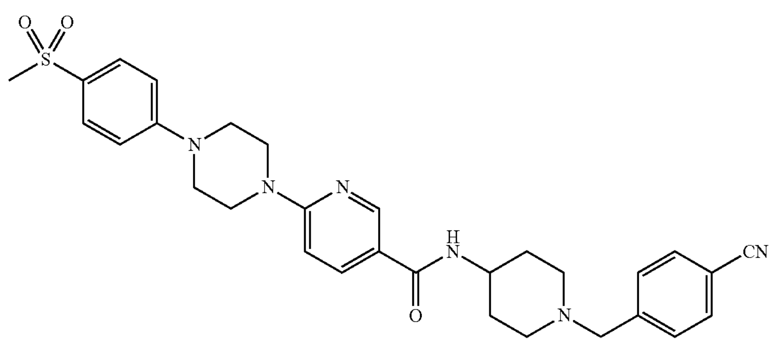 [SMILES: CS(=O)(=O)c1ccc(N2CCN(c3ccc(C(=O)NC4CCN(Cc5ccc(C#N)cc5)CC4)cn3)CC2)cc1] |
| 7-78 | N-((3,4-trans)-1-(4-cyanobenzyl)-3-methylpiperidin-4-yl)-6-(4-(4-methoxybenzoyl)piperidine-1-carbonyl)nicotinamide | 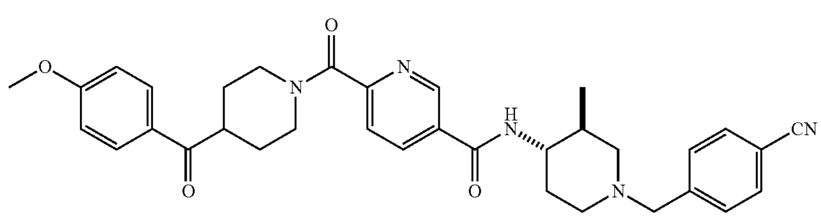 |
| 7-79 | N-(1-(4-cyanobenzyl)piperidin-4-yl)-6-(4-(4-(methylsulfonyl)benzyl)piperazin-1-yl)nicotinamide | 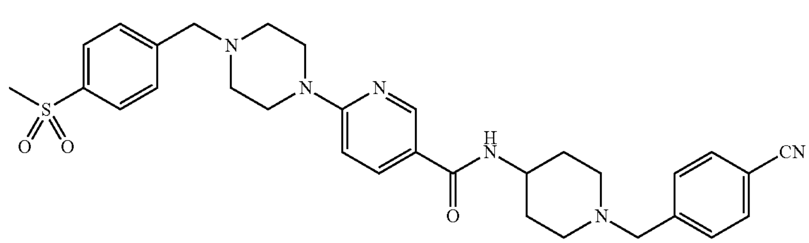 [SMILES: CS(=O)(=O)c1ccc(CN2CCN(c3ccc(C(=O)NC4CCN(Cc5ccc(C#N)cc5)CC4)cn3)CC2)cc1] |
| 7-80 | N-(1-(4-cyanobenzyl)piperidin-4-yl)-6-(4-(4-(methylsulfonyl)phenoxy)piperidin-1-yl)nicotinamide | 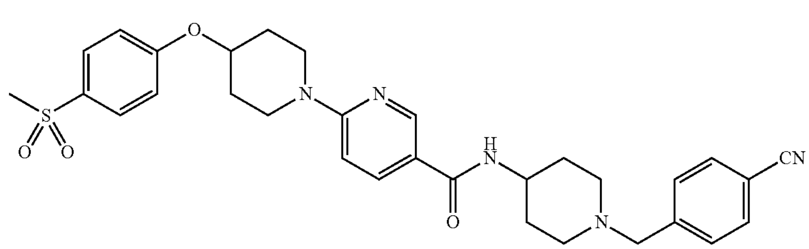 [SMILES: CS(=O)(=O)c1ccc(OC2CCN(c3ccc(C(=O)NC4CCN(Cc5ccc(C#N)cc5)CC4)cn3)CC2)cc1] |

TABLE 7-continued

| No. | Name | Structure |
|---|---|---|
| 7-81 | N-(1-(4-cyanobenzyl)piperidin-4-yl)-6-(4-(4-(cyclopropanecarbonyl)phenyl)piperazin-1-yl)nicotinamide | 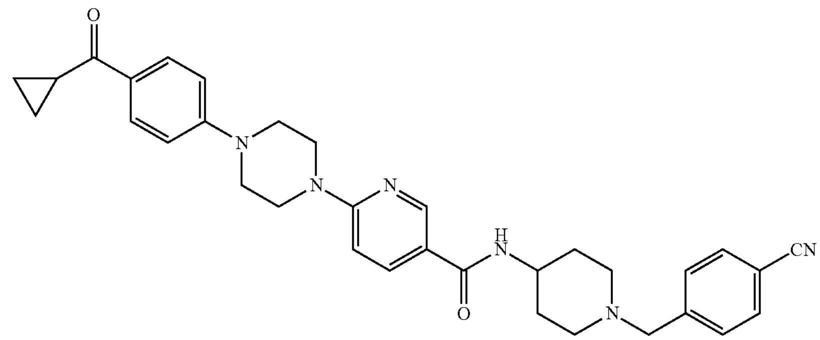 [SMILES: N#Cc1ccc(CN2CCC(NC(=O)c3ccc(N4CCN(c5ccc(C(=O)C6CC6)cc5)CC4)nc3)CC2)cc1] |
| 7-82 | N-(6-(4-acetylphenoxy)pyridin-3-yl)-6-(4-(4-(pyrrolidin-1-ylsulfonyl)phenyl)piperazine-1-carbonyl)nicotinamide | 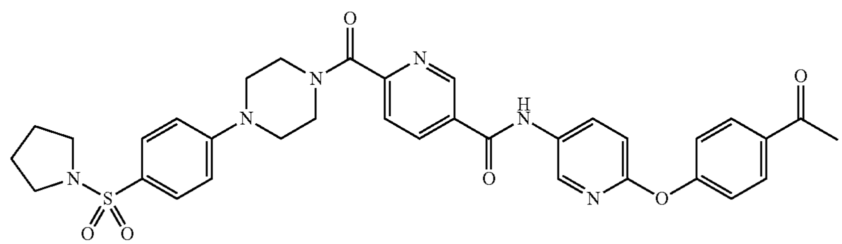 [SMILES: CC(=O)c1ccc(Oc2ccc(NC(=O)c3ccc(C(=O)N4CCN(c5ccc(S(=O)(=O)N6CCCC6)cc5)CC4)nc3)cn2)cc1] |
| 7-83 | N-(6-(4-acetylphenoxy)pyridin-3-yl)-6-(4-(4-(pyrrolidin-1-ylsulfonyl)benzyl)piperazine-1-carbonyl)nicotinamide | 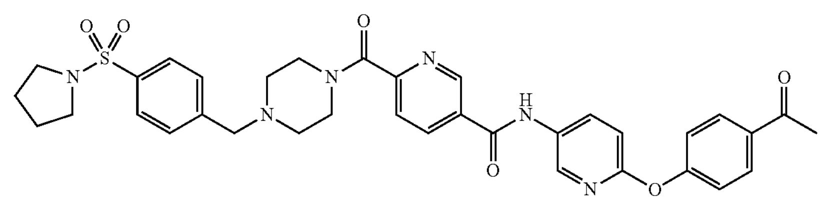 [SMILES: CC(=O)c1ccc(Oc2ccc(NC(=O)c3ccc(C(=O)N4CCN(Cc5ccc(S(=O)(=O)N6CCCC6)cc5)CC4)nc3)cn2)cc1] |
| 7-84 | N-(1-(4-cyanobenzyl)-3,3-dimethylpiperidin-4-yl)-6-(4-(4-methoxybenzoyl)piperidine-1-carbonyl)nicotinamide | 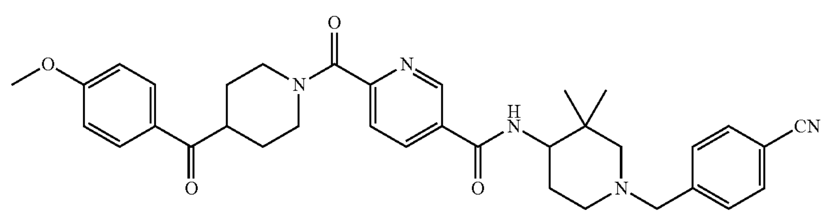 [SMILES: COc1ccc(C(=O)C2CCN(C(=O)c3ccc(C(=O)NC4CCN(Cc5ccc(C#N)cc5)CC4(C)C)cn3)CC2)cc1] |
| 7-85 | N-(3,3-dimethyl-1-(4-(trifluoromethoxy)benzyl)piperidin-4-yl)-6-(4-(4-methoxybenzoyl)piperidine-1-carbonyl)nicotinamide | 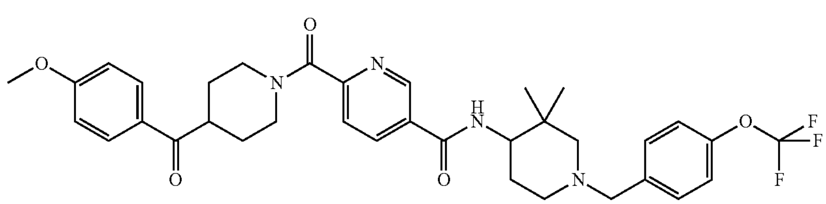 [SMILES: COc1ccc(C(=O)C2CCN(C(=O)c3ccc(C(=O)NC4CCN(Cc5ccc(OC(F)(F)F)cc5)CC4(C)C)cn3)CC2)cc1] |
| 7-86 | N-(1-(4-cyano-3-fluorobenzyl)-3,3-dimethylpiperidin-4-yl)-6-(4-(4-methoxybenzoyl)piperidine-1-carbonyl)nicotinamide | 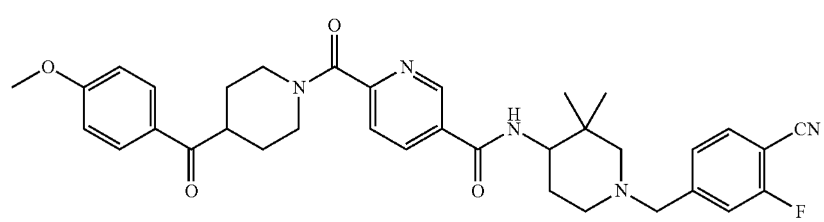 [SMILES: COc1ccc(C(=O)C2CCN(C(=O)c3ccc(C(=O)NC4CCN(Cc5ccc(C#N)c(F)c5)CC4(C)C)cn3)CC2)cc1] |

TABLE 7-continued

| No. | Name | Structure |
|---|---|---|
| 7-87 | N-(1-(4-fluoro-3-methoxybenzyl)-3,3-dimethylpiperidin-4-yl)-6-(4-(4-methoxybenzoyl)piperidine-1-carbonyl)nicotinamide | 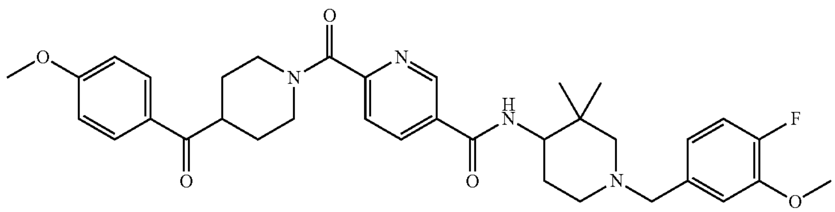 |
| 7-88 | 6-(4-(4-methoxybenzoyl)piperidine-1-carbonyl)nicotinic acid | 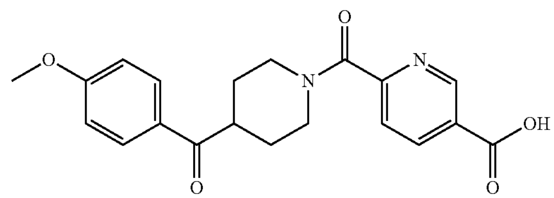 [SMILES: COc1ccc(C(=O)C2CCN(C(=O)c3ccc(C(=O)O)cn3)CC2)cc1] |
| 7-89 | N-(1-(4-cyano-3-methoxybenzyl)-3,3-dimethylpiperidin-4-yl)-6-(4-(4-methoxybenzoyl)piperidine-1-carbonyl)nicotinamide | 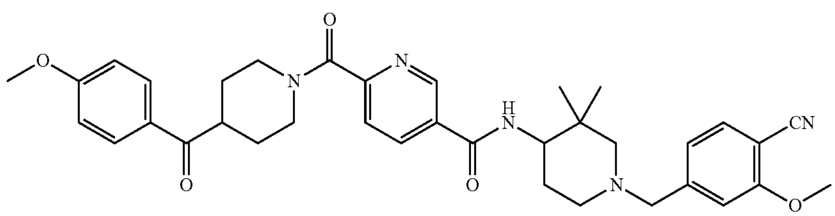 |
| 7-90 | N-(1-(3-cyano-4-methoxybenzyl)-3,3-dimethylpiperidin-4-yl)-6-(4-(4-methoxybenzoyl)piperidine-1-carbonyl)nicotinamide | 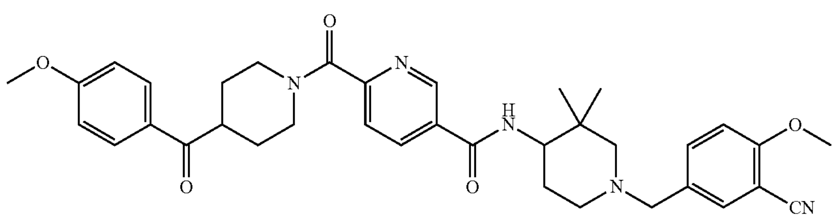 |
| 7-91 | N-ethyl-4-((4-(6-(4-(4-methoxybenzoyl)piperidine-1-carbonyl)nicotinoyl)piperazin-1-yl)methyl)benzenesulfonamide | 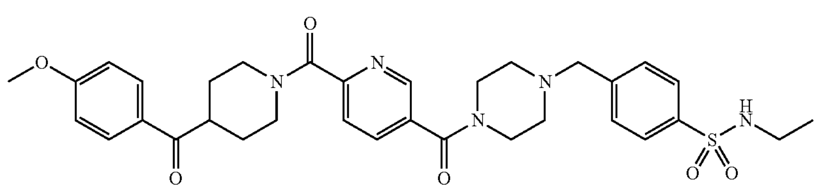 [SMILES: CCNS(=O)(=O)c1ccc(CN2CCN(C(=O)c3ccc(C(=O)N4CCC(C(=O)c5ccc(OC)cc5)CC4)nc3)CC2)cc1] |
| 7-92 | N-(6-(4-acetylphenoxy)pyridin-3-yl)-6-(4-(4-(N-ethylsulfamoyl)benzyl)piperazine-1-carbonyl)nicotinamide | 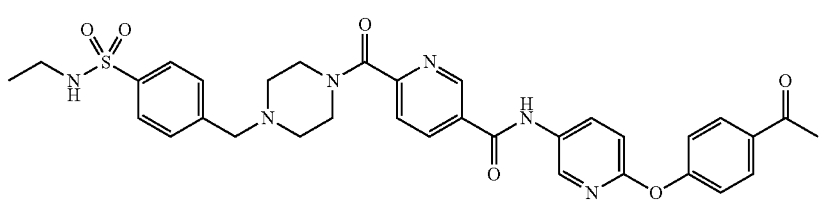 [SMILES: CCNS(=O)(=O)c1ccc(CN2CCN(C(=O)c3ccc(C(=O)Nc4ccc(Oc5ccc(C(C)=O)cc5)nc4)cn3)CC2)cc1] |
| 7-93 | N-((3,4-cis)-1-(4-cyanobenzyl)-3-methylpiperidin-4-yl)-6-(4-(4-methoxybenzoyl)piperidine-1-carbonyl)nicotinamide | 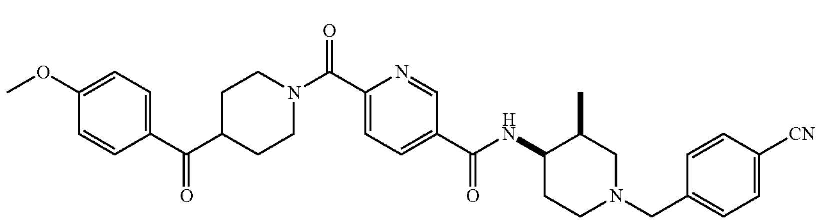 |

TABLE 7-continued

| No. | Name | Structure |
|---|---|---|
| 7-94 | 6-(4-(4-methoxybenzoyl)piperidine-1-carbonyl)-N-((3,4-cis)-3-methyl-1-(4-(trifluoromethoxy)benzyl)piperidin-4-yl)nicotinamide | 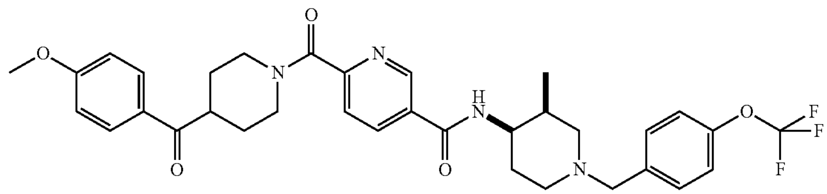 |
| 7-95 | N-(1-(3-fluoro-4-methoxybenzyl)-3,3-dimethylpiperidin-4-yl)-6-(4-(4-methoxybenzoyl)piperidine-1-carbonyl)nicotinamide | 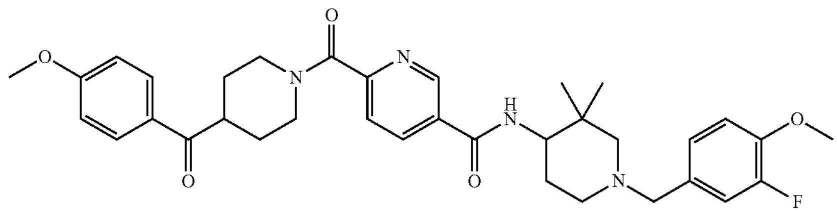 |
| 7-96 | N-((3,4-cis)-1-(3-fluoro-4-methoxybenzyl)-3-methylpiperidin-4-yl)-6-(4-(4-methoxybenzoyl)piperidine-1-carbonyl)nicotinamide | 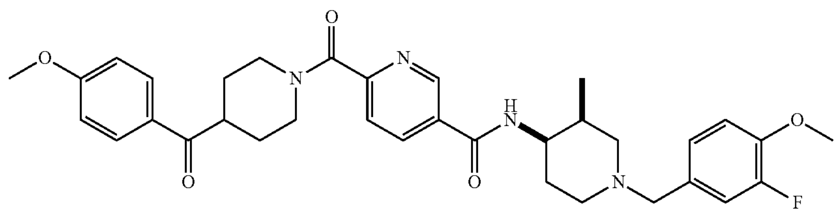 |
| 7-97 | N-((3,4-cis)-1-(4-fluoro-3-methoxybenzyl)-3-methylpiperidin-4-yl)-6-(4-(4-methoxybenzoyl)piperidine-1-carbonyl)nicotinamide | 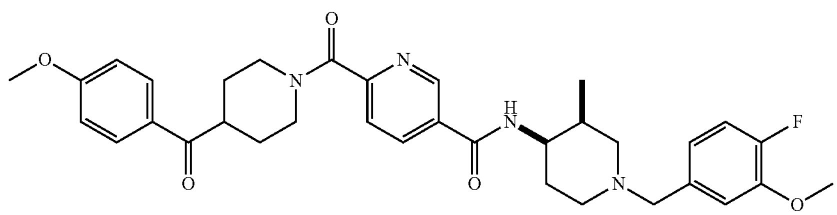 |
| 7-98 | N-((3,4-cis)-1-(4-cyano-3-fluorobenzyl)-3-methylpiperidin-4-yl)-6-(4-(4-methoxybenzoyl)piperidine-1-carbonyl)nicotinamide | 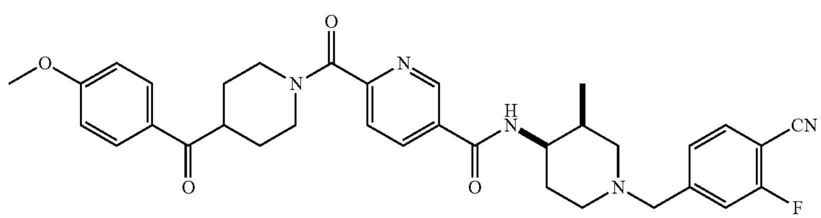 |
| 7-99 | N-((3,4-cis)-1-(4-cyano-3-methoxybenzyl)-3-methylpiperidin-4-yl)-6-(4-(4-methoxybenzoyl)piperidine-1-carbonyl)nicotinamide | 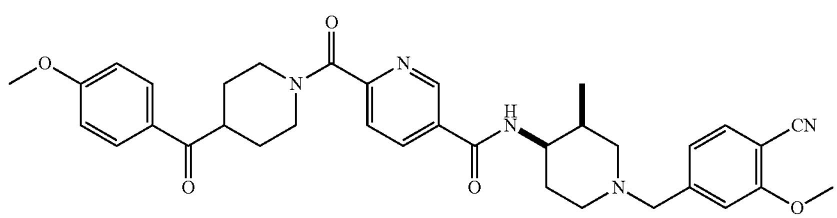 |
| 7-100 | N-((3,4-cis)-1-(3-cyano-4-methoxybenzyl)-3-methylpiperidin-4-yl)-6-(4-(4-methoxybenzoyl)piperidine-1-carbonyl)nicotinamide | 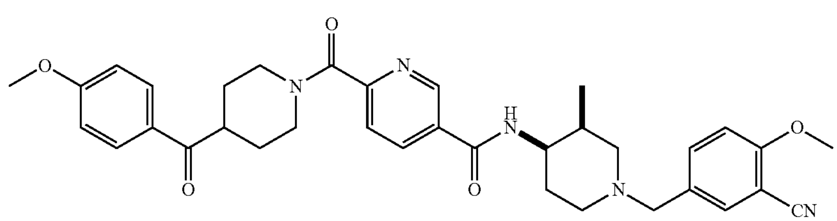 |

TABLE 7-continued

| No. | Name |
|---|---|
| 7-101 | N-((3,4-cis)-1-(4-cyanobenzyl)-3-(trifluoromethyl)piperidin-4-yl)-6-(4-(4-methoxybenzoyl)piperidine-1-carbonyl)nicotinamide |
| 7-102 | 6-(4-(4-methoxybenzoyl)piperidine-1-carbonyl)-N-((3,4-cis)-1-(4-methoxybenzyl)-3-(trifluoromethyl)piperidin-4-yl)nicotinamide |
| 7-103 | N-((3,5-cis)-1-(4-cyanobenzyl)-3,5-dimethylpiperidin-4-yl)-6-(4-(4-methoxybenzoyl)piperidine-1-carbonyl)nicotinamide |
| 7-104 | N-((3,5-cis)-3,5-dimethyl-1-(4-(trifluoromethoxy)benzyl)piperidin-4-yl)-6-(4-(4-methoxybenzoyl)piperidine-1-carbonyl)nicotinamide |
| 7-105 | N-(1-(4-cyanobenzyl)piperidin-4-yl)-6-(4-(4-methoxybenzoyl)piperidine-1-carbonyl)-4-methylnicotinamide |
| 7-106 | N-((3R,4R)-1-(4-cyanobenzyl)-3-fluoropiperidin-4-yl)-6-(4-(4-methoxybenzoyl)piperidine-1-carbonyl)nicotinamide |
| 7-107 | N-((3S,4S)-1-(4-cyanobenzyl)-3-fluoropiperidin-4-yl)-6-(4-(4-methoxybenzoyl)piperidine-1-carbonyl)nicotinamide |

TABLE 7-continued

| No. | Name |
|---|---|
| 7-108 | 6-(4-(3-(cyclopropanecarboxamido)phenoxy)piperidine-1-carbonyl)-N-(1-(4-(trifluoromethoxy)benzyl)piperidin-4-yl)nicotinamide |
| 7-109 | N-(1-(4-methoxybenzyl)piperidin-4-yl)-6-(4-(4-(pyrrolidin-1-yl)benzoyl)piperidine-1-carbonyl)nicotinamide |
| 7-110 | 6-(4-(4-(pyrrolidin-1-yl)benzoyl)piperidine-1-carbonyl)-N-(1-(4-(trifluoromethoxy)benzyl)piperidin-4-yl)nicotinamide |
| 7-111 | 6-(4-(4-(pyrrolidin-1-yl)benzoyl)piperidine-1-carbonyl)-N-(1-(3-(trifluoromethoxy)benzyl)piperidin-4-yl)nicotinamide |
| 7-112 | N-((cis)-4-(4-cyanophenoxy)cyclohexyl)-6-(4-(4-(pyrrolidin-1-yl)benzoyl)piperidine-1-carbonyl)nicotinamide |
| 7-113 | N-(1-(3-fluoro-4-methoxybenzyl)piperidin-4-yl)-6-(4-(4-(pyrrolidin-1-yl)benzoyl)piperidine-1-carbonyl)nicotinamide |
| 7-114 | 6-(4-(4-(pyrrolidin-1-yl)benzoyl)piperidine-1-carbonyl)-N-(1-(4-(pyrrolidin-1-yl)benzyl)piperidin-4-yl)nicotinamide |

TABLE 7-continued

| No. | Name | Structure |
|---|---|---|
| 7-115 | 6-(4-(4-methoxybenzoyl)piperidine-1-carbonyl)-N-(piperidin-4-yl)nicotinamide | 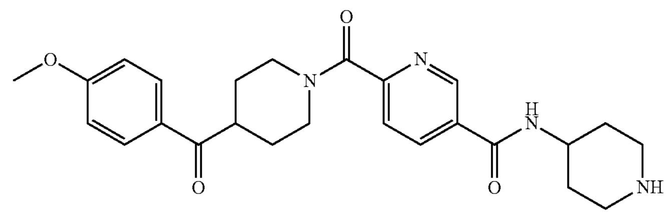 [SMILES: COc1ccc(C(=O)C2CCN(C(=O)c3ccc(C(=O)NC4CCNCC4)cn3)CC2)cc1] |
| 7-116 | N-(1-(4-isopropoxybenzyl)piperidin-4-yl)-6-(4-(4-(pyrrolidin-1-yl)benzoyl)piperidine-1-carbonyl)nicotinamide | 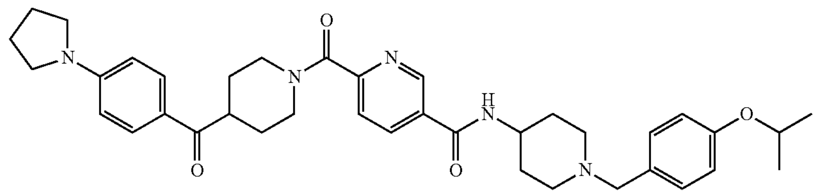 [SMILES: CC(C)Oc1ccc(CN2CCC(NC(=O)c3ccc(C(=O)N4CCC(C(=O)c5ccc(N6CCCC6)cc5)CC4)nc3)CC2)cc1] |
| 7-117 | N-(1-(4-cyano-3-fluorobenzyl)piperidin-4-yl)-6-(4-(4-(pyrrolidin-1-yl)benzoyl)piperidine-1-carbonyl)nicotinamide | 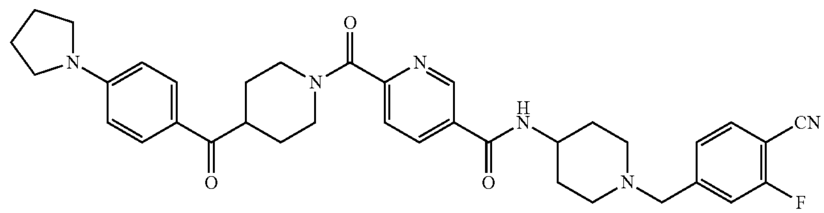 [SMILES: N#Cc1ccc(CN2CCC(NC(=O)c3ccc(C(=O)N4CCC(C(=O)c5ccc(N6CCCC6)cc5)CC4)nc3)CC2)cc1F] |
| 7-118 | N-(1-(4-cyanobenzyl)piperidin-4-yl)-6-(4-(4-(trifluoromethylsulfonyl)phenoxy)piperidine-1-carbonyl)nicotinamide | 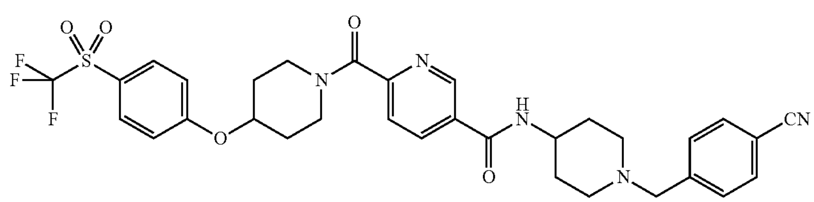 [SMILES: N#Cc1ccc(CN2CCC(NC(=O)c3ccc(C(=O)N4CCC(Oc5ccc(S(=O)(=O)C(F)(F)F)cc5)CC4)nc3)CC2)cc1] |
| 7-119 | N-((trans)-1-(4-cyanobenzyl)-3-fluoropiperidin-4-yl)-6-(4-(4-(trifluoromethylsulfonyl)phenoxy)piperidine-1-carbonyl)nicotinamide | 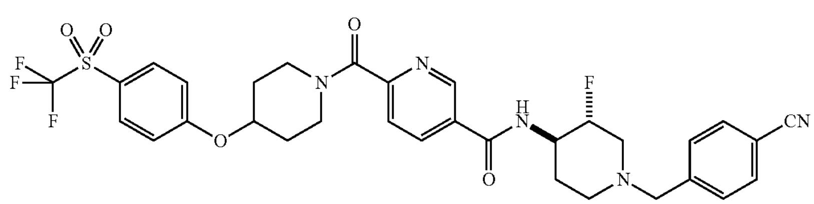 |
| 7-120 | 6-(4-(4-(cyclopropanecarbonyl)phenoxy)piperidine-1-carbonyl)-N-(1-(4-methoxybenzyl)piperidin-4-yl)nicotinamide | 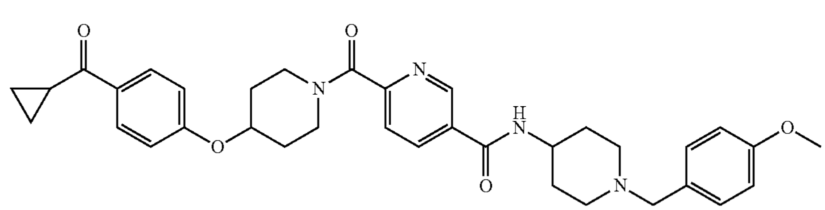 [SMILES: COc1ccc(CN2CCC(NC(=O)c3ccc(C(=O)N4CCC(Oc5ccc(C(=O)C6CC6)cc5)CC4)nc3)CC2)cc1] |

TABLE 7-continued

| No. | Name | Structure |
|---|---|---|
| 7-121 | N-(6-(4-cyanophenoxy)pyridin-3-yl)-6-(4-(4-(methylsulfonyl)phenoxy)piperidine-1-carbonyl)nicotinamide | 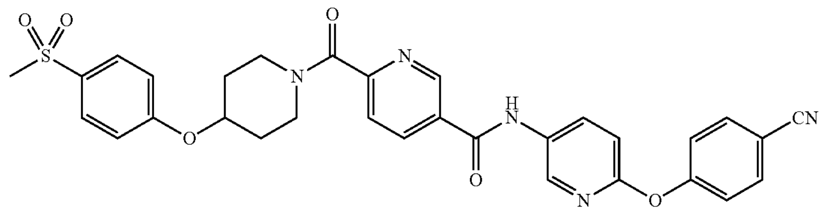 [SMILES: CS(=O)(=O)c1ccc(OC2CCN(C(=O)c3ccc(C(=O)Nc4ccc(Oc5ccc(C#N)cc5)nc4)cn3)CC2)cc1] |
| 7-122 | N-(6-(4-cyanophenoxy)pyridin-3-yl)-6-(4-(4-methoxybenzoyl)piperidine-1-carbonyl)nicotinamide | 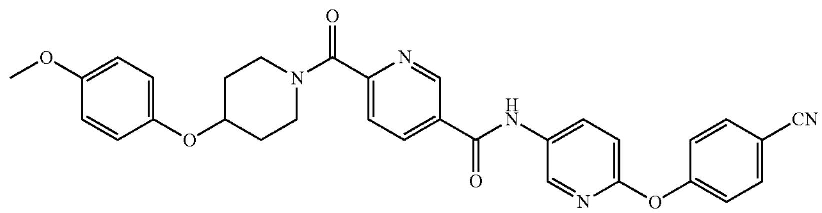 [SMILES: COc1ccc(OC2CCN(C(=O)c3ccc(C(=O)Nc4ccc(Oc5ccc(C#N)cc5)nc4)cn3)CC2)cc1] |
| 7-123 | N-((cis)-3-fluoro-1-(4-(trifluoromethoxy)benzyl)piperidin-4-yl)-6-(4-(4-methoxybenzoyl)piperidine-1-carbonyl)nicotinamide | 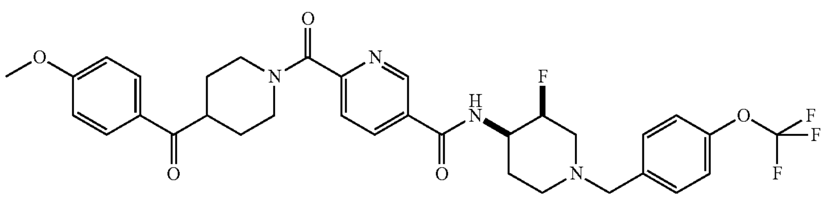 |

The present disclosure contemplates combinations of particularly described embodiments. For example, a first paragraph discloses certain embodiments of ring system "B" and a second paragraph discloses certain embodiments of T; also contemplated are embodiments in which ring system "B" is as described as in the first paragraph and T is as described in the second paragraph. This disclosure contemplates all such combinations, to the extent the definitions of the various structural features do not conflict with one another.

The compounds of the disclosure can be made using synthetic methodology familiar to the person of skill in the art, and using procedures analogous to those described in U.S. Patent Application Publications nos. 2009/0163511, 2009/0170829, 2009/0186894 and 2009/0275609, and in U.S. patent application Ser. Nos. 12/695,861 and 13/194,810, each of which is hereby incorporated by reference in its entirety.

The compounds disclosed herein can be made using procedures familiar to the person of ordinary skill in the art and as described herein. For example, compounds of structural formula (7-I) can be prepared according to Schemes 1-6, below, or analogous synthetic schemes:

Scheme 1

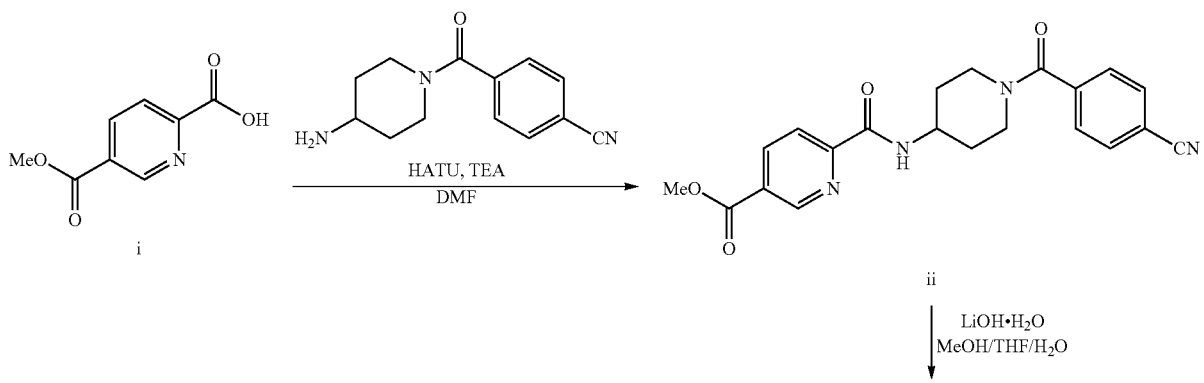

-continued

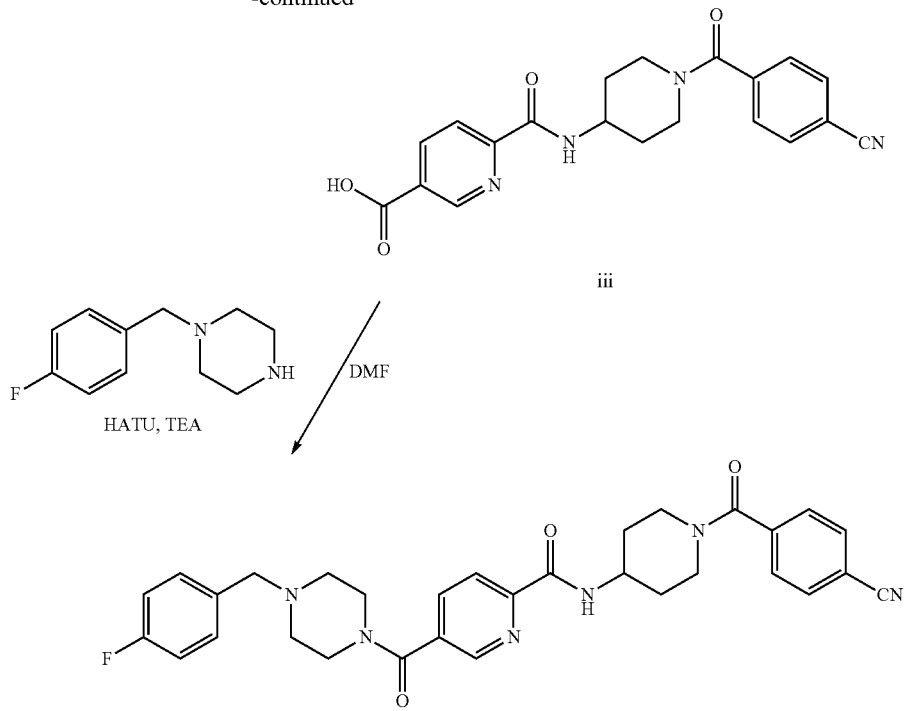

Referring to Scheme 1, a pyridinedicarboxylic acid monomethyl ester (i), for example, is coupled with an amine (here a substituted 1-benzoylpiperidine-4-amine) to form a carboxymethyl-substituted pyridinecarboxamide (ii). The ester is saponified to form the corresponding carboxylic acid (iii), which is then coupled with a suitable amine (in this case, a substituted 1-benzylpiperazine) to form a compound of structural formula (7-I).

Referring to Scheme 2, a bromopyridinedicarboxylic acid, for example, is coupled with an amine (here a substituted 1-benzylpiperidine-4-amine) to form a bromo-substituted pyridinecarboxamide (iv), which is then coupled with a suitable amine (in this case, a substituted 4-phenoxypiperidine) using a palladium catalyst to form a compound of structural formula (7-I).

Scheme 2

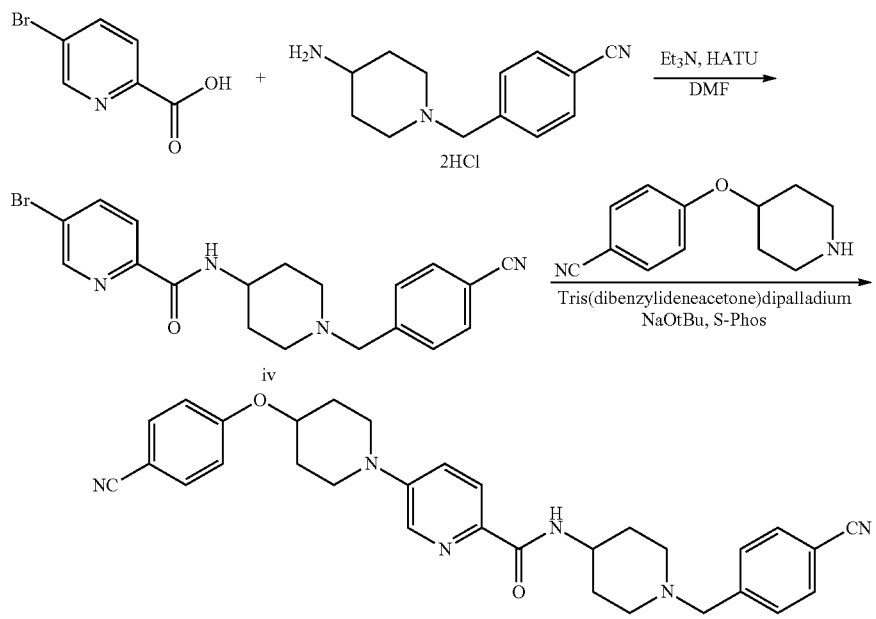

Scheme 3

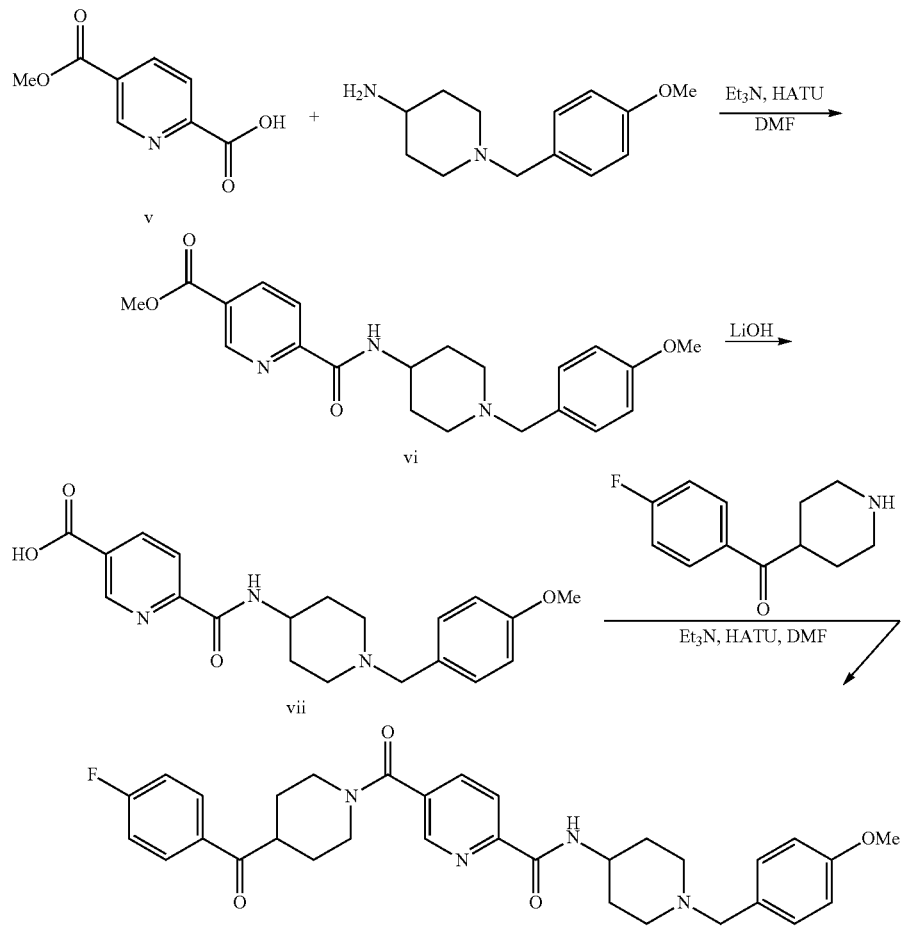

Referring to Scheme 3, a pyridinedicarboxylic acid monomethyl ester (v), for example, is coupled with an amine (here a substituted 1-benzylpiperidine-4-amine) to form a carboxymethyl-substituted pyridinecarboxamide (vi). The ester is saponified to form the corresponding carboxylic acid (vii), which is then coupled with a suitable amine (in this case, a substituted 4-benzoylpiperidine) to form a compound of structural formula (7-I).

Scheme 4

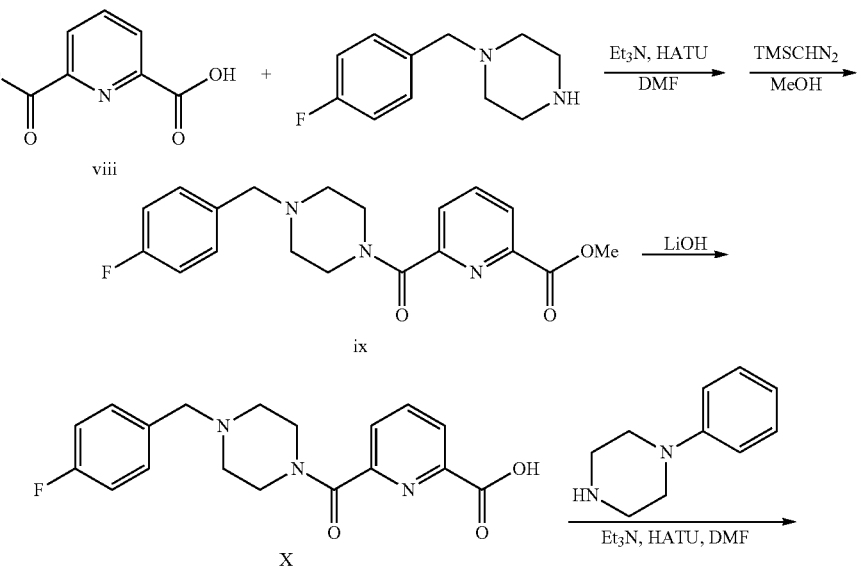

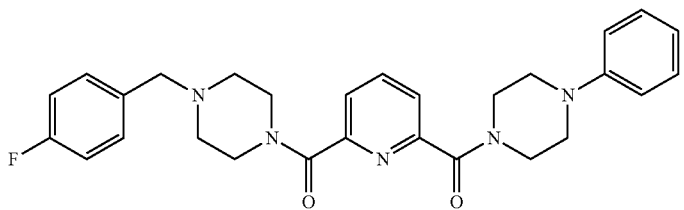

Referring to Scheme 4, a pyridine dicarboxylic acid (viii), for example, is coupled with one equivalent of an amine (here, a substituted 1-benzylepiperizine), then with methanol and trimethylsilyl(diazomethane) to form a carbomethoxy-substituted pyridinecarboxamide (ix), which is saponified to give a carboxylic acid-substituted pyridinecarboxamide (x). An amine (in this case, 1-phenylpiperazine) is coupled with the carboxylic acid-substituted pyridinecarboxamide (x) to form a compound of structural formula (7-I).

-continued

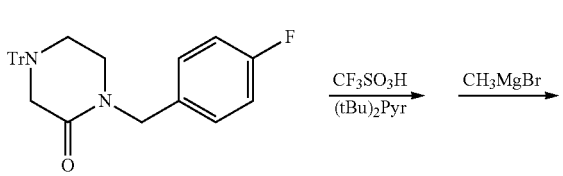

Scheme 5

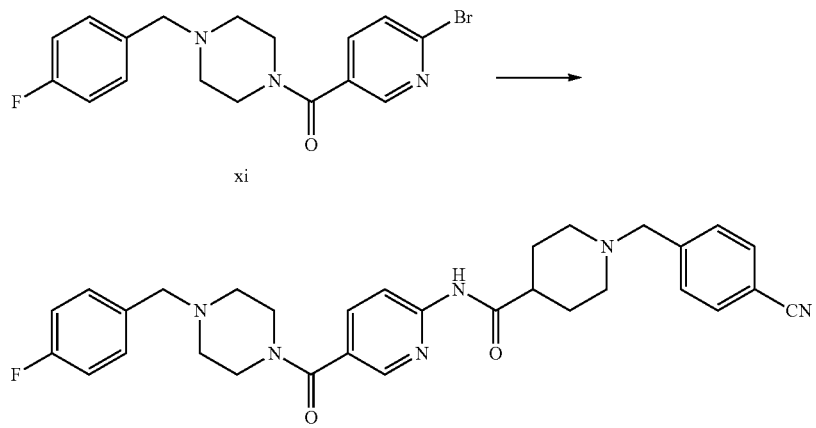

Referring to Scheme 5, a bromopyridinecarboxamide (xi) is coupled with a substituted 1-benzylpiperidine-4-carboxamide using a palladium catalyst to form Compound 46 of Table 1. Reactions of this general type are described in more detail, for example, in Wrona, Iwona E. et al., Journal of Organic Chemistry (2010), 75(9), 2820-2835.

-continued

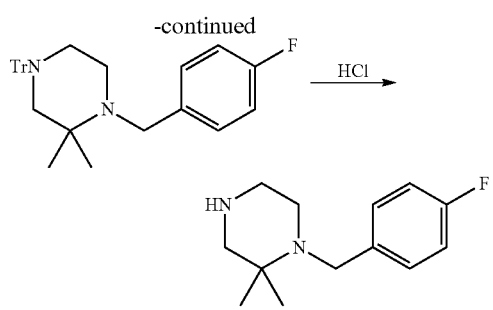

Scheme 6 describes a preparation that can be used to make gem-dimethylpiperazines for use in making compounds analogous to Compound 125 of Table 1. A piperazin-2-one is singly protected with trityl chloride, then coupled with an Scheme 6

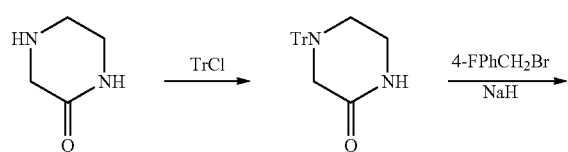

appropriate bromide (here, a substituted benzyl bromide) to form a 4-protected 1-(substituted benzyl)piperazin-2-one. The oxo is converted to a gem-dimethyl using Grignard chemistry, then the trityl is removed to yield the desired gem-dimethyl piperazine. Details are provided in the Examples below, and in Xiao, K-J.; Luo, J-M.; Ye, K-Y.; Wang, Y.; Huang, P-Q. *Angew. Chem. Int. Ed.* 2010, 49, 3037-3040.

Moreover, compounds with methyl-substituted piperidine moieties can be prepared using procedures analogous to those described in Scheme 7, below.

Scheme 7, a benzyl-protected piperidinone is methylated at the 3-position with iodomethane, and the benzyl protecting group is removed by hydrogenolysis and replaced with a butyloxycarbonyl (Boc) protecting group to form 1-Boc-3,3-dimethylpiperidin-4-one (a). The carbonyl can be reductively aminated with benzyl amine, which yields 1-Boc-3,3-dimethylpiperidin-4-amine (b) upon hydrogenolysis. In this example, 1-Boc-3,3-dimethylpiperidin-4-amine is coupled with a substituted pyridinecarboxylic acid (c), the Boc group is removed, and the piperidine nitrogen is alkylated to form Compound 7-83.

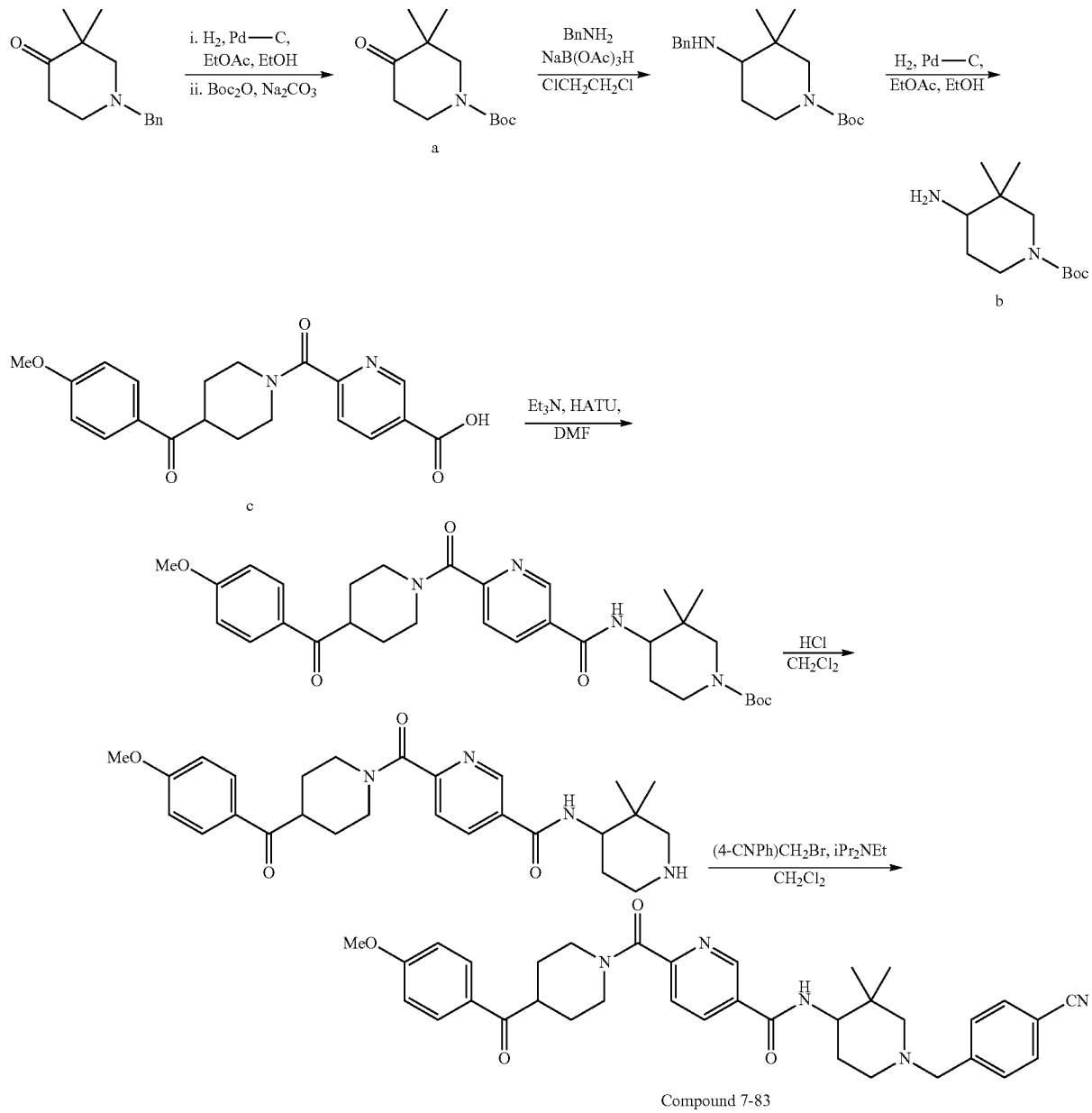

Scheme 7

Compound 7-83

Scheme 7 describes a preparation that can be used to make 1-Boc-3,3-dimethylpiperidin-4-one and 1-Boc-3,3-dimethylpiperidine-4-amine, which can further be elaborated into a variety of compounds, such as Compound 7-83 of Table 7. In Similar procedures can be used to convert commercially available 1-benzyl-3-methylpiperidin-4-one to 1-Boc-3-methylpiperidin-4-amine; using the procedures described herein, the major diastereomer is the cis diastereomer. Similarly, commercially available 1-Boc-3,3-difluoro can be converted to 1-Boc-3,3-difluoropiperidin-4-amine

Scheme 8

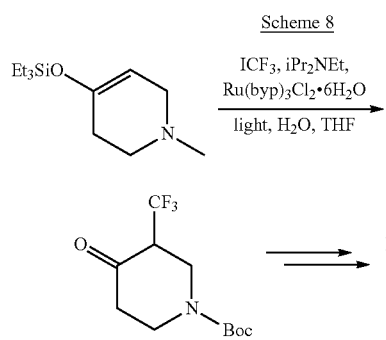

As shown in Scheme 8, similar procedures can be used to convert 1-Boc-3-trifluoromethylpiperidin-4-one to 1-Boc-3-trifluoromethylpiperidin-4-amine 1-Boc-3-trifluoromethylpiperidin-4-one can be prepared from 1-methyl-4-(triethylsilyloxy)-1,2,3,6-tetrahydropyridine as described in Pham, P. V., et al., Angew. Chem. Int. Ed. 2011, 50, 6119-6122, which is hereby incorporated herein by reference in its entirety.

Scheme 9

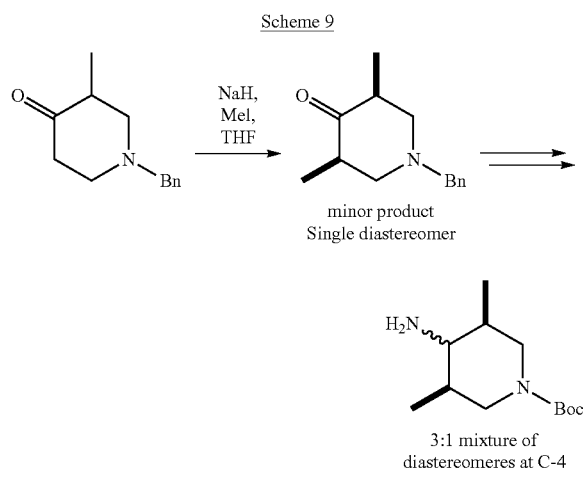

As shown in Scheme 9, similar procedures can be used to convert 1-benzyl-3,5-dimethylpiperidin-4-one amine to 1-Boc-3,5-dimethylpiperidin-4-amine; use of the procedures described herein, a 3:1 ratio of diastereomers at the 4-position is achieved. 1-Boc-3,5-dimethylpiperidin-4-amine can be prepared by alkylation of commercially available 1-benzyl-3-methylpiperidin-4-one; the syn diastereomer is a minor reaction product.

Scheme 10

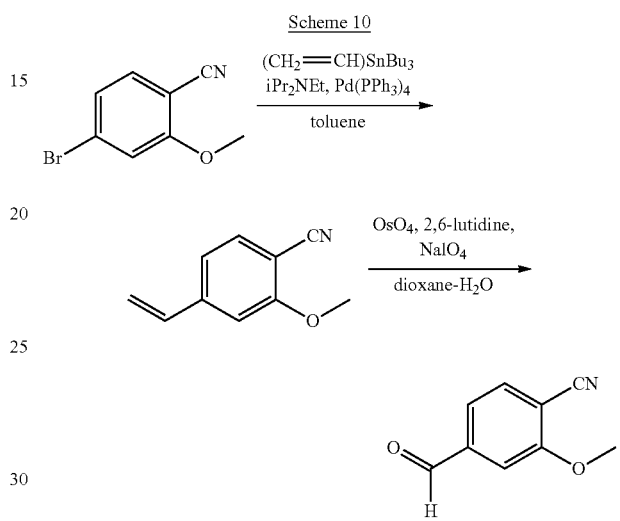

Scheme 10 describes a preparation that can be used to make substituted cyanobenzaldehydes that can be used in the construction of the G-$R^{17}$ moiety, for example, by reductive amination. For example, in Scheme 10, 4-bromo-2-methoxybenzonitrile is vinylated to form 1-vinyl-4-cyano-3-methoxybenzene. The vinyl double bond is cleaved with osmium tetraoxide. to form 4-cyano-3-methoxybenzaldehyde. Similarly, 4-cyano-3-methylbenzaldehyde, 3-cyano-4-methylbenzaldehyde, 4-cyano-2-methylbenzaldehyde, 3-cyano-4-methoxybenzaldehyde and 5-cyano-2-methoxybenzaldehyde can be prepared from their corresponding bromides.

For use in the synthesis of various compounds described above, (cis)- and (trans)-tert-butyl 4-amino-3-fluoropiperidine-1-carboxylate can be prepared as described in Scheme 11 below:

Scheme 11

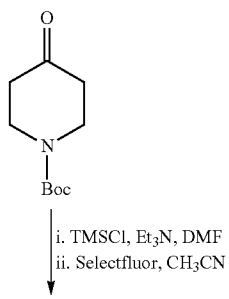

-continued
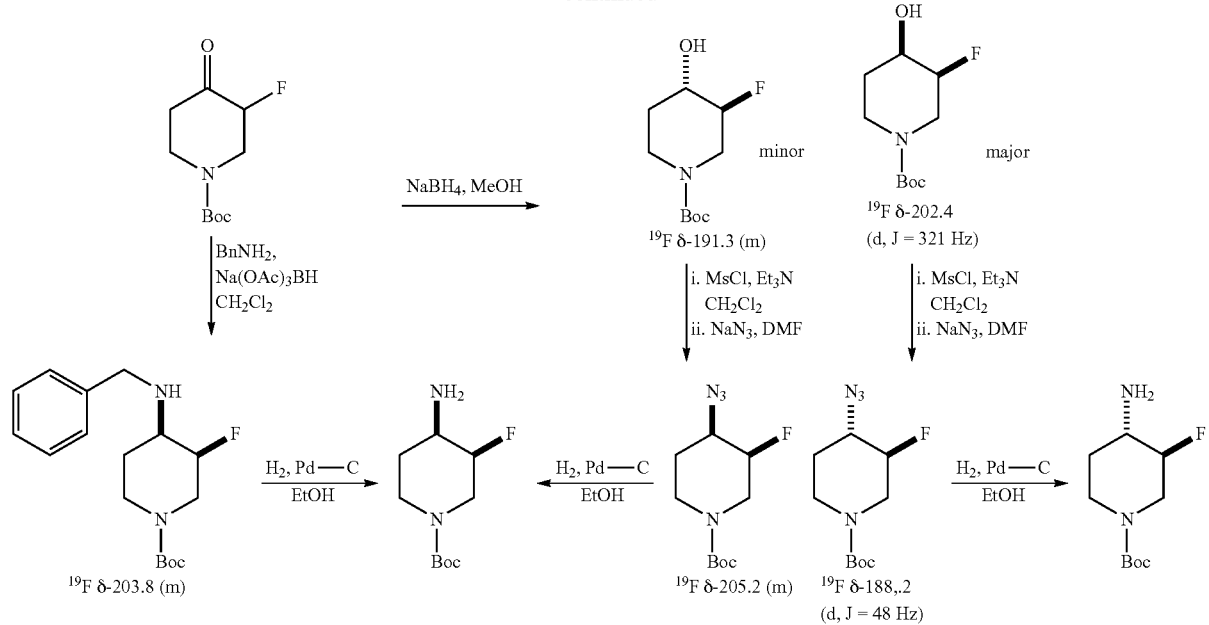
Scheme 12 provides an example of a synthetic route for the preparation of benzofurandicarboxamide compounds:
Scheme 12
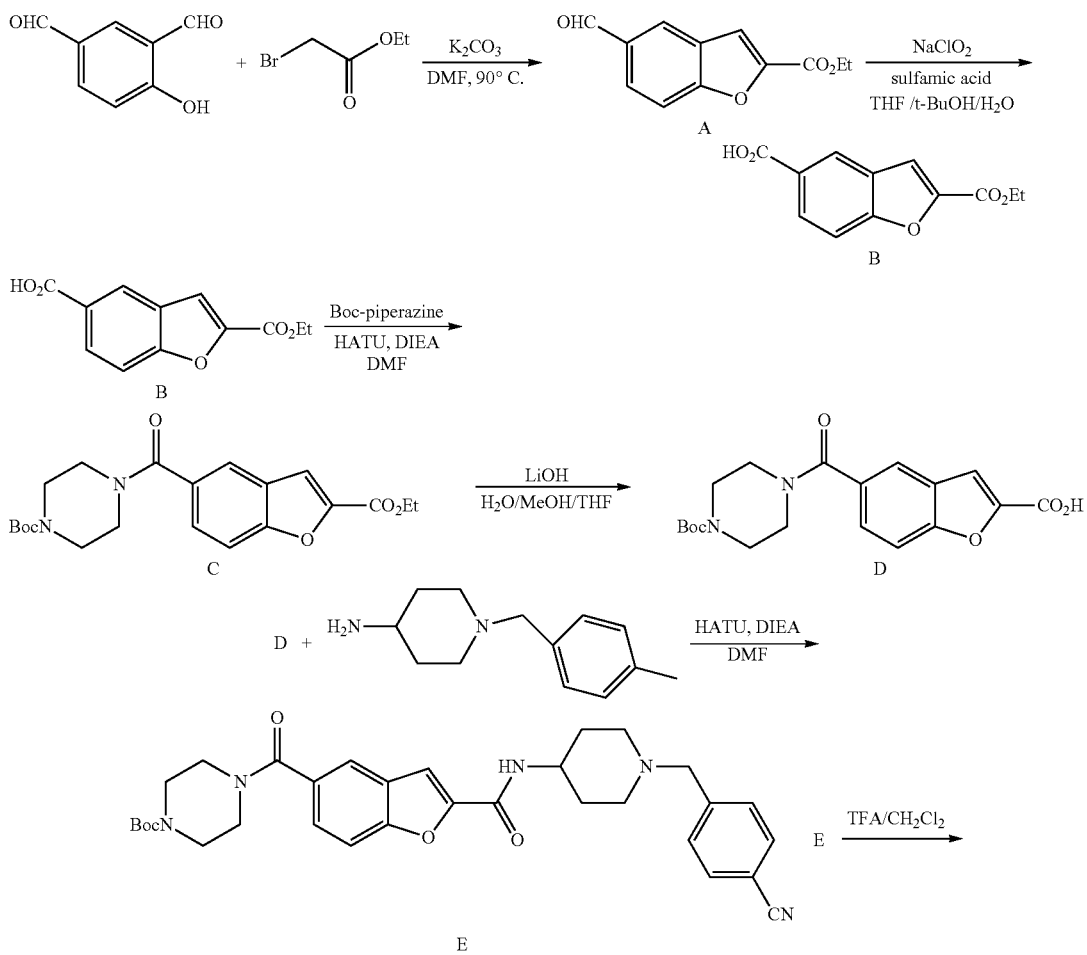

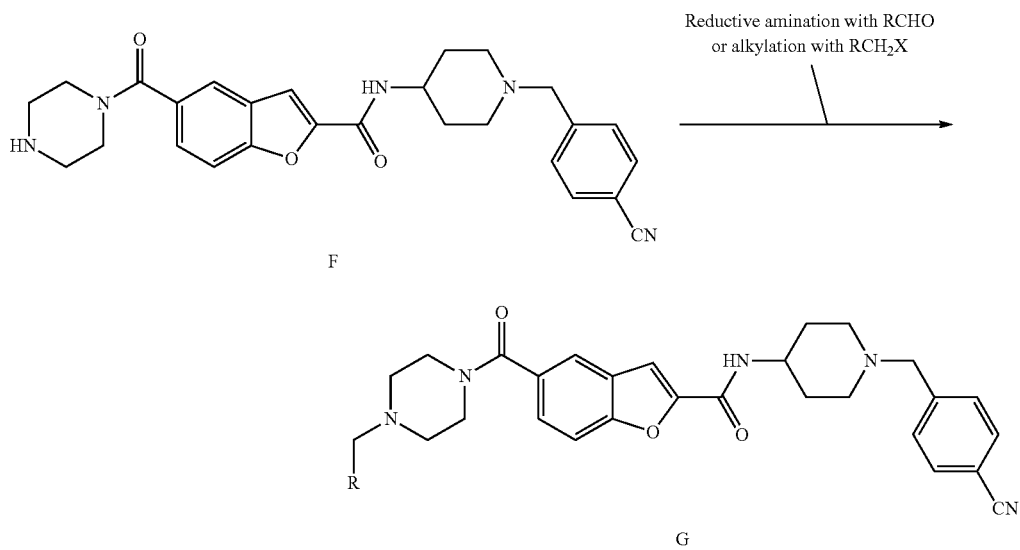
F
G
Scheme 13 provides an example of a synthetic route for the preparation of (carboxamido)benzofurancarboxamide compounds:
Scheme 13
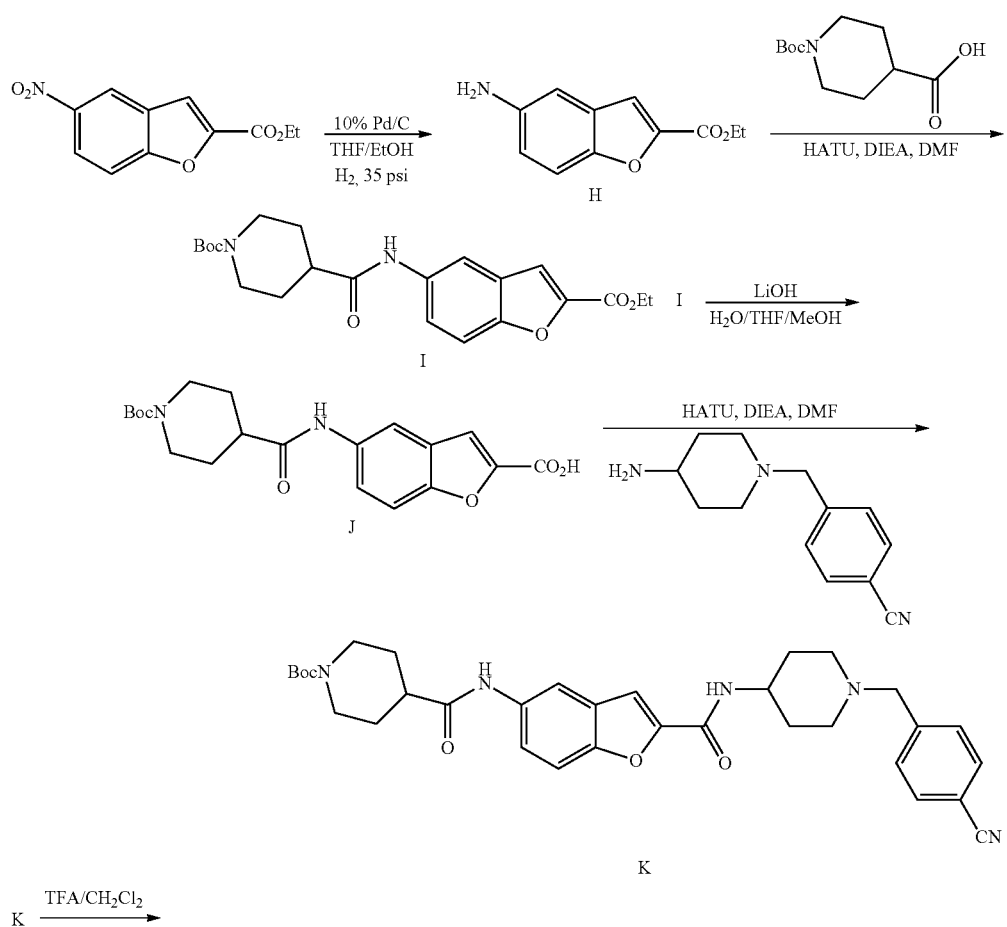

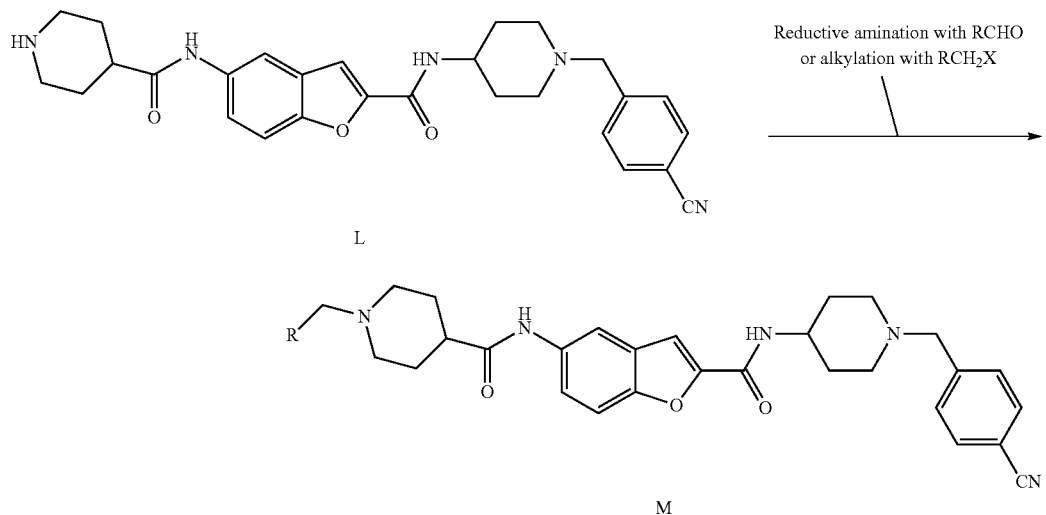
Scheme 14 provides an example of a synthetic route for the preparation of (3-fluoropiperidin-4-yl)oxybenzofurancarboxamide compounds:
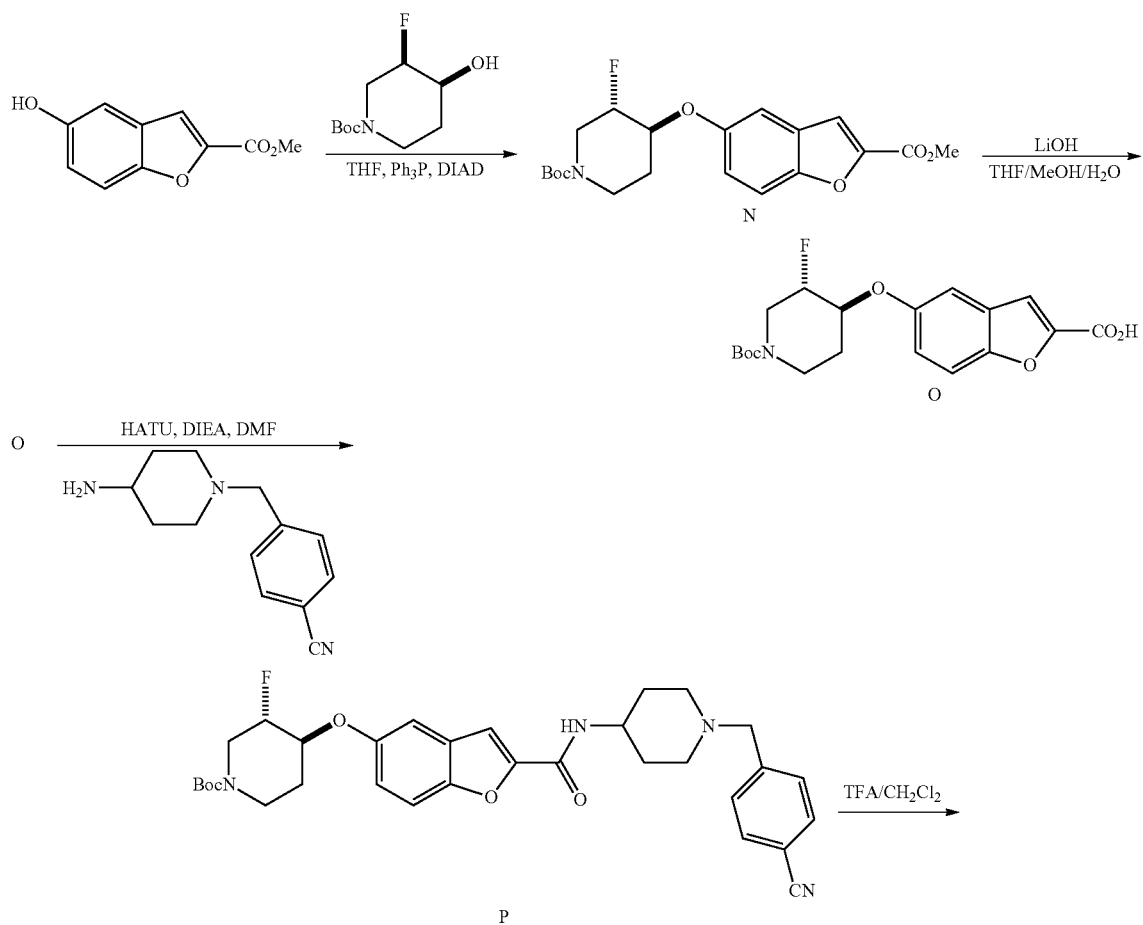

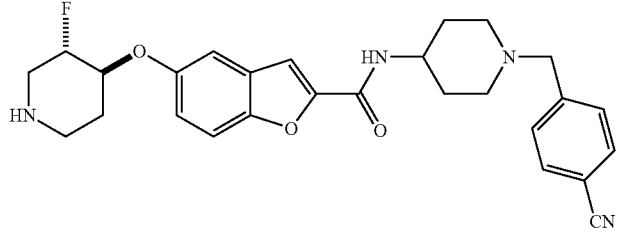

Q

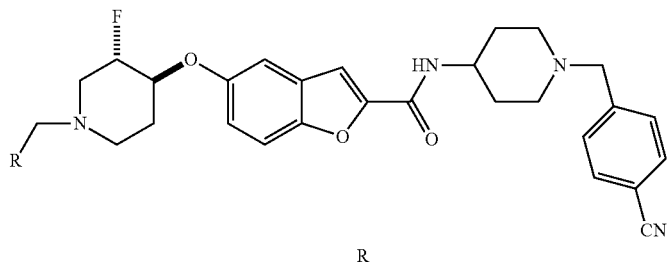

R

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. CH$_3$—CH$_2$—), in some circumstances a bivalent linking moiety can be "alkyl," in which case those skilled in the art will understand the alkyl to be a divalent radical (e.g., —CH$_2$—CH$_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as (A)$_a$-B-, wherein a is 0 or 1. In such instances, when a is 0 the moiety is B- and when a is 1 the moiety is A-B-.

As used herein, the term "alkyl" includes alkyl, alkenyl and alkynyl groups of a designed number of carbon atoms, desirably from 1 to about 12 carbons (i.e., inclusive of 1 and 12). The term "C$_m$-C$_n$ alkyl" means an alkyl group having from m to n carbon atoms (i.e., inclusive of m and n). The term "C$_m$-C$_n$ alkyl" means an alkyl group having from m to n carbon atoms. For example, "C$_1$-C$_6$ alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "C$_0$ alkyl"), the group is simply a single covalent bond if it is a divalent radical or is a hydrogen atom if it is a monovalent radical. For example, the moiety "—(C$_0$-C$_6$ alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 12 carbons.

The term "haloalkyl" is an alkyl group substituted with one or more halogen atoms, e.g. F, Cl, Br and I. A more specific term, e.g., "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like. In certain embodiments of the compounds disclosed herein, each haloalkyl is a fluoroalkyl.

The term "aryl" represents an aromatic ring system having a single ring (e.g., phenyl) which is optionally fused to other aromatic hydrocarbon rings or non-aromatic hydrocarbon rings. "Aryl" includes ring systems having multiple condensed rings and in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. In certain examples, aryl groups include those having a first carbocyclic, aromatic ring fused to an aromatic or aliphatic heterocycle, for example, 2,3-dihydrobenzofuranyl. The aryl groups herein are unsubstituted or, when specified as "optionally substituted", can unless stated otherwise be substituted in one or more substitutable positions with various groups, as described below.

The term "heteroaryl" refers to an aromatic ring system containing at least one heteroatom selected from nitrogen, oxygen and sulfur in an aromatic ring. The heteroaryl may be fused to one or more cycloalkyl or heterocycloalkyl rings. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" refers to a non-aromatic ring or ring system containing at least one heteroatom that is preferably selected from nitrogen, oxygen and sulfur, wherein said heteroatom is in a non-aromatic ring. The heterocycloalkyl may be saturated (i.e., a heterocycloalkyl) or partially unsaturated (i.e., a heterocycloalkenyl). Heterocycloalkyl includes monocyclic groups as well as bicyclic and polycyclic ring systems, including bridged and fused systems. The heterocycloalkyl ring is optionally fused to other heterocycloalkyl rings and/or non-aromatic hydrocarbon rings and/or phenyl rings. In certain embodiments, the heterocycloalkyl groups have from 3 to 7 members in a single ring. In other embodiments, heterocycloalkyl groups have 5 or 6 members in a single ring. Examples of heterocycloalkyl groups include, for example, azabicyclo[2.2.2]octyl (in each case also "quinuclidinyl" or a quinuclidine derivative), azabicyclo[3.2.1]octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butryolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as described below.

The term "cycloalkyl" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., bridged systems) to other cycloalkyl rings. Certain examples of cycloalkyl groups present in the disclosed compounds have from 3 to 7 members in a single ring, such as having 5 or 6 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups.

The term "ring system" encompasses monocycles, as well as fused and/or bridged polycycles.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "electron withdrawing group" means a group that withdraws electron density from the structure to which it is attached than would a similarly-attached hydrogen atom. For example, electron withdrawing groups can be selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), NO$_2$ and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group.

The term "substituted," when used to modify a specified group or radical, means that one or more hydrogen atoms of the specified group or radical are each, independently of one another, replaced with the same or different substituent groups as defined below.

Substituent groups for substituting for hydrogens on saturated carbon atoms in the specified group or radical are, unless otherwise specified, —$R^{60}$, halo, —O$^-$M$^+$, =O, —O$R^{70}$, —S$R^{70}$, —S$^-$M$^+$, =S, —N$R^{80}R^{80}$, =N$R^{70}$, =N—O$R^{70}$, trihalomethyl, —CF$_3$, —CN, —OCN, —SCN, —NO, —NO$_2$, =N$_2$, —N$_3$, —SO$_2R^{70}$, —SO$_2$O$^-$M$^+$, —SO$_2$O$R^{70}$, —OSO$_2R^{70}$, —OSO$_2$O$^-$M$^+$, —OSO$_2$O$R^{70}$, —P(O)(O$^-$)$_2$(M$^+$)$_2$, —P(O)(O$R^{70}$)O$^-$M$^+$, —P(O)(O$R^{70}$)$_2$, —C(O)$R^{70}$, —C(S)$R^{70}$, —C(N$R^{70}$)$R^{70}$, —C(O)O$^-$M$^+$, —C(O)O$R^{70}$, —C(S)O$R^{70}$, —C(O)N$R^{80}R^{80}$, —C(N$R^{70}$)N$R^{80}R^{80}$, —OC(O)$R^{70}$, —OC(S)$R^{70}$, —OC(O)O$^-$M$^+$, —OC(O)O$R^{70}$, —OC(S)O$R^{70}$, —N$R^{70}$C(O)$R^{70}$, —N$R^{70}$C(S)$R^{70}$, —N$R^{70}$CO$_2^-$M$^+$, —N$R^{70}$CO$_2R^{70}$, —N$R^{70}$C(S)O$R^{70}$, —N$R^{70}$C(O)N$R^{80}R^{80}$, —N$R^{70}$C(N$R^{70}$)$R^{70}$ and —N$R^{70}$C(N$R^{70}$)N$R^{80}R^{80}$. Each $R^{60}$ is independently selected from the group consisting of alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{71}$, —SR$^{71}$, —S$^-$M$^+$, =S, —NR$^{81}$R$^{81}$, =NR$^{71}$, =N—OR$^{71}$, trihalomethyl, —CF$_3$, —CN, —OCN, —SCN, —NO, —NO$_2$, =N$_2$, —N$_3$, —SO$_2$R$^{71}$, —SO$_2$O$^-$M$^+$, —SO$_2$OR$^{71}$, —OSO$_2$R$^{71}$, —OSO$_2$O$^-$M$^+$, —OSO$_2$OR$^{71}$, —P(O)(O$^-$)$_2$(M$^+$)$_2$, —P(O)(OR$^{71}$)O$^-$M$^+$, —P(O)(OR$^{71}$)$_2$, —C(O)R$^{71}$, —C(S)R$^{71}$, —C(NR$^{71}$)R$^{71}$, —C(O)O$^-$M$^+$, —C(O)OR$^{71}$, —C(S)OR$^{71}$, —C(O)NR$^{81}$R$^{81}$, —C(NR$^{71}$)NR$^{81}$R$^{81}$, —OC(O)R$^{71}$, —OC(S)R$^{71}$, —OC(O)O$^-$M$^+$, —OC(O)OR$^{71}$, —OC(S)OR$^{71}$, —NR$^{71}$C(O)R$^{71}$, —NR$^{71}$C(S)R$^{71}$, —NR$^{71}$CO$_2^-$M$^+$, —NR$^{71}$CO$_2$R$^{71}$, —NR$^{71}$C(S)OR$^{71}$, —NR$^{71}$C(O)NR$^{81}$R$^{81}$, —NR$^{71}$C(NR$^{71}$)R$^{71}$ and —NR$^{71}$C(NR$^{71}$)NR$^{81}$R$^{81}$. Each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each R$^{71}$ is independently hydrogen or R$^{61}$, in which R$^{61}$ is alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —O$^-$M$^+$, =O, —OR$^{72}$, —SR$^{72}$, —S$^-$M$^+$, =S, —NR$^{82}$R$^{82}$, =NR$^{72}$, =N—OR$^{72}$, trihalomethyl, —CF$_3$, —CN, —OCN, —SCN, —NO, —NO$_2$, =N$_2$, —N$_3$, —SO$_2$R$^{71}$, —SO$_2$O$^-$M$^+$, —SO$_2$OR$^{72}$, —OSO$_2$R$^{72}$, —OSO$_2$O$^-$M$^+$, —OSO$_2$OR$^{72}$, —P(O)(O$^-$)$_2$(M$^+$)$_2$, —P(O)(OR$^{72}$)O$^-$M$^+$, —P(O)(OR$^{72}$)$_2$, —C(O)R$^{72}$, —C(S)R$^{72}$, —C(NR$^{72}$)R$^{72}$, —C(O)O$^-$M$^+$, —C(O)OR$^{72}$, —C(S)OR$^{72}$, —C(O)NR$^{82}$R$^{82}$, —C(NR$^{72}$)NR$^{82}$R$^{82}$, —OC(O)R$^{72}$, —OC(S)R$^{72}$, —OC(O)O$^-$M$^+$, —OC(O)OR$^{72}$, —OC(S)OR$^{72}$, —NR$^{72}$C(O)R$^{72}$, —NR$^{72}$C(S)R$^{72}$, —NR$^{72}$CO$_2^-$M$^+$, —NR$^{72}$CO$_2$R$^{72}$, —NR$^{72}$C(S)OR$^{72}$, —NR$^{72}$C(O)NR$^{82}$R$^{82}$, —NR$^{72}$C(NR$^{72}$)R$^{72}$ and —NR$^{72}$C(NR$^{72}$)NR$^{82}$R$^{82}$; and each R$^{81}$ is independently R$^{71}$ or alternatively, two R$^{81}$s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution. Each R$^{72}$ is independently hydrogen, (C$_1$-C$_6$ alkyl) or (C$_1$-C$_6$ fluoroalkyl); each R$^{82}$ is independently R$^{72}$ or alternatively, two R$^{82}$s, taken together with the nitrogen atom to which they are bonded, form a 5-, 6- or 7-membered heterocycloalkyl which may optionally include 1, 2, 3 or 4 of the same or different additional heteroatoms selected from the group consisting of O, N and S, of which N may have —H or C$_1$-C$_3$ alkyl substitution. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means e.g. that one of the counter ions for such divalent alkali earth ions can be an ionized form of a presently disclosed compound and the other a typical counter ion such as chloride, or two ionized presently disclosed molecules can serve as counter ions for such divalent alkali earth ions, or a doubly ionized compound can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4-methyl-piperazin-1-yl and N-morpholinyl.

Substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

Substituent groups for hydrogens on nitrogen atoms in "substituted" heteroalkyl and heterocycloalkyl groups are, unless otherwise specified, —R$^{60}$, —O$^-$M$^+$, —OR$^{70}$, -SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In certain embodiments of the compounds disclosed herein, a group that is substituted has 1, 2, 3, or 4 substituents, 1, 2, or 3 substituents, 1 or 2 substituents, or 1 substituent.

In certain preferred embodiments, substituent groups on "substituted" alkyl, cycloalkyl, heterocycloalkyl, aryl and heteroaryl groups are -halo, —OH, —O—(C$_1$-C$_4$ alkyl), —O—(C$_1$-C$_4$ haloalkyl), —N(C$_0$-C$_4$ alkyl)(C$_0$-C$_4$ alkyl), —SH, —S(O)$_{0-2}$—(C$_1$-C$_4$ alkyl), —(C$_1$-C$_4$ alkyl), —(C$_1$-C$_4$ haloalkyl), —C(O)—(C$_0$-C$_4$ alkyl), —C(O)N(C$_0$-C$_4$ alkyl)(C$_0$-C$_4$ alkyl), —N(C$_0$-C$_4$ alkyl)C(O)(C$_0$-C$_4$ alkyl)(C$_0$-C$_4$ alkyl), —C(O)O—(C$_0$-C$_4$ alkyl), —OC(O)—(C$_0$-C$_4$ alkyl), S(O)$_2$—O(C$_0$-C$_4$ alkyl), and —NO$_2$, in which no alkyl is further substituted.

In certain embodiments of the compounds described herein, each R$^3$ is independently selected from —(C$_1$-C$_6$ alkyl), —(C$_1$-C$_6$ haloalkyl), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN.

In certain embodiments of the compounds described herein, each R$^{14}$ is independently selected from —(C$_1$-C$_6$ alkyl), —(C$_1$-C$_6$ haloalkyl), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN.

In certain embodiments of the compounds described herein, each R$^4$ is independently selected from —(C$_1$-C$_6$ alkyl), —(C$_1$-C$_6$ haloalkyl), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two R$^4$ on the same carbon optionally combine to form oxo;

In certain embodiments of the compounds described herein, each R$^5$ is independently selected from —(C$_1$-C$_6$ alkyl), —(C$_1$-C$_6$ haloalkyl), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, —(C$_0$-C$_6$ alkyl)-C(O)R$^{10}$, -halogen, —NO$_2$ and —CN.

In certain embodiments of the compounds described herein, each R$^{15}$ is independently selected from —(C$_1$-C$_6$ alkyl), —(C$_1$-C$_6$ haloalkyl), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)

$R^{10}$, —($C_0$-$C_6$ alkyl)-S(O)$_{0-2}R^{10}$, -halogen, —NO$_2$ and —CN, and two $R^{15}$ on the same carbon optionally combine to form oxo.

In certain embodiments of the compounds described herein, each $R^6$, $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-NR$^9$—($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), In certain embodiments of the compounds described herein, $R^9$ is independently selected from —H, —($C_1$-$C_4$ alkyl) and —C(O)O—($C_1$-$C_4$ alkyl), In certain embodiments of the compounds described herein, each $R^{16}$ is independently selected from —($C_1$-$C_6$ alkyl), —($C_1$-$C_6$ haloalkyl), —($C_0$-$C_6$ alkyl)-L-$R^7$, —($C_0$-$C_6$ alkyl)-NR$^8$R$^9$, —($C_0$-$C_6$ alkyl)-OR$^{10}$, —($C_0$-$C_6$ alkyl)-C(O)R$^{10}$, —($C_0$-$C_6$ alkyl)-S(O)$_{0-2}R^{10}$, -halogen, —NO$_2$ and —CN, and optionally two of $R^{16}$ on the same carbon combine to form oxo.

In certain embodiments of the compounds described herein, each Ar is an aryl optionally substituted with 1, 2, 3 or 4 optional substituents; each Het is a heteroaryl optionally substituted with 1, 2, 3 or 4 optional substituents; each Cak is cycloalkyl optionally substituted with 1, 2, 3 or 4 optional substituents; each Hca is heterocycloalkyl optionally substituted with 1, 2, 3 or 4 optional substituents, and each alkyl is optionally substituted with 1, 2, 3 or 4 optional substituents.

In certain embodiments of the compounds described herein, each $R^{60}$ is H, alkyl or heteroalkyl; each $R^{70}$ is H, alkyl or heteroalkyl; and each $R^{80}$ is H, alkyl or heteroalkyl or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution.

The compounds disclosed herein can also be provided as pharmaceutically acceptable salts. The term "pharmaceutically acceptable salts" or "a pharmaceutically acceptable salt thereof" refer to salts prepared from pharmaceutically acceptable non-toxic acids or bases including inorganic acids and bases and organic acids and bases. If the compound is basic, salts may be prepared from pharmaceutically acceptable non-toxic acids. Such salts may be, for example, acid addition salts of at least one of the following acids: benzenesulfonic acid, citric acid, α-glucoheptonic acid, D-gluconic acid, glycolic acid, lactic acid, malic acid, malonic acid, mandelic acid, phosphoric acid, propanoic acid, succinic acid, sulfuric acid, tartaric acid (d, l, or dl), tosic acid (toluenesulfonic acid), valeric acid, palmitic acid, pamoic acid, sebacic acid, stearic acid, lauric acid, acetic acid, adipic acid, carbonic acid, 4-chlorobenzenesulfonic acid, ethanedisulfonic acid, ethylsuccinic acid, fumaric acid, galactaric acid (mucic acid), D-glucuronic acid, 2-oxo-glutaric acid, glycerophosphoric acid, hippuric acid, isethionic acid (ethanolsulfonic acid), lactobionic acid, maleic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, hydriodic acid, hydrobromic acid, hydrochloric acid, methanesulfonic acid, nicotinic acid, nitric acid, orotic acid, oxalic acid, picric acid, L-pyroglutamic acid, saccharine, salicylic acid, gentisic acid, and/or 4-acetamidobenzoic acid.

The compounds described herein can also be provided in prodrug form. "Prodrug" refers to a derivative of an active compound (drug) that undergoes a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Specific examples of suitable progroups and their respective promoieties will be apparent to those of skill in the art.

The compounds disclosed herein can also be provided as N-oxides.

The presently disclosed compounds, salts, prodrugs and N-oxides can be provided, for example, in solvate or hydrate form.

One of ordinary skill in the art of medicinal chemistry also will appreciate that the disclosed structures are intended to include isotopically enriched forms of the present compounds. As used herein "isotopes" includes those atoms having the same atomic number but different mass numbers. As will be apparent to those of skill in the art upon consideration of the present compounds, certain atoms can be enriched an isotope of that atom. For example, compounds having a fluorine atom, may be synthesized in a form enriched in the radioactive fluorine isotope $^{18}$F. Similarly, compounds may be enriched in the heavy isotopes of hydrogen, deuterium and tritium, and can be enriched in a radioactive isotope of carbon, such as $^{13}$C. Such compounds can be useful, for example, in studying the AMPK pathway and its role in metabolism.

Compounds can be assayed for binding to a membrane-bound adiponectin receptor by performing a competitive binding assay with adiponectin. In one such procedure, HEK 293 cellular membrane is coated onto a COSTAR 384 plate, which is then blocked with 1% casein. Polyhistidine-tagged globular adiponectin and a candidate compound is incubated with the membrane in HEPES buffer. Unbound ligands are washed away and the degree of binding of the adiponectin is determined using horseradish peroxidase-conjugated anti-polyhistidine. Compounds that compete with adiponectin binding to the membrane (i.e., give a reduced signal compared to a control performed without a candidate compound)

can be chosen as hits and further screened using the below-described functional assays to identify adiponectin receptor agonists.

An in-cell western assay can be performed to demonstrate the activation of AMPK in human liver cells by globular adiponectin using glutathione S-transferase (GST). AMPK activity can be measured by the relative concentration of phosphorylated acetyl Co-A carboxylase, which is one of the products of AMPK. An increase in pACC correlates with an increase in the rate of fatty acid oxidation.

The compounds disclosed herein can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like.

Pharmaceutical compositions can be made using the presently disclosed compounds. For example, in one embodiment, a pharmaceutical composition includes a pharmaceutically acceptable carrier, diluent or excipient, and compound as described above.

In the pharmaceutical compositions disclosed herein, one or more of the presently disclosed compounds may be present in association with one or more pharmaceutically acceptable carriers, diluents or excipients, and, if desired, other active ingredients. The pharmaceutical compositions may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

The presently disclosed compounds can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

The presently disclosed compounds can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compounds disclosed herein can be made using procedures familiar to the person of ordinary skill in the art and as described, for example, in U.S. Patent Application Publications nos. 2009/0163511, 2009/0170829, 2009/0186894 and 2009/0275609, and in U.S. patent application Ser. No. 12/695,861, each of which is hereby incorporated by reference in its entirety. One of skill in the art can adapt the reaction sequences described therein to fit the desired target molecule. Of course, in certain situations one of skill in the art will use different reagents to affect one or more of the individual steps or to use protected versions of certain of the substituents. Additionally, one skilled in the art would recognize that the presently disclosed compounds can be synthesized using different routes altogether.

Compounds suitable for use in the presently disclosed pharmaceutical compositions include compounds of Tables 1-7, above.

While not intending to be bound by theory, the inventors surmise that the compounds described herein activate the AMPK pathway, for example by acting as mimics of adiponectin. Activation of the AMPK pathway has the effect of increasing glucose uptake, decreasing glycogen synthesis and increasing fatty acid oxidation, thereby reducing glycogen, intracellular triglyceride and fatty acid concentration and causing an increase in insulin sensitivity. Because they activate the AMPK pathway, the compounds described herein should also inhibit the inflammatory processes which occur during the early phases of atherosclerosis. Accordingly, the compounds described herein can be useful in the treatment of type II diabetes and in the treatment and prevention of atherosclerosis, cardiovascular disease, obesity and non-alcoholic fatty liver disease.

Accordingly, another aspect of the present disclosure relates to a method of activating the AMPK pathway. According to this aspect, a method for activating the AMPK pathway in a cell includes contacting the cell with an effective amount of a compound, pharmaceutically acceptable salt, N-oxide (or solvate or hydrate thereof) or composition described herein.

In one embodiment, a method of increasing fatty acid oxidation in a cell includes contacting the cell with an effective amount of a compound, pharmaceutically acceptable salt, N-oxide (or solvate or hydrate thereof) or composition described herein. Acetyl Co-A carboxylase (ACC) catalyzes the formation of malonyl Co-A, a potent inhibitor of fatty acid oxidation; phosphorylation of ACC greatly reduces its catalytic activity, thereby reducing the concentration of malonyl Co-A and increasing the rate of fatty acid oxidation. Because the presently disclosed compounds can increase the rate of phosphorylation of ACC, they can reduce the inhibition of fatty acid oxidation and therefore increase its overall rate.

In another embodiment, a method of decreasing glycogen concentration in a cell includes contacting the cell with an effective amount of a compound, pharmaceutically acceptable salt, N-oxide (or solvate or hydrate thereof) or composition described herein.

In another embodiment, a method of increasing glucose uptake in a cell includes contacting the cell with an effective amount of a compound, pharmaceutically acceptable salt, N-oxide (or solvate or hydrate thereof) or composition described herein.

In another embodiment, a method of reducing triglyceride levels in a subject includes administering to the subject an effective amount of a compound, pharmaceutically acceptable salt, N-oxide (or solvate or hydrate thereof) or composition described herein.

In another embodiment, a method of increasing insulin sensitivity of a subject includes administering to the subject an effective amount of a compound, pharmaceutically acceptable salt prodrug, N-oxide (or solvate or hydrate thereof) or composition described herein.

Accordingly, the compounds and compositions disclosed herein can be used to treat a variety of metabolic disorders. For example, in one embodiment, a method of treating type II diabetes in a subject in need of such treatment includes administering to the subject an effective amount of a compound, pharmaceutically acceptable salt, solvate, hydrate, N-oxide or composition described herein. In another embodiment, a method of treating or preventing atherosclerosis or cardiovascular disease in a subject includes administering to the subject an effective amount of a compound, pharmaceutically acceptable salt prodrug, N-oxide (or solvate or hydrate thereof) or composition described herein.

As described herein, the compounds disclosed herein can act as activators of the AMPK pathway. Accordingly, in another embodiment, a method comprises modulating the AMPK pathway (either in vitro or in vivo) by contacting a cell with a compound, pharmaceutically acceptable salt, N-oxide (or solvate or hydrate thereof) or composition described herein, or administering a compound, pharmaceutically acceptable salt, N-oxide (or solvate or hydrate thereof) or composition described herein to a mammal (for example, a human) in an amount sufficient to modulate the AMPK activity and study the effects thereby induced. Such methods are useful for studying the AMPK pathway and its role in biological mechanisms and disease states both in vitro and in vivo.

In certain embodiments, the compounds disclosed herein affect lipid signaling pathways. For example, in some embodiments, the compounds up-regulate ceramidase activity. Ceramide is a central player in sphingolipid metabolism, and is the immediate precursor of sphingomyelins and glycosphingolipids as well as the bioactive products sphingosine and sphingosine-1-phosphate. Moreover, endogenous ceramide itself mediates, at least in part, the actions of a variety of stimuli on cell differentiation, apoptosis, and growth suppression. Ceramide is deacylated by ceramidase to form sphingosine, which is in turn phosphorylated to sphingosine-1-phosphate by sphingosine kinase.

Elevated ceramide levels have been shown to induce cell apoptosis, differentiation and senescence. Moreover, elevated ceramide levels are linked to a variety of diseases and disorders, including, for example, Batten's disease, inflammatory bowel diseases, diffuse intravascular coagulation, fever, protein catabolism and/or lipid depletion, hepatosplenomegaly associated with inflammatory or metabolic liver diseases, endomyocarditis, endolithial cell and leucocyte activation, capillary thrombosis, meningo-encephalitis due to infectious agents, complications in organ transplantation, rheumatoid arthritis and connective tissue diseases, autoimmune diseases, hyperthyroidism, damage by radiation/chemotherapy agents and chronic fatigue syndrome.

Up-regulating ceramidase function (and therefore reducing the concentration of ceramide) can be used to treat disorders involving deficient cell proliferation (growth) or in which cell proliferation is otherwise desired, for example, degenerative disorders, growth deficiencies, lesions, physical trauma, and diseases in which ceramide accumulates within cells, such as Fabry disease. Other disorders that may benefit from the activation of ceramidase include neurodegenerative disorders such as Alzheimer's disease and amyotrophic lateral sclerosis and disorders of aging such as immune dysfunction, as well as disorders, such as those listed above, linked to elevated ceramide levels.

The compounds, salts, prodrugs, N-oxides, solvates and hydrates described herein can be administered, for example, to a mammalian host to retard cellular responses associated with the activation of the ceramide-mediated signal transduction pathway. The compounds can be useful, for example, in providing protection against cell senescence or apoptosis, such as occurs as a result of trauma (for example, radiation dermatitis) and aging (for example, of the skin or other organs).

Another embodiment is a method for up-regulating ceramidase function in a cell (either in vivo or in vitro), the method including contacting the cell with an effective amount of a compound, pharmaceutically acceptable salt, N-oxide (or solvate or hydrate thereof) or composition described herein.

In another embodiment, a method for decreasing ceramide concentration in a cell (either in vivo or in vitro) includes contacting the cell with an effective amount of a compound, pharmaceutically acceptable salt, N-oxide (or solvate or hydrate thereof) or composition described herein.

In another embodiment, a method for inhibiting ceramide-activated responses to stimuli in a cell (either in vivo or in vitro) includes contacting the cell with an effective amount of a compound, pharmaceutically acceptable salt, N-oxide (or solvate or hydrate thereof) or composition described herein. The stimuli can be, for example, stimuli for cell senescence and/or apoptosis.

Another embodiment is a method for treating or preventing a disease or disorder in which cell proliferation is deficient or desired in a subject, the method including administering to the subject an effective amount of a compound, pharmaceutically acceptable salt, N-oxide (or solvate or hydrate thereof) or composition described herein. Various applicable diseases and disorders are described herein.

Another embodiment is a method for treating a disease or disorder linked to elevated ceramide levels in a subject, the method including administering to the subject an effective amount of a compound, pharmaceutically acceptable salt, N-oxide (or solvate or hydrate thereof) or composition as described herein. Various applicable diseases and disorders are described herein. In certain embodiments, the subject has a ceramide level higher than about 50 pmol/$10^6$ cells.

Moreover, since some drugs can induce high levels of ceramide, the compounds, salts, prodrugs, N-oxides, solvates and hydrates described herein can be usefully co-administered with such drugs in order to at least partially ameliorate this effect. For example, in certain embodiments, an effective amount of a compound, pharmaceutically acceptable salt, N-oxide (or solvate or hydrate thereof) or composition as described herein is co-administered with a corticosteroid (for example, dexamethasone), an anti-inflammatory (for example, indomethacin), an antiviral (for example, interferon), an immunosuppressant (for example, cyclosporin), a chemotherapy agent (for example, adriamicin), and immunopotentiant (for example, an immunoglobulin or a vaccine), or an andocrinological agent (for example, metimazole). As the person of skill in the art will appreciate, co-administration contemplates not only administration at the same time, but also administration at different times, but with time-overlapping pharmacological effects.

Another embodiment is a method for reducing the effect of aging in the skin of a subject, the method including contacting the skin with a compound, pharmaceutically acceptable salt, N-oxide (or solvate or hydrate thereof) or composition as described herein.

Another embodiment is a method for treating or preventing radiation dermatitis in the skin of a subject, the method including contacting the skin with a compound, pharmaceutically acceptable salt, N-oxide (or solvate or hydrate thereof) or composition as described herein.

To identify and select therapeutic compounds for use in treating ceramide-associated conditions, cells (or intracellular components such as microsomes) which have not been exposed to a senescence or apoptosis-inducing agent (for example, cytokines such as TNF-α or exogenous stimuli such as heat, radiation or chemical agents) are exposed to such and agent and to the candidate compound. Inhibition of senescence or apoptosis is measured as a function of cell growth. The person of ordinary skill in the art will be familiar with techniques for obtaining such measurements.

For example, inhibition of cell senescence can be measured after serum deprivation in serum-dependent cells. Many cell types are dependent upon serum factors for growth. Thus, deprivation of such cells of serum provides a model for assessment of compounds to modulate cell responses to intracellular ceramide-mediated signal transduction. In particular, withdrawal of serum from serum-dependent cell cultures produces increased intracellular levels of endogenous ceramide and may also increase intracellular levels of endogenous diacyl glycerol (see, e.g., Jayadev, et al., J. Biol. Chem., 270, 2047-2052 (1995)). To evaluate the inhibitory effect of the compounds described herein on ceramide-associated conditions in vitro, the serum withdrawal model can be used. Specifically, 3T3 fibroblast cells can be seeded in 96 well microtiter plates in DMEM in the presence of 10% fetal bovine serum. The cells are incubated to 90% confluence. The medium is removed, and the cells washed and reincubated in serum-free DMEM. A test compound at a variety of concentrations (for example, 0, 4, 40 or 400 µM) and cell permeable ceramide (for example, 0, 5 or 10 µM) are added to the wells. After 24 hrs. incubation, 0.5 µCi of [$^3$H] thymidine is added to each well for 2 hrs. DNA synthesis in the tested cell population is assessed by conventional techniques for detection of [$^3$H] thymidine incorporation. The results of this assay can be used to establish the cell senescence inhibitory efficacy of the test compound.

Inhibition of cell apoptosis can be determined, for example, using CD95 stimulation. Engagement of cell surface receptor CD95 (also known as Fas/Apo-1 antigen) triggers cell apoptosis. DX2 is a functional anti-FAS (CD95) antibody which will, on binding of CD95, activate the sphingomyelinase catalysis of sphingomyelin hydrolysis and production of ceramide (see, with respect to DX2, Cifone, et al., J. Exp. Med., 177, 1547-1552 (1993)). Thus, binding of CD95 is a model for conduction of apoptosis via the sphingomyelin signal transduction pathway. To assess the inhibitory effect of the compounds disclosed herein on ceramide-mediated cell apoptosis, human T lymphoblasts (Jurkat) are suspended at 2×$10^6$ cells/mL in RPMI-1640 supplemented with insulin, transferrin, selenium and glutamine. After incubation for 2 hrs. at room temperature with a test compound, pentoxifylline or a control compound (Ro-1724), 25 ng/mL of anti-FAS antibody is added to each suspension. After another 2 hrs., cell apoptosis is measured as a function of the number of cells (counted by hemocytometer) that excluded the vital dye erythrosin B. The results of the experiment can be used to establish the apoptosis inhibitory efficacy of the test compound.

To assess the inhibitory effect of the compounds disclosed herein on death of human lymphocytes, human peripheral blood lymphocytes are isolated from normal human blood and depleted of monocytes by adherence to a plastic substrate. Lymphocytes are then cultured in RPMI-1640 medium with 10% autologous plasma at an initial concentration of $2 \times 10^6$ cells/mL. Aliquots of the cell samples are divided and one half of the samples are incubated with a test compound or 6,7-dimethoxy-1(2H)-isoquinoline (Aldrich) for four days. The remaining half of the samples are allowed to rest for four days. Cell viability after four days is determined by erythrosin B dye exclusion in a hemocytometer. The results of the experiment can be used to establish the apoptosis inhibitory efficacy of the test compound on human lymphocytes as compared to untreated lymphocytes.

Ceramide-activated protein kinase (CaPK) is a 97 kDa protein which is exclusively membrane-bound and is believed to serve a role in the sphingomyelin signal transduction pathway. In particular, CaPK is believed to mediate phosphorylation of a peptide derived from the amino acid sequence surrounding Thr.sup.669 of the epidermal growth factor receptor (i.e., amino acids 663-681). This site is also recognized by the mitogen-activated kinase MAP (also known as a family of extracellular signal-regulated kinases). Thus, the effect of the compounds disclosed herein on CaPK activity in cells can be indicative of the effect that the compounds exert on signal transduction in the sphingomyelin pathway. Accordingly, Jurkat cells are suspended at $2 \times 10^6$ cells/mL in RPMI-1640 medium as described herein with respect to the cell apoptosis experiment. After incubation for 2 hrs., either a test compound; 20 µM of ceramide or 25 ng/ml of anti-FAS antibody DX2 are added to each suspension and incubated for 15 mins. After centrifugation and washing, the cells were separately homogenized in a dounce homogenizer. Ceramide kinase levels in each test sample can be assayed as described by Liu, et al., J. Biol. Chem., 269, 3047-3052 (1994), which is hereby incorporated by reference herein in its entirety. Briefly, the membrane fraction is isolated from each test sample of treated cell homogenate by ultracentrifugation and run on a 10% PAGE gel. The gel is washed with guanadine-HCl, and renatured in HEPES buffer. Then [$^{32}$P]-ATP is added to the gel and left there for 10 mins. Thereafter, the gel is extensively washed with 5% TCA. Autophosphorylated kinase is detected by autoradiography. The results of this assay can be used to establish the CaPK inhibitory efficacy of the compounds disclosed herein.

Ceramidase activity can be measured in a variety of ways. For example, a sample from a subject or a sample of cells can be assayed in vitro for RNA or protein levels, structure, and/or activity of the expressed ceramidase RNA or protein. Many methods standard in the art can be thus employed, including but not limited to ceramidase enzyme assays.

Cellular ceramide levels can be monitored directly, or by indirectly monitoring the concentrations of a ceramide metabolite in a cell. For example, ceramide levels can be directly measured by isolating peripheral blood lymphocytes from a subject. The cells are centrifuged to remove supernatant, and lipids are removed from the cell pellet. The organic phase containing the ceramide can be assayed using the diacylglycerase kinase assay for phosphorylating the ceramide which is then evidenced by autoradiography. Methods for performing diacylglycerase kinase assays are described, for example, in Cifone, M. G. et al., J. Exp. Med., 180(4), 1547-52 (1993), Jayadev et al., J. Biol. Chem., 270, 2047-2052. (1995), and Perry, D. K. et al, Methods Enzymology, 312, 22-31 (2000), each of which is hereby incorporated by reference in its entirety.

Another embodiment is the use of a compound, pharmaceutically acceptable salt, N-oxide (or solvate or hydrate thereof) or composition as described herein in the manufacture of a medicament for any of the therapeutic purposes described herein. For example, the medicament can be for the reduction of triglyceride levels in a subject, the treatment of type II diabetes in a subject, or the treatment or prevention of atherosclerosis or cardiovascular disease in a subject. In other embodiments, the medicament can be used to reduce the levels of cellular ceramide in a subject, for example in the treatment of Batten's disease.

The presently disclosed compounds are useful for increasing metabolic efficiency, for example by increasing fiber oxidative capacity, endurance and aerobic workload. In particular, the present agonists are useful for treating and regulating disorders of mitochondrial function, including, without limitation, exercise intolerance, chronic fatigue syndrome, muscle weakness, myoclonus, myoclonus epilepsy, such as associated with ragged-red fibers syndrome, Kearns-Sayre syndrome, Leigh's syndrome, mitochondrial myopathy encephalopathy lactacidosis stroke (MELAS) syndrome and stroke like episodes. The disclosed agonists also are useful for treating muscular dystrophic states, such as Duchenne's and Becker's muscular dystrophies and Friedreich's ataxia.

The present agonists also function to reduce oxidative stress and secondary effects of such stress. Many diseases, including several of those listed above, have secondary effects caused by damage due to excessive oxidative stress which can be treated using the compounds disclosed herein. For example, free radical damage has been implicated in neurological disorders, such as Parkinson's disease, amyotrophic lateral sclerosis (Lou Gehrig's disease) and Alzheimers disease. Additional diseases in which excessive free radical damage occurs generally include hypoxic conditions and a variety of other disorders. More specifically, such disorders include ischemia, ischemic reperfusion injury (such as coronary or cerebral reperfusion injury), myocardial ischemia or infarction, cerebrovascular accidents (such as a thromboembolic or hemorrhagic stroke) that can lead to ischemia in the brain, operative ischemia, traumatic hemorrhage (for example, a hypovolemic stroke that can lead to CNS hypoxia or anoxia), resuscitation injury, spinal cord trauma, inflammatory diseases, autoimmune disorders (such as rheumatoid arthritis or systemic lupus erythematosis), Down's syndrome, Hallervorden-Spatz disease, Huntingtons chorea, Wilson's disease, diabetic angiopathy (such as peripheral vascular disease or retinal degeneration), uveitis, chronic obstructive pulmonary disease (COPD), including chronic bronchitis and emphysema, asthma, neoplasia, Crohn's disease, inflammatory bowel disease and pancreatitis. Free radical damage is also implicated in a variety of age-related disorders, particularly ophthalmic conditions such as cataracts and age-related macular degeneration.

In particular the present compounds are useful for treating neurological disorders associated with reduced mitochondrial function, oxidative stress, or both. For example, Alzheimer's disease, dementia and Parkinson's disease can be treated using the present compounds.

Metabolic efficiency is enhanced by the compounds disclosed herein. Thus the agonists can be administered to a subject to improve exercise efficiency and athletic performance. Moreover, conditions including, without limitation, hypoxic states, angina pectoris, coronary ischemia and organ damage secondary to coronary vessel occlusion, intermittent claudication, multi-infarct dementia, myocardial infarction, stroke, high altitude sickness and heart failure, including congestive heart failure can be treated using the disclosed compounds. In another aspect the present compounds are useful for treating conditions associated with chronic heart failure, including myopathy/muscle atrophy, chronic obstructive pulmonary disease (COPD) and kidney diseases.

In one aspect the present compounds stimulate increased nitric oxide production. Such compounds are useful for treating diseases associated with reduced circulation and reduced blood vessel function. For example, the present compounds are useful for the treatment of heart disease and cardiomyopathy.

In another aspect, the present compounds activate autophagy and/or apoptotic pathways. Accordingly the present compounds are useful in halting or slowing the progression of neurodegenerative diseases and hyperproliferative disorders, such as cancer.

Inflammatory disorders and effects can be treated using the present compounds For example, in one aspect, the present compounds are particularly useful for treating lung inflammation, such as is involved in asthma, COPD and transplant rejection. Similarly, the present compounds are useful in reducing organ inflammation, particularly macrophage-associated inflammation, such as inflammation of the kidney, liver and other organs. The anti-inflammatory activity of the presently disclosed compounds can be assessed as is known to those of skill in the art, for example, by using the mixed lymphocyte response in vitro.

Accordingly, one aspect of the disclosure relates to a method for treating or ameliorating a disorder or condition related to oxidative stress, mitochondrial dysfunction, free radical damage and/or metabolic inefficiency in a subject in need thereof, the method including administering to the subject an effective amount of a compound, pharmaceutically acceptable salt, N-oxide (or solvate or hydrate thereof) or pharmaceutical composition described herein.

Another aspect of the present disclosure relates to a method for the treatment or amelioration of a disorder of mitochondrial dysfunction in a subject in need thereof, the method including administering to the subject an effective amount of a compound, pharmaceutically acceptable salt, N-oxide (or solvate or hydrate thereof) or pharmaceutical composition described herein. In certain embodiments, the disorder is selected from the group consisting of exercise intolerance, chronic fatigue syndrome, muscle weakness, myoclonus, myoclonus epilepsy (such as associated with ragged-red fibers syndrome), Kearns-Sayre syndrome, Leigh's syndrome, mitochondrial myopathy encephalopathy lactacidosis stroke (MELAS) syndrome and stroke like episodes.

Another aspect of the disclosure relates to a method of increasing metabolic efficiency in a subject in need thereof, the method including administering to the subject an effective amount of a compound, pharmaceutically acceptable salt, N-oxide (or solvate or hydrate thereof) or pharmaceutical composition described herein. Such methods can be used to increase fiber oxidative capacity, endurance, aerobic workload, or any combination thereof. These methods can be used, for example, to improve exercise efficiency, exercise endurance and/or athletic performance in a subject.

Another aspect of the present disclosure relates to methods for mimicking the effects of exercise in a subject in need thereof, the method including administering to the subject an effective amount of a compound, pharmaceutically acceptable salt, N-oxide (or solvate or hydrate thereof) or pharmaceutical composition described herein.

Another aspect of the disclosure relates to a method for treating or ameliorating a disorder in a subject in need thereof, the disorder being selected from the group consisting of hypoxic states, angina pectoris, coronary ischemia and organ damage secondary to coronary vessel occlusion, intermittent claudication, multi-infarct dementia, myocardial infarction, stroke, high altitude sickness and heart failure, including congestive heart failure, the method including administering to the subject an effective amount of a compound, pharmaceutically acceptable salt, N-oxide (or solvate or hydrate thereof) or pharmaceutical composition described herein.

Another aspect of the disclosure relates to a method for the treatment of amelioration of a muscular dystrophic state in a subject in need thereof, the method including administering to the subject an effective amount of a compound, pharmaceutically acceptable salt, N-oxide (or solvate or hydrate thereof) or pharmaceutical composition described herein. In certain embodiments, the muscular dystrophic state is Duchenne's muscular dystrophy, Becker's muscular dystrophy, or Friedreich's ataxia.

Another aspect of the disclosure relates to a method for increasing oxidative capacity of a muscle fiber, the method including contacting the muscle fiber with a compound, pharmaceutically acceptable salt, N-oxide (or solvate or hydrate thereof) or pharmaceutical composition described herein. The contacting may be performed in vitro or in vivo.

Another aspect of the disclosure relates to a method for reducing oxidative stress in a subject in need thereof, the method including administering to the subject an effective amount of a compound, pharmaceutically acceptable salt, N-oxide (or solvate or hydrate thereof) or pharmaceutical composition described herein.

Another aspect of the disclosure relates to a method for reducing free radical damage in a subject in need thereof, the method including administering to the subject an effective amount of a compound, pharmaceutically acceptable salt, N-oxide (or solvate or hydrate thereof) or pharmaceutical composition described herein.

Another aspect of the disclosure relates to a method for treating or ameliorating a disorder or condition in a subject in need thereof, the disorder or condition selected from the group consisting of neurological disorders, hypoxic conditions, ischemia, ischemic reperfusion injury, myocardial ischemia or infarction, cerebrovascular accidents, operative ischemia, traumatic hemorrhage, resuscitation injury, spinal cord trauma, inflammatory diseases, autoimmune disorders, Down's syndrome, Hallervorden-Spatz disease, Huntingtons chorea, Wilson's disease, diabetic angiopathy, uveitis, chronic obstructive pulmonary disease (COPD), asthma, neoplasia, Crohn's disease, inflammatory bowel disease, pancreatitis and age-related disorders, the method including administering to the subject an effective amount of a compound, pharmaceutically acceptable salt, N-oxide (or solvate or hydrate thereof) or pharmaceutical composition described herein. Particular examples of such disorders and conditions are discussed above.

Another aspect of the disclosure is a method for treating or ameliorating a neurological disorder in a subject in need thereof, the neurological disorder being associated with reduced mitochondrial function, oxidative stress, or both, the method including administering to the subject an effective amount of a compound, pharmaceutically acceptable salt, N-oxide (or solvate or hydrate thereof) or pharmaceutical composition described herein. Particular examples of such neurological disorders are discussed above.

Another aspect of the disclosure relates to a method for reducing oxidative stress in a cell, the method including contacting the cell with a compound, pharmaceutically acceptable salt, N-oxide (or solvate or hydrate thereof) or pharmaceutical composition described herein. The contacting may be performed in vitro or in vivo.

Another aspect of the disclosure relates to a method for reducing free radical damage in a cell, the method including contacting the cell with a compound, pharmaceutically acceptable salt, N-oxide (or solvate or hydrate thereof) or pharmaceutical composition described herein. The contacting may be performed in vitro or in vivo.

Another aspect of the disclosure is a method for treating an inflammatory disorder or effect in a subject in need thereof, the method including administering to the subject an effective amount of a compound, pharmaceutically acceptable salt, N-oxide (or solvate or hydrate thereof) or pharmaceutical composition described herein. For example, in one embodiment, the inflammatory disorder or effect is lung inflammation, such as is involved in asthma, COPD and transplant rejection. In another embodiment, the inflammatory disorder or effect is organ inflammation, particularly macrophage-associated inflammation, such as inflammation of the kidney, liver and other organs.

Another aspect of the disclosure is a method of treating a disorder, the method including administering to a subject in need of treatment a compound selected from compounds 1-161-1-175 of Table 1, compounds 4-9-4-17 of Table 4, compounds 5-106-5-129 of Table 5, the compounds of Table 6, and the compounds of Table 7, or a pharmaceutically-acceptable salt or N-oxide thereof, or a solvate or hydrate thereof, the disorder being selected from Parkinson's disease, amyotrophic lateral sclerosis (Lou Gehrig's disease); Alzheimers disease; hypoxic conditions; ischemia, ischemic reperfusion injury (such as coronary or cerebral reperfusion injury), myocardial ischemia or infarction, cerebrovascular accidents (such as a thromboembolic or hemorrhagic stroke) that can lead to ischemia in the brain, operative ischemia, traumatic hemorrhage (for example, a hypovolemic stroke that can lead to CNS hypoxia or anoxia), resuscitation injury, spinal cord trauma, inflammatory diseases, autoimmune disorders (such as rheumatoid arthritis or systemic lupus erythematosis), Down's syndrome, Hallervorden-Spatz disease, Huntingtons chorea, Wilson's disease, diabetic angiopathy (such as peripheral vascular disease or retinal degeneration), uveitis, chronic obstructive pulmonary disease (COPD), including chronic bronchitis and emphysema, asthma, neoplasia, Crohn's disease, inflammatory bowel disease; pancreatitis, age-related disorders including ophthalmic conditions such as cataracts and age-related macular degeneration, neurological disorders associated with reduced mitochondrial function, oxidative stress, or both; Alzheimer's disease, dementia, Parkinson's disease, hypoxic states, angina pectoris, coronary ischemia and organ damage secondary to coronary vessel occlusion, intermittent claudication, multi-infarct dementia, myocardial infarction, stroke, high altitude sickness, heart failure (including congestive heart failure), myopathy/muscle atrophy, chronic obstructive pulmonary disease (COPD) and kidney diseases.

Another aspect of the disclosure is a method of improving exercise efficiency or athletic performance, the method including administering to a subject in need of treatment a compound selected from compounds 1-161-1-175 of Table 1, compounds 4-9-4-17 of Table 4, compounds 5-106-5-129 of Table 5, the compounds of Table 6, and the compounds of Table 7, or a pharmaceutically-acceptable salt or N-oxide thereof, or a solvate or hydrate thereof.

Other aspects of the disclosure relate to the use of a compound, pharmaceutically acceptable salt, N-oxide (or solvate or hydrate thereof) or composition as described herein in the manufacture of a medicament for any of the therapeutic purposes described herein. Still other aspects of the disclosure relate to the use of a compound, pharmaceutically acceptable salt, N-oxide (or solvate or hydrate thereof) or composition as described herein for the treatment of any of the therapeutic purposes described herein. In certain embodiments, the compounds used in the methods and uses disclosed herein have $EC_{50}$ values for AMPK activation less than 10 µM, less than 5 µM, or even less than 1 µM.

EXAMPLES

Synthesis of 1-Boc-3,3-Dimethyl-4-aminopiperidine

Synthesis of 1-Benzyl-3,3-dimethylpiperid-4-one

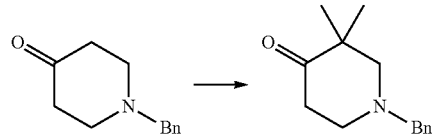 [SMILES: O=C1CCN(Cc2ccccc2)CC1 ; CC1(C)CN(Cc2ccccc2)CCC1=O]

1-Benzylpiperid-4-one (9.45 g, 8.92 mL, 49.98 mmol, 1.0 eq) was added to a suspension of sodium hydride (3.50 g of a 60% suspension in oil, 87.50 mmol, 1.75 eq) in tetrahydrofuran (100 mL). Iodomethane (9.84 g, 3.93 mL, 62.96 mmol, 1.26 eq) was added and the reaction heated to 60° C. for 5 hours. The reaction was filtered and the filtrate concentrated. The residue was partitioned between EtOAc (150 mL) and water (150 mL). The aqueous phase was extracted with EtOAc (150 mL). The organics were combined, washed with brine (150 mL), dried ($Na_2SO_4$), and concentrated under reduced pressure. Column chromatography (silica, 20→60% EtOAc-hexane) yielded the title compound as a colourless oil; $^1$H nmr (CDCl$_3$) δ 7.36-7.26 (5H, m, C$_6$H$_5$), 3.56 (2H, s, C$\underline{H}_2$C$_6$H$_5$), 2.72 (2H, t, J 6.0 Hz, pipH-5 or H-6), 2.51 (2H, t, J 6.0 Hz, pipH-5 or H-6), 2.41 (2H, s, pipH-2), 1.13 (6H, s, 2×CH$_3$); and 1-benzyl-3-methylpiperidin-4-one (3.12 g) as a colourless oil.

Synthesis of 1-Boc-3,3-dimethylpiperidin-4-one

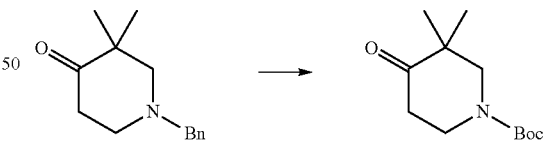

To a solution of 1-benzyl-3,3-dimethylpiperidin-4-one (0.217 g, 1.00 mmol, 1.0 eq) in ethyl acetate-ethanol (1:1, 10 mL) was added palladium on carbon (approximately 0.100 g). The reaction was purged with nitrogen followed by hydrogen and stirred under an atmosphere of hydrogen for 1 hour. The reaction was purged with nitrogen and di-tert-butyl carbonate (0.327 g, 1.50 mmol, 1.5 eq) and sodium carbonate (0.212 g, 2.00 mmol, 2.0 eq) were added. The solution was stirred at room temperature for 1.5 hours and the reaction filtered through Celite®, eluting with EtOAc (4×20 mL). The filtrate was concentrated under reduced pressure. MPLC (15→50% EtOAc-hexane) yielded the title compound (0.206 g, 91%) as a white solid; $^1$H nmr (CDCl$_3$) δ 3.69 (2H, dd, J 6.5, 6.0 Hz, pipH-6), 3.40 (2H, s, pipH-2), 2.46 (2H, t, J 6.5 Hz, pipH-5), 1.46 (9H, s, C(CH$_3$)$_3$), 1.08 (6H, s, 2×CH$_3$); $^{13}$C nmr (CDCl$_3$) δ 177.2, 154.7, 80.1, 54.9, 46.5, 43.4, 37.6, 28.3, 22.4; m/z 172 [M+H—C$_4$H$_8$]$^+$.

Synthesis of
1-Boc-3,3-dimethyl-4-N-benzylaminopiperidine

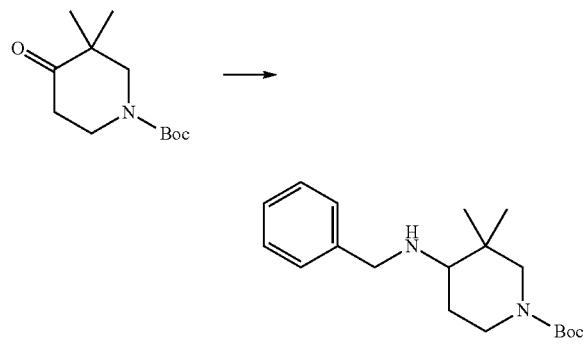

To a solution of the 1-Boc-3,3-dimethylpiperidin-4-one (1.45 g, 6.39 mmol, 1.0 eq) in 1,2-dichloroethane (60 mL) was added benzylamine (1.03 g, 1.04 mL, 9.58 mmol, 1.5 eq). The reaction was equilibrated at room temperature for 10 minutes before adding sodium triacetoxyborohydride (2.71 g, 12.78 mmol, 2.0 eq) and stirring at 6 hours. Rochelle's salt (30 mL) was added and the mixture stirred for 2 hours before pouring into NaHCO$_3$ (90 mL). The organics were extracted with CH$_2$Cl$_2$ (3×90 mL), combined, dried (Na$_2$SO$_4$) and concentrated under reduced pressure. MPLC (0→10% MeOH—CH$_2$Cl$_2$) yielded title compound (1.65 g, 81%) as a colourless oil; $^1$H nmr (CDCl$_3$) δ 7.33-7.23 (5H, m, ArH), 4.10 (1H, m, NH), 4.09 (1H, m, 1H of pipH-6), 3.92, 3.68 (2H, 2d AB system, J 13.5 Hz, NHCH$_2$Ph), 3.63 (1H, m, 1H of pipH-2), 2.74 (1H, m, 1H of pipH-6), 2.52 (1H, m, 1H of pipH-2), 2.25 (1H, dd, J 10.5, 4.0 Hz, pipH-4), 1.82 (1H, br d, J 11.0 Hz, 1H of pipH-5), 1.44 (9H, s, C(CH$_3$)$_3$), 1.35 (1H, m, 1H of pipH-5), 0.94 (3H, s, 1×CH$_3$) 0.86 (3H, s, 1×CH$_3$); $^{13}$C nmr (CDCl$_3$) δ 155.0, 141.0, 128.3, 128.0, 126.9, 79.2, 62.3, 51.9, 43.0, 35.7, 28.4, 27.3, 25.4, 18.2; m/z 319 [M+H]$^+$.

Synthesis of
1-Boc-3,3-dimethyl-4-N-benzylaminopiperidine

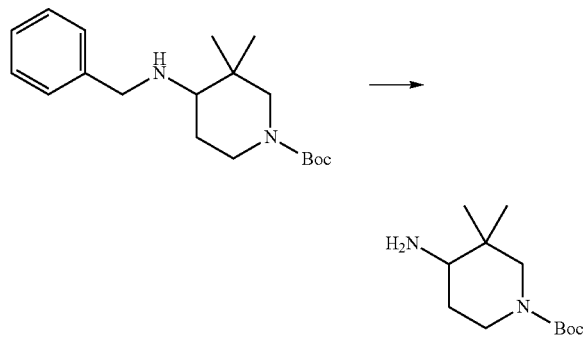

To a solution of the N-benzylaminopiperidine (1.65 g, 5.19 mmol mmol) in ethyl acetate-methanol (1:1, 50 mL) was added palladium on carbon (approximately 0.20 g). The flask was purged with nitrogen followed by hydrogen and stirred under an atmosphere of hydrogen for 5 hours. The reaction was purged with nitrogen and filtered through Celite®, eluting with 5% MeOH—CH$_2$Cl$_2$ (4×30 mL). The reaction was concentrated under reduced pressure to yield the title compound (1.29 g) as a colourless oil. The crude material was taken on without purification; $^1$H nmr (CDCl$_3$) δ 4.06 (1H, m, 1H of pipH-6), 3.65 (1H, m, 1H of pipH-2), 2.80 (1H, m, 1H of pipH-6), 2.50 (1H, dd, J 6.5, 4.0 Hz, pipH-4), 2.48 (1H, m, 1H of pipH-2), 1.63-1.56 (1H, m, 1H of pipH-5), 1.44 (9H, s, C(CH$_3$)$_3$), 1.37 (1H, m, 1H of pipH-5), 0.92 (3H, s, 1×CH$_3$), 0.82 (3H, s, 1×CH$_3$); $^{13}$C nmr (CDCl$_3$) δ 155.2, 79.3, 56.6, 55.0, 42.8, 35.7, 28.4, 25.0, 17.0; m/z 229 [M+H]$^+$, 173 [M+H—C$_4$H$_8$]$^+$.

Synthesis of
cis-3-trifluoromethyl-4-amino-1-Boc-piperidine

Synthesis of
3-trifluoromethyl-1-Boc-piperidin-4-one

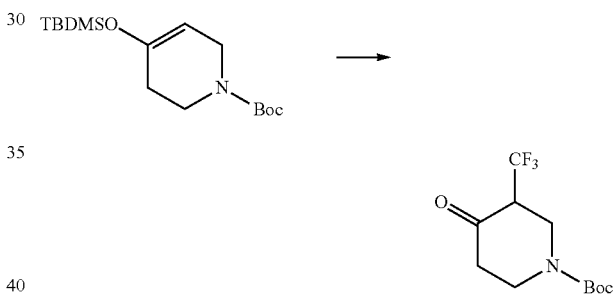

The following procedure is similar to the one reported in Pham, P. V.; Nagib, D. A.; MacMillan, D. W. C. *Angew. Chem. Int. Ed.* 2011, 50, 6119-6122, which is hereby incorporated herein by reference in its entirety. Tris(bipyridyl)dichlororuthenium (II) hexahydrate (0.012 g, 0.02 mmol, 0.005 eq) was added to the silyl enol ether (1.00 g, 3.19 mmol, 1.0 eq) in a borosilicate test tube. Tetrahydrofuran (16 mL) was added to form a brown solution to which was added diisopropylethylamine (1.14 mL, 6.39 mmol, 2.0 eq) and water (0.09 mL, 4.79 mmol, 1.5 eq). The reaction was cooled to −78° C. and degassed by vacuum evacuation/nitrogen backfill (3 times). Trifluoromethyliodide was condensed into a flask as added to the silyl enol ether solution. The reaction was sealed and stirred at room temperature in the presence of light for 23 hours. Et$_2$O (approximately 40 mL) was added and the reaction filtered through Celite® to remove the resulting precipitate. The filtrate was concentrated under reduced pressure. MPLC (10→50% EtOAc-hexane) yielded the title compound (0.105 g, 12%) as a pale yellow oil; $^1$H nmr (CDCl$_3$) δ 4.40-3.70 (2H, m, 2H of pipH-2, H-3, H-6), 3.56 (2H, m, 2H of pipH-2, H-3, H-6), 3.07 (1H, m, 1H of pipH-2, H-3, H-6), 2.46 (2H, m, pipH-5), 1.43 (9H, s, C(CH$_3$)$_3$); $^{19}$F nmr (CDCl$_3$) δ −66.8.

507

Synthesis of 3-trifluoromethyl-4-N-benzylamino-1-Boc-piperidine

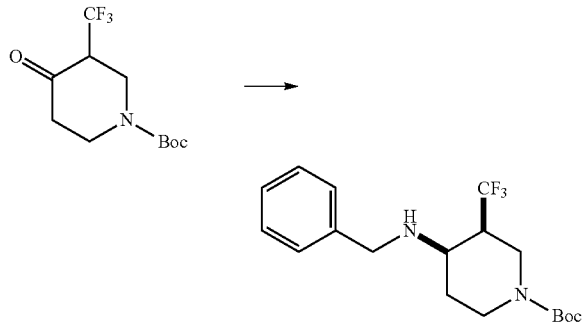

A solution of the piperidinone (0.105 g, 0.393 mmol, 1.0 eq) and benzylamine (0.064 mL, 0.599 mmol, 1.5 eq) in 1,2-dichloroethane (4.0 mL) was equilibrated at room temperature for 10 minutes before adding sodium triacetoxyborohydride (0.167 g, 0.787 mmol, 2.0 eq) and stirring at room temperature for 24 hours. Rochelle's salt (3 mL) was added and the reaction was stirred for 1 hour before pouring into $NaHCO_3$ (30 mL). The organics were extracted with $CH_2Cl_2$ (3×30 mL). The combined organics were dried ($Na_2SO_4$), and concentrated under reduced pressure. MPLC (0→10 MeOH—$CH_2Cl_2$) yielded the title compound (0.092 g, 65%) as a colourless oil; $^1$H nmr ($CDCl_3$) δ 7.32 (4H, m, 4H of $C_6H_5$), 7.28 (1H, m, 1H of $C_6H_5$), 3.84, 3.75 (2H, 2d AB system, J 13.0 Hz, $NCH_2C_6H_5$), 3.69-3.54 (2H, m, 2H of pipH-2, H-6), 3.44 (1H, m, 1H of pipH-2, H-6), 3.23 (1H, m, 1H of pipH-2, H-6), 2.41 (1H, m, pipH-3), 1.86 (1H, m, 1H of pipH5), 1.53 (1H, m, 1H of pipH-3), 1.46 (9H, s, $C(CH_3)_3$); m/z 359 $[M+H]^+$, 303 $[M+H-C_4H_8]^+$.

Synthesis of 3-trifluoromethyl-4-amino-1-Boc-piperidine

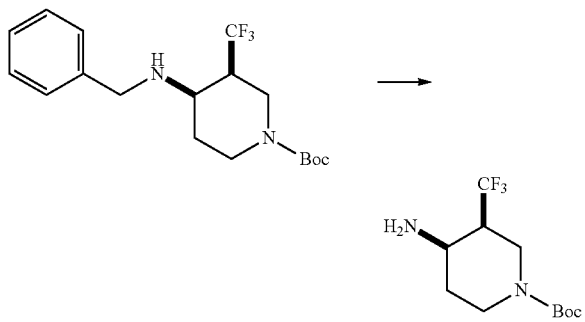

To a solution of the benzylaminopiperidine (0.092 g, 0.257 mmol, 1.0 eq) in ethyl acetate-ethanol (1:1, 4 mL) was added palladium on carbon (0.100 g). The reaction was purged with hydrogen and stirred under an atmosphere of hydrogen for 3 hours. The reaction was purged with nitrogen and filtered through Celite®, eluting with 5% MeOH—$CH_2Cl_2$ (3×15 mL). The filtrate was concentrated under reduced pressure and the crude material used without purification.

508

Synthesis of 4-Cyano-3-methoxybenzaldehyde

Synthesis of 1-Vinyl-4-cyano-3-methoxybenzene

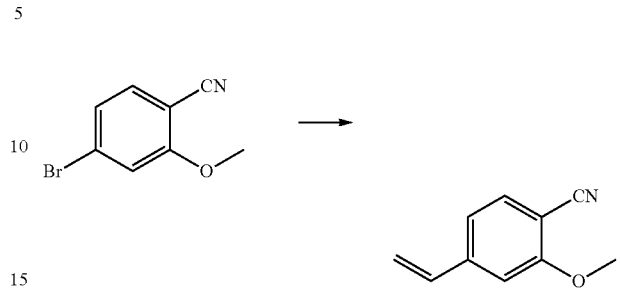

To a solution of 4-bromo-2-methoxybenzonitrile (~0.5 g, 2.36 mmol, 1.0 eq) in toluene (12 mL) was added diisopropylethylamine (0.61 g, 0.82 mL, 4.72 mmol, 2.0 eq), and tributyl(vinyl)tin (1.12 g, 1.03 mL, 3.54 mmol, 1.5 eq). The reaction mixture was degrassed by bubbling agron through the mixture. Tetrakis(triphenylphosphine)palladium (0.10 g, 0.12 mmol, 0.05 eq) was added and the reaction further degassed before heating to 90° C. for 16 hours. The reaction was cooled and partitioned between EtOAc (100 mL) and $NaHCO_3$ (100 mL). The organics were washed with brine (80 mL), dried ($Na_2SO_4$) and concentrated under reduced pressure. MPLC (5→30% EtOAc-hexane) yielded the title compound (0.343 g, 91%) as a white solid; $^1$H nmr ($CDCl_3$) δ 7.56-7.53 (2H, m, ArH-5, H-6), 6.92 (1H, d, J 9.0 Hz, ArH-2), 6.59 (1H, dd, J 17.5, 11.0 Hz, C$\underline{H}$=$CH_2$), 5.63 (1H, d, J 17.5 Hz, CH=C$\underline{H}_2$ trans), 5.23 (1H, d, J 11.0 Hz, CH=C$\underline{H}_2$ cis), 3.91 (3H, s, $OCH_3$); m/z 160 $[M+H]^+$.

Synthesis of 4-cyano-3-methoxybenzaldehyde

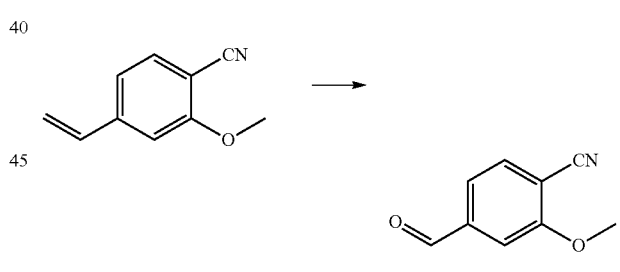

To a solution of 1-vinyl-4-cyano-3-methoxybenzene (0.343 g, 2.16 mmol, 1.0 eq) in dioxane (7 mL) was added 2,6-lutidine (0.461 g, 0.50 mL, 4.31 mmol, 2.0 eq) followed by osmium tetroxide (1.37 g, 1.32 mL of a 4% solution in water, 0.22 mmol, 0.1 eq). A brown/black solution resulted after 1→2 minutes. Sodium periodate (1.847 g, 8.63 mmol as a solution in 7 mL of water, 4.0 eq) was added forming a white precipitate. The mixture was stirred at room temperature for 35 minutes before partitioning between EtOAc (100 mL) and HCl (1M, 100 mL). The organics were washed with brine (100 mL), dried ($Na_2SO_4$) and concentrated under reduced pressure. MPLC (10→50% EtOAc-hexane) yielded the title compound as a white solid; $^1$H nmr ($CDCl_3$) d 9.89 (1H, s, CHO), 8.09 (2H, m, ArH-2, H-6), 7.12 (1H, d, J 9.5 Hz, ArH-3), 4.04 (3H, s, $OCH_3$); m/z 162 $[M+H]^+$.

Example Synthetic Procedures for the Preparation of Benzofurandicarboxamide Compounds Benzofurandicarboxamide compounds can be made using procedures analogous to those described in Scheme 12. Synthetic procedures for particular steps of Scheme 12 are provided below.

Ethyl 5-formylbenzofuran-2-carboxylate (compound A of Scheme 12): 4-Hydroxyisophthalaldehyde (TCI America) (10.75 g, 71.6 mmol) in $CH_3CN$ (150 mL) was treated with $K_2CO_3$ (10.1 g, 1 eq.) and ethyl bromoacetate (8.0 mL, 1 eq.). The mixture was heated at 90° C. for 18 h, then cooled and concentrated under vacuum. The residue was partitioned between EtOAc and water. The organic layer was dried over sodium sulfate and concentrated under vacuum. The crude product was purified on the Combiflash system with a 220 g silica gel column, eluting with hexanes/EtOAc. The product was obtained as a white solid, 3.8 g. $^1$H NMR ($CDCl_3$) 10.08 (s, 1H, CHO), 8.24 (m, 1H), 8.01 (m, 1H), 7.72 (d, 1H), 7.63 (m, 1H), 4.48 (q, 2H, $OCH_2$), 1.44 (t, 3H, $OCH_2CH_3$); m/z 218.94 [M+H]+.

Ethyl 5-carboxybenzofuran-2-carboxylate (compound B of Scheme 12): Ethyl 5-formylbenzofuran-2-carboxylate (3.8 g, 17.4 mmol) was dissolved in a mixture of THF (80 mL) and t-BuOH (20 mL). A solution of sulfamic acid (4.0 g, 41.2 mmol) and sodium chlorite (3.4 g, 37.6 mmol) in water (70 mL) was added dropwise at RT. After 3 h an additional portion of sulfamic acid (1.2 g) and sodium chlorite (1.4 g) in water was added in one portion. The reaction mixture was stirred overnight at RT, then extracted twice with EtOAc, dried over sodium sulfate and concentrated under vacuum to give the crude product, 4.87 g which was suitable for use without purification. $^1$H NMR (DMSO-$d_6$) 8.42 (m, 1H), 8.07 (m, 1H), 7.49-7.81 (m, 2H), 4.37 (q, 2H, $OCH_2$), 1.34 (t, 3H, $OCH_2CH_3$); m/z 234.94 [M+H]+.

5-(4-(tert-butoxycarbonyl)piperazine-1-carbonyl)benzofuran-2-carboxylic acid (compound D of Scheme 12): Ethyl 5-carboxybenzofuran-2-carboxylate (2.35 g, 10 mmol) was treated with mono-Boc-piperazine (2.03 g, 11 mmol), HATU (3.9 g, 10.2 mmol) and DIEA (3.5 mL, 2 eq.) in DMF (20 mL) at RT for 4.5 h. The mixture was diluted with EtOAc and washed with saturated aqueous sodium bicarbonate solution and brine (2×). The organic extract was dried over anhydrous sodium sulfate and concentrated under vacuum. LCMS analysis of the crude product showed 95% purity and the expected mass m/z 402.94 [M+H]+. The crude ester was dissolved in a mixture of THF (15 mL) and MeOH (15 mL) and treated with LiOH monohydrate (2.5 g, approx. 6 eq) in water (20 mL) with vigorous stirring at RT. After 2 h LCMS analysis showed the reaction was done. The mixture was concentrated under vacuum to remove the organic solvents, then acidified with ice-cold 10% aqueous HCl. The resulting precipitate was filtered off, washed well with water and air dried to give compound D as a white solid, 3.15 g. $^1$H NMR (DMSO-$d_6$) 7.82 (d, 1H), 7.68-7.74 (m, 1H), 7.61 (s, 1H), 7.50 (dd, 1H), 3.46 (m, 4H), 3.38 (m, 4H), 1.40 (s, 9H); m/z 374.91 [M+H]+.

N-(1-(4-cyanobenzyl)piperidin-4-yl)-5-(piperazine-1-carbonyl)benzofuran-2-carboxamide (compound F of Scheme 12): Compound D of Scheme 12 (1.0 g, 2.67 mmol) was dissolved in dry DMF and treated with 4-amino-1-(4-cyanobenzyl)piperidine dihydrochloride (0.86 g, 1.1 eq.), DIEA (1.4 mL, 3 eq.) and HATU (1.12 g, 1.1 eq.) at RT. After 3 h the reaction was complete as judged by LCMS. The reaction mixture was diluted with EtOAc and washed with saturated aqueous sodium bicarbonate solution and brine (2×). The organic extract was dried over anhydrous sodium sulfate and concentrated under vacuum. LCMS analysis of the crude product showed the expected mass m/z 572.03 [M+H]+. The Boc group was removed by treatment with TFA (5 mL) in $CH_2Cl_2$ (10 mL) at RT for 2 h. The solvent was removed under vacuum and the residue was partitioned between $CH_2Cl_2$ and saturated aqueous potassium carbonate solution. The organic layer was concentrated under vacuum to give compound F as a tan foam, 0.936 g. $^1$H NMR (DMSO-$d_6$) 8.37 (d, 1H), 7.74-7.77 (m, 3H), 7.66 (d, 1H), 7.49-7.57 (m, 3H), 7.43 (dd, 1H), 3.79 (m, 1H), 3.56 (s, 2H), 3.40 (m, 4H), 2.81-2.88 (m, 2H), 2.68 (m, 4H), 2.06-2.15 (m, 2H), 1.77-1.81 (m, 2H), 1.60-1.72 (m, 2H); m/z 471.96 [M+H]+. Reductive amination or alkylation can be performed as described elsewhere herein, as described in the referenced publications, or using methods familiar to the person of skill in the art.

Example Synthetic Procedures for the Preparation of (Carboxamido)Benzofurancarboxamide Compounds (Carboxamido)benzofurancarboxamide compounds can be made using procedures analogous to those described in Scheme 13. Synthetic procedures for particular steps of Scheme 13 are provided below.

Ethyl 5-aminobenzofuran-2-carboxylate (compound H of Scheme 13): Ethyl 5-nitrobenzofuran-2-carboxylate (Aldrich, 8.0 g) was dissolved in a mixture of EtOH and THF, treated with 10% Pd/C (wet, Degussa type E101, Aldrich) and hydrogenated on a Parr apparatus at 35 psi for 4 h. The reaction mixture was filtered over Celite, washed with THF and EtOH and concentrated under vacuum to give crude solid product, 6.3 g which was used without purification. $^1$H NMR ($CDCl_3$) 7.34-7.37 (m, 2H), 6.87 (d, 1H), 6.81 (dd, 1H), 4.41 (q, 2H, $OCH_2$), 3.60 (broad s, 2H, $NH_2$), 1.40 (t, 3H, $OCH_2CH_3$); m/z 206.39 [M+H]+

5-(1-(tert-butoxycarbonyl)piperidine-4-carboxamido)benzofuran-2-carboxylic acid (compound J of Scheme 13): Ethyl 5-aminobenzofuran-2-carboxylate (5.3 g, 25.8 mmol) was dissolved in $CH_2Cl_2$ (50 mL) and treated with 1-Boc-piperidine-4-carboxylic acid (5.95 g, 25.8 mmol), HATU (9.9 g, 25.9 mmol) and DIEA (13.6 mL, 3 eq.) at RT overnight. The reaction mixture was washed with water, 1M aqueous potassium hydrogen sulfate solution, and saturated sodium bicarbonate solution. The organic layer was dried over anhydrous sodium sulfate and concentrated under vacuum. Intermediate I showed >95% purity according to LCMS with the expected mass m/z 417.59 [M+H]+ The crude ester was dissolved in a mixture of THF (20 mL) and MeOH (20 mL) and treated with a solution of LiOH monohydrate (6 g, approx 6 eq.) in water (30 mL). After 5 h stirring at RT, the reaction was complete. The organic solvents were removed under vacuum and the residue was acidified with ice cold 10% aqueous HCl. A gummy precipitate formed which was filtered off, redissolved in a mixture of $CH_2Cl_2$ and MeOH and washed with brine. The organic phase was dried over anhydrous sodium sulfate and concentrated under vacuum to give compound J as a pinkish solid, 6.29 g. $^1$H NMR (DMSO-$d_6$) 10.18 (s, 1H, $CO_2H$), 8.16 (d, 1H), 7.61 (m, 1H), 7.59 (s, 1H), 7.52 (dd, 1H), 4.00 (m, 2H), 2.76 (m, 4H), 1.77 (m, 2H), 1.51 (m, 2H), 1.45 (s, 9H); m/z 389.38 [M+H]+

N-(2-(1-(4-cyanobenzyl)piperidin-4-ylcarbamoyl)benzofuran-5-yl)piperidine-4-carboxamide (compound L of Scheme 13): Compound J of Scheme 13 (3.19 g, 8.22 mmol) was dissolved in $CH_2Cl_2$ (50 mL) and treated with 4-amino-1-(4-cyanobenzyl)piperidine dihydrochloride (2.37 g, 8.2 mmol), HATU (3.2 g, 8.2 mmol) and DIEA (4.8 mL, 3.3 eq) at RT for 3 h. The reaction mixture was diluted with $CH_2Cl_2$ and MeOH (for added solubility) and washed with water, saturated sodium bicarbonate solution and brine. The organic layer was dried over anhydrous sodium sulfate and concentrated under reduced pressure. The crude product (compound K of Scheme 14) showed the expected mass m/z 586.73 [M+H]+. Compound K was then stirred at RT with a mixture of CH$_2$Cl$_2$/TFA (1/1, 40 mL) for 1 h. The solvents were removed under vacuum and the residue was partitioned between CH$_2$Cl$_2$ and saturated aqueous potassium carbonate. The organic layer was dried over anhydrous sodium sulfate and concentrated under vacuum to give Compound L as a pinkish solid, 3.13 g. $^1$H NMR (CDCl$_3$/MeOD$_4$) 7.85 (d, 1H), 7.54 (d, 2H), 7.43 (dd, 1H), 7.37 (d, 2H), 7.33 (d, 1H), 7.30 (s, 1H), 3.89 (m, 1H), 3.49 (s, 2H), 3.07 (m, 2H), 2.77 (m, 2H), 2.52-2.62 (m, 2H), 2.39 (m, 1H), 2.07-2.15 (m, 2H), 1.86-1.94 (m, 2H), 1.76-1.83 (m, 2H), 1.50-1.70 (m, 4H); m/z 486.64 [M+H]+. Reductive amination or alkylation can be performed as described elsewhere herein, as described in the referenced publications, or using methods familiar to the person of skill in the art.

Example Synthetic Procedures for the Preparation of (3-fluoropiperidin-4-yl)oxybenzofurancarboxamide Compounds (3-Fluoropiperidin-4-yl)oxybenzofurancarboxamide compounds can be made using procedures analogous to those described in Scheme 14. Synthetic procedures for particular steps of Scheme 14 are provided below.

(3,4-trans)-tert-butyl 3-fluoro-4-(2-(methoxycarbonyl) benzofuran-5-yloxy)piperidine-1-carboxylate (compound N of Scheme 14): Methyl 3-hydroxybenzofuran-2-carboxylate (2.22 g, 11.6 mmol) and racemic cis-1-Boc-3-fluoro-4-hydroxypiperidine (2.54 g, 11.6 mmol) and triphenylphosphine (3.04 g, 11.6 mmol) were dissolved in dry THF (40 mL) and then treated dropwise at RT with diisopropylazodicarboxylate (2.51 mL, 1.1 eq.). After 15 h, the reaction mixture was concentrated under vacuum. The residue was partitioned between diethyl ether and 1M aq. sodium hydroxide solution. The organic layer was dried over anhydrous sodium sulfate and concentrated under reduced pressure. The crude product was purified on the CombiFlash system with a 120 g silica gel column, eluting 10 to 70% EtOAc/hexanes. Compound N was obtained as a clear glass, 2.2 g. $^1$H NMR (CDCl$_3$) 7.50 (s, 1H), 7.45 (d, 1H), 7.18 (d, 1H), 7.09 (dd, 1H), 4.70 (m, 0.5H) and 4.55 (m, 0.5H) (piperidine-H-3), 4.41-4.48 (m, 1H), 3.96 (s, 3H), 3.78-3.92 (m, 1H), 3.54-3.72 (m, 2H), 3.44 (m, 1H), 2.05-2.15 (m, 1H), 1.72-1.83 (m, 1H), 1.46 (s, 9H); m/z 293.92 [M+H]+(-Boc)

5-((3,4-trans)-1-(tert-butoxycarbonyl)-3-fluoropiperidin-4-yloxy)benzofuran-2-carboxylic acid (compound 0 of Scheme 14): Compound N of Scheme 14 (2.2 g, 5.6 mmol) was dissolved in a mixture of THF (10 mL) and MeOH (10 mL) and treated with a solution of LiOH monohydrate (1.5 g, 6 eq.) in water (10 mL) at RT. After 2 h the organic solvents were removed under vacuum and the residue was treated with ice-cold 10% aqueous HCl. The precipitate was filtered off, washed well with water and air dried to give compound 0 as a white solid, 1.63 g. $^1$H NMR (DMSO-d$_6$) 7.60 (s, 1H), 7.54 (d, 1H), 7.39 (d, 1H), 7.16 (dd, 1H), 4.71 (m, 0.5H, one-half of piperidine-H3), 4.52-4.65 (m, 1.5H, one-half of piperidine-H3 and piperidine-H4), 3.76-3.89 (m, 1H), 3.41-3.55 (m, 2H), 3.25-3.34 (m, 1H), 1.97-2.06 (m, 1H), 1.57-1.67 (m, 1H), 1.41 (s, 9H); m/z 378.02 [M]$^-$.

N-(1-(4-cyanobenzyl)piperidin-4-yl)-5-((3,4-trans)-3-fluoropiperidin-4-yloxy)benzofuran-2-carboxamide (compound Q of Scheme 14): Compound O of Scheme 14 (0.80 g, 2.11 mmol) was dissolved in dry DMF (5 mL) and treated with 4-amino-1-(4-cyanobenzyl)piperidine dihydrochloride (0.67 g, 1.1 eq.), HATU (0.89 g, 1.1 eq.) and DIEA (1.1 mL, 3 eq). After 4 h the reaction mixture was diluted with EtOAc and washed with saturated aqueous sodium bicarbonate solution, water and brine (2×). The organic layer was dried over anhydrous sodium sulfate and concentrated under reduced pressure to give crude Compound P of Scheme 14, which showed LCMS m/z 577.48 [M+H]+ as required. Compound P was treated with CH$_2$Cl$_2$/TFA, 1/1 (10 mL) at RT for 3 h. The solvent was removed under vacuum and the residue was then partitioned between CH$_2$Cl$_2$ and saturated aqueous potassium carbonate. The organic layer was dried over anhydrous sodium sulfate to give compound Q as a yellow foam, 0.80 g. $^1$H NMR (DMSO-d$_6$) 8.27 (d, 1H), 7.75 (d, 2H), 7.50 (m, 3H), 7.40 (s, 1H), 7.33 (d, 1H), 7.07 (dd, 1H), 4.55 (m, 0.5H, one-half of piperidine-H3), 4.35-4.45 (m, 1.5H, one-half of piperidine-H3 and piperidine-H4), 3.73-3.80 (m, 1H), 3.56 (s, 2H), 3.13-3.22 (m, 3H), 2.77-2.88 (m, 3H), 2.55-2.62 (m, 1H), 2.05-2.13 (m, 4H), 1.59-1.80 (m, 4H); $^{19}$F NMR (DMSO-d$_6$)–186.39 (d, J=52.6 Hz); m/z 477.50 [M+H]+. Reductive amination or alkylation can be performed as described elsewhere herein, as described in the referenced publications, or using methods familiar to the person of skill in the art.

SYNTHETIC EXAMPLES

The following compounds were made using methods analogous to those described in the referenced publications and in Schemes 1-14; in certain cases, exemplary synthetic procedures are provided.

Compound 1-161 (as its formic acid salt): $^1$H NMR (CDCl$_3$) 7.73-7.77 (m, 2H), 7.61-7.65 (m, 3H), 7.50 (dd, 2H), 7.35-7.41 (m, 4H), 7.24 (m, 1H), 6.92 (s, 1H), 6.79 (dd, 1H), 4.44 (m, 1H), 3.90 (m, 1H), 3.83 (s, 2H), 3.56 (s, 2H), 2.80-2.97 (m, 6H), 2.21-2.25 (m, 2H), 2.10-2.17 (m, 2H), 1.87-1.97 (m, 4H), 1.58-1.68 (m, 2H); m/z 640.58[M+H].

Compound 1-162: $^1$H NMR (CDCl$_3$) 7.92 (s, 1H), 7.79 (d, 2H), 7.70 (d, 2H), 7.58 (d, 2H), 7.43 (d, 2H), 7.35 (d, 2H), 7.08 (d, 1H), 6.99 (dd, 1H), 6.51 (d, 1H), 4.31 (m, 1H), 3.99 (m, 1H), 3.53 (s, 2H), 3.50 (s, 2H), 2.76-2.82 (m, 4H), 2.30-2.37 (m, 2H), 2.15-2.22 (m, 2H), 1.88-1.99 (m, 4H), 1.77-1.82 (m, 2H), 1.54-1.67 (m, 2H); m/z 640.63[M+H].

Compound 1-163 (as its formic acid salt): $^1$H NMR (CDCl$_3$/MeOD$_4$) 7.92 (d, 1H), 7.66-7.71 (m, 3H), 7.56 (d, 2H), 7.42-7.48 (m, 4H), 7.31-7.38 (m, 2H), 7.10 (d, 1H), 6.99 (dd, 1H), 6.42 (m, 1H), 4.50 (m, 1H), 3.94 (m, 1H), 3.77 (m, 2H), 3.65 (s, 2H), 3.56 (m, 2H), 2.88-2.93 (m, 2H), 2.26-2.34 (m, 2H), 1.81-1.99 (m, 6H), 1.62-1.75 (m, 2H); m/z 629.58 [M+H].

Compound 1-168 (as its formic acid salt): $^1$H NMR (DMSO-d$_6$) 8.26 (d, 1H), 7.75 (d, 2H), 7.49 (d, 2H), 7.38-7.44 (m, 3H), 7.27-7.34 (m, 3H), 7.07 (dd, 1H), 4.71-4.77 (m, 0.5H, CHF), 4.53-4.60 (m, 0.5H, CHF), 4.33-4.44 (m, 1H), 3.68-3.82 (m, 1H), 3.60 (s, 2H), 3.56 (s, 2H), 2.93-3.07 (m, 1H), 2.67-2.80 (m, 3H), 2.19-2.42 (m, 2H), 2.06-2.13 (m, 2H), 1.59-1.79 (m, 6H); m/z 651.05[M+H].

Compound 1-169 (as its formic acid salt): $^1$H NMR (DMSO-d$_6$) 8.39 (m, 1H), 8.26 (d, 1H), 7.69-7.79 (m, 3H), 7.50 (d, 1H), 7.39-7.43 (m, 4H), 7.33 (d, 1H), 7.27 (d, 2H), 7.08 (dd, 1H), 6.50 (m, 1H), 4.75 (m, 0.5H, CHF), 4.58 (m, 0.5H, CHF), 4.39 (m, 1H), 3.77 (m, 1H), 3.61 (s, 2H), 3.50 (s, 2H), 3.04-3.10 (m, 1H), 2.70-2.82 (m, 3H), 2.21-2.36 (m, 2H), 2.08 (m, 2H), 1.57-1.79 (m, 6H); m/z 692.11[M+H].

Compound 1-171 (as its formic acid salt): $^1$H NMR (DMSO-d$_6$) 8.26 (d, 1H), 8.02 (m, 2H), 7.92 (m, 2H), 7.75 (s, 1H), 7.50 (d, 1H), 7.38-7.43 (m, 3H), 7.33 (d, 1H), 7.27 (d, 2H), 7.07 (dd, 1H), 4.74 (m, 0.5H, CHF), 4.58 (m, 0.5H, CHF), 4.31-4.41 (m, 1H), 3.77 (m, 1H), 3.57 (s, 2H), 3.50 (s, 2H), 3.06-3.10 (m, 1H), 2.73-2.82 (m, 2H), 2.23-2.41 (m, 2H), 2.03-2.06 (m, 2H), 1.58-1.79 (m, 6H); m/z 717.07[M+H].

Compound 4-9: $^1$H nmr (CDCl$_3$) δ 8.94 (1H, m, pyH-6), 8.15 (1H, dd, J 8.0, 2.0 Hz, pyH-4), 7.69 (1H, d, J 8.0 Hz, pyH-3), 7.68 (2H, d, J 9.0 Hz, 2H of C$_6$H$_4$SO$_2$N), 7.60 (2H, d, J 8.5 Hz, 2H of C$_6$H$_4$CN), 7.44 (2H, d, J 8.0 Hz, 2H of C$_6$H$_4$CN), 6.91 (2H, d, J 9.0 Hz, 2H of C$_6$H$_4$SO$_2$N), 6.54 (1H, d, J 7.5 Hz, NH), 4.01 (1H, m, pipH-4), 3.96 (2H, m, 2H of piz), 3.77 (2H, m, 2H of piz), 3.55 (2H, s, CH$_2$C$_6$H$_4$CN), 3.46 (2H, m, 2H of piz), 3.34 (2H, m, 2H of piz), 3.20, 3.18 (4H, 2d AB system, J 6.5 Hz, 4H of pyrrolidine), 2.83 (2H, m, 2H of pipH-3, H-5), 2.19 (2H, dd, J 11.5, 9.5 Hz, 2H of pipH-2, H-6), 2.02 (2H, m, 2H of pipH-3, H-5), 1.73 (4H, m, 4H of pyrrolidine), 1.63 (2H, m, 2H of pipH-3, H-5); m/z: 642 [M+H]$^+$.

Compound 4-10: $^1$H nmr (CDCl$_3$) δ 8.91 (1H, d, J 2.0 Hz, pyH-6), 8.11 (1H, dd, J 8.0, 2.0 Hz, pyH-4), 7.97 (2H, d, J 9.0 Hz, 2H of C$_6$H$_4$COcPr), 7.60 (1H, d, J 8.0 Hz, pyH-3), 7.33 (2H, d, J 9.0 Hz, 2H of C$_6$H$_4$OCF$_3$), 7.17 (2H, d, J 9.0 Hz, 2H of C$_6$H$_4$OCF$_3$), 7.13 (1H, d, J 8.0 Hz, NH), 6.89 (2H, d, J 9.0 Hz, 2H of C$_6$H$_4$COcPr), 4.58 (1H, dtd, J 50.0, 9.5, 5.0 Hz, pipH-3), 4.15 (1H, m, pipH-4), 3.97 (2H, m, 2H of piz), 3.72 (2H, m, 2H of piz), 3.61, 3.54 (2H, 2d AB system, J 13.5 Hz, CH$_2$C$_6$H$_4$OCF$_3$), 3.48 (2H, m, 2H of piz), 3.35 (2H, m, 2H of piz), 3.22 (1H, m, 1H of pipH-2), 2.83 (1H, m, 1H of pipH-6), 2.61 (1H, m, cPrH-1), 2.26-2.15 (3H, m, 1H of pipH-2, 1H of pipH-5, 1H of pipH-6), 1.65 (1H, m, 1H of pipH-5), 1.89 (2H, m, 2H of cPrH-2, H-3), 0.98 (2H, m, 2H of cPrH-2, H-3); $^{19}$F nmr (CDCl$_3$) δ −57.9, −188.4 (d, J 49.0 Hz); m/z: 655 [M+H]$^+$.

Compound 4-11: $^1$H nmr (CDCl$_3$) δ 8.93 (1H, d, J 2.0 Hz, pyH-6), 8.13 (1H, dd, J 8.0, 2.0 Hz, pyH-4), 7.71 (2H, d, J 9.0 Hz, 2H of C$_6$H$_4$SO$_2$iPr), 7.65 (1H, d, J 8.0 Hz, pyH-3), 7.33 (2H, d, J 9.0 Hz, 2H of C$_6$H$_4$OCF$_3$), 7.17 (2H, d, J 9.0 Hz, 2H of C$_6$H$_4$OCF$_3$), 6.94 (1H, m, NH), 6.92 (2H, d, J 9.5 Hz, 2H of C$_6$H$_4$SO$_2$iPr), 4.56 (1H, dtd, J 50.0, 9.5, 5.0 Hz, pipH-3), 4.16 (1H, m, pipH-4), 3.97 (2H, m, 2H of piz), 3.75 (2H, m, 2H of piz), 3.62, 3.55 (2H, 2d AB system, J 13.5 Hz, CH$_2$C$_6$H$_4$OCF$_3$), 3.50 (2H, m, 2H of piz), 3.38 (2H, m, 2H of piz), 3.21 (1H, m, 1H of pipH-2), 3.13 (1H, heptet, J 7.0 Hz, SO$_2$CH(CH$_3$)$_2$), 2.83 (1H, m, 1H of pipH-6), 2.26-2.15 (3H, m, 1H of pipH-2, 1H of pipH-5, 1H of pipH-6), 1.65 (1H, m, 1H of pipH-5), 1.27 (6H, d, J 7.0 Hz, SO$_2$CH(CH$_3$)$_2$); $^{19}$F nmr (CDCl$_3$) δ −57.9, 188.5 (d, J 50.0 Hz); m/z: 693 [M+H]$^+$.

Compound 4-12: $^1$H nmr (CDCl$_3$) δ 8.93 (1H, m, pyH-6), 8.14 (1H, dd, J 8.5, 2.0 Hz, pyH-4), 7.97 (2H, d, J 9.0 Hz, 2H of C$_6$H$_4$COcPr), 7.67 (1H, d, J 8.0 Hz, pyH-3), 7.62 (2H, d, J 8.0 Hz, 2H of C$_6$H$_4$CN), 7.44 (2H, d, J 8.5 Hz, 2H of C$_6$H$_4$CN), 6.90 (2H, d, J 9.0 Hz, 2H of C$_6$H$_4$COcPr), 6.87 (1H, d, J 8.0 Hz, NH), 4.58 (1H, dtd, J 50.0, 9.5, 5.0 Hz, pipH-3), 4.17 (1H, m, pipH-4), 3.98 (2H, m, 2H of piz), 3.75 (2H, m, 2H of piz), 3.67, 3.61 (2H, 2d AB system, J 14.0 Hz, CH$_2$C$_6$H$_4$CN), 3.49 (2H, m, 2H of piz), 3.37 (2H, m, 2H of piz), 3.19 (1H, m, 1H of pipH-2), 2.81 (1H, m, 1H of pipH-6), 4.62 (1H, tt, J 8.0, 5.0 Hz, cPrH-1), 2.31-2.19 (3H, m, 1H of pipH-2, 1H of pipH-5, 1H of pipH-6), 1.65 (1H, m, 1H of pipH-5), 1.19 (2H, m, 2H of cPrH-2, H-3), 0.98 (2H, m, 2H of cPrH-2, H-3); $^{19}$F nmr (CDCl$_3$) δ −188.5 (d, J 50.5 Hz); m/z: 595 [M+H]$^+$.

Compound 4-13: $^1$H nmr (CDCl$_3$) δ 8.89 (1H, m, pyH-6), 8.11 (1H, dd, J 8.0, 2.0 Hz, pyH-4), 7.90 (2H, d, J 8.5 Hz, 2H of C$_6$H$_4$SO$_2$Me), 7.63 (2H, d, J 8.0 Hz, 2H of C$_6$H$_4$CN), 7.60 (1H, d, J 8.0 Hz, pyH-3), 7.55 (2H, d, J 8.0 Hz, 2H of C$_6$H$_4$SO$_2$Me), 7.44 (2H, d, J 8.0 Hz, 2H of C$_6$H$_4$CN), 6.74 (1H, d, J 8.0 Hz, NH), 4.56 (1H, dtd, J 50.0, 9.5, 5.0 Hz, pipH-3), 4.15 (1H, m, pipH-4), 3.84 (2H, m, 2H of piz), 3.63 (4H, m, CH$_2$C$_6$H$_4$CN, CH$_2$C$_6$H$_4$SO$_2$Me), 3.53 (2H, m, 2H of piz), 3.18 (1H, m, 1H of pipH-2), 3.06 (3H, s, SO$_2$CH$_3$), 2.80 (1H, m, 1H of pipH-6), 2.58 (2H, m, 2H of piz), 2.44 (2H, m, 2H of piz), 2.31-2.18 (3H, m, 1H of pipH-2, 1H of pipH-45, 1H of pipH-6), 1.66 (1H, m, 1H of pipH-5); $^{19}$F nmr (CDCl$_3$) δ −188.6 (d, J 51.0 Hz); m/z: 620 [M+H]$^+$.

Compound 4-14: $^1$H nmr (CDCl$_3$) δ 8.93 (1H, m, pyH-6), 8.13 (1H, dd, J 8.5, 2.0 Hz, pyH-4), 7.70 (2H, d, J 9.0 Hz, 2H of C$_6$H$_4$SO$_2$N), 7.64 (1H, d, J 8.5 Hz, pyH-3), 7.34 (2H, d, J 8.5 Hz, 2H of C$_6$H$_4$OCF$_3$), 7.17 (2H, d, J 8.0 Hz, 2H of C$_6$H$_4$OCF$_3$), 6.93 (1H, m, NH), 6.91 (2H, d, J 9.0 Hz, 2H of C$_6$H$_4$SO$_2$N), 4.58 (1H, dtd, J 50.0, 9.5, 5.0 Hz, pipH-3), 4.15 (1H, m, pipH-4), 3.97 (2H, m, 2H of piz), 3.74 (2H, m, 2H of piz), 3.62, 3.55 (2H, 2d AB system, J 13.5 Hz, CH$_2$C$_6$H$_4$OCF$_3$), 3.47 (2H, m, 2H of piz), 3.34 (2H, m, 2H of piz), 3.20 (5H, m, 4H of pyrrolidine, 1H of pipH-2 or H-6), 2.83 (1H, m, 1H of pipH-2 or H-6), 2.27-2.15 (3H, m, 1H of pipH-2, 1H of pipH-5, 1H of pipH-6), 1.74 (4H, m, 4H of pyrrolidine), 1.68 (1H, m, 1H of pipH-5); $^{19}$F nmr (CDCl$_3$) δ −57.9, −188.5 (d, J 46.5 Hz); m/z: 719 [M+H]$^+$.

Compound 4-15: $^1$H nmr (CDCl$_3$) δ 8.88 (1H, d, J 2.0 Hz, pyH-6), 8.08 (1H, dd, J 8.0, 2.0 Hz, pyH-4), 7.78 (2H, d, J 8.5 Hz, 2H of C$_6$H$_4$SO$_2$N), 7.54 (1H, d, J 8.0 Hz, pyH-3), 7.49 (2H, d, J 8.5 Hz, 2H of C$_6$H$_4$SO$_2$N), 7.33 (2H, d, J 8.5 Hz, 2H of C$_6$H$_4$OCF$_3$), 7.17 (2H, d, J 8.5 Hz, 2H of C$_6$H$_4$OCF$_3$), 6.98 (1H, d, J 8.0 Hz, NH), 4.58 (1H, dtd, J 50.0, 9.5, 5.0 Hz, pipH-3), 4.15 (1H, m, pipH-4), 3.84 (2H, m, 2H of piz), 3.63-3.57 (4H, m, CH$_2$C$_6$H$_4$SO$_2$N, CH$_2$C$_6$H$_4$OCF$_3$), 3.51 (2H, m, 2H of piz), 3.24 (4H, m, 4H of pyrrolidine), 3.20 (1H, m, 1H of pipH-2 or pipH-6), 2.82 (1H, m, 1H of pipH-2 or H-6), 2.57 (2H, m, 2H of piz), 2.42 (2H, m, 2H of piz), 2.26-2.14 (3H, m, 1H of pipH-2, 1H of pipH-5, 1H of pipH-6), 1.75 (4H, m, 4H of pyrrolidine), 1.63 (1H, m, 1H of pipH-5); $^{19}$F nmr (CDCl$_3$) δ −57.9, −188.5 (d, J 46.5 Hz); m/z: 734 [M+H]$^+$.

Compound 4-16: $^1$H nmr (CDCl$_3$) δ 8.89 (1H, m, pyH-6), 8.11 (1H, dd, J 8.5, 2.0 Hz, pyH-4), 7.77 (2H, d, J 8.5 Hz, 2H of C$_6$H$_4$SO$_2$N), 7.59 (3H, m, pyH-3, 2H of C$_6$H$_4$CN), 7.48 (2H, d, J 8.0 Hz, 2H of C$_6$H$_4$CN or C$_6$H$_4$SO$_2$N), 7.44 (2H, d, J 8.0 Hz, 2H of C$_6$H$_4$CN or C$_6$H$_4$SO$_2$N), 6.51 (1H, d, J 8.0 Hz, NH), 4.00 (1H, m, pipH-4), 3.83 (2H, m, 2H of piz), 3.59 (2H, s, CH$_2$C$_6$H$_4$SO$_2$N or CH$_2$C$_6$H$_4$CN), 3.55-3.52 (4H, m, CH$_2$C$_6$H$_4$SO$_2$N or CH$_2$C$_6$H$_4$CN, 2H of piz), 3.23 (4H, m, 4H of pyrrolidine), 2.82 (2H, m, 2H of pipH-2, H-6), 2.57 (2H, m, 2H of piz), 2.42 (2H, m, 2H of piz), 2.19 (2H, dd, J 11.5, 9.5 Hz, 2H of pipH-2, H-6), 2.01 (2H, m, 2H of pipH-3, H-5), 1.75 (4H, m, 4H of pyrrolidine), 1.61 (2H, m, 2H of pipH-3, H-5); m/z: 656 [M+H]$^+$.

Compound 4-17: $^1$H nmr (CDCl$_3$) δ 8.90 (1H, m, pyH-6), 8.12 (1H, dd, J 8.0, 2.0 Hz, pyH-4), 7.81 (2H, d, J 8.5 Hz, 2H of C$_6$H$_4$SO$_2$N), 7.63 (1H, m, pyH-3), 7.60 (2H, d, J 8.0 Hz, 2H of C$_6$H$_4$CN), 7.48 (2H, d, J 9.0 Hz, 2H of C$_6$H$_4$SO$_2$N), 7.44 (2H, d, J 8.0 Hz, 2H of C$_6$H$_4$CN), 6.37 (1H, d, J 8.0 Hz, NH), 4.50 (1H, t, J 6.0 Hz, NHCH$_2$CH$_3$), 4.01 (1H, m, pipH-4), 3.83 (2H, m, 2H of piz), 3.60 (2H, s, CH$_2$C$_6$H$_4$SO$_2$N or CH$_2$C$_6$H$_4$CN), 3.56 (4H, m, 2H of piz, CH$_2$C$_6$H$_4$SO$_2$N or CH$_2$C$_6$H$_4$CN), 3.02 (2H, dq, J 6.0, 7.0 Hz, NHCH$_2$CH$_3$), 2.83 (2H, m, 2H of pipH-2, H-6), 2.57 (2H, m, 2H of piz), 2.43 (2H, m, 2H of piz), 2.20 (2H, dd, J 11.5, 9.5 Hz, 2H of pipH-2, H-6), 2.03 (2H, m, 2H of pipH-3, H-5), 1.61 (2H, m, 2H of pipH-3, H-5), 1.11 (3H, t, J 7.0 Hz, NHCH$_2$CH$_3$); m/z: 630 [M+H]$^+$.

Compound 6-1: $^1$H nmr (CDCl$_3$) δ 7.99 (2H, d, J 8.5 Hz, 2H of C$_6$H$_4$SO$_2$Me), 7.61 (2H, d, J 8.0 Hz, 2H of C$_6$H$_4$CN), 7.58 (2H, d, J 8.0 Hz, 2H of C$_6$H$_4$CN), 7.45 (2H, d, J 8.5 Hz, 2H of C$_6$H$_4$SO$_2$Me), 7.38 (2H, m, BzfuranH-3 or H-4, BzfuranH-7), 7.11 (1H, dd, J 7.0, 2.0 Hz, BzfuranH-6), 7.09 (1H, m, BzfuranH-3 or H-4), 6.46 (1H, d, J 8.5 Hz, NH), 4.02 (1H, m, pipH-4), 3.66 (2H, s, CH$_2$C$_6$H$_4$SO$_2$Me or CH$_2$C$_6$H$_4$CN), 3.56 (2H, s, CH$_2$C$_6$H$_4$SO$_2$Me or C H₂C₆H₄CN), 3.19 (4H, m, 4H of piz), 3.06 (3H, s, SO₂CH₃), 2.82 (2H, m, 2H of pipH-2, H-6), 2.66, 2.64 (4H, 2d AB system, J 5.0 Hz, 4H of piz), 2.22 (2H, dd, J 11.5, 9.5 Hz, 2H of pipH-2, H-6), 2.03 (2H, m, 2H of pipH-3, H-5), 1.62 (2H, m, 2H of pipH-3, H-5); m/z: 613 [M+H]⁺ (found [M+H]⁺, 612.2643, C₃₄H₃₇N₅O₄S requires [M+H]⁺612.2639).

Compound 6-2: ¹H nmr (CDCl₃) δ 7.90 (2H, d, J 8.5 Hz, 2H of C₆H₄SO₂Me), 7.68 (1H, d, J 8.5 Hz, BzfuranH-4), 7.61 (2H, d, J 8.5 Hz, 2H of C₆H₄CN), 7.57 (1H, s, BzfuranH-3), 7.54 (2H, d, J 8.5 Hz, 2H of C₆H₄SO₂Me), 7.46 (2H, d, J 8.5 Hz, 2H of C₆H₄CN), 7.45 (1H, d, J 1.0 Hz, BzfuranH-7), 7.32 (1H, dd, J 8.0, 1.0 Hz, BzfuranH-5), 6.52 (1H, d, J 8.5 Hz, NH), 4.03 (1H, m, pipH-4), 3.78 (2H, m, 2H of piz), 3.62 (2H, s, CH₂C₆H₄CN or CH₂C₆H₄SO₂Me), 3.56 (2H, s, CH₂C₆H₄CN or CH₂C₆H₄SO₂Me), 3.56-3.47 (2H, m, 2H of piz), 3.05 (3H, s, SO₂CH₃), 2.83 (2H, m, 2H of pipH-2, H-6), 2.48 (4H, m, 4H of piz), 2.22 (2H, dd, J 11.5, 9.5 Hz, 2H of pipH-2, H-6), 2.04 (2H, m, 2H of pipH-3, H-5), 1.63 (2H, m, 2H of pipH-3, H-5); m/z: 640 [M+H]⁺.

Compound 6-3: ¹H nmr (CDCl₃) δ 7.90 (2H, d, J 8.5 Hz, 2H of C₆H₄SO₂Me), 7.68 (1H, d, J 8.0 Hz, BzfuranH-4), 7.57 (1H, s, BzfuranH-3), 7.55 (2H, d, J 8.5 Hz, 2H of C₆H₄SO₂Me), 7.45 (1H, d, J 1.0 Hz, BzfuranH-7), 7.33 (1H, dd, J 8.0, 1.5 Hz, BzfuranH-5), 7.23 (2H, d, J 8.5 Hz, 2H of C₆H₄OCH₃), 6.86 (2H, d, J 8.5 Hz, 2H of C₆H₄OCH₃), 6.52 (1H, d, J 8.5 Hz, NH), 4.02 (1H, m, pipH-4), 3.86-3.74 (2H, m, 2H of piz), 3.80 (3H, s, OCH₃), 3.62 (2H, s, CH₂C₆H₄OCH₃ or CH₂C₆H₄SO₂Me), 3.55 (2H, m, 2H of piz), 3.48 (2H, s, CH₂C₆H₄OCH₃ or CH₂C₆H₄SO₂Me), 3.05 (3H, s, SO₂CH₃), 2.88 (2H, m, 2H of pipH-2, H-6), 2.48 (4H, m, 4H of piz), 2.18 (2H, dd, J 11.0, 10.0 Hz, 2H of pipH-2, H-6), 2.02 (2H, m, 2H of pipH-3, H-5), 1.63 (2H, m, 2H of pipH-3, H-5); m/z: 646 [M+H]⁺.

Compound 6-4: ¹H nmr (CDCl₃) δ 7.90 (2H, d, J 8.5 Hz, 2H of C₆H₄SO₂Me), 6.68 (1H, d, J 8.0 Hz, BzfuranH-4), 7.58 (1H, s, BzfuranH-3), 7.55 (2H, d, J 8.5 Hz, 2H of C₆H₄SO₂Me), 7.46 (1H, s, BzfuranH-7), 7.34 (3H, m, 2H of C₆H₄OCF₃, BzfuranH-5), 7.16 (2H, d, J 8.5 Hz, 2H of C₆H₄OCF₃), 6.51 (1H, d, J 8.0 Hz, NH), 4.03 (1H, m, pipH-4), 3.78 (2H, m, 2H of piz), 3.62 (2H, s, CH₂C₆H₄OCF₃ or CH₂C₆H₄SO₂Me), 3.51 (2H, s, CH₂C₆H₄OCF₃ or CH₂C₆H₄SO₂Me), 3.49 (2H, m, 2H of piz), 3.05 (3H, s, SO₂CH₃), 2.86 (2H, m, 2H of pipH-2, H-6), 2.48 (4H, m, 4H of piz), 2.19 (2H, dd, J 11.0, 10.0 Hz, 2H of pipH-2, H-6), 2.03 (2H, m, 2H of pipH-3, H-5), 1.63 (2H, m, 2H of pipH-3, H-5); ¹⁹F nmr (CDCl₃) δ −57.9; m/z: 699 [M+H]⁺.

Compound 6-5: ¹H nmr (CDCl₃) δ 7.89 (2H, d, J 8.5 Hz, 2H of C₆H₄SO₂Me), 7.66 (1H, d, J 8.0 Hz, BzfuranH-4), 7.56 (1H, s, BzfuranH-3), 7.54 (2H, d, J 8.5 Hz, 2H of C₆H₄SO₂Me), 7.44 (1H, d, J 1.0 Hz, BzfuranH-7), 7.31 (1H, dd, J 8.0, 1.5 Hz, BzfuranH-5), 7.08 (1H, dd, J 12.5, 1.5 Hz, C₆H₃(F)OMeH-2), 6.98 (1H, d, J 8.5 Hz, C₆H₃(F)OMeH-6), 6.89 (1H, dd, J 8.5 Hz, C₆H₃(F)OMeH-5), 6.56 (1H, d, J 8.5 Hz, NH), 4.01 (1H, m, pipH-4), 3.87 (3H, s, OCH3), 3.75 (2H, m, 2H of piz), 3.61 (2H, s, CH₂C₆H₄SO₂Me or CH₂C₆H₃(F)OMe), 3.50 (2H, m, 2H of piz), 3.44 (2H, s, CH₂C₆H₄SO₂Me or CH₂C₆H₃(F)OMe), 3.04 (3H, s, SO2CH3), 2.84 (2H, m, 2H of pipH-2, H-6), 2.48 (4H, m, 4H of piz), 2.16 (2H, dd, J 11.5, 10.0 Hz, 2H of pipH-2, H-6), 2.01 (2H, m, 2H of pipH-3, H-5), 1.62 (2H, m, 2H of pipH-3, H-5); ¹⁹F nmr (CDCl₃) δ −135.6; m/z: 664 [M+H]⁺.

Compound 6-6: ¹H nmr (CDCl₃) δ 8.48 (1H, s, NH), 8.43 (1H, d, J 2.5 Hz, N, O-pyH-6), 8.34 (1H, dd, J 9.0, 2.5 Hz, N, O-pyH-4), 8.02 (2H, d, J 9.0 Hz, 2H of C₆H₄SO₂Me), 7.90 (2H, d, J 8.5 Hz, 2H of C₆H₄Ac), 7.72 (1H, d, J 8.0 Hz, BzfuranH-4), 7.60 (1H, s, BzfuranH-3 or H-7), 7.55 (2H, d, J 8.0 Hz, 2H of C₆H₄SO₂Me), 7.46 (1H, s, BzfuranH-3 or H-7), 7.36 (1H, dd, J 8.5, 1.0 Hz, BzfuranH-5), 7.20 (2H, d, J 9.0 Hz, 2H of C₆H₄Ac), 7.06 (1H, d, J 9.0 Hz, N, O-pyH-3), 3.82 (2H, m, 2H of piz), 3.63 (2H, s, CH₂C₆H₄SO₂Me), 3.53 (2H, m, 2H of piz), 3.05 (3H, s, SO₂CH₃), 2.60 (3H, s, COCH₃), 2.48 (4H, m, 4H of piz); m/z: 653 [M+H]⁺.

Compound 6-7: ¹H nmr (CDCl₃) δ 7.90 (2H, d, J 8.0 Hz, 2H of C₆H₄SO₂Me), 7.68 (1H, d, J 8.0 Hz, BzfuranH-4), 7.58 (1H, s, BzfuranH-3 or H-7), 7.55 (2H, d, J 8.0 Hz, 2H of C₆H₄SO₂Me), 7.46 (1H, s, BzfuranH-3 or H-7), 7.36-7.31 (3H, m, 2H of C₆H₄OCF₂CF₂H, BzfuranH-5), 7.16 (2H, d, J 8.5 Hz, 2H of C₆H₄OCF₂CF₂H), 6.52 (1H, d, J 8.5 Hz, NH), 5.91 (1H, dt, J 53.5, 2.5 Hz, OCF₂CF₂H), 4.03 (1H, m, pipH-4), 3.80 (2H, m, 2H of piz), 3.63 (2H, s, CH₂C₆H₄OCF₂CF₂H or CH₂C₆H₄SO₂CH₃), 3.53 (2H, s, CH₂C₆H₄OCF₂CF₂H or CH₂C₆H₄SO₂CH₃), 3.60-3.410 (2H, br m, 2H of piz), 3.05 (3H, s, SO₂CH₃), 2.87 (2H, m, 2H of pipH-2, H-6), 2.49 (4H, m, 4H of piz), 2.21 (2H, t, J 11.0 Hz, 2H of pipH-2, H-6), 2.04 (2H, m, 2H of pipH-3, H-5), 1.64 (2H, m, 2H of pipH-3, H-5); ¹⁹F nmr (CDCl₃) δ −88.2, −136.8 (dt, J 53.5, 6.0 Hz); m/z: 731 [M+H]⁺.

Compound 6-8: ¹H nmr (CDCl₃) δ 8.58 (1H, s, NH), 8.45 (1H, m, N, O-pyH-6), 8.36 (1H, dd, J 9.0, 2.5 Hz, N, O-pyH-4), 7.90 (2H, d, J 8.5 Hz, 2H of C₆H₄SO₂Me), 7.72-7.66 (3H, m, 2H of C₆H₄CN, BzfuranH-4 or H-5), 7.61 (1H, s, BzfuranH-3 or H-7), 7.59 (1H, s, BzfuranH-3 or H-7), 7.55 (2H, d, J 8.5 Hz, 2H of C₆H₄SO₂Me), 7.34 (1H, d, J 8.0 Hz, BzfuranH-4 or H-5), 7.23 (2H, d, J 9.0 Hz, 2H of C₆H₄CN), 7.07 (1H, d, J 9.0 Hz, N, O-pyH-3), 3.82 (2H, m, 2H of piz), 3.63 (2H, s, CH₂C₆H₄SO₂CH₃), 3.50 (2H, m, 2H of piz), 3.05 (3H, s, SO₂CH₃), 2.49 (4H, m, 4H of piz); m/z: 636 [M+H]⁺.

Compound 6-9: ¹H nmr (CDCl₃) δ 7.80 (2H, d, J 9.0 Hz, 2H of C₆H₄SO₂Me), 7.62 (2H, d, J 8.5 Hz, 2H of C₆H₄CN), 7.46 (2H, d, J 8.5 Hz, 2H of C₆H₄CN), 7.41 (2H, m, 1H of BzfuranH-3 or H-4, 1H of BzfuranH-6 or H-7), 7.16 (2H, m, 1H of BzfuranH-3 or H-4, 1H of BzfuranH-6 or H-7), 7.00 (2H, d, J 9.0 Hz, 2H of C₆H₄SO₂Me), 6.47 (1H, d, J 8.0 Hz, NH), 4.03 (1H, m, pipH-4), 3.57 (2H, s, CH₂C₆H₄CN), 3.55 (4H, m, 4H of piz), 3.32, 3.30 (4H, 2d AB system, J 5.0 Hz, 4H of piz), 3.02 (3H, s, SO₂CH₃), 2.83 (2H, m, 2H of pipH-2, H-6), 2.22 (2H, dd, J 11.5, 9.5 Hz, 2H of pipH-2, H-6), 2.04 (2H, m, 2H of pipH-3, H-5), 1.63 (2H, m, 2H of pipH-3, H-5); m/z: 598 [M+H]⁺ (found [M+H]⁺, 598.2458, C₃₃H₃₅N₅O₄S requires [M+H]⁺598.2483).

Compound 6-11: ¹H NMR (CDCl₃) 7.69 (s, 1H), 7.58 (d, 2H), 7.43-7.51 (m, 5H), 7.26 (m, 2H), 7.00 (m, 2H), 6.50 (d, 1H), 4.02 (m, 1H), 3.61 (m, 4H), 3.49 (s, 2H), 3.44 (s, 2H), 2.80 (m, 2H), 2.45 (m, 4H), 2.25 (m, 2H), 2.03 (m, 2H), 1.65 (m, 22H).

Compound 6-12: ¹H NMR (CDCl₃) 8.31 (d, 1H), 7.39-7.62 (m, 3H), 7.48-7.57 (m, 3H), 7.24-7.33 (m, 4H), 6.97-7.10 (m, 6H), 3.62 (m, 4H), 3.48 (s, 2H), 2.46 (m, 4H).

Compound 6-13: ¹H NMR (CDCl₃) 7.60 (m, 3H), 7.39-7.46 (m, 5H), 7.25-7.27 (m, 2H), 6.98 (t, 2H), 6.43 (d, 1H), 4.02 (s, 1H), 3.58 (s, 2H), 3.54 (s, 2H), 3.47 (s, 2H), 2.82 (m, 2H), 2.58 (m, 8H), 2.26 (m, 2H), 2.05 (m, 2H), 1.65 (m, 2H).

Compound 6-14 (as its formic acid salt): ¹H NMR (CDCl₃) 7.53 (m, 3H), 7.47 (d, 2H), 7.33-7.40 (m, 5H), 6.86 (d, 2H), 4.36 (m, 1H), 3.92 (m, 1H), 3.59 (s, 2H), 3.51 (s, 2H), 2.71-2.80 (m, 2H), 2.65-2.68 (m, 2H), 2.36 (m, 2H), 2.15 (m, 2H), 1.95 (m, 4H), 1.79 (m, 2H), 1.60 (m, 2H).

Compound 6-15 (as its formic acid salt): ¹H NMR (CDCl₃/MeOD₄) 7.90-7.95 (m, 2H), 7.69 (d, 1H), 7.50-7.56 (m, 5H), 7.40-7.44 (m, 2H), 7.10 (t, 2H), 4.10 (s, 1H), 3.51 (m, 1H), 3.20 (m, 1H), 3.14 (m, 2H), 2.90 (m, 2H), 2.10 (m, 2H), 1.73-1.95 (m, 8H). m/z 569.70[M+H]+.

Compound 6-16 (as its formic acid salt): ¹H NMR (CDCl₃/MeOD₄) 7.88-7.93 (m, 2H), 7.66 (s, 1H), 7.60 (d, 2H), 7.46-

7.51 (m, 3H), 7.38-7.41 (m, 2H), 7.08 (t, 2H), 4.00 (m, 1H), 3.80 (s, 2H), 3.48 (m, 1H), 3.04-3.16 (m, 4H), 2.58 (m, 2H), 2.03 (m, 2H), 1.67-1.87 (m, 6H); m/z 593.72[M+H]+.

Compound 6-17 (as its formic acid salt): $^1$H NMR (CDCl$_3$/MeOD$_4$) 8.28 (dd, 1H), 7.88-7.93 (m, 3H), 7.65 (s, 1H), 7.36-7.62 (m, 5H), 6.99-7.24 (m, 4H), 6.98 (d, 1H), 4.42 (m, 1H), 3.47 (m, 2H), 3.12 (m, 2H), 1.69-1.83 (m, 4H). m/z 589.65[M+H]+.

Compound 6-18 (as its formic acid salt): $^1$H NMR (CDCl$_3$/MeOD$_4$) 8.44 (d, 2H), 7.67 (s, 1H), 7.50 (d, 1H), 7.40 (m, 2H), 7.28 (broad s, 2H), 6.86 (m, 2H), 6.82 (m, 2H), 4.42 (m, 1H), 3.96 (m, 1H), 3.74 (m, 1H), 3.54 (m, 3H), 2.24 (m, 2H), 1.64-2.00 (m, 8H); m/z 557.71 [M+H]+.

Compound 6-19 (as its formic acid salt): $^1$H NMR (CDCl$_3$/MeOD$_4$) 7.67 (s, 1H), 7.58 (d, 2H), 7.39-7.49 (m, 5H), 6.81-6.90 (m, 4H), 4.43 (m, 1H), 3.97 (m, 1H), 3.74 (m, 2H), 3.65 (s, 2H), 3.53 (m, 2H), 2.88-3.10 (m, 2H), 2.33 (m, 2H), 1.68-1.97 (m, 8H); m/z 581.75[M+H]+.

Compound 6-20 (as its formic acid salt): $^1$H NMR (CDCl$_3$/MeOD$_4$) 8.42 (s, 1H), 8.27 (d, 1H), 7.70 (s, 1H), 7.45-7.62 (m, 4H), 7.44 (d, 1H), 7.16 (d, 2H), 6.81-6.99 (m, 5H), 4.42 (m, 1H), 3.75 (m, 2H), 3.55 (m, 2H), 1.85 (m, 4H); m/z 577.66[M+H].

Compound 6-21 (as its formic acid salt): $^1$H NMR (CDCl$_3$/MeOD$_4$) 7.50 (s, 1H), 6.94-7.03 (m, 5H), 6.87 (d, 2H), 6.44-6.50 (m, 4H), 3.62 (m, 1H), 3.46 (m, 3H), 3.37 (s, 3H), 2.80 (m, 2H), 2.49-2.57 (m, 2H), 2.30 (m, 2H), 2.14 (m, 2H), 1.42-1.68 (m, 8H); m/z 592.69[M+H].

Compound 6-22 (as its formic acid salt): $^1$H NMR (DMSO-d$_6$) 9.85 (s, 1H), 8.06 (s, 1H), 7.62 (d, 2H), 7.52 (m, 4H), 7.34 (s, 1H), 7.18 (d, 2H), 7.01 (d, 2H), 4.81 (m, 1H), 3.94 (m, 4H), 3.60 (m, 2H), 2.92-3.00 (m, 2H), 2.60-2.69 (m, 1H), 2.05 (m, 2H), 1.90 (m, 2H), 1.71-1.80 (m, 4H); m/z 617.64[M+H].

Compound 6-23 (as its formic acid salt): $^1$H NMR (CDCl$_3$/MeOD$_4$) 7.72 (s, 1H), 7.62 (d, 2H), 7.34 (dd, 1H), 7.17 (d, 1H), 7.09 (d, 2H), 6.99 (d, 2H), 6.69-6.77 (m, 5H), 6.61 (d, 2H), 3.75 (m, 1H), 3.52 (2 overlapping s, 5H), 2.87 (m, 2H), 2.28 (m, 2H), 1.77 (m, 2H), 1.56 (m, 2H); m/z 594.64[M+H].

Compound 6-24 (as its formic acid salt): $^1$H NMR (CDCl$_3$/MeOD$_4$) 8.09 (s, 1H), 7.97 (m, 2H), 7.60-7.68 (m, 3H), 7.53 (d, 1H), 7.31 (s, 1H), 7.04-7.15 (m, 8H), 4.77 (m, 1H), 3.90-4.07 (m, 4H), 1.98-2.13 (m, 8H); m/z 619.58[M+H].

Compound 6-25: $^1$H NMR (CDCl$_3$) 7.73 (s, 1H), 7.44-7.55 (m, 5H), 7.24 (m, 2H), 6.98 (d, 2H), 6.85 (m, 2H), 6.44 (d, 1H), 4.65 (m, 1H), 4.04 (m, 1H), 3.80-3.85 (m, 2H), 3.82 (s, 3H), 3.64 (m, 2H), 3.47 (s, 2H), 2.83 (m, 2H), 2.17 (m, 2H), 1.87-2.00 (m, 6H), 1.59-1.69 (m, 2H); m/z 636.62[M+H].

Compound 6-26: $^1$H NMR (CDCl$_3$) 8.37 (m, 2H), 8.25 (dd, 1H), 7.77 (s, 1H), 7.50-7.58 (m, 5H), 7.06-7.12 (m, 3H), 6.97-7.04 (m, 3H), 4.66 (m, 1H), 3.81 (m, 2H), 3.66 (m, 2H), 1.88-1.99 (m, 4H); m/z 620.55[M+H].

Compound 6-27: $^1$H NMR (CDCl$_3$) 7.61 (m, 3H), 7.51 (d, 2H), 7.41-7.47 (m, 5H), 6.94 (d, 2H), 6.43 (d, 1H), 4.40 (m, 1H), 4.04 (m, 1H), 3.62 (s, 2H), 3.57 (s, 2H), 2.58-2.84 (m, 4H), 2.20-2.39 (m, 4H), 2.03-2.07 (m, 4H), 1.82-1.90 (m, 2H), 1.63-1.71 (m, 2H); m/z 617.57[M+H].

Compound 6-28 (as its formic acid salt): $^1$H NMR (CDCl$_3$) 7.59 (m, 1H), 7.34-7.41 (m, 5H), 6.81-6.88 (m, 4H), 6.63 (m, 1H), 4.41 (m, 1H), 3.92 (m, 1H), 3.82 (s, 2H), 3.50 (s, 2H), 2.71-2.87 (m, 4H), 2.60-2.68 (m, 2H), 2.18-2.26 (m, 2H), 1.88-2.03 (m, 6H), 1.62-1.71 (m, 2H); m/z 628.58[M+H].

Compound 6-29 (as its formic acid salt): $^1$H NMR (CDCl$_3$/MeOD$_4$) 8.18-8.31 (m, 1H), 7.61 9s, 1H), 7.40-7.45 (m, 5H), 6.99-7.04 (m, 4H), 6.88-6.92 (m, 4H), 4.36 (m, 1H), 3.60 (s, 2H), 2.68-2.74 (m, 2H), 2.30-2.34 (m, 2H), 1.93-1.99 (m, 2H), 1.80-1.85 (m, 2H); m/z 606.58[M+H].

Compound 6-30: $^1$H NMR (CDCl$_3$) 7.75 (s, 1H), 7.61 (d, 2H), 7.47-7.60 (m, 7H), 6.97 (d, 2H), 6.51 (d, 1H), 4.67 (m, 1H), 4.03 (m, 1H), 3.79 (m, 2H), 3.57 (s, 2H), 2.81 (m, 2H), 2.18-2.26 (m, 2H), 1.80-2.10 (m, 6H), 1.61.1.70 (m, 4H); m/z 632.59[M+H].

Compound 6-31: $^1$H NMR (CDCl$_3$) 7.75 (s, 1H), 7.47-7.57 (m, 7H), 6.94-6.99 (m, 4H), 6.60 (d, 1H), 4.68 (m, 1H), 4.62 (m, 1H), 4.12 (m, 1H), 3.40-4.00 (broad m, 4H), 1.71-2.15 (m, 12H); m/z 631.60[M+H].

Compound 6-32: $^1$H NMR (CDCl$_3$/MeOD$_4$) 7.85 (d, 1H), 7.54 (d, 2H), 7.43 (dd, 1H), 7.37 (d, 2H), 7.35 (m, 1H), 7.32 (d, 1H), 3.87 (m, 1H), 3.70 (s, 2H), 3.04-3.08 (m, 2H), 2.75-2.79 (m, 2H), 2.52-2.62 (m, 2H), 2.39 (m, 1H), 2.08-2.15 (m, 2H), 1.88-1.92 (m, 2H), 1.78-1.82 (m, 2H), 1.52-1.70 (m, 4H); m/z 486.64[M+H].

Compound 6-33 (as its formic acid salt): $^1$H NMR (CDCl$_3$/MeOD$_4$) 7.80 (s, 1H), 7.50 (d, 2H), 7.32-7.43 (m, 6H), 7.26-7.31 (m, 1H), 6.60 (d, 1H), 6.49 (m, 1H), 4.14-4.20 (m, 2H), 3.88 (m, 1H), 3.54 (s, 2H), 2.74-2.88 (m, 4H), 2.40-2.50 (m, 1H), 2.14-2.22 (m, 2H), 1.74-1.92 (m, 6H), 1.53-1.72 (m, 2H); m/z 531.61[M+H].

Compound 6-34: $^1$H NMR (CDCl$_3$/MeOD$_4$) 8.41 (d, 1H), 7.83 (s, 1H), 7.62 (dt, 1H), 7.54 (d, 2H), 7.31-7.45 (m, 6H), 7.12 (m, 1H), 3.92 (m, 1H), 3.59 (s, 2H), 3.50 (s, 2H), 2.88-2.92 (m, 2H), 2.71-2.78 (m, 2H), 2.06-2.25 (m, 5H), 1.80-1.96 (m, 6H), 1.55-1.65 (m, 2H); m/z 577.21[M+H].

Compound 6-35: $^1$H NMR (CDCl$_3$/MeOD$_4$) 8.38 (s, 1H), 8.35 (m, 1H), 7.80 (s, 1H), 7.64 (d, 1H), 7.52 (d, 2H), 7.43 (dd, 1H), 7.28-7.42 (m, 4H), 7.20 (dd, 1H), 3.88 (m, 1H), 3.48 (s, 2H), 3.44 (s, 2H), 2.83 (m, 2H), 2.74 (m, 2H), 2.14-2.25 (m, 3H), 1.99-2.11 (m, 4H), 1.79-1.97 (m, 4H), 1.54-1.62 (m, 2H); m/z 577.66[M+H].

Compound 6-36: $^1$H NMR (CDCl$_3$/MeOD$_4$) 7.79 (s, 1H), 7.50 (d, 2H), 7.40 (dd, 1H), 7.32-7.37 (m, 2H), 7.28 (d, 2H), 3.84 (m, 1H), 3.51 (s, 2H), 3.00-3.04 (m, 2H), 2.71-2.75 (m, 2H), 1.98-2.31 (m, 7H), 1.76-1.90 (m, 6H), 1.54-1.62 (m, 2H), 0.77 (m, 1H), 0.42 (m, 2H), 0.08 (m, 2H); m/z 540.67 [M+H].

Compound 6-37: $^1$H NMR (CDCl$_3$/MeOD$_4$) 7.82 (s, 1H), 7.54 (d, 2H), 7.44 (dd, 1H), 7.31-7.41 (m, 4H), 6.51 (m, 1H), 5.92 (m, 2H), 3.92 (m, 1H), 3.57 (s, 3H), 3.51 (s, 2H), 3.40 (s, 2H), 2.88-2.93 (m, 2H), 2.73-2.79 (m, 2H), 2.13-2.25 (m, 3H), 1.93-2.01 (m, 4H), 1.79-1.84 (m, 4H), 1.56-1.77 (m, 2H); m/z 579.70[M+H].

Compound 6-38: $^1$H NMR (CDCl$_3$/MeOD$_4$) 7.76 (d, 1H), 7.45 (d, 2H), 7.35 (dd, 1H), 7.21-7.32 (m, 4H), 6.70 (d, 2H), 3.79 (m, 1H), 3.55 (s, 3H), 3.50 (s, 2H), 3.40 (s, 2H), 2.66-2.70 (m, 4H), 2.06-2.16 (m, 3H), 1.90-2.03 (m, 2H), 1.81-1.85 (m, 2H), 1.63-1.71 (m, 4H), 1.49-1.56 (m, 2H); m/z 580.71[M+H].

Compound 6-39: $^1$H NMR (CDCl$_3$/MeOD$_4$) 8.76 (sharp s) and 8.60 (broad s, 1H combined, amide NH), 8.04 9s, 1H), 7.56-7.62 (m, 3H), 7.37-7.47 (m, 4H), 7.22 (d, 2H), 6.54 (d, 2H), 6.43 (d, 1H, amide NH), 4.03 (m, 1H), 3.78 (s, 2H), 3.57 (s, 2H), 3.22-3.31 (m, 6H), 2.80-2.84 (m, 2H), 2.37-2.47 (m, 5H), 2.21-2.29 (m, 2H), 1.98-2.06 (m, 8H), 1.63-1.71 (m, 2H); m/z 645.75[M+H].

Compound 6-40 (as its formic acid salt): $^1$H NMR (CDCl$_3$/MeOD$_4$) 7.88 (s, 1H), 7.56 (d, 2H), 7.32-7.47 (m, 5H), 7.27 (d, 2H), 6.84 (d, 2H), 3.92 (m, 1H), 3.90 (s, 2H), 3.74 (s, 3H), 3.55 (s, 2H), 3.19-3.24 (m, 2H), 2.70-2.80 (m, 4H), 2.50 (m, 1H), 2.21 (m, 2H), 1.93-2.10 (m, 6H), 1.64 (m, 2H); m/z 606.70[M+H].

Compound 6-41 (as its formic acid salt): $^1$H NMR (CDCl$_3$/MeOD$_4$) 8.58 (s, 1H), 8.32 (d, 1H), 8.22 (s, 2H), 7.87 (m, 2H), 7.71-7.78 (m, 2H), 7.55 (d, 2H), 7.31-7.45 (m, 3H), 7.15 (m, 1H), 3.96 (s, 2H), 3.92 (m, 1H), 3.58 (s, 2H), 3.29 (m, 2H), 2.70-2.90 (m, 4H), 2.51 (m, 1H), 2.20-2.27 (m, 2H), 1.93-2.19 (m, 6H), 1.66 (m, 2H); m/z 643.74[M+H].

Compound 6-42 (as its formic acid salt): $^1$H NMR (CDCl$_3$/MeOD$_4$) 8.04 9s, 1H), 7.74-7.84 (m, 3H), 7.62-7.70 (m, 3H), 7.54 (d, 2H), 7.32-7.46 (m, 4H), 3.92 (m, 1H), 3.61 (s, 2H), 3.52 (s, 2H), 3.05 (m, 2H), 2.76-2.80 (m, 2H), 2.15-2.36 (m, 5H), 1.94 (m, 6H), 1.58-1.65 (m, 2H); m/z 667.71[M+H].

Compound 6-43 (as its formic acid salt): $^1$H NMR (CDCl$_3$/MeOD$_4$) 7.81 (s, 1H), 7.52 (d, 2H), 7.38-7.44 (m, 3H), 7.34 (d, 2H), 7.11 (m, 1H), 6.94-7.02 (m, 2H), 3.89 (m, 1H), 3.51 (s, 2H), 3.47 (s, 2H), 2.88-2.92 (m, 2H), 2.75-2.79 (m, 2H), 2.19-2.28 (m, 1H), 2.09-2.16 (m, 4H), 1.81-1.93 (m, 6H), 1.57-1.65 (m, 2H); m/z 612.70[M+H].

Compound 6-44 (as its formic acid salt): $^1$H NMR (CDCl$_3$/MeOD$_4$) 7.82 (s, 1H), 7.49-7.53 (m, 4H), 7.25-7.43 (m, 8H), 6.91-6.95 (m, 4H), 3.89 (m, 1H), 3.76 (s, 2H), 3.53 (s, 2H), 3.08 (m, 2H), 2.74-2.81 (m, 2H), 2.39-2.49 (m, 3H), 2.14-2.22 (m, 2H), 1.95 (m, 6H), 1.57-1.65 (m, 2H); m/z 691.77[M+H].

Compound 6-45: $^1$H NMR (CDCl$_3$) 7.92 (s, 1H), 7.60 (d, 2H), 7.42-7.47 (m, 4H), 7.38 (s, 2H), 7.31 (s, 1H), 7.29 (s, 1H), 4.03 (m, 1H), 3.87 (s, 3H), 3.57 (s, 2H), 3.46 (s, 2H), 3.00-3.04 (m, 2H), 2.79-2.84 (m, 2H), 2.21-2.29 (m, 3H), 2.03-2.12 (m, 4H), 1.89-1.97 (m, 4H), 1.66 (m, 2H); m/z 580.71[M+H].

Compound 6-46 (as its formic acid salt): $^1$H NMR (CDCl$_3$/MeOD$_4$) 7.80 (s, 1H), 7.50 (d, 2H), 7.34-7.41 (m, 3H), 7.25-7.32 (m, 4H), 7.05 (d, 2H), 3.87 (m, 1H), 3.60 (s, 2H), 3.50 (s, 2H), 2.94-2.98 (m, 2H), 2.75-2.79 (m, 2H), 2.11-2.33 (m, 5H), 1.86-1.92 (m, 6H), 1.56-1.65 (m, 2H); m/z 660.72[M+H].

Compound 6-47: $^1$H NMR (CDCl$_3$/MeOD$_4$) 7.83 (s, 1H), 7.54 (d, 2H), 7.40-7.46 (m, 3H), 7.37 (d, 2H), 7.32 (m, 2H), 3.93 (m, 1H), 3.54 (s, 2H), 3.51 (s, 2H), 2.89-2.94 (m, 2H), 2.74-2.79 (m, 2H), 2.14-2.29 (m, 3H), 1.97-2.13 (m, 4H), 1.83-1.87 (m, 4H), 1.52-1.65 (m, 2H); m/z 566.72[M+H].

Compound 6-49 (as its formic acid salt): $^1$H NMR (CDCl$_3$/MeOD$_4$) 7.49 (s, 1H), 7.56-7.59 (m, 4H), 7.43-7.48 (m, 5H), 7.28-7.40 (m, 2H), 3.95 (m, 1H), 3.59 (s, 2H), 3.57 (s, 2H), 2.90-2.94 (m, 2H), 2.81-2.85 (m, 2H), 2.14-2.33 (m, 5H), 1.87-1.99 (m, 6H), 1.60-1.70 (m, 2H); m/z 601.70[M+H].

Compound 6-50 (as its formic acid salt): $^1$H NMR (CDCl$_3$/MeOD$_4$) 7.78 (s, 1H), 7.44-7.51 (m, 4H), 7.33-7.39 (m, 5H), 7.25-7.30 (m, 2H), 3.85 (m, 1H), 3.61 (s, 2H), 3.51 (s, 2H), 2.91-2.95 (m, 2H), 2.75-2.79 (m, 2H), 2.11-2.32 (m, 5H), 1.83-1.90 (m, 6H), 1.55-1.65 (m, 2H); m/z 644.00[M+H].

Compound 6-52 (as its formic acid salt): $^1$H NMR (CDCl$_3$/MeOD$_4$) 7.87 (s, 1H), 7.57 (d, 2H), 7.47 (dd, 1H), 7.40-7.44 (m, 3H), 7.34 (m, 1H), 4.47 (d, 1H), 3.93 (m, 1H), 3.55 (s, 2H), 2.84 (m, 1H), 2.60-2.80 (m, 4H), 2.51-2.57 (m, 1H), 2.16-2.24 (m, 2H), 1.98 (s, 3H), 1.58-1.93 (m, 8H); m/z 528.64[M+H].

Compound 6-53 (as its formic acid salt): $^1$H NMR (CDCl$_3$/MeOD$_4$) 7.87 (s, 1H), 7.58 (d, 2H), 7.28-7.50 (m, 9H), 3.93 (m, 1H), 3.54 (s, 2H), 3.30 (s, 2H), 2.75-2.83 (m, 2H), 2.15-2.23 (m, 2H), 1.93-1.98 (m, 2H), 1.57-1.68 (m, 2H);
m/z 494.48[M+H]

Compound 6-54 (as its formic acid salt): $^1$H NMR (CDCl$_3$/MeOD$_4$) 7.86 (s, 1H), 7.53-7.59 (m, 4H), 7.43-7.48 (m, 4H), 7.40 (d, 2H), 7.36 (m, 1H), 3.92 (m, 1H), 3.54 (s, 2H), 3.30 (s, 2H), 2.78-2.83 (m, 2H), 2.14-2.22 (m, 2H), 1.97 (m, 2H), 1.55-1.68 (m, 2H); m/z 561.53[M+H].

Compound 6-55 (as its formic acid salt): $^1$H NMR (CDCl$_3$/MeOD$_4$) 8.00-8.07 (m, 3H), 7.94 (s, 1H), 7.64 (dd, 1H), 7.58 (m, 2H), 7.43-7.52 (m, 5H), 7.33-7.39 (m, 1H), 7.15 (s, 1H), 3.96 (m, 1H), 3.61 (s, 2H), 2.85-2.90 (m, 2H), 2.22-2.31 (m, 2H), 1.96-2.00 (m, 2H), 1.63-1.75 (m, 2H); m/z 545.53[M+H]

Compound 6-56 (as its formic acid salt): $^1$H NMR (CDCl$_3$/MeOD$_4$) 7.94 (s, 1H), 7.56 (m, 3H), 7.40-7.45 (m, 3H), 7.37 (m, 1H), 3.94 (s, 1H), 3.57 (s, 2H), 2.86 (s, 3H), 2.84 (m, 2H), 2.22-2.26 (m, 2H), 1.95-1.98 (m, 2H), 1.58-1.71 (m, 2H); m/z 501.48[M+H].

Compound 6-57 (as its formic acid salt): $^1$H NMR (CDCl$_3$/MeOD$_4$) 7.98-8.02 (m, 3H), 7.71-7.75 (m, 2H), 7.63 (dd, 1H), 7.55-7.90 (m, 2H), 7.38-7.46 (m, 4H), 3.94 (s, 1H), 3.55 (s, 2H), 2.79-2.83 (m, 2H), 2.15-2.20 (m, 2H), 1.95-1.98 (m, 2H), 1.57-1.70 (m, 2H); m/z 504.52[M+H].

Compound 6-58 (as its formic acid salt): $^1$H NMR (CDCl$_3$/MeOD$_4$) 7.89 (s, 1H), 7.55-7.59 (m, 2H), 7.39-7.49 (m, 3H), 7.31-7.36 (m, 2H), 3.94 (m, 1H), 3.56 (s, 2H), 3.22 (m, 2H), 2.80-2.84 (m, 4H), 2.63 (s, 3H), 2.54-2.58 (m, 1H), 2.17-2.26 (m, 2H), 2.08 (m, 4H), 1.94-1.99 (m, 2H), 1.60-1.70 (m, 2H); m/z 500.57[M+H].

Compound 6-59 (as its formic acid salt): $^1$H NMR (CDCl$_3$/MeOD$_4$) 8.43 (s, 1H), 8.11 (s, 1H), 7.94 (s, 1H), 7.53-7.63 (m, 5H), 7.30-7.40 (m, 4H), 6.95 (d, 2H), 3.95 (m, 1H), 3.80 (s, 3H), 3.53 (s, 2H), 2.78-2.82 (m, 2H), 2.15-2.22 (m, 2H), 1.94-1.98 (m, 2H), 1.60-1.68 (m, 2H); m/z 575.58[M+H].

Compound 6-60 (as its formic acid salt): $^1$H NMR (CDCl$_3$/MeOD$_4$) 8.17 (s, 1H), 8.10 (d, 2H), 8.00 (d, 2H), 7.96 (s, 1H), 7.64 (m, 1H), 7.57 (d, 2H), 7.39-7.46 (m, 4H), 3.95 (m, 1H), 3.55 (s, 2H), 2.80-2.84 (m, 2H), 2.17-2.25 (m, 2H), 1.95-1.99 (m, 2H), 1.61-1.69 (m, 2H); m/z 546.57[M+H].

Compound 6-61 (as its formic acid salt): $^1$H NMR (CDCl$_3$/MeOD$_4$) 8.03 (s, 1H), 7.56-7.60 (m, 3H), 7.35-7.47 (m, 4H), 6.48 (s, 1H), 3.94 (m, 1H), 3.55 (s, 2H), 2.80-2.84 (m, 2H), 2.46 (s, 3H), 2.16-2.24 (m, 2H), 1.94-1.99 (m, 2H), 1.58-1.69 (m, 2H); m/z 484.51[M+H].

Compound 6-62 (as its formic acid salt): $^1$H NMR (CDCl$_3$/MeOD$_4$) 7.94 (m, 2H), 7.66 (m, 2H), 7.52-7.57 (m, 3H), 7.43 (d, 1H), 7.37 (m, 2H), 4.04 (m, 1H), 3.97 (s, 2H), 3.13-3.18 (m, 2H), 2.66-2.70 (m, 2H), 2.51 (s, 3H), 2.06-2.10 (m, 2H), 1.82-1.86 (m, 2H); m/z 483.53[M+H].

Compound 6-63 (as its formic acid salt): $^1$H NMR (CDCl$_3$/MeOD$_4$) 7.93 (s, 1H), 7.78 (d, 2H), 7.54-7.60 (m, 3H), 7.39-7.42 (m, 2H), 7.31 (d, 2H), 6.87 (d, 2H), 3.94 (m, 1H), 3.81 (m, 4H), 3.53 (s, 2H), 3.23 (m, 4H), 2.77-2.82 (m, 2H), 2.15-2.23 (m, 2H), 1.94-1.99 (m, 2H), 1.59-1.64 (m, 2H); m/z 564.58[M+H].

Compound 6-64 (as its formic acid salt): $^1$H NMR (CDCl$_3$/MeOD$_4$) 8.66 (d, 1H), 8.24 (dd, 1H), 7.97 (s, 1H), 7.56-7.63 (m, 3H), 7.36-7.44 (m, 4H), 7.02-7.07 (m, 4H), 6.92 (d, 1H), 3.95 (m, 1H), 3.55 (s, 2H), 2.79-2.84 (m, 2H), 2.16-2.24 (m, 2H), 1.94-1.99 (m, 2H), 1.58-1.69 (m, 2H); m/z 590.56[M+H].

Compound 6-66 (as its formic acid salt): $^1$H NMR (CDCl$_3$/MeOD$_4$) 8.54 (s, 1H), 8.17 (s, 1H), 7.97 (s, 1H), 7.56-7.68 (m, 5H), 7.37-7.44 (m, 4H), 7.10-7.16 (m, 2H), 3.94 (m, 1H), 3.55 (s, 2H), 2.80-2.84 (m, 2H), 2.15-2.23 (m, 2H), 1.94-1.98 (m, 2H), 1.59-1.69 (m, 2H); m/z 563.61[M+H].

Compound 6-68 (as its formic acid salt): $^1$H NMR (CDCl$_3$/MeOD$_4$) 7.93 (s, 1H), 7.76 (d, 2H), 7.56-7.61 (m, 3H), 7.40-7.44 (m, 2H), 7.35 (d, 2H), 6.53 (d, 2H), 3.94 (m, 1H), 3.55 (s, 2H), 3.34 (m, 4H), 2.79-2.84 (m, 2H), 2.16-2.24 (m, 2H), 1.94-2.02 (m, 6H), 1.58-1.69 (m, 2H); m/z 548.64[M+H].

Compound 6-69 (as its formic acid salt): $^1$H NMR (CDCl$_3$/MeOD$_4$) 7.87 (s, 1H), 7.56-7.60 (m, 2H), 7.51-7.54 (m, 2H), 7.40-7.48 (m, 3H), 7.34-7.37 (m, 2H), 6.94-6.98 (m, 2H), 4.61 (m, 1H), 3.93 (m, 1H), 3.52 (s, 2H), 2.79-2.84 (m, 2H), 2.38-2.44 (m, 1H), 1.93-2.20 (m, 8H), 1.58-1.78 (m, 6H); m/z 602.67[M+H].

Compound 6-70 (as its formic acid salt): ¹H NMR (CDCl₃/MeOD₄) 8.33 (s, 1H), 7.88 (s, 1H), 7.58 (m, 2H), 7.35-7.50 (m, 7H), 6.66 (d, 1H, NH), 4.41 (m, 2H), 3.93 (m, 1H), 3.56 (s, 2H), 3.03-3.10 (m, 2H), 2.80-2.84 (m, 2H), 2.58-2.63 (m, 1H), 2.16-2.20 (m, 2H), 1.80-1.96 (m, 6H), 1.62-1.66 (m, 2H); m/z 588.69[M+H].

Compound 6-71 (as its formic acid salt): ¹H NMR (CDCl₃/MeOD₄) 8.42 (s, 1H), 7.98-8.11 (m, 4H), 7.89 (d, 1H), 7.58-7.65 (m, 3H), 7.47 (m, 3H), 7.16-7.24 (m, 2H), 7.07 (m, 1H), 3.94 (m, 1H), 3.58 (s, 2H), 2.82-2.87 (m, 2H), 2.19-2.26 (m, 2H), 1.95-2.00 (m, 2H), 1.65-1.70 (m, 2H); m/z 597.62[M+H].

Compound 6-72 (as its formic acid salt): ¹H NMR (CDCl₃/MeOD₄) 8.09 (s, 1H), 8.02 (s, 2H), 7.92 (m, 1H), 7.56-7.60 (m, 4H), 7.40-7.46 (m, 3H), 7.33-7.37 (m, 3H), 5.36 (s, 2H), 3.94 (m, 1H), 3.58 (s, 2H), 2.82-2.86 (m, 2H), 2.18-2.26 (m, 2H), 1.94-1.99 (m, 2H), 1.63-1.70 (m, 2H); m/z 627.61[M+H].

Compound 6-75 (as its formic acid salt): ¹H NMR (CDCl₃) 7.84 (d, 2H), 7.74 (m, 1H), 7.62-7.66 (d, 2H), 7.46-7.56 (m, 5H), 7.02 (d, 2H), 6.80 (d, 1H, amide NH), 4.72 (m, 1H), 4.19 (m, 4H), 3.94 (m, 1H), 3.79 (s, 2H), 3.05-3.09 (m, 2H), 3.02 (s, 3H), 2.40-2.44 (m, 2H), 1.79-2.09 (m, 8H); m/z 627.61 [M+H].

Compound 6-78 (as its formic acid salt): ¹H NMR (CDCl₃/MeOD₄) 7.78 (d, 4H), 7.60 (d, 1H), 7.55 (s, 1H), 7.44-7.47 (d, 4H), 7.33-7.42 (m, 2H), 4.63 (s, 2H), 3.95 (m, 1H), 3.76-3.80 (m, 4H), 3.54 (s, 2H), 3.28 (s, 3H), 2.96 (m, 6H), 2.36 (m, 2H), 1.91-1.95 (m, 2H), 1.65-1.75 (m, 2H); m/z 640.60[M+H].

Compound 6-79 (as its formic acid salt): ¹H NMR (CDCl₃/MeOD₄) 7.83 (d, 1H), 7.61 (dd, 2H), 7.57 (d, 2H), 7.52 (d, 2H), 7.44 (d, 2H), 7.36-7.41 (m, 3H), 7.30-7.34 (m, 3H), 3.94 (m, 1H), 3.81 (m, 4H), 3.68 (s, 2H), 3.50 (s, 2H), 2.92-2.96 (m, 2H), 2.26-2.53 (m, 6H), 1.91-1.95 (m, 2H), 1.66-1.70 (m, 2H); m/z 628.71[M+H].

Compound 6-80 (as its formic acid salt): ¹H NMR (CDCl₃/MeOD₄) 7.63 (s, 1H), 7.58 9d, 2H), 7.34-7.49 (m, 5H), 7.06 (d, 2H), 6.44 (d, 2H), 3.94 (m, 1H), 3.68 (m, 6H), 3.56 (s, 2H), 3.15-3.20 (m, 4H), 2.91-2.95 (m, 2H), 2.55 (m, 4H), 2.28 (m, 2H), 1.88-1.97 (m, 6H), 1.60-1.80 (m, 2H); m/z 631.83[M+H].

Compound 6-81 (as its formic acid salt): ¹H NMR (CDCl₃/MeOD₄) 7.56 (s, 1H), 7.48 (d, 2H), 7.41 (d, 1H), 7.27-7.35 (m, 4H), 7.20 (m, 2H), 7.00 (d, 2H), 3.85 (m, 1H), 3.55-3.60 (m, 4H), 3.50 (s, 2H), 3.39 (s, 2H), 2.74-2.79 (m, 2H), 2.33 (m, 4H), 2.14-2.19 (m, 2H), 1.84-1.90 (m, 2H), 1.50-1.64 (m, 2H); m/z 646.59[M+H].

Compound 6-82 (as its formic acid salt): ¹H NMR (CDCl₃/MeOD₄) 8.51 (d, 1H), 7.99 (s, 1H), 7.77 (d, 2H), 7.57-7.68 (m, 3H), 7.51 (d, 2H), 7.43 (d, 1H), 7.29-7.37 (m, 5H), 7.12 (m, 1H), 3.88 (s, 1H), 3.50 (m, 8H), 2.76-2.80 (m, 2H), 2.41 (m, 4H), 2.13-2.20 (m, 2H), 1.88-1.92 (m, 2H), 1.53-1.65 (m, 2H); m/z 639.69[M+H].

Compound 6-84 (as its formic acid salt): ¹H NMR (DMSO-d₆) 8.28 (d, 1H), 8.08 (m, 1H), 7.77 (d, 2H), 7.68 (d, 2H), 7.47-7.55 (m, 4H), 7.09 (d, 2H), 4.00 (m, 1H), 3.81 (m, 1H), 3.58 (s, 2H), 3.07 (s, 3H), 2.99 (m, 2H), 2.79-2.84 (m, 2H), 2.04-2.16 (m, 2H), 1.90-1.94 (m, 2H), 1.64-1.82 (m, 6H); m/z 640.57[M+H].

Compound 6-85 (as its formic acid salt): ¹H NMR (DMSO-d₆) 8.32 (m, 1H), 8.18-8.23 (m, 3H), 8.08 (d, 2H), 7.73-7.79 (m, 3H), 7.64 (d, 1H), 7.53 (d, 2H), 3.81 (m, 1H), 3.58 (s, 2H), 3.27 (s, 3H), 2.80-2.84 (m, 2H), 2.09-2.17 (m, 2H), 1.79-1.84 (m, 2H), 1.64-1.74 (m, 2H); m/z 557.48[M+H].

Compound 6-87 (as its formic acid salt): ¹H NMR (DMSO-d₆) 8.39 (d, 1H), 7.86 (s, 1H), 7.76 (d, 2H), 7.67-7.70 (m, 3H), 7.49-7.56 (m, 4H), 7.06 (d, 2H), 3.78 (m, 1H), 3.65 (m, 4H), 3.57 (s, 2H), 3.43 (m, 4H), 3.17 (s, 3H), 2.78-2.82 (m, 2H), 2.03-2.15 (m, 2H), 1.77-1.82 (m, 2H), 1.64-1.72 (m, 2H); m/z 626.64[M+H]

Compound 6-88 (as its formic acid salt): ¹H NMR (DMSO-d₆) 8.36 (d, 1H), 7.80-7.83 (m, 3H), 7.67 (d, 1H), 7.54 (s, 1H), 7.48 (dd, 1H), 7.19 (m, 4H), 6.87 (d, 2H), 3.78 (m, 1H), 3.76 (s, 3H), 3.40 (s, 2H), 2.78-2.82 (m, 2H), 1.98-2.06 (m, 2H), 1.60-1.80 (m, 4H); m/z 645.94[M+H].

Compound 6-90 (as its formic acid salt): ¹H NMR (DMSO-d₆) 8.28 (broad s, 1H), 8.23 (d, 1H), 8.14 (d, 1H), 7.92 (dd, 1H), 7.74 (d, 2H), 7.64 (d, 2H), 7.49-7.55 (m, 4H), 7.02 (d, 2H), 4.10 (m, 1H), 3.94-3.94 (m, 2H), 3.80 (m, 1H), 3.58 (s, 2H), 2.78-2.83 (m, 2H), 2.09-2.17 (m, 2H), 1.91-1.94 (m, 2H), 1.79-1.82 (m, 2H), 1.62-1.73 (m, 4H); m/z 586.92 [M+H].

Compound 6-91 (as its formic acid salt): ¹H NMR (DMSO-d₆) 8.44 9s, 1H), 8.22 (d, 1H), 8.11 (s, 2H), 7.99-8.05 (m, 3H), 7.88-7.93 (m, 3H), 7.74 (d, 2H), 7.63 (d, 1H), 7.49-7.54 (m, 3H), 3.79 (m, 1H), 3.58 (s, 2H), 3.48 (s, 2H), 2.78-2.92 (m, 2H), 2.08-2.17 (m, 2H), 1.82 (m, 2H), 1.62-1.82 (m, 2H); m/z 666.94[M+H].

Compound 6-94 (as its formic acid salt): ¹H NMR (DMSO-d₆) 8.35 (d, 1H), 7.86 (d, 2H), 7.77 (s, 1H), 7.66 (d, 1H), 7.55 (d, 2H), 7.44 (dd, 1H), 7.20 (d, 2H), 6.86 (d, 2H), 3.77 (m, 1H), 3.73 (s, 3H), 3.62 (s, 2H), 3.51 (m, 4H), 3.42 (s, 2H), 3.15 (s, 3H), 2.79-2.84 (m, 2H), 2.42 (m, 4H), 2.01-2.09 (m, 2H), 1.76-1.80 (m, 2H), 1.60-1.65 (m, 2H); m/z 644.92 [M+H].

Compound 7-12: ¹H nmr (CDCl₃) δ 9.05 (1H, m, pyH-6), 8.64 (1H, s, NH), 8.29 (1H, s, N, O-pyH-3 or H-6), 8.26 (1H, dd, J 8.0, 2.0 Hz, pyH-4), 7.93 (2H, d, J 9.0 Hz, 2H of C₆$\underline{H}$₄OCH₃), 7.67 (2H, d, J 9.0 Hz, 2H of C₆H₄CN), 7.60 (1H, d, J 8.0 Hz, pyH-3), 7.23 (2H, d, J 8.5 Hz, 2H of C₆H₄CN), 6.96 (2H, d, J 9.0 Hz, 2H of C₆$\underline{H}$₄OCH₃), 6.94 (1H, s, N, O-pyH-3 or H-6), 4.64 (1H, m, 1H of BzpipH-2, H-6), 3.93 (1H, m, 1H of BzpipH-2, H-6), 3.88 (3H, s, OCH₃), 3.54 (1H, m, BzpipH-4), 3.26 (1H, m, 1H of BzpipH-2, H-6), 3.10 (1H, m, 1H of BzpipH-2, H-6), 2.38 (3H, s, N, O-pyCH₃), 2.02 (1H, m, 1H of BzpipH-3, H-5), 1.92-1.82 (3H, m, 3H of BzpipH-3, H-5); m/z: 576 [M+H]⁺.

Compound 7-13: ¹H nmr (CDCl₃) δ 8.91 (1H, m, pyH-6), 8.13 (1H, dd, J 8.0, 2.0 Hz, pyH-4), 7.95 (1H, d, J 9.5 Hz, C₆H₃MeSO₂CH₃H-5), 7.63 (1H, m, pyH-3), 7.60 (2H, d, J 8.5 Hz, 2H of C₆H₄CN), 7.45 (2H, d, J 8.5 Hz, 2H of C₆H₄CN), 6.86-6.82 (2H, m, C₆H₃MeSO₂CH₃H-2 and H-6), 6.41 (1H, m, NH), 4.71 (1H, m, PhOpipH-4), 4.01 (1H, m, pipH-4), 3.90 (2H, m, 2H of PhOpipH-2, H-6), 3.69 (1H, m, 1H of PhOpipH-2, H-6), 3.56 (2H, s, C$\underline{H}$₂C₆H₄CN), 3.52 (1H, m, 1H of PhOpipH-2, H-6), 3.05 (3H, s, SO₂CH₃), 2.83 (2H, m, 2H of pipH-2, H-6), 2.66 (3H, s, ArCH₃), 2.20 (2H, t, J 11.5 Hz, 2H of pipH-2, H-6), 2.12-1.96 (5H, m, 2H of pipH-3, H-5, 3H of PhOpipH-3, H-5), 1.86 (1H, m, 1H of PhOpipH-3, H-5), 1.62 (2H, m, 2H of pipH-3, H-5); m/z: 616 [M+H]⁺.

Compound 7-14: ¹H nmr (CDCl₃) δ 8.90 (1H, d, J 2.0 Hz, pyH-6), 8.11 (1H, dd, J 8.0, 2.0 Hz, pyH-4), 7.95 (1H, d, J 9.5 Hz, C₆H₃MeSO₂CH₃H-5), 7.60 (1H, d, J 8.5 Hz, pyH-3), 7.34 (2H, d, J 9.0 Hz, 2H of C₆H₄OCF₃), 7.15 (2H, d, J 8.0 Hz, C₆H₄OCF₃), 6.86-6.83 92H, m, C₆H₃MeSO₂CH₃H-2 and H-6), 6.47 (1H, d, J 8.0 Hz, NH), 4.71 (1H, m, PhOpipH-4), 4.01 (1H, m, pipH-4), 3.91 (2H, m, 2H of PhOpipH-2, H-6), 3.69 (1H, m, 1H of PhOpipH-2, H-6), 3.50 (3H, m, C$\underline{H}$₂C₆H₄OCF₃, 1H of PhOpipH-2, H-6), 3.04 (3H, s, SO₂CH₃), 2.85 (2H, m, 2H of pipH-2, H-6), 2.65 (3H, s, ArCH₃), 2.17 (2H, t, J 11.5 Hz, 2H of pipH-2, H-6), 2.02 (5H, m, 2H of pipH-3, H-5, 3H of PhOpipH-3, H-5), 1.86 (1H, m, 1H of PhOpipH-3, H-5), 1.61 (2H, m, 2H of pipH-3, H-5); ¹⁹F nmr (CDCl₃) δ −57.9; m/z: 675 [M+H]⁺.

Compound 7-15: ¹H nmr (CDCl₃) δ 9.65 (1H, s, NH), 8.95 (1H, m, pyH-6), 8.52 (1H, d, J 2.5 Hz, N, O-pyH-6), 8.44 (1H, dd, J 9.0, 2.5 Hz, N, O-pyH-4), 8.13 (1H, dd, J 8.5, 2.0 Hz, pyH-4), 7.96 (1H, d, J 9.0 Hz, C₆H₃MeSO₂CH₃H-5), 7.68 (2H, d, J 9.0 Hz, 2H of C₆H₄CN), 7.43 (1H, d, J 8.5 Hz, pyH-3), 7.23 (2H, d, J 8.5 Hz, 2H of C₆H₄CN), 7.07 (1H, d, J 8.5 Hz, N, O-pyH-3), 6.86-6.83 (2H, m, C₆H₃MeSO₂CH₃H-2, H-6), 4.73 (1H, m, PhOpipH-4), 4.03 (1H, m, 1H of PhOpipH-2, H-6), 3.86 (1H, m, 1H of PhOpipH-2, H-6), 3.65 (1H, m, 1H of PhOpipH-2, H-6), 3.44 (1H, m, 1H of PhOpipH-2, H-6), 3.05 (3H, s, SO₂CH₃), 2.66 (3H, s, ArCH₃), 2.12-1.96 (3H, m, 3H of PhOpipH-3, H-5), 1.88 (1H, m, 1H of PhOpipH-3, H-5); m/z: 612 [M+H]⁺.

Compound 7-16: ¹H nmr (CDCl₃) δ 8.90 (1H, d, J 2.0 Hz, pyH-6), 8.14 (1H, dd, J 8.5, 2.0 Hz, pyH-4), 7.96 (1H, d, J 9.0 Hz, C₆H₃MeSO₂CH₃H-5), 7.67 (1H, d, J 8.5 Hz, pyH-3), 7.23 (2H, d, J 9.0 Hz, 2H of C₆H₄OCH₃), 6.87-6.84 (4H, m, 2H of C₆H₄OCH₃, C₆H₃MeSO₂CH₃H-2, H-6), 6.17 (1H, d, J 8.0 Hz, NH), 4.71 (1H, m, PhOpipH-4), 4.02 (1H, m, pipH-4), 3.89 (2H, m, 2H of PhOpipH-2, H-6), 3.80 (3H, s, OCH₃), 3.72 (1H, m, 1H of PhOpipH-2, H-6), 3.54 (1H, m, 1H of PhOpipH-2, H-6), 3.48 (2H, s, C<u>H</u>₂C₆H₄OCH₃), 3.05 (3H, s, SO₂CH₃), 2.88 (2H, m, 2H of pipH-2, H-6), 2.66 (3H, s, ArCH₃), 2.17 (2H, t, J 11.5 Hz, 2H of pipH-2, H-6), 2.10-1.94 (5H, m, 2H of pipH-3, H-5, 3H of PhOpipH-3, H-5), 1.87 (1H, m, 1H of PhOpipH-3, H-5), 1.59 (2H, m, 2H of pipH-3, H-5); m/z: 622 [M+H]⁺.

Compound 7-17: ¹H nmr (CDCl₃, @ 50° C.) δ 8.57 (1H, dd, J 2.0, 1.0 Hz, 7.93 (2H, d, J 9.0 Hz, 2H of C₆H₄OCH₃), 7.77 (1H, dd, J 8.0, 2.0 Hz, pyH-4), 7.67 (1H, dd, J 8.0, 1.0 Hz, pyH-3), 7.59 (2H, d, J 7.5 Hz, 2H of C₆H₄CN), 7.41 (2H, d, J 8.0 Hz, 2H of C₆H₄CN), 6.96 (2H, d, J 9.0 Hz, 2H of C₆H₄OCH₃), 4.67 (1H, m, 1H of BzpipH-2, H-6), 4.03 (1H, m, 1H of BzpipH-2, H-6), 3.87 (3H, s, 1×OCH₃), 3.55 (6H, m, pipH-4, BzpipH-4, NC<u>H</u>₂C<u>H</u>₂OCH₃), 3.49 (2H, s, C₂C₆H₄CN), 3.33 (3H, s, 1×OCH₃), 3.30 (1H, m, 1H of BzpipH-2, H-6), 3.14 (1H, m, 1H of BzpipH-2, H-6), 2.84 (2H, m, 2H of pipH-2, H-6), 2.03-1.84 (8H, m, 2H of pipH-2, H-6, 2H of pipH-3, H-5, BzpipH-3, H-5), 1.67 (2H, m, 2H of pipH-3, H-5); m/z: 624 [M+H]⁺.

Compound 7-18: ¹H nmr (CDCl₃, @ 50° C.) δ 8.58 (1H, dd, J 2.0, 1.0 Hz, pyH-6), 7.94 (2H, d, J 9.0 Hz, 2H of C₆H₄OCH₃), 7.78 (1H, d,d J 8.0, 2.0 Hz, pyH-4), 7.68 (1H, d, J 8.0 Hz, pyH-3), 7.31 (2H, m, 2H of C₆H₄OCF₃), 7.14 (2H, d, J 8.0 Hz, 2H of C₆H₄OCF₃), 6.96 (2H, d, J 9.0 Hz, 2H of C₆H₄OCH₃), 4.68 (1H, m, 1H of BzpipH-2, H-6), 4.04 (1H, m, 1H of BzpipH-2, H-6), 3.88 (3H, s, 1×OCH₃), 3.55 (6H, m, pipH-4, BzpipH-4, NC<u>H</u>₂C<u>H</u>₂OCH₃), 3.33 (3H, s, 1×OCH3), 3.28 (1H, m, 1H of BzpipH-2, H-6), 3.14 (1H, m, 1H of BzpipH-2, H-6), 2.88 (2H, m, 2H of pipH-2, H-6), 2.06-1.82 (8H, m, 2H of pipH-2, H-6, 2H of pipH-3, H-5, BzpipH-3, H-5), 1.67 (2H, m, 2H of pipH-3, H-5); ¹⁹F nmr (CDCl₃) δ −57.9; m/z: 683 [M+H]⁺.

Compound 7-19: m/z: 1097 [M+H]⁺.

Compound 7-20: ¹H nmr (CDCl₃) δ 9.74 (1H, s, NH), 8.95 (1H, m, pyH-6), 8.54 (1H, d, J 2.5 Hz, N, O-pyH-6), 8.41 (1H, dd, J 9.0, 2.5 Hz, N, O-pyH-4), 8.11 (1H, dd, J 8.0, 2.0 Hz, pyH-4), 8.04 (2H, d, J 9.0 Hz, 2H of C₆H₄Ac), 7.68 (1H, d, J 9.0 Hz, BzthiazoleH-7), 7.46 (1H, d, J 2.5 Hz, BzthiazoleH-4), 7.41 (1H, d, J 8.5 Hz, pyH-3), 7.19 (2H, d, J 9.0 Hz, 2H of C₆H₄Ac), 7.04 (1H, d, J 9.0 Hz, N, O-pyH-3), 7.00 (1H, dd, J 9.0, 2.0 Hz, BzthiazoleH-6), 4.67 (1H, m, PhOpipH-4), 3.95 (2H, m, 2H of PhOpipH-2, H-6), 3.67 (1H, m, 1H of PhOpipH-2, H-6), 3.39 (1H, m, 1H of PhOpipH-2, H-6), 2.81 (3H, s, 1×CH₃), 2.59 (3H, s, 1×CH₃), 2.06-1.90 (4H, m, PhOpipH-3, H-5); m/z: 608 [M+H]⁺.

Compound 7-21: ¹H nmr (CDCl₃) δ 8.95 (1H, d, J 2.0 Hz, pyH-6), 8.17 (1H, dd, J 8.5, 2.0 Hz, pyH-4), 7.94 (2H, d, J 9.0 Hz, 2H of COC₆H₄OCH₃), 7.69 (1H, d, J 8.5 Hz, pyH-3), 7.24 (2H, d, J 8.5 Hz, 2H of CH₂C₆H₄OCH₃), 6.96 (2H, d, J 9.0 Hz, 2H of COC₆H₄OCH₃), 6.87 (2H, d, J 9.0 Hz, 2H of CH₂C₆H₄OCH₃), 6.49 (1H, d, J 9.0 Hz, NH), 4.85 (0.5H, br s, 0.5H of pipH-3), 4.70 (1.5H, m, 0.5H of pipH-3, 1H of BzpipH-2, H-6), 4.30-4.11 (1H, m, pipH-4), 3.96 (1H, m, 1H of BzpipH-2, H-6), 3.88 (3H, s, 1×OCH₃), 3.81 (3H, s, 1×OCH₃), 3.53 (3H, m, C<u>H</u>₂C₆H₄OCH₃, BzpipH-4), 3.31-3.21 (2H, m, 1H of pipH-2, 1H of BzpipH-2, H-6), 3.11 (1H, m, 1H of BzpipH-2, H-6), 2.96 (1H, m, 1H of pipH-6), 2.35 (0.5H, d, J 13.0 Hz, 0.5H of pipH-2), 2.20 (1.5H, m, 0.5H of pipH-2, 1H of pipH-6), 2.04-1.95 (2H, m, 2H of pipH-5, BzpipH-3, H-5), 1.92-1.81 (4H, m, 4H of pipH-5, BzpipH-3, H-5); m/z: 589 [M+H]⁺.

Compound 7-22: ¹H nmr (CDCl₃) δ 8.90 (1H, d, J 2.0 Hz, pyH-6), 8.11 (1H, dd, J 8.0, 2.0 Hz, pyH-4), 7.68 (1H, d, J 9.0 Hz, BzthiazoleH-7), 7.58 (3H, m, 2H of C₆H₄CN, pyH-3), 7.44 (3H, m, 2H of C₆H₄CN, BzthiazoleH-4), 7.00 (1H, dd, J 9.0, 2.5 Hz, BzthiazoleH-6), 6.58 (1H, d, J 8.0 Hz, NH), 4.66 (1H, m, PhOpipH-4), 4.01 (1H, m, pipH-4), 3.91 (2H, m, 2H of PhOpipH-2, H-6), 3.72 (1H, m, 1H of PhOpipH-2, H-6), 3.56 (2H, s, C<u>H</u>₂C₆H₄CN), 3.45 (1H, m, 1H of PhOpipH-2, H-6), 2.83 (2H, m pipH-2, H-6), 2.81 (3H, s, BzthiazoleCH₃), 2.20 (2H, m, 2H of pipH-2, H-6), 2.12-1.95 (5H, m, 2H of pipH-3, H-5, 3H of PhOpipH-3, H-5), 1.89 (1H, m, 1H of PhOpipH-3, H-5), 1.64 (2H, m, 2H of pipH-3, H-5); m/z: 595 [M+H]⁺.

Compound 7-23: ¹H nmr (CDCl₃) δ 8.88 (1H, m, pyH-6), 8.08 (1H, dd, J 8.5, 2.0 Hz, pyH-4), 7.67 (1H, d, J 8.5 Hz, BzthiazoleH-7), 7.52 (1H, d, J 8.0 Hz, pyH-3), 7.46 (1H, d, J 2.0 Hz, BzthiazoleH-4), 7.32 (2H, d, J 9.0 Hz, 2H of C₆H₄OCF₃), 7.13 (2H, d, J 8.0 Hz, 2H of C₆H₄OCF₃), 6.99 (1H, dd, J 9.0, 2.0 Hz, BzthiazoleH-6), 6.74 (1H, d, J 8.0 Hz, NH), 4.65 (1H, m, PhOpipH-4), 3.99 (1H, m, pipH-4), 3.91 (2H, m, 2H of PhOpipH-2, H-6), 3.70 (1H, m, 1H of PhOpipH-2, H-6), 3.49 (2H, s, C<u>H</u>₂C₆H₄OCF₃), 3.43 (1H, m, 1H of PhOpipH-2, H-6), 2.84 (2H, m, 2H of pipH-2, H-6), 2.80 (3H, s, BzthiazoleCH₃), 2.15 (2H, t, J 11.0 Hz, 2H of pipH-2, H-6), 2.09-1.94 (5H, m, 2H of pipH-3, H-5, 3H of PhOpipH-3, H-5), 1.88 (1H, m, 1H of PhOpipH-3, H-5), 1.62 (2H, m, 2H of pipH-3, H-5); ¹⁹F nmr (CDCl₃) δ −57.9; m/z: 654 [M+H]⁺.

Compound 7-24: ¹H nmr (CDCl₃) δ 8.89 (1H, m, pyH-6), 8.11 (1H, dd, J 8.0, 2.0 Hz, pyH-4), 7.67 (1H, d, 9.0 Hz, BzthiazoleH-7), 7.60 (1H, d, J 8.0 Hz, pyH-3), 7.46 (1H, d, J 2.5 Hz, BzthiazoleH-4), 7.22 (2H, d, J 9.0 Hz, 2H of C₆H₄OCH₃), 7.00 (1H, dd, J 9.0, 2.5 Hz, BzthiazoleH-6), 6.85 (2H, d, J 9.0 Hz, 2H of C₆H₄OCH₃), 6.41 (1H, d, J 8.0 Hz, NH), 4.66 (1H, m, PhOpipH-4), 4.00 (1H, m, pipH-4), 3.91 (2H, m, 2H of PhOpipH-2, H-6), 3.79 (3H, s, OCH₃), 3.72 (1H, m, 1H of PhOpipH-2, H-6), 3.47 (2H, s, C<u>H</u>₂C₆H₄OCH₃), 3.43 (1H, m, 1H of PhOpipH-2, H-6), 2.87 (2H, m, 2H of pipH-2, H-6), 2.81 (3H, s, BzthiazoleCH₃), 2.16 (2H, dd, J 11.5, 10.0 Hz, 2H of pipH-2, H-6), 2.09-1.88 (6H, m, 2H of pipH-3, H-5, PhOpipH-3, H-5), 1.60 (2H, m, 2H of pipH-3, H-5); m/z: 600 [M+H]⁺.

Compound 7-25: ¹H nmr (CDCl₃) δ 9.95 (1H, s, NH), 8.93 (1H, d, J 2.0 Hz, pyH-6), 8.57 (1H, d, J 2.5 Hz, N, O-pyH-6), 8.45 (1H, dd, J 9.0 2.5 Hz, N, O-pyH-4), 8.09 (1H, dd, J 8.0, 2.0 Hz, pyH-4), 7.67 (1H, d, J 8.5 Hz, 2H of C₆H₄CN), 7.66 (1H, d, J 8.5 Hz, BzthiazoleH-7), 7.46 (1H, d, J 2.0 Hz, BzthiazoleH-4), 7.37 (1H, d, J 8.0 Hz, pyH-3), 7.22 (2H, d, J 8.5 Hz, 2H of C₆H₄CN), 7.06 (1H, d, J 9.0 Hz, N, O-pyH-3), 7.00 (1H, dd, J 9.0, 2.0 Hz, BzthiazoleH-6), 4.68 (1H, m, PhOpipH-4), 3.97 (2H, m, 2H of PhOpipH-2, H-6), 3.66 (1H, m, 1H of PhOpipH-2, H-6), 3.38 (1H, m, 1H of PhOpipH-2, H-6), 2.82 (3H, s, BzthiazoleCH$_3$), 2.06 (2H, m, 2H of PhOpipH-3, H-5), 1.98-1.91 (2H, m, 2H of PhOpipH-3, H-5); m/z: 591 [M+H]$^+$.

Compound 7-26: $^1$H nmr (CDCl$_3$) δ 8.92 (1H, m, pyH-6), 8.15 (1H, dd, J 8.5, 2.0 Hz, pyH-4), 7.94 (2H, d, J 9.0 Hz, 2H of COC$_6$H$_4$OCH$_3$), 7.64 (1H, d, J 8.0 Hz, pyH-3), 7.21 (2H, d, J 9.0 Hz, 2H of CH$_2$C$_6$H$_4$OCH$_3$), 6.96 (2H, d, J 9.0 Hz, 2H of COC$_6$H$_4$OCH$_3$), 6.86 (2H, d, J 8.5 Hz, 2H of CH$_2$C$_6$H$_4$OCH$_3$), 6.40 (1H, d, J 8.0 Hz, NH), 4.69 (1H, m, 1H of BzpipH-2, H-6), 4.60, 4.44 (1H, 2m, pipH-3), 4.15 (1H, m, pipH-4), 3.93 (1H, m, 1H of BzpipH-2, H-6), 3.88 (3H, s, 1×OCH$_3$), 3.81 (3H, s, 1×OCH$_3$), 3.57, 3.49 (2H, 2d AB system, J 13.0 Hz, CH$_2$C$_6$H$_4$OCH$_3$), 3.48 (1H, m, BzpipH-4), 3.23 (2H, 1H of pipH-2 or H-6, 1H of BzpipH-2, H-6), 3.11 (1H, m, 1H of BzpipH-2, H-6), 2.83 (1H, m, pipH-2 or H-6), 2.24-2.13 (2H, m, 2H of pipH-2, H-6), 2.02 (1H, m, 1H of pipH-5, BzpipH-3, H-5), 1.93-1.80 (3H, m, 3H of pipH-5, BzpipH-3, H-5), 1.57 (2H, m, 2H of pipH-5, BzpipH-3, H-5); $^{19}$F nmr (CDCl$_3$) δ −188.6 (d, J 58.5 Hz); m/z: 589 [M+H]$^+$.

Compound 7-27: $^1$H nmr (CDCl$_3$) δ 8.96 (1H, m, pyH-6), 8.17 (1H, dd, J 8.5, 2.0 Hz, pyH-4), 7.94 (2H, d, J 9.0 Hz, 2H of C$_6$H$_4$OCH$_3$), 7.67 (2H, m, pyH-3, C$_6$H$_4$CNH-3), 7.57 (2H, m, C$_6$H$_4$CNH-4, H-6), 7.43 (1H, t, J 7.5 Hz, C$_6$H$_4$CNH-5), 6.95 (2H, d, J 9.0 Hz, 2H of C$_6$H$_4$OCH$_3$), 6.63 (1H, d, J 8.5 Hz, NH), 4.87 (0.5H, m, 0.5H of pipH-3), 4.69 (1.5H, m, 0.5H of pipH-3, 1H of BzpipH-2, H-6), 4.29, 4.18 (1H, 2m, pipH-4), 3.95 (1H, m, 1H of BzpipH-2, H-6), 3.87 (3H, s, OCH$_3$), 3.60 (2H, s, CH$_2$C$_6$H$_4$CN), 3.53 (1H, m, BzpipH-4), 3.31-3.18 (2H, m, 1H of pipH-2, 1H of BzpipH-2, H-6), 3.11 (1H, m, 1H of BzpipH-2, H-6), 2.92 (1H, m, 1H of pipH-6), 2.43 (0.5H, d, J 13.0 Hz, 0.5H of pipH2), 2.30 (0.5H, d, J 12.5 Hz, 0.5H of pipH-2), 2.26 (1H, t, J 11.5 Hz, 1H of pipH-6), 2.06-1.98 (2H, m, 2H of pipH-5, BzpipH-3, H-5), 1.96-1.82 (4H, m, 4H of pipH-5, BzpipH-3, H-5); $^{19}$F nmr (CDCl$_3$) δ −200.9; m/z: 584 [M+H]$^+$.

Compound 7-28: $^1$H nmr (CDCl$_3$) δ 8.96 (1H, m, pyH-6), 8.18 (1H, dd, J 8.5, 2.0 Hz, pyH-4), 7.94 (2H, d, J 9.0 Hz, 2H of C$_6$H$_4$OCH$_3$), 7.70 (1H, d, J 8.0 Hz, pyH-3), 7.59 (2H, d, J 8.0 Hz, 2H of C$_6$H$_4$CF$_3$), 7.47 (2H, d, J 8.0 Hz, 2H of C$_6$H$_4$CF$_3$), 6.96 (2H, d, J 8.5 Hz, 2H of C$_6$H$_4$OCH$_3$), 6.49 (1H, d, J 8.5 Hz, NH), 4.87 (0.5H, m, 0.5H of pipH-3), 4.69 (1.5H, m, 0.5H of pipH-3, 1H of BzpipH-2, H-6), 4.29, 4.19 (1H, 2m, pipH-4), 3.96 (1H, m, 1H of BzpipH-2, H-6), 3.88 (3H, s, OCH3), 3.66, 3.60 (2H, 2d AB system, J 14.0 Hz, CH$_2$C$_6$H$_4$CF$_3$), 3.53 (1H, m, BzpipH-4), 3.32-3.22 (2H, m, 1H of pipH-2, 1H of BzpipH-2, H-6), 3.11 (1H, m, 1H of BzpipH-2, H-6), 2.95 (1H, m, 1H of pipH-6), 2.41 (0.5H, d, J 13.0 Hz, 0.5H of pipH-2), 2.26 (1.5H, m, 0.5H of pipH-2, 1H of pipH-6), 2.06-1.98 (2H, m, 2H of pipH-5, BzpipH-3, H-5), 1.96-1.82 (4H, m, 4H of pipH-5, BzpipH-3, H-5); $^{19}$F nmr (CDCl$_3$) δ −62.5, −201.0; m/z: 627 [M+H]$^+$.

Compound 7-29: $^1$H nmr (CDCl$_3$) δ 8.89 (1H, m, pyH-6), 8.07 (1H, br d, J 8.0 Hz, pyH-4), 7.94 (2H, d, J 9.0 Hz, 2H of C$_6$H$_4$OCH$_3$), 7.66 (1H, s, C$_6$H$_4$CNH-2), 7.57-7.52 (2H, m, 2H of C$_6$H$_4$CNH-4, H-5, H-6), 7.48 (1H, d, J 8.5 Hz, pyH-3), 7.44-7.39 (2H, m, NH, 1H of C$_6$H$_4$CNH-4, H-5, H-6), 6.95 (2H, d, J 9.0 Hz, 2H of C$_6$H$_4$OCH$_3$), 4.71 (1.5H, m, 0.5H of pipH-3, 1H of BzpipH-2, H-6), 4.54 (0.5H, td, J 9.5, 5.0 Hz, 0.5H of pipH-3), 4.17 (1H, m, pipH-4), 3.87 (3H, s, OCH$_3$), 3.85 (1H, m, 1H of BzpipH-2, H-6), 3.64, 3.58 (2H, 2d AB system, CH$_2$C$_6$H$_4$CN), 3.56 (1H, m, BzpipH-4), 3.29-3.10 (3H, m, 1H of pipH-2, 2H of BzpipH-2, H-6), 2.80 (1H, d, J 10.0 Hz, 1H of pipH-6), 2.92-2.12 (3H, m, 1H of pipH-2, 1H of pipH-5, 1H of pipH-6), 2.03 (1H, m, 1H of BzpipH-3, H-5), 1.93-1.78 (3H, m, 3H of BzpipH-3, H-5), 1.69 (1H, m, 1H of pipH-5); $^{19}$F nmr (CDCl$_3$) δ −188.5 (d, J 55.0 Hz); m/z: 584 [M+H]$^+$.

Compound 7-30: $^1$H nmr (CDCl$_3$) δ 8.89 (1H, d, J 2.0 Hz, pyH-6), 8.09 (1H, dd, J 8.0, 2.0 Hz, pyH-4), 7.94 (2H, d, J 9.0 Hz, 2H of COC$_6$H$_4$OCH$_3$), 7.51 (1H, d, J 8.5 Hz, pyH-3), 7.22 (1H, t, J 8.0 Hz, CH$_2$C$_6$H$_4$OCH$_3$H-5), 7.10 (1H, d, J 7.5 Hz, NH), 6.95 (2H, d, J 9.0 Hz, 2H of COC$_6$H$_4$OCH$_3$), 6.88 (2H, m, CH$_2$C$_6$H$_4$OCH$_3$H-2, H-4 or H-6), 6.80 (1H, m, CH$_2$C$_6$H$_4$OCH$_3$H-4 or H-6), 4.68 (1.5H, m, 0.5H of pipH-3, 1H of BzpipH-2, H-6), 4.51 (0.5H, m, 0.5H of pipH-3), 4.14 (1H, m, pipH-4), 3.88 (1H, m, 1H of BzpipH-2, H-6), 3.87 (3H, s, 1×OCH$_3$), 3.80 (3H, s, 1×OCH$_3$), 3.59, 3.52 (2H, 2d AB system, J 13.0 Hz, CH$_2$C$_6$H$_4$OCH$_3$), 3.50 (1H, m, BzpipH-4), 3.23 (2H, m, 1H of pipH-2, 1H of BzpipH-2, H-6), 3.12 (1H, t, J 11.0 Hz, 1H of BzpipH-2, H-6), 2.84 (1H, m, 1H of pipH-6), 2.25-2.13 (3H, m, 1H of pipH-2, 1H of pipH-5, 1H of pipH-6), 2.02 (1H, m, 1H of BzpipH-3, H-5), 1.93-1.80 (3H, m, 3H of BzpipH-3, H-5), 1.66 (1H, m, 1H of pipH-5); $^{19}$F nmr (CDCl$_3$) δ −188.4 (d, J 50.0 Hz); m/z: 589 [M+H]$^+$.

Compound 7-31: $^1$H nmr (CDCl$_3$) δ 8.89 (1H, m, pyH-6), 8.09 (1H, dd, J 8.0, 2.0 Hz, pyH-4), 7.94 (2H, d, J 9.0 Hz, 2H of C$_6$H$_4$OCH$_3$), 7.57 (2H, d, J 8.0 Hz, 2H of C$_6$H$_4$CF$_3$), 7.52 (1H, d, J 8.5 Hz, pyH-3), 7.43 (2H, d, J 8.0 Hz, 2H of C$_6$H$_4$CF$_3$), 7.13 (1H, d, J 6.0 Hz, NH), 6.96 (2H, d, J 9.0 Hz, 2H of C$_6$H$_4$OCH$_3$), 4.69 (1.5H, m, 0.5H of pipH-3, 1H of BzpipH-2, H-6), 4.51 (1H, ddd, J 9.5, 9.0, 5.0 Hz, 0.5H of pipH-3), 4.15 (1H, m, pipH-4), 3.88 (3H, s, OCH$_3$), 3.86 (1H, m, 1H of BzpipH-2, H-6), 3.66, 3.60 (2H, 2d AB system, J 13.5 Hz, CH$_2$C$_6$H$_4$CF$_3$), 3.54 (1H, m, BzpipH-4), 3.29-3.17 (2H, m, 1H of pipH-2, 1H of BzpipH-2, H-6), 3.12 (1H, m, 1H of BzpipH-2, H-6), 2.82 (1H, m, 1H of pipH-6), 2.29-2.16 (3H, m, 1H of pipH-2, 1H of pipH-5, 1H of pipH-6), 2.03 (1H, m, 1H of BzpipH-3, H-5), 1.93-1.81 (3H, m, 3H of BzpipH-3, H-5), 1.64 (1H, m, 1H of pipH-5); $^{19}$F nmr (CDCl$_3$) δ −62.4, −188.5 (d, J 45.5 Hz); m/z: 628 [M+H]$^+$.

Compound 7-32: $^1$H nmr (CDCl$_3$) δ 8.91 (1H, d, J 2.0 Hz, pyH-6), 8.11 (1H, dd, J 8.5, 2.0 Hz, pyH-4), 7.94 (2H, d, J 9.5 Hz, 2H of C$_6$H$_4$OCH$_3$), 7.59 (1H, s, C$_6$H$_4$CF$_3$H-2), 7.56 (1H, d, J 8.5 Hz, pyH-3), 7.52, 7.41 (3H, m, C$_6$H$_4$CF$_3$H-4, H-5, H-6), 6.96 (2H, d, J 8.5 Hz, 2H of C$_6$H$_4$OCH$_3$), 6.86 (1H, d, J 7.5 Hz, NH), 4.68 (1.5H, m, 0.5H of pipH-3, 1H of BzpipH-2, H-6), 4.50 (0.5H, td, J 9.5, 5.0 Hz, 0.5H of pipH-3), 4.16 (1H, m, pipH-4), 3.90 (1H, m, 1H of BzpipH-2, H-6), 3.88 (3H, s, OCH$_3$), 3.67, 3.60 (2H, 2d AB system, J 13.5 Hz, CH$_2$C$_6$H$_4$CF$_3$), 3.53 (1H, m, BzpipH-4), 3.29-3.16 (2H, m, 1H of pipH-2, 1H of BzpipH-2, H-6), 3.12 (1H, m, 1H of BzpipH-2, H-6), 2.83 (1H, m, 1H of pipH-6), 2.30-2.16 (3H, m, 1H of pipH-2, 1H of pipH-5, 1H of pipH-6), 2.02 (1H, m, 1H of BzpipH-3, H-5), 1.93-1.81 (3H, m, 3H of BzpipH-3, H-5), 1.64 (1H, m, 1H of pipH-5); $^{19}$F nmr (CDCl$_3$) δ −62.5, −188.6 (d, J 48.0 Hz); m/z: 627 [M+H]$^+$.

Compound 7-33 (as its benzene sulfonic acid salt): $^1$H nmr (D$_6$-DMSO @ 60° C.) δ 9.00 (1H, s, pyH-6), 8.29 (1H, dd, J 8.5, 2.0 Hz, pyH-4), 7.97 (2H, d, J 8.5 Hz, 2H of C$_6$H$_4$OCH$_3$), 7.66 (3H, m, 2H of C$_6$H$_4$OCF$_3$, 1H of C$_6$H$_5$SO$_3$H), 7.61 (2H, m, pyH-3, 1H of C$_6$H$_5$SO$_3$H), 7.44 (2H, d, J 7.5 Hz, 2H of C$_6$H$_4$OCF$_3$), 7.31-7.26 (3H, m, 3H of C$_6$H$_5$SO$_3$H), 7.03 (2H, d, J 9.0 Hz, 2H of C$_6$H$_4$OCH$_3$), 3.84 (3H, s, OCH$_3$), remaining resonances very broad; $^{19}$F nmr (CDCl$_3$) δ −56.7, remaining resonance too broad to observe; m/z: 643 [M+H]$^+$ (found [M+H]$^+$, 603.1689, C$_{31}$H$_{27}$FN$_4$O$_6$S requires [M+H]$^+$ 603.1708).

Compound 7-34: $^1$H nmr (CDCl$_3$) δ 8.95 (1H, m, pyH-6), 8.16 (1H, dd, J 8.5, 2.0 Hz, pyH-4), 7.94 (2H, d, J 9.0 Hz, 2H of C$_6$H$_4$OCH$_3$), 7.65 (1H, d, J 8.0 Hz, pyH-3), 7.60 (1H, s, $C_6H_4CF_3H$-2), 7.53 (2H, m, 2H of $C_6H_4CF_3H$-4, H-5, H-6), 7.44 (1H, m, 1H of $C_6H_4CF_3H$-4, H-5, H-6), 6.95 (2H, d, J 8.5 Hz, 2H of $C_6\underline{H}_4OCH_3$), 6.73 (1H, d, J 9.0 Hz, NH), 4.87 (0.5H, br s, 0.5H of pipH-3), 4.69 (1.5H, m, 0.5H of pipH-3, 1H of BzpipH-2, H-6), 4.32-4.13 (1H, m, pipH-4), 3.94 (1H, m, 1H of BzpipH-2, H-6), 3.87 (3H, s, $OCH_3$), 3.63 (2H, s, C$\underline{H}_2C_6H_4CF_3$), 3.53 (1H, m, BzpipH-4), 3.30-3.20 (2H, m, 1H of pipH-2, 1H of BzpipH-2, H-6), 3.10 (1H, m, 1H of BzpipH-2, H-6), 2.94 (1H, m, 1H of pipH-6), 2.42 (0.5H, d, J 12.5 Hz, 0.5H of pipH-2), 2.26 (1.5H, m, 0.5H of pipH-2, 1H of pipH-6), 2.08-1.97 (2H, m, 1H of pipH-5, 1H of BzpipH-3, H-5), 1.91-1.81 (4H, m, 1H of pipH-5, 3H of BzpipH-3, H-5); $^{19}$F nmr ($CDCl_3$) δ −62.5, −200.7; m/z: 627 [M+H]$^+$.

Compounds 7-35 and 7-36 were separated from a racemic mixture using chiral chromatography on an (R, R)-Whelk-O 1 25 cm×10 mm column (silica modified with covalently bound 4-(3,5-dinitrobenzamido)tetrahydrophenanthrene), available from Regis Technologies. The instrument was a TharSFC semi-preparative HPLC system, and elution was performed isocratically using 50% MeOH with 0.1% diethylamine in supercritical carbon dioxide at 14 mL/min at 30° C. Compound 7-36 was the earlier-eluting peak and compound 7-35 was the later-eluting peak.

Compound 7-35 (single enantiomer): $^1$H nmr ($CDCl_3$) δ 8.93 (1H, s, pyH-6), 8.12 (1H, d, J 8.0 Hz, pyH-4), 7.94 (2H, d, J 9.0 Hz, 2H of $C_6\underline{H}_4OCH_3$), 7.53 (2H, m, pyH-3, NH), 7.33 (2H, d, J 9.0 Hz, 2H of $C_6H_4OCF_3$), 7.16 (2H, d, J 8.0 Hz, 2H of $C_6H_4OCF_3$), 6.96 (2H, d, J 8.5 Hz, 2H of $C_6\underline{H}_4OCH_3$), 4.68 (1.5H, m, 0.5H of pipH-3, 1H of BzpipH-2, H-6), 4.50 (0.5H, m, 0.5H of pipH-3), 4.16 (1H, m, pipH-4), 3.89 (1H, m, 1H of BzpipH-2, H-6), 3.88 (3H, s, $OCH_3$), 3.61, 3.55 (2H, 2d, J 13.5 Hz, C$\underline{H}_2C_6H_4OCF_3$), 3.53 (1H, m, BzpipH-4), 3.22 (2H, m, pipH-2, 1H of BzpipH-2, H-6), 3.12 (1H, m, 1H of BzpipH-2, H-6), 2.83 (1H, m, 1H of pipH-6), 2.25-2.12 (3H, m, 1H of pipH-2, 1H of pipH-5, 1H of pipH-6), 2.02 (1H, m, 1H of BzpipH-3, H-5), 1.90-1.76 (3H, m, 3H of BzpipH-3, H-5), 1.66 (1H, m, 1H of pipH-5); $^{19}$F nmr ($CDCl_3$) δ −57.9, −188.5 (d, J 52.5 Hz); m/z: 643 [M+H]$^+$.

Compound 7-36 (single enantiomer): $^1$H nmr ($CDCl_3$) δ 8.89 (1H, m, pyH-6), 8.10 (1H, dt, J 8.0, 2.5 Hz, pyH-4), 7.94 (2H, d, J 9.0 Hz, 2H of $C_6\underline{H}_4OCH_3$), 7.54 (1H, dd, J 8.0, 7.5 Hz, pyH-3), 7.33 (2H, d, J 9.0 Hz, 2H of $C_6H_4OCF_3$), 7.16 (2H, d, J 8.0 Hz, 2H of $C_6H_4OCF_3$), 7.03 (1H, m, NH), 6.96 (2H, d, J 8.5 Hz, 2H of $C_6\underline{H}_4OCH_3$), 4.69 (1.5H, m, 0.5H of pipH-3, 1H of BzpipH-2, H-6), 4.50 (0.5H, m, 0.5H of pipH-3), 4.15 (1H, m, pipH-4), 3.90 (1H, m, 1H of BzpipH-2, H-6), 3.88 (3H, s, $OCH_3$), 3.60, 3.54 (2H, 2d AB system, J 13.5 Hz, C$\underline{H}_2C_6H_4OCF_3$), 3.52 (1H, m, BzpipH-4), 3.27-3.16 (2H, m, 1H of pipH-2, 1H of BzpipH-2, H-6), 3.11 (1H, m, 1H of BzpipH-2, H-6), 2.83 (1H, m, 1H of pipH-6), 2.26-2.15 (3H, m, 1H of pipH-2, 1H of pipH-5, 1H of pipH-6), 2.02 (1H, m, 1H of BzpipH-3, H-5), 1.92-1.78 (3H, m, 3H of BzpipH-3, H-5), 1.67 (1H, m, 1H of pipH-5); $^{19}$F nmr ($CDCl_3$) δ −57.9, −188.5 (d, J 56.5 Hz); m/z: 643 [M+H]$^+$.

Compound 7-37: $^1$H nmr ($CDCl_3$) δ 8.88 (1H, m, pyH-6), 8.08 (1H, dd, J 8.0, 2.0 Hz, pyH-4), 7.94 (2H, d, J 9.0 Hz, 2H of $C_6H_4OCH_3$), 7.50 (1H, d, J 8.5 Hz, pyH-3), 7.18 (1H, d, J 7.0 Hz, NH), 7.11-7.04 (2H, m, 2H of $C_6H_3FMeH$-2, H-5, H-6), 6.95 (2H, d, J 9.0 Hz, 2H of $C_6\underline{H}_4OCH_3$), 6.92 (1H, m, 1H of $C_6H_3FMeH$-2, H-5, H-6), 4.68 (1.5H, m, 0.5H of pipH-3, 1H of BzpipH-2, H-6), 4.50 (0.5H, td, J 9.5, 2.0 Hz, 0.5H of pipH-3), 4.13 (1H, m, pipH-4), 3.88 (3H, s, OCH3), 3.84 (1H, m, 1H of BzpipH-2, H-6), 3.53 (1H, m, BzpipH-4), 3.52, 3.46 (2H, 2d AB system, J 13.0 Hz, $CH_2C_6H_3FMe$), 3.28-3.15 (2H, m, 1H of pipH-2, 1H of BzpipH-2, H-6), 3.11 (1H, m, 1H of BzpipH-2, H-6), 2.82 (1H, m, 1H of pipH-6), 2.25 (3H, d, J 1.5 Hz, ArCH3), 2.22-2.11 (3H, m, 1H of pipH-2, 1H of pipH-5, 1H of pipH-6), 2.20 (1H, m, 1H of BzpipH-3, H-5), 1.93-1.80 (3H, m, 3H of BzpipH-3, H-5), 1.65 (1H, m, 1H of pipH-5); $^{19}$F nmr ($CDCl_3$) δ −119.8, −188.4 (d, J 52.5 Hz); m/z: 591 [M+H]$^+$.

Compound 7-38: $^1$H nmr ($CDCl_3$) δ 8.90 (1H, m, pyH-6), 8.11 (1H, dd, J 8.5, 2.0 Hz, pyH-4), 7.81 (1H, s, BzimidH-2), 7.57 (2H, d, J 8.5 Hz, 2H of $C_6H_4CN$), 7.56 (1H, d, J 8.0 Hz, pyH-3), 7.43 (2H, d, J 8.5 Hz, 2H of $C_6H_4CN$), 7.31 (1H, d, J 2.0 Hz, BzimidH-4), 7.29 (1H, d, J 8.5 Hz, BzimidH-7), 6.98 (1H, dd, J 9.0, 2.0 Hz, BzimidH-6), 6.64 (1H, d, J 8.0 Hz, NH), 4.61 (1H, m, PhOpipH-4), 4.02 (1H, m, pipH-4), 3.91 (2H, m, 2H of PhOpipH-2, H-6), 3.82 (3H, s, $BzimidCH_3$), 3.73 (1H, m, 1H of PhOpipH-2, H-6), 3.55 (2H, s, C$\underline{H}_2C_6H_4CN$), 3.43 (1H, m, 1H of PhOpipH-2, H-6), 2.83 (2H, m, 2H of pipH-2, H-6), 2.19 (2H, dd, J 12.5, 9.5 Hz, 2H of pipH-2, H-6), 2.10-1.95 (4H, m, 2H of pipH-3, H-5, 2H of PhOpipH-3, H-5), 1.85 (2H, m, 2H of PhOpipH-3, H-5), 1.63 (2H, m, 2H of pipH-3, H-5); m/z: 578 [M+H]$^+$.

Compound 7-39: $^1$H nmr ($CDCl_3$) δ 8.90 (1H, m, pyH-6), 8.11 (1H, dd, J 8.0, 2.0 Hz, pyH-4), 7.80 (1H, s, BzimidH-2), 7.57 (1H, d, J 8.0 Hz, pyH-3), 7.35-7.29 (4H, m, 2H of $C_6H_4OCF_3$, BzimidH-4, H-7), 7.14 (2H, d, J 8.0 Hz, 2H of $C_6H_4OCF_3$), 6.98 (1H, dd, J 9.0, 2.0 Hz, BzimidH-6), 6.60 (2H, d, J 8.0 Hz, NH), 4.61 (1H, m, PhOpipH-4), 4.01 (1H, m, pipH-4), 3.95-3.88 (2H, m, 2H of PhOpipH-2, H-6), 3.81 (3H, s, $BzimidCH_3$), 3.72 (1H, m, 1H of PhOpipH-2, H-6), 3.50 (2H, s, C$\underline{H}_2C_6H_4OCF_3$), 3.43 (1H, m, 1H of PhOpipH-2, H-6), 2.85 (2H, m, 2H of pipH-2, H-6), 2.17 (2H, t, J 11.5 Hz, 2H of pipH-2, H-6), 2.10-1.83 (6H, m, 2H of pipH-3, H-5, PhOpipH-3, H-5), 1.61 (2H, m, 2H of pipH-3, H-5); $^{19}$F nmr ($CDCl_3$) δ −57.9; m/z: 638 [M+H]$^+$.

Compound 7-40: $^1$H nmr ($CDCl_3$) δ 8.99 (1H, d, J 2.0 Hz, pyH-6), 8.11 (1H, dd, J 8.0, 2.0 Hz, pyH-4), 7.80 (1H, s, BzimidH-2), 7.58 (1H, d, J 8.0 Hz, pyH-3), 7.30 (1H, d, J 2.0 Hz, BzimidH-4), 7.27 (1H, m, BzimidH-7), 7.22 (2H, d, J 8.5 Hz, 2H of $C_6\underline{H}_4OCH_3$), 6.98 (1H, dd, J 9.0, 2.0 Hz, BzimidH-6), 6.84 (2H, d, J 9.0 Hz, 2H of $C_6H_4OCH_3$), 6.53 (1H, d, J 8.0 Hz, NH), 4.60 (1H, m, PhOpipH-4), 4.00 (1H, m, pipH-4), 3.95-3.87 (2H, m, 2H of PhOpipH-2, H-6), 3.81 (3H, s, $OCH_3$ or $BzimidCH_3$), 3.89 (3H, s, $OCH_3$ or $BzimidCH_3$), 3.72 (1H, m, 1H of PhOpipH-2, H-6), 3.45 (2H, s, C$\underline{H}_2C_6H_4OCH_3$), 3.40 (1H, m, 1H of PhOpipH-2, H-6), 2.86 (2H, m, 2H of pipH-2, H-6), 2.14 (2H, t, J 11.5 Hz, 2H of pipH-2, H-6), 2.02-1.87 (6H, m, 2H of pipH-3, H-5, PhOpipH-3, H-5), 1.60 (2H, m, 2H of pipH-3, H-5); m/z: 583 [M+H]$^+$.

Compound 7-41: $^1$H nmr ($CDCl_3$) δ 8.90 (1H, d, J 2.0 Hz, pyH-6), 8.08 (1H, dd, J 8.0, 2.0 Hz, pyH-4), 7.94 (2H, d, J 9.0 Hz, 2H of $C_6\underline{H}_4OCH_3$), 7.92 (1H, m, pyrrazoleH-3 or H-5), 7.17 (1H, d, J 2.0 Hz, pyrazzoleH-3 or H-5), 7.64 (2H, d, J 8.5 Hz, 2H of $C_6H_4$pyrrazole), 7.51 (1H, d, J 8.0 Hz, pyH-3), 7.38 (2H, d, J 8.5 Hz, 2H of $C_6H_4$pyrrazole), 7.19 (1H, d, J 7.5 Hz, NH), 6.95 (2H, d, J 8.5 Hz, 2H of $C_6\underline{H}_4OCH_3$), 6.46 (1H, dd, J 2.0, 1.5 Hz, pyrrazoleH-4), 4.68 (1.5H, m, 0.5H of pipH-3, 1H of BzpipH-2, H-6), 4.55 (0.5H, dt, J 4.5, 9.5 Hz, 0.5H of pipH-3), 4.15 (1H, m, pipH-4), 3.87 (3H, s, $OCH_3$), 3.84 (1H, m, 1H of BzpipH-2, H-6), 3.64, 3.57 (2H, 2d AB system, J 13.5 Hz, C$\underline{H}_2C_6H_4$), 3.53 (1H, m, BzpipH-4), 3.22 (2H, m, 1H of pipH-2, 1H of BzpipH-2, H-6), 3.12 (1H, m, 1H of BzpipH-2, H-6), 2.85 (1H, m, 1H of pipH-6), 2.27-2.15 (3H, m, 1H of pipH-2, 1H of pipH-5, 1H of pipH-6), 2.02 (1H, m, 1H of BzpipH-3, H-5), 1.93-1.80 (3H, m, 3H of BzpipH-3, H-5), 1.65 (1H, m, 1H of pipH-5); $^{19}$F nmr ($CDCl_3$) δ −188.4 (d, J 46.5 Hz); m/z: 625 [M+H]$^+$.

Compound 7-42: $^1$H nmr ($CDCl_3$) δ 8.89 (1H, m, pyH-6), 8.09 (1H, dd, J 8.0, 2.0 Hz, pyH-4), 7.93 (2H, d, J 9.0 Hz, 2H of $C_6\underline{H}_4OCH_3$), 7.84 (1H, s, 1H of imid), 7.55 (1H, dd, J 8.0, 5.0 Hz, NH), 7.48 (1H, d, J 8.0 Hz, pyH-3), 7.42 (2H, d, J 9.0

Hz, 2H of $C_6H_4$imid), 7.33 (2H, d, J 8.5 Hz, 2H of $C_6H_4$imid), 7.27 (1H, m, 1H of imid), 7.19 (1H, s, 1H of imid), 6.95 (2H, d, J 9.0 Hz, 2H of $C_6\underline{H}_4OCH_3$), 4.69 (1.5H, m, 0.5H of pipH-3, 1H of BzpipH-2, H-6), 4.53 (0.5H, m, 0.5H of pipH-3), 4.16 (1H, m, pipH-4), 3.87 (3H, s, $OCH_3$), 3.82 (1H, m, 1H of BzpipH-2, H-6), 3.65, 3.58 (2H, 2d AB system, J 13.5 Hz, $C\underline{H}_2C_6H_4$), 3.54 (1H, m, BzpipH-4), 3.23 (2H, m, 1H of pipH-2, 1H of BzpipH-2, H-6), 3.11 (1H, m, 1H of BzpipH-2, H-6), 2.85 (1H, m, 1H of pipH-6), 2.28-2.16 (3H, m, 1H of pipH-2, 1H of pipH-5, 1H of pipH-6), 2.01 (1H, m, 1H of BzpipH-3, H-5), 1.93-1.82 (3H, m, 3H of BzpipH-3, H-5), 1.68 (1H, m, 1H of pipH-5); $^{19}F$ nmr ($CDCl_3$) δ –188.4 (d, J 45.5 Hz); m/z: 626 [M+H]$^+$ (found [M+H]$^+$, 614.2202, $C_{33}H_{29}F_2N_5O_5$ requires [M+H]$^+$614.2210).

Compound 7-43: $^1H$ nmr ($CDCl_3$) δ 8.88 (1H, m, pyH-6), 8.09 (1H, dd, J 8.0, 2.0 Hz, pyH-4), 7.94 (2H, d, J 9.0 Hz, 2H of $C_6\underline{H}_4OCH_3$), 7.52 (1H, d, J 8.0 Hz, pyH-3), 7.14 (1H, m, NH); 7.03-6.92 (4H, m, 2H of $C_6\underline{H}_4OCH_3$, 2H of $C_6\underline{H}_3(F)OCH_3$), 6.81 (1H, m, 1H of $C_6\underline{H}_3(F)OCH_3$), 4.68 (1.5H, m, 0.5H of pipH-3, 1H of BzpipH-2, H-6), 4.50 (0.5H, dt, J 5.0, 9.5 Hz, 0.5H of pipH-3), 4.15 (1H, m, pipH-4), 3.88 (6H, s, 2×$OCH_3$), 3.86 (1H, m, 1H of BzpipH-2, H-6), 3.55, 3.50 (2H, 2d AB system, J 13.0 Hz, $C\underline{H}_2C_6H_3(F)OCH_3$), 3.28-3.16 (2H, m, 1H of pipH-2, 1H of BzpipH-2, H-6), 3.11 (1H, m, 1H of BzpipH-2, H-6), 2.83 (1H, m, 1H of pipH-6), 2.24-2.13 (3H, m, 1H of pipH-2, 1H of pipH-5, 1H of pipH-6), 2.02 (1H, m, 1H of BzpipH-3, H-5), 1.94-1.80 (3H, m, 3H of BzpipH-3, H-5), 1.65 (1H, m, 1H of pipH-5); $^{19}F$ nmr ($CDCl_3$) δ –137.2, –188.4 (d, J 49.0 Hz); m/z: 607 [M+H]$^+$.

Compound 7-44: $^1H$ nmr ($CDCl_3$) δ 8.88 (1H, m, pyH-6), 8.06 (1H, d, J 8.5 Hz, pyH-4), 7.94 (2H, d, J 9.0 Hz, 2H of $C_6\underline{H}_4OCH_3$), 7.45 (1H, d, J 8.0 Hz, pyH-3), 7.43 (1H, d, J 7.0 Hz, NH), 7.06 (1H, d, J 12.0 Hz, $C_6H_3(F)OCH_3$-2), 6.98-6.94 (3H, m, 2H of $C_6\underline{H}_4OCH_3$, $C_6H_3(F)OCH_3$-6), 6.89 (1H, t, J 8.5 Hz, $C_6H_3(F)OCH_3$-5), 4.68 (1.5H, m, 0.5H of pipH-3, 1H of BzpipH-2, H-6), 4.51 (0.5H, dt, J 4.5, 9.5 Hz, 0.5H of pipH-3), 4.14 (1H, m, pipH-4), 3.87 (6H, 2s, 2×$OCH_3$), 3.83 (1H, m, 1H of BzpipH-2, H-6), 3.53, 3.46 (2H, 2d AB system, J 13.0 Hz, $C\underline{H}_2C_6H_3(F)OCH_3$), 3.53 (1H, m, BzpipH-4), 3.27-3.17 (2H, m, 1H of pipH-2, 1H of BzpipH-2, H-6), 3.12 (m, 1H of BzpipH-2, H-6), 2.81 (1H, m, 1H of pipH-6), 2.22-2.11 (3H, m, 1H of pipH-2, 1H of pipH-5, 1H of pipH-6), 2.02 (1H, m, 1H of BzpipH-3, H-5), 1.93-1.76 (3H, m, 3H of BzpipH-3, H-5), 1.65 (1H, m, 1H of pipH-5); $^{19}F$ nmr ($CDCl_3$) δ –135.4, –188.4 (d, J 51.0 Hz); m/z: 607 [M+H]$^+$.

Compound 7-45: $^1H$ nmr ($CDCl_3$) δ 8.89 (1H, d, J 2.0 Hz, pyH-6), 8.09 (1H, dd, J 8.5, 2.0 Hz, pyH-4), 7.94 (2H, d, J 9.0 Hz, 2H of $C_6\underline{H}_4OCH_3$), 7.56 (1H, d, J 7.0 Hz, $C_6H_3(F)CF_3H$-2), 7.52 (1H, d, J 8.5 Hz, pyH-3), 7.48 (1H, m, $C_6H_3(F)CF_3H$-6), 7.14 (1H, t, J 9.5 Hz, $C_6H_3(F)CF_3H$-5), 7.08 (1H, d, J 7.5 Hz, NH), 6.96 (2H, d, J 9.0 Hz, 2H of $C_6\underline{H}_4OCH_3$), 4.68 (1.5H, m, 0.5H of pipH-3, 1H of BzpipH-2, H-6), 4.51 (0.5H, dt, J 5.0, 9.5 Hz, 0.5H of pipH-3), 4.16 (1H, m, pipH-4), 3.88 (3H, s, $OCH_3$), 3.86 (1H, m, 1H of BzpipH-2, H-6), 3.61, 3.55 (2H, 2d AB system, J 13.5 Hz, $C\underline{H}_2C_6H_3(F)CF_3$), 3.53 (1H, m, BzpipH-4), 3.28-3.16 (2H, m, 1H of pipH-2, 1H of BzpipH-2, H-6), 3.12 (1H, m, 1H of BzpipH-2, H-6), 2.81 (1H, m, 1H of pipH-6), 2.29-2.17 (3H, m, 1H of pipH-2, 1H of pipH-5, 1H of pipH-6), 2.02 (1H, m, 1H of BzpipH-3, H-5), 1.92-1.80 (3H, m, 3H of BzpipH-3, H-5), 1.64 (1H, m, 1H of pipH-5); $^{19}F$ nmr ($CDCl_3$) δ –61.3, –116.6, –188.6 (d, J 55.0 Hz); m/z: 645 [M+H]$^+$.

Compound 7-46: $^1H$ nmr ($CD_3OD$ and $CDCl_3$) δ 9.05 (1H, m, N, O-pyH-6), 8.38 (1H, m, pyH-6), 8.31 (2H, m, N, O-pyH-4, pyH-4), 7.98 (2H, d, J 9.0 Hz, 2H of $C_6H_4Ac$), 7.80 (1H, s, BzimidH-2), 7.63 (1H, m, J 8.0 Hz, pyH-3), 7.27 (2H, m, BzimidH-4, H-7), 7.15 (2H, d, J 9.0 Hz, 2H of $C_6H_4Ac$), 6.99 (2H, m, N, O-pyH-3, BzimidH-6), 4.62 (1H, m, PhOpipH-4), 3.89 (2H, m, 2H of PhOpipH-2, H-6), 3.38 (2H, m, 2H of PhOpipH-2, H-6), 2.20 (3H, s, $COCH_3$), 1.22 (4H, m, PhOpipH-3, H-5); m/z: 591 [M+H]$^+$ (found [M+H]$^+$, 591.2322, $C_{33}H_{30}N_6O_5$ requires [M+H]$^+$591.2351).

Compound 7-47: $^1H$ nmr ($CDCl_3$) δ 8.88 (1H, d, J 2.0 Hz, pyH-6), 8.08 (1H, dd, J 8.0, 2.0 Hz, pyH-4), 7.96 (1H, d, J 9.5 Hz, $C_6H_3MeSO_2MeH$-5), 7.51 (1H, d, J 8.5 Hz, pyH-3), 7.33 (2H, d, J 9.0 Hz, 2H of $C_6H_4OCF_3$), 7.16 (2H, d, J 8.5 Hz, 2H of $C_6H_4OCF_3$, NH or $C_6H_3MeSO_2MeH$-2 or H-6), 6.85 (2H, m, 2H of NH, $C_6H_3MeSO_2MeH$-2, H-6), 4.71 (1H, m, PhOpipH-4), 4.67 (0.5H, m, 0.5H of pipH-3), 4.50 (0.5H, td, J 9.5, 5.0 Hz, 0.5H of pipH-3), 4.14 (1H, m, pipH-4), 3.94 (1H, m, 1H of PhOpipH-2, H-6), 3.88 (1H, m, 1H of PhOpipH-2, H-6), 3.65 (1H, m, 1H of PhOpipH-2, H-6), 3.61, 3.54 (2H, 2d AB system, J 13.5 Hz, $C\underline{H}_2C_6H_4OCF_3$), 3.44 (1H, m, 1H of PhOpipH-2, H-6), 3.21 (1H, m, 1H of pipH-2 or pipH-6), 3.05 (3H, s, $SO_2CH_3$), 2.83 (1H, m, 1H of pipH-2 or pipH-6), 2.66 (3H, s, $C_6H_3C\underline{H}_3SO_2CH_3$), 2.26-2.11 (3H, m, 1H of pipH-2, 1H of pipH-5, 1H of pipH-6), 2.10-1.93 (3H, m, 3H of PhOpipH-3, H-5), 1.85 (1H, m, 1H of PhOpipH-3, H-5), 1.65 (1H, m, 1H of pipH-5); $^{19}F$ nmr ($CDCl_3$) δ –57.9, –188.4 (d, J 51.0 Hz); m/z: 694 [M+H]$^+$.

Compound 7-48: $^1H$ nmr ($CDCl_3$) δ 8.88 (1H, d, J 2.0 Hz, pyH-6), 8.09 (1H, dd, J 8.0, 2.0 Hz, pyH-4), 7.82 (2H, d, J 9.0 Hz, 2H of $C_6H_4SO_2cPr$), 7.52 (1H, d, J 8.0 Hz, pyH-3), 7.33 (2H, d, J 9.0 Hz, 2H of $C_6H_4OCF_3$), 7.15 (3H, m, 2H of $C_6H_4OCF_3$, NH), 7.02 (2H, d, J 9.0 Hz, 2H of $C_6H_4SO_2cPr$), 4.73 (1H, m, PhOpipH-4), 4.67 (0.5H, td, J 9.5, 5.0 Hz, 0.5H of pipH-3), 4.50 (0.5H, td, J 9.5, 5.0 Hz, 0.5H of pipH-3), 4.14 (1H, m, pipH-4), 3.92 (2H, m, 2H of PhOpipH-2, H-6), 3.67 (1H, m, 1H of PhOpipH-2, H-6), 3.61, 3.54 (2H, 2d AB system, J 13.5 Hz, $C\underline{H}_2C_6H_4OCF_3$), 3.45 (1H, m, 1H of PhOpipH-2, H-6), 3.21 (1H, m, 1H of pipH-2 or pipH-6), 2.82 (1H, m, 1H of pipH-2 or pipH-6), 2.43 (1H, m, cPrH-1), 2.26-2.14 (3H, m, 1H of pipH-2, 1H of pipH-5, 1H of pipH-6), 2.10-1.94 (3H, m, 3H of PhOpipH-3, H-5), 1.87 (1H, m, 1H of PhOpipH-3, H-5), 1.65 (1H, m, 1H of pipH-5), 1.32 (2H, m, 2H of cPrH-2, H-3), 1.01 (2H, m, 2H of cPrH-2, H-3); $^{19}F$ nmr ($CDCl_3$) δ –57.9, –188.4 (d, J 49.0 Hz); m/z: 706 [M+H]$^+$.

Compound 7-49: $^1H$ nmr ($CDCl_3$) δ 8.90 (1H, d, J 2.0 Hz, pyH-6), 8.10 (1H, dd, J 8.5, 2.0 Hz, pyH-4), 7.87 (2H, d, J 9.0 Hz, 2H of $C_6\underline{H}_4SO_2CH_3$), 7.57 (1H, d, J 8.5 Hz, pyH-3), 7.33 (2H, d, J 8.5 Hz, 2H of $C_6H_4OCF_3$), 7.17 (2H, d, J 8.0 Hz, 2H of $C_6H_4OCF_3$), 7.03 (2H, d, J 9.0 Hz, 2H of $C_6\underline{H}_4SO_2CH_3$), 6.92 (1H, d, J 8.0 Hz, NH), 4.74 (1H, m, PhOpipH-4), 4.57 (1H, dtd, J 50.0, 9.5, 5.0 Hz, pipH-3), 4.15 (1H, m, pipH-4), 3.92 (2H, m, 2H of PhOpipH-2, H-6), 3.68 (1H, m, 1H of PhOpipH-2, H-6), 3.62, 3.54 (2H, 2d AB system, J 13.5 Hz, $C\underline{H}_2C_6H_4OCF_3$), 3.48 (1H, m, 1H of PhOpipH-2, H-6), 3.21 (1H, m, 1H of pipH-2 or pipH-6), 3.03 (3H, s, $SO_2CH_3$), 2.83 (1H, m, 1H of pipH-2 or pipH-6), 2.27-2.15 (3H, m, 1H of pipH-2, 1H of pipH-5, 1H of pipH-6), 2.12-1.94 (3H, m, 3H of PhOpipH-3, H-5), 1.88 (1H, m, 1H of PhOpipH-3, H-5), 1.65 (1H, m, 1H of pipH-5); $^{19}F$ nmr ($CDCl_3$) δ –57.9, –188.5 (d, J 48.5 Hz); m/z: 680 [M+H]$^+$.

Compound 7-50: $^1H$ nmr ($CDCl_3$) δ 8.88 (1H, d, J 2.0 Hz, pyH-6), 8.09 (1H, dd, J 8.0, 2.0 Hz, pyH-4), 7.96 (2H, d, J 9.5 Hz, 2H of $C_6H_4SO_2CF_3$), 7.54 (1H, d, J 8.0 Hz, pyH-3), 7.34 (2H, d, J 8.5 Hz, 2H of $C_6H_4OCF_3$), 7.17 (2H, d, J 8.5 Hz, 2H of $C_6H_4OCF_3$), 7.11 (3H, m, 2H of $C_6H_4SO_2CF_3$, NH), 4.79 (1H, m, PhOpipH-4), 4.58 (1H, dtd, J 50.0, 9.5, 5.0 Hz, pipH-3), 4.13 (1H, m, pipH-4), 3.94 (2H, m, 2H of PhOpipH-2, H-6), 3.68 (1H, m, 1H of PhOpipH-2, H-6), 3.61, 3.54 (2H, 2d AB system, J 13.5 Hz, $C\underline{H}_2C_6H_4OCF_3$), 3.49 (1H, m, 1H of PhOpipH-2, H-6), 3.21 (1H, m, 1H of pipH-2 or H-6), 2.83

(1H, m, 1H of pipH-2 or H-6), 2.26-2.14 (3H, m, 1H of pipH-2, 1H of pipH-5, 1H of pipH-6), 2.10-1.97 (3H, m, 3H of PhOpipH-3, H-5), 1.90 (1H, m, 1H of PhOpipH-3, H-5), 1.64 (1H, m, 1H of pipH-5); $^{19}$F nmr (CDCl$_3$) δ −57.9, −78.8, −188.5 (d, 47.5 Hz); m/z: 734 [M+H]$^+$.

Compound 7-51: $^1$H nmr (CDCl$_3$) δ 8.88 (1H, m, pyH-6), 8.08 (1H, dd, J 8.0, 2.0 Hz, pyH-4), 7.68 (1H, d, J 9.0 Hz, BzthiazoleH-7), 7.52 (1H, d, J 8.0 Hz, pyH-3), 7.47 (1H, d, J 2.0 Hz, BzthiazoleH-4), 7.32 (2H, d, J 9.0 Hz, 2H of C$_6$H$_4$OCF$_3$), 7.16 (2H, d, J 8.0 Hz, 2H of C$_6$H$_4$OCF$_3$), 7.07 (1H, d, J 7.5 Hz, NH), 7.00 (1H, dd, J 9.0, 2.0 Hz, BzthiazoleH-6), 4.67 (1.5H, m, 0.5H of pipH-3, PhOpipH-4), 4.50 (0.5H, td, J 9.5, 5.0 Hz, 0.5H of pipH-3), 4.15 (1H, m, pipH-4), 3.93 (2H, m, 2H of PhOpipH-2, H-6), 3.70 (1H, m, 1H of PhOpipH-2, H-6), 3.61, 3.54 (2H, 2d AB system, J 13.5 Hz, CH$_2$C$_6$H$_4$OCF$_3$), 3.44 (1H, m, 1H of PhOpipH-2, H-6), 3.21 (1H, m, 1H of pipH-2 or pipH-6), 2.83 (1H, m, 1H of pipH-2 or pipH-6), 2.81 (3H, s, BzthiazoleCH$_3$), 2.26-2.14 (3H, m, 1H of pipH-2, 1H of pipH-5, 1H of pipH-6), 2.12-1.97 (3H, m, 3H of PhOpipH-3, H-5), 1.89 (1H, m, 1H of PhOpipH-3, H-5), 1.65 (1H, m, 1H of pipH-5); $^{19}$F nmr (CDCl$_3$) δ −57.9, −188.5 (d, J 52.5 Hz); m/z: 673 [M+H]$^+$.

Compound 7-52: $^1$H nmr (CDCl$_3$) δ 8.89 (1H, m, pyH-6), 8.09 (1H, dd, J 8.0, 2.0 Hz, pyH-4), 7.94 (2H, d, J 9.0 Hz, 2H of C$_6$H$_4$Ac), 7.53 (1H, d, J 8.5 Hz, pyH-3), 7.33 (2H, d, J 9.0 Hz, 2H of C$_6$H$_4$OCF$_3$), 7.16 (2H, d, J 8.5 Hz, 2H of C$_6$H$_4$OCF$_3$), 7.06 (1H, d, J 7.5 Hz, NH), 6.95 (2H, d, J 9.0 Hz, 2H of C$_6$H$_4$Ac), 4.73 (1H, m, PhOpipH-4), 4.57 (1H, dtd, J 50.0, 9.5, 5.0 Hz, pipH-3), 4.15 (1H, m, pipH-4), 3.95 (1H, m, 1H of PhOpipH-2, H-6), 3.89 (1H, m, 1H of PhOpipH-2, H-6), 3.68 (1H, m, 1H of PhOpipH-2, H-6), 3.61, 3.54 (2H, 2d AB system, J 13.5 Hz, CH$_2$C$_6$H$_4$OCF$_3$), 3.46 (1H, m, 1H of PhOpipH-2, H-6), 3.21 (1H, m, 1H of pipH-2 or pipH-6), 2.83 (1H, m, 1H of pipH-2 or pipH-6), 2.55 (3H, s, COCH$_3$), 2.26-2.15 (3H, m, 1H of pipH-2, 1H of pipH-5, 1H of pipH-6), 2.10-1.95 (3H, m, 3H of PhOpipH-3, H-5), 1.87 (1H, m, 1H of PhOpipH-3, H-5), 1.65 (1H, m, 1H of pipH-5); $^{19}$F nmr (CDCl$_3$) δ −57.9, −188.5 (d, J 51.0 Hz); m/z: 643 [M+H]$^+$.

Compound 7-53: $^1$H nmr (CDCl$_3$) δ 8.87 (1H, m, pyH-6), 8.06 (1H, dd, J 8.0, 2.0 Hz, pyH-4), 7.89 (2H, d, J 9.0 Hz, 2H of C$_6$H$_4$morpholine), 7.45 (1H, d, J 8.0 Hz, pyH-3), 7.43 (1H, m, NH), 7.32 (2H, d, J 8.5 Hz, 2H of C$_6$H$_4$OCF$_3$), 7.15 (2H, d, J 8.0 Hz, 2H of C$_6$H$_4$OCF$_3$), 6.88 (2H, d, J 9.0 Hz, 2H of C$_6$H$_4$morpholine), 4.68 (1.5H, m, 0.5H of pipH-3, 1H of BzpipH-2, H-6), 4.53 (0.5H, td, J 9.5, 5.0 Hz, 0.5H of pipH-3), 4.15 (1H, m, pipH-4), 3.86, 3.84 (4H, 2d AB system, J 5.0 Hz, 4H of morpholine), 3.81 (1H, m, 1H of BzpipH-2, H-6), 3.60, 3.53 (2H, 2d AB system, J 13.5 Hz, CH$_2$C$_6$H$_4$OCF$_3$), 3.51 (1H, m, BzpipH-4), 3.32, 3.30 (4H, 2d AB system, J 5.0 Hz, 4H of morpholine), 3.11 (1H, m, 1H of pipH-2), 2.82 (1H, m, 1H of pipH-6), 2.25-2.12 (3H, m, 1H of pipH-2, 1H of pipH-5, 1H of pipH-6), 1.98 (1H, m, 1H of BzpipH-3, H-5), 1.90-1.74 (3H, m, 3H of BzpipH-3, H-5), 1.67 (1H, m, 1H of pipH-5); $^{19}$F nmr (CDCl$_3$) δ −57.8, −188.4 (d, J 50.0 Hz); m/z: 699 [M+H]$^+$.

Compound 7-54: $^1$H nmr (CDCl$_3$) δ 8.89 (1H, m, pyH-6), 8.09 (1H, dd, J 8.0, 2.0 Hz, pyH-4), 8.06 (2H, d, J 8.5 Hz, 2H of C$_6$H$_4$pyrrazole), 8.02 (1H, d, J 2.5 Hz, pyrazoleH-3 or H-5), 7.84 (2H, d, J 9.0 Hz, 2H of C$_6$H$_4$pyrrazole), 7.78 (1H, d, J 2.0 Hz, pyrrazoleH-3 or H-5), 7.74 (1H, d, J 8.0 Hz, pyH-3), 7.33 (2H, d, J 8.5 Hz, 2H of C$_6$H$_4$OCF$_3$), 7.16 (2H, d, J 8.0 Hz, 2H of C$_6$H$_4$OCF$_3$), 7.07 (1H, d, J 8.0 Hz, NH), 6.53 (1H, dd, J 2.5, 2.0 Hz, pyrrazoleH-4), 4.69 (1H, m, 1H of BzpipH-2, H-6), 4.59 (1H, dtd, J 50.0, 9.5, 5.0 Hz, pipH-3), 4.15 (1H, m, pipH-4), 3.90 (1H, m, 1H of BzpipH-2, H-6), 3.61, 3.54 (3H, 2d AB system, J 13.5 Hz, CH$_2$C$_6$H$_4$OCF$_3$, BzpipH-4), 3.31-3.11 (3H, m, 1H of pipH-2, 2H of BzpipH-2, H-6), 2.83 (1H, m, 1H of pipH-6), 2.26-2.15 (3H, m, 1H of pipH-2, 1H of pipH-5, 1H of pipH-6), 2.07 (1H, m, 1H of BzpipH-3, H-5), 1.98-1.82 (3H, m, 3H of BzpipH-3, H-5), 1.67 (1H, m, 1H of pipH-5); $^{19}$F nmr (CDCl$_3$) δ −57.9, −188.5 (d, J 54.5 Hz); m/z: 680 [M+H]$^+$.

Compound 7-55: $^1$H nmr (CDCl$_3$) δ 8.89 (1H, m, pyH-6), 8.07 (1H, d, J 8.0 Hz, pyH-4), 7.94 (2H, d, J 9.5 Hz, 2H of C$_6$H$_4$OCH$_3$), 7.54 (2H, m, NH, C$_6$H$_3$(CN)OCH$_3$H-2), 7.45 (2H, m, pyH-3, C$_6$H$_3$(CN)OCH$_3$H-5 or H-6), 6.95 (2H, d, J 9.0 Hz, 2H of C$_6$H$_4$OCH$_3$), 6.92 (1H, d, J 8.5 Hz, C$_6$H$_3$(CN)OCH$_3$H-5 or H-6), 4.70 (1.5H, m, 0.5H of pipH-3, 1H of BzpipH-2, H-6), 4.52 (0.5H, td, J 9.5, 5.0 Hz, 0.5H of pipH-3), 4.15 (1H, m, pipH-4), 3.91 (3H, s, 1×OCH$_3$), 3.87 (3H, s, 1×OCH$_3$), 3.83 (1H, m, 1H of BzpipH-2, H-6), 3.57 (1H, m, 1H of BzpipH-4), 3.54, 3.48 (2H, 2d AB system, J 13.5 Hz, CH$_2$C$_6$H$_4$OCF$_3$), 3.28-3.09 (3H, m, 1H of pipH-2, 2H of BzpipH-2, H-6), 2.79 (1H, m, 1H of pipH-6), 2.24 (3H, m, 1H of pip H-2, 1H of pipH-5, 1H of pipH-6), 2.03 (1H, m, 1H of BzpipH-3, H-5), 1.93-1.78 (3H, m, 3H of BzpipH-3, H-5), 1.67 (1H, m, 1H of pipH-5); $^{19}$F nmr (CDCl$_3$) δ −188.4 (d, J 47.5 Hz); m/z: 614 [M+H]$^+$.

Compound 7-56: $^1$H nmr (CDCl$_3$) δ 8.87 (1H, d, J 2.0 Hz, pyH-3), 8.06 (1H, dd, J 8.5, 2.0 Hz, pyH-4), 7.94 (2H, d, J 9.0 Hz, 2H of C$_6$H$_4$OCH$_3$), 7.46 (1H, d, J 8.5 Hz, pyH-3), 7.41 (2H, m, C$_6$H$_3$(CN)CH$_3$H-3, H-5 or H-6), 7.38 (2H, m, NH, C$_6$H$_3$(CN)CH$_3$H-5 or H-6), 6.96 (2H, d, J 9.0 Hz, 2H of C$_6$H$_4$OCH$_3$), 4.77 (1.5H, m, 0.5H of pipH-3, 1H of BzpipH-2, H-6), 4.50 (0.5H, td, J 9.5, 5.0 Hz, 0.5H of pipH-3), 4.16 (1H, m, pipH-4), 3.88 (3H, s, OCH$_3$), 3.84 (1H, m, 1H of BzpipH-2, H-6), 3.60, 3.53 (2H, 2d AB system, J 13.5 Hz, CH$_2$C$_6$H$_4$OCF$_3$), 3.53 (1H, m, BzpipH-4), 3.28-3.07 (3H, m, 1H of pipH-2, 2H of BzpipH-2, H-6), 2.79 (1H, m, 1H of pipH-6), 2.36 (3H, s, ArCH$_3$), 2.32-2.12 (3H, m, 1H of pipH-2, 1H of pipH-5, 1H of pipH-6), 2.00 (1H, m, 1H of BzpipH-3, H-5), 1.93-1.78 (3H, m, 3H of BzpipH-3, H-5), 1.65 (1H, m, 1H of pipH-5); $^{19}$F nmr (CDCl$_3$) δ −188.5 (d, J 50.0 Hz); m/z: 598 [M+H]$^+$.

Compound 7-57 (as its trifluoroacetic acid salt): $^1$H nmr (CDCl$_3$) δ 8.96 (1H, m, pyH-6), 8.17 (1H, dd, J 8.0, 2.0 Hz, pyH-4), 7.93 (1H, m, NH), 7.86 (2H, d, J 9.0 Hz, 2H of C$_6$H$_4$pyrrolidine), 7.56 (1H, d, J 8.0 Hz, pyH-3), 7.51 (2H, d, J 9.0 Hz, 2H of C$_6$H$_4$OCF$_3$), 7.30 (2H, d, J 8.0 Hz, 2H of C$_6$H$_4$OCF$_3$), 6.53 (2H, d, J 9.0 Hz, 2H of C$_6$H$_4$pyrrolidine), 5.09 (1H, m, pipH-3), 4.66 (1H, m, 1H of BzpipH-2, H-6), 4.45 (1H, m, pipH-4), 4.25 (2H, s, CH$_2$C$_6$H$_4$OCF$_3$), 3.79 (2H, m, 2H of pipH-2, pipH-6, BzpipH-2, H-4, H-6), 3.52 (2H of pipH-2, pipH-6, BzpipH-2, H-4, H-6), 3.37 (4H, m, 4H of pyrrolidine), 3.22 (1H, m, 1H of BzpipH-2, H-6), 3.08 (1H, of BzpipH-2, H-6), 2.89 (2H, m, 2H of pipH-2, pipH-6), 2.35 (1H, m, 1H of pipH-5, BzpipH-3, H-5), 2.20-1.97 (2H, m, 2H of pipH-5, BzpipH-3, H-5), 2.04 (4H, m, 4H of pyrrolidine), 1.90-1.76 (3H, m, 3H of pipH-5, BzpipH-3, H-5); $^{19}$F nmr (CDCl$_3$) δ −57.9, −75.8 (CF$_3$CO$_2$H), −188.5 (d, J 48.5 Hz); m/z: 683 [M+H]$^+$ (found [M+H]$^+$, 682.2917, C$_{36}$H$_{39}$F$_4$N$_5$O$_4$ requires [M+H]$^+$ 682.3011).

Compound 7-58: $^1$H nmr (CDCl$_3$) δ 8.90 (1H, m, pyH-6), 8.09 (1H, dd, J 8.5, 2.0 Hz, pyH-4), 7.94 (2H, d, J 9.0 Hz, 2H of C$_6$H$_4$OCH$_3$), 7.58 (1H, d, J 2.0 Hz, C$_6$H$_3$(CN)MeH-2), 7.51 (1H, d, J 8.0 Hz, pyH-3), 7.40 (1H, dd, J 8.0, 1.5 Hz, C$_6$H$_3$(CN)MeH-6), 7.26 (1H, d, J 8.0 Hz, C$_6$H$_3$(CN)MeH-5), 7.20 (1H, d, J 6.0 Hz, NH), 6.96 (2H, d, J 9.0 Hz, 2H of C$_6$H$_4$OCH$_3$), 4.69 (1.5H, m, 0.5H of pipH-3, 1H of BzpipH-2, H-6), 4.51 (0.5H, td, J 9.5, 5.0 Hz, 0.5H of pipH-3), 4.16 (1H, m, pipH-4), 3.88 (3H, s, OCH$_3$), 3.86 (1H, m, 1H of BzpipH-2, H-6), 3.59, 3.53 (2H, 2d AB system, J 13.5 Hz, CH$_2$C$_6$H$_4$OCH$_3$), 3.51 (1H, m, BzpipH-4), 3.29-3.10 (3H, m, 1H of pipH-2, 2H of BzpipH-2, H-6), 2.80 (1H, m, pipH-6), 2.52 (3H, s, ArCH$_3$), 2.27-2.12 (3H, m, 1H of pipH-2, 1H of pipH-5, 1H of pipH-6), 2.03 (1H, m, 1H of BzpipH-3, H-5), 1.94-1.78 (3H, m, 3H of BzpipH-3, H-5), 1.65 (1H, m, 1H of pipH-5); $^{19}$F nmr (CDCl$_3$) δ −188.5 (d, J 51.0 Hz); m/z: 598 [M+H]$^+$.

Compound 7-59: $^1$H nmr (CDCl$_3$) δ 8.88 (1H, d, J 2.0 Hz, pyH-6), 8.07 (1H, dd, J 8.0, 2.0 Hz, pyH-4), 7.94 (2H, d, J 8.5 Hz, 2H of C$_6$H$_4$OCH$_3$), 7.52 (1H, d, J 8.0 Hz, pyH-3), 7.49 (1H, d, J 8.5 Hz, C$_6$H$_3$(CN)MeH-5), 7.28-7.22 (3H, m, NH, C$_6$H$_3$(CN)MeH-2, H-6) 6.96 (2H, d, J 9.0 Hz, 2H of C$_6$H$_4$OCH$_3$), 4.69 (1.5H, m, 0.5H of pipH-3, 1H of BzpipH-2, H-6), 4.53 (0.5H, td, J 9.5, 5.0 Hz, 0.5H of pipH-3), 4.15 (1H, m, pipH-4), 3.88 (3H, s, OCH$_3$), 3.83 (1H, m, 1H of BzpipH-2, H-6), 3.61, 3.55 (2H, 2d AB system, J 14.0 Hz, CH$_2$C$_6$H$_4$OCF$_3$), 3.53 (1H, m, BzpipH-4), 3.28-3.07 (3H, m, 1H of pipH-2, 2H of BzpipH-2, H-6), 2.80 (1H, m, 1H of pipH-6), 2.53 (3H, s, ArCH$_3$), 2.28-2.15 (3H, m, 1H of pipH-2, 1H of pipH-5, 1H of pipH-6), 2.02 (1H, m, 1H of BzpipH-2, H-6), 1.94-1.78 (3H, m, 3H of BzpipH-3, H-5), 1.67 (1H, m, 1H of pipH-5); $^{19}$F nmr (CDCl$_3$) δ −188.4 (d, J 46.5 Hz); m/z: 598 [M+H]$^+$.

Compound 7-60: $^1$H nmr (CDCl$_3$) δ 8.91 (1H, m, pyH-6), 8.08 (1H, br d, J 8.5 Hz, pyH-4), 7.95 (2H, d, J 9.0 Hz, 2H of C$_6$H$_4$OCH$_3$), 7.68 (1H, d, J 1.5 Hz, C$_6$H$_3$(CN)OCH$_3$H-2), 7.54 (1H, dd, J 9.0, 2.0 Hz, C$_6$H$_3$(CN)OCH$_3$H-4), 6.95 (2H, d, J 9.0 Hz, 2H of C$_6$H$_4$OCH$_3$), 6.90 (1H, d, J 8.5 Hz, C$_6$H$_3$(CN)OCH$_3$H-5), 4.73 (1.5H, m, 0.5H of pipH-3, 1H of BzpipH-2, H-6), 4.57 (0.5H, m, 0.5H of pipH-3), 4.18 (1H, m, pipH-4), 3.88 (3H, s, 1×OCH$_3$), 3.87 (3H, s, 1×OCH$_3$), 3.84 (1H, m, 1H of BzpipH-2, H-4, H-6), 3.61 (2H, s, CH$_2$C$_6$H$_4$OCF$_3$), 3.56 (1H, m, 1H of BzpipH-2, H-4, H-6), 3.29-3.11 (3H, m, 1H of pipH-2, 2H of BzpipH-2, H-6), 2.83 (1H, m, 1H of pipH-6), 2.34-2.24 (2H, m, 2H of pipH-2, pipH-5, pipH-6), 2.16 (1H of pipH-2, pipH-5, pipH-6), 2.04 (1H, m, 1H of BzpipH-3, H-5), 1.94-1.78 (3H, m, 3H of BzpipH-3, H-5), 1.72 (1H, m, 1H of pipH-5); $^{19}$F nmr (CDCl$_3$) δ −188.4 (d, J 45.5 Hz); m/z: 615 [M+H]$^+$.

Compound 7-61: $^1$H nmr (CDCl$_3$) δ 8.87 (1H, m, pyH-6), 8.12, 8.09 (4H, 2d AB system, J 9.0 Hz, C$_6$H$_4$SO$_2$CH$_3$), 8.07 (1H, m, pyH-4), 7.49 (1H, d, J 8.5 Hz, pyH-3), 7.34 (2H, d, J 9.0 Hz, 2H of C$_6$H$_4$OCF$_3$), 7.17 (2H, d, J 8.5 Hz, 2H of C$_6$H$_4$OCF$_3$), 4.69 (1.5H, m, 0.5H of pipH-3, 1H of BzpipH-2, H-6), 5.52 (0.5H, td, J 9.5, 5.0 Hz, 0.5H of pipH-3), 4.15 (1H, m, pipH-4), 3.87 (1H, m, 1H of BzpipH-2, H-6), 3.62, 3.55 (2H, 2d AB system, J 13.5 Hz, CH$_2$C$_6$H$_4$OCF$_3$), 3.58 (1H, m, BzpipH-4), 3.30-3.15 (3H, m, 1H of pipH-2, 2H of BzpipH-2, H-6), 3.09 (3H, s, SO$_2$CH$_3$), 2.84 (1H, m, 1H of pipH-6), 2.26-2.14 (3H, m, 1H of pipH-2, 1H of pipH-5, 1H of pipH-6), 2.05 (1H, m, 1H of BzpipH-3, H-5), 1.95-1.84 (3H, m, 3H of BzpipH-3, H-5), 1.66 (1H, qd, J 12.5, 3.5 Hz, 1H of pipH-5); $^{19}$F nmr (CDCl$_3$) δ −57.9, −188.3 (d, J 51.0 Hz); m/z: 692 [M+H]$^+$.

Compound 7-62: $^1$H nmr (CDCl$_3$) δ 8.88 (1H, d, J 2.0 Hz, pyH-6), 8.08 (1H, dd, J 8.0, 2.0 Hz, pyH-4), 7.59 (2H, d, J 9.0 Hz, 2H of C$_6$H$_4$CN), 7.52 (1H, d, J 8.5 Hz, pyH-3), 7.33 (2H, d, J 8.5 Hz, 2H of C$_6$H$_4$OCF$_3$), 7.16 (2H, d, J 8.0 Hz, 2H of C$_6$H$_4$OCF$_3$), 7.12 (1H, d, J 8.0 Hz, NH), 6.96 (2H, d, J 9.0 Hz, 2H of C$_6$H$_4$CN), 4.68 (1.5H, m, 0.5H of pipH-3, PhOpipH-4), 4.50 (0.5H, td, J 9.5, 5.0 Hz, 0.5H of pipH-3), 4.15 (1H, m, pipH-4), 3.98-3.84 (2H, m, 2H of PhOpipH-2, H-6), 3.66 (1H, m, 1H of PhOpipH-2, H-6), 3.61, 3.54 (2H, 2d AB system, J 13.5 Hz, CH$_2$C$_6$H$_4$OCF$_3$), 3.46 (1H, m, 1H of PhOpipH-2, H-6), 3.21 (1H, m, 1H of pipH-2), 2.83 (1H, m, 1H of pipH-6), 2.26-2.13 (3H, m, 1H of pipH-2, 1H of pipH-5, 1H of pipH-6), 2.08-1.94 (3H, m, 3H of PhOpipH-3, H-5), 1.86 (1H, m, 1H of PhOpipH-3, H-5), 1.64 (1H, m, 1H of pipH-5); $^{19}$F nmr (CDCl$_3$) δ −57.9, −188.4 (d, J 49.0 Hz); m/z: 626 [M+H]$^+$.

Compound 7-63: $^1$H nmr (CDCl$_3$) δ 8.87 (1H, m, pyH-6), 8.08 (1H, dd, J 8.0, 2.0 Hz, pyH-4), 7.93 (2H, d, J 9.0 Hz, 2H of C$_6$H$_4$OCH$_3$), 7.50 (1H, d, J 8.0 Hz, pyH-3), 7.39 (1H, s, pyrazoleH-3 or H-5), 7.27 (1H, s, pyrazoleH-3 or H-5), 7.21 (1H, d, J 8.5 Hz, NH), 6.95 (2H, d, J 8.5 Hz, 2H of C$_6$H$_4$OCH$_3$), 4.65 (1.5H, m, 0.5H of pipH-3, 1H of BzpipH-2, H-6), 4.48 (0.5H, td, J 9.5, 5.0 Hz, 0.5H of pipH-3), 4.11 (1H, m, pipH-4), 3.87 (3H, s, OCH3), 3.82 (1H, m, 1H of BzpipH-2, H-6), 3.52 (1H, m, 1H of BzpipH-4), 3.51, 3.45 (2H, 2d, J 13.5 Hz, CH$_2$C$_6$H$_4$OCF$_3$), 3.28-3.17 (2H, m, 1H of pipH-2, 1H of BzpipH-2, H-6), 3.10 (1H, m, 1H of BzpipH-2, H-6), 2.85 (1H, m, 1H of pipH-6), 2.20-2.08 (3H, m, 1H of pipH-2, 1H of pipH-5, 1H of pipH-6), 2.00 (1H, m, 1H of BzpipH-3, H-5), 1.92-1.79 (3H, m, 3H of BzpipH-3, H-5), 1.62 (1H, m, 1H of pipH-5); $^{19}$F nmr (CDCl$_3$) δ −188.4 (d, J 51.0 Hz); m/z: 563 [M+H]$^+$.

Compound 7-64: $^1$H nmr (CDCl$_3$) δ 8.91 (1H, m, pyH-6), 7.14 (1H, dd, J 8.5, 2.0 Hz, pyH-4), 7.96 (1H, d, J 9.5 Hz, C$_6$H$_3$(SO$_2$Me)MeH-3), 7.65 (1H, d, J 8.0 Hz, pyH-3), 7.33 (2H, d, J 9.0 Hz, 2H of C$_6$H$_4$OCF$_2$CF$_2$H), 7.16 (2H, d, J 8.5 Hz, 2H of C$_6$H$_4$OCF$_2$CF$_2$H), 6.84 (2H, m, C$_6$H$_3$(SO$_2$Me)MeH-2, H-6), 6.24 (1H, d, J 7.5 Hz, NH), 5.90 (1H, tt, J 53.0, 3.0 Hz, CF$_2$H), 4.71 (1H, m, PhOpipH-4), 4.01 (1H, m, pipH-4), 3.95-3.83 (2H, m, 2H of PhOpipH-2, H-6), 3.71 (1H, m, 1H of PhOpipH-2, H-6), 3.52 (1H, m, 1H of PhOpipH-2, H-6), 3.51 (2H, s, CH$_2$C$_6$H$_4$OCF$_2$CF$_2$H), 3.05 (3H, s, SO$_2$CH$_3$), 2.86 (2H, m, 2H of pipH-2, H-6), 2.66 (3H, s, ArCH$_3$), 2.18 (2H, t, J 11.5 Hz, 2H of pipH-2, H-6), 2.08-1.94 (5H, m, 2H of pipH-3, H-5, 3H of PhOpipH-3, H-5), 1.87 (1H, m, 1H of PhOpipH-3, H-5), 1.60 (2H, m, 2H of pipH-3, H-5); $^{19}$F nmr (CDCl$_3$) δ −88.2, −136.8 (dt, J 53.5, 5.5 Hz); m/z: 708 [M+H]$^+$.

Compound 7-65: $^1$H nmr (CDCl$_3$) δ 8.89 (1H, m, pyH-6), 8.10 (1H, dd, J 8.0, 2.0 Hz, pyH-4), 7.93 (2H, d, J 9.0 Hz, 2H of C$_6$H$_4$OCH$_3$), 7.55 (1H, d, J 8.0 Hz, pyH-3), 7.33 (2H, d, J 8.5 Hz, 2H of C$_6$H$_4$OCF$_2$CF$_2$H), 7.14 (2H, d, J 8.5 Hz, 2H of C$_6$H$_4$OCF$_2$CF$_2$H), 6.95 (2H, d, J 9.0 Hz, 2H of C$_6$H$_4$OCH$_3$), 6.66 (1H, d, J 8.0 Hz, NH), 5.90 (1H, tt, J 53.0, 3.0 Hz, CF$_2$H), 4.68 (1H, m, 1H of BzpipH-2, H-6), 4.01 (1H, m, pipH-4), 3.89 (1H, m, 1H of BzpipH-2, H-6), 3.87 (3H, s, OCH$_3$), 3.53 (1H, m, BzpipH-4), 3.50 (2H, s, CH$_2$C$_6$H$_4$OCF$_2$CF$_2$H), 3.24 (1H, m, 1H of BzpipH-2, H-6), 3.10 (1H, m, 1H of BzpipH-2, H-6), 2.86 (2H, m, 2H of pipH-2, H-6), 2.17 (2H, dd, J 11.5, 9.5 Hz, 2H of pipH-2, H-6), 2.01 (3H, m, 2H of pipH-3, H-5, 1H of BzpipH-3, H-5), 1.92-1.78 (3H, m, 3H of BzpipH-3, H-5), 1.63 (2H, m, 2H of pipH-3, H-5); $^{19}$F nmr (CDCl$_3$) δ −88.2 (d, J 2.5 Hz), −136.7 (dt, J 52.5, 5.5 Hz); m/z: 658 [M+H]$^+$.

Compound 7-66: $^1$H nmr (CDCl$_3$) δ 8.87 (1H, m, pyH-6), 8.08 (1H, dd, J 8.0, 2.0 Hz, pyH-4), 7.94 (2H, d, J 9.0 Hz, 2H of C$_6$H$_4$OCH$_3$), 7.49 (1H, d, J 8.0 Hz, pyH-3 or C$_6$H$_3$(CN)OMeH-5), 7.48 (1H, d, J 8.0 Hz, pyH-3 or C$_6$H$_3$(CN)OMeH-5), 7.33 (1H, t, J 6.5 Hz, NH), 6.98-6.94 (4H, m, 2H of C$_6$H$_4$OCH$_3$, C$_6$H$_3$(CN)OMeH-2, H-6), 4.69 (1.5H, m, 0.5H of pipH-3, 1H of BzpipH-2, H-6), 4.54 (0.5H, td, J 9.5, 5.0 Hz, 0.5H of pipH-3), 4.15 (1H, m, pipH-4), 3.92 (3H, s, 1×OCH$_3$), 3.88 (3H, s, 1×OCH$_3$), 3.84 (1H, m, 1H of BzpipH-2, H-6), 3.63, 3.57 (2H, 2d AB system, J 14.0 Hz, CH$_2$C$_6$H$_3$(CN)OMe), 3.55 (1H, m, BzpipH-4), 3.28-3.18 (2H, m, 1H of pipH-2, 1H of BzpipH-2, H-6), 3.11 (1H, m, 1H of BzpipH-2, H-6), 2.81 (1H, m, 1H of pipH-6), 2.30-2.14 (3H, m, 1H of pipH-2, 1H of pipH-5, 1H of pipH-6), 2.02 (1H, m, 1H of BzpipH-3, H-5), 1.94-1.80 (3H, m, 3H of BzpipH-3, H-5), 1.68 (1H, m, 1H of pipH-5); $^{19}$F nmr (CDCl$_3$) δ −188.4 (d, J 55.5 Hz); m/z: 615 [M+H]$^+$.

Compound 7-67: $^1$H nmr (CDCl$_3$) δ 8.89 (1H, d, J 2.0 Hz, pyH-6), 8.09 (1H, dd, J 8.0, 2.0 Hz, pyH-4), 7.62 (2H, d, J 8.0 Hz, 2H of CH$_2$C$_6$H$_4$CN), 7.59 (2H, d, J 8.5 Hz, 2H of OC$_6$H$_4$CN), 7.54 (1H, d, J 8.5 Hz, pyH-4), 7.44 (2H, d, J 8.5 Hz, 2H of CH$_2$C$_6$H$_4$CN), 7.07 (1H, d, J 7.5 Hz, NH), 6.96 (2H, d, J 9.0 Hz, 2H of OC$_6$H$_4$CN), 4.69 (1.5H, m, 0.5H of pipH-3, PhOpipH-4), 4.51 (0.5H, td, J 9.5, 5.0 Hz, 0.5H of pipH-3), 4.15 (1H, m, pipH-4), 3.99-3.83 (2H, m, 2H of PhOpipH-2, H-6), 3.67 (1H, m, 1H of PhOpipH-2, H-6), 3.66, 3.61 (2H, 2d AB system, J 14.0 Hz, CH$_2$C$_6$H$_4$CN), 3.44 (1H, m, 1H of PhOpipH-2, H-6), 3.19 (1H, m, 1H of pipH-2), 2.80 (1H, m, 1H of pipH-6), 2.31-2.13 (3H, m, 1H of pipH-2, 1H of pipH-5, 1H of pipH-6), 2.10-1.92 (3H, m, 3H of PhOpipH-3, H-5), 1.86 (1H, m, 1H of PhOpipH-3, H-5), 1.65 (1H, m, 1H of pipH-5); $^{19}$F nmr (CDCl$_3$) δ −188.5 (d, J 50.0 Hz); m/z: 567 [M+H]$^+$.

Compound 7-68: $^1$H nmr (CDCl$_3$) δ 8.90 (1H, m, pyH-6), 8.11 (1H, dd, J 8.0, 2.0 Hz, pyH-4), 8.06 (2H, d, J 9.0 Hz, 2H of C$_6$H$_4$pyrazole), 8.02 (1H, d, J 2.5 Hz, pyrazoleH-3 or H-5), 7.84 (2H, d, J 9.0 Hz, 2H of C$_6$H$_4$pyrazole), 7.78 (1H, d, J 2.0 Hz, pyrazoleH-3 or H-5), 7.62 (2H, d, J 8.5 Hz, 2H of C$_6$H$_4$CN), 7.58 (1H, d, J 8.5 Hz, pyH-3), 7.44 (2H, d, J 8.5 Hz, 2H of C$_6$H$_4$CN), 6.84 (1H, m, NH), 6.53 (1H, dd, J 2.5, 2.0 Hz, pyrazoleH-4), 4.69 (1.5H, m, 0.5H of pipH-3, 1H of BzpipH-2, H-6), 4.50 (0.5H, td, J 9.5, 5.0 Hz, 0.5H of pipH-3), 4.16 (1H, m, pipH-4), 3.92 (1H, m, 1H of BzpipH-2, H-6), 3.67, 3.61 (2H, 2d AB system, J 14.0 Hz, CH$_2$C$_6$H$_4$CN), 3.54 (1H, m, 1H of BzpipH-2, H-6), 3.32-3.10 (3H, m, 1H of pipH-2, 2H of BzpipH-2, H-6), 2.80 (1H, m, 1H of pipH-6), 2.31-2.17 (3H, m, 1H of pipH-2, 1H of pipH-5, 1H of pipH-6), 2.06 (1H, m, 1H of BzpipH-3, H-5), 1.96-1.82 (3H, m, 3H of BzpipH-3, H-5), 1.64 (1H, m, 1H of pipH-5); $^{19}$F nmr (CDCl$_3$) δ −188.6 (d, J 50.0 Hz); m/z: 621 [M+H]$^+$ (found [M+H]$^+$, 620.2753, C$_{35}$H$_{34}$FN$_7$O$_3$ requires [M+H]$^+$ 620.2780).

Compound 7-69: $^1$H nmr (CDCl$_3$) δ 8.87 (1H, m, pyH-6), 8.07 (1H, dd, J 8.0, 2.0 Hz, pyH-4), 8.01 (2H, d, J 8.5 Hz, 2H of COC$_6$H$_4$OCF$_3$), 7.51 (1H, d, J 8.5 Hz, pyH-3), 7.33 (2H, d, J 8.5 Hz, 2H of COC$_6$H$_4$OCF$_3$), 7.31 (2H, d, J 8.0 Hz, 2H of CH$_2$C$_6$H$_4$OCF$_3$), 7.16 (2H, d, J 8.0 Hz, 2H of CH$_2$C$_6$H$_4$OCF$_3$), 7.15 (1H, m, NH), 4.69 (1.5H, m, 0.5H of pipH-3, 1H of BzpipH-2, H-6), 4.51 (0.5H, td, J 9.5, 5.0 Hz, 0.5H of pipH-3), 4.15 (1H, m, pipH-4), 3.88 (1H, m, 1H of BzpipH-2, H-6), 3.61, 3.55 (2H, 2d AB system, J 13.5 Hz, CH$_2$C$_6$H$_4$OCF$_3$), 3.54 (1H, m, BzpipH-4), 3.29-3.10 (3H, m, 1H of pipH-2, 2H of BzpipH-2, H-6), 2.83 (1H, m, 1H of pipH-6), 2.26-2.12 (3H, m, 1H of pipH-2, 1H of pipH-5, 1H of pipH-6), 2.03 (1H, m, 1H of BzpipH-3, H-5), 1.94-1.80 (3H, m, 3H of BzpipH-3, H-5), 1.65 (1H, m, 1H of pipH-5); $^{19}$F nmr (CDCl$_3$) δ −57.6, −57.9, −188.5 (d, J 47.5 Hz); m/z: 698 [M+H]$^+$.

Compound 7-70: $^1$H nmr (CDCl$_3$) δ 9.85 (1H, s, NH), 8.93 (1H, d, J 2.0 Hz, pyH-6), 8.54 (1H, d, J 2.5 Hz, N,O-pyH-6), 8.43 (1H, dd, J 9.0, 2.5 Hz, N,O-pyH-4), 8.10 (1H, dd, J 8.0, 2.0 Hz, pyH-4), 8.00 (2H, d, J 8.5 Hz, 2H of C$_6$H$_4$Ac or C$_6$H$_4$OCF$_3$), 7.99 (2H, d, J 9.0 Hz, 2H of C$_6$H$_4$Ac or C$_6$H$_4$OCF$_3$), 7.40 (1H, d, J 8.0 Hz, pyH-3), 7.32 (2H, d, J 8.5 Hz, 2H of C$_6$H$_4$Ac or C$_6$H$_4$OCF$_3$), 7.19 (2H, d, J 9.0 Hz, 2H of C$_6$H$_4$Ac or C$_6$H$_4$OCF$_3$), 7.04 (1H, d, J 9.0 Hz, pyH-3), 4.69 (1H, m, 1H of BzpipH-2, H-6), 3.81 (1H, m, 1H of BzpipH-2, H-6), 3.55 (1H, m, BzpipH-4), 3.25 (1H, m, 1H of BzpipH-2, H-6), 3.17 (1H, m, 1H of BzpipH-2, H-6), 2.59 (3H, s, COCH$_3$), 2.06 (1H, m, 1H of BzpipH-3, H-5), 1.95-1.82 (3H, m, 3H of BzpipH-3, H-6); $^{19}$F nmr (CDCl$_3$) δ −57.6; m/z: 633 [M+H]$^+$.

Compound 7-71: $^1$H nmr (CDCl$_3$) δ 8.87 (1H, s, pyH-6), 8.08 (1H, dd, J 8.0, 2.0 Hz, pyH-6), 8.01 (2H, d, J 8.5 Hz, 2H of C$_6$H$_4$OCF$_3$), 7.62 (2H, d, J 8.0 Hz, 2H of C$_6$H$_4$CN), 7.52 (1H, d, J 8.0 Hz, pyH-3), 7.44 (2H, d, J 8.5 Hz, 2H of C$_6$H$_4$CN), 7.32 (2H, d, J 9.0 Hz, 2H of C$_6$H$_4$OCF$_3$), 7.18 (1H, dd, J 7.0, 4.5 Hz, NH), 4.69 (1.5H, m, 0.5H of pipH-3, 1H of BzpipH-2, H-6), 4.52 (0.5H, td, J 9.5, 5.0 Hz, 0.5H of pipH-3), 4.15 (1H, m, pipH-4), 3.88 (1H, m, 1H of BzpipH-2, H-6), 3.66, 3.61 (2H, 2d AB system, J 14.0 Hz, CH$_2$C$_6$H$_4$CN), 3.54 (1H, m, BzpipH-4), 3.29-3.09 (3H, m, 1H of pipH-2, 2H of BzpipH-2, H-6), 2.80 (1H, m, 1H of pipH-6), 2.30-2.12 (3H, m, 1H of pipH-2, 1H of pipH-5, 1H of pipH-6), 2.04 (1H, m, 1H of BzpipH-3, H-5), 1.95-1.80 (3H, m, 3H of BzpipH-3, H-5), 1.68 (1H, m, 1H of pipH-5); $^{19}$F nmr (CDCl$_3$) δ −57.6, −188.5 (d, J 51.0 Hz); m/z: 638 [M+H]$^+$.

Compound 7-72 (as its trifluoroacetic acid salt): $^1$H nmr (CDCl$_3$) δ 8.93 (1H, m, pyH-6, 8.17 (1H, dd, J 8.0, 2.0 Hz, pyH-4, 7.85 (2H, d, J 8.5 Hz, 2H of C$_6$H$_4$pyrrolidine), 7.74 (2H, d, J 8.5 Hz, 2H of C$_6$H$_4$CN), 7.60 (2H, d, J 8.5 Hz, 2H of C$_6$H$_4$CN), 7.52 (1H, d, J 8.0 Hz, pyH-3), 6.53 (2H, d, J 9.5 Hz, 2H of C$_6$H$_4$pyrrolidine), 5.15, 4.89 (1H, 2m, pipH-3), 4.64 (1H, m, 1H of BzpipH-2, H-6), 4.44 (1H, m, pipH-4), 4.32 (2H, s, CH$_2$C$_6$H$_4$CN), 3.74 (2H, m, 1H of pipH-2, 1H of BzpipH-2, H-6), 3.52 (2H, m, 1H of pipH-6, BzpipH-4), 3.38, 3.6 (4H, 2d AB system, J 6.0 Hz, 4H of pyrrolidine), 3.22 (1H, m, 1H of BzpipH-2, H-6), 3.08 (1H, m, 1H of BzpipH-2, H-6), 2.99 (2H, m, 1H of pipH-2, 1H of pipH-6), 2.36 (1H, m, 1H of pipH-5), 2.12 (1H, m, 1H of pipH-5), 2.05, 2.03 (4H, 2d AB system, J 6.0 Hz, 4H of pyrrolidine), 1.98 (1H, m, 1H of BzpipH-3, H-5), 1.89-1.74 (3H, m, 3H of BzpipH-3, H-5); $^{19}$F nmr (CDCl$_3$) δ −75.7, −188.3; m/z: 624 [M+H]$^+$ (found [M+H]$^+$, 623.3118, C$_{36}$H$_{39}$FN$_6$O$_3$ requires [M+H]$^+$ 623.3141).

Compound 7-73: $^1$H nmr (CDCl$_3$) δ 8.90 (1H, d, J 2.0 Hz, pyH-6), 8.11 (1H, dd, J 8.0, 2.0 Hz, pyH-4), 7.82 (2H, d, J 9.0 Hz, 2H of C$_6$H$_4$SO$_2$cPr), 7.62 (2H, d, J 8.5 Hz, 2H of C$_6$H$_4$CN), 7.56 (1H, d, J 8.0 Hz, pyH-3), 7.44 (2H, d, J 8.0 Hz, 2H of C$_6$H$_4$CN), 7.04 (1H, m, NH), 7.02 (2H, d, J 9.0 Hz, 2H of C$_6$H$_4$SO$_2$cPr), 4.73 (1H, m, PhOpipH-4), 4.59 (1H, dtd, J 50.0, 9.5, 5.0 Hz, pipH-3), 4.15 (1H, m, pipH-4), 3.92 (2H, m, 2H of PhOpipH-2, H-6), 3.68 (1H, m, 1H of PhOpipH-2, H-6), 3.46, 3.61 (2H, 2d AB system, J 14.0 Hz, CH$_2$C$_6$H$_4$CN), 3.46 (1H, m, 1H of PhOpipH-2, H-6), 3.19 (1H, m, 1H of pipH-3), 2.80 (1H, m, 1H of pipH-2), 2.44 (1H, tt, J 8.0, 5.0 Hz, cPrH-1), 2.31-2.14 (3H, m, 1H of pipH-2, 1H of pipH-5, 1H of pipH-6), 2.10-1.92 (3H, m, 3H of PhOpipH-3, H-5), 1.88 (1H, m, 1H of PhOpipH-3, H-5), 1.68 (1H, m, 1H of pipH-5), 1.32 (2H, m, 2H of cPrH-2, H-3), 1.01 (2H, m, 2H of cPrH-2, H-3); $^{19}$F nmr (CDCl$_3$) δ −188.5 (d, J 51.0 Hz); m/z: 647 [M+H]$^+$.

Compound 7-74: $^1$H nmr (CDCl$_3$) δ 8.91 (1H, m, pyH-6), 8.11 (1H, dd, J 8.0, 2.0 Hz, pyH-4), 7.94 (2H, d, J 8.5 Hz, 2H of C$_6$H$_4$Ac), 7.61 (2H, d, J 8.5 Hz, 2H of C$_6$H$_4$CN), 7.53 (1H, d, J 8.5 Hz, pyH-3), 7.44 (2H, d, J 8.5 Hz, 2H of C$_6$H$_4$CN), 7.16 (1H, d, J 7.0 Hz, NH), 6.95 (2H, d, J 9.0 Hz, 2H of C$_6$H$_4$Ac), 4.70 (1.5H, m, 0.5H of pipH-3, PhOpipH-4), 4.53 (0.5H, td, J 9.5, 5.0 Hz, 0.5H of pipH-3), 4.16 (1H, m, pipH-4), 3.99-3.84 (2H, m, 2H of PhOpipH-2, H-6), 3.69 (1H, m, 1H of PhOpipH-2, H-6), 3.67, 3.61 (2H, 2d AB system, J 13.0 Hz, CH$_2$C$_6$H$_4$CN), 3.43 (1H, m, 1H of PhOpipH-2, H-6), 3.19 (1H, m, 1H of pipH-2), 2.81 (1H, m, 1H of pipH-6), 2.55 (3H, s, COCH$_3$), 2.30-2.14 (3H, m, 1H of pipH-2, 1H of pipH-5, 1H of pipH-6), 2.08-1.95 (3H, m, 3H of PhOpipH-3, H-5), 1.87 (1H, m, 1H of PhOpipH-3, H-5), 1.67 (1H, m, 1H of pipH-5); $^{19}$F nmr (CDCl$_3$) δ −188.5 (d, J 51.5 Hz); m/z: 584 [M+H]$^+$.

Compound 7-75: ¹H nmr (CDCl₃) δ 8.88 (1H, d, J 2.0 Hz, pyH-6), 8.07 (1H, dd, J 8.5, 2.0 Hz, pyH-4), 7.90 (2H, d, J 9.0 Hz, 2H of C₆H₄morpholine), 7.59 (2H, d, J 8.5 Hz, 2H of C₆H₄CN), 7.47 (1H, d, J 8.5 Hz, pyH-3), 7.43 (2H, d, J 8.0 Hz, 2H of C₆H₄CN), 7.36 (1H, dd, J 7.5, 3.5 Hz, NH), 6.89 (2H, d, J 8.5 Hz, 2H of C₆H₄morpholine), 4.69 (1.5H, m, 0.5H of pipH-3, 1H of BzpipH-2, H-6), 4.54 (0.5H, td, J 9.5, 5.0 Hz, 0.5H of pipH-3), 4.15 (1H, m, pipH-4), 3.86, 3.85 (4H, 2d AB system, J 5.0 Hz, 4H of morpholine), 3.84 (1H, m, 1H of BzpipH-2, H-6), 3.65, 3.60 (2H, 2d AB system, J 14.0 Hz, CH₂C₆H₄CN), 3.52 (1H, m, BzpipH-4), 3.33, 3.31 (4H, 2d, AB system, J 5.0 Hz, 4H of morpholine), 3.28-3.08 (3H, m, 1H of pipH-2, 2H of BzpipH-2, H-6), 2.80 (1H, m, 1H of pipH-6), 2.30-2.14 (3H, m, 1H of pipH-2, 1H of pipH-5, 1H of pipH-6), 2.01 (1H, m, 1H of BzpipH-3, H-5), 1.93-1.79 (3H, m, 3H of BzpipH-3, H-5), 1.67 (1H, m, 1H of pipH-5); ¹⁹F nmr (CDCl₃) δ −188.4 (d, J 51.5 Hz); m/z: 640 [M+H]⁺.

Compound 7-76: ¹H nmr (CDCl₃) δ 9.74 (1H, s, NH), 8.93 (1H, m, pyH-6), 8.50 (1H, d, J 2.5 Hz, N,O-pyH-6), 8.42 (1H, dd, J 9.0, 2.5 Hz, N,O-pyH-4), 8.10 (1H, dd, J 8.0, 2.0 Hz, pyH-4), 8.01 (2H, d, J 9.0 Hz, 2H of C₆H₄SO₂Me), 7.90 (2H, d, J 8.5 Hz, 2H of C₆H₄Ac), 7.54 (2H, d, J 8.5 Hz, 2H of C₆H₄Ac), 7.40 (1H, d, J 8.5 Hz, pyH-3), 7.18 (2H, d, J 9.0 Hz, 2H of C₆H₄SO₂Me), 7.03 (1H, d, J 9.0 Hz, N,O-pyH-3), 3.85 (2H, m, 2H of piz), 3.62 (2H, s, CH₂C₆H₄SO₂Me), 3.46 (2H, m, 2H of piz), 3.05 (3H, s, SO₂CH₃), 2.60 (3H, s, COCH₃), 2.57 (2H, m, 2H of piz), 2.43 (2H, m, 2H of piz); m/z: 614 [M+H]⁺.

Compound 7-77 (as its trifluoroacetic acid salt): ¹H nmr (CD₃OD) δ 8.31 (1H, d, J 2.5 Hz, pyH-6), 7.98 (1H, d, J 9.0 Hz, pyH-3), 7.87 (2H, d, J 8.5 Hz, 2H of C₆H₄CN), 7.77 (2H, d, J 9.0 Hz, 2H of C₆H₄SO₂Me), 7.71 (2H, d, J 8.5 Hz, 2H of C₆H₄CN), 7.46 (1H, dd, J 9.0, 2.5 Hz, pyH-4), 7.10 (2H, d, J 9.0 Hz, 2H of C₆H₄SO₂Me), 4.44 (2H, m, 2H of pipH-2, H-6), 4.14 (1H, m, pipH-4), 3.59 (6H, s, CH₂C₆H₄CN, 4H of piz), 3.23 (2H, m, 2H of pipH-2, H-6), 3.05 (3H, s, SO₂CH₃), 2.64 (4H, m, 4H of piz), 2.21 (2H, m, 2H of pipH-3, H-5), 1.93 (2H, m, 2H of pipH-3, H-5); m/z: 559 [M+H]⁺ (found [M+H]⁺, 559.2451, C₃₀H₃₄N₆O₃S requires [M+H]⁺ 559.2486).

Compound 7-78: ¹H nmr (CDCl₃) δ 8.92 (1H, m, pyH-6), 8.14 (1H, dd, J 8.5, 2.0 Hz, pyH-4), 7.94 (2H, d, J 9.0 Hz, 2H of C₆H₄OMe), 7.62 (3H, m, pyH-3, 2H of C₆H₄CN), 7.45 (2H, d, J 8.5 Hz, 2H of C₆H₄CN), 6.96 (2H, d, J 9.0 Hz, 2H of C₆H₄OMe), 6.25 (1H, d, J 9.0 Hz, NH), 4.70 (1H, m, 1H of BzpipH-2, H-6), 3.94 (1H, m, 1H of BzpipH-2, H-6), 3.88 (3H, s, OCH₃), 3.75 (1H, m, pipH-3), 3.55 (2H, s, CH₂C₆H₄CN), 3.52 (1H, m, BzpipH-4), 3.26 (1H, m, 1H of BzpipH-2, H-6), 3.11 (1H, m, 1H of BzpipH-2, H-6), 2.89-2.82 (2H, m, 1H of pipH-2, 1H of pipH-6), 2.17 (1H, td, J 12.0, 2.0 Hz, 1H of pipH-2 or pipH-6), 2.08-1.96 (2H, m, 1H of pipH-2 or pipH-6, 1H of pipH-5), 1.94-1.73 (4H, m, BzpipH-3, H-5), 1.60 (1H, m, 1H of pipH-5), 0.95 (3H, d, J 6.5 Hz, CH₃); m/z: 580 [M+H]⁺.

Compound 7-79: ¹H nmr (CDCl₃) δ 8.15 (1H, d, J 2.5 Hz, pyH-6), 8.02 (1H, d, J 9.0 Hz, pyH-3), 7.91 (2H, d, J 8.5 Hz, 2H of C₆H₄SO₂Me), 7.72 (1H, d, J 9.0 Hz, NH), 7.60 (2H, d, J 8.5 Hz, 2H of C₆H₄CN), 7.58 (2H, d, J 8.0 Hz, 2H of C₆H₄CN), 7.45 (2H, d, J 8.5 Hz, 2H of C₆H₄SO₂Me), 7.20 (1H, dd, J 9.0, 2.5 Hz, pyH-4), 3.97 (1H, m, pipH-4), 3.65 (2H, s, CH₂C₆H₄SO₂Me or CH₂C₆H₄CN), 3.55 (2H, s, CH₂C₆H₄SO₂Me or CH₂C₆H₄CN), 3.34, 3.32 (4H, 2d AB system, J 5.0 Hz, 4H of piz), 3.06 (3H, s, SO₂CH₃), 2.80 (2H, m, 2H of pipH-2, H-6), 2.63, 2.61 (4H, 2d AB system, J 5.0 Hz, 4H of piz), 2.21 (2H, dd, J 11.0, 9.5 Hz, 2H of pipH-2, H-6), 1.99 (2H, m, 2H of pipH-3, H-5), 1.61 (2H, m, 2H of pipH-3, H-5); m/z: 580 [M+H]⁺ (found [M+H]⁺, 573.2651, C₃₁H₃₆N₆O₃S requires [M+H]⁺573.2642).

Compound 7-80: ¹H nmr (CDCl₃) δ 8.19 (1H, d, J 3.0 Hz, pyH-6), 8.04 (1H, d, J 9.0 Hz, pyH-3), 7.88 (2H, d, J 9.0 Hz, 2H of C₆H₄SO₂Me), 7.72 (1H, d, J 8.5 Hz, NH), 7.61 (2H, d, J 8.5 Hz, 2H of C₆H₄CN), 7.45 (2H, d, J 8.5 Hz, 2H of C₆H₄CN), 7.25 (1H, dd, J 9.0, 2.5 Hz, pyH-4), 7.05 (2H, d, J 9.0 Hz, 2H of C₆H₄SO₂Me), 4.66 (1H, m, PhOpipH-4), 3.98 (1H, m, pipH-4), 3.60 (2H, m, 2H of PhOpipH-2, H-6), 3.56 (2H, s, CH₂C₆H₄SO₂Me or CH₂C₆H₄CN), 2.48 (2H, s, CH₂C₆H₄SO₂Me or CH₂C₆H₄CN), 3.35 (2H, m, 2H of PhOpipH-2, H-6), 3.04 (3H, s, SO2CH3), 2.80 (2H, m, 2H of pipH-2, H-6), 2.22 (2H, t, J 11.0, 2H of pipH-2, H-6), 2.18-2.10 (2H, m, 2H of PhOpipH-3, H-5), 2.01 (4H, m, 2H of pipH-3, H-5, 2H of PhOpipH-3, H-5), 1.62 (2H, m, 2H of pipH-3, H-5); m/z: 575 [M+H]⁺ (found [M+H]⁺, 574.2496, C₃₁H₃₅N₅O₄S requires [M+H]⁺574.2483).

Compound 7-81: ¹H nmr (CDCl₃) δ 8.20 (1H, d, J 2.5 Hz, pyH-6), 8.07 (1H, d, J 9.0 Hz, pyH-3), 7.99 (2H, d, J 9.0 Hz, C₆H₄COcPr), 7.74 (1H, d, J 8.5 Hz, NH), 7.61 (2H, d, J 8.5 Hz, 2H of C₆H₄CN), 7.45 (2H, d, J 8.0 Hz, 2H of C₆H₄CN), 7.25 (1H, dd, J 9.0, 3.0 Hz, pyH-4), 6.93 (2H, d, J 9.0 Hz, 2H of C₆H₄COcPr), 3.99 (1H, m, pipH-4), 3.56-3.47 (10H, m, 8H of piz, CH₂C₆H₄CN), 2.80 (2H, m, 2H of pipH-2, H-6), 2.62 (1H, m, cPrH-1), 2.22 (2H, dd, J 11.0, 9.5 Hz, 2H of pipH-2, H-6), 2.01 (2H, m, 2H of pipH-3, H-5), 1.63 (2H, m, 2H of pipH-3, H-5), 1.20 (2H, m, 2H of cPrH-2, H-3), 0.98 (2H, m, 2H of cPrH-2, H-3); m/z: 550 [M+H]⁺ (found [M+H]⁺, 549.2956, C₃₃H₃₆N₆O₂ requires [M+H]⁺ 549.2973).

Compound 7-82: ¹H nmr (CDCl₃) δ 9.60 (1H, s, NH), 9.00 (1H, s, pyH-6), 8.51 (1H, d, J 2.5 Hz, N,O-pyH-6), 8.41 (1H, dd, J 9.0, 2.5 Hz, N,O-pyH-4), 8.18 (1H, dd, J 8.5, 2.0 Hz, pyH-4), 8.00 (2H, d, J 9.0 Hz, 2H of C₆H₄Ac), 7.68 (2H, d, J 9.0 Hz, 2H of C₆H₄SO₂N), 7.53 (1H, d, J 8.5 Hz, pyH-3), 7.19 (2H, d, J 9.0 Hz, 2H of C₆H₄Ac), 7.04 (1H, d, J 9.0 Hz, N,O-pyH-3), 6.90 (2H, d, J 9.0 Hz, 2H of C₆H₄SO₂N), 3.98 (2H, m, 2H of piz), 3.70 (2H, m, 2H of piz), 3.47 (2H, m, 2H of piz), 3.34 (2H, m, 2H of piz), 3.20, 3.18 (4H, 2d AB system, J 6.5 Hz, 4H of pyrrolidine), 2.59 (3H, s, COCH₃), 1.74 (4H, m, 4H of pyrrolidine); m/z: 556 [M+H]⁺.

Compound 7-83: ¹H nmr (CDCl₃) δ 9.74 (1H, s, NH), 8.93 (1H, m, pyH-6), 8.51 (1H, d, J 2.5 Hz, N,O-pyH-6), 8.42 (1H, dd, J 9.0, 3.0 Hz, N,O-pyH-4), 8.09 (1H, dd, J 8.0, 2.0 Hz, pyH-4), 8.01 (2H, d, J 9.0 Hz, 2H of C₆H₄Ac), 7.78 (2H, d, J 8.5 Hz, 2H of C₆H₄SO₂N), 7.48 (2H, d, J 8.5 Hz, 2H of C₆H₄SO₂N), 7.40 (1H, d, J 8.0 Hz, pyH-3), 7.19 (2H, d, J 9.0 Hz, 2H of C₆H₄Ac), 7.03 (1H, d, J 9.0 Hz, N,O-pyH-3), 3.85 (2H, m, 2H of piz), 3.60 (2H, s, CH₂C₆H₄SO₂N), 3.46 (2H, m, 2H of piz), 3.25, 3.23 (4H, 2d AB system, J 6.5 Hz, 4H of pyrrolidine), 2.60 (3H, s, COCH₃), 2.58 (2H, m, 2H of piz), 2.42 (2H, m, 2H of piz), 1.76 (4H, m, 4H of pyrrolidine); m/z: 669 [M+H]⁺.

Compound 7-84 was synthesized as follows:

1-Boc-3,3-dimethyl-4-N-benzylaminopiperidine: To a solution of the 1-Boc-3,3-dimethylpiperidin-4-one (1.45 g, 6.39 mmol, 1.0 eq) in 1,2-dichloroethane (60 mL) was added benzylamine (1.03 g, 1.04 mL, 9.58 mmol, 1.5 eq). The reaction was equilibrated at room temperature for 10 minutes before adding sodium triacetoxyborohydride (2.71 g, 12.78 mmol, 2.0 eq) and stirring at 6 hours. Rochelle's salt (30 mL) was added and the mixture stirred for 2 hours before pouring into NaHCO₃ (90 mL). The organics were extracted with CH₂Cl₂ (3×90 mL), combined, dried (Na₂SO₄) and concentrated under reduced pressure. MPLC (0→10% MeOH—CH₂Cl₂) yielded title compound (1.65 g, 81%) as a colourless oil; ¹H nmr (CDCl₃) δ 7.33-7.23 (5H, m, ArH), 4.10 (1H, m, NH), 4.09 (1H, m, 1H of pipH-6), 3.92, 3.68 (2H, 2d AB system, J 13.5 Hz, NHC$\underline{H}_2$Ph), 3.63 (1H, m, 1H of pipH-2), 2.74 (1H, m, 1H of pipH-6), 2.52 (1H, m, 1H of pipH-2), 2.25 (1H, dd, J 10.5, 4.0 Hz, pipH-4), 1.82 (1H, br d, J 11.0 Hz, 1H of pipH-5), 1.44 (9H, s, C(CH$_3$)$_3$), 1.35 (1H, m, 1H of pipH-5), 0.94 (3H, s, 1×CH$_3$) 0.86 (3H, s, 1×CH$_3$); $^{13}$C nmr (CDCl$_3$) δ 155.0, 141.0, 128.3, 128.0, 126.9, 79.2, 62.3, 51.9, 43.0, 35.7, 28.4, 27.3, 25.4, 18.2; m/z 319 [M+H]$^+$.

1-Boc-3,3-dimethyl-4-N-benzylaminopiperidine: To a solution of the N-benzylaminopiperidine (1.65 g, 5.19 mmol mmol) in ethyl acetate-methanol (1:1, 50 mL) was added palladium on carbon (approximately 0.20 g). The flask was purged with nitrogen followed by hydrogen and stirred under an atmosphere of hydrogen for 5 hours. The reaction was purged with nitrogen and filtered through Celite®, eluting with 5% MeOH—CH$_2$Cl$_2$ (4×30 mL). The reaction was concentrated under reduced pressure to yield the title compound (1.29 g) as a colourless oil. The crude material was taken on without purification; $^1$H nmr (CDCl$_3$) δ 4.06 (1H, m, 1H of pipH-6), 3.65 (1H, m, 1H of pipH-2), 2.80 (1H, m, 1H of pipH-6), 2.50 (1H, dd, J 6.5, 4.0 Hz, pipH-4), 2.48 (1H, m, 1H of pipH-2), 1.63-1.56 (1H, m, 1H of pipH-5), 1.44 (9H, s, C(CH$_3$)$_3$), 1.37 (1H, m, 1H of pipH-5), 0.92 (3H, s, 1×CH$_3$), 0.82 (3H, s, 1×CH$_3$); $^{13}$C nmr (CDCl$_3$) δ 155.2, 79.3, 56.6, 55.0, 42.8, 35.7, 28.4, 25.0, 17.0; m/z 229 [M+H]$^+$, 173 [M+H—C$_4$H$_8$]$^+$.

tert-butyl 4-(6-(4-(4-methoxybenzoyl)piperidine-1-carbonyl)nicotinamido)-3,3-dimethylpiperidine-1-carboxylate: To a mixture of 6-(4-(4-methoxybenzoyl)piperidine-1-carbonyl)nicotinic acid (0.323 g, 0.877 mmol, 1.0 eq) and the aminopiperidine (0.200 g, 0.877 mmol, 1.0 eq) in dimethylformamide (5.0 mL) was added triethylamine (0.133 g, 0.183 mL, 1.316 mmol, 1.5 eq) followed by HATU (0.367 g, 0.965 mmol, 1.1 eq), The reaction was stirred at room temperature for 16 hours. The reaction was partitioned between EtOAc (120 mL) and water-NaHCO$_3$ (1:1, 120 mL). The organics were further washed with brine (100 mL), water (120 mL) and brine (100 mL) before drying (Na$_2$SO$_4$) and concentrated under reduced pressure. MPLC (0→10% MeOH—CH$_2$Cl$_2$) yielded the coupled compound (0.260 g, 51%) as a white solid; $^1$H nmr (CDCl$_3$) δ 8.93 (1H, br s, pyH-6), 8.15 (1H, br d, J 6.0 Hz, pyH-4), 7.93 (2H, d, J 9.0 Hz, 2H of C$_6$H$_4$OMe), 7.57 (1H, d, J 8.5 Hz, pyH-3), 6.94 (2H, d, J 9.0 Hz, 2H of C$_6$H$_4$OMe), 4.65 (1H, m, 1H of BzpipH-2, H-6), 4.05 (3H, m, pipH-4, 2H of pipH-2, H-5, H-6), 3.90 (1H, m, 1H of BzpipH-2, H-6), 3.86 (3H, s, OCH$_3$), 3.85-3.68 (2H, m, 2H of pipH-2, H-5, H-6), 3.52 (1H, m, BzpipH-4), 3.23 (1H, m, 1H of BzpipH-2, H-6), 3.09 (1H, t, J 12.0 Hz, 1H of BzpipH-2, H-6), 2.78 (1H, m, 1H of pipH-2, H-5, H-6), 2.68 (1H, m, 1H of pipH-2, H-5, H-6), 2.02 (1H, m, 1H of BzpipH-3, H-5), 1.90-1.75 (3H, m, 3H of BzpipH-3, H-5), 1.45 (9H, s, C(CH$_3$)$_3$), 0.96 (6H, s, 2×CH$_3$); m/z 579 [M+H]$^+$.

N-(3,3-dimethylpiperidin-4-yl)-6-(4-(4-methoxybenzoyl) piperidine-1-carbonyl)nicotinamide: To a solution of tert-butyl 4-(6-(4-(4-methoxybenzoyl)piperidine-1-carbonyl)nicotinamido)-3,3-dimethylpiperidine-1-carboxylate (0.260 g, 0.450 mmol, 1.0 eq) in dichloromethane (5.0 mL) was added hydrogen chloride (0.45 mL of a 4M solution in dioxane, 1.799 mmol, 4.0 eq). The reaction was stirred at room temperature for 6 hours before concentrating to dryness. The crude material was used without further purification.

Compound 7-84: To a suspension of the piperidine dihydrochloride (0.040 g, 0.073 mmol, 1.0 eq) in dichloromethane (1.0 mL) was added 4-cyanobenzyl bromide (0.017 g, 0.087 mmol, 1.2 eq) followed by diisopropylethylamine (0.037 g, 0.050 mL, 0.290 mmol, 4.0 eq). The resulting solution was stirred at room temperature for 14 hours before concentrating under reduced pressure. MPLC (0→10% MeOH—CH$_2$Cl$_2$) yielded Compound 7-84 as a white foam or oil; $^1$H nmr (CDCl$_3$) δ 8.91 (1H, d, J 2.0 Hz, pyH-6), 8.13 (1H, dd, J 8.0, 2.0 Hz, pyH-4), 7.94 (2H, d, J 9.0 Hz, 2H of C$_6$H$_4$OMe), 7.62 (1H, m, pyH-3), 7.60 (2H, d, J 8.0 Hz, 2H of C$_6$H$_4$CN), 7.45 (2H, d, J 8.0 Hz, 2H of C$_6$H$_4$CN), 6.95 (2H, d, J 9.0 Hz, 2H of C$_6$H$_4$OMe), 6.23 (1H, d, J 7.0 Hz, NH), 4.69 (1H, m, 1H of BzpipH-2, H-6), 4.01-3.90 (2H, m, 1H of pipH-4, 1H of BzpipH-2, H-6), 3.87 (3H, s, OCH$_3$), 3.53 (1H, m, BzpipH-4), 3.57, 3.45 (2H, 2d AB system, J 14.5 Hz, C$\underline{H}_2$C$_6$H$_4$CN), 3.25 (1H, m, 1H of BzpipH-2, H-6), 3.10 (1H, m, 1H of BzpipH-2, H-6), 2.84 (1H, m, 1H of pipH-2 or H-6), 2.42 (1H, d, J 11.5 Hz, 1H of pipH-2 or H-6), 2.21 (1H, td, J 11.0, 3.5 Hz, 1H of pipH-2 or H-6), 2.04-1.69 (7H, m, 1H of pipH-2 or H-6, pipH-5, BzpipH-3, H-5), 1.08 (3H, s, 1×CH$_3$), 0.92 (3H, s, 1×CH$_3$); m/z: 594 [M+H]$^+$.

Compound 7-85: $^1$H nmr (CDCl$_3$) δ 8.92 (1H, m, pyH-6), 8.14 (1H, dd, J 8.0, 2.0 Hz, pyH-4), 7.94 (2H, d, J 9.0 Hz, 2H of C$_6$H$_4$SO$_2$N), 7.65 (1H, d, J 8.0 Hz, pyH-3), 7.35 (2H, d, J 8.5 Hz, 2H of C$_6$H$_4$OCF$_3$), 7.15 (2H, d, J 8.0 Hz, 2H of C$_6$H$_4$OCF$_3$), 6.95 (2H, d, J 9.0 Hz, 2H of C$_6$H$_4$SO$_2$N), 6.14 (1H, d, J 9.5 Hz, NH), 4.69 (1H, m, 1H of BzpipH-2, H-6), 4.01-3.89 (2H, m, pipH-4, 1H of BzpipH-2, H-6), 3.87 (3H, s, OCH$_3$), 3.54 (1H, m, BzpipH-4), 3.51, 3.40 (2H, 2d AB system, J 13.5 Hz, C$\underline{H}_2$C$_6$H$_4$OCF$_3$), 3.26 (1H, m, 1H of BzpipH-2, H-6), 3.11 (1H, m, 1H of BzpipH-2, H-6), 2.85 (1H, m, 1H of pipH-2 or H-6), 2.45 (1H, d, J 11.0 Hz, 1H of pipH-2 or H-6), 2.17 (1H, dd, J 11.0, 9.0 Hz, 1H of pipH-2 or H-6), 2.04-1.71 (7H, m, 1H of pipH-2 or H-6, pipH-5, BzpipH-3, H-5), 1.08 (3H, s, 1×CH$_3$), 0.92 (3H, s, 1×CH$_3$); $^{19}$F nmr (CDCl$_3$) δ −57.7; m/z: 653 [M+H]$^+$.

Compound 7-86: $^1$H nmr (CDCl$_3$) δ 8.90 (1H, d, J 2.0 Hz, pyH-6), 8.12 (1H, dd, J 8.5, 2.0 Hz, pyH-4), 7.94 (2H, d, J 9.0 Hz, 2H of C$_6$H$_4$OMe), 7.60 (1H, d, J 8.0 Hz, pyH-3), 7.56 (1H, dd, J 7.5, 7.0 Hz, C$_6$H$_3$(F)CN H-5 or H-6), 7.29-7.21 (2H, m, C$_6$H$_3$(F)CN H-2, C$_6$H$_3$(F)CN H-5 or H-6), 6.95 (2H, d, J 9.0 Hz, 2H of C$_6$H$_4$OMe), 6.94 (1H, dd, J 9.0, 2.0 Hz, NH), 4.69 (1H, m, 1H of BzpipH-2, H-6), 4.01-3.91 (2H, m, pipH-4, 1H of BzpipH-2, H-6), 3.87 (3H, s, OCH$_3$), 3.57, 3.46 (2H, 2d AB system, J 15.0 Hz, C$\underline{H}_2$C$_6$H$_3$(F)CN), 3.52 (1H, m, BzpipH-4), 3.25 (1H, m, 1H of BzpipH-2, H-6), 3.10 (1H, m, 1H of BzpipH-2, H-6), 2.84 (1H, m, 1H of pipH-2 or H-6), 2.42 (1H, d, J 11.0 Hz, 1H of pipH-2 or H-6), 2.22 (1H, td, J 11.0, 4.0 Hz, 1H of pipH-2 or H-6), 2.07-1.96 (2H, m, 1H of pipH-2 or H-6, 1H of BzpipH-3, H-5), 1.93-1.75 (5H, m pipH-5, 3H of BzpipH-3, H-5), 1.10 (3H, s, 1×CH$_3$), 0.92 (3H, s, 1×CH$_3$); $^{19}$F nmr (CDCl$_3$) δ −106.9; m/z: 613 [M+H]$^+$.

Compound 7-87: $^1$H nmr (CDCl$_3$) δ 8.91 (1H, m, pyH-6), 8.14 (1H, dd, J 8.5, 2.0 Hz, pyH-4), 7.94 (2H, d, J 9.0 Hz, 2H of C$_6$H$_4$OMe), 7.64 (1H, d, J 8.0 Hz, pyH-3), 7.02-6.97 (2H, m, 2H of C$_6$H$_3$(F)OMe), 6.95 (2H, d, J 9.0 Hz, 2H of C$_6$H$_4$OMe), 6.84-6.79 (1H, m, 1H of C$_6$H$_3$(F)OMe), 6.16 (1H, d, J 9.0 Hz, NH), 4.69 (1H, m, 1H of BzpipH-2, H-6), 4.01-3.92 (2H, m, pipH-4, 1H of BzpipH-2, H-6), 3.88 (3H, s, OCH$_3$), 3.54 (1H, m, BzpipH-4), 3.50, 3.31 (2H, 2d AB system, J 13.5 Hz, C$\underline{H}_2$C$_6$H$_3$(F)OMe), 3.25 (1H, m, 1H of BzpipH-2, H-6), 3.10 (1H, m, 1H of BzpipH-2, H-6), 2.86 (1H, m, 1H of pipH-2 or H-6), 2.44 (1H, d, J 11.0 Hz, 1H of pipH-2 or H-6), 2.19 (1H, td, J 11.0, 2.5 Hz, 1H of pipH-2 or H-6), 2.02 (1H, m, 1H of BzpipH-3, H-5), 1.90 (1H, d, J 11.5 Hz, 1H of pipH-2 or H-6), 1.88-1.71 (5H, m, pipH-5, 3H of BzpipH-3, H-5), 1.07 (3H, s, 1×CH$_3$), 0.92 (3H, s, 1×CH$_3$); $^{19}$F nmr (CDCl$_3$) δ −138.0; m/z: 617 [M+H]$^+$.

Compound 7-88: $^1$H nmr (D$_6$-DMSO) δ 9.04 (1H, d, J 2.0 Hz, pyH-6), 8.35 (1H, dd, J 8.0, 2.0 Hz, pyH-4), 7.98 (2H, d, J 9.0 Hz, 2H of C$_6$H$_4$OMe), 7.66 (1H, d, J 8.0 Hz, pyH-3), 7.04 (2H, d, J 9.0 Hz, 2H of C$_6$H$_4$OMe), 4.50 (1H, m, 1H of BzpipH-2, H-6), 3.83 (3H, s, OCH$_3$), 3.72 (1H, tt, J 11.0, 3.5 Hz, BzpipH-4), 3.58 (1H, m, 1H of BzpipH-2, H-6), 3.21 (1H, m, 1H of BzpipH-2, H-6), 3.03 (1H, td, J 12.5, 2.5 Hz, 1H of BzpipH-2, H-6), 1.87 (1H, m, 1H of BzpipH-3, H-5), 1.68 (1H, m, 1H of BzpipH-3, H-5), 1.59-1.46 (2H, m, 2H of BzpipH-3, H-5); m/z: 369 [M+H]$^+$.

Compound 7-89: $^1$H nmr (CDCl$_3$) δ 8.92 (1H, m, pyH-6), 8.14 (1H, dd, J 8.0, 2.0 Hz, pyH-4), 7.94 (2H, d, J 9.0 Hz, 2H of C$_6$H$_4$OMe), 7.65 (1H, d, J 8.0 Hz, pyH-3), 7.55 (1H, d, J 2.0 Hz, C$_6$H$_3$(CN)OMeH-2), 7.47 (1H, dd, J 9.0, 2.0 Hz, C$_6$H$_3$(CN)OMeH-6), 6.95 (2H, d, J 9.0 Hz, 2H of C$_6$H$_4$OMe), 6.92 (1H, d, J 8.5 Hz, C$_6$H$_3$(CN)OMeH-5), 6.16 (1H, d, J 9.5 Hz, NH), 4.69 (1H, m, 1H of BzpipH-2, H-6), 3.96 (2H, m, pipH-4, 1H of BzpipH-2, H-6), 3.92 (3H, s, 1×OCH$_3$), 3.87 (3H, s, 1×OCH$_3$), 3.53 (1H, m, BzpipH-4), 3.45, 3.34 (2H, 2d AB system, J 13.0 Hz, C$\underline{H}_2$C$_6$H$_3$(CN)OMe), 3.26 (1H, m, 1H of BzpipH-2, H-6), 3.11 (1H, m, 1H of BzpipH-2, H-6), 2.83 (1H, m, 1H of pipH-2 or H-6), 2.41 (1H, d, J 11.0 Hz, 1H of pipH-2 or H-6), 2.16 (1H, td, J 11.0, 3.0 Hz, 1H of pipH-2 or H-6), 2.02 (1H, m, 1H of BzpipH-3, H-5), 1.93 (1H, d, J 11.0 Hz, 1H of pipH-2 or H-6), 1.91-1.70 (5H, m, pipH-5, 3H of BzpipH-3, H-5), 1.06 (3H, s, 1×CH$_3$), 0.92 (3H, s, 1×CH$_3$); m/z: 625 [M+H]$^+$.

Compound 7-90: $^1$H nmr (CDCl$_3$) δ 8.92 (1H, m, pyH-6), 8.14 (1H, dd, J 8.5, 2.0 Hz, pyH-4), 7.94 (2H, d, J 9.0 Hz, 2H of C$_6$H$_4$OMe), 7.64 (1H, d, J 8.0 Hz, pyH-3), 7.48 (1H, d, J 8.0 Hz, C$_6$H$_3$(CN)OMeH-5), 7.03 (1H, s, C$_6$H$_3$(CN)OMeH-2), 6.96 (1H, m, C$_6$H$_3$(CN)OMeH-6), 6.95 (2H, d, J 9.0 Hz, 2H of C$_6$H$_4$OMe), 6.20 (1H, d, J 9.0 Hz, NH), 4.69 (1H, m, 1H of BzpipH-2, H-6), 3.97 (2H, m, pipH-4, 1H of BzpipH-2, H-6), 3.92 (3H, s, 1×OCH$_3$), 3.87 (3H, s, 1×OCH$_3$), 3.58, 3.41 (2H, 2d AB system, J 14.5 Hz, C$\underline{H}_2$C$_6$H$_3$(CN)OMe), 3.53 (1H, m, BzpipH-4), 3.25 (1H, m, 1H of BzpipH-2, H-6), 3.10 (1H, m, 1H of BzpipH-2, H-6), 2.87 (1H, m, 1H of pipH-2 or H-6), 2.42 (1H, d, J 11.5 Hz, 1H of pipH-2 or H-6), 2.25 (1H, td, J 11.0, 3.5 Hz, 1H of pipH-2 or H-6), 2.04-1.75 (7H, m, 1H of pipH-2 or H-6, pipH-5, BzpipH-3, H-5), 1.10 (3H, s, 1×CH$_3$), 0.93 (3H, s, 1×CH$_3$); m/z: 625 [M+H]$^+$.

Compound 7-91: $^1$H nmr (CDCl$_3$) δ 8.62 (1H, m, pyH-6), 7.93 (2H, d, J 9.0 Hz, 2H of C$_6$H$_4$OMe), 7.84-7.80 (3H, m, 2H of C$_6$H$_4$SO$_2$N, pyH-4), 7.66 (2H, d, J 8.5 Hz, 2H of C$_6$H$_4$SO$_2$N), 6.95 (2H, d, J 9.0 Hz, 2H of C$_6$H$_4$OMe), 4.69 (1H, m, 1H of BzpipH-2, H-6), 4.56 (1H, m, SO$_2$NH), 3.98 (1H, m, 1H of BzpipH-2, H-6), 3.87 (3H, s, OCH$_3$), 3.80 (2H, m, 2H of piz), 3.60 (2H, s, C$\underline{H}_2$C$_6$H$_4$SO$_2$N), 3.52 (1H, m, BzpipH-4), 3.44 (2H, m, 2H of piz), 3.26 (1H, m, 1H of BzpipH-2, H-6), 3.09 (1H, m, 1H of BzpipH-2, H-6), 3.01 (2H, dq, J 6.0, 7.0 Hz, SO$_2$NHC$\underline{H}_2$CH$_3$), 2.54 (2H, m, 2H of piz), 2.42 (2H, m, 2H of piz), 2.01 (1H, m, 1H of BzpipH-3, H-5), 1.94-1.80 (3H, m, 3H of BzpipH-3, H-5), 1.10 (3H, t, J 7.0 Hz, SO$_2$NHCH$_2$C$\underline{H}_3$); m/z: 634 [M+H]$^+$.

Compound 7-92: $^1$H nmr (CDCl$_3$) δ 9.75 (1H, s, NH), 8.93 (1H, m, pyH-6), 8.50 (1H, d, J 2.5 Hz, N, O-pyH-6), 8.42 (1H, dd, J 9.0, 2.5 Hz, N, O-pyH-4), 8.10 (1H, dd, J 8.0, 2.0 Hz, pyH-4), 8.00 (2H, d, J 9.0 Hz, 2H of C$_6$H$_4$SO$_2$N or C$_6$H$_4$Ac), 7.81 (2H, d, J 8.5 Hz, 2H of C$_6$H$_4$SO$_2$N or C$_6$H$_4$Ac), 7.46 (2H, d, J 8.5 Hz, 2H of C$_6$H$_4$SO$_2$N or C$_6$H$_4$Ac), 7.40 (1H, d, J 9.0 Hz, pyH-3), 7.18 (2H, d, J 9.0 Hz, 2H of C$_6$H$_4$SO$_2$N or C$_6$H$_4$Ac), 7.03 (1H, d, J 9.5 Hz, N, O-pyH-6), 4.52 (1H, t, J 6.0 Hz, SO$_2$N$\underline{H}$CH$_2$CH$_3$), 3.84 (2H, m, 2H of piz), 3.59 (2H, s, C$\underline{H}_2$C$_6$H$_4$SO$_2$N), 3.46 (2H, m, 2H of piz), 3.02 (2H, dq, J 6.0, 7.0 Hz, SO$_2$NHC$\underline{H}_2$CH$_3$), 2.60 (3H, s, COCH$_3$), 2.56 (2H, m, 2H of piz), 2.42 (2H, m, 2H of piz), 1.11 (3H, t, J 7.0 Hz, SO$_2$NHCH$_2$C$\underline{H}_3$); m/z: 644 [M+H]$^+$.

Compound 7-93: $^1$H nmr (CDCl$_3$) δ 8.91 (1H, m, pyH-6), 8.14 (1H, dd, J 8.0, 2.0 Hz, pyH-4), 7.94 (2H, d, J 9.0 Hz, 2H of C$_6$H$_4$OMe), 7.64 (1H, d, J 8.5 Hz, pyH-3), 7.61 (2H, d, J 8.5 Hz, 2H of C$_6$H$_4$CN), 7.45 (2H, d, J 8.5 Hz, 2H of C$_6$H$_4$CN), 6.96 (2H, d, J 9.0 Hz, 2H of C$_6$H$_4$OMe), 6.33 (1H, d, J 8.5 Hz, NH), 4.69 (1H, m, 1H of BzpipH-2, H-6), 4.27 (1H, m, pipH-4), 3.96 (1H, m, 1H of BzpipH-2, H-6), 3.88 (3H, s, OCH$_3$), 3.57, 3.49 (2H, 2d AB system, J 14.0 Hz, C$\underline{H}_2$C$_6$H$_4$CN), 3.54 (1H, m, BzpipH-4), 3.26 (1H, m, 1H of BzpipH-2, H-6), 3.10 (1H, m, 1H of BzpipH-2, H-6), 2.55 (1H, m, 1H of pipH-2), 2.43 (2H, m, pipH-6), 2.34 (1H, m, 1H of pipH-2), 2.21 (1H, m, 1H of pipH-3), 2.01 (1H, m, 1H of BzpipH-3, H-5), 1.91-1.81 (5H, m, pipH-5, 3H of BzpipH-3, H-5), 1.03 (3H, d, J 6.5 Hz, CH$_3$); m/z: 580 [M+H]$^+$.

Compound 7-94: $^1$H nmr (CDCl$_3$) δ 8.92 (1H, d, J 2.0 Hz, pyH-6), 8.15 (1H, dd, J 8.5, 2.0 Hz, pyH-4), 7.94 (2H, d, J 9.5 Hz, 2H of C$_6$H$_4$OMe), 7.66 (1H, d, J 8.0 Hz, pyH-3), 7.35 (2H, d, J 8.5 Hz, 2H of C$_6$H$_4$OCF$_3$), 7.16 (2H, d, J 8.0 Hz, 2H of C$_6$H$_4$OCF$_3$), 6.96 (2H, d, J 9.0 Hz, 2H of C$_6$H$_4$OMe), 6.27 (1H, d, J 8.0 Hz, NH), 4.69 (1H, m, 1H of BzpipH-2, H-6), 4.27 (1H, m, pipH-4), 3.96 (1H, m, 1H of BzpipH-2, H-6), 3.88 (3H, s, OCH$_3$), 3.57-3.42 (3H, m, BzpipH-4, C$\underline{H}_2$C$_6$H$_4$OCF$_3$), 3.26 (1H, m, 1H of BzpipH-2, H-6), 3.11 (1H, m, 1H of BzpipH-2, H-6), 2.54-2.40 (3H, m, pipH-2, 1H of pipH-6), 2.31 (1H, m, 1H of pipH-6), 2.20 (1H, m, pipH-3), 2.02 (2H, m, 1H of BzpipH-3, H-5), 1.94-1.76 (5H, m, pipH-5, 3H of BzpipH-3, H-5), 1.02 (3H, d, J 7.0 Hz, CH$_3$); $^{19}$F nmr (CDCl$_3$) δ −57.9; m/z: 639 [M+H]$^+$.

Compound 7-95: $^1$H nmr (CDCl$_3$) δ 8.92 (1H, m, pyH-6), 8.14 (1H, dd, J 8.5, 2.0 Hz, pyH-4), 7.94 (2H, d, J 9.0 Hz, 2H of C$_6$H$_4$OMe), 7.66 (1H, d, J 8.0 Hz, pyH-3), 7.10 (1H, dd, J 12.5, 2.0 Hz, C$_6$H$_3$(F)OMeH-2), 6.98 (1H, m, C$_6$H$_3$(F)OMeH-6), 6.95 (2H, d, J 9.0 Hz, 2H of C$_6$H$_4$OMe), 6.89 (1H, t, J 8.5 Hz, C$_6$H$_3$(F)OMeH-5), 6.11 (1H, d, J 9.0 Hz, NH), 4.69 (1H, m, 1H of BzpipH-2, H-6), 3.96 (2H, m, pipH-4, 1H of BzpipH-2, H-6), 3.88 (3H, s, 1×OCH$_3$), 3.87 (3H, s, 1×OCH$_3$), 3.53 (1H, m, BzpipH-4), 3.45, 3.32 (2H, 2d AB system, J 13.5 Hz, C$\underline{H}_2$C$_6$H$_3$(F)OMe), 3.26 (1H, m, 1H of BzpipH-2, H-6), 3.11 (1H, m, 1H of BzpipH-2, H-6), 2.84 (1H, m, 1H of pipH-2 or H-6), 2.44 (1H, d, J 11.0 Hz, 1H of pipH-2 or H-6), 2.15 (1H, td, J 11.0, 3.0 Hz, 1H of pipH-2 or H-6), 2.20 (1H, m, 1H of BzpipH-3, H-5), 1.91 (1H, d, J 11.5 Hz, 1H of pipH-2, H-6), 1.89-1.69 (5H, m, pipH-5, 3H of BzpipH-3, H-5), 1.07 (3H, s, 1×CH$_3$), 0.92 (3H, s, 1×CH$_3$); $^{19}$F nmr (CDCl$_3$) δ −135.7; m/z: 617 [M+H]$^+$.

Compound 7-96: $^1$H nmr (CDCl$_3$) δ 8.92 (1H, m, pyH-6), 8.14 (1H, dd, J 8.0, 2.0 Hz, pyH-4), 7.94 (2H, d, J 8.5 Hz, 2H of C$_6$H$_4$OMe), 7.65 (1H, d, J 8.0 Hz, pyH-3), 7.09 (1H, dd, J 12.5, 1.5 Hz, C$_6$H$_3$(F)OMeH-2), 7.00-6.94 (3H, m, 2H of C$_6$H$_4$OMe, C$_6$H$_3$(F)OMeH-6), 6.89 (1H, t, J 8.5 Hz, C$_6$H$_3$(F)OMeH-5), 6.32 (1H, d, J 8.5 Hz, NH), 4.69 (1H, m, 1H of BzpipH-2, H-6), 4.26 (1H, m, pipH-4), 3.95 (1H, m, 1H of BzpipH-2, H-6), 3.87 (6H, s, 2×OCH$_3$), 3.53 (1H, m, BzpipH-4), 3.44, 3.37 (2H, 2d AB system, J 13.5 Hz, C$\underline{H}_2$C$_6$H$_3$(F)OMe), 3.26 (1H, m, 1H of BzpipH-2, H-6), 3.10 (1H, m, 1H of BzpipH-2, H-6), 2.54-2.36 (3H, m, 3H of pipH-2, H-6), 2.28 (1H, m, 1H of pipH-2 or pipH-6), 2.18 (1H, m, pipH-3), 2.02 (1H, m, 1H of BzpipH-3, H-5), 1.92-1.76 (5H, m, pipH-5, 3H of BzpipH-3, H-5), 1.01 (3H, d, J 6.5 Hz, CH$_3$); $^{19}$F nmr (CDCl$_3$) δ −135.6; m/z: 603 [M+H]$^+$.

Compound 7-97: $^1$H nmr (CDCl$_3$) δ 8.92 (1H, m, pyH-6), 8.15 (1H, dd, J 8.0, 2.0 Hz, pyH-4), 7.94 (2H, d, J 9.0 Hz, 2H of C$_6$H$_4$OMe), 7.68 (1H, d, J 8.0 Hz, pyH-3), 7.03-6.94 (4H, m, C$_6$H$_3$(F)OMeH-5 and H-2 or H-6, 2H C$_6$H$_4$OMe), 6.82 (1H, m, C$_6$H$_3$(F)OMeH-2 or H-6), 6.23 (1H, d, J 9.0 Hz, NH), 4.70 (1H, m, 1H of BzpipH-2, H-6), 4.27 (1H, m, pipH-4), 3.97 (1H, m, 1H of BzpipH-2, H-6), 3.89 (3H, s, 1×OCH$_3$), 3.88 (3H, s, 1×OCH$_3$), 3.53 (1H, m, BzpipH-4), 3.49, 3.38 (2H, 2d AB system, J 13.5 Hz, C$\underline{H}_2$C$_6$H$_3$(F)OMe), 3.27 (1H, m, 1H of BzpipH-2, H-6), 3.11 (1H, m, 1H of BzpipH-2, H-6), 2.54-2.38 (3H, m, 3H of pipH-2, H-6), 2.28 (1H, m, 1H of pipH-2 or H-6), 2.20 (pipH-3), 2.03 (1H, m, 1H of BzpipH-3, H-5), 1.93-1.80 (5H, m, pipH-5, 3H of BzpipH-3, H-5), 1.02 (3H, d, J 6.5 Hz, $CH_3$); $^{19}F$ nmr ($CDCl_3$) δ −137.8; m/z: 603 $[M+H]^+$.

Compound 7-98: $^1H$ nmr ($CDCl_3$) δ 8.92 (1H, m, pyH-6), 8.14 (1H, dd, J 8.5, 2.0 Hz, pyH-4), 7.94 (2H, d, J 9.0 Hz, 2H of $C_6H_4OMe$), 7.65 (1H, d, J 8.0 Hz, pyH-3), 7.56 (1H, dd, J 8.0, 6.5 Hz, $C_6H_3(F)CN$ H-5), 7.29-7.22 (2H, m, $C_6H_3(F)CN$ H-2 and H-6), 6.96 (2H, d, J 8.5 Hz, 2H of $C_6H_4OMe$), 6.33 (1H, d, J 8.0 Hz, NH), 4.69 (1H, m, 1H of BzpipH-2, H-6), 4.27 (1H, m, pipH-4), 3.95 (1H, m, 1H of BzpipH-2, H-6), 3.88 (3H, s, $OCH_3$), 3.56, 3.49 (2H, 2d AB system, J 14.0 Hz, $CH_2C_6H_3(F)CN$), 3.54 (1H, m, BzpipH-4), 3.26 (1H, m, 1H of BzpipH-2, H-6), 3.11 (1H, m, 1H of BzpipH-2, H-6), 2.57 (1H, m, 1H of pipH-2, H-6), 2.47-2.32 (3H, m, 3H of pipH-2, H-6), 2.23 (1H, m, pipH-3), 2.02 (1H, m, 1H of BzpipH-3, H-5), 1.82-1.78 (5H, pipH-5, 3H of BzpipH-3, H-5), 1.05 (3H, d, J 7.0 Hz, $CH_3$); $^{19}F$ nmr ($CDCl_3$) δ −106.8; m/z: 598 $[M+H]^+$.

Compound 7-99: $^1H$ nmr ($CDCl_3$) δ 8.92 (1H, m, pyH-6), 8.15 (1H, dd, J 8.5, 2.0 Hz, pyH-4), 7.94 (2H, d, J 9.0 Hz, 2H of $C_6H_4OMe$), 7.64 (1H, d, J 8.0 Hz, pyH-3), 7.48 (1H, d, J 7.5 Hz, $C_6H_3(CN)OMeH$-5), 7.04 (1H, br s, $C_6H_3(CN)OMeH$-2), 6.97 (1H, m, $C_6H_3(CN)OMeH$-6), 6.95 (2H, d, J 9.5 Hz, 2H of $C_6H_4OMe$), 6.35 (1H, br s, NH), 4.69 (1H, m, 1H of BzpipH-2, H-6), 4.27 (1H, m, pipH-4), 3.95 (1H, m, 1H of BzpipH-2, H-6), 3.93 (3H, s, 1×$OCH_3$), 3.87 (3H, s, 1×$OCH_3$), 3.60-3.44 (3H, m, BzpipH-4, $CH_2C_6H_3(CN)OMe$), 3.26 (1H, m, 1H of BzpipH-2, H-6), 3.10 (1H, m, 1H of BzpipH-2, H-6), 2.59 (1H, m, 1H of pipH-2 or H-6), 2.50-2.32 (3H, m, 3H of pipH-2, H-6), 2.23 (1H, m, pipH-3), 2.02 (1H, m, 1H of BzpipH-3, H-5), 1.91-1.74 (5H, m, pipH-5, 3H of BzpipH-3, H-5), 1.05 (3H, d, J 6.5 Hz, $CH_3$); m/z: 610 $[M+H]^+$.

Compound 7-100: $^1H$ nmr ($CDCl_3$) δ 8.92 (1H, m, pyH-6), 8.15 (1H, dd, J 8.5, 2.0 Hz, pyH-4), 7.94 (2H, d, J 9.0 Hz, 2H of $C_6H_4OMe$), 7.67 (1H, d, J 8.5 Hz, pyH-3), 7.54 (1H, d, J 2.0 Hz, $C_6H_3(CN)OMeH$-2), 7.48 (1H, dd, J 9.0, 2.0 Hz, $C_6H_3(CN)OMeH$-6), 6.95 (2H, d, J 9.0 Hz, 2H of $C_6H_4OMe$), 6.92 (1H, d, J 9.0 Hz, $C_6H_3(CN)OMeH$-5), 6.29 (1H, d, J 8.5 Hz, NH), 4.69 (1H, m, 1H of BzpipH-2, H-6), 4.26 (1H, m, pipH-4), 3.96 (1H, m, 1H of BzpipH-2, H-6), 3.92 (3H, s, 1×$OCH_3$), 3.88 (3H, s, 1×$OCH_3$), 3.53 (1H, m, BzpipH-4), 3.45, 3.38 (2H, 2d AB system, J 13.5 Hz, $CH_2C_6H_3(CN)OMe$), 3.26 (1H, m, 1H of BzpipH-2, H-6), 3.11 (1H, m, 1H of BzpipH-2, H-6), 2.49 (1H, m, 1H of pipH-2, H-6), 2.41 (2H, m, 2H of pipH-2, H-6), 2.29 (1H, m, 1H of pipH-2, H-6), 2.19 (1H, m, pipH-3), 2.02 (1H, m, 1H of BzpipH-3, H-5), 1.84-1.78 (5H, m, pipH-5, 3H of BzpipH-3, H-5), 1.02 (3H, d, J 7.0 Hz, $CH_3$); m/z: 610 $[M+H]^+$.

Compound 7-101 was synthesized as follows:

cis-tert-butyl 4-(6-(4-(4-methoxybenzoyl)piperidine-1-carbonyl)nicotinamido)-3-(trifluoromethyl)piperidine-1-carboxylate: To a mixture of 6-(4-(4-methoxybenzoyl)piperidine-1-carbonyl)nicotinic acid (0.094 g, 0.257 mmol, 1.0 eq), and 3-trifluoromethyl-4-amino-1-Boc-piperidine (0.257 mmol, 1.0 eq) was added dimethylformamide (2.5 mL) and triethylamine (0.054 mL, 0.386 mmol, 1.5 eq). HATU (0.107 g, 0.283 mmol, 1.1 eq) was added and the reaction was stirred at room temperature for 14 hours and partitioned between EtOAc (120 mL) and $NaHCO_3$-water (1:1, 120 mL). The organics were further washed with brine (100 mL), water (100 mL) and brine (100 mL), dried ($Na_2SO_4$) and concentrated under reduced pressure. MPLC (0→10% MeOH—$CH_2Cl_2$) yielded the coupled product (0.104 g, 68%) as a colourless oil; $^1H$ nmr ($CDCl_3$) δ 8.90 (1H, br s, pyH-6), 8.08 (1H, br d, J 7.0 Hz, pyH-4), 7.92 (2H, d, J 9.0 Hz, 2H of $C_6H_4OMe$), 7.50 (2H, m, pyH-3, NH), 6.94 (2H, d, J 9.0 Hz, 2H of $C_6H_4OMe$), 4.61 (2H, m, 1H of pipH-2, H-4, H-6, 1H of BzpipH-2, H-6), 3.86 (3H, s, $OCH_3$), 3.86-3.74 (2H, m, 1H of pipH-2, H-4, H-6, 1H of BzpipH-2, H-6), 3.52 (1H, m, BzpipH-4), 3.52-3.38 (2H, m, 2H of pipH-2, H-4, H-6), 3.26-3.04 (1H, m, 1H of pipH-2, H-3, H-4, H-6), 3.22 (1H, m, 1H of BzpipH-2, H-6), 3.12 (1H, t, J 11.5 Hz, 1H of BzpipH-2, H-6), 2.76 (1H, m, 1H of pipH-2, H-3, H-4, H-6), 2.00 (1H, m, 1H of BzpipH-3, H-5), 1.90-1.65 (5H, m, pipH-5, 3H of BzpipH-3, H-5), 1.45 (9H, s, $C(CH_3)_3$); $^{19}F$ nmr ($CDCl_3$) δ −62.7; m/z 619 $[M+H]^+$.

cis-6-(4-(4-Methoxybenzoyl)piperidine-1-carbonyl)-N-(3-(trifluoromethyl)piperidin-4-yl)nicotinamide, dihydrochloride salt: To a solution of the cis-tert-butyl 4-(6-(4-(4-methoxybenzoyl)piperidine-1-carbonyl)nicotinamido)-3-(trifluoromethyl)piperidine-1-carboxylate (0.104 g, 0.168 mmol, 1.0 eq) in dichloromethane (2.0 mL) was added hydrogen chloride (0.17 mL of a 4M solution in dioxane, 0.673 mmol, 4.0 eq). The reaction was stirred at room temperature of 4 hours and further hydrogen chloride (0.17 mL of a 4M solution in dioxane, 0673 mmol, 4.0 eq) added. The reaction was stirred for a further 2 hours before concentrating to dryness to yield a white solid, which was taken onto the next step without purification.

Compound 7-101: To a suspension of the cis-6-(4-(4-Methoxybenzoyl)piperidine-1-carbonyl)-N-(3-(trifluoromethyl)piperidin-4-yl)nicotinamide, dihydrochloride salt (0.084 mmol, 1.0 eq) in dichloromethane (1.0 mL) was added diisopropylethylamine (0.051 mL, 0.294 mmol, 3.5 eq) to form a clear pale orange solution to which was added a-bromo-p-benzonitrile (0.020 g, 0.101 mmol, 1.2 eq). The reaction was stirred at room temperature for 14 hours before concentrating onto silica. MPLC (0→10% MeOH—$CH_2Cl_2$) yielded the title compound as a white foam; $^1H$ nmr ($CDCl_3$, @50° C.) δ 8.81 (1H, m, pyH-6), 8.03 (1H, dd, J 8.5, 2.0 Hz, pyH-4), 7.85 (2H, d, J 9.0 Hz, 2H of $C_6H_4OMe$), 7.57-7.52 (3H, m, pyH-3, 2H of $C_6H_4CN$), 7.37 (2H, d, J 8.5 Hz, 2H of $C_6H_4CN$), 6.88 (2H, d, J 9.0 Hz, 2H of $C_6H_4OMe$), 6.53 (1H, d, J 8.0 Hz, NH), 4.57 (1H, m, 1H of BzpipH-2, H-6), 4.52 (1H, m, pipH-4), 3.88 (1H, m, 1H of BzpipH-2, H-6), 3.80 (3H, s, $OCH_3$), 3.57, 3.49 (2H, 2d AB system, J 14.0 Hz, $CH_2C_6H_4CN$), 3.45 (1H, m, BzpipH-4), 3.19 (1H, m, 1H of BzpipH-2, H-6), 3.06 (1H, m, 1H of BzpipH-2, H-6), 2.77 (1H, m, pipH-3), 2.73-2.50 (3H, m, 1H of pipH-2, pipH-6), 2.45 (1H, m, 1H of pipH-2), 2.01 (1H, m, 1H of pipH-5) 1.94 (1H, m, 1H of BzpipH-3, H-5), 1.85-1.17 (4H, 1H of pipH-5, 3H of BzpipH-3, H-5); $^{13}C$ nmr ($CDCl_3$) δ 200.0, 166.7 (2 carbons), 164.9, 163.7, 156.5, 147.0, 143.6, 136.0, 132.3, 130.6, 130.5, 128.5, 126.5 (d, J 281.5 Hz), 123.2, 123.1, 118.8, 114.0, 111.2, 62.1, 55.5, 50.4, 49.5, 46.7, 44.4, 42.7, 42.3 (d, J 24.5 Hz), 42.0, 29.2, 28.8, 28.5; $^{19}F$ nmr ($CDCl_3$, @50° C.) δ −64.1; m/z: 634 $[M+H]^+$ (found $[M+H]^+$, 634.2645, $C_{34}H_{34}F_3N_5O_4$ requires $[M+H]^+$634.2636).

Compound 7-102: $^1H$ nmr ($CDCl_3$, @50° C.) δ 8.96 (1H, m, pyH-6), 8.17 (1H, dd, J 8.0, 2.0 Hz, pyH-4), 7.99 (2H, d, J 9.0 Hz, 2H of $COC_6H_4OMe$), 7.74 (1H, d, J 8.5 Hz, pyH-3), 7.30 (2H, d, J 8.5 Hz, 2H of $CH_2C_6H_4OMe$), 7.02 (2H, d, J 9.0 Hz, 2H of $COC_6H_4OMe$ or $CH_2C_6H_4OMe$), 6.93 (2H, d, J 9.0 Hz, 2H of $COC_6H_4OMe$ or $CH_2C_6H_4OMe$), 4.45 (1H, d, J 8.0 Hz, NH), 4.76-4.64 (2H, m, pipH-4, 1H of BzpipH-2, H-6), 4.05 (1H, m, 1H of BzpipH-2, H-6), 3.94 (3H, s, 1×$OCH_3$), 3.86 (3H, s, 1×$OCH_3$), 3.60, 3.53 (2H, 2d AB system, J 13.0 Hz, $CH_2C_6H_4OMe$), 3.58 (1H, m, BzpipH-4), 3.33 (1H, m, 1H of BzpipH-2, H-6), 3.21 (1H, m, 1H of BzpipH-2, H-6), 2.92-2.80 (2H, m, 1H of pipH-3, 1H of pipH-2 or H-6), 2.70-2.60 (2H, m, 2H of pipH-2, H-6), 2.57-2.49 (1H, m, 1H of pipH-2, H-6), 2.16-2.04 (2H, m, 1H of pipH-5, 1H of BzpipH-3, H-5), 2.01-2.89 (4H, m, 1H of pipH-5, 3H of BzpipH-3, H-5); $^{19}$F nmr (CDCl$_3$, @50° C.) δ −65.0; m/z: 639 [M+H]$^+$ (found [M+H]$^+$, 639.2745, C$_{34}$H$_{37}$F$_3$N$_4$O$_5$ requires [M+H]$^+$ 639.2789).

Compound 7-103 (as an approximately 3:1 mixture of diastereomers): $^1$H nmr (CDCl$_3$) δ 8.92 (1H, m, pyH-6), 8.15 (1H, dd, J 8.0, 2.0 Hz, pyH-4), 7.94 (2H, d, J 9.0 Hz, 2H of C$_6$H$_4$OMe), 7.67-7.58 (3H, m, pyH-3, 2H of C$_6$H$_4$CN), 7.45 (2H, d, J 8.0 Hz, 2H of C$_6$H$_4$CN), 6.95 (2H, d, J 9.0 Hz, 2H of C$_6$H$_4$OMe), 6.37 (0.3H, d, J 9.0 Hz, NH minor), 6.15 (0.7H, d, J 9.0 Hz, NH major), 4.70 (1H, m, 1H of BzpipH-2, H-6), 4.41 (0.7H, dt, J 10.0, 3.5 Hz, pipH-4 major), 3.96 (1.3H, pipH-4 minor, 1H of BzpipH-2, H-6), 3.87 (3H, s, OCH$_3$), 3.58-3.41 (3H, m, CH$_2$C$_6$H$_4$CN, BzpipH-4), 3.26 (1H, m, 1H of BzpipH-2, H-6), 3.10 (1H, m, 1H of BzpipH-2, H-6), 2.76 (0.3H, m, 1H of pipH-2 or H-6 minor), 2.66-2.55 (1.7H, m, 1H of pipH-2, H-6 major, 1H of pipH-2, H-6), 2.34-2.10 (2H, m, 2H of pipH-2, H-6), 2.05-1.80 (6H, m, pipH-3, pipH-5, BzpipH-3, H-5), 1.08 (1H, d, J 7.0 Hz, 1×CH$_3$ minor), 0.95 (1H, d, J 6.0 Hz, 1×CH$_3$ minor), 0.89 (4H, d, J 6.5 Hz, 2×CH$_3$ major); m/z: 595 [M+H]$^+$.

Compound 7-104 (as an approximately 3:1 mixture of diastereomers): $^1$H nmr (CDCl$_3$) δ 8.93 (1H, m, pyH-6), 8.15 (1H, m, pyH-4), 7.95 (1.4H, d, J 9.0 Hz, 2H of C6H4OMe major), 7.94 (0.6H, d, J 9.0 Hz, 2H of C$_6$H$_4$OMe minor), 7.66 (0.7H, d, J 8.0 Hz, pyH-3 major), 7.62 (0.3H, d, J 8.5 Hz, pyH-3 minor), 7.33 (2H, d, J 8.0 Hz, 2H of C$_6$H$_4$OCF$_3$), 7.17 (1.4H, d, J 8.0 Hz, 2H of C$_6$H$_4$OCF$_3$ major), 7.15 (0.06H, d, J 7.5 Hz, 2H of C$_6$H$_4$OCF$_3$ minor), 6.95 (2H, d, J 9.0 Hz, 2H of C$_6$H$_4$OMe), 6.38 (0.3H, d, J 9.0 Hz, NH minor), 6.16 (0.7H, d, J 10.0 Hz, NH major), 4.70 (1H, m, 1H of BzpipH-2, H-6), 4.41 (0.7H, dt, J 10.0, 3.5 Hz, pipH-4 major), 3.99-3.90 (1.3H, m, pipH-4 minor, 1H of BzpipH-2, H-6), 3.87 (3H, s, OCH$_3$), 3.54, 3.38 (0.6H, 2d AB system, J 13.5 Hz, CH$_2$C$_6$H$_4$OCF$_3$ minor), 3.53 (1H, m, BzpipH-4), 3.49 (1.4H, s, CH$_2$C$_6$H$_4$OCF$_3$ major), 3.26 (1H, m, 1H of BzpipH-2, H-6), 3.11 (1H, m, 1H of BzpipH-2, H-6), 2.77 (0.3H, m, 1H of pipH-2, H-6 minor), 2.67 (1.4H, m, 2H of pipH-2, H-6 major), 2.58 (0.3H, m, 1H of pipH-2, H-6 minor), 2.31-2.09 (2H, m, 2H of pipH-2, H-6), 2.02 (1H, m, 1H of BzpipH-3, H-5), 1.96-1.76 (5H, m, pipH-3, pipH-5, 3H of BzpipH-3, H-5), 1.08 (1H, d, J 7.0 Hz, 1×CH$_3$ minor), 0.95 (1H, d, J 6.0 Hz, 1×CH$_3$ minor), 0.89 (4H, d, J 7.0 Hz, 2×CH$_3$ major); $^{19}$F nmr (CDCl$_3$) δ −57.9; m/z: 653 [M+H]$^+$.

Compound 7-105 was synthesized as follows:

2-(4-(4-methoxybenzoyl)piperidinylcarbonyl)-4-methyl-5-bromopyridine: To a mixture of 5-bromo-4-methylpyridine-2-carboxylic acid (0.400 g, 1.85 mmol, 1.0 eq) and 4-(4-methoxybenzoyl)piperidine hydrochloride (0.474 g, 1.85 mmol, 1.0 eq) was added dimethylformamide (10 mL) followed by triethylamine (0.64 mL, 4.36 mmol, 2.5 eq). HATU (0.774 g, 2.04 mmol, 1.1 eq) was added forming a yellow solution, which was stirred at room temperature for 1 day. The reaction was partitioned between EtOAc (120 mL) and water-NaHCO$_3$ (1:1, 120 mL). The organics were further washed with brine (120 mL), water (120 mL) and brine (100 mL), dried (Na$_2$SO$_4$) and concentrated under reduced pressure. MPLC (0→10% MeOH—CH$_2$Cl$_2$) yielded the title compound (0.693 g, 89%) as a yellow oil; $^1$H nmr (CDCl$_3$) δ 8.55 (1H, s, pyH-3 or H-6), 7.90 (2H, d, J 9.0 Hz, 2H of C$_6$H$_4$OMe), 7.48 (1H, s, pyH-3 or H-6), 6.91 (2H, d, J 9.0 Hz, 2H of C$_6$H$_4$OMe), 4.64 (1H, m, 1H of BzpipH-2, H-6), 4.01 (1H, m, 1H of BzpipH-2, H-6), 3.83 (3H, s, OCH$_3$), 3.49 (1H, m, BzpipH-4), 3.23 (1H, m, 1H of BzpipH-2, H-6), 3.03 (1H, m, 1H of BzpipH-2, H-6), 2.39 (3H, s, pyCH$_3$), 1.95 (1H, m, 1H of BzpipH-3, H-5), 1.86-1.75 (3H, s, 3H of BzpipH-3, H-5); m/z 417, 419 [M+H]+.

2-(4-(4-methoxybenzoyl)piperidinylcarbonyl)-4-methyl-5-vinylpyridine: A solution of the 5-bromopyridine (0.693 g, 1.66 mmol, 1.0 eq), diisopropylethylamine (0.58 mL, 3.32 mmol, 2.0 eq) and tributyl(vinyl)tin (0.58 mL, 2.99 mmol, 1.2 eq) in toluene (10 mL) was degassed by bubbling argon through the solution. Tetrakis(triphenylphosphine)palladium (0.058 g, 0.05 mmol, 0.03 eq) was added and the reaction further degassed before heating to 90° C. for 18 hours. The reaction was cooled and partitioned between EtOAc (100 mL) and NaHCO$_3$ (100 mL). The organics were washed with brine (90 mL), dried (Na$_2$SO$_4$) and concentrated under reduced pressure. MPLC (0→10% MeOH—CH$_2$Cl$_2$) yielded the title compound (0.573 g, 95%) as a colourless oil; $^1$H nmr (CDCl$_3$) δ 8.57 (1H, s, pyH-3 or H-6), 7.93 (2H, d, J 9.0 Hz, 2H of C$_6$H$_4$OMe), 7.41 (1H, s, pyH-3 or H-6), 6.94 (2H, d, J 9.0 Hz, 2H of C$_6$H$_4$OMe), 6.84 (1H, dd, J 17.5, 11.5 Hz, pyCH=CH$_2$), 5.75 (1H, dd, J 17.5, 1.0 Hz, pyCH=CH$_2$ trans), 5.45 (1H, dd, J 11.5, 1.0 Hz, pyCH=CH$_2$ cis), 4.69 (1H, m, 1H of BzpipH-2, H-6), 4.08 (1H, m, 1H of BzpipH-2, H-6), 3.86 (3H, s, OCH$_3$), 3.51 (1H, m, BzpipH-4), 3.27 (1H, m, 1H of BzpipH-2, H-6), 3.06 (1H, m, 1H of BzpipH-2, H-6), 2.37 (3H, s, pyCH$_3$), 1.99 (1H, m, 1H of BzpipH-3, H-5), 1.90-1.77 (3H, m, 3H of BzpipH-3, H-5); m/z 365 [M+H]$^+$.

2-(4-(4-methoxybenzoyl)piperidinylcarbonyl)-4-methylpyridine-5-carboxaldehyde: To a solution of the vinylpyridine (0.573 g, 1.57 mmol, 1.0 eq), in dioxane (9.0 mL) was added 2,6-lutidine (0.37 mL, 3.15 mmol, 2.0 eq). Osmium tetroxide (0.19 mL of a 4% solution in water, 0.03 mmol, 0.02 eq) was added and the reaction stirred at room temperature for 5 minutes before adding an aqueous solution of sodium periodate (1.347 g, 6.30 mmol, 4.0 eq) in water (7 mL). The reaction was stirred at room temperature for 1.5 hours before partitioning between EtOAc (250 mL) and HCl (1M, 200 mL). The organics were washed with HCl (1M, 200 mL) and brine (200 mL), dried (Na$_2$SO$_4$) and concentrated under reduced pressure. MPLC (0→10% MeOH—CH$_2$Cl$_2$) yielded the title compound (0.370 g, 65%); $^1$H nmr (CDCl$_3$) δ 10.31 (1H, s, CHO), 8.89 (1H, s, pyH-3 or H-6), 7.93 (2H, d, J 8.5 Hz, 2H of C$_6$H$_4$OMe), 7.52 (1H, s, pyH-3 or H-6), 6.95 (2H, d, J 9.0 Hz, 2H of C$_6$H$_4$OMe), 4.68 (1H, m, 1H of BzpipH-2, H-6), 3.94 (1H, m, 1H of BzpipH-2, H-6), 3.87 (3H, s, OCH$_3$), 3.53 (1H, m, BzpipH-4), 3.27 (1H, ddd, J 14.0, 10.5, 4.0 Hz, 1H of BzpipH2, H-6), 3.10 (1H, m, 1H of BzpipH-2, H-6), 2.71 (3H, s, pyCH$_3$), 2.03 (1H, m, 1H of BzpipH-3, H-5), 1.92-1.78 (3H, m, 3H of BzpipH-3, H-5); m/z 367 [M+H]$^+$.

2-(4-(4-methoxybenzoyl)piperidinylcarbonyl)-4-methylpyridine-5-carboxylic acid: To a solution of the pyridine carboxaldehyde (0.370 g, 1.01 mmol, 1.0 eq) in tetrahydrofuran-t-butanol (7:3, 10 mL) was added an aqueous solution of sodium chlorite (0.136 g, 1.52 mmool, 1.5 eq) and sulfamic acid (0.147 g, 1.52 mmol, 1.5 eq) in water (5 mL). The reaction was stirred at room temperature for 20 minutes before partitioning between EtOAc (70 mL) and brine (50 mL). The aqueous phase was extracted with EtOAc (70 mL). The combined organics were dried (Na$_2$SO$_4$) and concentrated under reduced pressure to yield the title compound (0.330 g, 85%) as a white solid, which was used without purification; m/z 383 [M+H]$^+$.

Compound 7-105: To a mixture of the pyridine carboxylic acid (0.050 g, 0.131 mmol, 1.0 eq), 1-(4-cyanobenzyl)-4-aminopiperidine dihydrochloride (0.045 g, 0.157 mmol, 1.2 eq) and HATU (0.055 g, 0.144 mmmol, 1.1 eq) was added dimethylformamide (1.0 mL) followed by triethylamine (0.064 mL, 0.458 mmol, 3.5 eq). The reaction was stirred at room temperature for 4 hours before partitioning between EtOAc (100 mL) and NaHCO$_3$-water (1:1, 100 mL). The organics were further washed with brine (100 mL), water (100 mL) and brine (100 mL) before drying (Na$_2$SO$_4$) and concentrating under reduced pressure. MPLC (0→10% MeOH—CH$_2$Cl$_2$) yielded the title compound as a colourless oil; $^1$H nmr (CDCl$_3$) δ 8.47 (1H, s, pyH-3 or H-6), 7.93 (2H, d, J 9.0 Hz, 2H of C$_6$H$_4$OMe), 7.59 (2H, d, J 8.0 Hz, 2H of C$_6$H$_4$CN), 7.44 (2H, d, J 8.5 Hz, 2H of C$_6$H$_4$CN), 7.38 (1H, s, pyH-3 or H-6), 6.95 (2H, d, J 9.0 Hz, 2H of C$_6$H$_4$OMe), 6.25 (1H, d, J 8.0 Hz, NH), 4.67 (1H, m, 1H of BzpipH-2, H-6), 4.02 (1H, m, pipH-4), 3.91 (1H, m, 1H of BzpipH-2, H-6), 3.87 (3H, s, OCH$_3$), 3.56 (2H, s, CH$_2$C$_6$H$_4$CN), 3.51 (1H, m, BzpipH-4), 3.22 (1H, m, 1H of BzpipH-2, H-6), 3.06 (1H, m, 1H of BzpipH-2, H-6), 2.82 (2H, m, 2H of pipH-2, H-6), 2.46 (3H, s, pyCH$_3$), 2.21 (2H, t, J 11.0 Hz, 2H of pipH-2, H-6), 2.07-1.98 (3H, m, 2H of pipH-3, H-5, 1H of BzpipH-3, H-5), 1.89-1.74 (3H, m, 3H of BzpipH-3, H-5), 1.61 (2H, m, 2H of pipH-3, H-5); m/z: 580 [M+H]$^+$.

Compounds 7-106 and 7-107 were prepared as follows:

Synthesis of N-((trans)-1-(4-cyanobenzyl)-3-fluoropiperidin-4-yl)-6-(4-(4-methoxybenzoyl)piperidine-1-carbonyl)nicotinamide ("the trans compound")

Coupling of the 1-tert-Butyloxycarbonyl-3-Fluoro-4-aminopiperidine

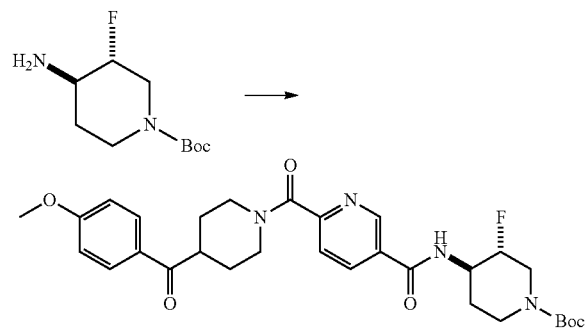

To a mixture of the crude pyridine carboxylic acid (2.15 g of approximately 66% purity, 3.86 mmol, 1.0 eq) and 1-tert-butyl-3-fluoro-4-aminopiperidine (0.84 g, 3.86 mmol, 1.0 eq) was added dimethylformamide (40 mL) followed by triethylamine (1.31 mL, 9.64 mmol, 2.5 eq). After the addition of HATU (1.47 g, 3.86 mmol, 1.0 eq) the reaction was stirred at room temperature for 4 hours before partitioning between EtOAc (300 mL) and water-NaHCO$_3$ (1:1, 300 mL). The organics were further washed with brine (250 mL), water (300 mL) and brine (250 mL) before drying (Na$_2$SO$_4$) and concentrating under reduced pressure. MPLC (0→10% MeOH—CH$_2$Cl$_2$) yielded the coupled material (1.41 g, 64%) as a pale yellow oil; $^1$H nmr (CDCl$_3$) δ 8.90 (1H, m, pyH-6), 8.11 (1H, dt, J 8.0, 2.0 Hz, pyH-4), 7.93 (2H, d, J 9.0 Hz, 2H of C$_6$H$_4$OCH$_3$), 7.56 (1H, d, J 6.0 Hz, NH), 7.50 (1H, dd, J 8.0, 2.0 Hz, pyH-3), 6.95 (2H, d, J 9.0 Hz, 2H of C$_6$H$_4$OCH$_3$), 4.65 (1H, m, 1H of BzpipH-2, H-6), 4.47 (0.5H, m, 0.5H of pipH-3), 4.31 (2.5H, m, 0.5H of pipH-3, pipH-4, 1H of pipH-2), 4.00 (1H, m, 1H of BzpipH-2, H-6), 3.87 (3H, s, OCH$_3$), 3.84 (1H, m, 1H of pipH-6), 3.53 (1H, m, BzpipH-4), 3.23 (1H, m, 1H of pipH-6), 3.11 (1H, m, 1H of BzpipH-2, H-6), 2.90 (2H, m, 1H of pipH-2, 1H of BzpipH-2, H-6), 2.08-1.92 (2H, m, 2H of pipH-5, BzpipH-3, H-5), 1.91-1.80 (4H, m, 4H of pipH-5, BzpipH-3, H-5), 1.47 (9H, s, C(CH$_3$)$_3$); $^{19}$F nmr (CDCl$_3$) δ −189.3 (d, J 47.5 Hz); m/z: 569 [M+H]$^+$.

Deprotection of the Tert-Butyloxycarbonyl Group

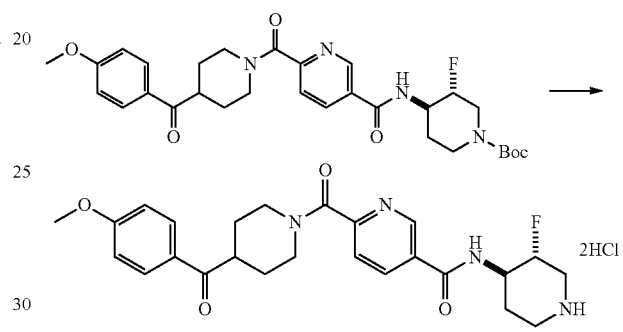

To a solution of the tert-butyloxycarbonylpiperidine (1.41 g, 2.48 mmol, 1.0 eq) in dichloromethane (25 mL) was added hydrogen chloride (2.5 mL of a 4.0M solution in dioxane, 9.93 mmol, 4.0 eq). The reaction was stirred at room temperature for 6 hours. A residue formed over the course of the reaction. Et$_2$O (100 mL) was added resulting in a precipitate after sonication, which was isolated by filtration. The resulting solid was dried under vacuum to yield the fluoropiperidine dihydrochloride as a pale orange solid (1.32 g, quantitative), which was used without further purification; $^1$H nmr (D$_6$-DMSO) δ 8.96 (2H, m, CONH, pyH-6), 8.30 (1H, dt, J 8.0, 2.0 Hz, pyH-4), 7.94 (2H, d, J 9.0 Hz, 2H of C$_6$H$_4$OCH$_3$), 7.62 (1H, dd, J 8.0 Hz, pyH-3), 6.99 (2H, d, J 9.5 Hz, 2H of C$_6$H$_4$OCH$_3$), 4.93, 4.75 (1H, 2m, pipH-3), 4.46 (1H, m, 1H of BzpipH-2, H-6), 4.32 (1H, m, pipH-4), 3.78 (3H, s, OCH$_3$), 3.69 (1H, m, BzpipH-4), 3.57-3.50 (2H, m, 1H of pipH-2, 1H of BzpipH-2, H-6), 3.28-3.10 (3H, m, 1H of pipH-2, 1H of pipH-6, 1H of BzpipH-2, H-6), 3.08-2.94 (2H, m, 1H of pipH-6, 1H of BzpipH-2, H-6), 2.02 (1H, m, 1H of pipH-5), 1.82 (2H, m, 1H of pipH-5, 1H of BzpipH-3, H-5), 1.63 (1H, m, 1H of BzpipH-3, H-5), 1.55-1.47 (2H, m, 2H of BzpipH-3, H-5); $^{19}$F nmr (D$_6$-DMSO) δ −188.6 (d, J 50.0 Hz); m/z: 469 [M+H]$^+$.

the Trans Compound

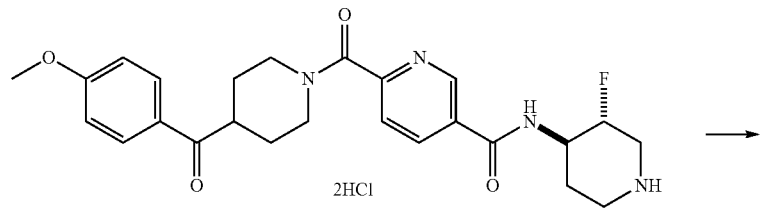

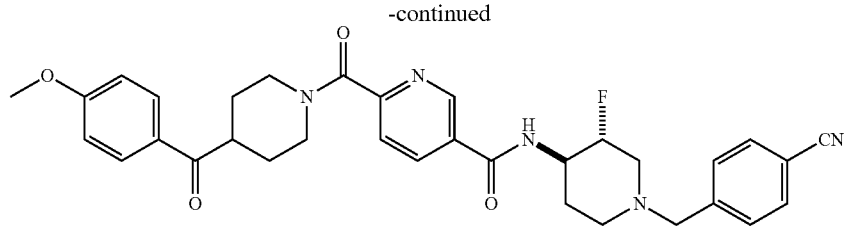

To a suspension of the fluoropiperidine dihydrochloride (0.250 g, 0.462 mmol, 1.0 eq) in dischlormethane (5.0 mL) was added diisopropylethylamine (0.28 mL, 1.617 mmol, 3.5 eq) to form a clear solution. 4-Cyanobenzyl bromide (0.100 g, 0.508 mmol, 1.1 eq) was added and the reaction stirred at room temperature for 5 hours before pouring into NaHCO$_3$ (40 mL). The organics were extracted with CH$_2$Cl$_2$ (3×40 mL), combined, dried (Na$_2$SO$_4$) and concentrated under reduced pressure. MPLC (3→5% MeOH—CH$_2$Cl$_2$) yielded the trans compound (0.162 g, 60%) as a white foam; IR (film) 3313, 2953, 1662, 1622, 1599, 1544, 1448, 1259, 1170, 1027, 971, 912, 848, 731 cm$^{-1}$; $^1$H nmr (CDCl$_3$) δ 8.88 (1H, d, J 2.0 Hz, pyH-6), 8.07 (1H, dd, J 8.5, 2.0 Hz, pyH-4), 7.94 (2H, d, J 9.0 Hz, 2H of C$_6$H$_4$OCH$_3$), 7.60 (2H, d, J 8.0 Hz, 2H of C$_6$H$_4$CN), 7.48 (1H, d, J 8.0 Hz, pyH-3), 7.43 (2H, d, J 8.0 Hz, 2H of C$_6$H$_4$CN), 7.33 (1H, m, NH), 6.96 (2H, d, J 9.0 Hz, 2H of C$_6$H$_4$OCH$_3$), 4.70 (1H, m, 1H of BzpipH-2, H-6), 4.70, 4.53 (1H, m, pipH-3), 4.15 (1H, m, pipH-4), 3.88 (3H, s, OCH$_3$), 3.82 (1H, m, 1H of BzpipH-2, H-6), 3.63 (2H, s, CH$_2$C$_6$H$_4$CN), 3.54 (1H, m, BzpipH-4), 3.28-3.09 (3H, m, 2H of BzpipH-2, H-6, 1H of pipH-6), 2.80 (1H, m, 1H of pipH-2), 2.30-2.17 (3H, m, 1H of pipH-6, 1H of pipH-5, 1H of pipH-2), 2.03 (1H, m, 1H of BzpipH-3, H-5), 1.93-1.82 (3H, m, 3H of BzpipH-3, H-5), 1.67 (1H, m, 1H of pipH-5); $^{13}$C nmr (CDCl$_3$) δ 199.9, 167.2, 165.3, 163.7, 155.8, 147.5, 143.8, 136.1, 132.2, 130.8, 130.6, 129.2, 128.5, 122.6, 118.8, 114.0, 111.1, 89.5 (90.7, 88.4, d, J 178.5 Hz), 61.7, 56.5 (56.7, 56.3, J 25.0 Hz), 55.5, 52.3 (52.4, 52.1, J 17.5 Hz), 51.7, 46.7, 42.6, 41.9, 29.9 (29.9, 29.8 J 6.5 Hz), 28.6 (28.8, 28.4, J 28.0 Hz); $^{19}$F nmr (CDCl$_3$) δ −188.5 (d, J=55 Hz); m/z: 584 [M+H]$^+$ (found [M+H]$^+$, 584.2711, C$_{33}$H$_{34}$FN$_5$O$_4$ requires [M+H]$^+$584.2668).

Compound 7-106 was separated from the racemic trans compound using chiral chromatography on an (R, R)-Whelk-O 1 25 cm×10 mm column (silica modified with covalently bound 4-(3,5-dinitrobenzamido)tetrahydrophenanthrene), available from Regis Technologies. The instrument was a TharSFC semi-preparative HPLC system, and elution was performed isocratically using 50% MeOH with 0.1% diethylamine in supercritical carbon dioxide at 14 mL/min at 30° C. Compound 7-106 was the later-eluting peak (at about 21 minutes under the conditions described above). The spectral data agree with the trans compound. Compound 7-106 was independently enantioselectively synthesized as described in the following scheme:

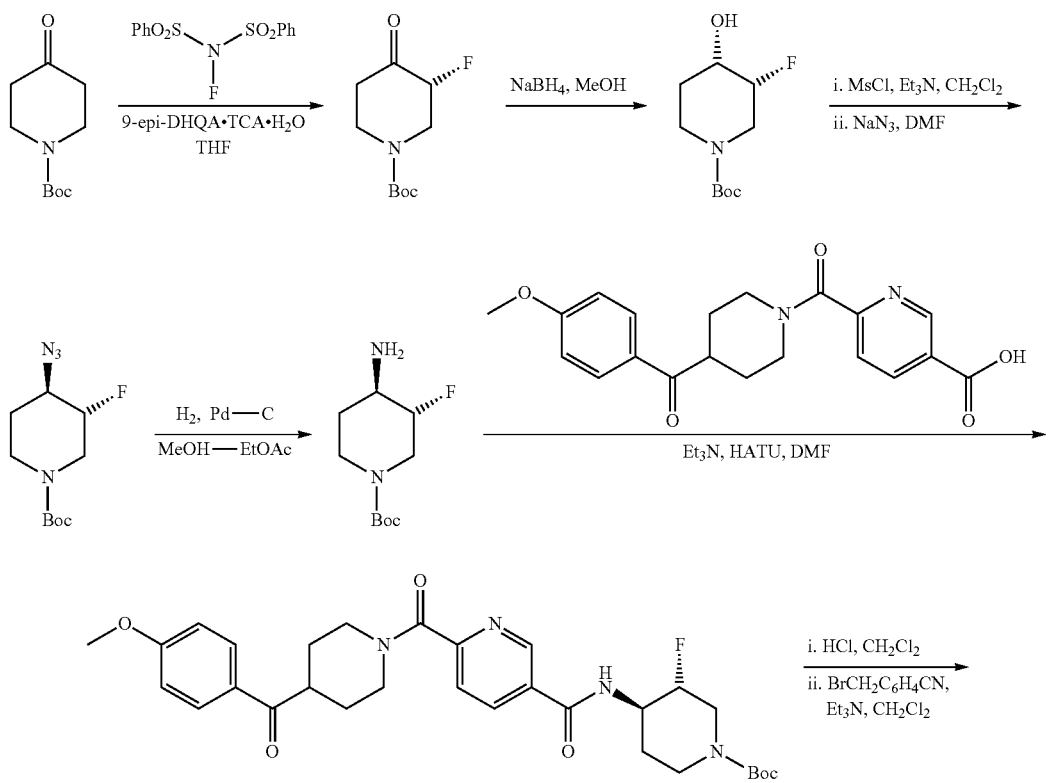

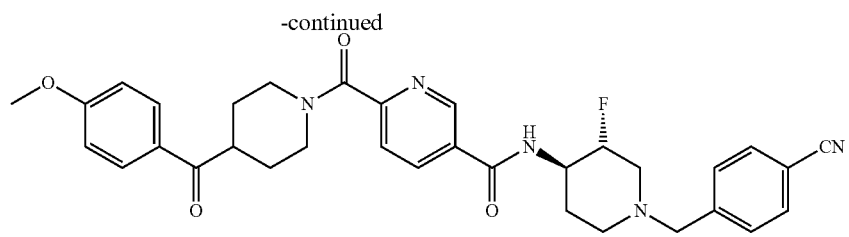

The first step of the synthesis followed the method of Kwiatkowski, P.; Beeson, T. D.; Conrad, J. C.; MacMillan, D. W. C., J. Am. Chem. Soc., 2011, 133(6), 1738-1741, which is hereby incorporated herein by reference in its entirety. 9-Epi-DHQA is (1R)-((2R)-5-ethylquinuclidin-2-yl)(6-methoxyquinolin-4-yl)methanamine. The optical rotation [α] of the (3R,4S)-tert-butyl 3-fluoro-4-hydroxypiperidine-1-carboxylate was −20.0° (c 0.33, $CH_2Cl_2$); the literature value for the corresponding (3S,4R) compound is +21.6°. See International Patent Application Publication no. WO 2010/128425.

Compound 7-107: N-((3S,4S)-1-(4-cyanobenzyl)-3-fluoropiperidin-4-yl)-6-(4-(4-methoxybenzoyl)piperidine-1-carbonyl)nicotinamide. Compound 7-107 was separated from the racemic mixture of the trans compound using chiral chromatography as described above with reference to Compound 7-107. Compound 7-107 was the earlier-eluting peak (at about 20 minutes under the conditions described above). The spectral data agree with the trans compound.

AMPK Activation

Compounds of Table 1 were assayed for their ability to activate AMPK using an enzyme-linked immunosorbent assay. The $EC_{50}$ values for AMPK activation for the tested compounds are presented in Table 8 below, in which "A" is less than 0.1 μM; "B" is 0.1-0.5 μM; "C" is 0.5-1 μM; "D" is 1-5 μM; "E" is 5-10 μM; and "F" is >10 μM.

TABLE 8

| Cpd No. | AMPK $EC_{50}$ |
|---|---|
| 1-1 | B |
| 1-2 | A |
| 1-3 | A |
| 1-4 | A |
| 1-5 | A |
| 1-6 | B |
| 1-7 | A |
| 1-8 | A |
| 1-9 | B |
| 1-10 | A |
| 1-11 | A |
| 1-12 | C |
| 1-13 | B |
| 1-14 | A |
| 1-15 | D |
| 1-16 | A |
| 1-17 | A |
| 1-18 | A |
| 1-19 | D |
| 1-20 | C |
| 1-21 | B |
| 1-22 | D |
| 1-23 | B |
| 1-24 | E |
| 1-25 | B |
| 1-26 | B |
| 1-27 | F |
| 1-28 | A |
| 1-29 | B |
| 1-30 | A |
| 1-31 | A |

TABLE 8-continued

| Cpd No. | AMPK $EC_{50}$ |
|---|---|
| 1-32 | B |
| 1-33 | C |
| 1-34 | C |
| 1-35 | B |
| 1-36 | C |
| 1-37 | C |
| 1-38 | D |
| 1-39 | B |
| 1-40 | A |
| 1-41 | B |
| 1-42 | D |
| 1-43 | D |
| 1-44 | B |
| 1-45 | F |
| 1-46 | D |
| 1-47 | D |
| 1-48 | D |
| 1-49 | A |
| 1-50 | D |
| 1-51 | B |
| 1-52 | B |
| 1-53 | B |
| 1-54 | D |
| 1-55 | D |
| 1-56 | E |
| 1-57 | C |
| 1-58 | A |
| 1-59 | B |
| 1-60 | F |
| 1-61 | B |
| 1-62 | E |
| 1-63 | A |
| 1-64 | A |
| 1-65 | A |
| 1-66 | A |
| 1-67 | A |
| 1-68 | A |
| 1-69 | A |
| 1-70 | A |
| 1-71 | A |
| 1-72 | B |
| 1-73 | C |
| 1-74 | B |
| 1-75 | A |
| 1-76 | B |
| 1-77 | B |
| 1-78 | A |
| 1-79 | B |
| 1-80 | A |
| 1-81 | B |
| 1-82 | B |
| 1-83 | B |
| 1-84 | E |
| 1-85 | C |
| 1-86 | F |
| 1-87 | A |
| 1-88 | A |
| 1-89 | A |
| 1-90 | A |
| 1-91 | F |
| 1-92 | C |
| 1-93 | B |
| 1-94 | A |
| 1-95 | A |

TABLE 8-continued

| Cpd No. | AMPK EC$_{50}$ |
|---|---|
| 1-96 | A |
| 1-97 | A |
| 1-98 | A |
| 1-99 | A |
| 1-100 | A |
| 1-101 | A |
| 1-102 | D |
| 1-103 | D |
| 1-104 | B |
| 1-105 | A |
| 1-106 | B |
| 1-107 | A |
| 1-108 | B |
| 1-109 | A |
| 1-110 | A |
| 1-111 | B |
| 1-112 | A |
| 1-113 | B |
| 1-114 | B |
| 1-115 | A |
| 1-116 | B |
| 1-117 | A |
| 1-118 | B |
| 1-119 | A |
| 1-120 | D |
| 1-121 | F |
| 1-122 | B |
| 1-123 | B |
| 1-124 | D |
| 1-125 | D |
| 1-126 | D |
| 1-127 | D |
| 1-128 | F |
| 1-129 | D |
| 1-130 | D |
| 1-131 | D |
| 1-137 | A |
| 1-138 | A |
| 1-139 | A |
| 1-140 | C |
| 1-141 | B |
| 1-144 | A |
| 1-145 | B |
| 1-146 | B |
| 1-147 | D |
| 1-148 | F |
| 1-149 | A |
| 1-150 | D |
| 1-151 | A |
| 1-152 | A |
| 1-153 | B |
| 1-154 | A |
| 1-155 | A |
| 1-156 | B |
| 1-157 | D |
| 1-158 | B |
| 1-159 | B |
| 1-160 | A |
| 1-161 | C |
| 1-162 | A |
| 1-163 | A |
| 1-164 | B |
| 1-165 | A |
| 1-166 | A |
| 1-167 | A |
| 1-168 | A |
| 1-169 | A |
| 1-170 | A |
| 1-171 | A |
| 1-172 | A |
| 1-173 | A |
| 1-174 | A |
| 1-175 | A |

Compounds of Table 2 were assayed for their ability to activate AMPK using an enzyme-linked immunosorbent assay. The EC$_{50}$ values for AMPK activation for the tested compounds are presented in Table 9 below, in which "A" is less than 0.5 µM; "B" is 0.5-1 µM; "C" is 1-5 µM; and "D" is 5-10 µM; "E" is 10-50 µM; and "F" is >100 µM:

TABLE 9

| Cpd No. | AMPK EC$_{50}$ |
|---|---|
| 2-1 | C |
| 2-2 | E |
| 2-3 | E |
| 2-4 | C |
| 2-5 | C |
| 2-6 | B |
| 2-7 | D |
| 2-8 | D |
| 2-9 | A |
| 2-10 | B |
| 2-11 | A |
| 2-12 | A |
| 2-13 | A |
| 2-14 | A |
| 2-15 | A |
| 2-16 | A |
| 2-17 | B |
| 2-18 | C |
| 2-19 | F |
| 2-20 | C |
| 2-21 | B |
| 2-22 | B |
| 2-23 | C |
| 2-24 | C |
| 2-25 | E |
| 2-26 | E |
| 2-27 | C |
| 2-28 | C |
| 2-29 | C |
| 2-30 | C |
| 2-31 | C |
| 2-32 | C |
| 2-33 | C |
| 2-24 | C |
| 2-35 | E |
| 2-36 | F |
| 2-37 | D |
| 2-38 | E |
| 2-39 | E |
| 2-40 | F |
| 2-41 | E |
| 2-43 | F |
| 2-44 | E |
| 2-45 | F |
| 2-46 | F |
| 2-47 | E |
| 2-48 | F |
| 2-49 | F |
| 2-50 | A |
| 2-51 | B |
| 2-52 | C |
| 2-53 | E |
| 2-54 | A |

Compounds of Table 3 were assayed for their ability to activate AMPK using an enzyme-linked immunosorbent assay. The EC$_{50}$ values for AMPK activation for the tested compounds are presented in Table 10 below, in which "A" is less than 0.1 µM; "B" is 0.1-1 µM; "C" is 1-10 µM; and "D" is 10-100 µM:

TABLE 10

| Cpd No. | AMPK EC$_{50}$ |
|---|---|
| 3-1 | A |
| 3-2 | A |
| 3-3 | A |
| 3-4 | A |
| 3-5 | D |

TABLE 10-continued

| Cpd No. | AMPK EC$_{50}$ |
|---|---|
| 3-6 | A |
| 3-7 | A |
| 3-8 | B |
| 3-9 | B |
| 3-10 | B |
| 3-11 | B |
| 3-12 | A |
| 3-13 | A |
| 3-14 | C |
| 3-15 | B |
| 3-16 | B |
| 3-17 | A |
| 3-18 | A |
| 3-19 | C |
| 3-20 | F |
| 3-21 | A |
| 3-22 | A |
| 3-23 | A |
| 3-24 | A |
| 3-25 | A |
| 3-26 | C |
| 3-27 | A |
| 3-28 | A |
| 3-29 | D |
| 3-30 | A |
| 3-31 | A |
| 3-32 | D |
| 3-33 | D |
| 3-34 | A |
| 3-35 | C |
| 3-36 | B |
| 3-37 | A |
| 3-38 | A |
| 3-39 | C |
| 3-40 | A |
| 3-41 | C |
| 3-42 | B |

Compounds of Table 4 were assayed for their ability to activate AMPK using an enzyme-linked immunosorbent assay. The EC$_{50}$ values for AMPK activation for the tested compounds are presented in Table 11 below, in which "A" is less than 0.5 µM; "B" is 0.5-1 µM; "C" is 1-5 µM; and "D" is 5-10 µM; "E" is 10-50 µM; and "F" is >100 µM:

TABLE 11

| Cpd No. | AMPK EC$_{50}$ |
|---|---|
| 4-1 | A |
| 4-2 | A |
| 4-3 | A |
| 4-4 | C |
| 4-5 | C |
| 4-6 | B |
| 4-7 | C |
| 4-8 | C |
| 4-9 | B |
| 4-10 | A |
| 4-11 | A |
| 4-12 | A |
| 4-13 | C |
| 4-14 | A |
| 4-15 | A |
| 4-16 | A |
| 4-17 | C |

Compounds of Table 5 were assayed for their ability to activate AMPK using an enzyme-linked immunosorbent assay. The EC$_{50}$ values for AMPK activation for the tested compounds are presented in Table 12 below, in which "A" is less than 1 µM; "B" is 1-10 µM; "C" is 10-20 µM; "D" is 20-50 µM; "E" is 50-100 µM, and "F" is >100 µM:

TABLE 12

| Cpd No. | AMPK EC$_{50}$ |
|---|---|
| 5-1 | A |
| 5-2 | A |
| 5-3 | B |
| 5-4 | F |
| 5-5 | E |
| 5-6 | A |
| 5-7 | A |
| 5-8 | B |
| 5-9 | D |
| 5-10 | B |
| 5-11 | B |
| 5-12 | B |
| 5-13 | D |
| 5-14 | A |
| 5-15 | A |
| 5-16 | A |
| 5-17 | A |
| 5-18 | A |
| 5-19 | A |
| 5-20 | A |
| 5-21 | B |
| 5-22 | B |
| 5-23 | A |
| 5-24 | C |
| 5-25 | F |
| 5-26 | A |
| 5-27 | A |
| 5-28 | A |
| 5-29 | A |
| 5-30 | A |
| 5-31 | A |
| 5-32 | A |
| 5-33 | A |
| 5-34 | A |
| 5-35 | B |
| 5-36 | A |
| 5-37 | A |
| 5-38 | B |
| 5-39 | B |
| 5-40 | A |
| 5-41 | A |
| 5-42 | A |
| 5-43 | A |
| 5-44 | A |
| 5-45 | A |
| 5-46 | A |
| 5-47 | A |
| 5-48 | A |
| 5-49 | A |
| 5-50 | B |
| 5-51 | A |
| 5-52 | B |
| 5-53 | C |
| 5-54 | A |
| 5-55 | A |
| 5-56 | A |
| 5-57 | A |
| 5-58 | B |
| 5-59 | A |
| 5-60 | A |
| 5-61 | A |
| 5-62 | A |
| 5-63 | A |
| 5-64 | A |
| 5-65 | A |
| 5-66 | A |
| 5-67 | A |
| 5-68 | A |
| 5-69 | A |
| 5-70 | A |
| 5-71 | A |
| 5-72 | A |
| 5-73 | A |
| 5-74 | A |
| 5-75 | A |
| 5-76 | A |
| 5-77 | A |
| 5-78 | A |

TABLE 12-continued

| Cpd No. | AMPK EC$_{50}$ |
|---|---|
| 5-79 | F |
| 5-80 | A |
| 5-81 | A |
| 5-82 | A |
| 5-83 | A |
| 5-84 | A |
| 5-85 | A |
| 5-86 | A |
| 5-87 | A |
| 5-88 | B |
| 5-89 | B |
| 5-90 | B |
| 5-91 | A |
| 5-92 | B |
| 5-93 | F |
| 5-94 | A |
| 5-95 | A |
| 5-96 | B |
| 5-97 | B |
| 5-98 | B |
| 5-99 | B |
| 5-100 | B |
| 5-101 | C |
| 5-102 | C |
| 5-103 | D |
| 5-104 | C |
| 5-105 | C |
| 5-106 | A |
| 5-107 | A |
| 5-108 | A |
| 5-109 | A |
| 5-110 | A |
| 5-111 | A |
| 5-112 | B |
| 5-113 | A |
| 5-114 | B |
| 5-115 | A |
| 5-116 | A |
| 5-117 | A |
| 5-118 | A |
| 5-119 | A |
| 5-120 | A |
| 5-121 | A |
| 5-122 | A |
| 5-123 | F |
| 5-124 | A |
| 5-125 | A |
| 5-126 | A |
| 5-127 | A |
| 5-128 | A |
| 5-129 | A |

Compounds of Table 6 were assayed for their ability to activate AMPK using an enzyme-linked immunosorbent assay. The EC$_{50}$ values for AMPK activation for the tested compounds are presented in Table 13 below, in which "A" is less than 0.1 µM; "B" is 0.1-1 µM; "C" is 1-10 µM; and "D" is 10-100 µM:

TABLE 13

| Cpd No. | AMPK EC$_{50}$ |
|---|---|
| 6-1 | A |
| 6-2 | B |
| 6-3 | A |
| 6-4 | B |
| 6-5 | A |
| 6-6 | A |
| 6-7 | A |
| 6-8 | A |
| 6-9 | B |
| 6-10 | A |
| 6-11 | A |
| 6-12 | A |

TABLE 13-continued

| Cpd No. | AMPK EC$_{50}$ |
|---|---|
| 6-13 | A |
| 6-14 | A |
| 6-15 | B |
| 6-16 | A |
| 6-17 | A |
| 6-18 | A |
| 6-19 | A |
| 6-20 | A |
| 6-21 | A |
| 6-22 | A |
| 6-23 | B |
| 6-24 | A |
| 6-25 | A |
| 6-26 | A |
| 6-27 | A |
| 6-28 | A |
| 6-29 | A |
| 6-30 | A |
| 6-31 | A |
| 6-33 | A |
| 6-40 | C |
| 6-41 | C |
| 6-42 | C |
| 6-43 | B |
| 6-44 | B |
| 6-46 | B |
| 6-48 | B |
| 6-49 | B |
| 6-50 | B |
| 6-54 | B |
| 6-55 | B |
| 6-56 | C |
| 6-57 | B |
| 6-59 | B |
| 6-60 | C |
| 6-61 | B |
| 6-64 | B |
| 6-65 | B |
| 6-66 | B |
| 6-67 | C |
| 6-68 | B |
| 6-69 | A |
| 6-70 | A |
| 6-71 | B |
| 6-72 | C |
| 6-73 | C |
| 6-74 | B |
| 6-75 | A |
| 6-76 | A |
| 6-77 | A |
| 6-78 | A |
| 6-79 | A |
| 6-80 | A |
| 6-81 | A |
| 6-82 | A |
| 6-83 | C |
| 6-84 | A |
| 6-85 | C |
| 6-86 | A |
| 6-87 | B |
| 6-88 | A |
| 6-89 | A |
| 6-90 | A |
| 6-91 | C |
| 6-92 | B |
| 6-93 | B |
| 6-94 | B |
| 6-95 | B |
| 6-96 | A |
| 6-97 | A |
| 6-98 | B |
| 6-99 | C |
| 6-100 | A |
| 6-101 | B |
| 6-102 | A |
| 6-103 | A |
| 6-104 | A |
| 6-105 | A |

TABLE 13-continued

| Cpd No. | AMPK EC$_{50}$ |
| --- | --- |
| 6-106 | A |
| 6-107 | A |
| 6-108 | A |
| 6-109 | A |
| 6-110 | B |
| 6-111 | B |
| 6-112 | A |
| 6-113 | A |
| 6-114 | A |
| 6-115 | A |
| 6-116 | A |
| 6-117 | C |
| 6-118 | A |
| 6-119 | A |
| 6-120 | A |
| 6-121 | A |
| 6-122 | B |
| 6-123 | A |
| 6-124 | A |
| 6-125 | A |
| 6-126 | A |
| 6-127 | A |
| 6-128 | A |
| 6-129 | A |
| 6-130 | A |
| 6-131 | A |
| 6-132 | A |
| 6-133 | A |
| 6-134 | A |
| 6-135 | A |
| 6-136 | A |
| 6-137 | A |
| 6-138 | A |
| 6-139 | A |
| 6-140 | A |
| 6-141 | A |
| 6-142 | A |
| 6-143 | A |
| 6-144 | A |
| 6-145 | A |
| 6-146 | A |
| 6-147 | A |
| 6-148 | A |
| 6-149 | A |
| 6-150 | A |
| 6-151 | A |
| 6-152 | B |
| 6-153 | A |
| 6-154 | A |
| 6-155 | A |
| 6-156 | A |
| 6-157 | A |
| 6-158 | B |
| 6-159 | C |
| 6-160 | A |
| 6-161 | A |
| 6-162 | A |
| 6-163 | A |
| 6-164 | A |

Compounds of Table 7 were assayed for their ability to activate AMPK using an enzyme-linked immunosorbent assay. The EC$_{50}$ values for AMPK activation for the tested compounds are presented in Table 14 below, in which "A" is less than 1 μM; "B" is 1-10 μM; "C" is 10-20 μM; "D" is 20-50 μM; "E" is 50-100 μM, and "F" is >100 μM:

TABLE 14

| Cpd No. | AMPK EC$_{50}$ |
| --- | --- |
| 7-1 | B |
| 7-2 | A |
| 7-3 | A |
| 7-4 | A |
| 7-5 | A |
| 7-6 | A |
| 7-7 | B |
| 7-8 | B |
| 7-9 | B |
| 7-10 | B |
| 7-11 | B |
| 7-13 | B |
| 7-14 | B |
| 7-15 | B |
| 7-16 | B |
| 7-17 | A |
| 7-18 | A |
| 7-19 | C |
| 7-20 | A |
| 7-21 | A |
| 7-22 | A |
| 7-23 | A |
| 7-24 | A |
| 7-25 | A |
| 7-26 | A |
| 7-27 | A |
| 7-28 | A |
| 7-29 | A |
| 7-30 | A |
| 7-31 | A |
| 7-32 | A |
| 7-33 | A |
| 7-34 | A |
| 7-35 | A |
| 7-36 | A |
| 7-37 | A |
| 7-38 | B |
| 7-39 | B |
| 7-40 | B |
| 7-41 | A |
| 7-42 | B |
| 7-43 | A |
| 7-44 | A |
| 7-45 | A |
| 7-46 | B |
| 7-47 | A |
| 7-48 | B |
| 7-49 | B |
| 7-50 | A |
| 7-51 | A |
| 7-52 | A |
| 7-53 | A |
| 7-54 | A |
| 7-55 | B |
| 7-56 | B |
| 7-57 | A |
| 7-58 | A |
| 7-59 | A |
| 7-60 | C |
| 7-61 | B |
| 7-62 | A |
| 7-63 | C |
| 7-64 | B |
| 7-65 | A |
| 7-66 | B |
| 7-67 | A |
| 7-68 | A |
| 7-69 | A |
| 7-70 | A |
| 7-71 | A |
| 7-72 | A |
| 7-73 | B |
| 7-74 | A |
| 7-75 | A |
| 7-76 | B |
| 7-77 | A |
| 7-78 | A |
| 7-79 | C |
| 7-80 | A |
| 7-81 | A |
| 7-82 | B |
| 7-83 | B |

TABLE 14-continued

| Cpd No. | AMPK EC$_{50}$ |
|---|---|
| 7-84 | A |
| 7-85 | A |
| 7-86 | A |
| 7-87 | B |
| 7-89 | B |
| 7-90 | B |
| 7-91 | C |
| 7-92 | B |
| 7-93 | A |
| 7-94 | A |
| 7-95 | A |
| 7-96 | A |
| 7-97 | A |
| 7-98 | A |
| 7-99 | A |
| 7-100 | A |
| 7-101 | A |
| 7-102 | A |
| 7-105 | A |
| 7-106 | A |
| 7-107 | A |
| 7-108 | A |
| 7-109 | A |
| 7-110 | A |
| 7-111 | A |
| 7-112 | A |
| 7-113 | A |
| 7-114 | A |
| 7-115 | E |
| 7-116 | A |
| 7-117 | A |
| 7-118 | A |
| 7-119 | A |
| 7-120 | A |
| 7-121 | A |
| 7-122 | A |
| 7-123 | A |

Endurance Testing

Male C57B/6J mice (8 weeks old) are randomly divided into at least four cohorts for exercise-trained and sedentary control and dosage groups.

Mice are acclimated to moderate treadmill running (10 m/min for 15 min) every other day for 1 week (day 1, 3, 5, 7). After acclimation, basal running endurances for the four groups are determined via a treadmill running test, where the speed is gradually increased from 0 to 15 m/min over the course of 15 min and then maintained constant until exhaustion. Treadmill to be used is 1012M-8-E52 Modular Enclosed Metabolic Treadmill for Mice, 8 Lanes w/Shock for Mice w/Shocker Detection & Software from Columbus Instruments or similar (with attached open-flow calorimeter for the measurement of respiratory metabolic performance while exercising). Exhaustion defined when mice are unable to avoid repetitive electrical shocks. Data are collected on total time and distance run as well as VO$_2$.

On day 8 dosing by gavage with the compounds begins for the sedentary and exercise-trained groups and dosing with vehicle only for the control sedentary and exercise-trained groups.

Beginning on day 9, the groups to be exercise-trained are subjected to 4 weeks (5 days/week) of exercise training. During all exercise sessions and treadmill tests, VO$_2$ is measured before, during, and after exercise by means of indirect calorimetry in metabolic treadmill chambers. The 5th day of training for each weekly exercise regime is used as a complete treadmill test where the speed is gradually increased from 0 to 15 m/min over the course of 15 min and then maintained constant until exhaustion. Day 9 exercise to consist of treadmill running of 10 m/min for 15 min with a treadmill incline of 5 degrees. Subsequent exercise-training is to be progressive with increasing intensity and time (also incline of 5 degrees on treadmill). Data are collected on total time and distance for each training session, with point of exhaustion noted for mice failing to complete exercise.

Treatment with the present compounds results in increased endurance for both the exercise-trained and sedentary groups.

What is claimed is:

1. A compound having the structural formula

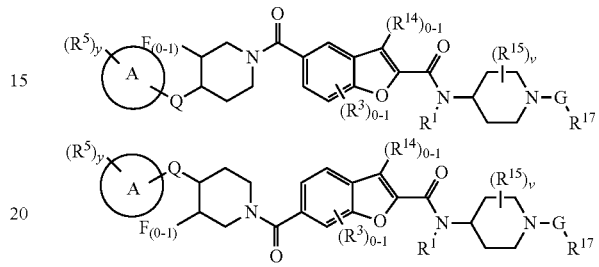

wherein
R$^1$ is H, —(C$_1$-C$_4$ alkyl), —C(O)—(C$_1$-C$_4$ alkyl) or —C(O)O—(C$_1$-C$_4$ alkyl);
G is a bond, —CH$_2$—, —C(O)—, —CH(CH$_3$)—, —O— or —S(O)$_2$—;
each R$^{15}$ is independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, and two R$^{15}$ on the same carbon optionally combine to form oxo; and
v is 0, 1, 2, 3 or 4;
R$^{17}$ is phenyl optionally substituted with 0, 1, 2 or 3 substituents independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —SF$_5$, —NO$_2$ and —CN;
R$^3$ is a substituent on a benzo carbon of the benzofuran ring system, which substituent is independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_6$ alkyl)-S(O)$_{0-2}$R$^{10}$, -halogen, —NO$_2$ and —CN;
R$^{14}$ is selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN;
Q is —CH$_2$—; a single bond; —S(O)$_2$—; —C(O)—; —O— or —CH(CH$_3$)—;
the ring system denoted by "A" is phenyl;
each R$^5$ is independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN; and
y is 0, 1, 2, 3 or 4;
in which
each L is independently selected from —NR$^9$C(O)O—, —OC(O)NR$^9$—, —NR$^9$C(O)—NR$^9$—, —NR$^9$C(O)S—, —SC(O)NR$^9$—, —NR$^9$C(O)—, —C(O)—NR$^9$—, —NR$^9$C(S)O—, —OC(S)

NR$^9$—, —NR$^9$C(S)—NR$^9$—, —NR$^9$C(S)S—, —SC(S)NR$^9$—, —C(S)NR$^9$—, —SC(O)NR$^9$—, —NR$^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR$^9$C(NR$^2$)NR$^9$—, —NR$^9$SO$_2$—, —SO$_2$NR$^9$— and —NR$^9$SO$_2$NR$^9$—, each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$—(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and each R$^9$ is independently selected from —H, —(C$_1$-C$_4$ alkyl) and —C(O)O—(C$_1$-C$_4$ alkyl), or a pharmaceutically-acceptable salt thereof.

2. A compound according to claim 1, wherein the

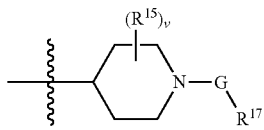

moiety is

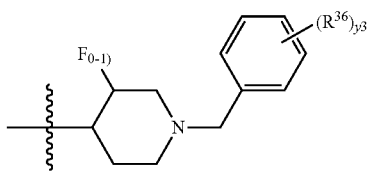

wherein y3 is 0, 1, 2 or 3, and each R$^{36}$ is independently selected from halo, cyano, —(C$_1$-C$_3$ haloalkyl), —O—(C$_1$-C$_2$ haloalkyl), —(C$_1$-C$_3$ alkyl), —O—(C$_1$-C$_2$ alkyl), —C(O)—(C$_0$-C$_2$ alkyl), —C(O)O—(C$_0$-C$_2$ alkyl), —C(O)N(C$_0$-C$_4$ alkyl)(C$_0$-C$_2$ alkyl), —S(O)$_2$(C$_1$-C$_2$ alkyl), —SF$_5$, and NO$_2$.

3. A compound according to claim 1, having the structural formula

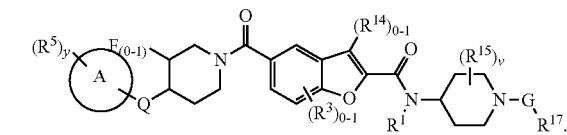

4. A compound according to claim 1, having the formula

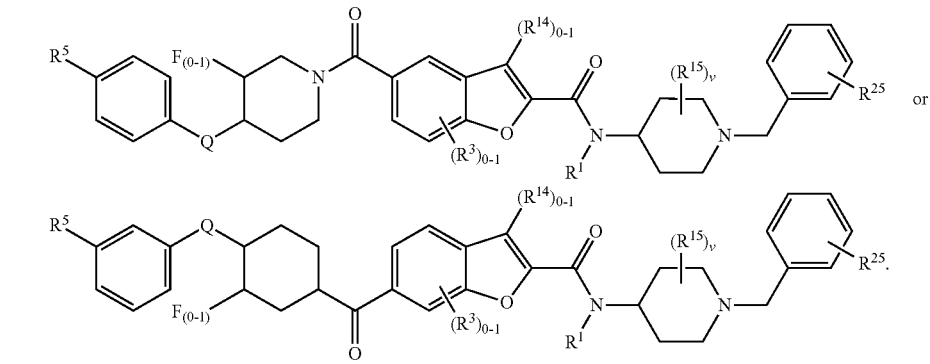

in which R$^{25}$ is selected from halo, cyano, —(C$_1$-C$_3$ haloalkyl), —O—(C$_1$-C$_2$ haloalkyl), —(C$_1$-C$_3$ alkyl), —O—(C$_1$-C$_2$ alkyl), —C(O)—(C$_0$-C$_2$ alkyl), —C(O)O—(C$_0$-C$_2$ alkyl), —C(O)N(C$_0$-C$_4$ alkyl)(C$_0$-C$_2$ alkyl), and NO$_2$.

5. A compound according to claim 1, wherein R$^1$ is H.
6. A compound according to claim 1, wherein (R$^3$)$_{0-1}$ is (R$^3$)$_0$.
7. A compound according to claim 1, wherein v is 0.
8. A compound according to claim 1, wherein (R$^{14}$)$_{0-1}$ is (R$^{14}$)$_0$.
9. A compound according to claim 1, wherein F$_{(0-1)}$ is F$_{(0)}$.
10. A compound according to claim 1, wherein (R$^3$)$_{0-1}$ is (R$^3$)$_0$, (R$^{14}$)$_{0-1}$ is (R$^{14}$)$_0$, and v is 0.
11. A compound according to claim 10, having the structural formula

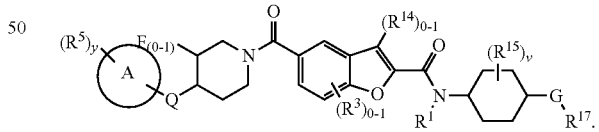

12. A compound according to claim 4, having the structural formula

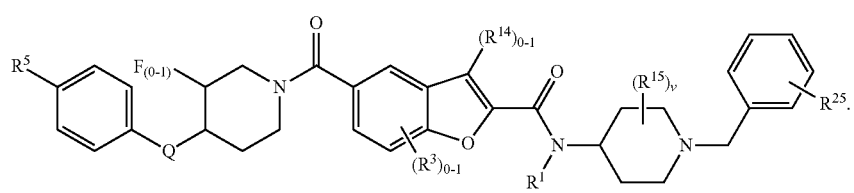

13. A compound according to claim 1, having the structural formula

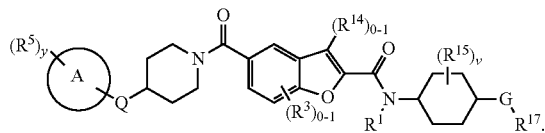

14. A compound according to claim 1, wherein Q is —CH$_2$—; a single bond; —S(O)$_2$—; —C(O)—; or —CH(CH$_3$)—.

15. A compound according to claim 1, selected from 5-(4-(4-fluorobenzoyl)piperidine-1-carbonyl)-N-(1-(pyridin-4-ylmethyl)piperidin-4-yl)benzofuran-2-carboxamide;

N-(1-(4-cyanobenzyl)piperidin-4-yl)-5-(4-(4-fluorobenzoyl)piperidine-1-carbonyl)benzofuran-2-carboxamide;

N-(6-(4-cyanophenoxy)pyridin-3-yl)-5-(4-(4-fluorobenzoyl)piperidine-1-carbonyl)benzofuran-2-carboxamide;

5-(4-(4-fluorophenoxy)piperidine-1-carbonyl)-N-(1-(pyridin-4-ylmethyl)piperidin-4-yl)benzofuran-2-carboxamide;

N-(1-(4-cyanobenzyl)piperidin-4-yl)-5-(4-(4-fluorophenoxy)piperidine-1-carbonyl)benzofuran-2-carboxamide;

5-(4-(4-fluorophenoxy)piperidine-1-carbonyl)-N-(6-(4-fluorophenoxy)pyridin-3-yl)benzofuran-2-carboxamide;

N-(1-(4-methoxybenzyl)piperidin-4-yl)-5-(4-(4-(trifluoromethyl)phenoxy)piperidine-1-carbonyl)benzofuran-2-carboxamide;

N-(6-(4-fluorophenoxy)pyridin-3-yl)-5-(4-(4-(trifluoromethyl)phenoxy)piperidine-1-carbonyl)benzofuran-2-carboxamide;

N-(1-(4-cyanobenzyl)piperidin-4-yl)-5-(4-(4-(trifluoromethyl)phenoxy)piperidine-1-carbonyl)benzofuran-2-carboxamide;

N-(1-(4-methoxybenzyl)piperidin-4-yl)-5-(4-(4-(methylsulfonyl)phenoxy)piperidine-1-carbonyl)benzofuran-2-carboxamide;

5-(4-(4-(methylsulfonyl)phenoxy)piperidine-1-carbonyl)-N-(1-(4-(trifluoromethoxy)benzyl)piperidin-4-yl)benzofuran-2-carboxamide;

N-(1-(4-cyanobenzyl)piperidin-4-yl)-5-((3,4-trans)-3-fluoro-4-(4-(methylsulfonyl)phenoxy)piperidine-1-carbonyl)benzofuran-2-carboxamide;

5-((3,4-trans)-3-fluoro-4-(4-(methylsulfonyl)phenoxy)piperidine-1-carbonyl)-N-(1-(4-methoxybenzyl)piperidin-4-yl)benzofuran-2-carboxamide;

5-((3,4-trans)-3-fluoro-4-(4-(methylsulfonyl)phenoxy)piperidine-1-carbonyl)-N-(1-(4-(trifluoromethoxy)benzyl)piperidin-4-yl)benzofuran-2-carboxamide;

N-(1-(4-cyanobenzyl)piperidin-4-yl)-5-(4-(4-fluorophenylsulfonyl)piperidine-1-carbonyl)benzofuran-2-carboxamide;

N-(1-(4-cyanobenzyl)piperidin-4-yl)-5-(4-(4-(trifluoromethylsulfonyl)phenoxy)piperidine-1-carbonyl)benzofuran-2-carboxamide;

N-(1-(4-cyanobenzyl)piperidin-4-yl)-5-(4-(4-(4-methoxyphenyl)-1H-pyrazol-1-yl)piperidine-1-carbonyl)benzofuran-2-carboxamide;

5-(4-(4-(methylsulfonyl)phenoxy)piperidine-1-carbonyl)-N-(1-(4-(trifluoromethoxy)benzyl)piperidin-4-yl)benzofuran-2-carboxamide;

N-(1-(4-(trifluoromethoxy)benzyl)piperidin-4-yl)-5-(4-(4-(trifluoromethylsulfonyl)phenoxy)piperidine-1-carbonyl)benzofuran-2-carboxamide;

N-(1-(3-fluoro-4-methoxybenzyl)piperidin-4-yl)-5-(4-(4-(trifluoromethylsulfonyl)phenoxy)piperidine-1-carbonyl)benzofuran-2-carboxamide;

and

N-(1-(4-methoxybenzyl)piperidin-4-yl)-5-(4-(4-(methylsulfonyl)phenoxy)piperidine-1-carbonyl)benzofuran-2-carboxamide;

or a pharmaceutically acceptable salt thereof.

16. A pharmaceutical composition comprising a compound of claim 1 or a pharmaceutically acceptable salt thereof, and at least one pharmaceutically acceptable carrier, diluent or excipient.

17. A method for
activating the AMPK pathway in a cell
comprising contacting the cell with an effective amount of a compound or salt of claim 1.

\* \* \* \* \*